US007951546B2

(12) United States Patent
Frantz et al.

(10) Patent No.: US 7,951,546 B2
(45) Date of Patent: May 31, 2011

(54) COMPOSITIONS AND METHODS FOR THE DIAGNOSIS AND TREATMENT OF TUMOR

(75) Inventors: Gretchen Frantz, San Francisco, CA (US); Kenneth J. Hillan, San Francisco, CA (US); Heidi Phillips, San Carlos, CA (US); Paul Polakis, Burlingame, CA (US); Susan D. Spencer, Tiburon, CA (US); P. Mickey Williams, Half Moon Bay, CA (US); Thomas D. Wu, San Francisco, CA (US); Zemin Zhang, Foster City, CA (US)

(73) Assignee: Genetech, Inc., South San Francisco, CA (US)

( * ) Notice: Subject to any disclaimer, the term of this patent is extended or adjusted under 35 U.S.C. 154(b) by 0 days.

(21) Appl. No.: 12/156,180

(22) Filed: May 29, 2008

(65) Prior Publication Data

US 2009/0075279 A1 Mar. 19, 2009

Related U.S. Application Data

(63) Continuation of application No. 11/804,045, filed on May 15, 2007, which is a continuation of application No. 10/872,972, filed on Jun. 21, 2004, now abandoned, which is a continuation of application No. 10/241,220, filed on Sep. 11, 2002, now abandoned.

(60) Provisional application No. 60/323,268, filed on Sep. 18, 2001, provisional application No. 60/339,227, filed on Oct. 19, 2001, provisional application No. 60/336,827, filed on Nov. 7, 2001, provisional application No. 60/331,906, filed on Nov. 20, 2001, provisional application No. 60/345,444, filed on Jan. 2, 2002, provisional application No. 60/369,724, filed on Apr. 3, 2002, provisional application No. 60/404,809, filed on Aug. 19, 2002.

(51) Int. Cl.
*G01N 33/53* (2006.01)

(52) U.S. Cl. .......................................................... 435/7.1

(58) Field of Classification Search ........................ None
See application file for complete search history.

(56) References Cited

U.S. PATENT DOCUMENTS

| | | | |
|---|---|---|---|
| 5,208,020 | A | 5/1993 | Chari et al. |
| 5,277,894 | A | 1/1994 | Strauss et al. |
| 5,773,001 | A | 6/1998 | Hamann et al. |
| 2003/0073129 | A1 | 4/2003 | Baker et al. |
| 2004/0058340 | A1 | 3/2004 | Dai et al. |

FOREIGN PATENT DOCUMENTS

| | | | | |
|---|---|---|---|---|
| EP | 1 126 028 | A1 | | 8/2001 |
| EP | 1 375 518 | | | 1/2004 |
| WO | WO 90/05540 | | | 5/1990 |
| WO | WO 00/12708 | | | 3/2000 |
| WO | WO 00/78961 | | | 12/2000 |
| WO | WO 01/42288 | A2 | | 6/2001 |
| WO | WO 0153312 | A1 | * | 7/2001 |
| WO | WO 01/60860 | | | 8/2001 |
| WO | WO 01/62273 | A1 | | 8/2001 |
| WO | WO 01/64882 | A2 | | 9/2001 |
| WO | WO 01/66689 | | | 9/2001 |
| WO | WO 01/66689 | A2 | * | 9/2001 |
| WO | WO 01/68848 | | | 9/2001 |
| WO | WO 02/059377 | A2 | | 8/2002 |
| WO | WO 03/018621 | | * | 3/2003 |
| WO | WO 03/042661 | | | 5/2003 |
| WO | WO 03/083074 | | | 10/2003 |
| WO | WO 2005/058028 | | | 6/2005 |

OTHER PUBLICATIONS

Stanton, P et al, 1994, Br J Cancer, 70: 427-433.*
Iehle, C et al, 1999, J Steroid Biochem Mol Biol, 68: 189-195.*
Abbaszadegan, M R, et al, 1994, Cancer Res, 54: 4676-4679.*
Stedman's medical dictionary, 25th ed, 1990, p. 1652-1653.*
Russo, V et al, 1995, Int J Cancer, 64: 216-221.*
Kibel, AS et al, 2000, J urol, 164(1): 192-6.*
Dong et al, 2000, Cancer Research, 60: 3880-3883.*
Banki et al, 1994, JBC, 269 (4): 2847-51.*
Bendayan et al, 1995, J Histochem Cytochem, 43(9): 881-886).*
Dahia, et al., "Mutation analysis of glial cell line-derived neurotrophic factor (GDNF), a ligand for the RET/GNDF receptor α complex, in sporadic phaeochromocytomas", Cancer Research, 57:310-313, (1997).
Kotani, et al., "The metastasis suppressor gene kiss-1 encodes kisspeptins, the natural ligands of the orphan G protein-coupled receptor GPR54", The journal of Biological Chemistry, vol. 276, No. 37, pp. 34631-34636, (2001).
Harms, et al., "Kiss-1 metastasis suppression and emergent pathways", Clinical & Experimental Metastasis, 20: 11-18, (2003).
Mason, "The RET receptor tyrosine kinase: activation, signalling and significance in neural development and disease", Pharmaceutica acta helvetiae, 74:261-264, (2000).
Marsh, et al., "Mutation analysis of glial cell line-derived neurotrophic factor, a ligand for an RET/Coreceptor complex, in multiple endocrine neoplasia type 2 and sporadic neuroendocrine tumors", JCEM, vol. 82, No. 9, pp. 3025-3028, (1997).
Mulligan, et al., "Investigation of the Genes for RET and its ligand complex, GDNF/GFRα-1, in small cell lung carcinoma", Genes, Chromosomes & Cancer, 21:326-332, (1998).
Steeg, et al., "Metastasis suppressor genes: basic biology and potential clinical use", Clinical Breast Cancer, vol. 4, No. 1, pp. 51-62, (2003).
Welch, et al., "Molecular biology of breast cancer metastasis genetic regulation of human breast carcinoma metastasis", Breast Cancer Research, 2: 408-416, (2000).
Caillou, et al., "Expression of reduced nicotinamide adenine dinucleotide phosphate oxidase (ThoX, LNOX, Duox) genes and proteins in human thyroid tissues", Journal of Clinical Endocrinology and Metabolism, vol. 86, No. 7, p. 3351-3358, (2001).

(Continued)

*Primary Examiner* — Sean E Aeder
(74) *Attorney, Agent, or Firm* — Mark T. Kresnak; James A. Fox; Arnold & Porter LLP

(57) ABSTRACT

The present invention is directed to compositions of matter useful for the diagnosis and treatment of tumor in mammals and to methods of using those compositions of matter for the same.

4 Claims, 136 Drawing Sheets

OTHER PUBLICATIONS

Yerushalmi, et al., "ERGL, a novel gene related to ERGIC-53 that is highly expressed in normal and neoplastic prostate and several other tissues", Gene, 265, pp. 55-60, (2001).
Accession No. AK000322; Sugano, et al., Feb. 15, 2000; Database: GBTRANS Search date: Nov. 18, 2003.
Accession No. NM_017763; Kawakami, et al.; Database: GBTRANS Search date: Nov. 18, 2003.
Accession No. Q9NXDO; Kawakami, et al.; Database: GBTRANS Search date: Oct. 1, 2000.
Bowie, et al., Science, 257:1306-1310, (1990).
Herbert, et al., The Dictionary of Immunology, Academic Press, $4^{th}$ Edition, pp. 58, (1995).
John Hopkins Pathology—Ovarian Cancer—http://www.ovariancancer.jhmi.edu/ca125qa.cfm, Web site, reviewed but cannot be published.
MPSRCH search report, US-10-241-220-93.rag, pp. 2-4, (2004).
Nishikawa, et al., European J. Biochem., 173(2): 389-394, (1988).
Roger, et al., Bioscience Reports, 8(4): 359-368, (1988).
TAT193 Sequence Alignment Report, date? page? reviewed but cannot be published.
Widschwendter, M., et al., Plosone—3(7)e2656:1-9 (2008).
Roger, I et al, 1988, Bioscience Reports, 8(4): 359-368.*
Herbert et al (The Dictionary of Immunology, Academic Press. 4th edition, 1995, p. 58).*
Bowie et al .Science, 1990, 257 : 1306-1310.*
White et al, 2001, Ann Rev Med, 52: 125-145.*
MPSRCH search report, 2004, us-10-241-220-93.rag, pp. 2-4.
Nishikawa, S, et al, 1988, European J. Biochem, 173(2); 389-394.
Breenbaum et al., (genome biology, 2003, vol. 4, issue 9, pp. 117.1-117.8).
Boon, 1992 (Adv. Can. Res., 58:177-210).
Crystal, 1995 (Science, vol. 270, p. 404-410).
Curti, 1993 (Crit. Rev. in Oncology/Hematology, 14:29-39).
Deonarain, 1998 (Expert Opin. Ther. Pat., vol. 8 pp. 53-69).
Ezzell, 1995 (J. NIH Res., 7:46-49).
Fu et al., 1996 (EMBO Jounrnal, vol. 15, pp. 4392-4401).
Guo et al., 2002 (Journal of Pharmacology and Experimental Therapeutics, vol. 300, pp. 206-212).
Gura, 1997 (Science, 278:1041-1042).
Hartwell et al. (Science, 1997, 278:1064-1068).
Hell et al., 1995 (Laboratory Investigation, vol. 73, pp. 492-496).
Jain, 1994 (Sci. Am., 271:58-65).
Miller, 1995 (FASEB J., vol. 9, pp. 190-199).
Sadek et al., "Osteopontin" Crit Rev Oral Biol Med., vol. 11, No. 3 pp. 279-303 (2000) XP001022167.
Sambrook et al., (Molecular Cloning, A Laboratory Manual, $2^{nd}$ Edition, Cold Springs Harbor Press, Cold Spring Harbor, p. 16.3-16.4).
Spitler, 1995 (Cancer Biotherapy, 10:1-3).
Thalmann et al., "Osteopontin: Possible Role in Prostate Cancer Progression", Clin. Cancer Research vol. 5, pp. 2271-2277 (1999) XP002348201.
Tokota, J et al., 1988 (Oncogene, vol. 3, pp. 471-475).
Verma, Sep. 1997 (Nature, vol. 389, pp. 239-242).
Weber et al., "The Metastasis Gene Osteopontin: A Candidate Target for Cancer Therapy" Biochimica et Biophysica Acta 1552 (2001) 61-85 XP004334757.
White et al., 2001 (Ann Rev Med., 52:125-145).
Zimmer, 1991 (Cell Motility and the Cytoskeleton, vol. 20, pp. 325-337).
U.S. Appl. No. 60/298,918 and MPSRCH search result, 2006, us-10-872-972.93.mpbm, pp. 1-5.

* cited by examiner

FIGURE 1

CTCCGGGTCCCCAGGGGCTGCGCCGGGCCGGCCTGGCAAGGGGGACGAGTCAGTGGACACTCCAGGAAGAGCGGCCC
CGCGGGGGGCGATGACCGTGCGCTGACCCTGACTCACTCCAGGTCCGGAGGCGGGGGCCCCCGGGGCGACTCGGGGG
CGGACCGCGGGGCGGAGCTGCCGCCCGTGAGTCCGGCCGAGCCACCTGAGCCCGAGCCGCGGGACACCGTCGCTCCT
GCTCTCCGA<u>ATG</u>CTGCGCACCGCGATGGGCCTGAGGAGCTGGCTCGCCGCCCCATGGGGCGCGCTGCCGCCTCGGCC
ACCGCTGCTGCTGCTCCTGCTGCTGCTGCTCCTGCTGCAGCCGCCGCCTCCGACCTGGGCGCTCAGCCCCCGGATCA
GCCTGCCTCTGGGCTCTGAAGAGCGGCCATTCCTCAGATTCGAAGCTGAACACATCTCCAACTACACAGCCCTTCTG
CTGAGCAGGGATGGCAGGACCCTGTACGTGGGTGCTCGAGAGGCCCTCTTTGCACTCAGTAGCAACCTCAGCTTCCT
GCCAGGCGGGGAGTACCAGGAGCTGCTTTGGGGTGCAGACGCAGAGAAGAAACAGCAGTGCAGCTTCAAGGGCAAGG
ACCCACAGCGCGACTGTCAAAACTACATCAAGATCCTCCTGCCGCTCAGCGGCAGTCACCTGTTCACCTGTGGCACA
GCAGCCTTCAGCCCCATGTGTACCTACATCAACATGGAGAACTTCACCCTGGCAAGGGACGAGAAGGGGAATGTCCT
CCTGGAAGATGGCAAGGGCCGTTGTCCCTTCGACCCGAATTTCAAGTCCACTGCCCTGGTGGTTGATGGCGAGCTCT
ACACTGGAACAGTCAGCAGCTTCCAAGGGAATGACCCGGCCATCTCGCGGAGCCAAAGCCTTCGCCCCACCAAGACC
GAGAGCTCCCTCAACTGGCTGCAAGACCCAGCTTTTGTGGCCTCAGCCTACATTCCTGAGAGCCTGGGCAGCTTGCA
AGGCGATGATGACAAGATCTACTTTTTCTTCAGCGAGACTGGCCAGGAATTTGAGTTCTTTGAGAACACCATTGTGT
CCCGCATTGCCCGCATCTGCAAGGGCGATGAGGGTGGAGAGCGGGTGCTACAGCAGCGCTGGACCTCCTTCCTCAAG
GCCCAGCTGCTGTGCTCACGGCCCGACGATGGCTTCCCCTTCAACGTGCTGCAGGATGTCTTCACGCTGAGCCCCAG
CCCCCAGGACTGGCGTGACACCCTTTTCTATGGGGTCTTCACTTCCCAGTGGCACAGGGGAACTACAGAAGGCTCTG
CCGTCTGTGTCTTCACAATGAAGGATGTGCAGAGAGTCTTCAGCGGCCTCTACAAGGAGGTGAACCGTGAGACACAG
CAGTGGTACACCGTGACCCACCCGGTGCCCACACCCCGGCCTGGAGCGTGCATCACCAACAGTGCCCGGGAAAGGAA
GATCAACTCATCCCTGCAGCTCCCAGACCGCGTGCTGAACTTCCTCAAGGACCACTTCCTGATGGACGGGCAGGTCC
GAAGCCGCATGCTGCTGCTGCAGCCCCAGGCTCGCTACCAGCGCGTGGCTGTACACCGCGTCCCTGGCCTGCACCAC
ACCTACGATGTCCTCTTCCTGGGCACTGGTGACGGCCGGCTCCACAAGGCAGTGAGCGTGGGCCCCCGGGTGCACAT
CATTGAGGAGCTGCAGATCTTCTCATCGGGACAGCCCGTGCAGAATCTGCTCCTGGACACCCACAGGGGGCTGCTGT
ATGCGGCCTCACACTCGGGCGTAGTCCAGGTGCCCATGGCCAACTGCAGCCTGTACCGGAGCTGTGGGGACTGCCTC
CTCGCCCGGGACCCCTACTGTGCTTGGAGCGGCTCCAGCTGCAAGCACGTCAGCCTCTACCAGCCTCAGCTGGCCAC
CAGGCCGTGGATCCAGGACATCGAGGGAGCCAGCGCCAAGGACCTTTGCAGCGCGTCTTCGGTTGTGTCCCCGTCTT
TTGTACCAACAGGGGAGAAGCCATGTGAGCAAGTCCAGTTCCAGCCCAACACAGTGAACACTTTGGCCTGCCCGCTC
CTCTCCAACCTGGCGACCCGACTCTGGCTACGCAACGGGGCCCCCGTCAATGCCTCGGCCTCCTGCCACGTGCTACC
CACTGGGGACCTGCTGCTGGTGGGCACCCAACAGCTGGGGGAGTTCCAGTGCTGGTCACTAGAGGAGGGCTTCCAGC
AGCTGGTAGCCAGCTACTGCCCAGAGGTGGTGGAGGACGGGGTGGCAGACCAAACAGATGAGGGTGGCAGTGTACCC
GTCATTATCAGCACATCGCGTGTGAGTGCACCAGCTGGTGGCAAGGCCAGCTGGGGTGCAGACAGGTCCTACTGGAA
GGAGTTCCTGGTGATGTGCACGCTCTTTGTGCTGGCCGTGCTGCTCCCAGTTTTATTCTTGCTCTACCGGCACCGGA
ACAGCATGAAAGTCTTCCTGAAGCAGGGGGAATGTGCCAGCGTGCACCCCAAGACCTGCCCTGTGGTGCTGCCCCCT
GAGACCCGCCCACTCAACGGCCTAGGGCCCCCTAGCACCCCGCTCGATCACCGAGGGTACCAGTCCCTGTCAGACAG
CCCCCCGGGGGCCCGAGTCTTCACTGAGTCAGAGAAGAGGCCACTCAGCATCCAAGACAGCTTCGTGGAGGTATCCC
CAGTGTGCCCCCGGCCCCGGGTCCGCCTTGGCTCGGAGATCCGTGACTCTGTGGTG<u>TGA</u>GAGCTGACTTCCAGAGGA
CGCTGCCCTGGCTTCAGGGGCTGTGAATGCTCGGAGAGGGTCAACTGGACCTCCCCTCCGCTCTGCTCTTCGTGGAA
CACGACCGTGGTGCCCGGCCCTTGGGAGCCTTGGAGCCAGCTGGCCTGCTGCTCTCCAGTCAAGTAGCGAAGCTCCT
ACCACCCAGACACCCAAACAGCCGTGGCCCCAGAGGTCCTGGCCAAATATGGGGGCCTGCCTAGGTTGGTGGAACAG
TGCTCCTTATGTAAACTGAGCCCTTTGTTTAAAAAACAATTCCAAATGTGAAACTAGAATGAGAGGGAAGAGATAGC
ATGGCATGCAGCACACACGGCTGCTCCAGTTCATGGCCTCCCAGGGGTGCTGGGGATGCATCCAAAGTGGTTGTCTG
AGACAGAGTTGGAAACCCTCACCAACTGGCCTCTTCACCTTCCACATTATCCCGCTGCCACCGGCTGCCCTGTCTCA
CTGCAGATTCAGGACCAGCTTGGGCTGCGTGCGTTCTGCCTTGCCAGTCAGCCGAGGATGTAGTTGTTGCTGCCGTC
GTCCCACCACCTCAGGGACCAGAGGGCTAGGTTGGCACTGCGGCCCTCACCAGGTCCTGGGCTCGGACCCAACTCCT
GGACCTTTCCAGCCTGTATCAGGCTGTGGCCACACGAGAGGACAGCGCGAGCTCAGGAGAGATTTCGTGACAATGTA
CGCCTTTCCCTCAGAATTCAGGGAAGAGACTGTCGCCTGCCTTCCTCCGTTGTTGCGTGAGAACCCGTGTGCCCCTT
CCCACCATATCCACCCTCGCTCCATCTTTGAACTCAAACACGAGGAACTAACTGCACCCTGGTCCTCTCCCCAGTCC
CCAGTTCACCCTCCATCCCTCACCTTCCTCCACTCTAAGGGATATCAACACTGCCCAGCACAGGGGCCCTGAATTTA
TGTGGTTTTTATACATTTTTTAATAAGATGCACTTTATGTCATTTTTTAATAAAGTCTGAAGAATTACTGTTTAAAA
AAAAAAAA

FIGURE 2

GGAAAGGCTGAGTCTCCAGCTCAAGGTCAAAACGTCCAAGGCCGAAAGCCCTCCAGTTTCCCCTGGACGCCTTGCTC
CTGCTTCTGCTACGACCTTCTGGGGAAAACGAATTTCTCATTTTCTTCTTAAATTGCCATTTTCGCTTTAGGAGATG
AATGTTTTCCTTTGGCTGTTTTGGCAATGACTCTGAATTAAAGCGATGCTAACGCCTCTTTTCCCCCTAATTGTTAA
AAGCTATGGACTGCAGGAAGATGGCCCGCTTCTCTTACAGTGTGATTTGGATCATGGCCATTTCTAAAGTCTTTGAA
CTGGGATTAGTTGCCGGGCTGGGCCATCAGGAATTTGCTCGTCCATCTCGGGGATACCTGGCCTTCAGAGATGACAG
CATTTGGCCCCAGGAGGAGCCTGCAATTCGGCCTCGGTCTTCCCAGCGTGTGCCGCCCATGGGGATACAGCACAGTA
AGGAGCTAAACAGAACCTGCTGCCTGAATGGGGGAACCTGCATGCTGGGGTCCTTTTGTGCCTGCCCTCCCTCCTTC
TACGGACGGAACTGTGAGCACGATGTGCGCAAAGAGAACTGTGGGTCTGTGCCCCATGACACCTGGCTGCCCAAGAA
GTGTTCCCTGTGTAAATGCTGGCACGGTCAGCTCCGCTGCTTTCCTCAGGCATTTCTACCCGGCTGTGATGGCCTTG
TGATGGATGAGCACCTCGTGGCTTCCAGGACTCCAGAACTACCACCGTCTGCACGTACTACCACTTTTATGCTAGTT
GGCATCTGCCTTTCTATACAAAGCTACTATTAATCGACATTGACCTATTTCCAGAAATACAATTTTAGATATCATGC
AAATTTCATGACCAGTAAAGGCTGCTGCTACAATGTCCTAACTGAAAGATGATCATTTGTAGTTGCCTTAAAATAAT
GAATACATTTCCAAAATGGTCTCTAACATTTCCTTACAGAACTACTTCTTACTTCTTTGCCCTGCCCTCTCCCAAAA
AACTACTTCTTTTTTCAAAAGAAAGTCAGCCATATCTCCATTGTGCCTAAGTCCAGTGTTTCTTTTTTTTTTTTTTT
TGAGACGGAGTCTCACTCTGTCACCCAGGCTGGACTGCAATGACGCGATCTTGGTTCACTGCAACCTCCGCATCCGG
GGTTCAAGCCATTCTCCTGCCTCAGCCTCCCAAGTAACTGGGATTACAGGCATGTGTCACCATGCCCAGCTAATTTT
TTTGTATTTTTAGTAGAGATGGGGTTTCACCATATTGGCCAGTCTGGTCTCGAACTCCTGACCTTGTGATCCACTC
GCCTCAGCCTCTCGAAGTGCTGAGATTACACACGTGAGCAACTGTGCAAGGCCTGGTGTTTCTTGATACATGTAATT
CTACCAAGGTCTTCTTAATATGTTCTTTTAAATGATTGAATTATATGTTCAGATTATTGGAGACTAATTCTAATGTG
GACCTTAGAATACAGTTTTGAGTAGAGTTGATCAAAATCAATTAAAATAGTCTCTTTAAAAGGAAAGAAAACATCTT
TAAGGGGAGGAACCAGAGTGCTGAAGGAATGGAAGTCCATCTGCGTGTGTGCAGGGAGACTGGGTAGGAAAGAGGAA
GCAAATAGAAGAGAGAGGTTGAAAAACAAAATGGGTTACTTGATTGGTGATTAGGTGGTGGTAGAGAAGCAAGTAAA
AAGGCTAAATGGAAGGGCAAGTTTCCATCATCTATAGAAAGCTATATAAGACAAGAACTCCCCTTTTTTTCCCAAAG
GCATTATAAAAAGAATGAAGCCTCCTTAGAAAAAAAATTATACCTCAATGTCCCCAACAAGATTGCTTAATAAATTG
TGTTTCCTCCAAGCTATTCAATTCTTTTAACTGTTGTAGAAGACAAAATGTTCACAATATATTTAGTTGTAAACCAA
GTGATCAAACTACATATTGTAAAGCCCATTTTTAAAATACATTGTATATATGTGTATGCACAGTAAAAATGGAAACT
ATATTGAA

FIGURE 3

GCCAGGAGGGAGAGCCTTCCCCAAGCAAACAATCCAGAGCAGCTGTGCAAACAACGGTGCATAAATGAGGCCTCCTG
GACCATGAAGCGAGTCCTGAGCTGCGTCCCGGAGCCCACGGTGGTCATGGCTGCCAGAGCGCTCTGCATGCTGGGGC
TGGTCCTGGCCTTGCTGTCCTCCAGCTCTGCTGAGGAGTACGTGGGCCTGTCTGCAAACCAGTGTGCCGTGCCAGCC
AAGGACAGGGTGGACTGCGGCTACCCCCATGTCACCCCCAAGGAGTGCAACAACCGGGGCTGCTGCTTTGACTCCAG
GATCCCTGGAGTGCCTTGGTGTTTCAAGCCCCTGCAGGAAGCAGAATGCACCTTCTGAGGCACCTCCAGCTGCCCCC
GGCCGGGGGATGCGAGGCTCGGAGCACCCTTGCCCGGCTGTGATTGCTGCCAGGCACTGTTCATCTCAGCTTTTCTG
TCCCTTTGCTCCCGGCAAGCGCTTCTGCTGAAAGTTCATATCTGGAGCCTGATGTCTTAACGAATAAAGGTCCCATG
CTCCACCCGA

FIGURE 4

GACCAGACTCGTCTCAGGCCAGTTGCAGCCTTCTCAGCCAAACGCCGACCAAGGAAAACTCACTACCATGAGAATTG
CAGTGATTTGCTTTTGCCTCCTAGGCATCACCTGTGCCATACCAGTTAAACAGGCTGATTCTGGAAGTTCTGAGGAA
AAGCAGCTTTACAACAAATACCCAGATGCTGTGGCCACATGGCTAAACCCTGACCCATCTCAGAAGCAGAATCTCCT
AGCCCCACAGAATGCTGTGTCCTCTGAAGAAACCAATGACTTTAAACAAGAGACCCTTCCAAGTAAGTCCAACGAAA
GCCATGACCACATGGATGATATGGATGATGAAGATGATGATGACCATGTGGACAGCCAGGACTCCATTGACTCGAAC
GACTCTGATGATGTAGATGACACTGATGATTCTCACCAGTCTGATGAGTCTCACCATTCTGATGAATCTGATGAACT
GGTCACTGATTTTCCCACGGACCTGCCAGCAACCGAAGTTTTCACTCCAGTTGTCCCCACAGTAGACACATATGATG
GCCGAGGTGATAGTGTGGTTTATGGACTGAGGTCAAAATCTAAGAAGTTTCGCAGACCTGACATCCAGTACCCTGAT
GCTACAGACGAGGACATCACCTCACACATGGAAAGCGAGGAGTTGAATGGTGCATACAAGGCCATCCCCGTTGCCCA
GGACCTGAACGCGCCTTCTGATTGGGACAGCCGTGGGAAGGACAGTTATGAAACGAGTCAGCTGGATGACCAGAGTG
CTGAAACCCACAGCCACAAGCAGTCCAGATTATATAAGCGGAAAGCCAATGATGAGAGCAATGAGCATTCCGATGTG
ATTGATAGTCAGGAACTTTCCAAAGTCAGCCGTGAATTCCACAGCCATGAATTTCACAGCCATGAAGATATGCTGGT
TGTAGACCCCAAAAGTAAGGAAGAAGATAAACACCTGAAATTTCGTATTTCTCATGAATTAGATAGTGCATCTTCTG
AGGTCAATTAAAAGGAGAAAAAATACAATTTCTCACTTTGCATTTAGTCAAAAGAAAAAATGCTTTATAGCAAAATG
AAAGAGAACATGAAATGCTTCTTTCTCAGTTTATTGGTTGAATGTGTATCTATTTGAGTCTGGAAATAACTAATGTG
TTTGATAATTAGTTTAGTTTGTGGCTTCATGGAAACTCCCTGTAAACTAAAAGCTTCAGGGTTATGTCTATGTTCAT
TCTATAGAAGAAATGCAAACTATCACTGTATTTTAATATTTGTTATTCTCTCATGAATAGAAATTTATGTAGAAGCA
AACAAAATACTTTTACCCACTTAAAAAGAGAATATAACATTTTATGTCACTATAATCTTTTGTTTTTTAAGTTAGTG
TATATTTTGTTGTGATTATCTTTTTGTGGTGTGAATAA

FIGURE 5

CGGACGCGTGGGCGGAGGGAAGAGGACCGCAAACCAACCCAGGACCCGCTCAGTTCCACGCGCGGCAGCCCTCCGTG
CGCGCAGGCTCGGTATGAGCCGCACAGCCTACACGGTGGGAGCCCTGCTTCTCCTCTTGGGGACCCTGCTGCCGGCT
GCTGAAGGGAAAAAGAAAGGGTCCCAAGGTGCCATCCCCCCGCCAGACAAGGCCCAGCACAATGACTCAGAGCAGAC
TCAGTCGCCCCAGCAGCCTGGCTCCAGGAACCGGGGGCGGGGCCAAGGGCGGGGCACTGCCATGCCCGGGGAGGAGG
TGCTGGAGTCCAGCCAAGAGGCCCTGCATGTGACGGAGCGCAAATACCTGAAGCGAGACTGGTGCAAAACCCAGCCG
CTTAAGCAGACCATCCACGAGGAAGGCTGCAACAGTCGCACCATCATCAACCGCTTCTGTTACGGCCAGTGCAACTC
TTTCTACATCCCCAGGCACATCCGGAAGGAGGAAGGTTCCTTTCAGTCCTGCTCCTTCTGCAAGCCCAAGAAATTCA
CTACCATGATGGTCACACTCAACTGCCCTGAACTACAGCCACCTACCAAGAAGAAGAGAGTCACACGTGTGAAGCAG
TGTCGTTGCATATCCATCGATTTGGATTAAGCCAAATCCAGGTGCACCCAGCATGTCCTAGGAATGCAGCCCCAGGA
AGTCCCAGACCTAAAACAACCAGATTCXXXXXXXXXXXXXXXXXXXXXXXXXXXXXXXXXXXXXXXXXAGACTTACG
ATGCATGTATACAAACGAATAGCAGATAATGATGACTAGTTCACACATAAAGTCCTTTTAAGGAGAAAATCTAAAAT
GAAAAGTGGATAAACAGAACATTTATAAGTGATCAGTTAATGCCTAAGAGTGAAAGTAGTTCTATTGACATTCCTCA
AGATATTTAATATCAACTGCATTATGTATTATGTCTGCTTAAATCATTTAAAAACGGCAAAGAATTATATAGACTAT
GAGGTACCTTGCTGTGTAGGAGGATGAAAGGGGAGTTGATAGTCTCATAAAACTAATTTGGCTTCAAGTTTCATGAA
TCTGTAACTAGAATTTAATTTTCACCCCAATAATGTTCTATATAGCCTTTGCTAAAGAGCAACTAATAAATTAAACC
TATTCTTTCAA

FIGURE 6

CGGACCTGAACCCCTAAAAGCGGAACCGCCTCCCGCCCTCGCCATCGCGGAGCTGAGTCGCCGGCGGCGGTGGCTGC
TGCCAGACCCGGAGTTTCCTCTTTCACTGGATGGAGCTGAACTTTGGGCGGCCAGAGCAGCACAGCTGTCCGGGGAT
CGCTGCATGCTGAGCTCCCTCGGCAAGACCCAGCGGCGGCTCGGGATTTTTTTGGGGGGGCGGGGACCAGCCCCGCG
CCGGCACCATGTTCCTGGCGACCCTGTACTTCGCGCTGCCGCTCTTGGACTTGCTCCTGTCGGCCGAAGTGAGCGGC
GGAGACCGCCTGGATTGCGTGAAAGCCAGTGATCAGTGCCTGAAGGAGCAGAGCTGCAGCACCAAGTACCGCACGCT
AAGGCAGTGCGTGGCGGGCAAGGAGACCAACTTCAGCCTGGCATCCGGCCTGGAGGCCAAGGATGAGTGCCGCAGCG
CCATGGAGGCCCTGAAGCAGAAGTCGCTCTACAACTGCCGCTGCAAGCGGGGTATGAAGAAGGAGAAGAACTGCCTG
CGCATTTACTGGAGCATGTACCAGAGCCTGCAGGGAAATGATCTGCTGGAGGATTCCCCATATGAACCAGTTAACAG
CAGATTGTCAGATATATTCCGGGTGGTCCCATTCATATCAGTGGAGCACATTCCCAAAGGGAACAACTGCCTGGATG
CAGCGAAGGCCTGCAACCTCGACGACATTTGCAAGAAGTACAGGTCGGCGTACATCACCCCGTGCACCACCAGCGTG
TCCAATGATGTCTGCAACCGCCGCAAGTGCCACAAGGCCCTCCGGCAGTTCTTTGACAAGGTCCCGGCCAAGCACAG
CTACGGAATGCTCTTCTGCTCCTGCCGGGACATCGCCTGCACAGAGCGGAGGCGACAGACCATCGTGCCTGTGTGCT
CCTATGAAGAGAGGGAGAAGCCCAACTGTTTGAATTTGCAGGACTCCTGCAAGACGAATTACATCTGCAGATCTCGC
CTTGCGGATTTTTTTACCAACTGCCAGCCAGAGTCAAGGTCTGTCAGCAGCTGTCTAAAGGAAAACTACGCTGACTG
CCTCCTCGCCTACTCGGGGCTTATTGGCACAGTCATGACCCCCAACTACATAGACTCCAGTAGCCTCAGTGTGGCCC
CATGGTGTGACTGCAGCAACAGTGGGAACGACCTAGAAGAGTGCTTGAAATTTTTGAATTTCTTCAAGGACAATACA
TGTCTTAAAAATGCAATTCAAGCCTTTGGCAATGGCTCCGATGTGACCGTGTGGCAGCCAGCCTTCCCAGTACAGAC
CACCACTGCCACTACCACCACTGCCCTCCGGGTTAAGAACAAGCCCCTGGGGCCAGCAGGGTCTGAGAATGAAATTC
CCACTCATGTTTTGCCACCGTGTGCAAATTTACAGGCACAGAAGCTGAAATCCAATGTGTCGGGCAATACACACCTC
TGTATTTCCAATGGTAATTATGAAAAAGAAGGTCTCGGTGCTTCCAGCCACATAACCACAAAATCAATGGCTGCTCC
TCCAAGCTGTGGTCTGAGCCCACTGCTGGTCCTGGTGGTAACCGCTCTGTCCACCCTATTATCTTTAACAGAAACAT
CATAGCTGCATTAAAAAAATACAATATGGACATGTAAAAAGACAAAAACCAAGTTATCTGTTTCCTGTTCTCTTGTA
TAGCTGAAATTCCAGTTTAGGAGCTCAGTTGAGAAACAGTTCCATTCAACTGGAACATTTTTTTTTTTTCCTTTTAA
GAAAGCTTCTTGTGATCCTTCGGGGCTTCTGTGAAAAACCTGATGCAGTGCTCCATCCAAACTCAGAAGGCTTTGGG
ATATGCTGTATTTTAAAGGGACAGTTTGTAACTTGGGCTGTAAAGCAAACTGGGGCTGTGTTTTCGATGATGATGAT
GATCATGATGATGATCATCATGATCATGATGATGATCATCATGATCATGATGATGATTTTAACAGTTTTACTTCTGG
CCTTTCCTAGCTAGAGAAGGAGTTAATATTTCTAAGGTAACTCCCATATCTCCTTTAATGACATTGATTTCTAATGA
TATAAATTTCAGCCTACATTGATGCCAAGCTTTTTTGCCACAAAGAAGATTCTTACCAAGAGTGGGCTTTGTGGAAA
CAGCTGGTACTGATGTTCACCTTTATATATGTACTAGCATTTTCCACGCTGATGTTTATGTACTGTAAACAGTTCTG
CACTCTTGTACAAAAGAAAAAACACCTGTCACATCCAAATATAAAA

FIGURE 7

ATGCAGCACCGAGGCTTCCTCCTCCTCACCCTCCTCGCCCTGCTGGCGCTCACCTCCGCGGTCGCCAAAAAGAAAGA
TAAGGTGAAGAAGGGCGGCCCGGGGAGCGAGTGCGCTGAGTGGGCCTGGGGGCCCTGCACCCCCAGCAGCAAGGATT
GCGGCGTGGGTTTCCGCGAGGGCACCTGCGGGGCCCAGACCCAGCGCATCCGGTGCAGGGTGCCCTGCAACTGGAAG
AAGGAGTTTGGAGCCGACTGCAAGTACAAGTTTGAGAACTGGGGTGCGTGTGATGGGGGCACAGGCACCAAAGTCCG
CCAAGGCACCCTGAAGAAGGCGCGCTACAATGCTCAGTGCCAGGAGACCATCCGCGTCACCAAGCCCTGCACCCCCA
AGACCAAAGCAAAGGCCAAAGCCAAGAAAGGGAAGGGAAAGGACTAGACGCCAAGCCTGGATGCCAAGGAGCCCCTG
GTGTCACATGGGGCCTGGCCCACGCCCTCCCTCTCCCAGGCCCGAGATGTGACCCACCAGTGCCTTCTGTCTGCTCG
TTAGCTTTAATCAATCATGCCCC

FIGURE 8

GCGGCAGCAGCGCGGGCCCCAGCAGCCTCGGCAGCCACAGCCGCTGCAGCCGGGGCAGCCTCCGCTGCTGTCGCCTC
CTCTGATGCGCTTGCCCTCTCCCGGCCCCGGGACTCCGGGAGAATGTGGGTCCTAGGCATCGCGGCAACTTTTTGCG
GATTGTTCTTGCTTCCAGGCTTTGCGCTGCAAATCCAGTGCTACCAGTGTGAAGAATTCCAGCTGAACAACGACTGC
TCCTCCCCCGAGTTCATTGTGAATTGCACGGTGAACGTTCAAGACATGTGTCAGAAAGAAGTGATGGAGCAAAGTGC
CGGGATCATGTACCGCAAGTCCTGTGCATCATCAGCGGCCTGTCTCATCGCCTCTGCCGGGTACCAGTCCTTCTGCT
CCCCAGGGAAACTGAACTCAGTTTGCATCAGCTGCTGCAACACCCCTCTTTGTAACGGGCCAAGGCCCAAGAAAAGG
GGAAGTTCTGCCTCGGCCCTCAGGCCAGGGCTCCGCACCACCATCCTGTTCCTCAAATTAGCCCTCTTCTCGGCACA
CTGCTGAAGCTGAAGGAGATGCCACCCCCTCCTGCATTGTTCTTCCAGCCCTCGCCCCCAACCCCCCACCTCCCTGA
GTGAGTTTCTTCTGGGTGTCCTTTTATTCTGGGTAGGGAGCGGGAGTCCGTGTTCTCTTTTGTTCCTGTGCAAATAA
TGAAAGAGCTCGGTAAAGCATTCTGAATAAATTCAGCCTGACTGAATTTTCAGTATGTACTTGAAGGAAGGAGGTGG
AGTGAAAGTTCACCCCCATGTCTGTGTAACCGGAGTCAAGGCCAGGCTGGCAGAGTCAGTCCTTAGAAGTCACTGAG
GTGGGCATCTGCCTTTTGTAAAGCCTCCAGTGTCCATTCCATCCCTGATGGGGGCATAGTTTGAGACTGCAGAGTGA
GAGTGACGTTTTCTTAGGGCTGGAGGGCCAGTTCCCACTCAAGGCTCCCTCGCTTGACATTCAAACTTCATGCTCCT
GAAAACCATTCTCTGCAGCAGAATTGGCTGGTTTCGCGCCTGAGTTGGGCTCTAGTGACTCGAGACTCAATGACTGG
GACTTAGACTGGGGCTCGGCCTCGCTCTGAAAAGTGCTTAAGAAAATCTTCTCAGTTCTCCTTGCAGAGGACTGGCG
CCGGGACGCGAAGAGCAACGGGCGCTGCACAAAGCGGGCGCTGTCGGTGGTGGAGTGCGCATGTACGCGCAGGCGCT
TCTCGTGGTTGGCGTGCTGCAGCGACAGGCGGCAGCACAGCACCTGCACGAACACCCGCCGAAACTGCTGCGAGGAC
ACCGTGTACAGGAGCGGGTTGATGACCGAGCTGAGGTAGAAAAACGTCTCCGAGAAGGGGAGGAGGATCATGTACGC
CCGGAAGTAGGACCTCGTCCAGTCGTGCTTGGGTTTGGCCGCAGCCATGATCCTCCGAATCTGGTTGGGCATCCAGC
ATACGGCCAATGTCACAACAATCAGCCCTGGGCAGACACGAGCAGGAGGGAGAGACAGAGA

FIGURE 9

CACCCTCCGTGGCAAGGCGAGGCCCCGGGGGCGGGCCGGGGTCACCACGCCTGCCCCAGGGAACCGCACAGACGGTA
CTCACCCTTCTTGCGATGATGTGAGATGATAAAATGCCTACATGATGAGATGAAGTGAGATGAAAAACATAGGCCTT
GTGATGGAATGGGAAATTCCAGAGATAATTTGCACGTGCGCTAAGCTGCGGCTACCCCCGCAAGCAACCTTCCAAGT
CCTTCGTGGCAATGGTGCTTCCGTGGGGACCGTGCTCATGTTCCGCTGCCCCTCCAACCACCAGATGGTGGGGTCTG
GGCTCCTCACCTGCACCTGGAAGGGGAGCATCGCTGAGTGGTCTTCAGGGTCCCCAGTGTGCAAACTGGTGCCACCA
CACGAGACCTTTGGCTTCAAGGTGGCCGTGATCGCCTCCATTGTGAGCTGTGCCATCATCCTGCTCATGTCCATGGC
CTTCCTCACCTGCTGCCTCCTCAAGTGCGTGAAGAAGAGCAAGCGGCGGCGCTCCAACAGGTCAGCCCAGCTGTGGT
CCCAGCTGAAAGATGAGGACTTGGAGACGGTGCAGGCCGCATACCTTGGCCTCAAGCACTTCAACAAACCCGTGAGC
GGGCCCAGCCAGGCGCACGACAACCACAGCTTCACCACAGACCATGGTGAGAGCACCAGCAAGCTGGCCAGTGTGAC
CCGCAGCGTGGACAAGGACCCTGGGATCCCCAGAGCTCTAAGCCTCAGTGGCTCCTCCAGCTCACCCCAAGCCCAGG
TGATGGTGCACATGGCAAACCCCAGACAGCCCCTGCCTGCCTCTGGGCTGGCCACAGGAATGCCACAACAGCCCGCA
GCATATGCCCTAGGGTGACCACGCAGTGAGGCTGGTGCCCATGCTCCACACTGGGAGGCCAGGCTGACCCCACCAGC
CAGTCAGCTACAACTCCACATCAACTCCACATGCGCCCAGCTCGAGACTGATGAGTGGAATCAGCTTCCAGGTGTAG
GGACCCCTTGAGGGGCCGAGCTGACATCCAAGGCTGAGGACCCCAGTGGGGAGTGTTCTGTTCCGGCATATCCTGGC
CGTAACGATTTTTATAGTTATGGACTACTTGAAACCACTACTGAGGGTAATTTACTAGCTGTGGCCTCCCACTAACT
AGCATTCCTTTAAAGAGACTGGGAAATGTTTTAAGCAAATCTAGTTTTGTATAATAAAATAAGAAAATAGCAATAAA
CTTCTTTTCAGCAACTACAAA

FIGURE 10A

CTGACTGCACTGGTGATGGTCCCTGGCAATCCAACCTGGCACCATCGCAGTTGGAGTACTATGCATCTTCACCAGAT
GAAAAGGCTCTAGTAGAAGCTGCTGCAAGGATTGGTATTGTGTTTATTGGCAATTCTGAAGAAACTATGGAGGTTAA
AACTCTTGGAAAACTGGAACGGTACAAACTGCTTCATATTCTGGAATTTGATTCAGATCGTAGGAGAATGAGTGTAA
TTGTTCAGGCACCTTCAGGTGAGAAGTTATTATTTGCTAAAGGAGCTGAGTCATCAATTCTCCCTAAATGTATAGGT
GGAGAAATAGAAAAAACCAGAATTCATGTAGATGAATTTGCTTTGAAAGGGCTAAGAACTCTGTGTATAGCATATAG
AAAATTTACATCAAAAGAGTATGAGGAAATAGATAAACGCATATTTGAAGCCAGGACTGCCTTGCAGCAGCGGGAAG
AGAAATTGGCAGCTGTTTTCCAGTTCATAGAGAAAGACCTGATATTACTTGGAGCCACAGCAGTAGAAGACAGACTA
CAAGATAAAGTTCGAGAAACTATTGAAGCATTGAGAATGGCTGGTATCAAAGTATGGGTACTTACTGGGGATAAACA
TGAAACAGCTGTTAGTGTGAGTTTATCATGTGGCCATTTTCATAGAACCATGAACATCCTTGAACTTATAAACCAGA
AATCAGACAGCGAGTGTGCTGAACAATTGAGGCAGCTTGCCAGAAGAATTACAGAGGATCATGTGATTCAGCATGGG
CTGGTAGTGGATGGGACCAGCCTATCTCTTGCACTCAGGGAGCATGAAAAACTATTTATGGAAGTTTGCAGAAATTG
TTCAGCTGTATTATGCTGTCGTATGGCTCCACTGCAGAAAGCAAAAGTAATAAGACTAATAAAAATATCACCTGAGA
AACCTATAACATTGGCTGTTGGTGATGGTGCTAATGACGTAAGCATGATACAAGAAGCCCATGTTGGCATAGGAATC
ATGGGTAAAGAAGGAAGACAGGCTGCAAGAAACAGTGACTATGCAATAGCCAGATTTAAGTTCCTCTCCAAATTGCT
TTTTGTTCATGGTCATTTTTATTATATTAGAATAGCTACCCTTGTACAGTATTTTTTTATAAGAATGTGTGCTTTA
TCACACCCCAGTTTTTATATCAGTTCTACTGTTTGTTTTCTCAGCAAACATTGTATGACAGCGTGTACCTGACTTTA
TACAATATTTGTTTTACTTCCCTACCTATTCTGATATATAGTCTTTTGGAACAGCATGTAGACCCTCATGTGTTACA
AAATAAGCCCACCCTTTATCGAGACATTAGTAAAAACCGCCTCTTAAGTATTAAAACATTTCTTTATTGGACCATCC
TGGGCTTCAGTCATGCCTTTATTTTCTTTTTTGGATCCTATTTACTAATAGGGAAAGATACATCTCTGCTTGGAAAT
GGCCAGATGTTTGGAAACTGGACATTTGGCACTTTGGTCTTCACAGTCATGGTTATTACAGTCACAGTAAAGATGGC
TCTGGAAACTCATTTTTGGACTTGGATCAACCATCTCGTTACCTGGGGATCTATTATATTTTATTTTGTATTTTCCT
TGTTTTATGGAGGGATTCTCTGGCCATTTTTGGGCTCCCAGAATATGTATTTTGTGTTTATTCAGCTCCTGTCAAGT
GGTTCTGCTTGGTTTGCCATAATCCTCATGGTTGTTACATGTCTATTTCTTGATATCATAAAGAAGGTCTTTGACCG
ACACCTCCACCCTACAAGTACTGAAAAGGCACAGCTTACTGAAACAAATGCAGGTATCAAGTGCTTGGACTCCATGT
GCTGTTTCCCGGAAGGAGAAGCAGCGTGTGCATCTGTTGGAAGAATGCTGGAACGAGTTATAGGAAGATGTAGTCCA
ACCCACATCAGCAGATCATGGAGTGCATCGGATCCTTTCTATACCAACGACAGGAGCATCTTGACTCTCTCCACAAT
GGACTCATCTACTTGTTAAAGGGGCAGTAGTACTTTGTGGGAGCCAGTTCACCTCCTTTCCTAAAATTCAGTGTGAT
CACCCTGTTAATGGCCACACTAGCTCTGAAATTAATTTCCAAAATCTTTGTAGTAGTTCATACCCACTCAGAGTTAT
AATGGCAAACAAACAGAAAGCATTAGTACAAGCCCCTCCCAACACCCTTAATTTGAATCTGAACATGTTAAAATTTG
AGAATAAAGAGACATTTTTCATCTCTTTGTCTGGTTTGTCCCTTGTGCTTATGGGACTCCTAATGGCATTTCAGTCT
GTTGCTGAGGCCATTATATTTTAATATAAATGTAGAAAAAAGAGAGAAATCTTAGTAAAGAGTATTTTTTAGTATTA
GCTTGATTATTGACTCTTCTATTTAAATCTGCTTCTGTAAATTATGCTGAAAGTTTGCCTTGAGAACTCTATTTTTT
TATTAGAGTTATATTTAAAGCTTTTCATGGAAAAGTTAATGTGAATACTGAGGAATTTTGGTCCCTCAGTGACCTG
TGTTGTTAATTCATTAATGCATTCTGAGTTCACAGAGCAAATTAGGAGAATCATTTCCAACCATTATTTACTGCAGT
ATGGGGAGTAAATTTATACCAATTCCTCTAACTGTACTGTAACACAGCCTGTAAAGTTAGCCATATAAATGCAAGGG
TATATCATATATACAAATCAGGAATCAGGTCCGTTCACCGAACTTCAAATTGATGTTTACTAATATTTTTGTGACAG
AGTATAAAGACCCTATAGTGGGTAAATTAGATACTATTAGCATATTATTAATTTAATGTCTTTATCATTGGATCTTT
TGCATGCTTTAATCTGGTTAACATATTTAAATTTGCTTTTTTTCTCTTTACCTGAAGGCTCTGTGTATAGTATTTCA
TGACATCGTTGTACAGTTTAACTATCAATAAAAAGTTTGGACAGTATTTAAATATTGCAAATATGTTTAATTATACA
AATCAGAATAGTATGGGTAATTAAATGAATACAAAAAGAAGAGCCTCTTTCTGCAGCCGACTTAGACATGCTCTTCC
CTTTCTATAAGCTAGATTTTAGAATAAAGGGTTTCAGTTAATAATCTTATTTTCAGGTTATGTCATCTAACTTATAG
CAAACTACCACAATACAGTGAGTTCTGCCAGTGTCCCAGTACAAGGCATATTTCAGGTGTGGCTGTGGAATGTAAAA
ATGCTCAACTTGTATCAGGTAATGTTAGCAATAAATTAAATGCTAAGAATGATTAATCGGGTACATGTTACTGTAAT
TAACTCATTGCACTTCAAAACCTAACTTCCATCCTGAATTTATCAAGTAGTTCAGTATTGTCATTTGTTTTTGTTTT
ATTGAAAAGTAATGTTGTCTTAAGATTTAGAAGTGATTATTAGCTTGAGAACTATTACCCAGCTCTAAGCAAATAAT
GATTGTATACATATTAAGATAATGGTTAAATGCGGTTTTACCAAGTTTTCCCTTGAAAATGTAATTCCTTTATGGAG
ATTTATTGTGCAGCCCTAAGCTTCCTTCCCATTTCATGAATATAAGGCTTCTAGAATTGGACTGGCAGGGGAAAGAA
TGGTAGAGACAGAAATTAAGACTTTATCCTTGTTTGCTTGTAAACTATTATTTTCTTGCTAATGTAACATTTGTCTG
TTCCAGTGATGTAAGGATATTAAGTTATTAAGCTAAATATTAATTTTCAAAAATAGTCCTTCTTTAACTTAGATATT
TCATAGCTGGATTTAGGAAGATCTGTTATTCTGGAAGTACTAAAAAGAATAATACAACGTACAATGTCTGCATTCAC
TAATTCATGTTCCAGAAGAGGAAATAATGAAGATATACTCAGTAGAGTACTAGGTGGAGGATATGGAAATTTGCTC
ATAAAATCTCTTATAAAACGTGCATATAACAAAATGACACCCAGTAGGCCTGCATTACATTTACATGAC

FIGURE 10B

CGTGTTTATTTGCCATCAAATAAACTGAGTACTGACACCAGACAAAGACTCCAAAGTCATAAAATAGCCTATGACCA
ACTGCAGCAAGACAGGAGGTCAGCTCGCCTATAATGGTGCTTAAAGTGTGATTGATGTAATTTTCTGTACTCACCAT
TTGAAGTTAGTTAAGGAGAACTTTATTTTTTTAAAAAAAGTAAATGGCAACCACTAGTGTGCTCATCCTGAACTGTT
ACTCCAAATCCACTCCGTTTTTAAAGCAAAATTATCTTGTGATTTTAAGAAAAGAGTTTTCTATTTATTTAAGAAAG
TAACAATGCAGTCTGCAAGCTTTCAGTAGTTTTCTAGTGCTATATTCATCCTGTAAAACTCTTACTACGTAACCAGT
AATCACAAGGAAAGTGTCCCCTTTGCATATTTCTTTAAAATTCTTTCTTTGGAAAGTATGATGTTGATAATTAACTT
ACCCTTATCTGCCAAAACCAGAGCAAAATGCTAAATACGTTATTGCTAATCAGTGGTCTCAAATCGATTTGCCTCCC
TTTGCCTCGTCTGAGGGCTGTAAGCCTGAAGATAGTGGCAAGCACCAAGTCAGTTTCCAAAATTGCCCCTCAGCTGC
TTTAAGTGACTCAGCACCCTGCCTCAGCTTCAGCAGGCGTAGGCTCACCCTGGGCGGAGCAAAGTATGGGCCAGGGA
GAACTACAGCTACGAAGACCTGCTGTCGAGTTGAGAAAAGGGGAGAATTTATGGTCTGAATTTTCTAACTGTCCTCT
TTCTTGGGTCTAAAGCTCATAATACACAAAGGCTTCCAGACCTGAGCCACACCCAGGCCCTATCCTGAACAGGAGAC
TAAACAGAGGCAAATCAACCCTAGGAAATACTTGCATTCTGCCCTACGGTTAGTACCAGGACTGAGGTCATTTCTAC
TGGAAAAGATTGTGAGATTGAACTTATCTGATCGCTTGAGACTCCTAATAGGCAGGAGTCAAGGCCACTAGAAAATT
GACAGTTAAGAGCCAAAAGTTTTTAAAATATGCTACTCTGAAAAATCTCGTGAAGGCTGTAGGAAAAGGGAGAATCT
TCCATGTTGGTGTTTTTCCTGTAAAGATCAGTTTGGGGTATGATATAAGCAGGTATTAATAAAAATAACACACCAAA
GAGTTACGTAAAACATGTTTTATTAATTTTGGTCCCCACGTACAGACATTTTATTTCTATTTTGAAATGAGTTATCT
ATTTTCATAAAAGTAAAACACTATTAAAGTGCTGTTTTATGTGAAATAACTTGAATGTTGTTCCTATAAAAAATAGA
TCATAACTCATGATATGTTTGTAATCATGGTAATTTAGATTTTTATGAGGAATGAGTATCTGGAAATATTGTAGCAA
TACTTGGTTTAAAATTTTGGACCTGAGACACTGTGGCTGTCTAATGTAATCCTTTAAAAATTCTCTGCATTGTCAGT
AAATGTAGTATATTATTGTACAGCTACTCATAATTTTTTAAAGTTTATGAAGTTATATTTATCAAATAAAAACTTTC
CTATAT

FIGURE 11A

ATGTGGGAAGAAGAAGACATTGCTATTCTGTTCAATAAAGAACCAGGAAAAACAGAGAATATTGAAAATAATCTAAG
TTCCAACCATAGAAGAAGCTGCAGAAGAAGTGAAGAAAGTGATGATGATTTGGATTTTGATATTGGTTTAGAAAACA
CAGGAGGAGACCCTCAAATTCTGAGATTTATTTCAGACTTCCTTGCTTTTTTGGTTCTCTACAATTTCATCATTCCA
ATTTCATTATATGTGACAGTCGAAATGCAGAAATTTCTTGGATCATTTTTTATTGGCTGGGATCTTGATCTGTATCA
TGAAGAATCAGATCAGAAAGCTCAAGTCAATACTTCCGATCTGAATGAAGAGCTTGGACAGGTAGAGTACGTGTTTA
CAGATAAAACTGGTACACTGACAGAAAATGAGATGCAGTTTCGGGAATGTTCAATTAATGGCATGAAATACCAAGAA
ATTAATGGTAGACTTGTACCCGAAGGACCAACACCAGACTCTTCAGAAGGAAACTTATCTTATCTTAGTAGTTTATC
CCATCTTAACAACTTATCCCATCTTACAACCAGTTCCTCTTTCAGAACCAGTCCTGAAAATGAAACTGAACTAATTA
AAGAACATGATCTCTTCTTTAAAGCAGTCAGTCTCTGTCACACTGTACAGATTAGCAATGTTCAAACTGACTGCACT
GGTGATGGTCCCTGGCAATCCAACCTGGCACCATCGCAGTTGGAGTACTATGCATCTTCACCAGATGAAAAGGCTCT
AGTAGAAGCTGCTGCAAGGTACAAACTGCTTCATATTCTGGAATTTGATTCAGATCGTAGGAGAATGAGTGTAATTG
TTCAGGCACCTTCAGGTGAGAAGTTATTATTTGCTAAAGGAGCTGAGTCATCAATTCTCCCTAAATGTATAGGTGGA
GAAATAGAAAAAACCAGAATTCATGTAGATGAATTTGCTTTGAAAGGGCTAAGAACTCTGTGTATAGCATATAGAAA
ATTTACATCAAAAGAGTATGAGGAAATAGATAAACGCATATTTGAAGCCAGGACTGCCTTGCAGCAGCGGGAAGAGA
AATTGGCAGCTGTTTTCCAGTTCATAGAGAAAGACCTGATATTACTTGGAGCCACAGCAGTAGAAGACAGACTACAA
GATAAAGTTCGAGAAACTATTGAAGCATTGAGAATGGCTGGTATCAAAGTATGGGTACTTACTGGGGATAAACATGA
AACAGCTGTTAGTGTGAGTTTATCATGTGGCCATTTTCATAGAACCATGAACATCCTTGAACTTATAAACCAGAAAT
CAGACAGCGAGTGTGCTGAACAATTGAGGCAGCTTGCCAGAAGAATTACAGAGGATCATGTGATTCAGCATGGGCTG
GTAGTGGATGGGACCAGCCTATCTCTTGCACTCAGGGAGCATGAAAAACTATTTATGGAAGTTTGCAGAAATTGTTC
AGCTGTATTATGCTGTCGTATGGCTCCACTGCAGAAAGCAAAAGTAATAAGACTAATAAAAATATCACCTGAGAAAC
CTATAACATTGGCTGTTGGTGATGGTGCTAATGACGTAAGCATGATACAAGAAGCCCATGTTGGCATAGGAATCATG
GGTAAAGAAGGAAGACAGGCTGCAAGAAACAGTGACTATGCAATAGCCAGATTTAAGTTCCTCTCCAAATTGCTTTT
TGTTCATGGTCATTTTTATTATATATTAGAATAGCTACCCTTGTACAGTATTTTTTTTATAAGAATGTGTGCTTTATCA
CACCCCAGTTTTTATATCAGTTCTACTGTTTGTTTTCTCAGCAAACATTGTATGACAGCGTGTACCTGACTTTATAC
AATATTTGTTTTACTTCCCTACCTATTCTGATATATAGTCTTTTGGAACAGCATGTAGACCCTCATGTGTTACAAAA
TAAGCCCACCCTTTATCGAGACATTAGTAAAAACCGCCTCTTAAGTATTAAAACATTTCTTTATTGGACCATCCTGG
GCTTCAGTCATGCCTTTATTTTCTTTTTTGGATCCTATTTACTAATAGGGAAAGATACATCTCTGCTTGGAAATGGC
CAGATGTTTGGAAACTGGACATTTGGCACTTTGGTCTTCACAGTCATGGTTATTACAGTCACAGTAAAGATGGCTCT
GGAAACTCATTTTTTGGACTTGGATCAACCATCTCGTTACCTGGGGATCTATTATATTTTATTTTGTATTTTCCTTGT
TTTATGGAGGGATTCTCTGGCCATTTTTGGGCTCCCAGAATATGTATTTTGTGTTTATTCAGCTCCTGTCAAGTGGT
TCTGCTTGGTTTGCCATAATCCTCATGGTTGTTACATGTCTATTTCTTGATATCATAAAGAAGGTCTTTGACCGACA
CCTCCACCCTACAAGTACTGAAAAGGCACAGCTTACTGAAACAAATGCAGGTATCAAGTGCTTGGACTCCATGTGCT
GTTTCCCGGAAGGAGAAGCAGCGTGTGCATCTGTTGGAAGAATGCTGGAACGAGTTATAGGAAGATGTAGTCCAACC
CACATCAGCAGATCATGGAGTGCATCGGATCCTTTCTATACCAACGACAGGAGCATCTTGACTCTCTCCACAATGGA
CTCATCTACTTGTTAAAGGGGCAGTAGTACTTTGTGGGAGCCAGTTCACCTCCTTTCCTAAAATTCAGTGTGATCAC
CCTGTTAATGGCCACACTAGCTCTGAAATTAATTTCCAAAATCTTTGTAGTAGTTCATACCCACTCAGAGTTATAAT
GGCAAACAAACAGAAAGCATTAGTACAAGCCCCTCCCAACACCCTTAATTTGAATCTGAACATGTTAAAATTTGAGA
ATAAAGAGACATTTTTCATCTCTTTGTCTGGTTTGTCCCTTGTGCTTATGGGACTCCTAATGGCATTTCAGTCTGTT
GCTGAGGCCATTATATTTTAATATAAATGTAGAAAAAAGAGAGAAATCTTAGTAAAGAGTATTTTTTAGTATTAGCT
TGATTATTGACTCTTCTATTTAAATCTGCTTCTGTAAATTATGCTGAAAGTTTGCCTTGAGAACTCTATTTTTTTAT
TAGAGTTATATTTAAAGCTTTTCATGGGAAAAGTTAATGTGAATACTGAGGAATTTTGGTCCCTCAGTGACCTGTGT
TGTTAATTCATTAATGCATTCTGAGTTCACAGAGCAAATTAGGAGAATCATTTCCAACCATTATTTACTGCAGTATG
GGGAGTAAATTTATACCAATTCCTCTAACTGTACTGTAACACAGCCTGTAAAGTTAGCCATATAAATGCAAGGGTAT
ATCATATATACAAATCAGGAATCAGGTCCGTTCACCGAACTTCAAATTGATGTTTACTAATATTTTTGTGACAGAGT
ATAAAGACCCTATAGTGGGTAAATTAGATACTATTAGCATATTATTAATTTAATGTCTTTATCATTGGATCTTTTGC
ATGCTTTAATCTGGTTAACATATTTAAATTTGCTTTTTTTCTCTTTACCTGAAGGCTCTGTGTATAGTATTTCATGA
CATCGTTGTACAGTTTAACTATCAATAAAAAGTTTGGACAGTATTTAAATATTGCAAATATGTTTAATTATACAAAT
CAGAATAGTATGGGTAATTAAATGAATACAAAAAGAAGAGCCTCTTTCTGCAGCCGACTTAGACATGCTCTTCCCTT
TCTATAAGCTAGATTTTAGAATAAAGGGTTTCAGTTAATAATCTTATTTTCAGGTTATGTCATCTAACTTATAGCAA
ACTACCACAATACAGTGAGTTCTGCCAGTGTCCCAGTACAAGGCATATTTCAGGTGTGGCTGTGGAATGTAAAAATG
CTCAACTTGTATCAGGTAATGTTAGCAATAAATTAAATGCTAAGAATGATTAATCGGGTACATGTTACTGTAATTAA
CTCATTGCACTTCAAAACCTAACTTCCATCCTGAATTTATCAAGTAGTTCAGTATTGTCATTTGTTTTT

FIGURE 11B

GTTTTATTGAAAAGTAATGTTGTCTTAAGATTTAGAAGTGATTATTAGCTTGAGAACTATTACCCAGCTCTAAGCAA
ATAATGATTGTATACATATTAAGATAATGGTTAAATGCGGTTTTACCAAGTTTTCCCTTGAAAATGTAATTCCTTTA
TGGAGATTTATTGTGCAGCCCTAAGCTTCCTTCCCATTTCATGAATATAAGGCTTCTAGAATTGGACTGGCAGGGGA
AAGAATGGTAGAGACAGAAATTAAGACTTTATCCTTGTTTGCTTGTAAACTATTATTTTCTTGCTAATGTAACATTT
GTCTGTTCCAGTGATGTAAGGATATTAAGTTATTAAGCTAAATATTAATTTTCAAAAATAGTCCTTCTTTAACTTAG
ATATTTCATAGCTGGATTTAGGAAGATCTGTTATTCTGGAAGTACTAAAAAGAATAATACAACGTACAATGTCTGCA
TTCACTAATTCATGTTCCAGAAGAGGAAATAATGAAGATATACTCAGTAGAGTACTAGGTGGGAGGATATGGAAATT
TGCTCATAAAATCTCTTATAAAACGTGCATATAACAAAATGACACCCAGTAGGCCTGCATTACATTTACATGACCGT
GTTTATTTGCCATCAAATAAACTGAGTACTGACACCAGACAAAGACTCCAAAGTCATAAAATAGCCTATGACCAACT
GCAGCAAGACAGGAGGTCAGCTCGCCTATAATGGTGCTTAAAGTGTGATTGATGTAATTTTCTGTACTCACCATTTG
AAGTTAGTTAAGGAGAACTTTATTTTTTTAAAAAAAGTAAATGGCAACCACTAGTGTGCTCATCCTGAACTGTTACT
CCAAATCCACTCCGTTTTTAAAGCAAAATTATCTTGTGATTTTAAGAAAAGAGTTTTCTATTTATTTAAGAAAGTAA
CAATGCAGTCTGCAAGCTTTCAGTAGTTTTCTAGTGCTATATTCATCCTGTAAAACTCTTACTACGTAACCAGTAAT
CACAAGGAAAGTGTCCCCTTTGCATATTTCTTTAAAATTCTTTCTTTGGAAAGTATGATGTTGATAATTAACTTACC
CTTATCTGCCAAAACCAGAGCAAAATGCTAAATACGTTATTGCTAATCAGTGGTCTCAAATCGATTTGCCTCCCTTT
GCCTCGTCTGAGGGCTGTAAGCCTGAAGATAGTGGCAAGCACCAAGTCAGTTTCCAAAATTGCCCCTCAGCTGCTTT
AAGTGACTCAGCACCCTGCCTCAGCTTCAGCAGGCGTAGGCTCACCCTGGGCGGAGCAAAGTATGGGCCAGGGAGAA
CTACAGCTACGAAGACCTGCTGTCGAGTTGAGAAAAGGGGAGAATTTATGGTCTGAATTTTCTAACTGTCCTCTTTC
TTGGGTCTAAAGCTCATAATACACAAAGGCTTCCAGACCTGAGCCACACCCAGGCCCTATCCTGAACAGGAGACTAA
ACAGAGGCAAATCAACCCTAGGAAATACTTGCATTCTGCCCTACGGTTAGTACCAGGACTGAGGTCATTTCTACTGG
AAAAGATTGTGAGATTGAACTTATCTGATCGCTTGAGACTCCTAATAGGCAGGAGTCAAGGCCACTAGAAAATTGAC
AGTTAAGAGCCAAAAGTTTTTAAAATATGCTACTCTGAAAAATCTCGTGAAGGCTGTAGGAAAAGGGAGAATCTTCC
ATGTTGGTGTTTTTCCTGTAAAGATCAGTTTGGGGTATGATATAAGCAGGTATTAATAAAAATAACACACCAAAGAG
TTACGTAAAACATGTTTTATTAATTTTGGTCCCCACGTACAGACATTTTATTTCTATTTTGAAATGAGTTATCTATT
TTCATAAAAGTAAAACACTATTAAAGTGCTGTTTTATGTGAAATAACTTGAATGTTGTTCCTATAAAAAATAGATCA
TAACTCATGATATGTTTGTAATCATGGTAATTTAGATTTTTATGAGGAATGAGTATCTGGAAATATTGTAGCAATAC
TTGGTTTAAAATTTTGGACCTGAGACACTGTGGCTGTCTAATGTAATCCTTTAAAAATTCTCTGCATTGTCAGTAAA
TGTAGTATATTATTGTACAGCTACTCATAATTTTTTAAAGTTTATGAAGTTATATTTATCAAATAAAAACTTTCCTA
TAT

FIGURE 12

```
GCACGAGGGCGCTTTTGTCTCCGGTGAGTTTTGTGGCGGGAAGCTTCTGCGCTGGTGCTTAGTAACCGACTTTCCTC
CGGACTCCTGCACGACCTGCTCCTACAGCCGGCGATCCACTCCCGGCTGTTCCCCCGGAGGGTCCAGAGGCCTTTCA
GAAGGAGAAGGCAGCTCTGTTTCTCTGCAGAGGAGTAGGGTCCTTTCAGCCATGAAGCATGTGTTGAACCTCTACCT
GTTAGGTGTGGTACTGACCCTACTCTCCATCTTCGTTAGAGTGATGGAGTCCCTAGAAGGCTTACTAGAGAGCCCAT
CGCCTGGGACCTCCTGGACCACCAGAAGCCAACTAGCCAACACAGAGCCCACCAAGGGCCTTCCAGACCATCCATCC
AGAAGCATGTGATAAGACCTCCTTCCATACTGGCCATATTTTGGAACACTGACCTAGACATGTCCAGATGGGAGTCC
CATTCCTAGCAGACAAGCTGAGCACCGTTGTAACCAGAGAACTATTACTAGGCCTTGAAGAACCTGTCTAACTGGAT
GCTCATTGCCTGGGCAAGGCCTGTTTAGGCCGGTTGCGGTGGCTCATGCCTGTAATCCTAGCACTTTGGGAGGCTGA
GGTGGGTGGATCACCTGAGGTCAGGAGTTCGAGACCAGCCTCGCCAACATGGCGAAACCCCATCTCTACTAAAAATA
CAAAAGTTAGCTGGGTGTGGTGGCAGAGGCCTGTAATCCCAGTTCCTTGGGAGGCTGAGGCGGGAGAATTGCTTGAA
CCCGGGGACGGAGGTTGCAGTGAACCGAGATCGCACTGCTGTACCCAGCCTGGGCCACAGTGCAAGACTCCATCTCA
AAAAAAAAAAGAAAAGAAAAAGCCTGTTTAATGCACAGGTGTGAGTGGATTGCTTATGGCTATGAGATAGGTTGATC
TCGCCCTTACCCCGGGGTCTGGTGTATGCTGTGCTTTCCTCAGCAGTATGGCTCTGACATCTCTTAGATGTCCCAAC
TTCAGCTGTTGGGAGATGGTGATATTTTCAACCCTACTTCCTAAACATCTGTCTGGGGTTCCTTTAGTCTTGAATGT
CTTATGCTCAATTATTTGGTGTTGAGCCTCTCTTCCACAAGAGCTCCTCCATGTTTGGATAGCAGTTGAAGAGGTTG
TGTGGGTGGGCTGTTGGGAGTGAGGATGGAGTGTTCAGTGCCCATTTCTCATTTTACATTTTAAAGTCGTTCCTCCA
ACATAGTGTGTATTGGTCTGAAGGGGGTGGTGGGATGCCAAAGCCTGCTCAAGTTATGGACATTGTGGCCACCATGT
GGCTTAAATGATTTTTTCTAACTAATAAAGTGGAATATATATTTCAAAAAAAAAAAAAAAAAA
```

FIGURE 13

ATACGACTCACTATAGGGCGAATTGGGTACCGGGCCCCCCCTCGNGTCGACGGTATCGATAAGCTTGATATCGAATT
CGGCCACACTGGCCGGATCCTCTAGAGATCCCTCGACCTCGACCCACGCGTCCGCCCACGCGTCCGATGTGCCTCTG
GGCAAAGAAGCAGAGCTAACGAGGAAAGGGATTTAAAGAGTTTTTCTTGGGTGTTTGTCAAACTTTTATTCCCTGTC
TGTGTGCAGAGGGGATTCAACTTCAATTTTTCTGCAGTGGCTCTGAGTCCAGCCCCTTACTTAAAGATCTGGAAAGC
ATGAAGACTGGGCTTTTTTTCCTATGTCTCTTGGGAACTGCAGCTGCAATCCCGACAAATGCAAGATTATTATCTGA
TCATTCCAAACCAACTGCTGAAACGGTAGCACCCGACAACACTGCAATCCCCAGTTTAAGGGCTGAAGATGAAGAAA
ATGAAAAAGAAACAGCAGTATCCACAGAAGACGATTCCCACCATAAGGCTGAAAAATCATCAGTACTAAAGTCAAAA
GAGGAAAGCCATGAACAGTCAGCAGAACAGGGCAAGAGTTCTAGCCAAGAGCTGGGATTGAAGGATCAAGANGACAG
TGATGGTGACTTAAGTGTGAATTTGGAGTATGCACCAACTGAAGGTACATTGGACATAAAAGAAGATATGAGTGAGC
CTCAGGAGAAAAACTCTCAGANACACTGATTTTTTGGCTCCTGGGTAGTTCCTTCCAGATTCTACCACAGAAGTTT

FIGURE 14

CGCGGGCCATGGCTCCCTGGGCGGAGGCCGAGCACTCGGCGCTGAACCCGCTGCGCGCGGTGTGGCTCACGCTGACC
GCCGCCTTCCTGCTGACCCTACTGCTGCAGCTCCTGCCGCCCGGCCTGCTCCCGGGCTGCGCGATCTTCCAGGACCT
GATCCGCTATGGGAAAACCAAGTGTGGGGAGCCGTCGCGCCCCGCCGCCTGCCGAGCCTTTGATGTCCCCAAGAGAT
ATTTTTCCCACTTTTATATCATCTCAGTGCTGTGGAATGGCTTCCTGCTTTGGTGCCTTACTCAATCTCTGTTCCTG
GGAGCACCTTTTCCAAGCTGGCTTCATGGTTTGCTCAGAATTCTCGGGGCGGCACAGTTCCAGGGAGGGGAGCTGGC
ACTGTCTGCATTCTTAGTGCTAGTATTTCTGTGGCTGCACAGCTTACGAAGACTCTTCGAGTGCCTCTACGTCAGTG
TCTTCTCCAATGTCATGATTCACGTCGTGCAGTACTGTTTTGGACTTGTCTATTATGTCCTTGTTGGCCTAACTGTG
CTGAGCCAAGTGCCAATGGATGGCAGGAATGCCTACATAACAGGGAAAAATCTATTGATGCAAGCACGGTGGTTCCA
TATTCTTGGGATGATGATGTTCATCTGGTCATCTGCCCATCAGTATAAGTGCCATGTTATTCTCGGCAATCTCAGGA
AAAATAAAGCAGGAGTGGTCATTCACTGTAACCACAGGATCCCATTTGGAGACTGGTTTGAATATGTTTCTTCCCCT
AACTACTTAGCAGAGCTGATGATCTACGTTTCCATGGCCGTCACCTTTGGGTTCCACAACTTAACTTGGTGGCTAGT
GGTGACAAATGTCTTCTTTAATCAGGCCCTGTCTGCCTTTCTCAGCCACCAATTCTACAAAAGCAAATTTGTCTCTT
ACCCGAAGCATAGGAAAGCTTTCCTACCATTTTTGTTTTAAGTTAACCTCAGTCATGAAGAATGCAAACCAGGTGAT
GGTTTCAATGCCTAAGGACAGTGAAGTCTGGAGCCCAAAGTACAGTTTCAGCAAAGCTGTTTGAAACTCTCCATTCC
ATTTCTATACCCCACAAGTTTTCACTGAATGAGCATGGCAGTGCCACTCAATAAAATGAATCTCCAAAGTATCTTCA
AAGAATAAATACTAATGGCAAAAAAAAAAAAA

FIGURE 15

TCCACACACACAAAAAACCTGCGCGTGAGGGGGGAGGAAAAGCAGGGCCTTTAAAAAGGCAATCACAACAACTTTTG
CTGCCAGGATGCCCTTGCTTTGGCTGAGAGGATTTCTGTTGGCAAGTTGCTGGATTATAGTGAGGAGTTCCCCCACC
CCAGGATCCGAGGGGCACAGCGCGGCCCCCGACTGTCCGTCCTGTGCGCTGGCCGCCCTCCCAAAGGATGTACCCAA
CTCTCAGCCAGAGATGGTGGAGGCCGTCAAGAAGCACATTTTAAACATGCTGCACTTGAAGAAGAGACCCGATGTCA
CCCAGCCGGTACCCAAGGCGGCGCTTCTGAACGCGATCAGAAAGCTTCATGTGGGCAAAGTCGGGGAGAACGGGTAT
GTGGAGATAGAGGATGACATTGGAAGGAGGGCAGAAATGAATGAACTTATGGAGCAGACCTCGGAGATCATCACGTT
TGCCGAGTCAGGAACAGCCAGGAAGACGCTGCACTTCGAGATTTCCAAGGAAGGCAGTGACCTGTCAGTGGTGGAGC
GTGCAGAAGTCTGGCTCTTCCTAAAAGTCCCCAAGGCCAACAGGACCAGGACCAAAGTCACCATCCGCCTCTTCCAG
CAGCAGAAGCACCCGCAGGGCAGCTTGGACACAGGGGAAGAGGCCGAGGAAGTGGGCTTAAAGGGGGAGAGGAGTGA
ACTGTTGCTCTCTGAAAAAGTAGTAGACGCTCGGAAGAGCACCTGGCATGTCTTCCCTGTCTCCAGCAGCATCCAGC
GGTTGCTGGACCAGGGCAAGAGCTCCCTGGACGTTCGGATTGCCTGTGAGCAGTGCCAGGAGAGTGGCGCCAGCTTG
GTTCTCCTGGGCAAGAAGAAGAAGAAAGAAGAGGAGGGGGAAGGGAAAAAGAAGGGCGGAGGTGAAGGTGGGGCAGG
AGCAGATGAGGAAAAGGAGCAGTCGCACAGACCTTTCCTCATGCTGCAGGCCCGGCAGTCTGAAGACCACCCTCATC
GCCGGCGTCGGCGGGGCTTGGAGTGTGATGGCAAGGTCAACATCTGCTGTAAGAAACAGTTCTTTGTCAGTTTCAAG
GACATCGGCTGGAATGACTGGATCATTGCTCCCTCTGGCTATCATGCCAACTACTGCGAGGGTGAGTGCCCGAGCCA
TATAGCAGGCACGTCCGGGTCCTCACTGTCCTTCCACTCAACAGTCATCAACCACTACCGCATGCGGGGCCATAGCC
CCTTTGCCAACCTCAAATCGTGCTGTGTGCCCACCAAGCTGAGACCCATGTCCATGTTGTACTATGATGATGGTCAA
AACATCATCAAAAAGGACATTCAGAACATGATCGTGGAGGAGTGTGGGTGCTCATAGAGTTGCCCAGCCCAGGGGGA
AAGGGAGCAAGAGTTGTCCAGAGAAGACAGTGGCAAAATGAAGAAATTTTTAAGGTTTCTGAGTTAACCAGAAAAAT
AGAAATTAAAAACAAAACAAAACAAAAAAAAAAACAAAAAAAAACAAAAGTAAATTAAAAACAAACCTGATGAAACA
GATGAAACAGATGAAGGAAGATGTGGAAATCTTAGCCTGCCTTAGCCAGGCCTCAGAGATGAAGCAGTGAAGAGACA
GATTGGGAGGGAAAGGGAGAATGGTGTACCCTTTATTTCTTCTGAAATCACACTGATGACATCAGTTGTTTAAACGG
GGTATTGTCCTTTCCCCCCTTGAGGTTCCCTTGTGAGCTTGAATCAACCAATCTGATCTGCAGTAGTGTGGACTAGA
ACAACCCAAATAGCATCTAGAAAGCCATGAGTTTGAAAGGGCCCATCACAGGCACTTTCCTAGCCTAAT

FIGURE 16

```
GCGGAGAAGCCGGGAGCGCGGGGCTCAGTCGGGGGGCGGCGGCGGCGGCGGCTCCGGGGATGGCGGCGGCTCCGCTG
CTGCTGCTGCTGCTGCTCGTGCCCGTGCCGCTGCTGCCGCTGCTGGCCCAAGGGCCCGGAGGGGCGCTGGGAAACCG
GCATGCGGTGTACTGGAACAGCTCCAACCAGCACCTGCGGCGAGAGGGCTACACCGTGCAGGTGAACGTGAACGACT
ATCTGGATATTTACTGCCCGCACTACAACAGCTCGGGGGTGGGCCCCGGGGCGGGACCGGGGCCCGGAGGCGGGGCA
GAGCAGTACGTGCTGTACATGGTGAGCCGCAACGGCTACCGCACCTGCAACGCCAGCCAGGGCTTCAAGCGCTGGGA
GTGCAACCGGCCGCACGCCCCGCACAGCCCCATCAAGTTCTCGGAGAAGTTCCAGCGCTACAGCGCCTTCTCTCTGG
GCTACGAGTTCCACGCCGGCCACGAGTACTACTACATCTCCACGCCCACTCACAACCTGCACTGGAAGTGTCTGAGG
ATGAAGGTGTTCGTCTGCTGCGCCTCCACATCGCACTCCGGGGAGAAGCCGGTCCCCACTCTCCCCCAGTTCACCAT
GGGCCCCAATGTGAAGATCAACGTGCTGGAAGACTTTGAGGGAGAGAACCCTCAGGTGCCCAAGCTTGAGAAGAGCA
TCAGCGGGACCAGCCCCAAACGGGAACACCTGCCCCTGGCCGTGGGCATCGCCTTCTTCCTCATGACGTTCTTGGCC
TCCTAGCTCTGCCCCCTCCCTGGGGGGGAGAGATGGGCGGGGCTTGGAACGAGCAGGGAGCCTTTGGCCTCTCC
AAGGGAAGCCTAGTGGGCCTAGACCCCTCCTCCCATGGCTAGAAGTGGGGCCTGCACCATACATCTGTGTCCGCCCC
CTCTACCCCTTCCCCCCACGTAGGGCACTGTAGTGGACCAAGCACGGGGACAGCCATGGGTCCCGGCGGCCTTGTG
GCTCTGGTAATGTTTGGTACCAAACTTGGGGGCCAAAAAGGGCAGTGCTCAGGACTCCCTGGCCCCTGGTACCTTTC
CCTGACTCCTGGTGCCCTCTCCCTTTGTCCCCCCAGAGAGACATATGCCCCAGAGAGAGCAAATCGAAGCGTGGGA
GGCACCCCCATTGCTCTCCTCCAGGGGCAGAACATGGGGAGGGGACTAGATGGGCAAGGGGCAGCACTGCCTGCTGC
TTCCTTCCCCTGTTTACAGCAATAAAGCACGTCCTCCTCCCCCACTCCCACTTCCAGGATTGTGGTTTGGATTGAAA
CCAAGTTTACAAGTAGACACCCCTGGGGGGGCGGGCAGTGGACAAGGATGGCAAGGGGTGGGCATTGGGGTGCCAGG
CAGGCATGTACAGACTCTATATCTCTATATATAATGTACAGACAGACAGAGTCCCTTCCCTCTTTAACCCCCTGACC
TTTCTTGACTTCCCCTTCAGCTTCAGACCCCTTCCCCACCAGGCTTAGGCCCCCCACACCTTGGGGGACCCCCCT
GGCCCCTCTTTTGTCTTCTGTGAAGACAGGACCTATGCAACGCACAGACACTTTTGGAGACCGTAAAACAACAGCGC
CCCCTCCCTTCCAGCCCTGAGCCGGGAACCATCTCCCAGGACCTTGCCCTGCTCACCCTATGTGGTCCCACCTATCC
TCCTGGGCCTTTTTCAAGTGCTTTGGCTGTGACTTTCATACTCTGCTCTTAGTCTAAAAAAAATAAACTGGAGATAA
```

FIGURE 17A

CGCTCGCCATGGGCCACTCCCCACCTGTCCTGCCTTTGTGTGCCTCTGTGTCTTTGCTGGGTGGCCTGACCTTTGGT
TATGAACTGGCAGTCATATCAGGTGCCCTGCTGCCACTGCAGCTTGACTTTGGGCTAAGCTGCTTGGAGCAGGAGTT
CCTGGTGGGCAGCCTGCTCCTGGGGGCTCTCCTCGCCTCCCTGGTTGGTGGCTTCCTCATTGACTGCTATGGCAGGA
AGCAAGCCATCCTCGGGAGCAACTTGGTGCTGCTGGCAGGCAGCCTGACCCTGGGCCTGGCTGGTTCCCTGGCCTGG
CTGGTCCTGGGCCGCGCTGTGGTTGGCTTCGCCATTTCCCTCTCCTCCATGGCTTGCTGTATCTACGTGTCAGAGCT
GGTGGGGCCACGGCAGCGGGGAGTGCTGGTGTCCCTCTATGAGGCAGGCATCACCGTGGGCATCCTGCTCTCCTATG
CCCTCAACTATGCACTGGCTGGTACCCCCTGGGGATGGAGGCACATGTTCGGCTGGGCCACTGCACCTGCTGTCCTG
CAATCCCTCAGCCTCCTCTTCCTCCCTGCTGGTACAGATGAGACTGCAACACACAAGGACCTCATCCCACTCCAGGG
AGGTGAGGCCCCCAAGCTGGGCCCGGGGAGGCCACGGTACTCCTTTCTGGACCTCTTCAGGGCACGCGATAACATGC
GAGGCCGGACCACAGTGGGCCTGGGGCTGGTGCTCTTCCAGCAACTAACAGGGCAGCCCAACGTGCTGTGCTATGCC
TCCACCATCTTCAGCTCCGTTGGTTTCCATGGGGGATCCTCAGCCGTGCTGGCCTCTGTGGGGCTTGGCGCAGTGAA
GGTGGCAGCTACCCTGACCGCCATGGGGCTGGTGGACCGTGCAGGCCGCAGGGCTCTGTTGCTAGCTGGCTGTGCCC
TCATGGCCCTGTCCGTCAGTGGCATAGGCCTCGTCAGCTTTGCCGTGCCCATGGACTCAGGCCCAAGCTGTCTGGCT
GTGCCCAATGCCACCGGGCAGACAGGCCTCCCTGGAGACTCTGGCCTGCTGCAGGACTCCTCTCTACCTCCCATTCC
AAGGACCAATGAGGACCAAAGGGAGCCAATCTTGTCCACTGCTAAGAAAACCAAGCCCCATCCCAGATCTGGAGACC
CCTCAGCCCCTCCTCGGCTGGCCCTGAGCTCTGCCCTCCCTGGGCCCCCTCTGCCCGCTCGGGGGCATGCACTGCTG
CGCTGGACCGCACTGCTGTGCCTGATGGTCTTTGTCAGTGCCTTCTCCTTTGGGTTTGGGCCAGTGACCTGGCTTGT
CCTCAGCGAGATCTACCCTGTGGAGATACGAGGAAGAGCCTTCGCCTTCTGCAACAGCTTCAACTGGGCGGCCAACC
TCTTCATCAGCCTCTCCTTCCTCGATCTCATTGGCACCATCGGCTTGTCCTGGACCTTCCTGCTCTACGGACTGACC
GCTGTCCTCGGCCTGGGCTTCATCTATTTATTTGTTCCTGAAACAAAAGGCCAGTCGTTGGCAGAGATAGACCAGCA
GTTCCAGAAGAGACGGTTCACCCTGAGCTTTGGCCACAGGCAGAACTCCACTGGCATCCCGTACAGCCGCATCGAGA
TCTCTGCGGCCTCCTGAGGAATCCGTCTGCCTGGAAATTCTGGAACTGTGGCTTTGGCAGACCATCTCCAGCATCCT
GCTTCCTAGGCCCCAGAGCACAAGTTCCAGCTGGTCTTTTGGGAGTGGCCCCTGCCCCCAAAGGTGGTCTGCTTTTG
CTGGGGTAAAAAGGATGAAAGTCTGAGAATGCCCAACTCTTCATTTTGAGTCTCAGGCCCTGAAGGTTCCTGAGGAT
CTAGCTTCATGCCTCAGTTTCCCCATTGACTTGCACATCTCTGCAGTATTTATAAGAAGAATATTCTATGAAGTCTT
TGTTGCACCATGGACTTTTCTCAAAGAATCTCAAGGGTACCAATCCTGGCAGGAAGTCTCTCCCGATATCACCCCTA
AATCCAAATGAGGATATCATCTTTTCTAATCTCTTTTTTCAACTGGCTGGGACATTTTCGGAAGGGGGAAGTCTCTT
TTTTTACTCTTATCATTTTTTTTTTTTTGAGGTGGAGTCTCATTCTGTTGCCCAGGCTGGCCTGATCTTGGCTCACTG
CAACCTCCACCTCCTGAGTTCAAGCGATTCTTGTGCCTCAGCCTCCTAAGCAGCTGGGACTACAGGCGCATGCAACC
ATACCCAGCTAATTTATTTTTAGCAGAGATGGGGTTTCACTGTGTTGGCCAGGCTGGTCGTGAACTCCTGAGCTCAA
GTGATCCACCCACCTCAGCCTCCCAGAGTGCTAGGATTACAGGCCTTTTGACTCTTTTATCTGAGTTTTATTGACCC
CTCTAATTCTCTTACCCAGAATATTTATCCTTCACCAGCAACTCTGACTCTTTGACGGGAGGCCTCAGTTCTAGTCC
TTGGTCTGCTGGTGTCATTGCTGTAGGAATGACCACGGGCCTCAGTTTCCCCATTTGTATAATGGGAAGCCTGTACC
AGGTCATTCTTAAGATTTCTCCTGACTCCAGTGAGCTGGAATTCTAAATGCTGGTCTAGGAGCTGTCTCCAGGATGG
TGCAGGATGGCTTTGCGGAAAGGAGATGGGTTTGGAGGCCAACAAACCTGCTTGTCAATATTGCCTTTGCCTCTTGG
CAGCCCTTGAACTTGAGTAAATAACAACTCCCTGAACCTCAGTTTCCTCATCTGCAGAATGGGGATAATTATGTCCC
AGGGGTATATTTAGACCCTGTTTCCTTTCAGGAGGGTCCCCAGCTGGTCCAGGGCCTGGGAAATTTCTACTTATCCT
CATTACCCAGGTCCCTCCTTTGGACCCTGTAAAGGGTCAGGGTGAATCAGATGGGGGACTGAGCAAGTAGCTATGAC
TGCAGATCATGTAAGGAAGGGACTGACAAGAAGCTCCCAGATGCTGGGGAGAATGAAGAGCTAAAATAGATCCTAGG
TGCTGGATGCTTTGTCATCCATGCGTGCACATATGGGTGCTGGCAGAGCCCCCAAGGACTCTGGCCTCTCGAGTTCT
CCTATCTTCTCCATTCTAGATGCTTCCCTTGTATCCAGTGATGTGCTGGAGCTGGCTTTGCCAAGCTTGTGAGAGCT
GGTTGCTACATTTTCAGGATTTTTACAAGTTGGTAAACACAGCCATTATAAAAAATTAAATGATTTAAATTTATAAT
TAAGTAAATTACATTAAAACAAAAAAATTATACTCAAAATTCATTACTTAATTTTACTACCTGTTACTATTATCTGT
GCTTTTGAGGCTATTTCTACATAGTAACTCTTATGGAGACCTAGGGGAGACACCGCGCATCTCTTCCTGATTCCCCA
CTCAATGACATCATGTTAGTCTTTGGTTGCTTAACTGGCTGTGGGGAGTGTTTTTGTATCACAAAGATTAGAGAGGA
CTACACATCAGGGCTTGATTTATTGTTTGTTGATTTTCTAGACTTCAGAACATGCTGGATAAAATGTCAGTAATGCA
AATTAAACTTTAAAGTATGTCTTGTTTGTAGCCAATACATGGTGTATAGCACCAAAAAATGGAGGGATTATTCTTCC
AGTAGTTGAACACTGTCATCCGTTTCAGCTGACAGCTGCTCAAATCATTTAAGAAGGAGTTCTGACATTCATTTTCA
TTGTTTTACTTTTGTCTTCCTCACTAGTGTAAACAAAAATTTCAACCAGCATTCATGCCGAACCTATACCCATTCTT
CAGTGCCTAGCTGTACAGTTATCAGGGATTTTTATTTGTAGTCTAATTTTGTCAAATCATGGCCAAATCGCAGTGAT
AGTTGACTTTGGATACAAGGTTTGGCAAAAAAAAAAATATTAACAAAATATTCTGTAAGAATCAATTGTCTATATGG
AATTTAGGATAAAGAATATTTACAATAAAGAATATTTACAATAAAGAGTTTATTATTATTTGTAAGTTG

FIGURE 17B

TGTGCAACAAACATACCCTTTATCTCTGTAAAATTTATACACACAAAAATTAACAAAAGATTCTGTAAGAATTAATT
GGCTATATGGAATTTAGGATAGAATATTTACAATAAAGAGTATTTACAATAAA

FIGURE 18A

GCTTCAGTCCCGCGACCGAAGCAGGGCGCGCAGCAGCGCTGAGTGCCCCGGAACGTGCGTCGCGCCCCCAGTGTCCG
TCGCGTCCGCCGCGCCCCGGGCGGGGATGGGCGGCCAGACTGAGCGCCGCACCCGCCATCCAGACCCGCCGGCCCT
AGCCGCAGTCCCTCCAGCCGTGGCCCCAGCGCGCACGGGCGATGGCGAAGGCGACGTCCGGTGCCGCGGGGCTGCGT
CTGCTGTTGCTGCTGCTGCTGCCGCTGCTAGGCAAAGTGGCATTGGGCCTCTACTTCTCGAGGGATGCTTACTGGGA
GAAGCTGTATGTGGACCAGGCGGCCGGCACGCCCTTGCTGTACGTCCATGCCCTGCGGGACGCCCCTGAGGAGGTGC
CCAGCTTCCGCCTGGGCCAGCATCTCTACGGCACGTACCGCACXCGGCTGCATGAGAACAACTGGATCTGCATCCAG
GAGGACACCGGCCTCCTCTACCTTAACCGGAGCCTGGACCATAGCTCCTGGGAGAAGCTCAGTGTCCGCAACCGCGG
CTTTCCCCTGCTCACCGTCTACCTCAAGGTCTTCCTGTCACCCACATCCCTTCGTGAGGGCGAGTGCCAGTGGCCAG
GCTGTGCCCGCGTATACTTCTCCTTCTTCAACACCTCCTTTCCAGCCTGCAGCTCCCTCAAGCCCCGGGAGCTCTGC
TTCCCAGAGACAAGGCCCTCCTTCCGCATTCGGGAGAACCGACCCCCAGGCACCTTCCACCAGTTCCGCCTGCTGCC
TGTGCAGTTCTTGTGCCCCAACATCAGCGTGGCCTACAGGCTCCTGGAGGGTGAGGGTCTGCCCTTCCGCTGCGCCC
CGGACAGCCTGGAGGTGAGCACGCGCTGGGCCCTGGACCGCGAGCAGCGGGAGAAGTACGAGCTGGTGGCCGTGTGC
ACCGTGCACGCCGGCGCGCGCGAGGAGGTGGTGATGGTGCCCTTCCCGGTGACCGTGTACGACGAGGACGACTCGGC
GCCCACCTTCCCCGCGGGCGTCGACACCGCCAGCGCCGTGGTGGAGTTCAAGCGGAAGGAGGACACCGTGGTGGCCA
CGCTGCGTGTCTTCGATGCAGACGTGGTACCTGCATCAGGGGAGCTGGTGAGGCGGTACACAAGCACGCTGCTCCCC
GGGGACACCTGGGCCCAGCAGACCTTCCGGGTGGAACACTGGCCCAACGAGACCTCGGTCCAGGCCAACGGCAGCTT
CGTGCGGGCGACCGTACATGACTATAGGCTGGTTCTCAACCGGAACCTCTCCATCTCGGAGAACCGCACCATGCAGC
TGGCGGTGCTGGTCAATGACTCAGACTTCCAGGGCCCAGGAGCGGGCGTCCTCTTGCTCCACTTCAACGTGTCGGTG
CTGCCGGTCAGCCTGCACCTGCCCAGTACCTACTCCCTCTCCGTGAGCAGGAGGGCTCGCCGATTTGCCCAGATCGG
GAAAGTCTGTGTGGAAAACTGCCAGGCGTTCAGTGGCATCAACGTCCAGTACAAGCTGCATTCCTCTGGTGCCAACT
GCAGCACGCTAGGGGTGGTCACCTCAGCCGAGGACACCTCGGGGATCCTGTTTGTGAATGACACCAAGGCCCTGCGG
CGGCCCAAGTGTGCCGAACTTCACTACATGGTGGTGGCCACCGACCAGCAGACCTCTAGGCAGGCCCAGGCCCAGCT
GCTTGTAACAGTGGAGGGGTCATATGTGGCCGAGGAGGCGGGCTGCCCCCTGTCCTGTGCAGTCAGCAAGAGACGGC
TGGAGTGTGAGGAGTGTGGCGGCCTGGGCTCCCCAACAGGCAGGTGTGAGTGGAGGCAAGGAGATGGCAAAGGGATC
ACCAGGAACTTCTCCACCTGCTCTCCCAGCACCAAGACCTGCCCCGACGGCCACTGCGATGTTGTGGAGACCCAAGA
CATCAACATTTGCCCTCAGGACTGCCTCCGGGGCAGCATTGTTGGGGGACACGAGCCTGGGGAGCCCCGGGGGATTA
AAGCTGGCTATGGCACCTGCAACTGCTTCCCTGAGGAGGAGAAGTGCTTCTGCGAGCCCGAAGACATCCAGGATCCA
CTGTGCGACGAGCTGTGCCGCACGGTGATCGCAGCCGCTGTCCTCTTCTCCTTCATCGTCTCGGTGCTGCTGTCTGC
CTTCTGCATCCACTGCTACCACAAGTTTGCCCACAAGCCACCCATCTCCTCAGCTGAGATGACCTTCCGGAGGCCCG
CCCAGGCCTTCCCGGTCAGCTACTCCTCTTCCGGTGCCCGCCGGCCCTCGCTGGACTCCATGGAGAACCAGGTCTCC
GTCGATGCCTTCAAGATCCTGGAGGATCCAAAGTGGGAATTCCCTCGGAAGAACTTGGTTCTTGGAAAAACTCTAGG
AGAAGGCGAATTTGGAAAAGTGGTCAAGGCAACGGCCTTCCATCTGAAAGGCAGAGCAGGGTACACCACGGTGGCCG
TGAAGATGCTGAAAGAGAACGCCTCCCCGAGTGAGCTTCGAGACCTGCTGTCAGAGTTCAACGTCCTGAAGCAGGTC
AACCACCCACATGTCATCAAATTGTATGGGGCCTGCAGCCAGGATGGCCCGCTCCTCCTCATCGTGGAGTACGCCAA
ATACGGCTCCCTGCGGGGCTTCCTCCGCGAGAGCCGCAAAGTGGGGCCTGGCTACCTGGGCAGTGGAGGCAGCCGCA
ACTCCAGCTCCCTGGACCACCCGGATGAGCGGGCCCTCACCATGGGCGACCTCATCTCATTTGCCTGGCAGATCTCA
CAGGGGATGCAGTATCTGGCCGAGATGAAGCTCGTTCATCGGGACTTGGCAGCCAGAAACATCCTGGTAGCTGAGGG
GCGGAAGATGAAGATTTCGGATTTCGGCTTGTCCCGAGATGTTTATGAAGAGGATTCCTACGTGAAGAGGAGCCAGG
GTCGGATTCCAGTTAAATGGATGGCAATTGAATCCCTTTTTGATCATATCTACACCACGCAAAGTGATGTATGGTCT
TTTGGTGTCCTGCTGTGGGAGATCGTGACCCTAGGGGGAAACCCCTATCCTGGGATTCCTCCTGAGCGGCTCTTCAA
CCTTCTGAAGACCGGCCACCGGATGGAGAGGCCAGACAACTGCAGCGAGGAGATGTACCGCCTGATGCTGCAATGCT
GGAAGCAGGAGCCGGACAAAAGGCCGGTGTTTGCGGACATCAGCAAAGACCTGGAGAAGATGATGGTTAAGAGGAGA
GACTACTTGGACCTTGCGGCGTCCACTCCATCTGACTCCCTGATTTATGACGACGGCCTCTCAGAGGAGGAGACACC
GCTGGTGGACTGTAATAATGCCCCCCTCCCTCGAGCCCTCCCTTCCACATGGATTGAAAACAAACTCTATGGCATGT
CAGACCCGAACTGGCCTGGAGAGAGTCCTGTACCACTCACGAGAGCTGATGGCACTAACACTGGGTTTCCAAGATAT
CCAAATGATAGTGTATATGCTAACTGGATGCTTTCACCCTCAGCGGCAAAATTAATGGACACGTTTGATAGTTAACA
TTTCTTTGTGAAAGGTAATGGACTCACAAGGGGAAGAAACATGCTGAGAATGGAAAGTCTACCGGCCCTTTCTTTGT
GAACGTCACATTGGCCGAGCCGTGTTCAGTTCCCAGGTGGCAGACTCGTTTTTGGTAGTTTGTTTTAACTTCCAAGG
TGGTTTTACTTCTGATAGCCGGTGATTTTCCCTCCTAGCAGACATGCCACACCGGGTAAGAGCTCTGAGTCTTAGTG
GTTAAGCATTCCTTTCTCTTCAGTGCCCAGCAGCACCCAGTGTTGGTCTGTGTCCATCAGTGACCACCAACATTCTG
TGTTCACATGTGTGGGTCCAACACTTACTACCTGGTGTATGAAATTGGACCTGAACTGTTGGATTTTTCTAGTTGCC
GCCAAACAAGGCAAAAAAATTTAAACATGAAGCACACACACAAAAAAGGCAGTAGGAAAAATGCTGGCC

FIGURE 18B

```
CTGATGACCTGTCCTTATTCAGAATGAGAGACTGCGGGGGGGGCCTGGGGGTAGTGTCAATGCCCCTCCAGGGCTGG
AGGGGAAGAGGGGCCCCGAGGATGGGCCTGGGCTCAGCATTCGAGATCTTGAGAATGATTTTTTTTAAATCATGCAA
CCTTTCCTTAGGAAGACATTTGGTTTTCATCATGATTAAGATGATTCCTAGATTTAGCACAATGGAGAGATTCCATG
CCATCTTTACTATGTGGATGGTGGTATCAGGGAAGAGGGCTCACAAGACACATTTGTCCCCCGGGCCCACCACATCA
TCCTCACGTGTTCGGTACTGAGCAGCCACTACCCCTGATGAGAACAGTATGAAGAAAGGGGGCTGTTGGAGTCCCAG
AATTGCTGACAGCAGAGGCTTTGCTGCTGTGAATCCCACCTGCCACCAGCCTGCAGCACACCCCACAGCCAAGTAGA
GGCGAAACGAGTGGCTCATCCTACCTGTTAGGAGCAGGTAGGGCTTGTACTCACTTTAATTTGAATCTTATCAACTT
ACTCATAAAGGGACAGGCTAGCTAGCTGTGTCAGAAGTAGCAATGACAATGACCAAGGACTGCTACACCTCTGATTA
CAATTCTGATGTGAAAAAGATGGTGTTTGGCTCTTATAGAGCCTGTGTGAAAGGCCCATGGATCAGCTCTTCCTGTG
TTTGTAATTTAATGCTGCTACAAGATGTTTCTGTTTCTTAGATTCTGACCATGACTCATAAGCTTCTTGTCATTCTT
CATTGCTTGTTTGTGGTCACAGATGCACAACACTCCTCCAGTCTTGTGGGGGCAGCTTTTGGGAAGTCTCAGCAGCT
CTTCTGGCTGTGTTGTCAGCACTGTAACTTCGCAGAAAAGAGTCGGATTACCAAAACACTGCCTGCTCTTCAGACTT
AAAGCACTGATAGGACTTAAAATAGTCTCATTCAAATACTGTATTTTATATAGGCATTTCACAAAAACAGCAAAATT
GTGGCATTTTGTGAGGCCAAGGCTTGGATGCGTGTGTAATAGAGCCTTATGGTGTGTGCGCACACACCCAGAGGAGA
GTTTGAAAAATGCTTATTGGACACGTAACCTGGCTCTAATTTGGGCTGTTTTTCAGATACACTGTGATAAGTTCTTT
TACAAATATCTATAGACATGGTAAACTTTTGGTTTTCAGATATGCTTAATGATAGTCTTACTAAATGCAGAAATAAG
AATAAACTTTCTCAAATTATTAAAAATGCCTACACAGTAAGTGTGAATTGCTGCAACAGGTTTGTTCTCAGGAGGGT
AAGAACTCCAGGTCTAAACAGCTGACCCAGTGATGGGGAATTTATCCTTGACCAATTTATCCTTGACCAATAACCTA
ATTGTCTATTCCTGAGTTATAAAGGTCCCCATCCTTATTAGCTCTACTGGAATTTTCATACACGTAAATGCAGAAGT
TACTAAGTATTAAGTATTACTGAGTATTAAGTAGTAATCTGTCAGTTATTAAAATTTGTAAAATCTATTTATGAAAG
GTCATTAAACCAGATCATGTTCCTTTTTTTGTAATCAAGGTGACTAAGAAAATCAGTTGTGTAAATAAAATCATGTA
TC
```

FIGURE 19A

TGAGAGCCAAGCAAAGAACATTAAGGAAGGAAGGAGGAATGAGGCTGGATACGGTGCAGTGAAAAAGGCACTTCCAA
GAGTGGGGCACTCACTACGCACAGACTCGACGGTGCCATCAGCATGAGAACTTACCGCTACTTCTTGCTGCTCTTTT
GGGTGGGCCAGCCCTACCCAACTCTCTCAACTCCACTATCAAAGAGGACTAGTGGTTTCCCAGCAAAGAAAAGGGCC
CTGGAGCTCTCTGGAAACAGCAAAAATGAGCTGAACCGTTCAAAAAGGAGCTGGATGTGGAATCAGTTCTTTCTCCT
GGAGGAATACACAGGATCCGATTATCAGTATGTGGGCAAGTTACATTCAGACCAGGATAGAGGAGATGGATCACTTA
AATATATCCTTTCAGGAGATGGAGCAGGAGATCTCTTCATTATTAATGAAAACACAGGCGACATACAGGCCACCAAG
AGGCTGGACAGGGAAGAAAAACCCGTTTACATCCTTCGAGCTCAAGCTATAAACAGAAGGACAGGGAGACCCGTGGA
GCCCGAGTCTGAATTCATCATCAAGATCCATGACATCAATGACAATGAACCAATATTCACCAAGGAGGTTTACACAG
CCACTGTCCCTGAAATGTCTGATGTCGGTACATTTGTTGTCCAAGTCACTGCGACGGATGCAGATGATCCAACATAT
GGGAACAGTGCTAAAGTTGTCTACAGTATTCTACAGGGACAGCCCTATTTTTCAGTTGAATCAGAAACAGGTATTAT
CAAGACAGCTTTGCTCAACATGGATCGAGAAAACAGGGAGCAGTACCAAGTGGTGATTCAAGCCAAGGATATGGGCG
GCCAGATGGGAGGATTATCTGGGACCACCACCGTGAACATCACACTGACTGATGTCAACGACAACCCTCCCCGATTC
CCCCAGAGTACATACCAGTTTAAAACTCCTGAATCTTCTCCACCGGGGACACCAATTGGCAGAATCAAAGCCAGCGA
CGCTGATGTGGGAGAAAATGCTGAAATTGAGTACAGCATCACAGACGGTGAGGGGCTGGATATGTTTGATGTCATCA
CCGACCAGGAAACCCAGGAAGGGATTATAACTGTCAAAAAGCTCTTGGACTTTGAAAAGAAGAAAGTGTATACCCTT
AAAGTGGAAGCCTCCAATCCTTATGTTGAGCCACGATTTCTCTACTTGGGGCCTTTCAAAGATTCAGCCACGGTTAG
AATTGTGGTGGAGGATGTAGATGAGCCACCTGTCTTCAGCAAACTGGCCTACATCTTACAAATAAGAGAAGATGCTC
AGATAAACACCACAATAGGCTCCGTCACAGCCCAAGATCCAGATGCTGCCAGGAATCCTGTCAAGTACTCTGTAGAT
CGACACACAGATATGGACAGAATATTCAACATTGATTCTGGAAATGGTTCGATTTTTACATCGAAACTTCTTGACCG
AGAAACACTGCTATGGCACAACATTACAGTGATAGCAACAGAGATCAATAATCCAAAGCAAAGTAGTCGAGTACCTC
TATATATTAAAGTTCTAGATGTCAATGACAACGCCCCAGAATTTGCTGAGTTCTATGAAACTTTTGTCTGTGAAAAA
GCAAAGGCAGATCAGTTGATTCAGACCCTGCATGCTGTTGACAAGGATGACCCTTATAGTGGACACCAATTTTCGTT
TTCCTTGGCCCCTGAAGCAGCCAGTGGCTCAAACTTTACCATTCAAGACAACAAAGACAACACGGCGGGAATCTTAA
CTCGGAAAAATGGCTATAATAGACACGAGATGAGCACCTATCTCTTGCCTGTGGTCATTTCAGACAACGACTACCCA
GTTCAAAGCAGCACTGGGACAGTGACTGTCCGGGTCTGTGCATGTGACCACCACGGGAACATGCAATCCTGCCATGC
GGAGGCGCTCATCCACCCCACGGACTGAGCACGGGGGCTCTGGTTGCCATCCTTCTGTGCATCGTGATCCTACTAG
TGACAGTGGTGCTGTTTGCAGCTCTGAGGCGGCAGCGAAAAAAAGAGCCTTTGATCATTTCCAAAGAGGACATCAGA
GATAACATTGTCAGTTACAACGACGAAGGTGGTGGAGAGGAGGACACCCAGGCTTTTGATATCGGCACCCTGAGGAA
TCCTGAAGCCATAGAGGACAACAAATTACGAAGGGACATTGTGCCCGAAGCCCTTTTCCTACCCCGACGGACTCCAA
CAGCTCGCGACAACACCGATGTCAGAGATTTCATTAACCAAAGGTTAAAGGAAAATGACACGGACCCCACTGCCCCG
CCATACGACTCCTTGGCCACTTACGCCTATGAAGGCACTGGCTCCGTGGCGGATTCCCTGAGCTCGCTGGAGTCAGT
GACCACGGATGCAGATCAAGACTATGATTACCTTAGTGACTGGGGACCTCGATTCAAAAAGCTTGCAGATATGTATG
GAGGAGTGGACAGTGACAAAGACTCCTAATCTGTTGCCTTTTTCATTTTCCAATACGACACTGAAATATGTGAAGTG
GCTATTTCTTTATATTTATCCACTACTCCGTGAAGGCTTCTCTGTTCTACCCGTTCCAAAAGCCAATGGCTGCAGTC
CGTGTGGATCCAATGTTAGAGACTTTTTTCTAGTACACTTTTATGAGCTTCCAAGGGGCAAATTTTTATTTTTTAGT
GCATCCAGTTAACCAAGTCAGCCCAACAGGCAGGTGCCGGAGGGGAGGACAGGGAACAGTATTTCCACTTGTTCTCA
GGGCAGCGTGCCCGCTTCCGCTGTCCTGGTGTTTTACTACACTCCATGTCAGGTCAGCCAACTGCCCTAACTGTACA
TTTCACAGGCTAATGGGATAAAGGACTGTGCTTTAAAGATAAAAATATCATCATAGTAAAAGAAATGAGGCATATC
GGCTCACAAAGAGATAAACTACATAGGGGTGTTTATTTGTGTCACAAAGAATTTAAAATAACACTTGCCCATGCTAT
TTGTTCTTCAAGAACTTTCTCTGCCATCAACTACTATTCAAAACCTCAAATCCACCCATATGTTAAAATTCTCATTA
CTCTTAAGGAATAGAAGCAAATTAAACGGTAACATCCAAAAGCAACCACAAACCTAGTACGACTTCATTCCTTCCAC
TAACTCATAGTTTGTTATATCCTAGACTAGACATGCGAAAGTTTGCCTTTGTACCATATAAAGGGGGAGGGAAATAG
CTAATAATGTTAACCAAGGAAATATATTTTACCATACATTTAAAGTTTTGGCCACCACATGTATCACGGGTCACTTG
AAATTCTTTCAGCTATCAGTAGGCTAATGTCAAAATTGTTTAAAAATTCTTGAAAGAATTTTCCTGAGACAAATTTT
AACTTCTTGTCTATAGTTGTCAGTATTATTCTACTATACTGTACATGAAAGTAGCAGTGTGAAGTACAATAATTCAT
ATTCTTCATATCCTTCTTACACGACTAAGTTGAATTAGTAAAGTTAGATTAAATAAAACTTAAATCTCACTCTAGGA
GTTCAGTGGAGAGGTTAGAGCCAGCCACACTTGAACCTAATACCCTGCCCTTGACATCTGGAAACCTCTACATATTT
ATATAACGTGATACATTTGGATAAACAACATTGAGATTATGATGAAAACCTACATATTCCATGTTTGGAAGACCCTT
GGAAGAGGAAAATTGGATTCCCTTAAACAAAAGTGTTTAAGATTGTAATTAAAATGATAGTTGATTTTCAAAAGCAT
TAATTTTTTTTCATTGTTTTTAACTTTGCTTTCATGACCATCCTGCCATCCTTGACTTTGAACTAATGATAAAGTAA
TGATCTCAAACTATGACAGAAAAGTAATGTAAAATCCATCCAATCTATTATTTCTCTAATTATGCAATTAGCCTCAT
AGTTATTATCCAGAGGACCCAACTGAACTGAACTAATCCTTCTGGCAGATTCAAATCGTTTATTTCACA

FIGURE 19B

CGCTGTTCTAATGGCACTTATCATTAGAATCTTACCTTGTGCAGTCATCAGAAATTCCAGCGTACTATAATGAAAAC
ATCCTTGTTTTGAAAACCTAAAAGACAGGCTCTGTATATATATATACTTAAGAATATGCTGACTTCACTTATTAGTC
TTAGGGATTTATTTTCAATTAATATTAATTTTCTACAAATAATTTTAGTGTCATTTCCATTTGGGGATATTGTCATA
TCAGCACATATTTTCTGTTTGGAAACACACTGTTGTTTAGTTAAGTTTTAAATAGGTGTATTACCCAAGAAGTAAAG
ATGGAAACGTT

FIGURE 20

CGGTGGAGGCCACAGACACCTCAAACCTGGATTCCACAATTCTACGTTAAGTGTTGGAGTTTTTATTACTCTGCTGT
AGGAAAGCCTTTGCCAATGCTTACAAGGAACTGTTTATCCCTGCTTCTCTGGGTTCTGTTTGATGGAGGTCTCCTAA
CACCACTACAACCACAGCCACAGCAGACTTTAGCCACAGAGCCAAGAGAAAATGTTATCCATCTGCCAGGACAACGG
TCACATTTCCAACGTGTTAAACGTGGCTGGGTATGGAATCAATTTTTTGTGCTGGAAGAATACGTGGGCTCCGAGCC
TCAGTATGTGGGAAAGCTCCATTCCGACTTAGACAAGGGAGAGGGCACTGTGAAATACACCCTCTCAGGAGATGGCG
CTGGCACCGTTTTTACCATTGATGAAACCACAGGGGACATTCATGCAATAAGGAGCCTAGATAGAGAAGAGAAACCT
TTCTACACTCTTCGTGCTCAGGCTGTGGACATAGAAACCAGAAAGCCCCTGGAGCCTGAATCAGAATTCATCATCAA
AGTGCAGGATATTAATGATAATGAGCCAAAGTTTTTGGATGGACCTTATGTTGCTACTGTTCCAGAAATGTCTCCTG
TGGGTGCATATGTACTCCAGGTCAAGGCCACAGATGCAGATGACCCGACCTATGGAAACAGTGCCAGAGTCGTTTAC
AGCATTCTTCAGGGACAACCTTATTTCTCTATTGATCCCAAGACAGGTGTTATTAGAACAGCTTTGCCAAACATGGA
CAGAGAAGTCAAAGAACAATATCAAGTACTCATCCAAGCCAAGGATATGGGAGGACAGCTTGGAGGATTAGCCGGAA
CAACAATAGTCAACATCACTCTCACCGATGTCAATGACAATCCACCTCGATTCCCCAAAAGCATCTTCCACTTGAAA
GTTCCTGAGTCTTCCCCTATTGGTTCAGCTATTGGAAGAATAAGAGCTGTGGATCCTGATTTTGGACAAAATGCAGA
AATTGAATACAATATTGTTCCAGGAGATGGGGGAAATTTGTTTGACATCGTCACAGATGAGGATACACAAGAGGGAG
TCATCAAATTGAAAAAGCCTTTAGATTTTGAAACAAAGAAGGCATACACTTTCAAAGTTGAGGCTTCCAACCTTCAC
CTTGACCACCGGTTTCACTCGGCGGGCCCTTTCAAAGACACAGCTACGGTGAAGATCAGCGTGCTGGACGTAGATGA
GCCACCGGTTTTCAGCAAGCCGCTCTACACCATGGAGGTTTATGAAGACACTCCGGTAGGGACCATCATTGGCGCTG
TCACTGCTCAAGACCTGGATGTAGGCAGCGGTGCTGTTAGGTACTTCATAGATTGGAAGAGTGATGGGGACAGCTAC
TTTACAATAGATGGAAATGAAGGAACCATCGCCACTAATGAATTACTAGACAGAGAAAGCACTGCGCAGTATAATTT
CTCCATAATTGCGAGTAAAGTTAGTAACCCTTTATTGACCAGCAAAGTCAATATACTGATTAATGTCTTAGATGTAA
ATGAATTTCCTCCAGAAATATCTGTGCCATATGAGACAGCCGTGTGTGAAAATGCCAAGCCAGGACAGATAATTCAG
ATAGTCAGTGCTGCAGACCGAGATCTTTCACCTGCTGGGCAACAATTCTCCTTTAGATTATCACCTGAGGCTGCTAT
CAAACCAAATTTTACAGTTCGTGACTTCAGAAACAACACAGCGGGGATTGAAACCCGAAGAAATGGATACAGCCGCA
GGCAGCAAGAGTTGTATTTCCTCCCTGTTGTAATAGAAGACAGCAGCTACCCTGTCCAGAGCAGCACAAACACAATG
ACTATTCGAGTCTGTAGATGTGACTCTGATGGCACCATCCTGTCTTGTAATGTGGAAGCAATTTTTCTACCTGTAGG
ACTTAGCACTGGGGCGTTGATTGCAATTCTACTATGCATTGTTATACTCTTAGCCATAGTTGTACTGTATGTAGCAC
TGCGAAGGCAGAAGAAAAAGCACACCCTGATGACCTCTAAAGAAGACATCAGAGACAACGTCATCCATTACGATGAT
GAAGGAGGTGGGGAGGAAGATACCCAGGCTTTCGACATCGGGGCTCTGAGAAACCCAAAAGTGATTGAGGAGAACAA
AATTCGCAGGGATATAAAACCAGACTCTCTCTGTTTACCTCGTCAGAGACCACCCATGGAAGATAACACAGACATAA
GGGATTTCATTCATCAAAGGCTACAGGAAAATGATGTAGATCCAACTGCCCCACCAATCGATTCACTGGCCACATAT
GCCTACGAAGGGAGTGGGTCCGTGGCAGAGTCCCTCAGCTCTATAGACTCTCTCACCACAGAAGCCGACCAGGACTA
TGACTATCTGACAGACTGGGGACCCCGCTTTAAAGTCTTGGCAGACATGTTTGGCGAAGAAGAGAGTTATAACCCTG
ATAAAGTCACTTAAGGGAGTCGTGGAGGCTAAAATACAACCGAGAGGGGAGATTTTT

FIGURE 21

GGCTCTCACCCTCCTCTCCTGCAGCTCCAGCTCTGTGCTCTGCCTCTGAGGAGACCATGGCCCGGCCTCTGTGTACC
CTGCTACTCCTGATGGCTACCCTGGCTGGGGCTCTGGCCTCGAGCTCCAAGGAGGAGAATAGGATAATCCCAGGTGG
CATCTATGATGCAGACCTCAATGATGAGTGGGTACAGCGTGCCCTTCACTTCGCCATCAGCGAGTACAACAAGGCCA
CCGAAGATGAGTACTACAGACGCCCGCTGCAGGTGCTGCGAGCCAGGGAGCAGACCTTTGGGGGGTGAATTACTTC
TTCGACGTAGAGGTGGGCCGCACCATATGTACCAAGTCCCAGCCCAACTTGGACACCTGTGCCTTCCATGAACAGCC
AGAACTGCAGAAGAAACAGTTATGCTCTTTCGAGATCTACGAAGTTCCCTGGGAGGACAGAATGTCCCTGGTGAATT
CCAGGTGTCAAGAAGCCTAGGGGTCTGTGCCAGGCCAGTCACACCGACCACCACCCACTCCCACCCCCTGTAGTGCT
CCCACCCCTGGACTGGTGGCCCCCACCCTGCGGGAGGCCTCCCCATGTGCCTGTGCCAAGAGACAGACAGAGAAGGC
TGCAGGAGTCCTTTGTTGCTCAGCAGGGCGCTCTGCCCTCCCTCCTTCCTTCTTGCTTCTAATAGACCTGGTACATG
GTACACACACCCCCACCTCCTGCAATTAAACAGTAGCATCGCC

FIGURE 22

GGCAGCGGTGGCAGGGGCTGCAGGAGCAAGTGACCAGGAGCAGGACTGGGGACAGGCCTGATCGCCCCTGCACGAAC
CAGACCCTTCGCCGCCCTCACGATGACTACCTCTCCGATCCTGCAGCTGCTGCTGCGGCTCTCACTGTGCGGGCTGC
TGCTCCAGAGGGCGGAGACAGGCTCTAAGGGGCAGACGGCGGGGGAGCTGTACCAGCGCTGGGAACGGTACCGCAGG
GAGTGCCAGGAGACCTTGGCAGCCGCGGAACCGCCTTCAGGCCTCGCCTGTAACGGGTCCTTCGATATGTACGTCTG
CTGGGACTATGCTGCACCCAATGCCACTGCCCGTGCGTCCTGCCCCTGGTACCTGCCCTGGCACCACCATGTGGCTG
CAGGTTTCGTCCTCCGCCAGTGTGGCAGTGATGGCCAATGGGGACTTTGGAGAGACCATACACAATGTGAGAACCCA
GAGAAGAATGAGGCCTTTCTGGACCAAAGGCTCATCTTGGAGCGGTTGCAGGTCATGTACACTGTCGGCTACTCCCT
GTCTCTCGCCACACTGCTGCTAGCCCTGCTCATCTTGAGTTTGTTCAGGCGGCTACATTGCACTAGAAACTATATCC
ACATCAACCTGTTCACGTCTTTCATGCTGCGAGCTGCGGCCATTCTCAGCCGAGACCGTCTGCTACCTCGACCTGGC
CCCTACCTTGGGGACCAGGCCCTTGCGCTGTGGAACCAGGCCCTCGCTGCCTGCCGCACGGCCCAGATCGTGACCCA
GTACTGCGTGGGTGCCAACTACACGTGGCTGCTGGTGGAGGGCGTCTACCTGCACAGTCTCCTGGTGCTCGTGGGAG
GCTCCGAGGAGGGCCACTTCCGCTACTACCTGCTCCTCGGCTGGGGGGCCCCCGCGCTTTTCGTCATTCCCTGGGTG
ATCGTCAGGTACCTGTACGAGAACACGCAGTGCTGGGAGCGCAACGAAGTCAAGGCCATTTGGTGGATTATACGGAC
CCCCATCCTCATGACCATCTTGATTAATTTCCTCATTTTTATCCGCATTCTTGGCATTCTCCTGTCCAAGCTGAGGA
CACGGCAAATGCGCTGCCGGGATTACCGGCTGAGGCTGGCTCGCTCCACGCTGACGCTGGTGCCCCTGCTGGGTGTC
CACGAGGTGGTGTTTGCTCCCGTGACAGAGGAACAGGCCCGGGGCGCCCTGCGCTTCGCCAAGCTCGGCTTTGAGAT
CTTCCTCAGCTCCTTCCAGGGCTTCCTGGTCAGCGTCCTCTACTGCTTCATCAACAAGGAGGTGCAGTCGGAGATCC
GCCGTGGCTGGCACCACTGCCGCCTGCGCCGCAGCCTGGGCGAGGAGCAACGCCAGCTCCCGGAGCGCGCCTTCCGG
GCCCTGCCCTCCGGCTCCGGCCCGGGCGAGGTCCCCACCAGCCGCGGCTTGTCCTCGGGGACCCTCCCAGGGCCTGG
GAATGAGGCCAGCCGGGAGTTGGAAAGTTACTGCTAGGGGGCGGGATCCCCGTGTCTGTTCAGTTAGCATGGATTTA
TTGAGTGCCAACTGCGTGCCAGGCCCAGTACGGAGGACGCTGGGGAAATGGTGAAGGAAACAGAAAAAAGGTCCCTG
CCCTTCTGGAGATGACAACTGAGTGGGGAAAACAGACCGTGAACACAAAACATCAAGTTCCACACACGCTATGGAAT
GGTTATGAAGGGAAGCGAGAAGGGGGCCTAGGGTGGTCTGGGAGGCGTCTCCAAGGAGGTGACACTTAAGCCATCCC
CGAAAGAGGTGAAAGAGATCACTTTGGGGAGAGCTGGAGAACAGGATTCTAGGCGGAAGCGATAGCATAGGCAAAGG
CCCTTGGGCAGGAAGGCGCTCAGCCTTGGCTGGAGTAGAATTAAGTCAGAGCCAACAGGTTGGGGAGAGACAGAGAA
GTGGGCAGGGGCACCCAAGTTGGGATTTCATTTCAGGTGCATTGGAGATTCTTAGGAGTGTCTCTTGGGGGTAATAT
TTTATTTTTTAAAAAATGAGGAT

FIGURE 23

GCCAGAGCGTGAGCCGCGACCTCCGCGCAGGTGGTCGCGCCGGTCTCCGCGGAAATGTTGTCCAAAGTTCTTCCAGT
CCTCCTAGGCATCTTATTGATCCTCCAGTCGAGGGTCGAGGGACCTCAGACTGAATCAAAGAATGAAGCCTCTTCCC
GTGATGTTGTCTATGGCCCCCAGCCCCAGCCTCTGGAAAATCAGCTCCTCTCTGAGGAAACAAAGTCAACTGAGACT
GAGACTGGGAGCAGAGTTGGCAAACTGCCAGAAGCCTCTCGCATCCTGAACACTATCCTGAGTAATTATGACCACAA
ACTGCGCCCTGGCATTGGAGAGAAGCCCACTGTGGTCACTGTTGAGATCGCCGTCAACAGCCTTGGTCCTCTCTCTA
TCCTAGACATGGAATACACCATTGACATCATCTTCTCCCAGACCTGGTACGACGAACGCCTCTGTTACAACGACACC
TTTGAGTCTCTTGTTCTGAATGGCAATGTGGTGAGCCAGCTATGGATCCCGGACACCTTTTTTAGGAATTCTAAGAG
GACCCACGAGCATGAGATCACCATGCCCAACCAGATGGTCCGCATCTACAAGGATGGCAAGGTGTTGTACACAATTA
GGATGACCATTGATGCCGGATGCTCACTCCACATGCTCAGATTTCCAATGGATTCTCACTCTTGCCCTCTATCTTTC
TCTAGCTTTTCCTATCCTGAGAATGAGATGATCTACAAGTGGGAAAATTTCAAGCTTGAAATCAATGAGAAGAACTC
CTGGAAGCTCTTCCAGTTTGATTTTACAGGAGTGAGCAACAAAACTGAAATAATCACAACCCCAGTTGGTGACTTCA
TGGTCATGACGATTTTCTTCAATGTGAGCAGGCGGTTTGGCTATGTTGCCTTTCAAAACTATGTCCCTTCTTCCGTG
ACCACGATGCTCTCCTGGGTTTCCTTTTGGATCAAGACAGAGTCTGCTCCAGCCCGGACCTCTCTAGGGATCACCTC
TGTTCTGACCATGACCACGTTGGGCACCTTTTCTCGTAAGAATTTCCCGCGTGTCTCCTATATCACAGCCTTGGATT
TCTATATCGCCATCTGCTTCGTCTTCTGCTTCTGCGCTCTGTTGGAGTTTGCTGTGCTCAACTTCCTGATCTACAAC
CAGACAAAAGCCCATGCTTCTCCTAAACTCCGCCATCCTCGTATCAATAGCCGTGCCCATGCCCGTACCCGTGCACG
TTCCCGAGCCTGTGCCCGCCAACATCAGGAAGCTTTTGTGTGCCAGATTGTCACCACTGAGGGAAGTGATGGAGAGG
AGCGCCCGTCTTGCTCAGCCCAGCAGCCCCCTAGCCCAGGTAGCCCTGAGGGTCCCCGCAGCCTCTGCTCCAAGCTG
GCCTGCTGTGAGTGGTGCAAGCGTTTTAAGAAGTACTTCTGCATGGTCCCCGATTGTGAGGGCAGTACCTGGCAGCA
GGGCCGCCTCTGCATCCATGTCTACCGCCTGGATAACTACTCGAGAGTTGTTTTCCCAGTGACTTTCTTCTTCTTCA
ATGTGCTCTACTGGCTTGTTTGCCTTAACTTGTAGGTACCAGCTGGTACCCTGTGGGGCAACCTCTCCAGTTCCCCA
GGAGGTCCAAGCCCCTTGCCAAGGGAGTTGGGGGAAAGCAGCAGCAGCAGCAGGAGCGACTAGAGTTTTTCCTGCCC
CATTCCCCAAACAGAAGCTTGCAGAGGGTTTGTCTTTGCTGCCCCTCTCCCCTACCTGGCCCATTCACTGAGTCTTC
TCAGCAGACCATTTCAAATTATTAATAAATGGGCCACCTCCCTCTTCTTCAAGGAGCATCCGTGATGCTCAGTGTTC
AAAACCACAGCCACTTAGTGATCAGCTCCCTAAAACCATGCCTAAGTACAGGCGGATTAGCTATCTTCCAACAATGC
TGACCACCAGACAATTACTGCATTTTTCCAGAAGCCCACTATTGCCTTTGTAGTGCTTTCGGCCCAGTTCTGGCCTC
AGCCTCAAAGTGCACCGACTAGTTGCTTGCCTATACCTGGCACCTCATTAAGATGCTGGGCAGCAGTATAACAGGAG
GAAGAGATCCCTCTCCTTTGGTCAGATTATTATGTTCTCAGTTCTCTCTCCCTGCTACCCCTTTCTCTGCAGATAGA
TAGACACTGGCATTATCCCTTTAGGAAGAGGGGGGGCAGCAAGAGAGCCTATTTGGGACAGCATTCCTCTCTCTCT
GCTGCTGTGACATCTCCCTCTCCTTGCTGGCTCCATCTTTCGTCTGCACTACCAATTCAATGCCCTTCATCCAATGG
GTATCTATTTTTGTGTGTGATTATAGTAACTACTCCCTGCTTTATATGCCACCCTCTTCCTTCTCTTTGACCCCTGT
GACTCTTTCTGTAACTTTCCCAGTGACTTCCCCTAGCCCTGACCCAGGCACTAGGCCTTGGTGACTTCCTGGGGCCA
AGAAACTAAGGAAACTCGGCTTTGCAACAGGCATTACTCGCCATTGATTGGTGCCCACCCAGGGCACACTGTCGGAG
TTCTATCACTTGCTTGACCCCTGGACCCATAAACCAGTCCACTGTTATACCCGGGGCACTCTAACCATCACAATCAA
TCAATCAAATTCCCTTAAATTTGTATGGCACTGGAACTTTGGCAAAGCACTTTTGACAAGTTGTGTCTGATTGGAGC
TTCATGATAGCCTTGTGACATCTTTAGGGCAGGATTCTTATCCCCATTTTGCAGATGAAAACCCTGAGTCACAGATT
TCTGTGGGACTGTGGATCTCACTGGAAGCTATCCAAGAGCCCACTGTCACCTTCTAGACCACATGATAGGGCTAGAC
AGCTCAGTTCACCATGATTCTCTTCTGTCACCTCTGCTGGCACACCAGTGGCAAGGCCCAGAATGGCGACCTCTCTT
TAGCTCAATTTCTGGGCCTGAGGTGCTCAGACTGCCCCCAAGATCAAATCTCTCCTGGCTGTAGTAACCCAGTGGAA
TGAATTTGGACATGCCCCAATGCTTCTATATGCTAAGTGAAATCTGTGTCTGTAATTTGTTGGGGGGTGGATAGGGT
GGGGTCTCCATCTACTTTTTGTCACCATCATCTGAAATGGGGAAATATGTAAATAAATATATCAGCAAAGCAAAAAG
AAAAAAAAAAA

FIGURE 24A

GGTGGCCTCTGTGGCCGTCCAGGCTAGCGGCGGCCCGCAGGCGGCGGGGAGAAAGACTCTCTCACCTGGTCTTGCGG
CTGTGGCCACCGCCGGCCAGGGGTGTGGAGGGCGTGCTGCCGGAGACGTCCGCCGGGCTCTGCAGTTCCGCCGGGGG
TCGGGCAGCTATGGAGCCGCGGCCCACGGCGCCCTCCTCCGGCGCCCCGGGACTGGCCGGGGTCGGGGAGACGCCGT
CAGCCGCTGCGCTGGCCGCAGCCAGGGTGGAACTGCCCGGCACGGCTGTGCCCTCGGTGCCGGAGGATGCTGCGCCC
GCGAGCCGGGACGGCGGCGGGGTCCGCGATGAGGGCCCCGCGGCGGCCGGGGACGGGCTGGGCAGACCCTTGGGGCC
CACCCCGAGCCAGAGCCGTTTCCAGGTGGACCTGGTTTCCGAGAACGCCGGGCGGGCCGCTGCTGCGGCGGCGGCGG
CGGCGGCGGCAGCGGCGGCGGCTGGTGCTGGGGCGGGGGCCAAGCAGACCCCCGCGGACGGGGAAGCCAGCGGCGAG
AGCGAGCCAGCTAAAGGCAGCGAGGAAGCCAAGGGCCGCTTCCGCGTGAACTTCGTGGACCCAGCTGCCTCCTCGTC
GGCTGAAGACAGCCTGTCAGATGCTGCCGGGGTCGGAGTCGACGGGCCCAACGTGAGCTTCCAGAACGGCGGGGACA
CGGTGCTGAGCGAGGGCAGCAGCCTGCACTCCGGCGGCGGCGGCGGCAGTGGGCACCACCAGCACTACTATTATGAT
ACCCACACCAACACCTACTACCTGCGCACCTTCGGCCACAACACCATGGACGCTGTGCCCAGGATCGATCACTACCG
GCACACAGCCGCGCAGCTGGGCGAGAAGCTGCTCCGGCCTAGCCTGGCGGAGCTCCACGACGAGCTGGAAAAGGAAC
CTTTTGAGGATGGCTTTGCAAATGGGGAAGAAAGTACTCCAACCAGAGATGCTGTGGTCACGTATACTGCAGAAAGT
AAAGGAGTCGTGAAGTTTGGCTGGATCAAGGGTGTATTAGTACGTTGTATGTTAAACATTTGGGGTGTGATGCTTTT
CATTAGATTGTCATGGATTGTGGGTCAAGCTGGAATAGGTCTATCAGTCCTTGTAATAATGATGGCCACTGTTGTGA
CAACTATCACAGGATTGTCTACTTCAGCAATAGCAACTAATGGATTTGTAAGAGGAGGAGGAGCATATTATTTAATA
TCTAGAAGTCTAGGGCCAGAATTTGGTGGTGCAATTGGTCTAATCTTCGCCTTTGCCAACGCTGTTGCAGTTGCTAT
GTATGTGGTTGGATTTGCAGAAACCGTGGTGGAGTTGCTTAAGGAACATTCCATACTTATGATAGATGAAATCAATG
ATATCCGAATTATTGGAGCCATTACAGTCGTGATTCTTTTAGGTATCTCAGTAGCTGGAATGGAGTGGGAAGCAAAA
GCTCAGATTGTTCTTTTGGTGATCCTACTTCTTGCTATTGGTGATTTCGTCATAGGAACATTTATCCCACTGGAGAG
CAAGAAGCCAAAAGGGTTTTTTGGTTATAAATCTGAAATATTTAATGAGAACTTTGGGCCCGATTTTCGAGAGGAAG
AGACTTTCTTTTCTGTATTTGCCATCTTTTTTCCTGCTGCAACTGGTATTCTGGCTGGAGCAAATATCTCAGGTGAT
CTTGCAGATCCTCAGTCAGCCATACCCAAAGGAACACTCCTAGCCATTTTAATTACTACATTGGTTTACGTAGGAAT
TGCAGTATCTGTAGGTTCTTGTGTTGTTCGAGATGCCACTGGAAACGTTAATGACACTATCGTAACAGAGCTAACAA
ACTGTACTTCTGCAGCCTGCAAATTAAACTTTGATTTTTCATCTTGTGAAAGCAGTCCTTGTTCCTATGGCCTAATG
AACAACTTCCAGGTAATGAGTATGGTGTCAGGATTTACACCACTAATTTCTGCAGGTATATTTTCAGCCACTCTTTC
TTCAGCATTAGCATCCCTAGTGAGTGCTCCCAAAATATTTCAGGCTCTATGTAAGGACAACATCTACCCAGCTTTCC
AGATGTTTGCTAAAGGTTATGGGAAAAATAATGAACCTCTTCGTGGCTACATCTTAACATTCTTAATTGCACTTGGA
TTCATCTTAATTGCTGAACTGAATGTTATTGCACCAATTATCTCAAACTTCTTCCTTGCATCATATGCATTGATCAA
TTTTTCAGTATTCCATGCATCACTTGCAAAATCTCCAGGATGGCGTCCTGCATTCAAATACTACAACATGTGGATAT
CACTTCTTGGAGCAATTCTTTGTTGCATAGTAATGTTCGTCATTAACTGGTGGGCTGCATTGCTAACATATGTGATA
GTCCTTGGGCTGTATATTTATGTTACCTACAAAAAACCAGATGTGAATTGGGGATCCTCTACACAAGCCCTGACTTA
CCTGAATGCACTGCAGCATTCAATTCGTCTTTCTGGAGTGGAAGACCACGTGAAAAACTTTAGGCCACAGTGTCTTG
TTATGACAGGTGCTCCAAACTCACGTCCAGCTTTACTTCATCTTGTTCATGATTTCACAAAAAATGTTGGTTTGATG
ATCTGTGGCCATGTACATATGGGTCCTCGAAGACAAGCCATGAAAGAGATGTCCATCGATCAAGCCAAATATCAGCG
ATGGCTTATTAAGAACAAAATGAAGGCATTTTATGCTCCAGTACATGCAGATGACTTGAGAGAAGGTGCACAGTATT
TGATGCAGGCTGCTGGTCTTGGTCGTATGAAGCCAAACACACTTGTCCTTGGATTTAAGAAAGATTGGTTGCAAGCA
GATATGAGGGATGTGGATATGTATATAAACTTATTTCATGATGCTTTTGACATACAATATGGAGTAGTGGTTATTCG
CCTAAAAGAAGGTCTGGATATATCTCATCTTCAAGGACAAGAAGAATTATTGTCATCACAAGAGAAATCTCCTGGCA
CCAAGGATGTGGTAGTAAGTGTGGAATATAGTAAAAAGTCCGATTTAGATACTTCCAAACCACTCAGTGAAAAACCA
ATTACACACAAAGTTGAGGAAGAGGATGGCAAGACTGCAACTCAACCACTGTTGAAAAAAGAATCCAAAGGCCCTAT
TGTGCCTTTAAATGTAGCTGACCAAAAGCTTCTTGAAGCTAGTACACAGTTTCAGAAAAAACAAGGAAAGAATACTA
TTGATGTCTGGTGGCTTTTTGATGATGGAGGTTTGACCTTATTGATACCTTACCTTCTGACGACCAAGAAAAAATGG
AAAGACTGTAAGATCAGAGTATTCATTGGTGGAAAGATAAACAGAATAGACCATGACCGGAGAGCGATGGCTACTTT
GCTTAGCAAGTTCCGGATAGACTTTTCTGATATCATGGTTCTAGGAGATATCAATACCAAACCAAAGAAAGAAAATA
TTATAGCTTTTGAGGAAATCATTGAGCCATACAGACTTCATGAAGATGATAAAGAGCAAGATATTGCAGATAAAATG
AAAGAAGATGAACCATGGCGAATAACAGATAATGAGCTTGAACTTTATAAGACCAAGACATACCGGCAGATCAGGTT
AAATGAGTTATTAAAGGAACATTCAAGCACAGCTAATATTATTGTCATGAGTCTCCCAGTTGCACGAAAAGGTGCTG
TGTCTAGTGCTCTCTACATGGCATGGTTAGAAGCTCTATCTAAGGACCTACCACCAATCCTCCTAGTTCGTGGAAT
CATCAGAGTGTCCTTACCTTCTATTCATAAATGTTCTATACAGTGGACAGCCCTCCAGAATGGTACTTCAGTGCCTA
GTGTAGTAACCTGAAATCTTCAATGACACATTAACATCACAATGGCGAATGGTGACTTTTCTTTCACGATTTCATTA
ATTTGAAAGCACACAGGAAAGCTTGCTCCATTGATAACGTGTATGGAGACTTCGGTTTTAGTCAATTCC

FIGURE 24B

ATATCTCAATCTTAATGGTGATTCTTCTCTGTTGAACTGAAGTTTGTGAGAGTAGTTTTCCTTTGCTACTTGAATAG
CAATAAAAGCGTGTTAACTTTTTGG

FIGURE 25A

GAGCTTGTCCAGACGAAGCCTCGCAGGGATGGGTTGGAGCCTGGGCCGTGCTTCGCTCAGGCAGCGTTTGAGGCAGA
CCCAGCAGGGTCCTCCTGGGGCCTTCCTGCCTTTGAACTGCGGTGGCGGGCGGGCGCACGGTCTCCTGTACGCCCTA
GACTAGGGGCCGCCATCTCCATGGCCACGGCCGTGAGCCGGCCCTGCGCCGGCAGGTCGCGGGACATACTGTGGCGC
GTTTTGGGCTGGAGGATAGTTGCAAGTATTGTTTGGTCAGTGCTATTTCTACCCATCTGCACCACAGTATTTATAAT
TTTCAGCAGGATTGATTTGTTTCATCCTATACAGTGGCTGTCTGATTCTTTCAGTGACCTGTATAGTTCCTATGTAA
TCTTTTACTTCCTGCTGCTGTCAGTGGTAATAATAATAATAAGTATTTTCAATGTGGAGTTCTATGCAGTTGTGCCT
TCTATTCCTTGCTCCAGACTAGCTCTGATAGGGAAGATCATTCATCCTCAGCAACTCATGCACTCATTTATTCATGC
TGCAATGGGAATGGTGATGGCCTGGTGTGCTGCAGTGATAACCCAGGGCCAGTACAGCTTTCTTGTGGTTCCCTGCA
CTGGTACTAACAGCTTTGGTAGCCCTGCTGCGCAAACCTGCTTAAATGAATATCATCTTTTTTTCCTACTGACTGGA
GCATTTATGGGCTATAGCTATAGCCTCCTGTATTTTGTTAACAACATGAACTATCTTCCATTTCCCATCATACAGCA
ATACAAGTTCTTGCGTTTTAGGAGATCTCTGCTCTTATTAGTTAAACACAGTTGTGTGGAATCACTGTTCCTGGTTA
GAAATTTCTGCATTTTATATTATTTTCTTGGCTATATTCCCAAAGCTTGGATTAGCACTGCTATGAACCTTCACATA
GATGAGCAGGTTCATAGGCCACTTGACACAGTGAGTGGCCTCTTAAATCTCTCGTTACTCTACCATGTCTGGCTGTG
TGGTGTCTTTCTCCTGACGACTTGGTATGTCTCATGGATACTCTTCAAAATCTATGCCACAGAGGCTCATGTGTTTC
CTGTTCAACCACCATTTGCAGAAGGGTCAGATGAGTGCCTTCCAAAAGTGTTAAATAGCAATCCTCCCCCCATCATA
AAGTATTTAGCCTTGCAGGACCTGATGTTGCTTTCTCAATATTCTCCTTCACGAAGACAAGAAGTTTTCAGCCTCAG
CCAACCAGGTGGACATCCCCACAATTGGACAGCCATTTCAAGGGAGTGTTTGAATCTTTTAAATGGTATGACTCAGA
AACTGATTCTCTATCAAGAAGCTGCTGCTACGAATGGGAGAGTGTCTTCATCTTACCCAGTGGAACCTAAGAAATTA
AATTCTCCAGAAGAAACTGCTTTTCAGACACCAAAATCTAGCCAGATGCCTCGGCCTTCAGTGCCACCATTAGTTAA
AACATCACTGTTTTCTTCAAAATTATCTACACCTGATGTTGTGAGCCCATTTGGGACCCCATTTGGCTCTAGTGTAA
TGAATCGGATGGCTGGAATTTTTGATGTAAACACCTGCTATGGGTCACCGCAAAGTCCTCAGCTAATAAGAAGGGGG
CCAAGATTGTGGACATCAGCTTCTGATCAGCAAATGACTGAATTTTCTAATCCTTCTCCATCTACCTCTATTAGTGC
TGAGGGTAAGACAATGAGACAACCCAGTGTGATTTATTCATGGATTCAGAATAAACGTGAACAGATTAAGAATTTCT
TGTCAAAACGGGTGCTGATAATGTATTTTTTCAGTAAGCACCCAGAGGCCTCCATTCAGGCTGTTTTTTCAGATGCC
CAAATGCATATTTGGGCATTAGAAGGTCTGTCGCACTTAGTAGCAGCATCATTTACAGAGGATAGATTTGGAGTTGT
CCAGACGACACTACCAGCTATCCTTAATACTTTGTTGACACTGCAAGAGGCAGTCGACAAGTACTTTAAGCTTCCTC
ATGCTTCCAGTAAACCACCCCGGATTTCAGGAAGCCTTGTGGACACTTCATATAAAACATTAAGATTTGCATTCAGA
GCATCACTGAAAACTGCCATCTATCGAATAACTACTACATTTGGTGAACATCTGAATGCTGTGCAAGCATCTGCAGA
ACATCAGAAAAGACTTCAACAGTTCTTGGAGTTCAAAGAATAGTTAAGTAATATAAACTGTGTTCATTACACTGCTG
ATACAACTACAGATGGGACAGTAAATGTTCAGCATTCTTGGATCAGAAGAAAACGGACTAATTAGATGCTTCCTTTG
TCGTGGTGGTTGCTTTGAAAACTATACTTTAATGGGAGAAATCATGGAAAGAAATTCTCAACAGAATAACTGAAAAC
TGCCTTTTCTGTACCGATTGCTTTTTGTGTGTGTGGTATAATAAAATCTTTATTCAATTTTACAGAAGCATTGATGG
CAGTCGAAATGTCTCTAGCTCATATAACTTAATAGTAATAACTAAAAAACTTTTAGAATTTACTTTTGAAAGGAGGG
AAGCCAGTTCTGAAATGAGTATAGGTTGATTTCATAGTCTTCTTAATTAAGAGTTTAGCTCTTTGTAAACTCAAAAT
ACATAAACTTTTTAAGTGTAGTTTCATTTACTGAAGGATAAAAATGGTAACAGTGCAGCAATATTCACAAAAAATAT
TGTCTAACGGACATATTTTGTTAATCTGTTAGGTTGGGTTTTTGTTTCCAGGGACAAATTAAATTTGTATGATTACC
CAAAAAAGGGTCTCAGTTTACAGATGCTAACTCTATATAAAGGAATGTGGAAAAACTCAGTTCTTAAGTTACAAGAT
TAAAAATTCACATTTGGTCTTTAAGAAACAATTGACTGACATCTATGAATTTATTTTGTATCATGCTAGTAAACACG
AAGTATTAATGTATGGGTATTTTCCCAGCTAGTTTTGCTTTCTTTTTCTGGAGCAAAACATTAAGTGATTGCAGAGT
TTTTCAAGCAAGAGAAAAAGGTTTGCAAAAAAACCCAGGAAATGTTCCCTTTTTTCCCCACCATTCATCTTCATTAG
ATCAAATTCTGTGAAACTTGTCTGGTCTCTCAAAGGGAGCAGCCTCTGTAGTGTTAAATGGCTAATTAAAATAGGAA
GATCTTTATAGCCAGAAACAACTTAGTCATCAAATAGCAAGTGAAACCAAAACGTCAGAGGGATTACTGTACTTGGA
AGTATGTTGTGTGTCCCAAATGTGAACGAAGTATTGTTAGAATTTATTAGATCAGCTTCTTTGGAGATCAAAGATTG
GAAATCCTAGTCATAGATATTCACTGGACTGGCTTTGGACTGAAATGCTCCTTTGTAATTCTTTTCCTATTGTCTTT
TCCTTCTAGTGTCCCAAAATATTTTCTTTAAAGTCAGCACAGTACTGTATATGAATCTTTAATGTGGTATCATATAT
GTCTACTTTTGTCTGATTCATCGATGTATTATATCTTTATAATTGAATATTTTAGCTCCGGGTCCTGTTGCCCCTTC
AAGCAGTACATGCCAAATTATAAATAGGTGCTACTGGCCTTGAGCATATCACTGTGGCACAGTTCCCCAATTGTCAA
GTGTTTAGATATGTAGACTATTGCCATTTGTTTTTTTGTTTTGGTTTTGCTTTGTGTCTGAAGCTGAATTGATTTCT
TTTTTTTGAATGTGAAAGTTGAATTTCAAACGTAGTCATTTCTTACAGATGGCCAAGACAGAAAATTGTGGCTAGGT
TGACTGAGAACTGTTGTCTTCCATGTATTAACACAATTAAGCTTTTTATATTCCACTCTCTGTGCTGACCCTGGCTG
AGGCATTTTGGGAGACAAGGACTCTGAATCTTCTGCTTCCATTAAAGAAGAACTGTGATATTCAACATTGGATTTCT
GAGAATAAAGATAGGATGATTCCTTTGAACTTTGACTTACTTGTATAAAATGTCCAGCTAGGTTAGGTT

FIGURE 25B

TTTGCCATTTCCTATATACTTTGGGTAAAGCTACATTTGATGAGCAATGTGAATGTTTCTGAGAATGTTCATTCCTG
TTTTCTCTTAAGAGAATGTGCTGTGTACTAAATACAGGCCACATAGTGTCTGCCTGTTGAAGATCTGGAAACTGCCT
CCCCAGATCTGTATTGTATTTGGTAGGTAAGGGGGTCAGTTTCTTTTTCTCATTGTGTGTTGATAATCTACACACCA
TCTGTTGGAACCAGGGTGTTATTATGGGGAACTCCTCCTGTGTACTAGGAGGAGGACCTTAGGGAGACCAAGAGGAG
AGAAGCATTTCCTTTGATGAAGTCACATCCTGTCTATGAGCCCACTAATGCTGTAACATTGGCCTGAAAGAGAGTGT
TCTTTAAAAGCCTTTCTCGGCTGTTAGTATAAAAACATGATGGTATCAGCTCTTAGCATGTTTGCTTGACCCTTATG
GAAGGTATAAATCCACAGAACTTCCTTCCCAGAGAACTGGGAAATTGTCCTAGAAATAAACCTTGTACAGTTGAGTG
GACATGGATAAGCAACAATTTGTTACTTTGCAGGATTTGTTCCTTGGTAATTGTTTGGTGTGTCATCCTGTAAATAT
TCATGATAGTCTGTTTATATCCTTTTGTATATCGTTGATACTGGATTGGGTAGAAAAATAAATTGGCAATTTAAAAA
AATGGAACAGTTAATTGAAA

FIGURE 26A

GATGGGGGCCCCGTTTGTCTGGGCCTTGGGCCTTTTGATGCTGCAGATGCTGCTCTTTGTGGCTGGGGAACAGGGCA
CACAGGATATCACCGATGCCAGCGAAAGGGGGCTCCACATGCAGAAGCTGGGGTCTGGGTCAGTGCAGGCTGCGCTG
GCGGAGCTGGTGGCCCTGCCCTGTCTCTTTACCCTGCAGCCACGGCCAAGCGCAGCCCGAGATGCCCCTCGGATAAA
GTGGACCAAGGTGCGGACTGCGTCGGGCCAGCGACAGGACTTGCCCATCCTGGTGGCCAAGGACAATGTCGTGAGGG
TGGCCAAAAGCTGGCAGGGACGAGTGTCACTGCCTTCCTACCCCCGGCGCCGAGCCAACGCCACGCTACTTCTGGGG
CCACTGAGGGCCAGTGACTCTGGGCTGTACCGCTGCCAGGTGGTGAGGGGCATCGAGGATGAGCAGGACCTGGTGCC
CTTGGAGGTGACAGGTGTTGTGTTCCACTACCGATCAGCCCGGGACCGCTATGCACTGACCTTCGCTGAGGCCCAGG
AGGCCTGCCGTCTCAGCTCAGCCATCATTGCAGCCCCTCGGCATCTACAGGCTGCCTTTGAGGATGGCTTTGACAAC
TGTGATGCTGGCTGGCTCTCTGACCGCACTGTTCGGTATCCTATCACCCAGTCCCGTCCTGGTTGCTATGGCGACCG
TAGCAGCCTTCCAGGGGTTCGGAGCTATGGAGGCGCAACCCACAGGAACTCTACGATGTGTATTGCTTTGCCCGGG
AGCTGGGGGGCGAGGTCTTCTACGTGGGCCCGGCCCGCCGCCTGACACTGGCCGGCGCGCGTGCACAGTGCCGCCGC
CAGGGTGCCGCGCTGGCCTCGGTGGGACAGCTGCACCTGGCCTGGCATGAGGGCCTGGACCAGTGCGACCCGGGCTG
GCTGGCCGACGGCAGCGTGCGCTACCCGATCCAGACGCCGCGCCGGCGCTGCGGGGGCCCAGCCCCGGGCGTGCGCA
CCGTCTACCGCTTCGCTAACCGGACCGGCTTCCCCTCACCCGCCGAGCGCTTCGACGCCTACTGCTTCCGAGCTCAT
CACCCCACGTCACAACATGGAGACCTAGAGACCCCATCCTCTGGGGATGAGGGGGAGATTCTGTCAGCAGAGGGGCC
CCCAGTTAGAGAACTGGAGCCCACCCTGGAGGAGGAAGAGGTGGTCACCCCTGACTTCCAGGAGCCTCTGGTGTCCA
GTGGGAAGAAGAAACCCTGATTTTGGAGGAGAAGCAGGAGTCTCAACAGACCCTCAGCCCTACCCCTGGGACCCC
ATGCTGGCCTCATGGCCCACTGGGGAAGTGTGGCTAAGCACGGTGGCCCCCAGCCCTAGCGACATGGGGGCAGGCAC
TGCAGCAAGTTCACACACGGAGGTGGCCCCAACTGACCCTATGCCTAGGAGAAGGGGGCGCTTCAAAGGGTTGAATG
GGCGCTACTTCCAGCAGCAGGAACCGGAGCCGGGGCTGCAAGGGGGGATGGAGGCCAGCGCCCAGCCCCCCACCTCA
GAGGCTGCAGTGAACCAAATGGAGCCTCCGTTGGCCATGGCAGTCACAGAGATGTTGGGCAGTGGCCAGAGCCGGAG
CCCCTGGGCTGATCTGACCAATGAGGTGGATATGCCTGGAGCTGGTTCTGCTGGTGGCAAGAGCTCCCCAGAGCCCT
GGCTGTGGCCCCCTACCATGGTCCCACCCAGCATCTCAGGCCACAGCAGGGCCCCTGTCCTGGAGCTAGAGAAAGCC
GAGGGCCCCAGTGCCAGGCCAGCCACCCCAGACCTGTTTTGGTCCCCCTTGGAGGCCACTGTCTCAGCTCCCAGCCC
TGCCCCCTGGGAGGCATTCCCTGTGGCCACCTCCCCAGATCTCCCTATGATGGCCATGCTGCGTGGTCCCAAAGAGT
GGATGCTACCACACCCCACCCCCATCTCCACCGAGGCCAATAGAGTTGAGGCACATGGTGAGGCCACCGCCACGGCT
CCACCCTCCCCTGCTGCAGAGACCAAGGTGTATTCCCTGCCTCTCTCTTTGACCCCAACAGGACAGGGTGGAGAGGC
CATGCCCACAACACCTGAGTCCCCCAGGGCAGACTTCAGAGAAACTGGGGAGACCAGCCCTGCTCAGGTCAACAAAG
CTGAGCACTCCAGCTCCAGCCCATGGCCTTCTGTAAACAGGAATGTGGCTGTAGGTTTTGTCCCCACTGAGACTGCC
ACTGAGCCAACGGGCCTCAGGGGTATCCCGGGGTCTGAGTCTGGGGTCTTCGACACAGCAGAAAGCCCCACTTCTGG
CTTGCAGGCCACTGTAGATGAGGTGCAGGACCCCTGGCCCTCAGTGTACAGCAAAGGGCTGGATGCAAGTTCCCCAT
CTGCCCCCCTGGGGAGCCCTGGAGTCTTCTTGGTACCCAAAGTCACCCCAAATTTGGAGCCTTGGGTTGCTACAGAT
GAAGGACCCACTGTGAATCCCATGGATTCCACAGTCACGCCGGCCCCCAGTGATGCTAGTGGAATTTGGGAACCTGG
ATCCCAGGTGTTTGAAGAAGCCGAAAGCACCACCTTGAGCCCTCAGGTGGCCCTGGATACAAGCATTGTGACGCCCC
TCACGACCCTGGAGCAGGGGGACAAGGTTGGAGTTCCAGCCATGTCTACACTGGGCTCCTCAAGCTCCCAACCCCAC
CCAGAGCCAGAGGATCAGGTGGAGACCCAGGGAACATCAGGAGCTTCAGTGCCTCCGCATCAGAGCAGTCCCCTAGG
GAAACCGGCTGTTCCTCCTGGGACACCGACTGCAGCCAGTGTGGGCGAGTCTGCCTCAGTTTCCTCAGGGGAGCCTA
CGGTACCGTGGGACCCCTCCAGCACCCTGCTGCCTGTCACCCTGGGCATAGAGGACTTCGAACTGGAGGTCCTGGCA
GGGAGCCCGGGTGTAGAGAGCTTCTGGGAGGAGGTGGCAAGTGGAGAGGAGCCAGCCCTGCCAGGGACCCCTATGAA
TGCAGGTGCGGAGGAGGTGCACTCAGATCCCTGTGAGAACAACCCTTGTCTTCATGGAGGGACATGTAATGCCAATG
GCACCATGTATGGCTGTAGCTGTGATCAGGGCTTCGCCGGGGAGAACTGTGAGATTGACATTGATGACTGCCTCTGC
AGCCCCTGTGAGAATGGAGGCACCTGTATTGATGAGGTCAATGGCTTTGTCTGCCTTTGCCTCCCCAGCTATGGGGG
CAGCTTTTGTGAGAAAGACACCGAGGGCTGTGACCGCGGCTGGCATAAGTTCCAGGGCCACTGTTACCGCTATTTTG
CCCACCGGAGGGCATGGGAAGATGCCGAGAAGGACTGCCGCCGCCGCTCCGGCCACCTGACCAGCGTCCACTCACCG
GAGGAACACAGCTTCATTAATAGCTTTGGGCATGAAAACACGTGGATCGGCCTGAACGACAGGATCGTGGAGAGAGA
TTTCCAGTGGACGGACAACACCGGGCTGCAATTTGAGAACTGGCGAGAGAACCAGCCGGACAATTTCTTCGCGGGTG
GCGAGGACTGTGTGGTGATGGTGGCGCATGAAAGCGGGCGCTGGAACGATGTCCCCTGCAACTACAACCTACCCTAT
GTCTGCAAGAAGGGCACAGTGCTCTGTGGTCCCCCTCCGGCAGTGGAGAATGCCTCACTCATCGGTGCCCGCAAGGC
CAAGAACAATGTCCATGCCACTGTAAGGTACCAGTGCAATGAAGGATTTGCCCAGCACCATGTGGTCACCATTCGAT
GCCGGAGCAATGGCAAGTGGGACAGGCCCCAAATTGTCTGCACCAAACCCAGACGTTCACATCGGATGCGGGACAC
CACCACCACCACCAACACCACCACCAGCATCACCACCACAAATCCCGCAAGGAGCGCAGAAAACACAAGAAACACCC
AACGGAGGACTGGAGAAGGACGAAGGGAATTTTTGCTGAAGAACCAGAAAAAGAAAGCACAACACCT

FIGURE 26B

TTCCCATGCCTCCTCTGGAGCCTTCGCCTGGGGAGACAGAACCCAGAGAGAAACAAGAGAGTCCAGAAGTCCCTGAA
CCCCAAACTGTTCTCGCAAAAAAAATATTCCTTTGAACAAAGGTCTTCTTTTCCTTTTTTTACATACACAAGATCTT
CTTGGCAGGTGGAGCCAGGTGTCTGAAAAGTTCATTCTCGTCTGGCTGAACTCTGGGAGTGTGTCCCAGCTGAGGGA
AGCACAAGTAGCAAAGCTCATTGGTCTGGTCTCTTGTTTGCCAGGCTGATTGAAGCAGGCCTTGATGAGGGTGCATG
AGTGTATGTTTGCATTCACATGAAGGAATTGCTTTTCACACCAGAAATTCAGACTTAGTCAATGTTGGCTGAATTCC
TAAATCCAGGAAGAAGCCTGGACGTAGGGTCATTAGCTTTGGGAATAGAAGGCTACACAGAAGCACACTGTTTTTGA
ACTTGACAACAGCTCTCCCTTTACCCTGGACTTCAGCCCAAGTTCCGTCTTTGGTCTTGGTGGATAAACACACAGTG
TGGAGATCCCACGTACTGCATTTTAGGGATGTTTTTAGGACAACCTCCCTCCATGCCTTCAGAGTTAGGAGTGAGAA
TGATCAAAGCAATATGTAGGTGATGGAGGGAGAGTGTATTGCTAACCCTTCCAGGTCTAGTCCAGCGCTGAGATTTG
GTGGTTCTGCATGTGTGATGAATCTCTTTCACACAAATAGACGAGAGGATATTTAGGGCTAGATGAGCCCAGATTTC
TTCCCCCTCCATCTCTCAGGGAGACAAAGAACCTCCTTCCTGGACCAAGGAGGTGCTGCCAAGTTTTCTAGCCCAGT
GCACATACCCAGTCCTTAAGCAGACATTGGTAGTGCCCCTGCCCTGGGTCCCACTCCTGCCCCACCCCACCCTTGTC
CCTGGCCATTGCCTGGTGGTCTAGAAACACTTAAAACTTGAAGTAGTGACACCTACCTGCGGTCATATTGTAGAGAG
ATGCTCAGTGTTAAAACTGAAACACACAAACACACACACACACACATTTTTCTCTTGTAGATTTTAATTTTTTAAGT
GGGAAAGAACTCACCTTGCCTTCCTCCCCCAAATGTGCAACCTGTAAAAGGTCTCTCCACACCAGGGGCCAGGATCC
AGTTCCCTCATCTCTGGCAGGAAAGATCCACAGCTTTTCCTCCATGTCTGTTACTCACTTTCAGCAGTCCGGGTAAA
ATCTGTGGATCAGGGTTAAAAAAGCACCGTGGAGAATGGCCCTCTTCAGGAAAGAAAAATAAGCAAATGAATGGTCC
ACCTAGGGGTTCAGTAAAGAAAGAAATGTGTTAACTGAGCCTGAATCCCTTCTGGGAAGTAATAATGACCATTGACA
ACTAAGAAGTAGACACCATGCTAAAGACTTACATACAATCTCCTTGAATCTTCTCAATAGCCCATTGACTTAGAAAC
TGTTACTTTCCCATTTTACACACAGTGAAACTGAGGCTCAGATATAAAGGAAAGGTACTGGCTTGAAGTCACAACCA
CGACAGGAGTAAGGATTTGGAATAAGGATTTGGTCCTGTTTTCTGGACCAAATCCTTACTCTGGCTCTGCTTACACT
TTCTCTCCATCACCAAATCCTTACTCCAAATCCAGAAGTCAGAGCCAACTCCCATCTTGGTTCTGACCCAAATCCTG
CTCTGGACTCTGGAGAGGAGATTGAAATATAATTGCACCCTCATACACATTTAGGAAATGGTTAAGAAGTGTAAACT
GAACCCTTATCCTTGTCTTCAATCTTCCTCCCTGTAGACATCTATCTTATTATGGTTATTATTCAGAAAACCCAGGG
ATACAGGTTTGTCTTCTTACTTTGATAACTCTTCTTAGTTTAAAATAATAATAATAACACATCTTTGGTCATCTATG
TCACACAAAAATTTTCCTTTGTTTGCGGGGGGCTGGGGATGCAGTGTTTTTTGGGGGGTCTTGGTTTATGCTCCCTG
CCCTTGAGCCCCTCAGCCGTTTGCCCTGCCCCCACCTCGGCTCCATGGTGGGAGGGGGCTCTGGTCTTTTCTAAAGT
GGGCGGTTTGTCTTTTGATCTTTCCCTTTTGGATGTGCGTGTGTGTCTGCGTGTGCCATGTGCGTGGCACGCATATG
AGTGTGTGTGCGTGTGAACGGCTTTGGGTCCTGCTGGTTTTGCTGTGAGCTGCAGTGTTCTGTGGGTCTGTGGTATC
TGACACTGTGGACATTAATGTACTTCTTGGACATTTTAATAAATTTTTTAACAGTTCAAAAAAAAAAAAAAAAAAAA
AAAA

FIGURE 27A

ACTAGAGATGGCGGGCGGGCTGCTCTGAAGAGACCTCGGCGGCGGCGGAGGAGGAGAGAAGCGCAGCGCCGCGCCGC
GCCGGGGCCCATGTGGGGAGGAGTCGGAGTCGCTGTTGCCGCCGCCGCCTGTAGCTGCTGGACCCGAGTGGGAGTGA
GGGGGAAACGGCAGGATGAAGTTCGCCGAGCACCTCTCCGCGCACATCACTCCCGAGTGGAGGAAGCAATACATCCA
GTATGAGGCTTTCAAGGATATGCTGTATTCAGCTCAGGACCAGGCACCTTCTGTGGAAGTTACAGATGAGGACACAG
TAAAGAGGTATTTTGCCAAGTTTGAAGAGAAGTTTTTCCAAACCTGTGAAAAAGAACTTGCCAAAATCAACACATTT
TATTCAGAGAAGCTCGCAGAGGCTCAGCGCAGGTTTGCTACACTTCAGAATGAGCTTCAGTCATCACTGGATGCACA
GAAAGAAAGCACTGGTGTTACTACGCTGCGACAACGCAGAAAGCCAGTCTTCCACTTGTCCCATGAGGAACGTGTCC
AACATAGAAATATTAAAGACCTTAAACTGGCCTTCAGTGAGTTCTACCTCAGTCTAATCCTGCTGCAGAACTATCAG
AATCTGAATTTTACAGGGTTTCGAAAAATCCTGAAAAAGCATGACAAGATCCTGGAAACATCTCGTGGAGCAGATTG
GCGAGTGGCTCACGTAGAGGTGGCCCCATTTTATACATGCAAGAAAATCAACCAGCTTATCTCTGAAACTGAGGCTG
TAGTGACCAATGAACTTGAAGATGGTGACAGACAAAAGGCTATGAAGCGTTTACGTGTCCCCCCTTTGGGAGCTGCT
CAGCCTGCACCAGCATGGACTACTTTTAGAGTTGGCCTATTTTGTGGAATATTCATTGTACTGAATATTACCCTTGT
GCTTGCCGCTGTATTTAAACTTGAAACAGATAGAAGTATATGGCCCTTGATAAGAATCTATCGGGGTGGCTTTCTTC
TGATTGAATTCCTTTTTCTACTGGGCATCAACACGTATGGTTGGAGACAGGCTGGAGTAAACCATGTACTCATCTTT
GAACTTAATCCGAGAAGCAATTTGTCTCATCAACATCTCTTTGAGATTGCTGGATTCCTCGGGATATTGTGGTGCCT
GAGCCTTCTGGCATGCTTCTTTGCTCCAATTAGTGTCATCCCCACATATGTGTATCCACTTGCCCTTTATGGATTTA
TGGTTTTCTTCCTTATCAACCCCACCAAAACTTTCTACTATAAATCCCGGTTTTGGCTGCTTAAACTGCTGTTTCGA
GTATTTACAGCCCCCTTCCATAAGGTAGGCTTTGCTGATTTCTGGCTGGCGGATCAGCTGAACAGCCTGTCAGTGAT
ACTGATGGACCTGGAATATATGATCTGCTTCTACAGTTTGGAGCTCAAATGGGATGAAAGTAAGGGCCTGTTGCCAA
ATAATTCAGAAGAATCAGGAATTTGCCACAAATATACATATGGTGTGCGGGCCATTGTTCAGTGCATTCCTGCTTGG
CTTCGCTTCATCCAGTGCCTGCGCCGATATCGAGACACAAAAAGGGCCTTTCCTCATTTAGTTAATGCTGGCAAGTA
CTCCACAACTTTCTTCATGGTGGCGTTTGCAGCCCTTTACAGCACTCACAAAGAACGAGGTCACTCGGACACTATGG
TGTTCTTTTACCTGTGGATTGTCTTTTATATCATCAGTTCCTGCTATACCCTCATCTGGGATCTCAAGATGGACTGG
GGTCTCTTCGATAAGAATGCTGGAGAGAACACTTTCCTCCGGGAAGAGATTGTATACCCCCAAAAAGCCTACTACTA
CTGTGCCATAATAGAGGATGTGATTCTGCGCTTTGCTTGGACTATCCAAATCTCGATTACCTCTACAACTTTGTTGC
CTCATTCTGGGGACATCATTGCTACTGTCTTTGCCCCACTTGAGGTTTTCCGGCGATTTGTGTGGAACTTCTTCCGC
CTGGAGAATGAACATCTGAATAACTGTGGTGAATTCCGTGCTGTGCGGGACATCTCTGTGGCCCCCCTGAACGCAGA
TGATCAGACTCTCCTAGAACAGATGATGGACCAGGATGATGGGGTACGAAACCGCCAGAAGAATCGGTCATGGAAGT
ACAACCAGAGCATATCCCTGCGCCGGCCTCGCCTCGCTTCTCAATCCAAGGCTCGTGACACTAAGGTATTGATAGAA
GACACAGATGATGAAGCTAACACTTGAATTTTCTGAAGTCTAGCTTAACATCTTTGGTTTTCCTACTCTACAATCCT
TTCCTCGACCAACGCAACCTCTAGTACCTTTCCAGCCGAAAACAGGAGAAAACACATAACACATTTTCCGAGCTCTT
CCGGATCGGATCCTATGGACTCCAAACAAGCTCACTGTGTTTCTTTTCTTTTCTTCTGGTTTAATTTTAATTTTCTA
TTTTCAAAACAAGTATTTACTTCATTTGCCAATCAGAGGATGTTTTAAGAAACAAAACATAGTATCTTATGGATTGT
TTACAATCACAAGGACATAGATACCTATCAGGATGAAGAACAGGCATTGCAAGGACCCTCTGATGGGACGGTACTGA
GATATCTCGGCTTCCGCTCAGCCCGGTTTTGAATGGTTGAAACCGGACATTGGTTTTTAAATTTTTTGTCAGTTTAT
GTGGAGAATTTTTTTCTTTCCTTCATACCCAGCGCAAAGGCACTGGCCGCACTTGCAGGAAAAGTGCAACTTAAAGC
AGTACCTTCATTCATGAAGCTACTTTTTAATTTGATGTAACTTTTCTTATTTGGGAAGGGTTGCTGGTGGGTGGG
AAATATGATGTATTTGTTACACATAGTTTTCTCATTATTTATGAAACTTAACCATACAGAATGATATAACTCCTGTG
CAATGAAGGTGATAACAGTAAAACTGATATAACTCCTGTGCAATGAAGGTGATAACAGTAAAAGAAGGCAGGGGAAA
CTTACGTTGGATGACATTTATGAGGGTCAGTCCCACATACCTCTTTCAGGAGACAACTTGCACCAGTTTGACCTTTT
CTTTTCTTTGTTTTTATTTTAAGCCAAAGTTTCATTGCTAACTTCTTAAGTTGCTGCTGCTTTAGAGTCCTGAGCAT
ATCTCTCATAACAAGGAATCCCACACTTCACACCACCGGCTGAATTTCATGGAAGAGGTTCTGATAATTTTTTTAAC
TTTTTAAGGAACAGATGTGGAATACACTGGCCCATATTTCAACCTTAACAGCTGAAGCTATGCCTTATTATGCATCC
ACATGTATGGTCCCTGTAGCGTGACCTTTACTAGCTCTGAATCAGAAGACAGAGCTATTTCAGAGGCTCTGTGTGCC
CTCACTAGATAGTTTTTCTTCTGGGTTCAACCACTTTAGCCAGAATTTGATCAAATTAAAAGTCTGTCATGGGGAAA
CTATATTTTTGAGCACATGGAACAAATTATACTTCCTCATTCATATTATGTTGATACAAAAGACCTTGGCAGCCATT
TCTCCCAGCAGTTTTAAAGGATGAACATTGGATTTCATGCCATCCCATAGAAAACCTGTTTTAAAATTTTAGGGATC
TTTACTTGGTCATACATGAAAAGTACACTGCTTAGAAATTATAGACTATTATGATCTGTCCACAGTGCCCATTGTCA
CTTCTTTGTCTCATTTCTTCCCTTTGTTCCTTAGTCATCCAAATAAGCCTGAAAACCATAAGAGATATTACTTTATT
GAATATGGTTGGCATTAAATTTAGCATTTCATTATCTAACAAAATTAATATAAATTCCAGGACATGGTAAAATGTGT
TTTAATAACCCCCAGACCCAAATGAAAATTTCAAAGTCAATACCAGCAGATTCATGAAAGTAAATTTAGTCCTATAA
TTTTCAGCTTAATTATAAACAAAGGAACAAATAAGTGGAAGGGCAGCTATTACCATTCGCTTAGTCAAA

FIGURE 27B

ACATTCGGTTACTGCCCTTTAATACACTCCTATCATCAGCACTTCCACCATGTATTACAAGTCTTGACCCATCCCTG
TCGTAACTCCAGTAAAAGTTACTGTTACTAGAAAATTTTTATCAATTAACTGACAAATAGTTTCTTTTTAAAGTAGT
TTCTTCCATCTTTATTCTGACTAGCTTCCAAAATGTGTTCCCTTTTTGAATCGAGGTTTTTTTGTTTTGTTTTGTTT
TCTGAAAAAATCATACAACTTTGTGCTTCTATTGCTTTTTTGTGTTTTGTTAAGCATGTCCCTTGGCCCAAATGGAA
GAGGAAATGTTTAATTAATGCTTTTTAGTTTAAATAAATTGAATCATTTATAATAATCAGTGTTAACAATTTAGTGA
CCCTTGGTAGGTTAAAGGTTGCATTATTTATACTTGAGATTTTTTTCCCCTAACTATTCTGTTTTTTGTACTTTAAA
ACTATGGGGGAAATATCACTGGTCTGTCAAGAAACAGCAGTAATTATTACTGAGTTAAATTGAAAAGTCCAGTGGAC
CAGGCATTTCTTATATAAATAAAATTGGTGGTACTAATGTGT

FIGURE 28

CCCTTGCTGGACCCGAGTGGGAGTGAGGGGGAAACGGCAGGATGAAGTTCGCCGAGCACCTCTCCGCGCACATCACT
CCCGAGTGGAGGAAGCAATACATCCAGTATGAGGCTTTCAAGGATATGCTGTATTCAGCTCAGGACCAGGCACCTTC
TGTGGAAGTTACAGATGAGGACACAGTAAAGAGGTATTTTGCCAAGTTTGAAGAGAAGTTTTTCCAAACCTGTGAAA
AAGAACTTGCCAAAATCAACACATTTTATTCAGAGAAGCTCGCAGAGGCTCAGCGCAGGTTTGCTACACTTCAGAAT
GAGCTTCAGTCATCACTGGATGCACAGAAAGAAAGCACTGGTGTTACTACGCTGCGACAACGCAGAAAGCCAGTCTT
CCACTTGTCCCATGAGGAACGTGTCCAACATAGAAATATTAAAGACCTTAAACTGGCCTTCAGTGAGTTCTACCTCA
GTCTAATCCTGCTGCAGAACTATCAGAATCTGAATTTTACAGGGTTTCGAAAAATCCTGAAAAAGCATGACAAGATC
CTGGAAACATCTCGTGGAGCAGATTGGCGAGTGGCTCACGTAGAGGTGGCCCCATTTTATACATGCAAGAAAATCAA
CCAGCTTATCTCTGAAACTGAGGCTGTAGTGACCAATGAACTTGAAGATGGTGACAGACAAAAGGCTATGAAGCGTT
TACGTGTCCCCCCTTTGGGAGCTGCTCAGCCTGCACCAGCATGGACTACTTTTAGAGTTGGCCTATTTTGTGGAATA
TTCATTGTACTGAATATTACCCTTGTGCTTGCCGCTGTATTTAAACTTGAAACAGATAGAAGTATATGGCCCTTGAT
AAGAATCTATCGGGGTGGCTTTCTTCTGATTGAATTCCTTTTTCTACTGGGCATCAACACGTATGGTTGGAGACAGG
CTGGAGTAAACCATGTACTCATCTTTGAACTTAATCCGAGAAGCAATTTGTCTCATCAACATCTCTTTGAGATTGCT
GGATTCCTCGGGATATTGTGGTGCCTGAGCCTTCTGGCATGCTTCTTTGCTCCAATTAGTGTCATCCCCACATATGT
GTATCCACTTGCCCTTTATGGATTTATGGTTTTCTTCCTTATCAACCCCACCAAAACTTTCTACTATAAATCCCGGT
TTTGGCTGCTTAAACTGCTGTTTCGAGTATTTACAGCCCCCTTCCATAAGGTAGGCTTTGCTGATTTCTGGCTGGCG
GATCAGCTGAACAGCCTGTCAGTGATACTGATGGACCTGGAATATATGATCTGCTTCTACAGTTTGGAGCTCAAATG
GGATGAAAGTAAGGGCCTGTTGCCAAATAATTCAGAAGAATCAGGAATTTGCCACAAATATACATATGGTGTGCGGG
CCATTGTTCAGTGCATTCCTGCTTGGCTTCGCTTCATCCAGTGCCTGCGCCGATATCGAGACACAAAAAGGGCCTTT
CCTCATTTAGTTAATGCTGGCAAATACTCCACAACTTTCTTCATGGTGACGTTTGCAGCCCTTTACAGCACTCACAA
AGAACGAGGTCACTCGGACACTATGGTGTTCTTTTACCTGTGGATTGTCTTTTATATCATCAGTTCCTGCTATACCC
TCATCTGGGATCTCAAGATGGACTGGGGTCTCTTCGATAAGAATGCTGGAGAGAACACTTTCCTCCGGGAAGAGATT
GTATACCCCCAAAAAGCCTACTACTACTGTGCCATAATAGAGGATGTGATTCTGCGCTTTGCTTGGACTATCCAAAT
CTCGATTACCTCTACAACTTTGTTGCCTCATTCTGGGGACATCATTGCTACTGTCTTTGCCCCACTTGAGGTTTTCC
GGCGATTTGTGTGGAACTTCTTCCGCCTGGAGAATGAACATCTGAATAACTGTGGTGAATTCCGTGCTGTGCGGGAC
ATCTCTGTGGCCCCCCTGAACGCAGATGATCAGACTCTCCTAGAACAGATGATGGACCAGGATGATGGGGTACGAAA
CCGCCAGAAGAATCGGTCATGGAAGTACAACCAGAGCATATCCCTGCGCCGGCCTCGCCTCGCTTCTCAATCCAAGG
CTCGTGACACTAAGGTATTGATAGAAGACACAGATGATGAAGCTAACACTTGAATTTTCTGAAGTCTAGCTTAACAT
CTTTGGTTTTCCTACTCTACAATCCTTTCCTCGACCAACGCAAGGGC

FIGURE 29

GCGCCCTAGCCCTCTTTCGGGGATACTGGCCGACCCCCTCTTCCTTTTCCCCTTTAGTGAAGGCCTCCCCCGTCGCC
GCGCGGCTTCCCGGAGCCGACTGCAGACTCCCTCAGCCCGGTGTTCCCCGCGTCCGGACGCCGAGGTCGCGGCTTCG
CAGAAACTCGGGCCCCTCCATCCGCCCTCAGAAAAGGGAGCGATGTTGATCTCAGGAAGCACAAAGGGACCTTCCTA
GCTCTGACTGAACCACGGAGCTCACCCTGGACAGTATCACTCCGTGGAGGAAGACTGTGAGACTGTGGCTGGAAGCC
AGATTGTAGCCACACATCCGCCCCTGCCCTACCCCAGAGCCCTGGAGCAGCAACTGGCTGCAGATCACAGACACAGT
GAGGATATGAGTGTAGGGGTGAGCACCTCAGCCCCTCTTTCCCCAACCTCGGGCACAAGCGTGGGCATGTCTACCTT
CTCCATCATGGACTATGTGGTGTTCGTCCTGCTGCTGGTTCTCTCTCTTGCCATTGGGCTCTACCATGCTTGTCGTG
GCTGGGGCCGGCATACTGTTGGTGAGCTGCTGATGGCGGACCGCAAAATGGGCTGCCTTCCGGTGGCACTGTCCCTG
CTGGCCACCTTCCAGTCAGCCGTGGCCATCCTGGGTGTGCCGTCAGAGATCTACCGATTTGGGACCCAATATTGGTT
CCTGGGCTGCTGCTACTTTCTGGGGCTGCTGATACCTGCACACATCTTCATCCCCGTTTTCTACCGCCTGCATCTCA
CCAGTGCCTATGAGTACCTGGAGCTTCGATTCAATAAAACTGTGCGAGTGTGTGGAACTGTGACCTTCATCTTTCAG
ATGGTGATCTACATGGGAGTTGTGCTCTATGCTCCGTCATTGGCTCTCAATGCAGTGACTGGCTTTGATCTGTGGCCT
GTCCGTGCTGGCCCTGGGCATTGTCTGTACCGTCTATACAGCTCTGGGTGGGCTGAAGGCCGTCATCTGGACAGATG
TGTTCCAGACACTGGTCATGTTCCTCGGGCAGCTGGCAGTTATCATCGTGGGGTCAGCCAAGGTGGGCGGCTTGGGG
CGTGTGTGGGCCGTGGCTTCCCAGCACGGCCGCATCTCTGGGTTTGAGCTGGATCCAGACCCCTTTGTGCGGCACAC
CTTCTGGACCTTGGCCTTCGGGGGTGTCTTCATGATGCTCTCCTTATACGGGGTGAACCAGGCTCAGGTGCAGCGGT
ACCTCAGTTCCCGCACGGAGAAGGCTGCTGTGCTCTCCTGTTATGCAGTGTTCCCCTTCCAGCAGGTGTCCCTCTGC
GTGGGCTGCCTCATTGGCCTGGTCATGTTCGCGTATTACCAGGAGTATCCCATGAGCATTCAGCAGGCTCAGGCAGC
CCCAGACCAGTTCGTCCTGTACTTTGTGATGGATCTCCTGAAGGGCCTGCCAGGCCTGCCAGGGCTCTTCATTGCCT
GCCTCTTCAGCGGCTCTCTCAGCACTATATCCTCTGCTTTTAATTCATTGGCAACTGTTACGATGGAAGACCTGATT
CGACCTTGGTTCCCTGAGTTCTCTGAAGCCCGGGCCATCATGCTTTCCAGAGGCCTTGCCTTTGGCTATGGGCTGCT
TTGTCTAGGAATGGCCTATATTTCCTCCCAGATGGGACCTGTGCTGCAGGCAGCAATCAGCATCTTTGGCATGGTTG
GGGGACCGCTGCTGGGACTCTTCTGCCTTGGAATGTTCTTTCCATGTGCTAACCCTCCTGGTGCTGTTGTGGGCCTG
TTGGCTGGGCTCGTCATGGCCTTCTGGATTGGCATCGGGAGCATCGTGACCAGCATGGGCTTCAGCATGCCACCCTC
TCCCTCTAATGGGTCCAGCTTCTCCCTGCCCACCAATCTAACCGTTGCCACTGTGACCACACTGATGCCCTTGACTA
CCTTCTCCAAGCCCACAGGGCTGCAGCGGTTCTATTCCTTGTCTTACTTATGGTACAGTGCTCACAACTCCACCACA
GTGATTGTGGTGGGCCTGATTGTCAGTCTACTCACTGGGAGAATGCGAGGCCGGTCCCTGAACCCTGCAACCATTTA
CCCAGTGTTGCCAAAGCTCCTGTCCCTCCTTCCGTTGTCCTGTCAGAAGCGGCTCCACTGCAGGAGCTACGGCCAGG
ACCACCTCGACACTGGCCTGTTTCCTGAGAAGCCGAGGAATGGTGTGCTGGGGGACAGCAGAGACAAGGAGGCCATG
GCCCTGGATGGCACAGCCTATCAGGGGAGCAGCTCCACCTGCATCCTCCAGGAGACCTCCCTGTGATGTTGACTCAG
GACCCCGCCTCTGTCCTCACTGTGCCAGGCCATAGCCAGAGGCCACCCTGTAGTACAGGGATGAGTCTTGGTGTGTT
CTGCAGGGACAGGCCTGGATGATCTAGCTCATACCAAAGGACCTTGTTCTGAGAGGTTCTTGCCTGCAGGAGAAGCT
GTCACATCTCAAGCATGTGAGGCACCGTTTTTCTCGTCGCTTGCCAATCTGTTTTTTAAAGGATCAGGCTCGTAGGG
AGCAGGATCATGCCAGAAATAGGGATGGAAGTGCATCCTCTGGGAAAAAGATAATGGCTTCTGATTCAACATAGCCA
TAGTCCTTTGAAGTAAGTGGCTAGAAACAGCACTCTGGTTATAATTGCCCCAGGGCCTGATTCAGGACTGACTCTCC
ACCATAAAACTGGAAGCTGCTTCCCCTGTAGTCCCCATTTCAGTACCAGTTCTGCCAGCCACAGTGAGCCCCTATTA
TTACTTTCAGATTGTCTGTGACACTCAAGCCCCTCTCATTTTTATCTGTCTACCTCCATTCTGAAGAGGGAGGTTTT
GGTGTCCCTGGTCCTCTGGGAATAGAAGATCCATTTGTCTTTGTGTAGAGCAAGCACGTTTTCCACCTCACTGTCTC
CATCCTCCACCTCTGAGATGGACACTTAAGAGACGGGGCAAATGTGGATCCAAGAAACCAGGGCCATGACCAGGTCC
ACTGTGGAGCAGCCATCTATCTACCTGACTCCTGAGCCAGGCTGCCGTGGTGTCATTTCTGTCATCCGTGCTCTGTT
TCCTTTTGGAGTTTCTTCTCCACATTATCTTTGTTCCTGGGGAATAAAAACTACCATTGGACCTAAAAAAAAAAAAA
AAAAA

FIGURE 30

GCGGGCGCCCAGTGCACCGGAGGAGGTGAGCGCCAGGTCGCCTTCGCGGCCCGGGGACACAGGCAGGGACGCGGGAG
CTGATGCGGCTGGACCGGCCGGGGAAACAGTATTTTCTGGAAGGGGGCCCCTCTGAAGCGGTCCAGGATCCTGCACA
TGGCGCTGACCGGGGCCTCAGACCCCTCTGCAGAGGCAGAGGCCAACGGGGAGAAGCCCTTTCTGCTGCGGGCATTG
CAGATCGCGCTGGTGGTCTCCCTCTACTGGGTCACCTCCATCTCCATGGTGTTCCTTAATAAGTACCTGCTGGACAG
CCCCTCCCTGCGGCTGGACACCCCCATCTTCGTCACCTTCTACCAGTGCCTGGTGACCACGCTGCTGTGCAAAGGCC
TCAGCGCTCTGGCCGCCTGCTGCCCTGGTGCCGTGGACTTCCCCAGCTTGCGCCTGGACCTCAGGGTGGCCCGCAGC
GTCCTGCCCCTGTCGGTGGTCTTCATCGGCATGATCACCTTCAATAACCTCTGCCTCAAGTACGTCGGTGTGGCCTT
CTACAATGTGGGCCGCTCACTCACCACCGTCTTCAACGTGCTGCTCTCCTACCTGCTGCTCAAGCAGACCACCTCCT
TCTATGCCCTGCTCACCTGCGGTATCATCATCGGGGGCTTCTGGCTTGGTGTGGACCAGGAGGGGGCAGAAGGCACC
CTGTCGTGGCTGGGCACCGTCTTCGGCGTGCTGGCTAGCCTCTGTGTCTCGCTCAACGCCATCTACACCACGAAGGT
GCTCCCGGCGGTGGACGGCAGCATCTGGCGCCTGACTTTCTACAACAACGTCAACGCCTGCATCCTCTTCCTGCCCC
TGCTCCTGCTGCTCGGGGAGCTTCAGGCCCTGCGTGACCTTGCCCAGCTGGGCAGTGCCCACTTCTGGGGGATGATG
ACGCTGGGCGGCCTGTTTGGCTTTGCCATCGGCTACGTGACAGGACTGCAGATCAAGTTCACCAGTCCGCTGACCCA
CAATGTGTCGGGCACGGCCAAGGCCTGTGCCCAGACAGTGCTGGCCGTGCTCTACTACGAGGAGACCAAGAGCTTCC
TCTGGTGGACGAGCAACATGATGGTGCTGGGCGGCTCCTCCGCCTACACCTGGGTCAGGGGCTGGGAGATGAAGAAG
ACTCCGGAGGAGCCCAGCCCCAAAGACAGCGAGAAGAGCGCCATGGGGGTGTGAGCACCACAGGCACCCTGGATGGC
CCGGCCCCGGGGCCCGTACACAGGCGGGGCCAGCACAGTAGTGAAGGCGGTCTCCTGGACCCCAGAAGCGTGCTGTG
GTGTGGACTGGGTGCTACTTATAGACCCAATCAGAATACGGTGGTTGAGAAGGAACCAGTGTTTACAAGTAATATCA
GAAAGTTGAAGGAACCAGTGTTTACAAGTAATACCAGAAAGTTGCC

FIGURE 31

GCCCTTATCCTGCACATGGCGCTGACCGGGGCCTCAGACCCCTCTGCAGAGGCAGAGGCCAACGGGGAGAAGCCCTT
TCTGCTGCGGGCATTGCAGATCGCGCTGGTGGTCTCCCTCTACTGGGTCACCTCCATCTCCATGGTGTTCCTTAATA
AGTACCTGCTGGACAGCCCCTCCCTGCGGCTGGACACCCCCATCTTCGTCACCTTCTACCAGTGCCTGGTGACCACG
CTGCTGTGCAAAGGCCTCAGCGCTCTGGCCGCCTGCTGCCCTGGTGCCGTGGACTTCCCCAGCTTGCGCCTGGACCT
CAGGGTGGCCCGCAGCGTCCTGCCCCTGTCGGTGGTCTTCATCGGCATGATCACCTTCAATAACCTCTGCCTCAAGT
ACGTCGGTGTGGCCTTCTACAATGTGGGCCGCTCACTCACCACCGTCTTCAACGTGCTGCTCTCCTACCTGCTGCTC
AAGCAGACCACCTCCTTCTATGCCCTGCTCACCTGCGGTATCATCATCGGGGGCTTCTGGCTTGGTGTGGACCAGGA
GGGGGCAGAAGGCACCCTGTCGTGGCTGGGCACCGTCTTCGGCGTGCTGGCTAGCCTCTGTGTCTCGCTCAACGCCA
TCTACACCACGAAGGTGCTCCCGGCGGTGGACGGCAGCATCTGGCGCCTGACTTTCTACAACAACGTCAACGCCTGC
ATCCTCTTCCTGCCCCTGCTCCTGCTGCTCGGGGAGCTTCAGGCCCTGCGTGACTTTGCCCAGCTGGGCAGTGCCCA
CTTCTGGGGGATGATGACGCTGGGCGGCCTGTTTGGCTTTGCCATCGGCTACGTGACAGGACTGCAGATCAAGTTCA
CCAGTCCGCTGACCCACAATGTGTCGGGCACGGCCAAGGCCTGTGCCCAGACAGTGCTGGCCGTGCTCTACTACGAG
GAGACCAAGAGCTTCCTCTGGTGGACGAGCAACATGATGGTGCTGGGCGGCTCCTCCGCCTACACCTGGGTCAGGGG
CTGGGAGATGAAGAAGACTCCGGAGGAGCCCAGCCCCAAAGACAGCGAGAAGAGCGCCATGGGGGTGTGAGCACCAC
AGGCACCCTGAAGGGC

FIGURE 32

CCGAGCGCGGGGCACCGGGGGCCTCCTGTATAGGCGGGCACCATGGGCTCCTGCTCCGGCCGCTGCGCGCTCGTCGT
CCTCTGCGCTTTTCAGCTGGTCGCCGCCCTGGAGAGGCAGGTGTTTGACTTCCTGGGCTACCAGTGGGCGCCCATCC
TGGCCAACTTTGTCCACATCATCATCGTCATCCTGGGACTCTTCGGCACCATCCAGTACCGGCTGCGCTACGTCATG
GTGTACACGCTGTGGGCAGCCGTCTGGGTCACCTGGAACGTCTTCATCATCTGCTTCTACCTGGAAGTCGGTGGCCT
CTTACAGGACAGCGAGCTACTGACCTTCAGCCTCTCCCGGCATCGCTCCTGGTGGCGTGAGCGCTGGCCAGGCTGTC
TGCATGAGGAGGTGCCAGCAGTGGGCCTCGGGGCCCCCCATGGCCAGGCCCTGGTGTCAGGTGCTGGCTGTGCCCTG
GAGCCCAGCTATGTGGAGGCCCTACACAGTGGCCTGCAGATCCTGATCGCGCTTCTGGGCTTTGTCTGTGGCTGCCA
GGTGGTCAGCGTGTTTACGGAGGAAGAGGACAGCTTTGATTTCATTGGTGGATTTGATCCATTTCCTCTCTACCATG
TCAATGAAAAGCCATCCAGTCTCTTGTCCAAGCAGGTGTACTTGCCTGCGTAAGTGAGGAAACAGCTGATCCTGCTC
CTGTGGCCTCCAGCCTCAGCGACCGACCAGTGACAATGACAGGAGCTCCCAGGCCTTGGGACGCGCCCCCACCCAGC
ACCCCCCAGGCGGCCGGCAGCACCTGCCCTGGGTTCTAAGTACTGGACACCAGCCAGGGCGGCAGGGCAGTGCCACG
GCTGGCTGCAGCGTCAAGAGAGTTTGTAATTTCCTTTCTCTTAAAAAAAAAAA

FIGURE 33

CTCCTGTATAGGCGGGCACCATGGGCTCCTGCTCCGGCCGCTGCGCGCTCGTCGTCCTCTGCGCTTTTCAGCTGGTC
GCCGCCCTGGAGAGGCAGGTGTTTGACTTCCTGGGCTACCAGTGGGCGCCCATCCTGGCCAACTTTGTCCACATCAT
CATCGTCATCCTGGGACTCTTCGGCACCATCCAGTACCGGCTGCGCTATGTCATGGTGTACACGCTGTGGGCAGCCG
TCTGGGTCACCTGGAACGTCTTCATCATCTGCTTCTACCTGGAAGTCGGTGGCCTCTTAAAGGACAGCGAGCTACTG
ACCTTCAGCCTCTCCCGGCATCGCTCCTGGTGGCGTGAGCGCTGGCCAGGCTGTCTGCATGAGGAGGTGCCAGCAGT
GGGCCTCGGGGCCCCCATGGCCAGGCCCTGGTGTCAGGTGCTGGCTGTGCCCTGGAGCCCAGCTATGTGGAGGCCC
TACACAGTTGCCTGCAGATCCTGATCGCGCTTCTGGGCTTTGTCTGTGGCTGCCAGGTGGTCAGCGTGTTTACGGAG
GAAGAGGACAGCTTTGATTTCATTGGTGGATTTGATCCATTTCCTCTCTACCATGTCAATGAAAAGCCATCCAGTCT
CTTGTCCAAGCAGGTGTACTTGCCTGCGTAAGTGAGGAAACAGCTGATCC

FIGURE 34

CTCCTGTATAGGCGGGCACCATGGGCTCCTGCTCCGGCCGCTGCGCGCTCGTCGTCCTCTGCGCTTTTCAGCTGGTC
GCCGCCCTGGAGAGGCAGGTGTTTGACTTCCTGGGCTACCAGTGGGCGCCCATCCTGGCCAACTTTGTCCACATCAT
CATCGTCATCCTGGGACTCTTCGGCACCATCCAGTACCGGCTGCGCTATGTCATGGTGTACACGCTGTGGGCAGCCG
TCTGGGTCACCTGGAACGTCTTCATCATCTGCTTCTACCTGGAAGTCGGTGGCCTCTTAAAGGACAGCGAGCTACTG
ACCTTCAGCCTCTCCCGGCATCGCTCCTGGTGGCGTGAGCGCTGGCCAGGCTGTCTGCATGAGGAGGTGCCAGCAGT
GGGCCTCGGGGCCCCCCATGGCCAGGCCCTGGTGTCAGGTGCTGGCTGTGCCCTGGAGCCCAGCTATGTGGAGGCCC
TACACAGTTGCCTGCAGATCCTGATCGCGCTTCTGGGCTTTGTCTGTGGCTGCCAGGTGGTCAGCGTGTTTACGGAG
GAAGAGGACAGCTGCCTGCGTAAGTGAGGAAACAGCTGATCCA

FIGURE 35

CTCCTGTATAGGCGGGCACCATGGGCTCCTGCTCCGGCCGCTGCGCGCTCGTCGTCCTCTGCGCTTTTCAGCTGGTC

GCCGCCCTGGAGAGGCAGGTGTTTGACTTCCTGGGCTACCAGTGGGCGCCCATCCTGGCCAACTTTGTCCACATCAT

CATCGTCATCCTGGGACTCTTCGGCACCATCCAGTACCGGCTGCGCTACGTCATGGTGTACACGCTGTGGGCAGCCC

TCTGGGTCACCTGGAACGTCTTCATCATCTGCTTCTACCTGGAAGTCGGTGGCCTCTTACAGGACAGCGAGCTACTG

ACCTTCAGCCTCTCCCGGCATCGCTCCTGGTGGCGTGAGCGCTGGCCAGGCTGTCTGCATGAGGAGGTGCCAGCAGT

GGGCCTCGGGGCCCCCCATGGCCAGGCCCTGGTGTCAGGTGCTGGCTGTGCCCTGGAGCCCAGCTATGTGGAGGCCC

TACACAGTGGCCTGCAGATCCTGATCGCGCTTCTGGGCTTTGTCTGTGGCTGCCAGGTGGTCAGCGTGTTTACGGAG

GAAGAGGACAGCTGCCTGCGTAAGTGAGGAAACAGCTGATCCA

FIGURE 36

GCATGGAAAGTCTTTATTTGAGCCCCTTAGCTGATGTGGAATCAGAAGAGCAAAAAGGTCATCTTCAGAGTGGCCTG
GGCTGGGTCCTTTTCTCTCCAGGATAGAAAAGTGGTGGTCACTTTATCCCTAGTAGACATGCTGCTGGGCTTTATCG
CCCCAGCATTCCCATCCCCTCCAGAGCCCCTTGTCACTCCAGACCAGCGAGTGTGGGCCTTTATCTGGACTCTGCTT
CCTCCCTGGGGACACCAGGTCTTGGAGCAAGAGAACTTGGCAGGCTCTCCCCATGGCAGTCTTATTCCTCCTCCTGT
TCCTATGTGGAACTCCCCAGGCTGCAGACAACATGCAGGCCATCTATGTGGCCTTGGGGGAGGCAGTAGAGCTGCCA
TGTCCCTCACCACCTACTCTACATGGGGACGAACACCTGTCATGGTTCTGCAGCCCTGCAGCAGGCTCCTTCACCAC
CCTGGTAGCCCAAGTCCAAGTGGGCAGGCCAGCCCCAGACCCTGGAAAACCAGGAAGGGAATCCAGGCTCAGACTGC
TGGGGAACTATTCTTTGTGGTTGGAGGGATCCAAAGAGGAAGATGCCGGGCGGTACTGGTGCGCTGTGCTAGGTCAG
CACCACAACTACCAGAACTGGAGGGTGTACGACGTCTTGGTGCTCAAAGGATCCCAGTTATCTGCAAGGGCTGCAGA
TGGATCCCCCTGCAATGTCCTCCTGTGCTCTGTGGTCCCCAGCAGACGCATGGACTCTGTGACCTGGCAGGAAGGGA
AGGGTCCCGTGAGGGGCCGTGTTCAGTCCTTCTGGGGCAGTGAGGCTGCCCTGCTCTTGGTGTGTCCTGGGGAGGGG
CTTTCTGAGCCCAGGAGCCGAAGACCAAGAATCATCCGCTGCCTCATGACTCACAACAAAGGGGTCAGCTTTAGCCT
GGCAGCCTCCATCGATGCTTCTCCTGCCCTCTGTGCCCCTTCCACGGGCTGGGACATGCCTTGGATTCTGATGCTGC
TGCTCACAATGGGCCAGGGAGTTGTCATCCTGGCCCTCAGCATCGTGCTCTGGAGGCAGAGGGTCCGTGGGGCTCCA
GGCAGAGGAAACCGAATGCGGTGCTACAACTGTGGTGGAAGCCCCAGCAGTTCTTGCAAAGAGGCCGTGACCACCTG
TGGCGAGGGCAGACCCCAGCCAGGCCTGGAACAGATCAAGCTACCTGGAAACCCCCCAGTGACCTTGATTCACCAAC
ATCCAGCCTGCGTCGCAGCCCATCATTGCAATCAAGTGGAGACAGAGTCGGTGGGAGACGTGACTTATCCAGCCCAC
AGGGACTGCTACCTGGGAGACCTGTGCAACAGCGCCGTGGCAAGCCATGTGGCCCCTGCAGGCATTTTGGCTGCAGC
AGCTACCGCCCTGACCTGTCTCTTGCCAGGACTGTGGAGCGGATAGGGGGAGTAGGAGTAGAGAAGGGAACAAGGGA
GCAAGGGAACAAGGGACATCTGAACATCTAATGTGAGAAGAGAAACATCCTTCTGTGAGTCATTAAAATCTATGAAC
CACTCT

FIGURE 37A

CTTTAGAGAAAGGAAGGGCCAAAACTACGACTTGGCTTTCTGAAACGGAAGCATAAATGTTCTTTTCCTCCATTTGT
CTGGATCTGAGAACCTGCATTTGGTATTAGCTAGTGGAAGCAGTATGTATGGTTGAAGTGCATTGCTGCAGCTGGTA
GCATGAGTGGTGGCCACCAGCTGCAGCTGGCTGCCCTCTGGCCCTGGCTGCTGATGGCTACCCTGCAGGCAGGCTTT
GGACGCACAGGACTGGTACTGGCAGCAGCGGTGGAGTCTGAAAGATCAGCAGAACAGAAAGCTGTTATCAGAGTGAT
CCCCTTGAAAATGGACCCCACAGGAAAACTGAATCTCACTTTGGAAGGTGTGTTTGCTGGTGTTGCTGAAATAACTC
CAGCAGAAGGAAAATTAATGCAGTCCCACCCACTGTACCTGTGCAATGCCAGTGATGACGACAATCTGGAGCCTGGA
TTCATCAGCATCGTCAAGCTGGAGAGTCCTCGACGGGCCCCCCGCCCCTGCCTGTCACTGGCTAGCAAGGCTCGGAT
GGCGGGTGAGCGAGGAGCCAGTGCTGTCCTCTTTGACATCACTGAGGATCGAGCTGCTGCTGAGCAGCTGCAGCAGC
CGCTGGGGCTGACCTGGCCAGTGGTGTTGATCTGGGGTAATGACGCTGAGAAGCTGATGGAGTTTGTGTACAAGAAC
CAAAAGGCCCATGTGAGGATTGAGCTGAAGGAGCCCCCGGCCTGGCCAGATTATGATGTGTGGATCCTAATGACAGT
GGTGGGCACCATCTTTGTGATCATCCTGGCTTCGGTGCTGCGCATCCGGTGCCGCCCCCGCCACAGCAGGCCGGATC
CGCTTCAGCAGAGAACAGCCTGGGCCATCAGCCAGCTGGCCACCAGGAGGTACCAGGCCAGCTGCAGGCAGGCCCGG
GGTGAGTGGCCAGACTCAGGGAGCAGCTGCAGCTCAGCCCCTGTGTGTGCCATCTGTCTGGAGGAGTTCTCTGAGGG
GCAGGAGCTACGGGTCATTTCCTGCCTCCATGAGTTCCATCGTAACTGTGTGGACCCCTGGTTACATCAGCATCGGA
CTTGCCCCCTCTGCGTGTTCAACATCACAGAGGGAGATTCATTTTCCCAGTCCCTGGGACCCTCTCGATCTTACCAA
GAACCAGGTCGAAGACTCCACCTCATTCGCCAGCATCCCGGCCATGCCCACTACCACCTCCCTGCTGCCTACCTGTT
GGGCCCTTCCCGGAGTGCAGTGGCTCGGCCCCCACGACCTGGTCCCTTCCTGCCATCCCAGGAGCCAGGCATGGGCC
CTCGGCATCACCGCTTCCCCAGAGCTGCACATCCCCGGGCTCCAGGAGAGCAGCAGCGCCTGGCAGGAGCCCAGCAC
CCCTATGCACAAGGCTGGGGAATGAGCCACCTCCAATCCACCTCACAGCACCCTGCTGCTTGCCCAGTGCCCCTACG
CCGGGCCAGGCCCCCTGACAGCAGTGGATCTGGAGAAAGCTATTGCACAGAACGCAGTGGGTACCTGGCAGATGGGC
CAGCCAGTGACTCCAGCTCAGGGCCCTGTCATGGCTCTTCCAGTGACTCTGTGGTCAACTGCACGGACATCAGCCTA
CAGGGGGTCCATGGCAGCAGTTCTACTTTCTGCAGCTCCCTAAGCAGTGACTTTGACCCCCTAGTGTACTGCAGCCC
TAAAGGGGATCCCCAGCGAGTGGACATGCAGCCTAGTGTGACCTCTCGGCCTCGTTCCTTGGACTCGGTGGTGCCCA
CAGGGGAAACCCAGGTTTCCAGCCATGTCCACTACCACCGCCACCGGCACCACCACTACAAAAAGCGGTTCCAGTGG
CATGGCAGGAAGCCTGGCCCAGAAACCGGAGTCCCCCAGTCCAGGCCTCCTATTCCTCGGACACAGCCCCAGCCAGA
GCCACCTTCTCCTGATCAGCAAGTCACCGGATCCAACTCAGCAGCCCCTTCGGGGCGGCTCTCTAACCCACAGTGCC
CCAGGGCCCTCCCTGAGCCAGCCCCTGGCCCAGTTGACGCCTCCAGCATCTGCCCCAGTACCAGCAGTCTGTTCAAC
TTGCAAAAATCCAGCCTCTCTGCCCGACACCCACAGAGGAAAAGGCGGGGGGTCCCTCCGAGCCCACCCCTGGCTC
TCGGCCCCAGGATGCAACTGTGCACCCAGCTTGCCAGATTTTTCCCCATTACACCCCCAGTGTGGCATATCCTTGGT
CCCCAGAGGCACACCCCTTGATCTGTGGACCTCCAGGCCTGGACAAGAGGCTGCTACCAGAAACCCCAGGCCCCTGT
TACTCAAATTCACAGCCAGTGTGGTTGTGCCTGACTCCTCGCCAGCCCCTGGAACCACATCCACCTGGGGAGGGGCC
TTCTGAATGGAGTTCTGACACCGCAGAGGGCAGGCCATGCCCTTATCCGCACTGCCAGGTGCTGTCGGCCCAGCCTG
GCTCAGAGGAGGAACTCGAGGAGCTGTGTGAACAGGCTGTGTGAGATGTTCAGGCCTAGCTCCAACCAAGAGTGTGC
TCCAGATGTGTTTGGGCCCTACCTGGCACAGAGTCCTGCTCCTGGGAAAGGAAAGGACCACAGCAAACACCATTCTT
TTTGCCGTACTTCCTAGAAGCACTGGAAGAGGACTGGTGATGGTGGAGGGTGAGAGGGTGCCGTTTCCTGCTCCAGC
TCCAGACCTTGTCTGCAGAAAACATCTGCAGTGCAGCAAATCCATGTCCAGCCAGGCAACCAGCTGCTGCCTGTGGC
GTGTGTGGGCTGGATCCCTTGAAGGCTGAGTTTTTGAGGGCAGAAAGCTAGCTATGGGTAGCCAGGTGTTACAAAGG
TGCTGCTCCTTCTCCAACCCCTACTTGGTTTCCCTCACCCCAAGCCTCATGTTCATACCAGCCAGTGGGTTCAGCAG
AACGCATGACACCTTATCACCTCCCTCCTTGGGTGAGCTCTGAACACCAGCTTTGGCCCCTCCACAGTAAGGCTGCT
ACATCAGGGGCAACCCTGGCTCTATCATTTTCCTTTTTTGCCAAAAGGACCAGTAGCATAGGTGAGCCCTGAGCACT
AAAAGGAGGGGTCCCTGAAGCTTTCCCACTATAGTGTGGAGTTCTGTCCCTGAGGTGGGTACAGCAGCCTTGGTTCC
TCTGGGGGTTGAGAATAAGAATAGTGGGCAGGGAAAAACTCCTCCTTGAAGATTTCCTGTCTCAGAGTCCCAGAGAG
GTAGAAAGGAGGAATTTCTGCTGGACTTCATCTGGGCAGAGGAAGGATGGAATGAAGGTAGAAAAGGCAGAATTACA
GCTGAGCGGGGACAACAAAGAGTTCTTCTCTGGGAAAAGTTTTGTCTTAGAGCAAGGATGGAAAATGGGGACAACAA
AGGAAAAGCAAAGTGTGACCCTTGGGTTTGGACAGCCCAGAGGCCCAGCTCCCCAGTATAAGCCATACAGGCCAGGG
ACCCACAGGAGAGTGGATTAGAGCACAAGTCTGGCCTCACTGAGTGGACAAGAGCTGATGGGCCTCATCAGGGTGAC
ATTCACCCCAGGGCAGCCTGACCACTCTTGGCCCCTCAGGCATTATCCCATTTGGAATGTGAATGTGGTGGCAAAGT
GGGCAGAGGACCCCACCTGGGAACCTTTTTCCCTCAGTTAGTGGGGAGACTAGCACCTAGGTACCCACATGGGTATT
TATATCTGAACCAGACAGACGCTTGAATCAGGCACTATGTTAAGAAATATATTTATTTGCTAATATATTTATCCACA
AATGTGGTCTGGTCTTGTGGTTTTGTTCTGTCGTGACTGTCACTCAGGGTAACAACGTCATCTCTTTCTACATCAAG
AGAAGTAAATTATTTATGTTATCAGAGGCTAGGCTCCGATTCATGAAAGGATAGGGTAGAGTAGAGGGCTTGGCAAT
AAGAACTGGTTTGTAAGCCCCTAAAAGTGTGGCTTAGTGAGATCAGGGAAGGAGAAAGCATGACTGGAT

FIGURE 37B

TCTTACTGTGCTTCAGTCATTATTATTATACTGTTCACTTCACACATTATCATACTTCAGTGACTYAGACCTTGGGC
AAATACTCTGTGCCTCGCTTTTTCAGTCCATAAAATGGGCCTACTTAATAGTTGTTGCAGGACTTACATGAGATAAT
AGAGTGTAGAAAATATGTTCCAAAGTGGAAAGTTTTATTCAGTGATAGAAAACATCCAAACCTGTCACAGAGCCCAT
CTGAACACAGCATGGGACCGCCAACAAGAAGAAAGCCCGCCCGGAAGCAGCTCAATCAGGAGGCTGGGCTGGAATGA
CAGCGCAGCGGGGCCTGAAACTATTTATATCCCAAAGCTCCTCTCAGATAAACACAAATGACTGCGTTCTGCCTGCA
CTCGGGCTATTGCGAGGACAGAGAGCTGGTGCTCCATTGGCGTGAAGTCTCCAGGGCCAGAAGGGGCCTTTGTCGCT
TCCTCACAAGGCACAAGTTCCCCTTCTGCTTCCCCGAGAAAGGTTTGGTAGGGGTGGTGGTTTAGTGCCTATAGAAC
AAGGCATTTCGCTTCCTAGACGGTGAAATGAAAGGGAAAAAAAGGACACCTAATCTCCTACAAATGGTCTTTAGTAA
AGGAACC

FIGURE 38

GCAGCTCTGGGGGAGCTCGGAGCTCCCGATCACGGCTTCTTGGGGGTAGCTACGGCTGGGTGTGTAGAACGGGGCCG
GGGCTGGGGCTGGGTCCCCTAGTGGAGACCCAAGTGCGAGAGGCAAGAACTCTGCAGCTTCCTGCCTTCTGGTCAG
TTCCTTATTCAAGTCTGCAGCCGGCTCCCAGGGAGATCTCGGTGGAACTTCAGAAACGCTGGGCAGTCTGCCTTTCA
ACCATGCCCCTGTCCCTGGGAGCCGAGATGTGGGGGCCTGAGGCCTGGCTGCTGCTGCTGCTACTGCTGGCATCATT
TACAGGCCGGTGCCCCGCGGGTGAGCTGGAGACCTCAGACGTGGTAACTGTGGTGCTGGGCCAGGACGCAAAACTGC
CCTGCTTCTACCGAGGGGACTCCGGCGAGCAAGTGGGGCAAGTGGCATGGGCTCGGGTGGACGCGGGCGAAGGCGCC
CAGGAACTAGCGCTACTGCACTCCAAATACGGGCTTCATGTGAGCCCGGCTTACGAGGGCCGCGTGGAGCAGCCGCC
GCCCCCACGCAACCCCCTGGACGGCTCAGTGCTCCTGCGCAACGCAGTGCAGGCGGATGAGGGCGAGTACGAGTGCC
GGGTCAGCACCTTCCCCGCCGGCAGCTTCCAGGCGCGGCTGCGGCTCCGAGTGCTGGTGCCTCCCCTGCCCTCACTG
AATCCTGGTCCAGCACTAGAAGAGGGCCAGGGCCTGACCCTGGCAGCCTCCTGCACAGCTGAGGGCAGCCCAGCCCC
CAGCGTGACCTGGGACACGGAGGTCAAAGGCACAACGTCCAGCCGTTCCTTCAAGCACTCCCGCTCTGCTGCCGTCA
CCTCAGAGTTCCACTTGGTGCCTAGCCGCAGCATGAATGGGCAGCCACTGACTTGTGTGGTGTCCCATCCTGGCCTG
CTCCAGGACCAAAGGATCACCCACATCCTCCACGTGTCCTTCCTTGCTGAGGCCTCTGTGAGGGGCCTTGAAGACCA
AAATCTGTGGCACATTGGCAGAGAAGGAGCTATGCTCAAGTGCCTGAGTGAAGGGCAGCCCCCTCCCTCATACAACT
GGACACGGCTGGATGGCCCTCTGCCCAGTGGGGTACGAGTGGATGGGGACACTTTGGGCTTTCCCCCACTGACCACT
GAGCACAGCGGCATCTACGTCTGCCATGTCAGCAATGAGTTCTCCTCAAGGGATTCTCAGGTCACTGTGGATGTTCT
TGACCCCCAGGAAGACTCTGGGAAGCAGGTGGACCTAGTGTCAGCCTCGGTGGTGGTGGTGGGTGTGATCGCCGCAC
TCTTGTTCTGCCTTCTGGTGGTGGTGGTGGTGCTCATGTCCCGATACCATCGGCGCAAGGCCCAGCAGATGACCCAG
AAATATGAGGAGGAGCTGACCCTGACCAGGGAGAACTCCATCCGGAGGCTGCATTCCCATCACACGGACCCCAGGAG
CCAGCCGGAGGAGAGTGTAGGGCTGAGAGCCGAGGGCCACCCTGATAGTCTCAAGGACAACAGTAGCTGCTCTGTGA
TGAGTGAAGAGCCCGAGGGCCGCAGTTACTCCACGCTGACCACGGTGAGGGAGATAGAAACACAGACTGAACTGCTG
TCTCCAGGCTCTGGGCGGGCCGAGGAGGAGGAAGATCAGGATGAAGGCATCAAACAGGCCATGAACCATTTTGTTCA
GGAGAATGGGACCCTACGGGCCAAGCCCACGGGCAATGGCATCTACATCAATGGGCGGGGACACCTGGTCTGACCCA
GGCCTGCCTCCCTTCCCTAGGCCTGGCTCCTTCTGTTGACATGGGAGATTTTAGCTCATCTTGGGGGCCTCCTTAAA
CACCCCCATTTCTTGCGGAAGATGCTCCCCATCCCACTGACTGCTTGACCTTTACCTCCAACCCTTCTGTTCATCGG
GAGGGCTCCACCAATTGAGTCTCTCCCACCATGCATGCAGGTCACTGTGTGTGTGCATGTGTGCCTGTGTGAGTGTT
GACTGACTGTGTGTGTGTGGAGGGGTGACTGTCCGTGGAGGGGTGACTGTGTCCGTGGTGTGTATTATGCTGTCATA
TCAGAGTCAAGTGAACTGTGGTGTATGTGCCACGGGATTTGAGTGGTTGCGTGGGCAACACTGTCAGGGTTTGGCGT
GTGTGTCATGTGGCTGTGTGTGACCTCTGCCTGAAAAAGCAGGTATTTTCTCAGACCCCAGAGCAGTATTAATGATG
CAGAGGTTGGAGGAGAGAGGTGGAGACTGTGGCTCAGACCCAGGTGTGCGGGCATAGCTGGAGCTGGAATCTGCCTC
CGGTGTGAGGGAACCTGTCTCCTACCACTTCGGAGCCATGGGGGCAAGTGTGAAGCAGCCAGTCCCTGGGTCAGCCA
GAGGCTTGAACTGTTACAGAAGCCCTCTGCCCTCTGGTGGCCTCTGGGCCTGCTGCATGTACATATTTTCTGTAAAT
ATACATGCGCCGGGAGCTTCTTGCAGGAATACTGCTCCGAATCACTTTTAATTTTTTTCTTTTTTTTTTCTTGCCCT
TTCCATTAGTTGTATTTTTTATTTATTTTTATTTTTATTTTTTTTTAGAGATGGAGTCTCACTATGTTGCTCAGGCT
GGCCTTGAACTCCTGGGCTCAAGCAATCCTCCTGCCTCAGCCTCCCTAGTAGCTGGGACTTTAAGTGTACACCACTG
TGCCTGCTTTGAATCCTTTACGAAGAGAAAAAAAAAATTAAAGAAAGCCTTTAGATTTATCCAATGTTTACTACTGG
GATTGCTTAAAGTGAGGCCCCTCCAACACCAGGGGGTTAATTCCTGTGATTGTGAAAGGGGCTACTTCCAAGGCATC
TTCATGCAGGCAGCCCCTTGGGAGGGCACCTGAGAGCTGGTAGAGTCTGAAATTAGGGATGTGAGCCTCGTGGTTAC
TGAGTAAGGTAAAATTGCATCCACCATTGTTTGTGATACCTTAGGGAATTGCTTGGACCTGGTGACAAGGGCTCCTG
TTCAATAGTGGTGTTGGGGAGAGAGAGAGCAGTGATTATAGACCGAGAGAGTAGGAGTTGAGGTGAGGTGAAGGAGG
TGCTGGGGGTGAGAATGTCGCCTTTCCCCCTGGGTTTTGGATCACTAATTCAAGGCTCTTCTGGATGTTTCTCTGGG
TTGGGGCTGGAGTTCAATGAGGTTTATTTTTAGCTGGCCCACCCAGATACACTCAGCCAGAATACCTAGATTTAGTA
CCCAAACTCTTCTTAGTCTGAAATCTGCTGGATTTCTGGCCTAAGGGAGAGGCTCCCATCCTTCGTTCCCCAGCCAG
CCTAGGACTTCGAATGTGGAGCCTGAAGATCTAAGATCCTAACATGTACATTTTATGTAAATATGTGCATATTTGTA
CATAAAATGATATTCTGTTTTTAAATAAACAGACAAAACTTGAAAAAAAAAAAAAAAAAAAAAAAAAAAAAAAAAAAA
AAAAAAAAAAAAAAAAAAAAAAAAAAAAAAAAAAAAAAAAAAAA

FIGURE 39

TTGGGGGTTTATTCTCTTCCCTTCTAACTTGACAGGGTCTTGCTCTGTCATTCAGGCAAGAGTGCAGTAGTGTGATC
ACTTCTTACTGCCGCCTCAAGCTTCCAGCCTCAACTCAAGCAATCCTCCCACCTCAGCCACCCAAGTGGCTGGGACT
ACAGATTAAGAATGACCCAAAATAAATTAAAGCTTTGTTCCAAAGCCAATGTGTATACTGAAGTGCCTGATGGAGGA
TGGGGCTGGGCGGTAGCTGTTTCATTTTTCTTCGTTGAAGTCTTCACCTACGGCATCATCAAGACATTTGGTGTCTT
CTTTAATGACTTAATGGACAGTTTTAATGAATCCAATAGCAGGATCTCATGGATAATCTCAATCTGTGTGTTTGTCT
TAACATTTTCAGCTCCCCTCGCCACAGTCCTGAGCAATCGTTTCGGACACCGTCTGGTAGTGATGTTGGGGGGCTA
CTTGTCAGCACCGGGATGGTGGCCGCCTCCTTCTCACAAGAGGTTTCTCATATGTACGTCGCCATCGGCATCATCTC
TGGTCTGGGATACTGCTTTAGTTTTCTCCCAACTGTAACCATCCTATCACAATATTTTGGCAAAAGACGTTCCATAG
TCACTGCAGTTGCTTCCACAGGAGAATGTTTCGCTGTGTTTGCTTTCGCACCAGCAATCATGGCTCTGAAGGAGCGC
ATTGGCTGGAGATACAGCCTCCTCTTCGTGGGCCTACTACAGTTAAACATTGTCATCTTCGGAGCACTGCTCAGACC
CATCATTATCAGAGGACCAGCGTCACCGAAAATAGTCATCCAGGAAAATCGGAAAGAAGCGCAGTATATGCTTGAAA
ATGAGAAAACACGAACCTCAATAGACTCCATTGACTCAGGAGTAGAACTAACTACCTCACCTAAAAATGTGCCTACT
CACACTAACCTGGAACTGGAGCCGAAGGCCGACATGCAGCAGGTCCTGGTGAAGACCAGCCCCAGGCCAAGCGAAAA
GAAAGCCCCGCTATTAGACTTCTCCATTTTGAAAGAGAAAAGTTTTATTTGTTATGCATTATTTGGTCTCTTTGCAA
CACTGGGATTCTTTGCACCTTCCTTGTACATCATTCCTCTGGGCATTAGTCTGGGCATTGACCAGGACCGCGCTGCT
TTTTTATTATCTACGATGGCCATTGCAGAAGTTTTCGGAAGGATCGGAGCTGGTTTTGTCCTCAACAGGGAGCCCAT
TCGTAAGATTTACATTGACCTCATCTGCGTCATCTTATTGACTGTGTCTCTGTTTGCCTTTACTTTTGCTACTGAAT
TCTGGGGTCTAATGTCATGCAGCATATTTTTTGGGTTTATGGTTGGAACAATAGGAGGACTCACATTCCACTGCTTG
CTGAAGATGATGTCGTGGGCATTGCAGAAGATGTCTTCTGCAGCTGGGGTCTACATCTTCATTCAGAGCATAGCAGG
ACTGGCTGGACCGCCCCTTGCAGGTTTGTTGGTGGACCAAAGTAAGATCTACAGCAGGGCCTTCTACTCCTGCGCAG
CTGGCATGGCCCTGGCTGCTGTGTGCCTCGCCCTGGTGAGACCGTGTAAGATGGGACTGTGCCAGCGTCATCACTCA
GGTGAAACAAAGGTAGTGAGCCATCGTGGGAAGACTTTACAGGACATACCTGAAGACTTTCTGGAAATGGATCTTGC
AAAAAATGAGCACAGAGTTCACGTGCAAATGGAGCCGGTATGACACACTTTCTTACAACAACAGCCACTGTGTTGGC
TGGAGAGGGATGGGGTGGCCCAACGGGGACACAAGGAGGCAGAGGAGCTAACCCCTCTACTCCACTTTCAAAACTA
CATTTTAAAGGGAATGTGTATGTGAAGAGCACTACCAACATCGCTTTTGTTTTGTTTTGTTTTGTTTTAAGCTTTTT
TTTTTTGCTTGTTTTTAAAGCCAAAACAAAAAACAACCAAGCACTCTTCCATATATAAATCTGGCTGTATTCAGTAG
CAATACAAGAGATATGTAGAAAGACTCTTTGGTTCACATTCCGATATTAAAATAGTGACATGAACTGGCAAAGTGGT
TTTAAAAGCTTTCACGTGGATAAATGATTTTCTTTTTTTCTTTTCTTTCTTCCTATGGTCTTGTCTGAATAAACTA
CTCTCCTGAATAAAACAACATCCAACCCAGGTCATTGAAATGAAATTGGCCAGTC

FIGURE 40

GATGTGCTCCTTGGAGCTGGTGTGCAGTGTCCTGACTGTAAGATCAAGTCCAAACCTGTTTTGGAATTGAGGAAACT
TCTCTTTTGATCTCAGCCCTTGGTGGTCCAGGTCTTCATGCTGCTGTGGGTGATATTACTGGTCCTGGCTCCTGTCA
GTGGACAGTTTGCAAGGACACCCAGGCCCATTATTTCCTCCAGCCTCCATGGACCACAGTCTTCCAAGGAGAGAGA
GTGACCCTCACTTGCAAGGGATTTCGCTTCTACTCACCACAGAAAACAAAATGGTACCATCGGTACCTTGGGAAAGA
AATACTAAGAGAAACCCCAGACAATATCCTTGAGGTTCAGGAATCTGGAGAGTACAGATGCCAGGCCCAGGGCTCCC
CTCTCAGTAGCCCTGTGCACTTGGATTTTTCTTCAGAGATGGGATTTCCTCATGCTGCCCAGGCTAATGTTGAACTC
CTGGGCTCAAGTGATCTGCTCACCTAGGCCTCTCAAAGCGCTGGGATTACAGCTTCGCTGATCCTGCAAGCTCCACT
TTCTGTGTTTGAAGGAGACTCTGTGGTTCTGAGGTGCCGGGCAAAGGCGGAAGTAACACTGAATAATACTATTTACA
AGAATGATAATGTCCTGGCATTCCTTAATAAAAGAACTGACTTCCAAAAAAAAAAAAAAAAAAAAAAAA

FIGURE 41A

AATTCACTAATGCATTCTGCTCTTTTTGAGAGCACAGCTTCTCAGATGTGCTCCTTGGAGCTGGTGTGCAGTGTCCT
GACTGTAAGATCAAGTCCAAACCTGTTTTGGAATTGAGGAAACTTCTCTTTTGATCTCAGCCCTTGGTGGTCCAGGT
CTTCATGCTGCTGTGGGTGATATTACTGGTCCTGGCTCCTGTCAGTGGACAGTTTGCAAGGACACCCAGGCCCATTA
TTTTCCTCCAGCCTCCATGGACCACAGTCTTCCAAGGAGAGAGAGTGACCCTCACTTGCAAGGGATTTCGCTTCTAC
TCACCACAGAAAACAAAATGGTACCATCGGTACCTCGGGAAAGAAATACTAAGAGAAACCCCAGACAATATCCTTGA
GGTTCAGGAATCTGGAGAGTACAGATGCCAGGCCCAGGGCTCCCCTCTCAGTAGCCCTGTGCACTTGGATTTTTCTT
CAGCTTCGCTGATCCTGCAAGCTCCACTTTCTGTGTTTGAAGGAGACTCTGTGGTTCTGAGGTGCCGGGCAAAGGCG
GAAGTAACACTGAATAATACTATTTACAAGAATGATAATGTCCTGGCATTCCTTAATAAAAGAACTGACTTCCATAT
TCCTCATGCATGTCTCAAGGACAATGGTGCATATCGCTGTACTGGATATAAGGAAAGTTGTTGCCCTGTTTCTTCCA
ATACAGTCAAAATCCAAGTCCAAGAGCCATTTACACGTCCAGTGCTGAGAGCCAGCTCCTTCCAGCCCATCAGCGGG
AACCCAGTGACCCTGACCTGTGAGACCCAGCTCTCTCTAGAGAGGTCAGATGTCCCGCTCCGGTTCCGCTTCTTCAG
AGATGACCAGACCCTGGGATTAGGCTGGAGTCTCTCCCCGAATTTCCAGATTACTGCCATGTGGAGTAAAGATTCAG
GGTTCTACTGGTGTAAGGCAGCAACAATGCCTCACAGCGTCATATCTGACAGCCCGAGATCCTGGATACAGGTGCAG
ATCCCTGCATCTCATCCTGTCCTCACTCTCAGCCCTGAAAAGGCTCTGAATTTTGAGGGAACCAAGGTGACACTTCA
CTGTGAAACCCAGGAAGATTCTCTGCGCACTTTGTACAGGTTTTATCATGAGGGTGTCCCCCTGAGGCACAAGTCAG
TCCGCTGTGAAAGGGGAGCATCCATCAGCTTCTCACTGACTACAGAGAATTCAGGGAACTACTACTGCACAGCTGAC
AATGGCCTTGGCGCCAAGCCCAGTAAGGCTGTGAGCCTCTCAGTCACTGTTCCCGTGTCTCATCCTGTCCTCAACCT
CAGCTCTCCTGAGGACCTGATTTTTGAGGGAGCCAAGGTGACACTTCACTGTGAAGCCCAGAGAGGTTCACTCCCCA
TCCTGTACCAGTTTCATCATGAGGATGCTGCCCTGGAGCGTAGGTCGGCCAACTCTGCAGGAGGAGTGGCCATCAGC
TTCTCTCTGACTGCAGAGCATTCAGGGAACTACTACTGCACAGCTGACAATGGCTTTGGCCCCCAGCGCAGTAAGGC
GGTGAGCCTCTCCATCACTGTCCCTGTGTCTCATCCTGTCCTCACCCTCAGCTCTGCTGAGGCCCTGACTTTTGAAG
GAGCCACTGTGACACTTCACTGTGAAGTCCAGAGAGGTTCCCCACAAATCCTATACCAGTTTTATCATGAGGACATG
CCCCTGTGGAGCAGCTCAACACCCTCTGTGGGAAGAGTGTCCTTCAGCTTCTCTCTGACTGAAGGACATTCAGGGAA
TTACTACTGCACAGCTGACAATGGCTTTGGTCCCCAGCGCAGTGAAGTGGTGAGCCTTTTTGTCACTGTTCCAGTGT
CTCGCCCCATCCTCACCCTCAGGGTTCCCAGGGCCCAGGCTGTGGTGGGGGACCTGCTGGAGCTTCACTGTGAGGCC
CCGAGAGGCTCTCCCCCAATCCTGTACTGGTTTTATCATGAGGATGTCACCCTGGGGAGCAGCTCAGCCCCCTCTGG
AGGAGAAGCTTCTTTCAACCTCTCTCTGACTGCAGAACATTCTGGAAACTACTCATGTGAGGCCAACAATGGCCTAG
TGGCCCAGCACAGTGACACAATATCACTCAGTGTTATAGTTCCAGTATCTCGTCCCATCCTCACCTTCAGGGCTCCC
AGGGCCCAGGCTGTGGTGGGGGACCTGCTGGAGCTTCACTGTGAGGCCCTGAGAGGCTCCTCCCCAATCCTGTACTG
GTTTTATCATGAAGATGTCACCCTGGGTAAGATCTCAGCCCCCTCTGGAGGAGGGGCCTCCTTCAACCTCTCTCTGA
CTACAGAACATTCTGGAATCTACTCCTGTGAGGCAGACAATGGTCCGGAGGCCCAGCGCAGTGAGATGGTGACACTG
AAAGTTGCAGTTCCGGTGTCTCGCCCGGTCCTCACCCTCAGGGCTCCCGGGACCCATGCTGCGGTGGGGGACCTGCT
GGAGCTTCACTGTGAGGCCCTGAGAGGCTCTCCCCTGATCCTGTACCGGTTTTTTCATGAGGATGTCACCCTAGGAA
ATAGGTCGTCCCCCTCTGGAGGAGCGTCCTTAAACCTCTCTCTGACTGCAGAGCACTCTGGAAACTACTCCTGTGAG
GCCGACAATGGCCTCGGGGCCCAGCGCAGTGAGACAGTGACACTTTATATCACAGGGCTGACCGCGAACAGAAGTGG
CCCTTTTGCCACAGGAGTCGCCGGGGGCCTGCTCAGCATAGCAGGCCTTGCTGCGGGGGCACTGCTGCTCTACTGCT
GGCTCTCGAGAAAAGCAGGGAGAAAGCCTGCCTCTGACCCCGCCAGGAGCCCTCCAGACTCGGACTCCCAAGAGCCC
ACCTATCACAATGTACCAGCCTGGGAAGAGCTGCAACCAGTGTACACTAATGCAAATCCTAGAGGAGAAAATGTGGT
TTACTCAGAAGTACGGATCATCCAAGAGAAAAAGAAACATGCAGTGGCCTCTGACCCCAGGCATCTCAGGAACAAGG
GTTCCCCTATCATCTACTCTGAAGTTAAGGTGGCGTCAACCCCGGTTTCCGGATCCCTGTTCTTGGCTTCCTCAGCT
CCTCACAGATGAGTCCACACGTCTCTCCAACTGCTGTTTCAGCCTCTGCACCCCAAAGTTCCCCTTGGGGGAGAAGC
AGCATTGAAGTGGGAAGATTTAGGCTGCCCCAGACCATATCTACTGGCCTTTGTTTCACATGTCCTCATTCTCAGTC
TGACCAGAATGCAGGGCCCTGCTGGACTGTCACCTGTTTCCCAGTTAAAGCCCTGACTGGCAGGTTTTTAATCCAG
TGGCAAGGTGCTCCCACTCCAGGGCCCAGCACATCTCCTGGATTCCTTAGTGGGCTTCAGCTGTGATTGCTGTTCTG
AGTACTGCTCTCATCACACCCCCACAGAGGGGGTCTTACCACACAAAGGGAGAGTGGGCCTTCAGGAGATGCCGGGC
TGGCCTAACAGCTCAGGTGCTCCTAAACTCCGACACAGAGTTCCTGCTTTGGGTGGATGCATTTCTCAATTGTCATC
AGCCTGGTGGGGCTACTGCAGTGTGCTGCCAAATGGGACAGCACACAGCCTGTGCACATGGGACATGTGATGGGTCT
CCCCACGGGGGCTGCATTTCACACTCCTCCACCTGTCTCAAACTCTAAGGTCGGCACTTGACACCAAGGTAACTTCT
CTCCTGCTCATGTGTCAGTGTCTACCTGCCCAAGTAAGTGGCTTTCATACACCAAGTCCCAAGTTCTTCCCATCCTA
ACAGAAGTAACCCAGCAAGTCAAGGCCAGGAGGACCAGGGGTGCAGACAGAACACATACTGGAACACAGGAGGTGCT
CAATTACTATTTGACTGACTGACTGAATGAATGAATGAATGAGGAAGAAAACTGTGGGTAATCAAACTGGCATAAAA
TCCAGTGCACTCCCTAGGAAATCCGGGAGGTATTCTGGCTTCCCTAAGAAACAACGGAAGAGAAGGAGC

FIGURE 41B

TTGGATGAGGAAACTGTTCAGCAAGAGGAAGGGCTTCTCACACTTTCATGTGCTTGTGGATCACCTGAGGATCCTGT
GAAAATACAGATACTGATTCAGTGGGTCTGTGTAGAGCCTGAGACTGCCATTCTAACATGTTCCCAGGGGATGCTGA
TGCTGCTGGCCCTGGGACTGCACTGCATGCATGTGAAGCCCTATAGGTCTCAGCAGAGGCCCATGGAGAGGGAATGT
GTGGCTCTGGCTGCCCAGGGCCCAACTCGGTTCACACGGATCGTGCTGCTCCCTGGCCAGCCTTTGGCCACAGCACC
ACCAGCTGCTGTTGCTGAGAGAGCTTCTTCTCTGTGACATGTTGGCTTTCATCAGCCACCCTGGGAAGCGGAAAGTA
GCTGCCACTATCTTTGTTTCCCCACCTCAGGCCTCACACTTTCCCATGAAAAGGGTGAATGTATATAACCTGAGCCC
TCTCCATTCAGAGTTGTTCTCCCATCTCTGAGCAATGGGATGTTCTGTTCCGCTTTTATGATATCCATCACATCTTA
TCTTGATCTTTGCTCCCAGTGGATTGTACAGTGATGACTTTTAAGCCCCACGGCCCTGAAATAAAATCCTTCCAAGG
GCATTGGAAGCTCTCTCCACCTGAACCATGGCTTTTCATGCTTCCAAGTGTCAGGGCCTTGCCCAGATAGACAGGGC
TGACTCTGCTGCCCCAACCTTTCAAGGAGGAAACCAGACACCTGAGACAGGAGCCTGTATGCAGCCCAGTGCAGCCT
TGCAGAGGACAAGGCTGGAGGCATTTGTCATCACTACAGATATGCAACTAAAATAGACGTGGAGCAAGAGAAATGCA
TTCCCACCGAGGCCGCTTTTTTAGGCCTAGTTGAAAGTCAAGAAGGACAGCAGCAAGCATAGGCTCAGGATTAAAGA
AAAAAATCTGCTCACAGTTTGTTCTGGAGGTCACATCACCAACAAAGCTCACGCCCTATGCAGTTCTGAGAAGGTGG
AGGCACCAGGCTCAAAAGAGGAAATTTAGAATTTCTCATTGGGAGAGTAAGGTACCCCCATCCCAGAATGATAACTG
CACAGTGGCAGAACAAACTCCACCCTAATGTGGGTGGACCCCATCCAGTCTGTTGAAGGCCTGAGTGTAACAAAAGG
GCTTATTCTTCCTCAAGTAAGGGGGAACTCCTGCTTTGGGCTGGGACATAAGTTTTTCTGCTTTCAGACGCAAACTG
AAAAATGGCTCTTCTTGGGTCTTGAGCTTGCTGGCATATGGACTGAAAGAAACTATGCTATTGGATCTCCTGGATCT
CCAGCTTGCTGACTGCAGATCTTGAGATATGTCAGCCTCTACAGTCACAAGAGCTAATTCATTCTAATAAACCAATC
TTTCTGTAAA

FIGURE 42

GGACCTGGGAAGGAGCATAGGACAGGGCAAGGCGGGATAAGGAGGGGCACCACAGCCCTTAAGGCACGAGGGAACCT
CACTGCGCATGCTCCTTTGGTGCCCACCTCAGTGCGCATGTTCACTGGGCGTCTTCCCATCGGCCCCTTCGCCAGTG
TGGGGAACGCGGCGGAGCTGTGAGCCGGCGACTCGGGTCCCTGAGGTCTGGATTCTTTCTCCGCTACTGAGACACGG
CGGACACACACAAACACAGAACCACACAGCCAGTCCCAGGAGCCCAGTAATGGAGAGCCCCAAAAAGAAGAACCAGC
AGCTGAAAGTCGGGATCCTACACCTGGGCAGCAGACAGAAGAAGATCAGGATACAGCTGAGATCCCAGTGCGCGACA
TGGAAGGTGATCTGCAAGAGCTGCATCAGTCAAACACCGGGGATAAATCTGGATTTGGGTTCCGGCGTCAAGGTGAA
GATAATACCTAAAGAGGAACACTGTAAAATGCCAGAAGCAGGTGAAGAGCAACCACAAGTTTAAATGAAGACAAGCT
GAAACAACGCAAGCTGGTTTTATATTAGATATTTGACTTAAACTATCTCAATAAAGTTTTGCAGCTTTCACCAAAAA
AAAAAAAAAA

FIGURE 43

AGCGGCTGGCGAGCCGGCGCCGGCCGAGCTGCGGGAGCCGCGGAGAGCACCAGCTGTCGCCGCGGGAGCTGCTCCGG
CCGCACCATGCGGGAGCTGGCCATTGAGATCGGGGTGCGAGCCCTGCTCTTCGGAGTCTTCGTTTTTACAGAGTTTT
TGGATCCGTTCCAGAGAGTCATCCAGCCAGAAGAGATCTGGCTCTATAAAAATCCTTTGGTGCAATCAGATAACATA
CCTACCCGCCTCATGTTTGCAATTTCTTTCCTCACACCCCTGGCTGTTATTTGTGTGGTGAAAATTATCCGGCGAAC
AGACAAGACTGAAATTAAGGAAGCCTTCTTAGCGGTGTCCTTGGCTCTTGCTTTGAATGGAGTCTGCACAAACACTA
TTAAATTAATAGTGGGAAGACCTCGCGCCGATTTCTTTTACCGCTGCTTTCCAGATGGAGTGATGAACTCGGAAATG
CATTGCACAGGTGACCCCGATCTGGTGTCCGAGGGCCGCAAAAGCTTCCCCAGCATCCATTCCTCCTTTGCCTTTTC
GGGCCTTGGCTTCACGACGTTCTACTTGGCGGGCAAGCTGCACTGCTTCACCGAGAGTGGGCGGGGAAAGAGCTGGC
GGCTCTGTGCTGCCATCCTGCCCTTGTACTGCGCCATGATGATTGCCCTGTCCCGCATGTGCGACTACAAGCATCAC
TGGCAAGATTCCTTTGTGGGTGGAGTCATCGCGCTCATTTTTGCATACATTTGCTACAGACAGCACTATCCTCCTCT
GGGCCAACACAGCTTGCCATAAACCCTACGTTAGTCTGCGAGTTTGCCATAAACCCTACGTTAGTCTGCGAGTCCCA
GCCTCACTGAAGAAAGAGGAGAGGCCCACAGCTGACAGCGCACCCAGCTTGCCTCTGGAGGGGATCACCGAAGGCCC
GGTATGACCAGTGTCCTGGGAGGATGGACACTAAGCCCTGGGCACATCTGCCACCCTGACATCATAACACAATAGAA
ATGGTTTTCTGTAGTGTATTTTTCATCAGTTGTTTCTCAAAGTCATCGTACTTCTGCTTCTGTTTCACTGATGGTGT
TCCTGCTACTTTAAATGTCTACTTCCAACATCCTTGAATTTGCAAGTGAAGGACAACAATCTCTGAGAGACGTGTGG
AAGAGGCTGCGAAGGTGGGGTTTGGGGAGCTTCGCCGATTCGTCTATCTGAAATGTTTGCTGTAACAGCCACCTTCC
TATGTTTTCATGGTTAGTAAACATAATAAAACCTCCCATCGGGAAAAAATACAAAATTCATTGATTTAGGAATATAT
ATATAATATTCACATGTGTAATTCCCCCCCTCCCTTTAGTGAGGGTAATTCAAGATCCTTCTCAACTGCTTTGTGCG
ACTTAGACTTTATGTTGCAGCAGACTTTTTTATTTTACTTATAGCGCGGAATCCGTGTTTCCTCAGAATCAGGGAAT
CCGCCCGAAAATCTGTTACAAAGGCCGCCAAGTGACATAACT

FIGURE 44

TCCTTGGGTTCGGGTGAAAGCGCCTGGGGGTTCGTGGCCATGATCCCCGAGCTGCTGGAGAACTGAAGGCGGACAGT
CTCCTGCGAAACCAGGCAATGGCGGAGCTGGAGTTTGTTCAGATCATCATCATCGTGGTGGTGATGATGGTGATGGT
GGTGGTGATCACGTGCCTGCTGAGCCACTACAAGCTGTCTGCACGGTCCTTCATCAGCCGGCACAGCCAGGGGCGGA
GGAGAGAAGATGCCCTGTCCTCAGAAGGATGCCTGTGGCCCTCGGAGAGCACAGTGTCAGGCAACGGAATCCCAGAG
CCGCAGGTCTACGCCCCGCCTCGGCCCACCGACCGCCTGGCCGTGCCGCCCTTCGCCCAGCGGAGCGCTTCCACCG
CTTCCAGCCCACCTATCCGTACCTGCAGCACGAGATCGACCTGCCACCCACCATCTCGCTGTCAGACGGGGAGGAGC
CCCCACCCTACCAGGGCCCCTGCACCCTCCAGCTTCGGGACCCCGAGCAGCAGCTGGAACTGAACCGGGAGTCGGTG
CGCGCACCCCCAAACAGAACCATCTTCGACAGTGACCTGATGGATAGTGCCAGGCTGGGCGGCCCCTGCCCCCCCAG
CAGTAACTCGGGCATCAGCGCCACGTGCTACGGCAGCGGCGGGCGCATGGAGGGGCCGCCGCCCACCTACAGCGAGG
TCATCGGCCACTACCCGGGGTCCTCCTTCCAGCACCAGCAGAGCAGTGGGCCGCCCTCCTTGCTGGAGGGGACCCGG
CTCCACCACACACACATCGCGCCCCTAGAGAGCGCAGCCATCTGGAGCAAAGAGAAGGATAAACAGAAAGGACACCC
TCTCTAGGGTCCCCAGGGGGGCCGGGCTGGGGCTGCGTAGGTGAAAAGGCAGAACACTCCGCGCTTCTTAGAAGAGG
AGTGAGAGGAAGGCGGGGGCGCAGCAACGCATCGTGTGGCCCTCCCCTCCCACCTCCCTGTGTATAAATATTTACA
TGTGATGTCTGGTCTGAATGCACAAGCTAAGAGAGCTTGCAAAAAAAAAAAGAAAAAAGAAAAAAAAAAACCACGTT
TCTTTGTTGAGCTGTGTCTTGAAGGCAAAAGAAAAAAAATTTCTACAGTAGTCTTTCTTGTTTCTAGTTGAGCTGCG
TGCGTGAATGCTTATTTTCTTTTGTTTATGATAATTTCACTTAACTTTAAAGACATATTTGCACAAAACCTTTGTTT
AAAGATCTGCAATATTATATATATAAATATATATAAGATAAGAGAAACTGTATGTGCGAGGGCAGGAGTATTTTTGT
ATTAGAAGAGGCCTATTAAAAAAAAAAGTTGTTTTCTGAACTAGAAGAGGAAAAAAATGGCAATTTTTGAGTGCCAA
GTCAGAAAGTGTGTATTACCTTGTAAAGAAAAAAATTACAAAGCAGGGGTTTAGAGTTATTTATATAAATGTTGAGA
TTTTGCACTATTTTTTAATATAAATATGTCAGTGCTTGCTTGATGGAAACTTCTCTTGTGTCTGTTGAGACTTTAAG
GGAGAAATGTCGGAATTTCAGAGTCGCCTGACGGCAGAGGGTGAGCCCCCGTGGAGTCTGCAGAGAGGCCTTGGCCA
GGAGCGGCGGGCTTTCCCGAGGGGCCACTGTCCCTGCAGAGTGGATGCTTCTGCCTAGTGACAGGTTATCACCACGT
TATATATTCCCTACCGAAGGAGACACCTTTTCCCCCCTGACCCAGAACAGCCTTTAAATCACAAGCAAAATAGGAAA
GTTAACCACGGAGGCACCGAGTTCCAGGTAGTGGTTTTGCCTTTCCCAAAAATGAAAATAAACTGTTACCGAAGGAA
TT

FIGURE 45

GCCCTTCGGACAGTCTCCTGCGAAACCAGGCAATGGCGGAGCTGGAGTTTGTTCAGATCATCATCATCGTGGTGGTG
ATGATGGTGATGGTGGTGGTGATCACGTGCCTGCTGAGCCACTACAAGCTGTCTGCACGGTCCTTCATCAGCCGGCA
CAGCCAGGGGCGGAGGAGAGAAGATGCCCTGTCCTCAGAAGGATGCCTGTGGCCCTCGGAGAGCACAGTGTCAGGCA
ACGGAATCCCAGAGCCGCAGGTCTACGCCCCGCCTCGGCCCACCGACCGCCTGGCCGTGCCGCCCTTCGCCCAGCGG
GAGCGCTTCCACCGCTTCCAGCCCACCTATCCGTACCTGCAGCACGAGATCGACCTGCCGCCCACCATCTCGCTGTC
AGACGGGGAGGAGCCCCCACCCTACCAGGGCCCCTGCACCCTCCAGCTTCGGGACCCCGAGCAGCAGCTGGAACTGA
ACCGGGAGTCGGTGCGCGCACCCCCAAACAGAACCATCTTCGACAGTGACCTGATGGATAGTGCCAGGCTGGGCGGC
CCCTGCCCCCCCAGCAGTAACTCGGGCATCAGCGCCACGTGCTACGGCAGCGGCGGGCGCATGGAGGGGCCGCCGCC
CACCTACAGCGAGGTCATCGGCCACTACCCGGGGTCCTCCTTCCAGCACCAGCAGAGCAGTGGGCCGCCCTCCTTGC
TGGAGGGGACCCGGCTCCACCACACACACATCGCGCCCCTAGAGAGCGCAGCCATCTGGAGCAAAGAGAAGGATAAA
CAGAAAGGACACCCTCTCTAGGGTCCCCAGAAGGGC

FIGURE 46

GGCGAGAGGCGGGCTGAGGCGGCCCAGCGGCGGCAGGTGAGGCGGAACCAACCCTCCTGGCCATGGGAGGGGCCGTG
GTGGACGAGGGCCCCACAGGCGTCAAGGCCCCTGACGGCGGCTGGGGCTGGGCCGTGCTCTTCGGCTGTTTCGTCAT
CACTGGCTTCTCCTACGCCTTCCCCAAGGCCGTCAGTGTCTTCTTCAAGGAGCTCATACAGGAGTTTGGGATCGGCT
ACAGCGACACAGCCTGGATCTCCTCCATCCTGCTGGCCATGCTCTACGGGACAGGTCCGCTCTGCAGTGTGTGCGTG
AACCGCTTTGGCTGCCGGCCCGTCATGCTTGTGGGGGGTCTCTTTGCGTCGCTGGGCATGGTGGCTGCGTCCTTTTG
CCGGAGCATCATCCAGGTCTACCTCACCACTGGGGTCATCACGGGGTTGGGTTTGGCACTCAACTTCCAGCCCTCGC
TCATCATGCTGAACCGCTACTTCAGCAAGCGGCGCCCCATGGCCAACGGGCTGGCGGCAGCAGGTAGCCCTGTCTTC
CTGTGTGCCCTGAGCCCGCTGGGGCAGCTGCTGCAGGACCGCTACGGCTGGCGGGGCGGCTTCCTCATCCTGGGCGG
CCTGCTGCTCAACTGCTGCGTGTGTGCCGCACTCATGAGGCCCCTGGTGGTCACGGCCCAGCCGGGCTCGGGGCCGC
CGCGACCCTCCCGGCGCCTGCTAGACCTGAGCGTCTTCCGGGACCGCGGCTTTGTGCTTTACGCCGTGGCCGCCTCG
GTCATGGTGCTGGGGCTCTTCGTCCCGCCCGTGTTCGTGGTGAGCTACGCCAAGGACCTGGGCGTGCCCGACACCAA
GGCCGCCTTCCTGCTCACCATCCTGGGCTTCATTGACATCTTCGCGCGGCCGGCCGCGGGCTTCGTGGCGGGGCTTG
GGAAGGTGCGGCCCTACTCCGTCTACCTCTTCAGCTTCTCCATGTTCTTCAACGGCCTCGCGGACCTGGCGGGCTCT
ACGGCGGGCGACTACGGCGGCCTCGTGGTCTTCTGCATCTTCTTTGGCATCTCCTACGGCATGGTGGGGGCCCTGCA
GTTCGAGGTGCTCATGGCCATCGTGGGCACCCACAAGTTCTCCAGTGCCATTGGCCTGGTGCTGCTGATGGAGGCGG
TGGCCGTGCTCGTCGGGCCCCCTTCGGGAGGCAAACTCCTGGATGCGACCCACGTCTACATGTACGTGTTCATCCTG
GCGGGGGCCGAGGTGCTCACCTCCTCCCTGATTTTGCTGCTGGGCAACTTCTTCTGCATTAGGAAGAAGCCCAAAGA
GCCACAGCCTGAGGTGGCGGCCGCGGAGGAGGAGAAGCTCCACAAGCCTCCTGCAGACTCGGGGGTGGACTTGCGGG
AGGTGGAGCATTTCCTGAAGGCTGAGCCTGAGAAAAACGGGGAGGTGGTTCACACCCCGGAAACAAGTGTCTGAGTG
GCTGGGCGGGGCCGGCAGGCACAGGGAGGAGGTACAGAAGCCGGCAACGCTTGCTATTTATTTTACAAACTGGACTG
GCTCAGGCAGGGCCACGGCTGGGCTCCAGCTGCCGGCCCAGCGGATCGTCGCCCGATCAGTGTTTTGAGGGGGAAGG
TGGCGGGGTGGGAACCGTGTCATTCCAGAGTGGATCTGCGGTGAAGCCAAGCCGCAAGGTTACAAGGCATCCTCACC
AGGGGCCCCGCCTGCTGCTCCCAGGTGGCCTGCGGCCACTGCTATGCTCAAGGACCTGGAAACCCATGCTTCGAGAC
AACGTGACTTTAATGGAGGGTGGGTGGGCCGCAGACAGGCTGGCAGGGCAGGTGCTGCGTGGGGCCCTCTCCAGCC
CGTCCTACCCTGGGCTCACATGGGGCCTGTGCCCACCCCTCTTGAGTGTCTTGGGGACAGCTCTTTCCACCCCTGGA
AGATGGAAATAAACCTGCGTGTGGGTGGAGTGTTCTCGTGCCGAATTCAAAAAGCTT

FIGURE 47

CCCACGCGTCCGCCCACGCGTCCGCCGGGTCCTGCGCGCTCCGGACTGAGGTGGCGTCCCTGGGCCGGACGGCGGTG
TCCCGGCGTGGCGGGAAGCCGGCACTGGAGCGGGAGCGCACTGGGCGCGGGACCGGGAGGCGCAGGGACCGGACGGC
TCCCGAGTCGCCCACCTGACGGTACCGAGAGGGCGGCGCCCCTCCGAGCAGAGCCGTCCCGGCCACTCCCCTGGGAT
CTGACTTGGCTCTTGCGGTCGCGGGCACCGTGAAGCCCTGGGGTGTGCGTGGCTCCTCCTGGTAGGCGCCCTTTCCC
GGCGTCCGGCTTGGGGTGGTGGTGGCGTTGACTCCAGCCCCGCCTCTCCCTGGAGAGGAGGGCTCCACTCGCTCCTT
CGGCCTCCTCCCCTGGGGCCGCAGCGACTCGGGCCGGCTTCCTGCTTCCCTGCCTGCCGGCGGTCCCGCTGGCTAGA
AGAAGTCTTCACTTCCCAGGAGAGCCAAAGCGTGTCTGGCCCTAGGTGGGAAAAGAACTGGCTGTGACCTTTGCCCT
GACCTGGAAGGGCCCAGCCTTGGGCTGAATGGCAGCACCCACGCCCGCCCGTCCGGTGCTGACCCACCTGCTGGTGG
CTCTCTTCGGCATGGGCTCCTGGGCTGCGGTCAATGGGATCTGGGTGGAGCTACCTGTGGTGGTCAAAGAGCTTCCA
GAGGGTTGGAGCCTCCCCTCTTACGTCTCTGTGCTTGTGGCTCTGGGGAACCTGGGTCTGCTGGTGGTGACCCTCTG
GAGGAGGCTGGCCCCAGGAAAGGACGAGCAGGTCCCCATCCGGGTGGTGCAGGTGCTGGGCATGGTGGGCACAGCCC
TGCTGGCCTCTCTGTGGCACCATGTGGCCCCAGTGGCAGGACAGTTGCATTCTGTGGCCTTCTTAGCACTGGCCTTT
GTGCTGGCACTGGCATGCTGTGCCTCGAATGTCACTTTCCTGCCCTTCTTGAGCCACCTGCCACCTCGCTTCTTACG
GTCATTCTTCCTGGGTCAAGGCCTGAGTGCCCTGCTGCCCTGCGTGCTGGCCCTAGTGCAGGGTGTGGGCCGCCTCG
AGTGCCCGCCAGCCCCCATCAACGGCACCCCTGGCCCCCCGCTCGACTTCCTTGAGCGTTTTCCCGCCAGCACCTTC
TTCTGGGCACTGACTGCCCTTCTGGTCGCTTCAGCTGCTGCCTTCCAGGGTCTTCTGCTGCTGTTGCCGCCACCACC
ATCTGTACCCACAGGGGAGTTAGGATCAGGCCTCCAGGTGGGAGCCCCAGGAGCAGAGGAAGAGGTGGAAGAGTCCT
CACCACTGCAAGAGCCACCAAGCCAGGCAGCAGGCACCACCCCTGGTCCAGACCCTAAGGCCTATCAGCTTCTATCA
GCCCGCAGTGCCTGCCTGCTGGGCCTGTTGGCCGCCACCAACGCGCTGACCAATGGCGTGCTGCCTGCCGTGCAGAG
CTTTTCCTGCTTACCCTACGGGCGTCTGGCCTACCACCTGGCTGTGGTGCTGGGCAGTGCTGCCAATCCCCTGGCCT
GCTTCCTGGCCATGGGTGTGCTGTGCAGGTCCTTGGCAGGGCTGGGCGGCCTCTCTCTGCTGGGCGTGTTCTGTGGG
GGCTACCTGATGGCGCTGGCAGTCCTGAGCCCCTGCCCGCCCCTGGTGGGCACCTCGGCGGGGGTGGTCCTCGTGGT
GCTGTCGTGGGTGCTGTGTCTTGGCGTGTTCTCCTACGTGAAGGTGGCAGCCAGCTCCCTGCTGCATGGCGGGGGCC
GGCCGGCATTGCTGGCAGCCGGCGTGGCCATCCAGGTGGGCTCTCTGCTCGGCGCTGTTGCTATGTTCCCCCCGACC
AGCATCTATCACGTGTTCCACAGCAGAAAGGACTGTGCAGACCCCTGTGACTCCTGAGCCTGGGCAGGTGGGACCC
CGCTCCCCAACACCTGTCTTTCCCTCAATGCTGCCACCATGCCTGAGTGCCTGCAGCCCAGGAGGCCCGCACACCGG
TACACTCGTGGACACCTACACACTCCATAGGAGATCCTGGCTTTCCAGGGTGGGCAAGGGCAAGGAGCAGGCTTGGA
GCCAGGGACCAGTGGGGGCTGTAGGGTAAGCCCCTGAGCCTGGGACCTACATGTGGTTTGCGTAATAAAACATTTGT
ATTTAAAAAAAAAAAA

FIGURE 48

GCCAGCACAGCTGCCCTCTGGACCCTGCGGACCCCAGCCGAGCCCCTTCCTGAGTTCCACAGGCGCAGCCCCCGGGC
GGTCGGGCGGAGGGGTCCCCGGGGCGGTGCCAGGCGCAATCCTGGAGGGCGGCCGGGAGGAGGAGGTGCGCGCGGCC
ATGCACACCGTGGCTACGTCCGGACCCAACGCGTCCTGGGGGGCACCGGCCAACGCCTCCGGCTGCCCGGGCTGTGG
CGCCAACGCCTCGGACGGCCCAGTCCCTTCGCCGCGGGCCGTGGACGCCTGGCTCGTGCCGCTCTTCTTCGCGGCGC
TGATGCTGCTGGGCCTGGTGGGGAACTCGCTGGTCATCTACGTCATCTGCCGCCACAAGCCGATGCGGACCGTGACC
AACTTCTACATCGCCAACCTGGCGGCCACGGACGTGACCTTCCTCCTGTGCTGCGTCCCCTTCACGGCCCTGCTGTA
CCCGCTGCCCGGCTGGGTGCTGGGCGACTTCATGTGCAAGTTCGTCAACTACATCCAGCAGGTCTCGGTGCAGGCCA
CGTGTGCCACTCTGACCGCCATGAGTGTGGACCGCTGGTACGTGACGGTGTTCCCGTTGCGCGCCCTGCACCGCCGC
ACGCCCCGCCTGGCGCTGGCTGTCAGCCTCAGCATCTGGGTAGGCTCTGCGGCGGTGTCTGCGCCGGTGCTCGCCCT
GCACCGCCTGTCACCCGGGCCGCGCGCCTACTGCAGTGAGGCCTTCCCCAGCCGCGCCCTGGAGCGCGCCTTCGCAC
TGTACAACCTGCTGGCGCTGTACCTGCTGCCGCTGCTCGCCACCTGCGCCTGCTATGCGGCCATGCTGCGCCACCTG
GGCCGGGTCGCCGTGCGCCCCGCGCCCGCCGATAGCGCCCTGCAGGGGCAGGTGCTGGCAGAGCGCGCAGGCGCCGT
GCGGGCCAAGGTCTCGCGGCTGGTGGCGGCCGTGGTCCTGCTCTTCGCCGCCTGCTGGGGCCCCATCCAGCTGTTCC
TGGTGCTGCAGGCGCTGGGCCCCGCGGGCTCCTGGCACCCACGCAGCTACGCCGCCTACGCGCTTAAGACCTGGGCT
CACTGCATGTCCTACAGCAACTCCGCGCTGAACCCGCTGCTCTACGCCTTCCTGGGCTCGCACTTCCGACAGGCCTT
CCGCCGCGTCTGCCCCTGCGCGCCGCGCCGCCCCCGCCGCCCCCGCCGGCCCGGACCCTCGGACCCCGCAGCCCCAC
ACGCGGAGCTGCACCGCCTGGGGTCCCACCCGGCCCCCGCCAGGGCGCAGAAGCCAGGGAGCAGTGGGCTGGCCGCG
CGCGGGCTGTGCGTCCTGGGGGAGGACAACGCCCCTCTTTGAGCGGACCCGGTGGGAATCCGAGCGGCTCCCTCGGG
AGCGGGGACTGCTGGAACAGCGGCTATTCTTCTGTTATTAGTATTTTTTTACTGTCCAAGATCAACTGTGGAAATA
TTTTGGTCTCTTGTGACGTTCGGTGCAGTTTCGTTGTGAAGTTTGCTATTGATATTGAAATTATGACTTCTGTGTTT
CCTGAAATTAAACATGTGTCAACACAGGACTTTTTGGATCATTCCAGAAAGTGTCAGACGTTTAAAAAAAAAAAAAA

FIGURE 49

GGCGCGGGGCGCCATGGCACACCGAGCGGCTCCGTCTTCTGCTCCTCAGAGAGCCCGGCTGGCGGCCTGGGATGACA
AGATGTCTGGACTGCAATCCTGCACAGTTTTGAGAGGGAGATGACTTGAGTGGTTGGCTTTTATCTCCACAACAATG
TCCATGAACAATTCCAAACAGCTAGTGTCTCCTGCAGCTGCGCTTCTTTCAAACACAACCTGCCAGACGGAAAACCG
GCTTTCCGTATTTTTTTCAGTAATCTTCATGACAGTGGGAATCTTGTCAAACAGCCTTGCCATCGCCATTCTCATGA
AGGCATATCAGAGATTTAGACAGAAGTCCAAGGCATCGTTTCTGCTTTTGGCCAGCGGCCTGGTAATCACTGATTTC
TTTGGCCATCTCATCAATGGAGCCATAGCAGTATTTGTATATGCTTCTGATAAAGAATGGATCCGCTTTGACCAATC
AAATGTCCTTTGCAGTATTTTTGGTATCTGCATGGTGTTTTCTGGTCTGTGCCCACTTCTTCTAGGCAGTGTGATGG
CCATTGAGCGGTGTATTGGAGTCACAAAACCAATATTTCATTCTACGAAAATTACATCCAAACATGTGAAAATGATG
TTAAGTGGTGTGTGCTTGTTTGCTGTTTTCATAGCTTTGCTGCCCATCCTTGGACATCGAGACTATAAAATTCAGGC
GTCGAGGACCTGGTGTTTCTACAACACAGAAGACATCAAAGACTGGGAAGATAGATTTTATCTTCTACTTTTTTCTT
TTCTGGGGCTCTTAGCCCTTGGTGTTTCATTGTTGTGCAATGCAATCACAGGAATTACACTTTTAAGAGTTAAATTT
AAAAGTCAGCAGCACAGACAAGGCAGATCTCATCATTTGGAAATGGTAATCCAGCTCCTGGCGATAATGTGTGTCTC
CTGTATTTGTTGGAGCCCATTTCTGGTTACAATGGCCAACATTGGAATAAATGGAAATCATTCTCTGGAAACCTGTG
AAACAACACTTTTTGCTCTCCGAATGGCAACATGGAATCAAATCTTAGATCCTTGGGTATATATTCTTCTACGAAAG
GCTGTCCTTAAGAATCTCTATAAGCTTGCCAGTCAATGCTGTGGAGTGCATGTCATCAGCTTACATATTTGGGAGCT
TAGTTCCATTAAAAATTCCTTAAAGGTTGCTGCTATTTCTGAGTCACCAGTTGCAGAGAAATCAGCAAGCACCTAGC
TTAATAGGACAGTAAATCTGTGTGGGGCTAGAACAAAAATTAAGACATGTTTGGCAATATTTCAGTTAGTTAAATAC
CTGTAGCCTAACTGGAAAATTCAGGCTTCATCATGTAGTTTGAAGATACTATTGTCAGATTCAGGTTTTGAAATTTG
TCAAATAAACAGGATAACTGTACATTTTCAACTTGTTTTTGCCAATGGGAGGTAGACACAATAAAATAATGCCATGG
GAGTCACACTGAAAGCAATTTTGAGCTTATCTGTCTTATTTATGCTTTGAGTGAATCATCTGTTGAGGTCTAATGCC
TCTACTTGGCCTATTTGCCAGAGAACATCTTAATGCAGCCTGCATAGTGAAATGGTTATTTTGAGATCACCGCTCTG
TAGCTAACCCTTATAAACTAGGCTCAGTAAAATAAAGCACTCTTATTTTTTGATCTGGCCTATTTTGCCCCTCATTG
TGTAGCCTCAATTAACACATGCATGGTCATGACACCCAGAATTCATGATGGTTTGTTATAACAACCTCTGCATATTC
CAGGTCTGGCAGACAGGTTGCCTGACCCTGCAATCCTATCTAGAATGGGCCCATTCTTGTCACATTTGACAAATAGG
ACTGCCTACATTTATTATTATGAAGGTCGATTGTTGTTGGAAGTGTTTTTTCATGTCATAGATTAGCAATTTTCAAA
TAATTATTTTTTCTCTGAAAATTTTGTGTGTGATTGCACAATAAATAATTTTTAGAGAAACAAAGGCTCTTTCTCAG
CACATTGATGGGCAACTAGAATTACAGCAGTTTCAAACTCTACCATGGATAATGCAAACAAACCGAAGCTACATGCC
AATGATAGGTGCAAAGAATATTGGCAAAAGGTGCTTTACCTTGAGCCATTATTTGTGTCAGAGAACAAAAGAAACAG
AATCAATATATAAATTCAAAGACTATCTGCAGCTAGTGTGTTTCTTCTTTACACACATATACACACAGACATCAGAA
AATTCTGTTGAGAGCAGGTTCATTAAATTTGTAAGATGGCATATTCTAAAGCCTGTGCTACCAGTACTAAGAGGGGA
AGACTGGCAATTTGCCAAGCACTTGGGGATTATTATAACAATTAACTAGGAGATCAAGAGATAATAATCTCTCCCCA
AATTTTCCAATAATAATTGAGACTTTTTCTTTGCTTGTTTGTGTAATTCAACCAAAAGAATTTCAATACCCATTCAA
ATTGTCCTAGGTCTATCAGAAATTAGGGAAGGTAGTCCTGCTTTATAATAGGAAAATGTATTTCTGTATAAGATTTC
TTTGCTTTCATTAAAAATGGGATTCATTTAAAAATTAATCTTTCCCTGTTAGGCTGATTTCAGATTCTCTAGGAAAT
CTGGTGAAGTAACCAGAAGACTTTCAGATGGTTTATTTGCTTTCAGCAGAGAATTTATTTCATACAGTTACTTAAGA
GTGTTGATGTCTTGTGAACAGAGATATAAGGAACCATTCTCCATCCTTCCTTATCATGCTGGGTACAATGCTTCTAT
GAATATTTCCATGTATTTTGACTGGGGAGAGGCATGGAGAAGAAACTCTCATTCAGGGGCTCCAGGATCCTTCTCCT
TGAGGCTTCTAAATAAATGGCAGAATTCTTGCTGTATTGCCATGATGTCACCCTGGCCATGTGTACTGACTTGAGGA
GATCTTGCAACATGGCCATGTGCAAGGCTTTAAGGAGTGAGAGAGATGTGTACATATCTTAGGAGGGTTATCTATGT
TATCTGAGTATATGTTTGGGTAACCAAATTGGTCTTAAAAATGATGTTAACCCAAGAAGTAGACATCAAAAATTAAA
AAAAAAAAAAAAAAA

FIGURE 50A

ATGTCACGCATGAGCCGGCATCCAGACAAGGACCTGGCCCAGGGTCCCTTCAACACCTGCTGTGGCTGCACCTTAAT
GGCTAGTCCTGCTAATCTCCCTCCGAACACTCAAGCAGCTGCAGAAAGGGCCCTTTCCCAGAGCAGGTGGAAGAGGG
TGCAAGTGCCCGCCCCGGCATCCCTGTCCCCTTTCCCACTGGCCATGGCTTCAGTTGCCTTCTGGATCAGCATCCTG
ATTGGCTGCGAGGAACAGACTCTCTGCAGAGGCTGGCGTAGCCCAGTCGGGGATGGCTGTGCTCATGTGCCTCCCCA
GGAGCGAGCGACCGCAGAGGCAGACCCTCCAGGGCGGTGCAGCACCTCCACGGCGTCGTCTACCATCTGTGGCCTGT
GGCATTTGTCCCCACGGCTGCAGCTCCTCCCACCTCTGCATTCCAGGCAGGGAGAAGAGTCGGGCAAAACTGAGAAG
GTGCTTCTCTGGGGAAGAGAGGGCCTCCATGTGTGGAAACCCGGAGTCCTGCAGCCCGATGTCCACGGCACCTCCAA
CCTGGGGAACTGCTCCTTCCTGCACGGCCTGGTTACGGCTCCCTCTTGTCCACGGCGGGCGGGCGCCGAGCTGCTGA
ATTCTTTAGGAAGTCAGTTTGCCATTAGCCTTTTTGAAGTTCAGAGTGGAACTGAGCCCAGCATTACAGGTGTGGCC
ACGTCAGGGCAGTGCAGGGCTATGCCACTGAAGCATTATCTCCTTTTGCTGGTGGGCTGCCAAGCCTGGGGTGCAGG
GTTGGCCTACCATGGCTGCCCTAGCGAGTGTACCTGCTCCAGGGCCTCCCAGGTGGAGTGCACCGGGGCACGCATTG
TGGCGGTGCCCACCCCTCTGCCCTGGAACGCCATGAGCCTGCAGATCCTCAACACGCACATCACTGAACTCAATGAG
TCCCCGTTCCTCAATATTTCAGCCCTCATCGCCCTGAGGATTGAGAAGAATGAGCTGTCGCGCATCACGCCTGGGGC
CTTCCGAAACCTGGGCTCGCTGCGCTATCTCAGCCTCGCCAACAACAAGCTGCAGGTTCTGCCCATCGGCCTCTTCC
AGGGCCTGGACAGCCTTGAGTCTCTCCTTCTGTCCAGTAACCAGCTGTTGCAGATCCAGCCGGCCCACTTCTCCCAG
TGCAGCAACCTCAAGGAGCTGCAGTTGCACGGCAACCACCTGGAATACATCCCTGACGGAGCCTTCGACCACCTGGT
AGGACTCACGAAGCTCAATCTGGGCAAGAATAGCCTCACCCACATCTCACCCAGGGTCTTCCAGCACCTGGGCAATC
TCCAGGTCCTCCGGCTGTATGAGAACAGGCTCACGGATATCCCCATGGGCACTTTTGATGGGCTTGTTAACCTGCAG
GAACTGGCTCTACAGCAGAACCAGATTGGACTGCTCTCCCCTGGTCTCTTCCACAACAACCACAACCTCCAGAGACT
CTACCTGTCCAACAACCACATCTCCCAGCTGCCACCCAGCATCTTCATGCAGCTGCCCCAGCTCAACCGTCTTACTC
TCTTTGGGAATTCCCTGAAGGAGCTCTCTCTGGGGATCTTCGGGCCCATGCCCAACCTGCGGGAGCTTTGGCTCTAT
GACAACCACATCTCTTCTCTACCCGACAATGTCTTCAGCAACCTCCGCCAGTTGCAGGTCCTGATTCTTAGCCGCAA
TCAGATCAGCTTCATCTCCCCGGGTGCCTTCAACGGGCTAACGGAGCTTCGGGAGCTGTCCCTCCACACCAACGCAC
TGCAGGACCTGGACGGGAATGTCTTCCGCATGTTGGCCAACCTGCAGAACATCTCCCTGCAGAACAATCGCCTCAGA
CAGCTCCCAGGGAATATCTTCGCCAACGTCAATGGCCTCATGGCCATCCAGCTGCAGAACAACCAGCTGGAGAACTT
GCCCCTCGGCATCTTCGATCACCTGGGGAAACTGTGTGAGCTGCGGCTGTATGACAATCCCTGGAGGTGTGACTCAG
ACATCCTTCCGCTCCGCAACTGGCTCCTGCTCAACCAGCCTAGGTTAGGGACGGACACTGTACCTGTGTGTTTCAGC
CCAGCCAATGTCCGAGGCCAGTCCCTCATTATCATCAATGTCAACGTTGCTGTTCCAAGCGTCCATGTACCTGAGGT
GCCTAGTTACCCAGAAACACCATGGTACCCAGACACACCCAGTTACCCTGACACCACATCCGTCTCTTCTACCACTG
AGCTAACCAGCCCTGTGGAAGACTACACTGATCTGACTACCATTCAGGTCACTGATGACCGCAGCGTTTGGGGCATG
ACCCATGCCCATAGCGGGCTGGCCATTGCCGCCATTGTAATTGGCATTGTCGCCCTGGCCTGCTCCCTGGCTGCCTG
CGTCGGCTGTTGCTGCTGCAAGAAGAGGAGCCAAGCTGTCCTGATGCAGATGAAGGCACCCAATGAGTGTTAAAGAG
GCAGGCTGGAGCAGGGCTGGGGAATGATGGGACTGGAGGACCTGGGAATTTCATCTTTCTGCCTCCACCCCTGGGTC
CATGGAGCTTTCCCGTGATTGCTCTTTCTGGCCCTAGATAAAGGTGTGCCTACCTCTTCCTGACTTGCCTGATTCTC
CCGTAGAGAAGCAGGTCGTGCCGGACCTTCCTACAATCAGGAAGATAGATCCAACTGGCCATGGCAAAAGCCCTGGG
GATTTCCGATTCATACCCCTGGGCTTCCTTCGAGAGGGCTCTTCCTCCAAATCCTCCCCACCTGTCCTCCAAGAACA
GCCTTCCCTGCGCCCAGGCCCCCTCCGGGCCTCTGTAGACTCAGTTAGTCCACAGCCTGCTCACTTCGTGGAATAG
TTCTCCGCTGAGATAGCCCCTCTCGCCTAAGTATTATGTAAGTTGATTTCCCTTCTTTTGTTTCTCTTGTTTGTGCT
ATGGCTTGACCCAGCATGTCCCCTCAAATGAAAGTTCTCCCCTTGATTTTCTGCTCCTGAAGGCAGGGTGAGTTCTC
TCCTCAAAGAAGACTTCAAACCATTTAACTGGTTTCTTAAGAGCCGTCAATCAGCCTGGTTTTGGGGATGCTATGAA
AGAGAGAAGGAAAATCATGCCGCTCAGTTCCTGGAGACAGAAGAGCCGTCATCAGTGTCTCACTTGTGATTTTTATC
TGGAAAAGGAAGAAACACCCCAGCACAGCAAGCTCAGCCTTTTAGAGAAGGATATTTCCAAACTGCAAACTTTGCTT
TGAAAAGTTTAGCCCTTTAAGGAATGAAATCATGTAGAATTTTGGACTTCTAAAAACATTAAAATCAGCTTATTAAT
ACGGGATAGAGAAAGAAATCTGGTGCCTGGGGGTCCCTGTGTTCACCCCTAGAGTTTGTTTTAAAATTTTTAATTGA
AGCATGTGAAGTGTACCTGCAGAAAAGTGGGAACATGATAGTGTATGGCTTGGTGGATTTTCACAAACTGAACATAC
CTGTGTAATCAGCATCTAGACCCAGACCCAGAGCGTCACAAATATCCCCCATCCTGGGCTTTTCCCAGAGGAGATGG
GGGCTTCTGAAGATGGACTTACCTGGGACCTGCCCCCCATGAGCCAGGACGGTCCCCCCACAGTCAGCCTGTGCAAA
GGCCCCGTGGCCAGGGGTGGAGGAGAATATGTGGGTGTGGACAGGATGGGAGACTGTGGCCTGAACAGGAGATTTTA
TTATATCTGGAGACCCTGAGAGACCCTGAGACCTGGGGCACCCTGGCTGGCCAGGTCAGAAGCATCCTGACTGCAGA
GGTCCGTGCAGCCACACCCTCTTCCCTGCCAGCAAGCTGTCTGCGGCTCATCGGAGGCCCCTCCGCCTGGAGCCTTC
TATGGACGTGATATGCCTGTATCTGTTTTTAATTTTCATTCTTCACTTAGGGGAAGTGAAATCGCTCAGAGATGAGA
TCCTTTAATTGAAAACGAAGTGTAACGGAATCTAGTGTCTTTCTAATGTGGTAAAATTCTCCATCAACA

FIGURE 50B

TCACAGTCAGCTGGCAGCTGAACTTCAGAATCTCACTTACAGCAGGCGACACGGGGGTACACCGATGGGTCACACTG
GGTCTGGGGGCTCCCTGGAGCTCCTCCTGCGTGTGGTCTGGTTAGGAGTTGAGTTGTTTGCTCCAGGGTTATTCTCC
TCCTCGAGTCACAGTCACACGAATACCTGCCTTCTCTGGCTTTCCTGCTATACACATATTCACATGGCGCTCAAGAA
GTTAGGCTCATGGCAACGTGTGTCTTTCTCTGGACAACTGGCCCAGTTTACAGTGAAATGGAGAATTTCAGGTCTCC
ACGTCTGCCCAGGAAAGAACTTCAGCTGACTCCACGGGGATCTGGAAATCCACGACCAATCCCGATCGGCTCTTATT
AGCTCCCCGCTCCACAAGACACCTGTGCTTTGGAAATCCACCACCAATCCCGATCGGCTCTTATTAGCTCCCCGCTC
CACAAGACACCTGTGATCTGGAAATCTACCACCAATCCCGATCGGCTCTTATTAGCTCCCCGCTCCACAAGACACCT
GTGACATCCTCCAGGGCCACAGGAGCACGTGCTGACCAGTTTTCCCTTCCAGTTCCTGCACAAAAAGTGTCCAGAGG
GCTGTTTGCAAACACTAGTGCACTTTGTAGCTTTTCACCCTCTGTCCCAGGGAATCTAGGAGAGATGAGGCCCGTCA
GAGTCAAGAGATGTCATCCCCCCAGGGTCTCCAAGGCATTTCCACACTATTGGTGGCACCTGGAGGACATGCACCAA
GGCTTGCCAGAGCCAACAGGAAGTGAGCCCAGAGCATGGCACATGAGCATCACCCGCTGATGGTGGCCTGCTGTGCC
TGGTGCCAACAGGGGCATCCCGGCCCATACCCCTCCAGACAGGAAGCATGGGTTTGCCCACAGACCTGTCGGGTGCT
CCTGTGAGTGGCCTCCAGATGTCTTTGTGCATAGGCACAAGTGGGCCAGGGCTGGAGGGAGGTGGGAAACCTCATCA
TCCGGTGGGCCCTGCCAATCTTAACCCAGAACCCTTAGGTATTCCTGGCAGTAGCCATGACATTGGAGCACCTTCCT
CTCCAGCCAGAGGCTGACCTGAGGGCCACTGTCCTCAGATGACACCACCCAGGAGCACCCTAGGTGAGGGGTGAGGG
CCCCCTTATGTGAACCTCTTGCCTCTTCCTTTCTCCCATCAGAGTGGTTGGATGGAGCCATTGGCCTCCTTTTCTTC
AGCGGGCCCTTCAACCTCTCTGCACCATGTTGTCTGGCTGAGGAGCTACTAGAAAAGCTGAGTGGAGTCTCCTTTCC
AACAGGATGATGCATTTGCTCAATTCTCAGGGCTGGAATGAGCCGGCTGGTCCCCCAGAAAGCTGGAGTGGGGTACA
GAGTTCAGTTTTCCTCTCTGTTTACAGCTCCTTGACAGTCCCACGCCCATCTGGAGTGGGAGCTGGGAGTCAGTGTT
GGAGAAGAAACAACAAAAGCCAATTAGAACCACTATTTTTAAAAAGTGCTTACTGTGCACAGATACTCTTCAAGCAC
TGGACGTGGATTCTCTCTCTAGCCCTCAGCACCCCTGCGGTAGGAGTGCCGCCTCTACCCACTTGTGATGGGGTACA
GAGGCACTTGCTCTTCTGCATGGTGTTCAATAGGCTGGGAGTTTTATTTATCTCTTCAAACTTTGTACAAGAGCTCA
TGGCTTGTCTTGGGCTTTCGTCATTAAACCAAAGGAAATGGAAGCCATTCCCCTGTTGCTCTCCTTAGTCTTGGTCA
TCAGAACCTCACTTGGTACCATATAGATCAAAAGCTTTGTAACCACAGGAAAAAATAAACTCTTCCATCCCTTAAAG
AATAGAATAGTTTGTCCCTCTCATGGGAATTGGGCTGTATGTATATTGTTCTTCCTCCTTAGAATTTAGAGATACAA
GAGTTCTACTTAGAACTTTTCATGGACACAATTTCCACAACCTTTCAGATGCTGATGTAGAGCTATTGGGAAAGAAC
TTCCAAACTCAGGAAGTTTGCAGAGAGCAGACAGCTAGAGATAACTCGGGACCCAGAGTTGGTCGACAGATGTTAGA
TGTATCCTAGCTTTTAGCTATAAACCACTCAAAGATTCAGCCCCCAGATCCCACAGTCAGAACTGAATCTGCGTTGT
TGGGAAGCCAGCAGTGGCCTTGGGAAGGAAGCCATGGCTGTGGTTCAGAGAGGGTGGGCTGGCAAGCCACTTCCGGG
GAAAACTCCTTCCGCCCCAGGTTTCTTCTTCTCTTAAGGAGAGATTATTCTCACCAACCCGCTGCCTTCATGCTGCC
TTCAAAGCTAGATCATGTTTGCCTTGCTTAGAGAATTACTGCAAATCAGCCCCAGTGCTTGGCGATGCATTTACAGA
TTTCTAGGCCCTCAGGGTTTTGTAGAGTGTGAGCCCTGGTGGGCAGGGTTGGGGGGTCTGTCTTCTGCTGGATGCTG
CTTGTAATCCATTTGG

FIGURE 51A

ATGGCGCCGCCGCCGCCGCCCGTGCTGCCCGTGCTGCTGCTCCTGGCCGCCGCCGCCGCCCTGCCGGCGATGGGGCT
GCGAGCGGCCGCCTGGGAGCCGCGCGTACCCGGCGGACCCGCGCCTTCGCCCTCCGGCCCGGCTGTACCTACGCGG
TGGGCGCCGCTTGCACGCCCCGGGCGCCGCGGGAGCTGCTGGACGTGGGCCGCGATGGGCGGCTGGCAGGACGTCGG
CGCGTCTCGGGCGCGGGGCGCCCGCTGCCGCTGCAAGTCCGCTTGGTGGCCCGCAGTGCCCCGACGGCGCTGAGCCG
CCGCCTGCGGGCGCGCACGCACCTTCCCGGCTGCGGAGCCCGTGCCCGGCTCTGCGGAACCGGTGCCCGGCTCTGCG
GGGCGCTCTGCTTCCCCGTCCCCGGCGGCTGCGCGGCCGCGCAGCATTCGGCGCTCGCAGCTCCGACCACCTTACCC
GCCTGCCGCTGCCCGCCGCGCCCCAGGCCCCGCTGTCCCGGCCGTCCCATCTGCCTGCCGCCGGGCGGCTCGGTCCG
CCTGCGTCTGCTGTGCGCCCTGCGGCGCGCGGCTGGCGCCGTCCGGGTGGACTGGCGCTGGAGGCCGCCACCGCGG
GGACGCCCTCCGCGTCGCCATCCCCATCGCCGCCCCTGCCGCCGAACTTGCCCGAAGCCCGGGCGGGGCCGGCGCGA
CGGGCCCGGCGGGGCACGAGCGGCAGAGGGAGCCTGAAGTTTCCGATGCCCAACTACCAGGTGGCGTTGTTTGAGAA
CGAACCGGCGGGCACCCTCATCCTCCAGCTGCACGCGCACTACACCATCGAGGGCGAGGAGGAGCGCGTGAGCTATT
ACATGGAGGGGCTGTTCGACGAGCGCTCCCGGGGCTACTTCCGAATCGACTCTGCCACGGGCGCCGTGAGCACGGAC
AGCGTACTGGACCGCGAGACCAAGGAGACGCACGTCCTCAGGGTGAAAGCCGTGGACTACAGTACGCCGCCGCGCTC
GGCCACCACCTACATCACTGTCTTGGTCAAAGACACCAACGACCACAGCCCGGTCTTCGAGCAGTCGGAGTACCGCG
AGCGCGTGCGGGAGAACCTGGAGGTGGGCTACGAGGTGCTGACCATCCGCGCCAGCGACCGCGACTCGCCCATCAAC
GCCAACTTGCGTTACCGCGTGTTGGGGGGCGCGTGGGACGTCTTCCAGCTCAACGAGAGCTCTGGCGTGGTGAGCAC
ACGGGCGGTGCTGGACCGGGAGGAGGCGGCCGAGTACCAGCTCCTGGTGGAGGCCAACGACCAGGGGCGCAATCCGG
GCCCGCTCAGTGCCACGGCCACCGTGTACATCGAGGTGGAGGACGAGAACGACAACTACCCCCAGTTCAGCGAGCAG
AACTACGTGGTCCAGGTGCCCGAGGACGTGGGGCTCAACACGGCTGTGCTGCGAGTGCAGGCCACGGACCGGGACCA
GGGCCAGAACGCGGCCATTCACTACAGCATCCTCAGCGGGAACGTGGCCGGCCAGTTCTACCTGCACTCGCTGAGCG
GGATCCTGGATGTGATCAACCCCTTGGATTTCGAGGATGTCCAGAAATACTCGCTGAGCATTAAGGCCCAGGATGGG
GGCCGGCCCCCGCTCATCAATTCTTCAGGGGTGGTGTCTGTGCAGGTGCTGGATGTCAACGACAACGAGCCTATCTT
TGTGAGCAGCCCCTTCCAGGCCACGGTGCTGGAGAATGTGCCCCTGGGCTACCCCGTGGTGCACATTCAGGCGGTGG
ACGCGGACTCTGGAGAGAACGCCCGGCTGCACTATCGCCTGGTGGACACGGCCTCCACCTTTCTGGGGGGCGGCAGC
GCTGGGCCTAAGAATCCTGCCCCCACCCCTGACTTCCCCTTCCAGATCCACAACAGCTCCGGTTGGATCACAGTGTG
TGCCGAGCTGGACCGCGAGGAGGTGGAGCACTACAGCTTCGGGGTGGAGGCGGTGGACCACGGCTCGCCCCCCATGA
GCTCCTCCACCAGCGTGTCCATCACGGTGCTGGACGTGAATGACAACGACCCGGTGTTCACGCAGCCCACCTACGAG
CTTCGTCTGAATGAGGATGCGGCCGTGGGGAGCAGCGTGCTGACCCTGCAGGCCCGCGACCGTGACGCCAACAGTGT
GATTACCTACCAGCTCACAGGCGGCAACACCCGGAACCGCTTTGCACTCAGCAGCCAGAGAGGGGGCGGCCTCATCA
CCCTGGCGCTACCTCTGGACTACAAGCAGGAGCAGCAGTACGTGCTGGCGGTGACAGCATCCGACGGCACACGGTCG
CACACTGCGCATGTCCTAATCAACGTCACTGATGCCAACACCCACAGGCCTGTCTTTCAGAGCTCCCATTACACAGT
GAGTGTCAGTGAGGACAGGCCTGTGGGCACCTCCATTGCTACCCTCAGTGCCAACGATGAGGACACAGGAGAGAATG
CCCGCATCACCTACGTGATTCAGGACCCCGTGCCGCAGTTCCGCATTGACCCCGACAGTGGCACCATGTACACCATG
ATGGAGCTGGACTATGAGAACCAGGTCGCCTACACGCTGACCATCATGGCCCAGGACAACGGCATCCCGCAGAAATC
AGACACCACCACCCTAGAGATCCTCATCCTCGATGCCAATGACAATGCACCCCAGTTCCTGTGGGATTTCTACCAGG
GTTCCATCTTTGAGGATGCTCCACCCTCGACCAGCATCCTCCAGGTCTCTGCCACGGACCGGGACTCAGGTCCCAAT
GGGCGTCTGCTGTACACCTTCCAGGGTGGGGACGACGGCGATGGGGACTTCTACATCGAGCCCACGTCCGGTGTGAT
TCGCACCCAGCGCCGGCTGGACCGGGAGAATGTGGCCGTGTACAACCTTTGGGCTCTGGCTGTGGATCGGGGCAGTC
CCACTCCCCTTAGCGCCTCGGTAGAAATCCAGGTGACCATCTTGGACATTAATGACAATGCCCCCATGTTTGAGAAG
GACGAACTGGAGCTGTTTGTTGAGGAGAACAACCCAGTGGGGTCGGTGGTGGCAAAGATTCGTGCTAACGACCCTGA
TGAAGGCCCTAATGCCCAGATCATGTATCAGATTGTGGAAGGGGACATGCGGCATTTCTTCCAGCTGGACCTGCTCA
ACGGGGACCTGCGTGCCATGGTGGAGCTGGACTTTGAGGTCCGGCGGGAGTATGTGCTGGTGGTGCAGGCCACGTCG
GCTCCGCTGGTGAGCCGAGCCACGGTGCACATCCTTCTCGTGGACCAGAATGACAACCCGCCTGTGCTGCCCGACTT
CCAGATCCTCTTCAACAACTATGTCACCAACAAGTCCAACAGTTTCCCCACCGGCGTGATCGGCTGCATCCCGGCCC
ATGACCCCGACGTGTCAGACAGCCTCAACTACACCTTCGTGCAGGGCAACGAGCTGCGCCTGTTGCTGCTGGACCCC
GCCACGGGCGAACTGCAGCTCAGCCGCGACCTGGACAACAACCGGCCGCTGGAGGCGCTCATGGAGGTGTCTGTGTC
TGATGGCATCCACAGCGTCACGGCCTTCTGCACCCTGCGTGTCACCATCATCACGGACGACATGCTGACCAACAGCA
TCACTGTCCGCCTGGAGAACATGTCCCAGGAGAAGTTCCTGTCCCCGCTGCTGGCCCTCTTCGTGGAGGGGGTGGCC
GCCGTGCTGTCCACCACCAAGGACGACGTCTTCGTCTTCAACGTCCAGAACGACACCGACGTCAGCTCCAACATCCT
GAACGTGACCTTCTCGGCGCTGCTGCCTGGCGGCGTCCGCGGCCAGTTCTTCCCGTCGGAGGACCTGCAGGAGCAGA
TCTACCTGAATCGGACGCTGCTGACCACCATCTCCACGCAGCGCGTGCTGCCCTTCGACGACAACATCTGCCTGCGC
GAGCCCTGCGAGAACTACATGAAGTGCGTGTCCGTTCTGCGATTCGACAGCTCCGCGCCCTTCCTCAGC

FIGURE 51B

TCCACCACCGTGCTCTTCCGGCCCATCCACCCCATCAACGGCCTGCGCTGCCGCTGCCCGCCCGGCTTCACCGGCGA
CTACTGCGAGACGGAGATCGACCTCTGCTACTCCGACCCGTGCGGCGCCAACGGCCGCTGCCGCAGCCGCGAGGGCG
GCTACACCTGCGAGTGCTTCGAGGACTTCACTGGAGAGCACTGTGAGGTGGATGCCCGCTCAGGCCGCTGTGCCAAC
GGGGTGTGCAAGAACGGGGGCACCTGCGTGAACCTGCTCATCGGCGGCTTCCACTGCGTGTGTCCTCCTGGCGAGTA
TGAGAGGCCCTACTGTGAGGTGACCACCAGGAGCTTCCCGCCCCAGTCCTTCGTCACCTTCCGGGGCCTGAGACAGC
GCTTCCACTTCACCATCTCCCTCACGTTTGCCACTCAGGAAAGGAACGGCTTGCTTCTCTACAACGGCCGCTTCAAT
GAGAAGCACGACTTCATCGCCCTGGAGATCGTGGACGAGCAGGTGCAGCTCACCTTCTCTGCAGGCGAGACAACAAC
GACCGTGGCACCGAAGGTTCCCAGTGGTGTGAGTGACGGGCGGTGGCACTCTGTGCAGGTGCAGTACTACAACAAGC
CCAATATTGGCCACCTGGGCCTGCCCCATGGGCCGTCCGGGGAAAAGATGGCCGTGGTGACAGTGGATGATTGTGAC
ACAACCATGGCTGTGCGCTTTGGAAAGGACATCGGGAACTACAGCTGCGCTGCCCAGGGCACTCAGACCGGCTCCAA
GAAGTCCCTGGATCTGACCGGCCCTCTACTCCTGGGGGGTGTCCCCAACCTGCCAGAAGACTTCCCAGTGCACAACC
GGCAGTTCGTGGGCTGCATGCGGAACCTGTCAGTCGACGGCAAAAATGTGGACATGGCCGGATTCATCGCCAACAAT
GGCACCCGGGAAGGCTGCGCTGCTCGGAGGAACTTCTGCGATGGGAGGCGGTGTCAGAATGGAGGCACCTGTGTCAA
CAGGTGGAATATGTATCTGTGTGAGTGTCCACTCCGATTCGGCGGGAAGAACTGTGAGCAAGCCATGCCTCACCCCC
AGCTCTTCAGCGGTGAGAGCGTCGTGTCCTGGAGTGACCTGAACATCATCATCTCTGTGCCCTGGTACCTGGGGCTC
ATGTTCCGGACCCGGAAGGAGGACAGCGTTCTGATGGAGGCCACCAGTGGTGGGCCCACCAGCTTTCGCCTCCAGAT
CCTGAACAACTACCTCCAGTTTGAGGTGTCCCACGGCCCCTCCGATGTGGAGTCCGTGATGCTGTCCGGGTTGCGGG
TGACCGACGGGGAGTGGCACCACCTGCTGATCGAGCTGAAGAATGTTAAGGAGGACAGTGAGATGAAGCACCTGGTC
ACCATGACCTTGGACTATGGGATGGACCAGAACAAGGCAGATATCGGGGGCATGCTTCCCGGGCTGACGGTAAGGAG
CGTGGTGGTCGGAGGCGCCTCTGAAGACAAGGTCTCCGTGCGCCGTGGATTCCGAGGCTGCATGCAGGGAGTGAGGA
TGGGGGGGACGCCCACCAACGTCGCCACCCTGAACATGAACAACGCACTCAAGGTCAGGGTGAAGGACGGCTGTGAT
GTGGACGACCCCTGTACCTCGAGCCCCTGTCCCCCCAATAGCCGCTGCCACGACGCCTGGGAGGACTACAGCTGCGT
CTGTGACAAAGGGTACCTTGGAATAAACTGTGTGGATGCCTGTCACCTGAACCCCTGCGAGAACATGGGGGCCTGCG
TGCGCTCCCCCGGCTCCCCGCAGGGCTACGTGTGCGAGTGTGGGCCCAGTCACTACGGGCCGTACTGTGAGAACAAA
CTCGACCTTCCGTGCCCCAGAGGCTGGTGGGGAACCCCGTCTGTGGACCCTGCCACTGTGCCGTCAGCAAAGGCTT
TGATCCCGACTGTAATAAGACCAACGGCCAGTGCCAATGCAAGGAGAATTACTACAAGCTCCTAGCCCAGGACACCT
GTCTGCCCTGCGACTGCTTCCCCCATGGCTCCCACAGCCGCACTTGCGACATGGCCACCGGGCAGTGTGCCTGCAAG
CCCGGCGTCATCGGCCGCCAGTGCAACCGCTGCGACAACCCGTTTGCCGAGGTCACCACGCTCGGCTGTGAAGTGAT
CTACAATGGCTGTCCCAAAGCATTTGAGGCCGGCATCTGGTGGCCACAGACCAAGTTCGGGCAGCCGGCTGCGGTGC
CATGCCCTAAGGGATCCGTTGGAAATGCGGTCCGACACTGCAGCGGGGAGAAGGGCTGGCTGCCCCCAGAGCTCTTT
AACTGTACCACCATCTCCTTCGTGGACCTCAGGGCCATGAATGAGAAGCTGAGCCGCAATGAGACGCAGGTGGACGG
CGCCAGGGCCCTGCAGCTGGTGAGGGCGCTGCGCAGTGCTACACAGCACACGGGCACGCTCTTTGGCAATGACGTGC
GCACGGCCTACCAGCTGCTGGGCCACGTCCTTCAGCACGAGAGCTGGCAGCAGGGCTTCGACCTGGCAGCCACGCAG
GACGCCGACTTTCACGAGGACGTCATCCACTCGGGCAGCGCCCTCCTGGCCCCAGCCACCAGGGCGGCGTGGGAGCA
GATCCAGCGGAGCGAGGGCGGCACGGCACAGCTGCTCCGGCGCCTCGAGGGCTACTTCAGCAACGTGGCACGCAACG
TGCGGCGGACGTACCTGCGGCCCTTCGTCATCGTCACCGCCAACATGATTCTTGCTGTCGACATCTTTGACAAGTTC
AACTTTACGGGAGCCAGGGTCCCGCGATTCGACACCATCCATGAAGAGTTCCCCAGGGAGCTGGAGTCCTCCGTCTC
CTTCCCAGCCGACTTCTTCAGACCACCTGAAGAAAAAGAAGGCCCCCTGCTGAGGCCGGCTGGCCGGAGGACCACCC
CGCAGACCACGCGCCCGGGGCCTGGCACCGAGAGGGAGGCCCCGATCAGCAGGCGGAGGCGACACCCTGATGACGCT
GGCCAGTTCGCCGTCGCTCTGGTCATCATTTACCGCACCCTGGGGCAGCTCCTGCCCGAGCGCTACGACCCCGACCG
TCGCAGCCTCCGGTTGCCTCACCGGCCCATCATTAATACCCCGATGGTGAGCACGCTGGTGTACAGCGAGGGGGCTC
CGCTCCCGAGACCCCTGGAGAGGCCCGTCCTGGTGGAGTTCGCCCTGCTGGAGGTGGAGGAGCGAACCAAGCCTGTC
TGCGTGTTCTGGAACCACTCCCTGGCCGTTGGTGGACGGAGGGTGGTCTGCCCGGGGCTGCGAGCTCCTGTCCAG
GAACCGGACACATGTCGCCTGCCAGTGCAGCCACACAGCCAGCTTTGCGGTGCTCATGGATATCTCCAGGCGTGAGA
ACGGGGAGGTCCTGCCTCTGAAGATTGTCACCTATGCCGCTGTGTCCTTGTCACTGGCAGCCCTGCTGGTGGCCTTC
GTCCTCCTGAGCCTGGTCCGCATGCTGCGCTCCAACCTGCACAGCATTCACAAGCACCTCGCCGTGGCGCTCTTCCT
CTCTCAGCTGGTGTTCGTGATTGGGATCAACCAGACGGAAAACCCGTTTCTGTGCACAGTGGTTGCCATCCTCCTCC
ACTACATCTACATGAGCACCTTTGCCTGGACCCTCGTGGAGAGCCTGCATGTCTACCGCATGCTGACCGAGGTGCGC
AACATCGACACGGGGCCCATGCGGTTCTACTACGTCGTGGGCTGGGGCATCCCGGCCATTGTCACAGGACTGGCGGT
CGGCCTGGACCCCCAGGGCTACGGGAACCCCGACTTCTGCTGGCTGTCGCTTCAAGACACCCTGATTTGGAGCTTTG
CGGGGCCCATCGGAGCTGTTATAATCATCAACACAGTCACTTCTGTCCTATCTGCAAAGGTTTCCTGCCAAAGAAAG
CACCATTATTATGGAAAAAAGGATCGTCTCCCTGCTGAGGACCGCATTCCTCCTGCTGCTGCTCATC

FIGURE 51C

AGCGCCACCTGGCTGCTGGGGCTGCTGGCTGTGAACCGCGATGCACTGAGCTTTCACTACCTCTTCGCCATCTTCAG
CGGCTTACAGGGCCCCTTCGTCCTCCTTTTCCACTGCGTGCTCAACCAGGAGGTCCGGAAGCACCTGAAGGGCGTGC
TCGGCGGGAGGAAGCTGCACCTGGAGGACTCCGCCACCACCAGGGCCACCCTGCTGACGCGCTCCCTCAACTGCAAC
ACCACCTTCGGTGACGGGCCTGACATGCTGCGCACAGACTTGGGCGAGTCCACCGCCTCGCTGGACAGCATCGTCAG
GGATGAAGGGATCCAGAAGCTCGGCGTGTCCTCTGGGCTGGTGAGGGGCAGCCACGGAGAGCCAGACGCGTCCCTCA
TGCCCAGGAGCTGCAAGGATCCCCCTGGCCACGATTCCGACTCAGATAGCGAGCTGTCCCTGGATGAGCAGAGCAGC
TCTTACGCCTCCTCACACTCGTCAGACAGCGAGGACGATGGGGTGGGAGCTGAGGAAAAATGGGACCCGGCCAGGGG
CGCCGTCCACAGCACCCCCAAAGGGGACGCTGTGGCCAACCACGTTCCGGCCGGCTGGCCCGACCAGAGCCTGGCTG
AGAGTGACAGTGAGGACCCCAGCGGCAAGCCCCGCCTGAAGGTGGAGACCAAGGTCAGCGTGGAGCTGCACCGCGAG
GAGCAGGGCAGTCACCGTGGAGAGTACCCCCCGGACCAGGAGAGCGGGGGCGCAGCCAGGCTTGCTAGCAGCCAGCC
CCCAGAGCAGAGGAAAGGCATCTTGAAAAATAAAGTCACCTACCCGCCGCCGCTGACGCTGACGGAGCAGACGCTGA
AGGGCCGGCTCCGGGAGAAGCTGGCCGACTGTGAGCAGAGCCCCACATCCTCGCGCACGTCTTCCCTGGGCTCTGGC
GGCCCCGACTGCGCCATCACAGTCAAGAGCCCTGGGAGGGAGCCGGGGCGTGACCACCTCAACGGGGTGGCCATGAA
TGTGCGCACTGGGAGCGCCCAGGCCGATGGCTCCGACTCTGAGAAACCGTGAGGCAAGCCCGTCACCCCACACAGGC
TGCGGCATCACCCTCAGACCTTGGAGCCCAAGGGGCCACTGCCCTTGAAGTGGAGTGGGCCCAGAGTGTGGCGGTCC
CCATGGTGGCAGCCCCCCGACTGATCATCCAGACACAAAGGTCTTGGTTCTCCCAGGAGCTCAGGGCCTGTCAGACC
TGGTGACAAGTGCCAAAGGCCACAGGCATGAGGGAGGCGTGGACCACTGGGCCAGCACCGCTGAGTCCTAAGACTGC
AGTCAAAGCCAGAACTGAGAGGGGACCCCAGACTGGGCCCAGAGGCTGGCCAGAGTTCAGGAACGCCGGGCACAGAC
CAAAGACCGCGGTCCAGCCCCGCCCAGGCGGGCATCTCATGGCAGTGCGGACCCGTGGCTGGCAGCCCGGGCAGTCC
TTTGCAAAGGCACCCCTTGTCTTAAAATCACTTCGCTATGTGGGAAAGGTGGAGATACTTTTATATATTTGTATGGG
ACTCTGAGGAGGTGCAACCTGTATATATATTGCATTCGTGCTGACTTTGTTATCCCGAGAGATCCATGCAATGATCT
CTTGCTGTCTTCTCTGTCAAGATTGCACAGTTGTACTTGAATCTGGCATGTGTTGACGAAACTGGTGCCCCAGCAGA
TCAAAGGTGGGAAATACGTCAGCAGTGGGGCTAAAACCAAGCGGCTAGAAGCCCTACAGCTGCCTTCGGCCAGGAAG
TGAGGATGGTGTGGGCCCTCCCCGCCGGCCCCCTGGGTCCCCAGTGTTCGCTGTGTGTGCGTTTGTCCTCTGCTGCC
ATCTGCCCCGGCTGTGTGAATTCAAGACAGGGCAGTGCAGCACTAGGCAGGTGTGAGGAGCCCTGCTGAGGTCACTG
TGGGGCACGGTTGCCACACGGCTGTCATTTTTCACCTGGTCATTCTGTGACCACCACCCCCTCCCCTCACCGCCTCC
CAGGTGGCCCGGGAGCTGCAGGTGGGATGGCTTTGTCCTTTGCTCCTGCTCCCCGTGGGACCTGGACCTTAAAGC
GTTGCAGGTTCCTGATTTGGACAGAGGTGTGGGGCCTTCCAGGCCGTTACATACCTCCTGCCAATTCTCTAACTCTC
TGAGACTGCGAGGATCTCCAGGCAGGGTTCTCCCCTCTGGAGTCTGACCAATTACTTCATTTTGCTTCAAATGGCCA
ATTGTGCAGAGGGACAAAGCCACAGCCACACTCTTCAACGGTTACCAAACTGTTTTTGGAAATTCACACCAAGGTCG
GGCCCACTGCAGGCAGCTGGCACAGCGTGGCCCGAGGGGCTGTGGAACGGGTCCCGGAACTGTCAGACATGTTTGAT
TTTAGCGTTTCCTTTGTTCTTCAAATCAGGTGCCCAAATAAGTGATCAGCACAGCTGCTTCCAAATAGGAGAAACCA
TAAAATAGGATGAAAATCAAGTAAAATGCAAAGATGTCCACACTGTTTTAAACTTGACCCTGATGAAAATGTGAGCA
CTGTTAGCAGATGCCTATGGGAGAGGAAAAGCGTATCTGAAAATGGTCCAGGACAGGAGGATGAAATGAGATCCCAG
AGTCCTCACACCTGAATGAATTATACATGTGCCTTACCAGGTGAGTGGTCTTTCGAAGATAAAAAACTCTAGTCCCT
TTAAACGTTTGCCCCTGGCGTTTCCTAAGTACGAAAAGGTTTTAAGTCTTCGAACAGTCTCCTTTCATGACTTTAA
CAGGATTCTGCCCCCTGAGGTGTAATTTTTTTGTTCTATTTTTTTCCACGTACTCCACAGCCAACATCACGAGGTGT
AATTTTTAATTTGATCAGAACTGTTACCAAAAAACAACTGTCAGTTTTATTGAGATGGAAAAATGTAAACCTATTT
TTATTACTTAAGACTTTATGGGAGAGATTAGACACTGGAGGTTTTAACAGAACGTGTATTTATTAATGTTCAAAAC
ACTGGAATTACAAATGAGAAGAGTCTACAATAAATTAAGATTTTTGAATTTGTACTTCTGCGGTGCTGGTTTTTCTC
CACAAACACCCCCGCCCCTCCCCATGCCCAGGGTGGCCGTGGAAGGGACGGTTTACGGACGTGCAGCTGAGCTGTCC
GTGTCCCATGCTCCCTCAGCCAGTGGAACGTGCCGGAACTTTTGTCCATTCCCTAGTAGGCCTGCCACAGCCTAGA
TGGGCAGTTTTTGTCTTTCACCAAATTTGAGGACTTTTTTTTTTTGCCATTATTTCTTCAGTTTTCTTTTCTTGCAC
TGATCTTTCTCCTCTCCTTCTGTGACTCCAGTGACTCAGACGTTAGACCTCTTGATGTTTTCCCACTGGTCCCTGAG
GCTCTGTTC

FIGURE 52

CGGCCTAAGGTAGCGACGGGACTGGCCGGGGCGGCAGGACCCGAAGGCGCTAGGCGGATTCACCGGATGGGAGTTG
AATCGCGTCCCGGTCTTTCTAGCTGTGCCCGGAAATCGGGCGTGCGGGCAGCTACAGCAGAGAATCGGACAAGGAGG
GAAGAAAGAGATGGTNNNNNNNNNNNNNNNNNNNNNNNNNNNNNNNNNNNNNNNGAAGTGAGTGCAAGAGGAGCCGG
CTTAGCATCTAAACTGATTCTACCATCAGAAAAGAGGCCAAACTTCTATCATC<u>ATG</u>GTGGATGTGAAGTGTCTGAGT
GACTGTAAATTGCAGAACCAACTTGAGAAGCTTGGATTTTCACCTGGCCCAATACTACCTTCCACCAGAAAGTTGTA
TGAAAAAAGTTAGTACAGTTGTTGGTCTCACCTCCCTGTGCACCACCTGTGATGAATGGACCCAGAGAGCTGGATG
GAGCGCAGGACAGTGATGACAGCGAAGAGCTTAATATCATTTTGCAAGGAAATATCATACTCTCAACAGAAAAAAGC
AAGAAACTCAAAAAATGGCCTGAGGCTTCCACCACTAAACGCAAAGCTGTAGATACCTATTGCTTGGATTATAAGCC
TTCCAAGGGAAGAAGGTGGGCTGCAAGAGCACCAAGCACCAGAATCACATATGGGACTATCACCAAAGAGAGAGACT
ACTGCGCGGAAGACCAGACTATCGAGAGCTGGAGAGAAGAAGGTTTCCCAGTGGGCTTGAAGCTTGCTGTGCTTGGT
ATTTTCATCATTGTGGTGTTTGTCTACCTGACTGTGGAAAATAAGTCGCTGTTTGGT<u>TAA</u>GTAATTTAGGAGCAAAG
CAATGCTCCAAGCGAGGCCTCCTGCTTCAGGAAAGAACCAAAACACTACCCTGAAGGGCCAGCCTAGCCTGCAGCCC
TCCCTTGCAGGGAGCCTTCCCTTGCACTGTGCTGCTCTCACAGATCGGTGTCTGGGCTCAGCCAGGTGGAAGGAACC
TGCCTAACCAGGCACCTGTGTTAAGAGCATGATGGTTAGGAAATCCCCCAAGTCATGTCAACTCTCATTAAAGGTGC
TTCCATATTTGAGCAGGCGTCAAACAAGG

FIGURE 53

ACCGCTCCGGAGCGGGAGGGGAGGCTTCGCGGAACGCTCTCGGCGCCAGGACTCGCGTGCAAAGCCCAGGCCCGGGC
GGCCAGACCAAGAGGGAAGAAGCACAGAATTCCTCAACTCCCAGTGTGCCCATGAGTAAGAGCAAATGCTCCGTGGG
ACTCATGTCTTCCGTGGTGGCCCCGGCTAAGGAGCCCAATGCCGTGGGCCCGAAGGAGGTGGAGCTCATCCTTGTCA
AGGAGCAGAACGGAGTGCAGCTCACCAGCTCCACCCTCACCAACCCGCGGCAGAGCCCCGTGGAGGCCCAGGATCGG
GAGACCTGGGGCAAGAAGATCGACTTTCTCCTGTCCGTCATTGGCTTTGCTGTGGACCTGGCCAACGTCTGGCGGTT
CCCCTACCTGTGCTACAAAAATGGTGGCGGTGCCTTCCTGGTCCCCTACCTGCTCTTCATGGTCATTGCTGGGATGC
CACTTTTCTACATGGAGCTGGCCCTCGGCCAGTTCAACAGGGAAGGGGCCGCTGGTGTCTGGAAGATCTGCCCCATA
CTGAAAGGTGTGGGCTTCACGGTCATCCTCATCTCACTGTATGTCGGCTTCTTCTACAACGTCATCATCGCCTGGGC
GCTGCACTATCTCTTCTCCTCCTTCACCACGGAGCTCCCCTGGATCCACTGCAACAACTCCTGGAACAGCCCCAACT
GCTCGGATGCCCATCCTGGTGACTCCAGTGGAGACAGCTCGGGCCTCAACGACACTTTTGGGACCACACCTGCTGCC
GAGTACTTTGAACGTGGCGTGCTGCACCTCCACCAGAGCCATGGCATCGACGACCTGGGGCCTCCGCGGTGGCAGCT
CACAGCCTGCCTGGTGCTGGTCATCGTGCTGCTCTACTTCAGCCTCTGGAAGGGCGTGAAGACCTCAGGGAAGGTGG
TATGGATCACAGCCACCATGCCATACGTGGTCCTCACTGCCCTGCTCCTGCGTGGGGTCACCCTCCCTGGAGCCATA
GACGGCATCAGAGCATACCTGAGCGTTGACTTCTACCGGCTCTGCGAGGCGTCTGTTTGGATTGACGCGGCCACCCA
GGTGTGCTTCTCCCTGGGCGTGGGGTTCGGGGTGCTGATCGCCTTCTCCAGCTACAACAAGTTCACCAACAACTGCT
ACAGGGACGCGATTGTCACCACCTCCATCAACTCCCTGACGAGCTTCTCCTCCGGCTTCGTCGTCTTCTCCTTCCTG
GGGTACATGGCACAGAAGCACAGTGTGCCCATCGGGGACGTGGCCAAGGACGGGCCAGGGCTGATCTTCATCATCTA
CCCGGAAGCCATCGCCACGCTCCCTCTGTCCTCAGCCTGGGCCGTGGTCTTCTTCATCATGCTGCTCACCCTGGGTA
TCGACAGCGCCATGGGTGGTATGGAGTCAGTGATCACCGGGCTCATCGATGAGTTCCAGCTGCTGCACAGACACCGT
GAGCTCTTCACGCTCTTCATCGTCCTGGCGACCTTCCTCCTGTCCCTGTTCTGCGTCACCAACGGTGGCATCTACGT
CTTCACGCTCCTGGACCATTTTGCAGCCGGCACGTCCATCCTCTTTGGAGTGCTCATCGAAGCCATCGGAGTGGCCT
GGTTCTATGGTGTTGGGCAGTTCAGCGACGACATCCAGCAGATGACCGGGCAGCGGCCCAGCCTGTACTGGCGGCTG
TGCTGGAAGCTGGTCAGCCCCTGCTTTCTCCTGTTCGTGGTCGTGGTCAGCATTGTGACCTTCAGACCCCCCCACTA
CGGAGCCTACATCTTCCCCGACTGGGCCAACGCGCTGGGCTGGGTCATCGCCACATCCTCCATGGCCATGGTGCCCA
TCTATGCGGCCTACAAGTTCTGCAGCCTGCCTGGGTCCTTTCGAGAGAAACTGGCCTACGCCATTGCACCCGAGAAG
GACCGTGAGCTGGTGGACAGAGGGGAGGTGCGCCAGTTCACGCTCCGCCACTGGCTCAAGGTGTAGAGGGAGCAGAG
ACGAAGACCCCAGGAAGTCATCCTGCAATGGGAGAGACACGAACAAACCAAGGAAATCTAAGTTTCGAGAGAAAGGA
GGGCAACTTCTACTCTTCAACCTCTACTGAAAACACAAACAACAAAGCAGAAGACTCCTCTCTTCTGACTGTTTACA
CCTTTCCGTGCCGGGAGCGCACCTCGCCGTGTCTTGTGTTGCTGTAATAACGACGTAGATCTGTGCAGCGAGGTCCA
CCCCGTTGTTGTCCCTGCAGGGCAGAAAAACGTCTAACTTCATGCTGTCTGTGTGAGGCTCCCTCCCTCCCTGCTCC
CTGCTCCCGGCTCTGAGGCTGCCCCAGGGGCACTGTGTTCTCAGGCGGGGATCACGATCCTTGTAGACGCACCTGCT
GAGAATCCCCGTGCTCACAGTAGCTTCCTAGACCATTTACTTTGCCCATATTAAAAAGCCAAGTGTCCTGCTTGGTT
TAGCTGTGCAGAAGGTGAAATGGAGGAAACCACAAATTCATGCAAAGTCCTTTCCCGATGCGTGGCTCCCAGCAGAG
GCCGTAAATTGAGCGTTCAGTTGACACATTGCACACACAGTCTGTTCAGAGGCATTGGAGGATGGGGGTCCTGGTAT
GTCTCACCAGGAAATTCTGTTTATGTTCTTGCAGCAGAGAGAAATAAAACTCCTTGAAACCAGCTCAGGCTACTGCC
ACTCAGGCAGCCTGTGGGTCCTTGTGGTGTAGGGAACGGCCTGAGAGGAGCGTGTCCTATCCCCGGACGCATGCAGG
GCCCCCACAGGAGCGTGTCCTATCCCCGGACGCATGCAGGGCCCCCACAGGAGCATGTCCTATCCCTGGACGCATGC
AGGGCCCCCACAGGAGCGTGTACTACCCCAGAACGCATGCAGGGCCCCCACAGGAGCGTGTACTACCCCAGGACGCA
TGCAGGGCCCCCACTGGAGCGTGTACTACCCCAGGACGCATGCAGGGCCCCCACAGGAGCGTGTCCTATCCCCGGAC
CGGACGCATGCAGGGCCCCCACAGGAGCGTGTACTACCCCAGGACGCATGCAGGGCCCCCACAGGAGCGTGTACTAC
CCCAGGATGCATGCAGGGCCCCCACAGGAGCGTGTACTACCCCAGGACGCATGCAGGGCCCCCATGCAGGCAGCCTG
CAGACCAACACTCTGCCTGGCCTTGAGCCGTGACCTCCAGGAAGGGACCCCACTGGAATTTTATTTCTCTCAGGTGC
GTGCCACATCAATAACAACAGTTTTTATGTTTGCGAATGGCTTTTTAAAATCATATTTACCTGTGAATCAAAACAAA
TTCAAGAATGCAGTATCCGCGAGCCTGCTTGCTGATATTGCAGTTTTTGTTTACAAGAATAATTAGCAATACTGAGT
GAAGGATGTTGGCCAAAAGCTGCTTTCCATGGCACACTGCCCTCTGCCACTGACAGGAAAGTGGATGCCATAGTTTG
AATTCATGCCTCAAGTCGGTGGGCCTGCCTACGTGCTGCCCGAGGGCAGGGGCCGTGCAGGGCCAGTCATGGCTGTC
CCCTGCAAGTGGACGTGGGCTCCAGGGACTGGAGTGTAATGCTCGGTGGGAGCCGTCAGCCTGTGAACTGCCAGGCA
GCTGCAGTTAGCACAGAGGATGGCTTCCCCATTGCCTTCTGGGGAGGGACACAGAGGACGGCTTCCCCATCGCCTTC
TGGCCGCTGCAGTCAGCACAGAGAGCGGCTTCCCCATTGCCTTCTGGGGAGGGACACAGAGGACAGTTTCCCCATCG
CCTTCTGGTTGTTGAAGACAGCACAGAGAGCGGCTTCCCCATCGCCTTCTGGGGAGGGGCTCCGTGTAGCAACCCAG
GTGTTGTCCGTGTCTGTTGACCAATCTCTATTCAGCATCGTGTGGGTCCCTAAGCACAATAAAAGACATCCACAATG
GAAAAAAAAAAAGGAATTC

FIGURE 54

CGGACGCGTGGGTGAGCAGGGACGGTGCACCGGACGGCGGGATCGAGCAAATGGGTCTGGCCATGGAGCACGGAGGG
TCCTACGCTCGGGCGGGGGGCAGCTCTCGGGGCTGCTGGTATTACCTGCGCTACTTCTTCCTCTTCGTCTCCCTCAT
CCAATTCCTCATCATCCTGGGGCTCGTGCTCTTCATGGTCTATGGCAACGTGCACGTGAGCACAGAGTCCAACCTGC
AGGCCACCGAGCGCCGAGCCGAGGGCCTATACAGTCAGCTCCTAGGGCTCACGGCCTCCCAGTCCAACTTGACCAAG
GAGCTCAACTTCACCACCCGCGCCAAGGATGCCATCATGCAGATGTGGCTGAATGCTCGCCGCGACCTGGACCGCAT
CAATGCCAGCTTCCGCCAGTGCCAGGGTGACCGGGTCATCTACACGAACAATCAGAGGTACATGGCTGCCATCATCT
TGAGTGAGAAGCAATGCAGAGATCAATTCAAGGACATGAACAAGAGCTGCGATGCCTTGCTCTTCATGCTGAATCAG
AAGGTGAAGACGCTGGAGGTGGAGATAGCCAAGGAGAAGACCATTTGCACTAAGGATAAGGAAAGCGTGCTGCTGAA
CAAACGCGTGGCGGAGGAACAGCTGGTTGAATGCGTGAAAACCCGGGAGCTGCAGCACCAAGAGCGCCAGCTGGCCA
AGGAGCAACTGCAAAAGGTGCAAGCCCTCTGCCTGCCCCTGGACAAGGACAAGTTTGAGATGGACCTTCGTAACCTG
TGGAGGGACTCCATTATCCCACGCAGCCTGGACAACCTGGGTTACAACCTCTACCATCCCCTGGGCTCGGAATTGGC
CTCCATCCGCAGAGCCTGCGACCACATGCCCAGCCTCATGAGCTCCAAGGTGGAGGAGCTGGCCCGGAGCCTCCGGG
CGGATATCGAACGCGTGGCCCGCGAGAACTCAGACCTCCAACGCCAGAAGCTGGAAGCCCAGCAGGGCCTGCGGGCC
AGTCAGGAGGCGAAACAGAAGGTGGAGAAGGAGGCTCAGGCCCGGGAGGCCAAGCTCCAAGCTGAATGCTCCCGGCA
GACCCAGCTAGCGCTGGAGGAGAAGGCGGTGCTGCGGAAGGAACGAGACAACCTGGCCAAGGAGCTGGAAGAGAAGA
AGAGGGAGGCGGAGCAGCTCAGGATGGAGCTGGCCATCAGAAACTCAGCCCTGGACACCTGCATCAAGACCAAGTCG
CAGCCGATGATGCCAGTGTCAAGGCCCATGGGCCCTGTCCCCAACCCCCAGCCCATCGACCCAGCTAGCCTGGAGGA
GTTCAAGAGGAAGATCCTGGAGTCCCAGAGGCCCCCTGCAGGCATCCCTGTAGCCCCATCCAGTGGCTGAGGAGGCT
CCAGGCCTGAGGACCAAGGGATGGCCCGACTCGGCGGTTTGCGGAGGATGCAGGGATATGCTCACAGCGCCCGACAC
AACCCCCTCCCGCCGCCCCCAACCACCCAGGGCCACCATCAGACAACTCCCTGCATGCAAACCCCTAGTACCCTCTC
ACACCCGCACCCGCGCCTCACGATCCCTCACCCAGAGCACACGGCCGCGGAGATGACGTCACGCAAGCAACGGCGCT
GACGTCACATATCACCGTGGTGATGGCGTCACGTGGCCATGTAGACGTCACGAAGAGATATAGCGATGGCGTCGTGC
AGATGCAGCACGTCGCACACAGACATGGGGAACTTGGCATGACGTCACACCGAGATGCAGCAACGACGTCACGGGCC
ATGTCGACGTCACACATATTAATGTCACACAGACGCGGCGATGGCATCACACAGACGGTGATGATGTCACACACAGA
CACAGTGACAACACACACCATGACAACGACACCTATAGATATGGCACCAACATCACATGCACGCATGCCCTTTCACA
CACACTTTCTACCCAATTCTCACCTAGTGTCACGTTCCCCCGACCCTGGCACACGGGCCAAGGTACCCACAGGATCC
CATCCCCTCCCGCACAGCCCTGGGCCCCAGCACCTCCCCTCCTCCAGCTTCCTGGCCTCCCAGCCACTTCCTCACCC
CCAGTGCCTGGACCCGGAGGTGAGAACAGGAAGCCATTCACCTCCGCTCCTTGAGCGTGAGTGTTTCCAGGACCCCC
TCGGGGCCCTGAGCCGGGGGTGAGGGTCACCTGTTGTCGGGAGGGGAGCCACTCCTTCTCCCCCAACTCCCAGCCCT
GCCTGTGGCCCGTTGAAATGTTGGTGGCACTTAATAAATATTAGTAAATCCTTAAAAAAAAAAAAAAAAAAAAAAAA
AAAAAAA

FIGURE 55

CGGACTTGGCTTGTTAGAAGGCTGAAAGATGATGGCAGGAATGAAAATCCAGCTTGTATGCATGCTACTCCTGGCTT
TCAGCTCCTGGAGTCTGTGCTCAGATTCAGAAGAGGAAATGAAAGCATTAGAAGCAGATTTCTTGACCAATATGCAT
ACATCAAAGATTAGTAAAGCACATGTTCCCTCTTGGAAGATGACTCTGCTAAATGTTTGCAGTCTTGTAAATAATTT
GAACAGCCCAGCTGAGGAAACAGGAGAAGTTCATGAAGAGGAGCTTGTTGCAAGAAGGAAACTTCCTACTGCTTTAG
ATGGCTTTAGCTTGGAAGCAATGTTGACAATATACCAGCTCCACAAAATCTGTCACAGCAGGGCTTTTCAACACTGG
GAGTTAATCCAGGAAGATATTCTTGATACTGGAAATGACAAAAATGGAAAGGAAGAAGTCATAAAGAGAAAAATTCC
TTATATTCTGAAACGGCAGCTGTATGAGAATAAACCCAGAAGACCCTACATACTCAAAAGAGATTCTTACTATTACT
GAGAGAATAAATCATTTATTTACATGTGATTGTGATTCATCATCCCTTAATTAAATATCAAATTATATTTGTGTGAA
AATGTGACAAACACACTTATCTGTCTCTTCTACAATTGTGGTTTATTGAATGTGTTTTTCTGCACTAATAGAAATTA
GACTAAGTGTTTTCAAATAAATCTAAATCTTCAAAAAAAAAAAAAAAAAAATGGGGCCGCAATT

FIGURE 56

CGCGGGGCGCGGAGTCGGCGGGGCCTCGCGGGACGCGGGCAGTGCGGAGACCGCGGCGCTGAGGACGCGGGAGCCGG
GAGCGCACGCGCGGGGTGGAGTTCAGCCTACTCTTTCTTAGATGTGAAAGGAAAGGAAGATCATTTCATGCCTTGTT
GATAAAGGTTCAGACTTCTGCTGATTCATAACCATTTGGCTCTGAGCTATGACAAGAGAGGAAACAAAAAGTTAAAC
TTACAAGCCTGCCATAAGTGAGAAGCAAACTTCCTTGATAACATGCTTTTGCGAAGTGCAGGAAAATTAAATGTGGG
CACCAAGAAAGAGGATGGTGAGAGTACAGCCCCCACCCCCCGTCCAAAGGTCTTGCGTTGTAAATGCCACCACCATT
GTCCAGAAGACTCAGTCAACAATATTTGCAGCACAGACGGATATTGTTTCACGATGATAGAAGAGGATGACTCTGGG
TTGCCTGTGGTCACTTCTGGTTGCCTAGGACTAGAAGGCTCAGATTTTCAGTGTCGGGACACTCCCATTCCTCATCA
AAGAAGATCAATTGAATGCTGCACAGAAAGGAACGAATGTAATAAAGACCTACACCCTACACTGCCTCCATTGAAAA
ACAGAGATTTTGTTGATGGACCTATACACCACAGGGCTTTACTTATATCTGTGACTGTCTGTAGTTTGCTCTTGGTC
CTTATCATATTATTTTGTTACTTCCGGTATAAAAGACAAGAAACCAGACCTCGATACAGCATTGGGTTAGAACAGGA
TGAAACTTACATTCCTCCTGGAGAATCCCTGAGAGACTTAATTGAGCAGTCTCAGAGCTCAGGAAGTGGATCAGGCC
TCCCTCTGCTGGTCCAAAGGACTATAGCTAAGCAGATTCAGATGGTGAAACAGATTGGAAAAGGTCGCTATGGGGAA
GTTTGGATGGGAAAGTGGCGTGGCGAAAAGGTAGCTGTGAAAGTGTTCTTCACCACAGAGGAAGCCAGCTGGTTCAG
AGAGACAGAAATATATCAGACAGTGTTGATGAGGCATGAAAACATTTTGGGTTTCATTGCTGCAGATATCAAAGGGA
CAGGGTCCTGGACCCAGTTGTACCTAATCACAGACTATCATGAAAATGGTTCCCTTTATGATTATCTGAAGTCCACC
ACCCTAGACGCTAAATCAATGCTGAAGTTAGCCTACTCTTCTGTCAGTGGCTTATGTCATTTACACACAGAAATCTT
TAGTACTCAAGGCAAACCAGCAATTGCCCATCGAGATCTGAAAAGTAAAAACATTCTGGTGAAGAAAAATGGAACTT
GCTGTATTGCTGACCTGGGCCTGGCTGTTAAATTTATTAGTGATACAAATGAAGTTGACATACCACCTAACACTCGA
GTTGGCACCAAACGCTATATGCCTCCAGAAGTGTTGGACGAGAGCTTGAACAGAAATCACTTCCAGTCTTACATCAT
GGCTGACATGTATAGTTTTGGCCTCATCCTTTGGGAGGTTGCTAGGAGATGTGTATCAGGAGGTATAGTGGAAGAAT
ACCAGCTTCCTTATCATGACCTAGTGCCCAGTGACCCCTCTTATGAGGACATGAGGGAGATTGTGTGCATCAAGAAG
TTACGCCCCTCATTCCCAAACCGGTGGAGCAGTGATGAGTGTCTAAGGCAGATGGGAAAACTCATGACAGAATGCTG
GGCTCACAATCCTGCATCAAGGCTGACAGCCCTGCGGGTTAAGAAAACACTTGCCAAAATGTCAGAGTCCCAGGACA
TTAAACTCTGATAGGAGAGGAAAAGTAAGCATCTCTGCAGAAAGCCAACAGGTACTCTTCTGTTTGTGGGCAGAGCA
AAAGACATCAAATAAGCATCCACAGTACAAGCCTTGAACATCGTCCTGCTTCCCAGTGGGTTCAGACCTCACCTTTC
AGGGAGCGACCTGGGCAAAGACAGAGAAGCTCCCAGAAGGAGAGATTGATCCATGTCTGTTTGTAGGACGGAGAAAC
CGCTTGGGTAACTTGTTCAAGATATGATGCATGTTGCTTTCTAAGAAAGCCCTGTATTTTGTGATTGCCTTTTTTTT
TTTTTAAGATGCTTTCATTTTGCCAAAATAAAACAGATAATGTGGATGGTTTAAGGGTTATAGTATTATAGTTTAAA
TAATAACAACAAAATTCTTCCCAGGAACTCTGCTGGAAGGTAAATTAAAATACTTGTTTTTCCATTGGTAAAATATT
GTTGCACTCTGTGAACCAAAAGACAGTCTAAGTTGGAGGACATAGAACGGAACTCATCTTAAACATACTCCCCACCC
CGTCTTGGCCTCCTCAGACCACTTTGGCCATCCCTGCATTTGGGGCCGCTATGGTAATGTGAATGCACTGGGTACAA
ACACCGCCTGTCTAGGACCACATTTGGAATTCCTGCAGGTGGCCTTTTGCAGCTTCAGGCAATATGGAACAAATGAA
GGTTTATGTGACTCTAATAGAAGTAATTGTTGATAGGTGTTTTTCAGATCCACTTCTGTTTCTGATTGAGTTAGGCA
TCTCTTTCATGGTAAAACCCTTTTCATTAAACACAAAAAAAGCTTTTTTTTTTTTTTTTTTTTTTTTTTTTTTTTAA
TGTGCAGAGGATTGACCTGTGCATGCTTTTGATCTCTCATTCAAAGGATCAATATTAAATAAAATTGTCATGAGCTG
TGTTGAAGACAGGGTGCTTTCAAATAGAGGTAATTTGCTCTTGTGTTGTAAGAGGAACATGTCAACAAAGATAGGAA
ATGAGGGTGATCGTGCAGATGGCTTGTATCTTATATATGCAAAGGAGCCAATCTCAGAAGCACAAAGAAAAAAGTGT
GCATACCTTATTTTGTACAGATAAAGATGATGTCTTTTTGTTATTGTCTGTCTGTTTTGTATGTGTCTGAGATAAGG
GATAGAGAGGAAACATCCGTCAGGCTAATTTAACTACATTTTATTTTAAAAATAGAGAAACATAACCTCTAGATGGG
ACAGCAGAGGACAGTTAGTAGAGGCCACAAACTGTTATGGGCTGCTGTGTTTTGTTCTAAAATCAATATGGTTGGAG
CATGTATATCTTAGGTGATCATTTCACATCTTAGGAATGCCTACTCATTTTATTTTATTCTAGTGATGCTCAATTCA
CTATTTAATTTATTATATTTTCTCTTCTGTGGCACTTATACAAAATATCTCTTCACCTACTTAGTTCTACAGGGTTT
TAACTTTGGAGCAACATGAATAAAATCATCGAGAAGGCCAATATTGTTTAGCAACATGAATACAATACAGTTTAAAG
TTGTACACATCCTGCTCAACTTTATTCATATACATTTCCTTTCTGTGGTTTTCTTTTGCTTCTTAGAAATTCTGTTA
GTGGTTAGTAAAGAATTTGAAAGTACTTTCTCCTTGCTGTTTTTTTTTTTTTTTAAGACATTCCTCCCAGAATACTC
CAGGGGGCAGTGTTTTATAACACATTTTCCCCACTGGGTGATTGAAGGATGGAGGATTTTTGAAAATTTGACAGCTA
CATGAAACATGAGAAAACATTTTCCTCACTTCTGAAGTCGGTTTGCAGCTGGTAACTTGTTCATCCAGAAAACATTC
TAAAGCAATGAGACTTTGTGAGCTGTGCTTACAGTTTGGGAGAATCATGAAGATTCTTTCTATATTTTGCATTTACT
TCCCAGTGCTTCATAGCTGCATTTTG

FIGURE 57

MLRTAMGLRSWLAAPWGALPPRPPLLLLLLLLLLLQPPPPTWALSPRISLPLGSEERPFLRFEAEHISNYTALLLSR
DGRTLYVGAREALFALSSNLSFLPGGEYQELLWGADAEKKQQCSFKGKDPQRDCQNYIKILLPLSGSHLFTCGTAAF
SPMCTYINMENFTLARDEKGNVLLEDGKGRCPFDPNFKSTALVVDGELYTGTVSSFQGNDPAISRSQSLRPTKTESS
LNWLQDPAFVASAYIPESLGSLQGDDDKIYFFFSETGQEFEFFENTIVSRIARICKGDEGGERVLQQRWTSFLKAQL
LCSRPDDGFPFNVLQDVFTLSPSPQDWRDTLFYGVFTSQWHRGTTEGSAVCVFTMKDVQRVFSGLYKEVNRETQQWY
TVTHPVPTPRPGACITNSARERKINSSLQLPDRVLNFLKDHFLMDGQVRSRMLLLQPQARYQRVAVHRVPGLHHTYD
VLFLGTGDGRLHKAVSVGPRVHIIEELQIFSSGQPVQNLLLDTHRGLLYAASHSGVVQVPMANCSLYRSCGDCLLAR
DPYCAWSGSSCKHVSLYQPQLATRPWIQDIEGASAKDLCSASSVVSPSFVPTGEKPCEQVQFQPNTVNTLACPLLSN
LATRLWLRNGAPVNASASCHVLPTGDLLLVGTQQLGEFQCWSLEEGFQQLVASYCPEVVEDGVADQTDEGGSVPVII
STSRVSAPAGGKASWGADRSYWKEFLVMCTLFVLAVLLPVLFLLYRHRNSMKVFLKQGECASVHPKTCPVVLPPETR
PLNGLGPPSTPLDHRGYQSLSDSPPGARVFTESEKRPLSIQDSFVEVSPVCPRPRV
RLGSEIRDSVV

Signal sequence.

amino acids 1-37

Transmembrane domain.

amino acids 717-737

N-glycosylation sites.

amino acids 69-72, 96-99, 165-168, 410-413, 525-528, 630-633

N-myristoylation sites.

amino acids 85-90, 205-210, 212-217, 251-256, 342-347, 351-356, 355-360, 397-402, 431-436, 456-461, 467-472, 508-513, 626-631, 703-708, 709-714

Leucine zipper pattern.

amino acids 12-33

FIGURE 58

MDCRKMARFSYSVIWIMAISKVFELGLVAGLGHQEFARPSRGYLAFRDDSIWPQEEPAIRPRSSQRVPPMGIQHSKE
LNRTCCLNGGTCMLGSFCACPPSFYGRNCEHDVRKENCGSVPHDTWLPKKCSLCKCWHGQLRCFPQAFLPGCDGLVM
DEHLVASRTPELPPSARTTTFMLVGICLSIQSYY

Transmembrane domain.

amino acids 7-27

N-glycosylation site.

amino acids 79-82

N-myristoylation sites.

amino acids 26-31, 71-76, 92-97, 136-141, 179-184

EGF-like domain cysteine pattern signature.

amino acids 95-107

FIGURE 59

MAARALCMLGLVLALLSSSSAEEYVGLSANQCAVPAKDRVDCGYPHVTPKECNNRGCCFDSRIPGVPWCFKPLQEAE
CTF

Signal sequence.
amino acids 1-21

Tyrosine kinase phosphorylation site.
amino acids 37-44

N-myristoylation sites.
amino acids 10-15, 26-31, 65-70

P-type 'Trefoil' domain signature.
amino acids 39-59

Trefoil (P-type) domain.
amino acids 31-72

FIGURE 60

MRIAVICFCLLGITCAIPVKQADSGSSEEKQLYNKYPDAVATWLNPDPSQKQNLLAPQNAVSSEETNDFKQETLPSK
SNESHDHMDDMDDEDDDDHVDSQDSIDSNDSDDVDDTDDSHQSDESHHSDESDELVTDFPTDLPATEVFTPVVPTVD
TYDGRGDSVVYGLRSKSKKFRRPDIQYPDATDEDITSHMESEELNGAYKAIPVAQDLNAPSDWDSRGKDSYETSQLD
DQSAETHSHKQSRLYKRKANDESNEHSDVIDSQELSKVSREFHSHEFHSHEDMLVVDPKSKEEDKHLKFRISHELDS
ASSEVN

Signal sequence.

amino acids 1-16

N-glycosylation sites.

amino acids 79-82, 106-109

Tyrosine kinase phosphorylation site.

amino acids 175-181

N-myristoylation sites.

amino acids 12-17, 200-205

Cell attachment sequence.

amino acids 159-161

Osteopontin signature.

amino acids 20-30

Osteopontin.

amino acids 1-314

FIGURE 61

MSRTAYTVGALLLLLGTLLPAAEGKKKGSQGAIPPPDKAQHNDSEQTQSPQQPGSRNRGRGQGRGTAMPGEEVLESS
QEALHVTERKYLKRDWCKTQPLKQTIHEEGCNSRTIINRFCYGQCNSFYIPRHIRKEEGSFQSCSFCKPKKFTTMMV
TLNCPELQPPTKKKRVTRVKQCRCISIDLD

Signal sequence.
amino acids 1-24

N-glycosylation site.
amino acids 42-45 cAMP- and cGMP-dependent protein kinase phosphorylation sites.
amino acids 26-29, 147-150, 168-171

N-myristoylation site.
amino acids 28-33, 61-66, 120-125, 136-141

Amidation site.
amino acids 23-26

DAN domain.
amino acids 58-184

FIGURE 62

MFLATLYFALPLLDLLLSAEVSGGDRLDCVKASDQCLKEQSCSTKYRTLRQCVAGKETNFSLASGLEAKDECRSAME
ALKQKSLYNCRCKRGMKKEKNCLRIYWSMYQSLQGNDLLEDSPYEPVNSRLSDIFRVVPFISVEHIPKGNNCLDAAK
ACNLDDICKKYRSAYITPCTTSVSNDVCNRRKCHKALRQFFDKVPAKHSYGMLFCSCRDIACTERRRQTIVPVCSYE
EREKPNCLNLQDSCKTNYICRSRLADFFTNCQPESRSVSSCLKENYADCLLAYSGLIGTVMTPNYIDSSSLSVAPWC
DCSNSGNDLEECLKFLNFFKDNTCLKNAIQAFGNGSDVTVWQPAFPVQTTTATTTTALRVKNKPLGPAGSENEIPTH
VLPPCANLQAQKLKSNVSGNTHLCISNGNYEKEGLGASSHITTKSMAAPPSCGLSPLLVLVVTALSTLLSLTETS

Signal sequence.
amino acids 1-23

Transmembrane domain.
amino acids 434-454

N-glycosylation sites.
amino acids 59-62, 342-345, 401-404 cAMP- and cGMP-dependent protein kinase phosphorylation site.
amino acids 220-223

N-myristoylation sites.
amino acids 205-210, 286-291, 343-348, 419-424

GDNF receptor family.
amino acids 1-415

FIGURE 63

MQHRGFLLLTLLALLALTSAVAKKKDKVKKGGPGSECAEWAWGPCTPSSKDCGVGFREGTCGAQTQRIRCRVPCNWK
KEFGADCKYKFENWGACDGGTGTKVRQGTLKKARYNAQCQETIRVTKPCTPKTKAKAKAKKGKGKD

Signal sequence.
amino acids 1-20

N-myristoylation sites.
amino acids 31-36, 34-39, 59-64, 92-97, 96-101

PTN/MK heparin-binding protein family signature 1.
amino acids 35-59

PTN/MK heparin-binding protein family signature 2.
amino acids 70-94

PTN/MK heparin-binding protein family.
amino acids 1-143

FIGURE 64

MWVLGIAATFCGLFLLPGFALQIQCYQCEEFQLNNDCSSPEFIVNCTVNVQDMCQKEVMEQSAGIMYRKSCASSAAC
LIASAGYQSFCSPGKLNSVCISCCNTPLCNGPRPKKRGSSASALRPGLRTTILFLKLALFSAHC

Signal sequence.
amino acids 1-22

Transmembrane domain.
amino acids 121-140

N-glycosylation site.
amino acids 45-48 cAMP- and cGMP-dependent protein kinase phosphorylation site.
amino acids 113-116

N-myristoylation sites.
amino acids 5-10, 115-120, 124-129

FIGURE 65

MKNIGLVMEWEIPEIICTCAKLRLPPQATFQVLRGNGASVGTVLMFRCPSNHQMVGSGLLTCTWKGSIAEWSSGSPV
CKLVPPHETFGFKVAVIASIVSCAIILLMSMAFLTCCLLKCVKKSKRRRSNRSAQLWSQLKDEDLETVQAAYLGLKH
FNKPVSGPSQAHDNHSFTTDHGESTSKLASVTRSVDKDPGIPRALSLSGSSSSPQAQVMVHMANPRQPLPASGLATG
MPQQPAAYALG

Transmembrane domain.

amino acids 93-113

N-glycosylation sites.

amino acids 128-131, 168-171 cAMP- and cGMP-dependent protein kinase phosphorylation site.

amino acids 124-127

N-myristoylation sites.

amino acids 35-40, 37-42, 58-63, 74-79, 194-199, 227-232

FIGURE 66

DCTGDGPWQSNLAPSQLEYYASSPDEKALVEAAARIGIVFIGNSEETMEVKTLGKLERYKLLHILEFDSDRRRMSVI
VQAPSGEKLLFAKGAESSILPKCIGGEIEKTRIHVDEFALKGLRTLCIAYRKFTSKEYEEIDKRIFEARTALQQREE
KLAAVFQFIEKDLILLGATAVEDRLQDKVRETIEALRMAGIKVWVLTGDKHETAVSVSLSCGHFHRTMNILELINQK
SDSECAEQLRQLARRITEDHVIQHGLVVDGTSLSLALREHEKLFMEVCRNCSAVLCCRMAPLQKAKVIRLIKISPEK
PITLAVGDGANDVSMIQEAHVGIGIMGKEGRQAARNSDYAIARFKFLSKLLFVHGHFYYIRIATLVQYFFYKNVCFI
TPQFLYQFYCLFSQQTLYDSVYLTLYNICFTSLPILIYSLLEQHVDPHVLQNKPTLYRDISKNRLLSIKTFLYWTIL
GFSHAFIFFFGSYLLIGKDTSLLGNGQMFGNWTFGTLVFTVMVITVTVKMALETHFWTWINHLVTWGSIIFYFVFSL
FYGGILWPFLGSQNMYFVFIQLLSSGSAWFAIILMVVTCLFLDIIKKVFDRHLHPTSTEKAQLTETNAGIKCLDSMC
CFPEGEAACASVGRMLERVIGRCSPTHISRSWSASDPFYTNDRSILTLSTMDSSTC

Transmembrane domains.
amino acids 352-372, 369-389, 405-425, 453-473, 487-507, 503-523, 522-542, 538-558, 561-581

N-glycosylation sites.
amino acids 281-284, 493-496 cAMP- and cGMP-dependent protein kinase phosphorylation sites.
amino acids 72-75, 128-131, 245-248

N-myristoylation sites.
amino acids 91-96, 261-266, 488-493

FIGURE 67

MWEEEDIAILFNKEPGKTENIENNLSSNHRRSCRRSEESDDDLDFDIGLENTGGDPQILRFISDFLAFLVLYNFIIP
ISLYVTVEMQKFLGSFFIGWDLDLYHEESDQKAQVNTSDLNEELGQVEYVFTDKTGTLTENEMQFRECSINGMKYQE
INGRLVPEGPTPDSSEGNLSYLSSLSHLNNLSHLTTSSSFRTSPENETELIKEHDLFFKAVSLCHTVQISNVQTDCT
GDGPWQSNLAPSQLEYYASSPDEKALVEAAARYKLLHILEFDSDRRRMSVIVQAPSGEKLLFAKGAESSILPKCIGG
EIEKTRIHVDEFALKGLRTLCIAYRKFTSKEYEEIDKRIFEARTALQQREEKLAAVFQFIEKDLILLGATAVEDRLQ
DKVRETIEALRMAGIKVWVLTGDKHETAVSVSLSCGHFHRTMNILELINQKSDSECAEQLRQLARRITEDHVIQHGL
VVDGTSLSLALREHEKLFMEVCRNCSAVLCCRMAPLQKAKVIRLIKISPEKPITLAVGDGANDVSMIQEAHVGIGIM
GKEGRQAARNSDYAIARFKFLSKLLFVHGHFYYIRIATLVQYFFYKNVCFITPQFLYQFYCLFSQQTLYDSVYLTLY
NICFTSLPILIYSLLEQHVDPHVLQNKPTLYRDISKNRLLSIKTFLYWTILGFSHAFIFFFGSYLLIGKDTSLLGNG
QMFGNWTFGTLVFTVMVITVTVKMALETHFWTWINHLVTWGSIIFYFVFSLFYGGILWPFLGSQNMYFVFIQLLSSG
SAWFAIILMVVTCLFLDIIKKVFDRHLHPTSTEKAQLTETNAGIKCLDSMCCFPEGEAACASVGRMLERVIGRCSPT
HISRSWSASDPFYTNDRSILTLSTMDSSTC

Transmembrane domains.
amino acids 61-81, 575-595, 610-630, 658-678, 698-718, 727-747, 743-763, 766-786

N-glycosylation sites.
amino acids 24-27, 113-116, 172-175, 184-187, 200-203, 486-489, 698-701 cAMP- and cGMP-dependent protein kinase phosphorylation sites.
amino acids 277-280, 333-336, 450-453

N-myristoylation sites.
amino acids 48-53, 296-301, 466-471, 693-698

E1-E2 ATPases phosphorylation site.
amino acids 130-136

Haloacid dehalogenase-like hydrolase.
amino acids 124-542

E1-E2 ATPases phosphoryl.
amino acids 105-142, 374-417, 516-539

FIGURE 68

MKHVLNLYLLGVVLTLLSIFVRVMESLEGLLESPSPGTSWTTRSQLANTEPTKGLPDHPSRSM

Signal sequence.

amino acids 1-18

N-myristoylation sites.

amino acids 11-16, 37-42

FIGURE 69

MKTGLFFLCLLGTAAAIPTNARLLSDHSKPTAETVAPDNTAIPSLRAEDEENEKETAVSTEDDSHHKAEKSSVLKSK
EESHEQSAEQGKSSSQELGLKDQXDSDGDLSVNLEYAPTEGTLDIKEDMSEPQEKNSQXH

Signal sequence.
amino acids 1-16

N-myristoylation site.
amino acids 12-17

FIGURE 70

MAPWAEAEHSALNPLRAVWLTLTAAFLLTLLLQLLPPGLLPGCAIFQDLIRYGKTKCGEPSRPAACRAFDVPKRYFS
HFYIISVLWNGFLLWCLTQSLFLGAPFPSWLHGLLRILGAAQFQGGELALSAFLVLVFLWLHSLRRLFECLYVSVFS
NVMIHVVQYCFGLVYYVLVGLTVLSQVPMDGRNAYITGKNLLMQARWFHILGMMMFIWSSAHQYKCHVILGNLRKNK
AGVVIHCNHRIPFGDWFEYVSSPNYLAELMIYVSMAVTFGFHNLTWWLVVTNVFFNQALSAFLSHQFYKSKFVSYPK·
HRKAFLPFLF

Transmembrane domains.
amino acids 20-40, 76-96, 118-138, 158-178, 193-213, 272-292

N-glycosylation site.
amino acids 274-277

Tyrosine kinase phosphorylation sites.
amino acids 143-149

N-myristoylation sites.
amino acids 38-43, 122-127

3-oxo-5-alpha-steroid 4-dehydrogenase.
amino acids 145-318

FIGURE 71

MPLLWLRGFLLASCWIIVRSSPTPGSEGHSAAPDCPSCALAALPKDVPNSQPEMVEAVKKHILNMLHLKKRPDVTQP
VPKAALLNAIRKLHVGKVGENGYVEIEDDIGRRAEMNELMEQTSEIITFAESGTARKTLHFEISKEGSDLSVVERAE
VWLFLKVPKANRTRTKVTIRLFQQQKHPQGSLDTGEEAEEVGLKGERSELLLSEKVVDARKSTWHVFPVSSSIQRLL
DQGKSSLDVRIACEQCQESGASLVLLGKKKKKEEEGEGKKKGGGEGGAGADEEKEQSHRPFLMLQARQSEDHPHRRR
RRGLECDGKVNICCKKQFFVSFKDIGWNDWIIAPSGYHANYCEGECPSHIAGTSGSSLSFHSTVINHYRMRGHSPFA
NLKSCCVPTKLRPMSMLYYDDGQNIIKKDIQNMIVEECGCS

Signal sequence.
amino acids 1-20

N-glycosylation site.
amino acids 165-168 cAMP- and cGMP-dependent protein kinase phosphorylation site.
amino acids 214-217

Tyrosine kinase phosphorylation site.
amino acids 94-100

N-myristoylation sites.
amino acids 144-149, 184-189, 273-278, 274-279, 277-282, 360-365, 363-368

Amidation sites.
amino acids 107-110, 257-260, 268-271

TGF-beta family signature.
amino acids 339-354

Transforming growth factor beta like.
amino acids 318-426

TGF-beta propeptide.
amino acids 42-274

FIGURE 72

MAAAPLLLLLLLVPVPLLPLLAQGPGGALGNRHAVYWNSSNQHLRREGYTVQVNVNDYLDIYCPHYNSSGVGPGAGP
GPGGGAEQYVLYMVSRNGYRTCNASQGFKRWECNRPHAPHSPIKFSEKFQRYSAFSLGYEFHAGHEYYYISTPTHNL
HWKCLRMKVFVCCASTSHSGEKPVPTLPQFTMGPNVKINVLEDFEGENPQVPKLEKSISGTSPKREHLPLAVGIAFF
LMTFLAS

Signal sequence.
amino acids 1-30

Transmembrane domain.
amino acids 224-237

N-glycosylation sites.
amino acids 38-41, 67-70, 100-103

Glycosaminoglycan attachment site.
amino acids 69-73

N-myristoylation sites.
amino acids 26-31, 27-32, 30-35, 70-75

Ephrin.
amino acids 27-171

FIGURE 73

MGHSPPVLPLCASVSLLGGLTFGYELAVISGALLPLQLDFGLSCLEQEFLVGSLLLGALLASLVGGFLIDCYGRKQA
ILGSNLVLLAGSLTLGLAGSLAWLVLGRAVVGFAISLSSMACCIYVSELVGPRQRGVLVSLYEAGITVGILLSYALN
YALAGTPWGWRHMFGWATAPAVLQSLSLLFLPAGTDETATHKDLIPLQGGEAPKLGPGRPRYSFLDLFRARDNMRGR
TTVGLGLVLFQQLTGQPNVLCYASTIFSSVGFHGGSSAVLASVGLGAVKVAATLTAMGLVDRAGRRALLLAGCALMA
LSVSGIGLVSFAVPMDSGPSCLAVPNATGQTGLPGDSGLLQDSSLPPIPRTNEDQREPILSTAKKTKPHPRSGDPSA
PPRLALSSALPGPPLPARGHALLRWTALLCLMVFVSAFSFGFGPVTWLVLSEIYPVEIRGRAFAFCNSFNWAANLFI
SLSFLDLIGTIGLSWTFLLYGLTAVLGLGFIYLFVPETKGQSLAEIDQQFQKRRFTLSFGHRQNSTGIPYSRIEISA
AS

Transmembrane domains.

amino acids 11-31, 45-65, 83-103, 136-156, 168-188, 231-251, 265-285, 296-316, 410-430, 456-476, 473-493

N-glycosylation sites.

amino acids 334-337, 526-529

Glycosaminoglycan attachment site.

amino acids 312-315 cAMP- and cGMP-dependent protein kinase phosphorylation site.

amino acids 515-518

N-myristoylation sites.

amino acids 19-24, 57-62, 93-98, 133-138, 142-147, 146-151, 159-164, 188-193, 265-270, 474-479, 502-507, 529-534

Amidation sites.

amino acids 72-75, 294-297

Sugar (and other) transporter.

amino acids 10-512

FIGURE 74

MAKATSGAAGLRLLLLLLLPLLGKVALGLYFSRDAYWEKLYVDQAAGTPLLYVHALRDAPEEVPSFRLGQHLYGTYR
TRLHENNWICIQEDTGLLYLNRSLDHSSWEKLSVRNRGFPLLTVYLKVFLSPTSLREGECQWPGCARVYFSFFNTSF
PACSSLKPRELCFPETRPSFRIRENRPPGTFHQFRLLPVQFLCPNISVAYRLLEGEGLPFRCAPDSLEVSTRWALDR
EQREKYELVAVCTVHAGAREEVVMVPFPVTVYDEDDSAPTFPAGVDTASAVVEFKRKEDTVVATLRVFDADVVPASG
ELVRRYTSTLLPGDTWAQQTFRVEHWPNETSVQANGSFVRATVHDYRLVLNRNLSISENRTMQLAVLVNDSDFQGPG
AGVLLLHFNVSVLPVSLHLPSTYSLSVSRRARRFAQIGKVCVENCQAFSGINVQYKLHSSGANCSTLGVVTSAEDTS
GILFVNDTKALRRPKCAELHYMVVATDQQTSRQAQAQLLVTVEGSYVAEEAGCPLSCAVSKRRLECEECGGLGSPTG
RCEWRQGDGKGITRNFSTCSPSTKTCPDGHCDVVETQDINICPQDCLRGSIVGGHEPGEPRGIKAGYGTCNCFPEEE
KCFCEPEDIQDPLCDELCRTVIAAAVLFSFIVSVLLSAFCIHCYHKFAHKPPISSAEMTFRRPAQAFPVSYSSSGAR
RPSLDSMENQVSVDAFKILEDPKWEFPRKNLVLGKTLGEGEFGKVVKATAFHLKGRAGYTTVAVKMLKENASPSELR
DLLSEFNVLKQVNHPHVIKLYGACSQDGPLLLIVEYAKYGSLRGFLRESRKVGPGYLGSGGSRNSSSLDHPDERALT
MGDLISFAWQISQGMQYLAEMKLVHRDLAARNILVAEGRKMKISDFGLSRDVYEEDSYVKRSQGRIPVKWMAIESLF
DHIYTTQSDVWSFGVLLWEIVTLGGNPYPGIPPERLFNLLKTGHRMERPDNCSEEMYRLMLQCWKQEPDKRPVFADI
SKDLEKMMVKRRDYLDLAASTPSDSLIYDDGLSEEETPLVDCNNAPLPRALPSTWIENKLYGMSDPNWPGESPVPLT
RADGTNTGFPRYPNDSVYANWMLSPSAAKLMDTFDS

Signal sequence.

amino acids 1-23

Transmembrane domains.

amino acids 386-406, 633-653

N-glycosylation sites.

amino acids 98-101, 151-154, 199-202, 336-339, 343-346, 361-364, 367-370, 377-380, 394-397, 448-451, 468-471, 554-557, 834-837, 975-978, 1092-1095 cAMP- and cGMP-dependent protein kinase phosphorylation sites.

amino acids 312-315, 693-696

Tyrosine kinase phosphorylation sites.

amino acids 477-483, 897-905, 1089-1096

N-myristoylation sites.

amino acids 28-33, 74-79, 275-280, 446-451, 453-458, 506-511, 514-519, 535-540, 550-555, 588-593, 601-606, 607-612, 810-815, 828-833, 830-835, 831-836, 1082-1087

Amidation site.

amino acids 884-887

Tyrosine protein kinases specific active-site signature.

amino acids 870-882

Protein kinase domain.

amino acids 724-1005

Cadherin domain.

amino acids 172-261

FIGURE 75

MRTYRYFLLLFWVGQPYPTLSTPLSKRTSGFPAKKRALELSGNSKNELNRSKRSWMWNQFFLLEEYTGSDYQYVGKL
HSDQDRGDGSLKYILSGDGAGDLFIINENTGDIQATKRLDREEKPVYILRAQAINRRTGRPVEPESEFIIKIHDIND
NEPIFTKEVYTATVPEMSDVGTFVVQVTATDADDPTYGNSAKVVYSILQGQPYFSVESETGIIKTALLNMDRENREQ
YQVVIQAKDMGGQMGGLSGTTTVNITLTDVNDNPPRFPQSTYQFKTPESSPPGTPIGRIKASDADVGENAEIEYSIT
DGEGLDMFDVITDQETQEGIITVKKLLDFEKKKVYTLKVEASNPYVEPRFLYLGPFKDSATVRIVVEDVDEPPVFSK
LAYILQIREDAQINTTIGSVTAQDPDAARNPVKYSVDRHTDMDRIFNIDSGNGSIFTSKLLDRETLLWHNITVIATE
INNPKQSSRVPLYIKVLDVNDNAPEFAEFYETFVCEKAKADQLIQTLHAVDKDDPYSGHQFSFSLAPEAASGSNFTI
QDNKDNTAGILTRKNGYNRHEMSTYLLPVVISDNDYPVQSSTGTVTVRVCACDHHGNMQSCHAEALIHPTGLSTGAL
VAILLCIVILLVTVVLFAALRRQRKKEPLIISKEDIRDNIVSYNDEGGGEEDTQAFDIGTLRNPEAIEDNKLRRDIV
PEALFLPRRTPTARDNTDVRDFINQRLKENDTDPTAPPYDSLATYAYEGTGSVADSLSSLESVTTDADQDYDYLSDW
GPRFKKLADMYGGVDSDKDS

Transmembrane domain.

amino acids 611-631

N-glycosylation sites.

amino acids 49-52, 255-258, 399-402, 437-440, 455-458, 536-539, 723-726

Glycosaminoglycan attachment sites.

amino acids 93-96, 435-438 cAMP- and cGMP-dependent protein kinase phosphorylation site.

amino acids 26-29

N-myristoylation sites.

amino acids 42-47, 215-220, 242-247, 243-248, 246-251, 247-252, 284-289, 403-408, 438-443, 534-539, 595-598, 610-615, 614-619, 782-787

Cell attachment sequence.

amino acids 83-85

Cadherins extracellular repeated domain signature.

amino acids 147-157, 256-266, 476-486

Cadherin cytoplasmic region.

amino acids 638-784

Cadherin domains.

amino acids 58-150, 164-259, 273-375, 388-479, 492-589

FIGURE 76

MLTRNCLSLLLWVLFDGGLLTPLQPQPQQTLATEPRENVIHLPGQRSHFQRVKRGWVWNQFFVLEEYVGSEPQYVGK
LHSDLDKGEGTVKYTLSGDGAGTVFTIDETTGDIHAIRSLDREEKPFYTLRAQAVDIETRKPLEPESEFIIKVQDIN
DNEPKFLDGPYVATVPEMSPVGAYVLQVKATDADDPTYGNSARVVYSILQGQPYFSIDPKTGVIRTALPNMDREVKE
QYQVLIQAKDMGGQLGGLAGTTIVNITLTDVNDNPPRFPKSIFHLKVPESSPIGSAIGRIRAVDPDFGQNAEIEYNI
VPGDGGNLFDIVTDEDTQEGVIKLKKPLDFETKKAYTFKVEASNLHLDHRFHSAGPFKDTATVKISVLDVDEPPVFS
KPLYTMEVYEDTPVGTIIGAVTAQDLDVGSGAVRYFIDWKSDGDSYFTIDGNEGTIATNELLDRESTAQYNFSIIAS
KVSNPLLTSKVNILINVLDVNEFPPEISVPYETAVCENAKPGQIIQIVSAADRDLSPAGQQFSFRLSPEAAIKPNFT
VRDFRNNTAGIETRRNGYSRRQQELYFLPVVIEDSSYPVQSSTNTMTIRVCRCDSDGTILSCNVEAIFLPVGLSTGA
LIAILLCIVILLAIVVLYVALRRQKKKHTLMTSKEDIRDNVIHYDDEGGGEEDTQAFDIGALRNPKVIEENKIRRDI
KPDSLCLPRQRPPMEDNTDIRDFIHQRLQENDVDPTAPPIDSLATYAYEGSGSVAESLSSIDSLTTEADQDYDYLTD
WGPRFKVLADMFGEEESYNPDKVT

Signal sequence.
amino acids 1-25
Transmembrane domain.
amino acids 612-632
N-glycosylation sites.
amino acids 256-259, 456-459, 537-540, 545-548
Glycosaminoglycan attachment site.
amino acids 94-97
cAMP- and cGMP-dependent protein kinase phosphorylation site.
amino acids 642-645
Tyrosine kinase phosphorylation site.
amino acids 159-165
N-myristoylation sites.
amino acids 99-104, 216-221, 243-248, 244-249, 247-252, 248-253, 285-290, 400-405, 404-409, 436-441, 439-444, 521-526, 596-601, 611-616, 615-620
Cadherins extracellular repeated domain signature.
amino acids 148-158, 257-267
Cadherin cytoplasmic region.
amino acids 639-785
Cadherin domain.
amino acids 59-151, 165-260, 274-376, 389-480, 493-590

FIGURE 77

MARPLCTLLLLMATLAGALASSSKEENRIIPGGIYDADLNDEWVQRALHFAISEYNKATEDEYYRRPLQVLRAREQT
FGGVNYFFDVEVGRTICTKSQPNLDTCAFHEQPELQKKQLCSFEIYEVPWEDRMSLVNSRCQEA

Signal sequence.

amino acids 1-20

Tyrosine kinase phosphorylation site.

amino acids 57-64

N-myristoylation sites.

amino acids 17-22, 33-38

Cystatin domain.

amino acids 32-137

FIGURE 78

MTTSPILQLLLRLSLCGLLLQRAETGSKGQTAGELYQRWERYRRECQETLAAAEPPSGLACNGSFDMYVCWDYAAPN
ATARASCPWYLPWHHHVAAGFVLRQCGSDGQWGLWRDHTQCENPEKNEAFLDQRLILERLQVMYTVGYSLSLATLLL
ALLILSLFRRLHCTRNYIHINLFTSFMLRAAAILSRDRLLPRPGPYLGDQALALWNQALAACRTAQIVTQYCVGANY
TWLLVEGVYLHSLLVLVGGSEEGHFRYYLLLGWGAPALFVIPWVIVRYLYENTQCWERNEVKAIWWIIRTPILMTIL
INFLIFIRILGILLSKLRTRQMRCRDYRLRLARSTLTLVPLLGVHEVVFAPVTEEQARGALRFAKLGFEIFLSSFQG
FLVSVLYCFINKEVQSEIRRGWHHCRLRRSLGEEQRQLPERAFRALPSGSGPGEVPTSRGLSSGTLPGPGNEASREL
ESYC

Transmembrane domains.
amino acids 1-20, 141-161, 169-189, 227-247, 259-279, 300-320, 338-358, 377-397

N-glycosylation sites.
amino acids 62-65, 77-80, 230-233

Glycosaminoglycan attachment sites.
amino acids 433-436, 435-438

N-myristoylation sites.
amino acids 29-34, 58-63, 228-233, 250-255, 319-324, 434-439, 445-450, 455-460

G-protein coupled receptors family 2 signature 1.
amino acids 61-85

G-protein coupled receptors family 2 signature 2.
amino acids 384-399

7 transmembrane receptor (Secretin family).
amino acids 134-399

Hormone receptor domain.
amino acids 58-123

FIGURE 79

MLSKVLPVLLGILLILQSRVEGPQTESKNEASSRDVVYGPQPQPLENQLLSEETKSTETETGSRVGKLPEASRILNT
ILSNYDHKLRPGIGEKPTVVTVEIAVNSLGPLSILDMEYTIDIIFSQTWYDERLCYNDTFESLVLNGNVVSQLWIPD
TFFRNSKRTHEHEITMPNQMVRIYKDGKVLYTIRMTIDAGCSLHMLRFPMDSHSCPLSFSSFSYPENEMIYKWENFK
LEINEKNSWKLFQFDFTGVSNKTEIITTPVGDFMVMTIFFNVSRRFGYVAFQNYVPSSVTTMLSWVSFWIKTESAPA
RTSLGITSVLTMTTLGTFSRKNFPRVSYITALDFYIAICFVFCFCALLEFAVLNFLIYNQTKAHASPKLRHPRINSR
AHARTRARSRACARQHQEAFVCQIVTTEGSDGEERPSCSAQQPPSPGSPEGPRSLCSKLACCEWCKRFKKYFCMVPD
CEGSTWQQGRLCIHVYRLDNYSRVVFPVTFFFFNVLYWLVCLNL

Signal sequence.

amino acids 1-18

Transmembrane domains.

amino acids 305-325, 335-355, 351-371, 485-505

N-glycosylation sites.

amino acids 134-137, 252-255, 272-275, 367-370, 482-485

N-myristoylation sites.

amino acids 62-67, 144-149

Neurotransmitter-gated ion-channels signature.

amino acids 195-209

FIGURE 80

MEPRPTAPSSGAPGLAGVGETPSAAALAAARVELPGTAVPSVPEDAAPASRDGGGVRDEGPAAAGDGLGRPLGPTPS
QSRFQVDLVSENAGRAAAAAAAAAAAAAAAAGAGAGAKQTPADGEASGESEPAKGSEEAKGRFRVNFVDPAASSSAED
SLSDAAGVGVDGPNVSFQNGGDTVLSEGSSLHSGGGGGSGHHQHYYYDTHTNTYYLRTFGHNTMDAVPRIDHYRHTA
AQLGEKLLRPSLAELHDELEKEPFEDGFANGEESTPTRDAVVTYTAESKGVVKFGWIKGVLVRCMLNIWGVMLFIRL
SWIVGQAGIGLSVLVIMMATVVTTITGLSTSAIATNGFVRGGGAYYLISRSLGPEFGGAIGLIFAFANAVAVAMYVV
GFAETVVELLKEHSILMIDEINDIRIIGAITVVILLGISVAGMEWEAKAQIVLLVILLLAIGDFVIGTFIPLESKKP
KGFFGYKSEIFNENFGPDFREEETFFSVFAIFFPAATGILAGANISGDLADPQSAIPKGTLLAILITTLVYVGIAVS
VGSCVVRDATGNVNDTIVTELTNCTSAACKLNFDFSSCESSPCSYGLMNNFQVMSMVSGFTPLISAGIFSATLSSAL
ASLVSAPKIFQALCKDNIYPAFQMFAKGYGKNNEPLRGYILTFLIALGFILIAELNVIAPIISNFFLASYALINFSV
FHASLAKSPGWRPAFKYYNMWISLLGAILCCIVMFVINWWAALLTYVIVLGLYIYVTYKKPDVNWGSSTQALTYLNA
LQHSIRLSGVEDHVKNFRPQCLVMTGAPNSRPALLHLVHDFTKNVGLMICGHVHMGPRRQAMKEMSIDQAKYQRWLI
KNKMKAFYAPVHADDLREGAQYLMQAAGLGRMKPNTLVLGFKKDWLQADMRDVDMYINLFHDAFDIQYGVVVIRLKE
GLDISHLQGQEELLSSQEKSPGTKDVVVSVEYSKKSDLDTSKPLSEKPITHKVEEEDGKTATQPLLKKESKGPIVPL
NVADQKLLEASTQFQKKQGKNTIDVWWLFDDGGLTLLIPYLLTTKKKWKDCKIRVFIGGKINRIDHDRRAMATLLSK
FRIDFSDIMVLGDINTKPKKENIIAFEEIIEPYRLHEDDKEQDIADKMKEDEPWRITDNELELYKTKTYRQIRLNEL
LKEHSSTANIIVMSLPVARKGAVSSALYMAWLEALSKDLPPILLVRGNHQSVLTFYS

Transmembrane domains.

amino acids 89-109, 315-335, 365-385, 402-422, 433-453, 484-504, 520-540, 653-673, 670-690, 708-728, 724-744

N-glycosylation sites.

amino acids 168-171, 506-509, 553-556, 562-565, 690-693

Glycosaminoglycan attachment site.

amino acids 187-190 cAMP- and cGMP-dependent protein kinase phosphorylation site.

amino acids 991-994

N-myristoylation sites.

amino acids 108-113, 131-136, 188-193, 189-194, 190-195, 316-321, 335-340, 365-370, 369-374, 422-427, 500-505, 504-509, 521-526, 535-540, 585-590, 606-611, 719-724, 796-801, 816-821, 925-930, 1059-1064, 1176-1181, 1202-1207

FIGURE 81

MATAVSRPCAGRSRDILWRVLGWRIVASIVWSVLFLPICTTVFIIFSRIDLFHPIQWLSDSFSDLYSSYVIFYFLLL
SVVIIIISIFNVEFYAVVPSIPCSRLALIGKIIHPQQLMHSFIHAAMGMVMAWCAAVITQGQYSFLVVPCTGTNSFG
SPAAQTCLNEYHLFFLLTGAFMGYSYSLLYFVNNMNYLPFPIIQQYKFLRFRRSLLLLVKHSCVESLFLVRNFCILY
YFLGYIPKAWISTAMNLHIDEQVHRPLDTVSGLLNLSLLYHVWLCGVFLLTTWYVSWILFKIYATEAHVFPVQPPFA
EGSDECLPKVLNSNPPPIIKYLALQDLMLLSQYSPSRRQEVFSLSQPGGHPHNWTAISRECLNLLNGMTQKLILYQE
AAATNGRVSSSYPVEPKKLNSPEETAFQTPKSSQMPRPSVPPLVKTSLFSSKLSTPDVVSPFGTPFGSSVMNRMAGI
FDVNTCYGSPQSPQLIRRGPRLWTSASDQQMTEFSNPSPSTSISAEGKTMRQPSVIYSWIQNKREQIKNFLSKRVLI
MYFFSKHPEASIQAVFSDAQMHIWALEGLSHLVAASFTEDRFGVVQTTLPAILNTLLTLQEAVDKYFKLPHASSKPP
RISGSLVDTSYKTLRFAFRASLKTAIYRITTTFGEHLNAVQASAEHQKRLQQFLEFKE

Transmembrane domains.

amino acids 24-44, 68-88, 109-129, 126-146, 161-181, 178-198, 221-241, 261-281

N-glycosylation sites.

amino acids 266-269, 361-364

N-myristoylation sites.

amino acids 125-130, 154-159, 173-178, 310-315, 448-453, 582-587

FIGURE 82

MGAPFVWALGLLMLQMLLFVAGEQGTQDITDASERGLHMQKLGSGSVQAALAELVALPCLFTLQPRPSAARDAPRIK
WTKVRTASGQRQDLPILVAKDNVVRVAKSWQGRVSLPSYPRRRANATLLLGPLRASDSGLYRCQVVRGIEDEQDLVP
LEVTGVVFHYRSARDRYALTFAEAQEACRLSSAIIAAPRHLQAAFEDGFDNCDAGWLSDRTVRYPITQSRPGCYGDR
SSLPGVRSYGRRNPQELYDVYCFARELGGEVFYVGPARRLTLAGARAQCRRQGAALASVGQLHLAWHEGLDQCDPGW
LADGSVRYPIQTPRRRCGGPAPGVRTVYRFANRTGFPSPAERFDAYCFRAHHPTSQHGDLETPSSGDEGEILSAEGP
PVRELEPTLEEEEVVTPDFQEPLVSSGEEETLILEEKQESQQTLSPTPGDPMLASWPTGEVWLSTVAPSPSDMGAGT
AASSHTEVAPTDPMPRRRGRFKGLNGRYFQQQEPEPGLQGGMEASAQPPTSEAAVNQMEPPLAMAVTEMLGSGQSRS
PWADLTNEVDMPGAGSAGGKSSPEPWLWPPTMVPPSISGHSRAPVLELEKAEGPSARPATPDLFWSPLEATVSAPSP
APWEAFPVATSPDLPMMAMLRGPKEWMLPHPTPISTEANRVEAHGEATATAPPSPAAETKVYSLPLSLTPTGQGGEA
MPTTPESPRADFRETGETSPAQVNKAEHSSSSPWPSVNRNVAVGFVPTETATEPTGLRGIPGSESGVFDTAESPTSG
LQATVDEVQDPWPSVYSKGLDASSPSAPLGSPGVFLVPKVTPNLEPWVATDEGPTVNPMDSTVTPAPSDASGIWEPG
SQVFEEAESTTLSPQVALDTSIVTPLTTLEQGDKVGVPAMSTLGSSSSQPHPEPEDQVETQGTSGASVPPHQSSPLG
KPAVPPGTPTAASVGESASVSSGEPTVPWDPSSTLLPVTLGIEDFELEVLAGSPGVESFWEEVASGEEPALPGTPMN
AGAEEVHSDPCENNPCLHGGTCNANGTMYGCSCDQGFAGENCEIDIDDCLCSPCENGGTCIDEVNGFVCLCLPSYGG
SFCEKDTEGCDRGWHKFQGHCYRYFAHRRAWEDAEKDCRRRSGHLTSVHSPEEHSFINSFGHENTWIGLNDRIVERD
FQWTDNTGLQFENWRENQPDNFFAGGEDCVVMVAHESGRWNDVPCNYNLPYVCKKGTVLCGPPPAVENASLIGARKA
KNNVHATVRYQCNEGFAQHHVVTIRCRSNGKWDRPQIVCTKPRRSHRMRGHHHHHQHHHQHHHHKSRKERRKHKKHP
TEDWEKDEGNFC

Signal sequence.
amino acids 1-22
N-glycosylation sites.
amino acids 122-125, 340-343, 1026-1029, 1223-1226
cAMP- and cGMP-dependent protein kinase phosphorylation sites.
amino acids 269-272, 1117-1120, 1209-1212
Tyrosine kinase phosphorylation site.
amino acids 131-138
N-myristoylation sites.
amino acids 45-50, 136-141, 284-289, 300-305, 459-464, 461-466, 499-504, 502-507, 503-508, 533-538, 552-557, 554-559, 752-757, 755-760, 759-764, 770-775, 789-794, 891-896, 909-914, 931-936, 997-1002, 1020-1025, 1021-1026, 1027-1032, 1077-1082, 1087-1092, 1180-1185, 1211-1216, 1228-1233
Amidation site.
amino acids 240-243
Aspartic acid and asparagine hydroxylation site.
amino acids 1061-1072
ATP/GTP-binding site motif A (P-loop).
amino acids 553-560
EGF-like domain cysteine pattern signature.
amino acids 1032-1043, 1050-1061, 1070-1081
C-type lectin domain signature.
amino acids 1184-1208
Extracellular link domain.
amino acids 159-254, 260-356
Lectin C-type domain.
amino acids 1105-1210
Sushi domain (SCR repeat).
amino acids 1215-1271
EGF-like domain.
amino acids 1012-1043, 1050-1081
Immunoglobulin domain.
amino acids 52-142

FIGURE 83

MKFAEHLSAHITPEWRKQYIQYEAFKDMLYSAQDQAPSVEVTDEDTVKRYFAKFEEKFFQTCEKELAKINTFYSEKL
AEAQRRFATLQNELQSSLDAQKESTGVTTLRQRRKPVFHLSHEERVQHRNIKDLKLAFSEFYLSLILLQNYQNLNFT
GFRKILKKHDKILETSRGADWRVAHVEVAPFYTCKKINQLISETEAVVTNELEDGDRQKAMKRLRVPPLGAAQPAPA
WTTFRVGLFCGIFIVLNITLVLAAVFKLETDRSIWPLIRIYRGGFLLIEFLFLLGINTYGWRQAGVNHVLIFELNPR
SNLSHQHLFEIAGFLGILWCLSLLACFFAPISVIPTYVYPLALYGFMVFFLINPTKTFYYKSRFWLLKLLFRVFTAP
FHKVGFADFWLADQLNSLSVILMDLEYMICFYSLELKWDESKGLLPNNSEESGICHKYTYGVRAIVQCIPAWLRFIQ
CLRRYRDTKRAFPHLVNAGKYSTTFFMVAFAALYSTHKERGHSDTMVFFYLWIVFYIISSCYTLIWDLKMDWGLFDK
NAGENTFLREEIVYPQKAYYYCAIIEDVILRFAWTIQISITSTTLLPHSGDIIATVFAPLEVFRRFVWNFFRLENEH
LNNCGEFRAVRDISVAPLNADDQTLLEQMMDQDDGVRNRQKNRSWKYNQSISLRRPRLASQSKARDTKVLIEDTDDE
ANT

Transmembrane domains.
amino acids 235-255, 276-296, 314-334, 332-352, 348-368, 368-388, 438-458, 475-495, 507-527

N-glycosylation sites.
amino acids 152-155, 248-251, 310-313, 432-435, 658-661, 664-667

N-myristoylation sites.
amino acids 238-243, 324-329, 428-433

Crystallins beta and gamma 'Greek key' motif signature.
amino acids 145-160

EXS family.
amino acids 439-617

SPX domain.
amino acids 1-180

FIGURE 84

MKFAEHLSAHITPEWRKQYIQYEAFKDMLYSAQDQAPSVEVTDEDTVKRYFAKFEEKFFQTCEKELAKINTFYSEKL
AEAQRRFATLQNELQSSLDAQKESTGVTTLRQRRKPVFHLSHEERVQHRNIKDLKLAFSEFYLSLILLQNYQNLNFT
GFRKILKKHDKILETSRGADWRVAHVEVAPFYTCKKINQLISETEAVVTNELEDGDRQKAMKRLRVPPLGAAQPAPA
WTTFRVGLFCGIFIVLNITLVLAAVFKLETDRSIWPLIRIYRGGFLLIEFLFLLGINTYGWRQAGVNHVLIFELNPR
SNLSHQHLFEIAGFLGILWCLSLLACFFAPISVIPTYVYPLALYGFMVFFLINPTKTFYYKSRFWLLKLLFRVFTAP
FHKVGFADFWLADQLNSLSVILMDLEYMICFYSLELKWDESKGLLPNNSEESGICHKYTYGVRAIVQCIPAWLRFIQ
CLRRYRDTKRAFPHLVNAGKYSTTFFMVTFAALYSTHKERGHSDTMVFFYLWIVFYIISSCYTLIWDLKMDWGLFDK
NAGENTFLREEIVYPQKAYYYCAIIEDVILRFAWTIQISITSTTLLPHSGDIIATVFAPLEVFRRFVWNFFRLENEH
LNNCGEFRAVRDISVAPLNADDQTLLEQMMDQDDGVRNRQKNRSWKYNQSISLRRPRLASQSKARDTKVLIEDTDDE
ANT

Transmembrane domains.
amino acids 235-255, 276-296, 314-334, 332-352, 348-368, 368-388, 438-458, 475-495, 507-527

N-glycosylation sites.
amino acids 152-155, 248-251, 310-313, 432-435, 658-661, 664-667

N-myristoylation sites.
amino acids 238-243, 324-329, 428-433

Crystallins beta and gamma 'Greek key' motif signature.
amino acids 145-160

EXS family.
amino acids 439-617

SPX domain.
amino acids 1-180

FIGURE 85

MSVGVSTSAPLSPTSGTSVGMSTFSIMDYVVFVLLLVLSLAIGLYHACRGWGRHTVGELLMADRKMGCLPVALSLLA
TFQSAVAILGVPSEIYRFGTQYWFLGCCYFLGLLIPAHIFIPVFYRLHLTSAYEYLELRFNKTVRVCGTVTFIFQMV
IYMGVVLYAPSLALNAVTGFDLWLSVLALGIVCTVYTALGGLKAVIWTDVFQTLVMFLGQLAVIIVGSAKVGGLGRV
WAVASQHGRISGFELDPDPFVRHTFWTLAFGGVFMMLSLYGVNQAQVQRYLSSRTEKAAVLSCYAVFPFQQVSLCVG
CLIGLVMFAYYQEYPMSIQQAQAAPDQFVLYFVMDLLKGLPGLPGLFIACLFSGSLSTISSAFNSLATVTMEDLIRP
WFPEFSEARAIMLSRGLAFGYGLLCLGMAYISSQMGPVLQAAISIFGMVGGPLLGLFCLGMFFPCANPPGAVVGLLA
GLVMAFWIGIGSIVTSMGFSMPPSPSNGSSFSLPTNLTVATVTTLMPLTTFSKPTGLQRFYSLSYLWYSAHNSTTVI
VVGLIVSLLTGRMRGRSLNPATIYPVLPKLLSLLPLSCQKRLHCRSYGQDHLDTGLFPEKPRNGVLGDSRDKEAMAL
DGTAYQGSSSTCILQETSL

Transmembrane domains.

amino acids 24-44, 64-84, 103-123, 140-160, 171-191, 206-226, 252-272, 294-314, 339-359, 394-414, 423-443, 455-475, 491-511, 527-547, 557-577

N-glycosylation sites.

amino acids 138-141, 489-492, 498-501, 534-537

N-myristoylation sites.

amino acids 4-9, 16-21, 43-48, 184-189, 194-199, 272-277, 308-313, 353-358, 362-367, 401-406, 455-460, 459-464, 463-468, 473-478, 490-495, 542-547, 623-628

Sodium:solute symporter family.

amino acids 61-463

FIGURE 86

MALTGASDPSAEAEANGEKPFLLRALQIALVVSLYWVTSISMVFLNKYLLDSPSLRLDTPIFVTFYQCLVTTLLCKG
LSALAACCPGAVDFPSLRLDLRVARSVLPLSVVFIGMITFNNLCLKYVGVAFYNVGRSLTTVFNVLLSYLLLKQTTS
FYALLTCGIIIGGFWLGVDQEGAEGTLSWLGTVFGVLASLCVSLNAIYTTKVLPAVDGSIWRLTFYNNVNACILFLP
LLLLLGELQALRDLAQLGSAHFWGMMTLGGLFGFAIGYVTGLQIKFTSPLTHNVSGTAKACAQTVLAVLYYEETKSF
LWWTSNMMVLGGSSAYTWVRGWEMKKTPEEPSPKDSEKSAMGV

Transmembrane domains.
amino acids 24-44, 61-81, 98-118, 139-159, 182-202, 220-240, 255-275

N-glycosylation site.
amino acids 284-287

N-myristoylation sites.
amino acids 162-167, 176-181, 185-190, 189-194, 260-265, 287-292, 319-324

FIGURE 87

MALTGASDPSAEAEANGEKPFLLRALQIALVVSLYWVTSISMVFLNKYLLDSPSLRLDTPIFVTFYQCLVTTLLCKG
LSALAACCPGAVDFPSLRLDLRVARSVLPLSVVFIGMITFNNLCLKYVGVAFYNVGRSLTTVFNVLLSYLLLKQTTS
FYALLTCGIIIGGFWLGVDQEGAEGTLSWLGTVFGVLASLCVSLNAIYTTKVLPAVDGSIWRLTFYNNVNACILFLP
LLLLLGELQALRDFAQLGSAHFWGMMTLGGLFGFAIGYVTGLQIKFTSPLTHNVSGTAKACAQTVLAVLYYEETKSF
LWWTSNMMVLGGSSAYTWVRGWEMKKTPEEPSPKDSEKSAMGV

Transmembrane domains.

amino acids 24-44, 61-81, 98-118, 139-159, 182-202, 219-239, 255-275

N-glycosylation site.

amino acids 284-287

N-myristoylation sites.

amino acids 162-167, 176-181, 185-190, 189-194, 260-265, 287-292, 319-324

FIGURE 88

MGSCSGRCALVVLCAFQLVAALERQVFDFLGYQWAPILANFVHIIIVILGLFGTIQYRLRYVMVYTLWAAVWVTWNV
FIICFYLEVGGLLQDSELLTFSLSRHRSWWRERWPGCLHEEVPAVGLGAPHGQALVSGAGCALEPSYVEALHSGLQI
LIALLGFVCGCQVVSVFTEEEDSFDFIGGFDPFPLYHVNEKPSSLLSKQVYLPA

Transmembrane domains.

amino acids 1-21, 34-54, 74-94, 147-167

Glycosaminoglycan attachment site.

amino acids 134-137

Tyrosine kinase phosphorylation site.

amino acids 24-32

N-myristoylation sites.

amino acids 2-7, 50-55, 125-130, 135-140

FIGURE 89

MGSCSGRCALVVLCAFQLVAALERQVFDFLGYQWAPILANFVHIIIVILGLFGTIQYRLRYVMVYTLWAAVWVTWNV
FIICFYLEVGGLLKDSELLTFSLSRHRSWWRERWPGCLHEEVPAVGLGAPHGQALVSGAGCALEPSYVEALHSCLQI
LIALLGFVCGCQVVSVFTEEEDSFDFIGGFDPFPLYHVNEKPSSLLSKQVYLPA

Signal sequence.
amino acids 1-21

Transmembrane domains.
amino acids 34-54, 74-94, 147-167

Glycosaminoglycan attachment site.
amino acids 134-137

Tyrosine kinase phosphorylation site.
amino acids 24-33

N-myristoylation sites.
amino acids 2-7, 50-55, 125-130, 135-140

FIGURE 90

MGSCSGRCALVVLCAFQLVAALERQVFDFLGYQWAPILANFVHIIIVILGLFGTIQYRLRYVMVYTLWAAVWVTWNV
FIICFYLEVGGLLKDSELLTFSLSRHRSWWRERWPGCLHEEVPAVGLGAPHGQALVSGAGCALEPSYVEALHSCLQI
LIALLGFVCGCQVVSVFTEEEDSCLRK

Signal sequence.
amino acids 1-21

Transmembrane domains.
amino acids 34-54, 73-93, 148-168

Glycosaminoglycan attachment site.
amino acids 134-137

Tyrosine kinase phosphorylation site.
amino acids 24-32

N-myristoylation sites.
amino acids 2-7, 50-55, 125-130, 135-140

FIGURE 91

MGSCSGRCALVVLCAFQLVAALERQVFDFLGYQWAPILANFVHIIIVILGLFGTIQYRLRYVMVYTLWAAVWVTWNV
FIICFYLEVGGLLQDSELLTFSLSRHRSWWRERWPGCLHEEVPAVGLGAPHGQALVSGAGCALEPSYVEALHSGLQI
LIALLGFVCGCQVVSVFTEEEDSCLRK

Signal sequence.
amino acids 1-21

Transmembrane domains.
amino acids 34-54, 73-93, 148-168

Glycosaminoglycan attachment site.
amino acids 134-137

Tyrosine kinase phosphorylation site.
amino acids 24-32

N-myristoylation sites.
amino acids 2-7, 50-55, 125-130, 135-140

FIGURE 92

MAVLFLLLFLCGTPQAADNMQAIYVALGEAVELPCPSPPTLHGDEHLSWFCSPAAGSFTTLVAQVQVGRPAPDPGKP
GRESRLRLLGNYSLWLEGSKEEDAGRYWCAVLGQHHNYQNWRVYDVLVLKGSQLSARAADGSPCNVLLCSVVPSRRM
DSVTWQEGKGPVRGRVQSFWGSEAALLLVCPGEGLSEPRSRRPRIIRCLMTHNKGVSFSLAASIDASPALCAPSTGW
DMPWILMLLLTMGQGVVILALSIVLWRQRVRGAPGRGNRMRCYNCGGSPSSSCKEAVTTCGEGRPQPGLEQIKLPGN
PPVTLIHQHPACVAAHHCNQVETESVGDVTYPAHRDCYLGDLCNSAVASHVAPAGILAAAATALTCLLPGLWSG

Signal sequence.
amino acids 1-15

Transmembrane domains.
amino acids 234-254, 354-374

N-glycosylation site.
amino acids 88-91

Tyrosine kinase phosphorylation site.
amino acids 97-104

N-myristoylation sites.
amino acids 12-17, 56-61, 110-115, 128-133, 138-143, 175-180, 209-214, 277-282, 278-283, 363-368

FIGURE 93

MSGGHQLQLAALWPWLLMATLQAGFGRTGLVLAAAVESERSAEQKAVIRVIPLKMDPTGKLNLTLEGVFAGVAEITP
AEGKLMQSHPLYLCNASDDDNLEPGFISIVKLESPRRAPRPCLSLASKARMAGERGASAVLFDITEDRAAAEQLQQP
LGLTWPVVLIWGNDAEKLMEFVYKNQKAHVRIELKEPPAWPDYDVWILMTVVGTIFVIILASVLRIRCRPRHSRPDP
LQQRTAWAISQLATRRYQASCRQARGEWPDSGSSCSSAPVCAICLEEFSEGQELRVISCLHEFHRNCVDPWLHQHRT
CPLCVFNITEGDSFSQSLGPSRSYQEPGRRLHLIRQHPGHAHYHLPAAYLLGPSRSAVARPPRPGPFLPSQEPGMGP
RHHRFPRAAHPRAPGEQQRLAGAQHPYAQGWGMSHLQSTSQHPAACPVPLRRARPPDSSGSGESYCTERSGYLADGP
ASDSSSGPCHGSSSDSVVNCTDISLQGVHGSSSTFCSSLSSDFDPLVYCSPKGDPQRVDMQPSVTSRPRSLDSVVPT
GETQVSSHVHYHRHRHHHYKKRFQWHGRKPGPETGVPQSRPPIPRTQPQPEPPSPDQQVTGSNSAAPSGRLSNPQCP
RALPEPAPGPVDASSICPSTSSLFNLQKSSLSARHPQRKRRGGPSEPTPGSRPQDATVHPACQIFPHYTPSVAYPWS
PEAHPLICGPPGLDKRLLPETPGPCYSNSQPVWLCLTPRQPLEPHPPGEGPSEWSSDTAEGRPCPYPHCQVLSAQPG
SEEELEELCEQAV

Transmembrane domains.

amino acids 5-25, 198-218

N-glycosylation sites.

amino acids 62-65, 92-97, 315-320, 481-486

Glycosaminoglycan attachment site.

amino acids 444-449

Tyrosine kinase phosphorylation site.

amino acids 171-177

N-myristoylation sites.

amino acids 29-34, 67-72, 263-268, 445-450, 489-494, 492-497, 574-579, 600-605

Amidation sites.

amino acids 335-338, 565-568

Zinc finger, C3HC4 type (RING finger).

amino acids 272-312

FIGURE 94

MPLSLGAEMWGPEAWLLLLLLLASFTGRCPAGELETSDVVTVVLGQDAKLPCFYRGDSGEQVGQVAWARVDAGEGAQ
ELALLHSKYGLHVSPAYEGRVEQPPPPRNPLDGSVLLRNAVQADEGEYECRVSTFPAGSFQARLRLRVLVPPLPSLN
PGPALEEGQGLTLAASCTAEGSPAPSVTWDTEVKGTTSSRSFKHSRSAAVTSEFHLVPSRSMNGQPLTCVVSHPGLL
QDQRITHILHVSFLAEASVRGLEDQNLWHIGREGAMLKCLSEGQPPPSYNWTRLDGPLPSGVRVDGDTLGFPPLTTE
HSGIYVCHVSNEFSSRDSQVTVDVLDPQEDSGKQVDLVSASVVVVGVIAALLFCLLVVVVVLMSRYHRRKAQQMTQK
YEEELTLTRENSIRRLHSHHTDPRSQPEESVGLRAEGHPDSLKDNSSCSVMSEEPEGRSYSTLTTVREIETQTELLS
PGSGRAEEEEDQDEGIKQAMNHFVQENGTLRAKPTGNGIYINGRGHLV

Signal sequence.
amino acids 1-26

Transmembrane domain.
amino acids 348-368

N-glycosylation sites.
amino acids 281-284, 430-433, 489-492

N-myristoylation sites.
amino acids 135-140, 162-167, 164-169, 189-194, 218-223, 311-316, 354-359, 464-469, 477-482, 490-495, 500-505

Cell attachment sequence.
amino acids 55-57

Immunoglobulin domains.
amino acids 45-129, 162-225, 263-317

FIGURE 95

MTQNKLKLCSKANVYTEVPDGGWGWAVAVSFFFVEVFTYGIIKTFGVFFNDLMDSFNESNSRISWIISICVFVLTFS
APLATVLSNRFGHRLVVMLGGLLVSTGMVAASFSQEVSHMYVAIGIISGLGYCFSFLPTVTILSQYFGKRRSIVTAV
ASTGECFAVFAFAPAIMALKERIGWRYSLLFVGLLQLNIVIFGALLRPIIIRGPASPKIVIQENRKEAQYMLENEKT
RTSIDSIDSGVELTTSPKNVPTHTNLELEPKADMQQVLVKTSPRPSEKKAPLLDFSILKEKSFICYALFGLFATLGF
FAPSLYIIPLGISLGIDQDRAAFLLSTMAIAEVFGRIGAGFVLNREPIRKIYIELICVILLTVSLFAFTFATEFWGL
MSCSIFFGFMVGTIGGLTFHCLLKMMSWALQKMSSAAGVYIFIQSIAGLAGPPLAGLLVDQSKIYSRAFYSCAAGMA
LAAVCLALVRPCKMGLCQRHHSGETKVVSHRGKTLQDIPEDFLEMDLAKNEHRVHVQMEPV

Transmembrane domains.
amino acids 23-43, 61-81; 85-105, 119-139, 148-168, 181-201, 293-313, 325-345, 358-378, 389-409, 422-442, 452-472

N-glycosylation site.
amino acids 57-60

Glycosaminoglycan attachment site.
amino acids 125-128 cAMP- and cGMP-dependent protein kinase phosphorylation site.
amino acids 146-149

N-myristoylation sites.
amino acids 40-45, 46-51, 98-103, 104-109, 122-127, 126-131, 241-246, 301-306, 319-324, 384-389, 397-402, 460-465

Amidation site.
amino acids 144-147

FIGURE 96

MLLWVILLVLAPVSGQFARTPRPIIFLQPPWTTVFQGERVTLTCKGFRFYSPQKTKWYHRYLGKEILRETPDNILEV
QESGEYRCQAQGSPLSSPVHLDFSSEMGFPHAAQANVELLGSSDLLT

Signal sequence.
amino acids 1-15

N-myristoylation site.
amino acids 89-94

FIGURE 97

MLLWVILLVLAPVSGQFARTPRPIIFLQPPWTTVFQGERVTLTCKGFRFYSPQKTKWYHRYLGKEILRETPDNILEV
QESGEYRCQAQGSPLSSPVHLDFSSASLILQAPLSVFEGDSVVLRCRAKAEVTLNNTIYKNDNVLAFLNKRTDFHIP
HACLKDNGAYRCTGYKESCCPVSSNTVKIQVQEPFTRPVLRASSFQPISGNPVTLTCETQLSLERSDVPLRFRFFRD
DQTLGLGWSLSPNFQITAMWSKDSGFYWCKAATMPHSVISDSPRSWIQVQIPASHPVLTLSPEKALNFEGTKVTLHC
ETQEDSLRTLYRFYHEGVPLRHKSVRCERGASISFSLTTENSGNYYCTADNGLGAKPSKAVSLSVTVPVSHPVLNLS
SPEDLIFEGAKVTLHCEAQRGSLPILYQFHHEDAALERRSANSAGGVAISFSLTAEHSGNYYCTADNGFGPQRSKAV
SLSITVPVSHPVLTLSSAEALTFEGATVTLHCEVQRGSPQILYQFYHEDMPLWSSSTPSVGRVSFSFSLTEGHSGNY
YCTADNGFGPQRSEVVSLFVTVPVSRPILTLRVPRAQAVVGDLLELHCEAPRGSPPILYWFYHEDVTLGSSSAPSGG
EASFNLSLTAEHSGNYSCEANNGLVAQHSDTISLSVIVPVSRPILTFRAPRAQAVVGDLLELHCEALRGSSPILYWF
YHEDVTLGKISAPSGGGASFNLSLTTEHSGIYSCEADNGPEAQRSEMVTLKVAVPVSRPVLTLRAPGTHAAVGDLLE
LHCEALRGSPLILYRFFHEDVTLGNRSSPSGGASLNLSLTAEHSGNYSCEADNGLGAQRSETVTLYITGLTANRSGP
FATGVAGGLLSIAGLAAGALLLYCWLSRKAGRKPASDPARSPPDSDSQEPTYHNVPAWEELQPVYTNANPRGENVVY
SEVRIIQEKKKHAVASDPRHLRNKGSPIIYSEVKVASTPVSGSLFLASSAPHR

Signal sequence.

amino acids 1-15

Transmembrane domain.

amino acids 851-871

N-glycosylation sites.

amino acids 132-135, 383-386, 621-624, 631-634, 714-717, 795-798, 806-809, 816-819, 843-846

Glycosaminoglycan attachment site.

amino acids 707-710

N-myristoylation sites.

amino acids 89-94, 162-167, 204-209, 236-241, 301-306, 338-343, 351-356, 362-367, 394-399, 431-436, 444-449, 487-492, 537-542, 615-620, 630-635, 708-703, 710-715, 723-728, 760-765, 802-807, 815-820, 826-831, 839-844, 851-856, 854-859, 861-866

Amidation site.

amino acids 877-880

Immunoglobulin domains.

amino acids 37-87, 116-168, 204-262, 301-357, 394-450, 487-543, 580-636, 673-729, 766-821

FIGURE 98

MLLWCPPQCACSLGVFPSAPSPVWGTRRSCEPATRVPEVWILSPLLRHGGHTQTQNHTASPRSPVMESPKKKNQQLK
VGILHLGSRQKKIRIQLRSQCATWKVICKSCISQTPGINLDLGSGVKVKIIPKEEHCKMPEAGEEQPQV

Signal sequence.
amino acids 1-25

N-glycosylation site.
amino acids 56-59

N-myristoylation sites.
amino acids 14-19, 25-30

FIGURE 99

MRELAIEIGVRALLFGVFVFTEFLDPFQRVIQPEEIWLYKNPLVQSDNIPTRLMFAISFLTPLAVICVVKIIRRTDK
TEIKEAFLAVSLALALNGVCTNTIKLIVGRPRADFFYRCFPDGVMNSEMHCTGDPDLVSEGRKSFPSIHSSFAFSGL
GFTTFYLAGKLHCFTESGRGKSWRLCAAILPLYCAMMIALSRMCDYKHHWQDSFVGGVIALIFAYICYRQHYPPLGQ
HSLPO

Transmembrane domains.
amino acids 4-24, 47-67, 82-102, 145-165, 175-195

Glycosaminoglycan attachment sites.
amino acids 152-155, 171-174

Tyrosine kinase phosphorylation site.
amino acids 107-114

N-myristoylation sites.
amino acids 95-100, 120-125, 153-158, 210-215

Amidation site.
amino acids 137-140

Tubulin-beta mRNA autoregulation signal.
amino acids 1-4

PAP2 superfamily.
amino acids 82-230

FIGURE 100

MAELEFVQIIIIVVVMMVMVVVITCLLSHYKLSARSFISRHSQGRRREDALSSEGCLWPSESTVSGNGIPEPQVYAP
PRPTDRLAVPPFAQRERFHRFQPTYPYLQHEIDLPPTISLSDGEEPPPYQGPCTLQLRDPEQQLELNRESVRAPPNR
TIFDSDLMDSARLGGPCPPSSNSGISATCYGSGGRMEGPPPTYSEVIGHYPGSSFQHQQSSGPPSLLEGTRLHHTHI
APLESAAIWSKEKDKQKGHPL

Transmembrane domain.
amino acids 7-27

N-glycosylation site.
amino acids 153-156

Glycosaminoglycan attachment site.
amino acids 65-68

N-myristoylation site.
amino acids 178-183

Amidation site.
amino acids 43-46

FIGURE 101

MAELEFVQIIIIVVVMMVMVVVITCLLSHYKLSARSFISRHSQGRRREDALSSEGCLWPSESTVSGNGIPEPQVYAP
PRPTDRLAVPPFAQRERFHRFQPTYPYLQHEIDLPPTISLSDGEEPPPYQGPCTLQLRDPEQQLELNRESVRAPPNR
TIFDSDLMDSARLGGPCPPSSNSGISATCYGSGGRMEGPPPTYSEVIGHYPGSSFQHQQSSGPPSLLEGTRLHHTHI
APLESAAIWSKEKDKQKGHPL

Transmembrane domain.
amino acids 7-27

N-glycosylation site.
amino acids 153-156

Glycosaminoglycan attachment site.
amino acids 65-68

N-myristoylation site.
amino acids 178-183

Amidation site.
amino acids 43-46

FIGURE 102

MGGAVVDEGPTGVKAPDGGWGWAVLFGCFVITGFSYAFPKAVSVFFKELIQEFGIGYSDTAWISSILLAMLYGTGPL
CSVCVNRFGCRPVMLVGGLFASLGMVAASFCRSIIQVYLTTGVITGLGLALNFQPSLIMLNRYFSKRRPMANGLAAA
GSPVFLCALSPLGQLLQDRYGWRGGFLILGGLLLNCCVCAALMRPLVVTAQPGSGPPRPSRRLLDLSVFRDRGFVLY
AVAASVMVLGLFVPPVFVVSYAKDLGVPDTKAAFLLTILGFIDIFARPAAGFVAGLGKVRPYSVYLFSFSMFFNGLA
DLAGSTAGDYGGLVVFCIFFGISYGMVGALQFEVLMAIVGTHKFSSAIGLVLLMEAVAVLVGPPSGGKLLDATHVYM
YVFILAGAEVLTSSLILLLGNFFCIRKKPKEPQPEVAAAEEEKLHKPPADSGVDLREVEHFLKAEPEKNGEVVHTPE
TSV

Transmembrane domains.

amino acids 20-40, 55-75, 114-134, 146-166, 180-200, 223-243, 262-282, 292-312, 318-338, 348-368, 385-405

N-myristoylation sites.

amino acids 54-59, 94-99, 95-100, 101-106, 119-124, 123-128, 125-130, 150-155, 185-190, 257-262, 312-317, 329-334, 333-338, 405-410

FIGURE 103

MAAPTPARPVLTHLLVALFGMGSWAAVNGIWVELPVVVKELPEGWSLPSYVSVLVALGNLGLLVVTLWRRLAPGKDE
QVPIRVVQVLGMVGTALLASLWHHVAPVAGQLHSVAFLALAFVLALACCASNVTFLPFLSHLPPRFLRSFFLGQGLS
ALLPCVLALVQGVGRLECPPAPINGTPGPPLDFLERFPASTFFWALTALLVASAAAFQGLLLLLPPPPSVPTGELGS
GLQVGAPGAEEEVEESSPLQEPPSQAAGTTPGPDPKAYQLLSARSACLLGLLAATNALTNGVLPAVQSFSCLPYGRL
AYHLAVVLGSAANPLACFLAMGVLCRSLAGLGGLSLLGVFCGGYLMALAVLSPCPPLVGTSAGVVLVVLSWVLCLGV
FSYVKVAASSLLHGGGRPALLAAGVAIQVGSLLGAVAMFPPTSIYHVFHSRKDCADPCDS

Transmembrane domains.
amino acids 9-29, 47-67, 81-101, 111-131, 146-166, 197-217, 272-292, 305-325, 332-352, 368-388, 404-424

N-glycosylation site.
amino acids 129-132

Protein kinase C phosphorylation sites.
amino acids 273-275, 435-437

N-myristoylation sites.
amino acids 22-27, 88-93, 107-112, 150-155, 232-237, 236-241, 281-286, 292-297, 346-351, 367-372, 400-405, 415-420

Leucine zipper pattern.
amino acids 149-170

FIGURE 104

MHTVATSGPNASWGAPANASGCPGCGANASDGPVPSPRAVDAWLVPLFFAALMLLGLVGNSLVIYVICRHKPMRTVT
NFYIANLAATDVTFLLCCVPFTALLYPLPGWVLGDFMCKFVNYIQQVSVQATCATLTAMSVDRWYVTVFPLRALHRR
TPRLALAVSLSIWVGSAAVSAPVLALHRLSPGPRAYCSEAFPSRALERAFALYNLLALYLLPLLATCACYAAMLRHL
GRVAVRPAPADSALQGQVLAERAGAVRAKVSRLVAAVVLLFAACWGPIQLFLVLQALGPAGSWHPRSYAAYALKTWA
HCMSYSNSALNPLLYAFLGSHFRQAFRRVCPCAPRRPRRPRRPGPSDPAAPHAELHRLGSHPAPARAQKPGSSGLAA
RGLCVLGEDNAPL

Transmembrane domains.

amino acids 42-62, 84-104, 125-145, 159-179, 202-222, 265-285, 307-327

N-glycosylation sites.

amino acids 10-13, 18-21, 28-31

N-myristoylation sites.

amino acids 14-19, 21-26, 24-29, 26-31, 56-61, 247-252, 255-260

7 transmembrane receptor (rhodopsin family).

amino acids 59-323

FIGURE 105

MSMNNSKQLVSPAAALLSNTTCQTENRLSVFFSVIFMTVGILSNSLAIAILMKAYQRFRQKSKASFLLLASGLVITD
FFGHLINGAIAVFVYASDKEWIRFDQSNVLCSIFGICMVFSGLCPLLLGSVMAIERCIGVTKPIFHSTKITSKHVKM
MLSGVCLFAVFIALLPILGHRDYKIQASRTWCFYNTEDIKDWEDRFYLLLFSFLGLLALGVSLLCNAITGITLLRVK
FKSQQHRQGRSHHLEMVIQLLAIMCVSCICWSPFLVTMANIGINGNHSLETCETTLFALRMATWNQILDPWVYILLR
KAVLKNLYKLASQCCGVHVISLHIWELSSIKNSLKVAAISESPVAEKSAST

Transmembrane domains.

amino acids 29-49, 67-87, 108-128, 152-172, 201-221, 244-264

N-glycosylation sites.

amino acids 4-7, 19-22, 277-280

Tyrosine kinase phosphorylation site.

amino acids 194-201

N-myristoylation sites.

amino acids 40-45, 72-77, 126-131, 273-278

7 transmembrane receptor (rhodopsin).

amino acids 104-304

FIGURE 106

MSRMSRHPDKDLAQGPFNTCCGCTLMASPANLPPNTQAAAERALSQSRWKRVQVPAPASLSPFPLAMASVAFWISIL
IGCEEQTLCRGWRSPVGDGCAHVPPQERATAEADPPGRCSTSTASSTICGLWHLSPRLQLLPPLHSRQGEESGKTEK
VLLWGREGLHVWKPGVLQPDVHGTSNLGNCSFLHGLVTAPSCPRRAGAELLNSLGSQFAISLFEVQSGTEPSITGVA
TSGQCRAMPLKHYLLLLVGCQAWGAGLAYHGCPSECTCSRASQVECTGARIVAVPTPLPWNAMSLQILNTHITELNE
SPFLNISALIALRIEKNELSRITPGAFRNLGSLRYLSLANNKLQVLPIGLFQGLDSLESLLLSSNQLLQIQPAHFSQ
CSNLKELQLHGNHLEYIPDGAFDHLVGLTKLNLGKNSLTHISPRVFQHLGNLQVLRLYENRLTDIPMGTFDGLVNLQ
ELALQQNQIGLLSPGLFHNNHNLQRLYLSNNHISQLPPSIFMQLPQLNRLTLFGNSLKELSLGIFGPMPNLRELWLY
DNHISSLPDNVFSNLRQLQVLILSRNQISFISPGAFNGLTELRELSLHTNALQDLDGNVFRMLANLQNISLQNNRLR
QLPGNIFANVNGLMAIQLQNNQLENLPLGIFDHLGKLCELRLYDNPWRCDSDILPLRNWLLLNQPRLGTDTVPVCFS
PANVRGQSLIIINVNVAVPSVHVPEVPSYPETPWYPDTPSYPDTTSVSSTTELTSPVEDYTDLTTIQVTDDRSVWGM
THAHSGLAIAAIVIGIVALACSLAACVGCCCCKKRSQAVLMQMKAPNEC

Transmembrane domains.

amino acids 57-77, 239-259, 775-795

N-glycosylation sites.

amino acids 183-186, 313-316, 607-610 cAMP- and cGMP-dependent protein kinase phosphorylation site.

amino acids 803-806

Tyrosine kinase phosphorylation site.

amino acids 652-659

N-myristoylation sites.

amino acids 209-214, 222-227, 229-234, 234-239, 255-260, 333-338, 357-362, 453-458, 477-482, 573-578, 620-625, 769-774, 776-781, 798-803

Leucine zipper pattern.

amino acids 344-365

Leucine rich repeat N-terminal domain.

amino acids 262-290

Leucine rich repeats.

amino acids 316-339, 340-363, 364-387, 388-411, 412-435, 436-459, 460-483, 484-507, 508-531, 532-555, 556-579, 580-603, 604-627, 628-651

Leucine rich repeat C-terminal domain amino acids 661-713

FIGURE 107A

MAPPPPPVLPVLLLLAAAAALPAMGLRAAAWEPRVPGGTRAFALRPGCTYAVGAACTPRAPRELLDVGRDGRLAGRR
RVSGAGRPLPLQVRLVARSAPTALSRRLRARTHLPGCGARARLCGTGARLCGALCFPVPGGCAAAQHSALAAPTTLP
ACRCPPRPRPRCPGRPICLPPGGSVRLRLLCALRRAAGAVRVGLALEAATAGTPSASPSPSPPLPPNLPEARAGPAR
RARRGTSGRGSLKFPMPNYQVALFENEPAGTLILQLHAHYTIEGEEERVSYYMEGLFDERSRGYFRIDSATGAVSTD
SVLDRETKETHVLRVKAVDYSTPPRSATTYITVLVKDTNDHSPVFEQSEYRERVRENLEVGYEVLTIRASDRDSPIN
ANLRYRVLGGAWDVFQLNESSGVVSTRAVLDREEAAEYQLLVEANDQGRNPGPLSATATVYIEVEDENDNYPQFSEQ
NYVVQVPEDVGLNTAVLRVQATDRDQGQNAAIHYSILSGNVAGQFYLHSLSGILDVINPLDFEDVQKYSLSIKAQDG
GRPPLINSSGVVSVQVLDVNDNEPIFVSSPFQATVLENVPLGYPVVHIQAVDADSGENARLHYRLVDTASTFLGGGS
AGPKNPAPTPDFPFQIHNSSGWITVCAELDREEVEHYSFGVEAVDHGSPPMSSSTSVSITVLDVNDNDPVFTQPTYE
LRLNEDAAVGSSVLTLQARDRDANSVITYQLTGGNTRNRFALSSQRGGGLITLALPLDYKQEQQYVLAVTASDGTRS
HTAHVLINVTDANTHRPVFQSSHYTVSVSEDRPVGTSIATLSANDEDTGENARITYVIQDPVPQFRIDPDSGTMYTM
MELDYENQVAYTLTIMAQDNGIPQKSDTTTLEILILDANDNAPQFLWDFYQGSIFEDAPPSTSILQVSATDRDSGPN
GRLLYTFQGGDDGDGDFYIEPTSGVIRTQRRLDRENVAVYNLWALAVDRGSPTPLSASVEIQVTILDINDNAPMFEK
DELELFVEENNPVGSVVAKIRANDPDEGPNAQIMYQIVEGDMRHFFQLDLLNGDLRAMVELDFEVRREYVLVVQATS
APLVSRATVHILLVDQNDNPPVLPDFQILFNNYVTNKSNSFPTGVIGCIPAHDPDVSDSLNYTFVQGNELRLLLLDP
ATGELQLSRDLDNNRPLEALMEVSVSDGIHSVTAFCTLRVTIITDDMLTNSITVRLENMSQEKFLSPLLALFVEGVA
AVLSTTKDDVFVFNVQNDTDVSSNILNVTFSALLPGGVRGQFFPSEDLQEQIYLNRTLLTTISTQRVLPFDDNICLR
EPCENYMKCVSVLRFDSSAPFLSSTTVLFRPIHPINGLRCRCPPGFTGDYCETEIDLCYSDPCGANGRCRSREGGYT
CECFEDFTGEHCEVDARSGRCANGVCKNGGTCVNLLIGGFHCVCPPGEYERPYCEVTTRSFPPQSFVTFRGLRQRFH
FTISLTFATQERNGLLLYNGRFNEKHDFIALEIVDEQVQLTFSAGETTTTVAPKVPSGVSDGRWHSVQVQYYNKPNI
GHLGLPHGPSGEKMAVVTVDDCDTTMAVRFGKDIGNYSCAAQGTQTGSKKSLDLTGPLLLGGVPNLPEDFPVHNRQF
VGCMRNLSVDGKNVDMAGFIANNGTREGCAARRNFCDGRRCQNGGTCVNRWNMYLCECPLRFGGKNCEQAMPHPQLF
SGESVVSWSDLNIIISVPWYLGLMFRTRKEDSVLMEATSGGPTSFRLQILNNYLQFEVSHGPSDVESVMLSGLRVTD
GEWHHLLIELKNVKEDSEMKHLVTMTLDYGMDQNKADIGGMLPGLTVRSVVVGGASEDKVSVRRGFRGCMQGVRMGG
TPTNVATLNMNNALKVRVKDGCDVDDPCTSSPCPPNSRCHDAWEDYSCVCDKGYLGINCVDACHLNPCENMGACVRS
PGSPQGYVCECGPSHYGPYCENKLDLPCPRGWWGNPVCGPCHCAVSKGFDPDCNKTNGQCQCKENYYKLLAQDTCLP
CDCFPHGSHSRTCDMATGQCACKPGVIGRQCNRCDNPFAEVTTLGCEVIYNGCPKAFEAGIWWPQTKFGQPAAVPCP
KGSVGNAVRHCSGEKGWLPPELFNCTTISFVDLRAMNEKLSRNETQVDGARALQLVRALRSATQHTGTLFGNDVRTA
YQLLGHVLQHESWQQGFDLAATQDADFHEDVIHSGSALLAPATRAAWEQIQRSEGGTAQLLRRLEGYFSNVARNVRR
TYLRPFVIVTANMILAVDIFDKFNFTGARVPRFDTIHEEFPRELESSVSFPADFFRPPEEKEGPLLRPAGRRTTPQT
TRPGPGTEREAPISRRRRHPDDAGQFAVALVIIYRTLGQLLPERYDPDRRSLRLPHRPIINTPMVSTLVYSEGAPLP
RPLERPVLVEFALLEVEERTKPVCVFWNHSLAVGGTGGWSARGCELLSRNRTHVACQCSHTASFAVLMDISRRENGE
VLPLKIVTYAAVSLSLAALLVAFVLLSLVRMLRSNLHSIHKHLAVALFLSQLVFVIGINQTENPFLCTVVAILLHYI
YMSTFAWTLVESLHVYRMLTEVRNIDTGPMRFYYVVGWGIPAIVTGLAVGLDPQGYGNPDFCWLSLQDTLIWSFAGP
IGAVIIINTVTSVLSAKVSCQRKHHYYGKKGIVSLLRTAFLLLLLISATWLLGLLAVNRDALSFHYLFAIFSGLQGP
FVLLFHCVLNQEVRKHLKGVLGGRKLHLEDSATTRATLLTRSLNCNTTFGDGPDMLRTDLGESTASLDSIVRDEGIQ
KLGVSSGLVRGSHGEPDASLMPRSCKDPPGHDSDSDSELSLDEQSSSYASSHSSDSEDDGVGAEEKWDPARGAVHST
PKGDAVANHVPAGWPDQSLAESDSEDPSGKPRLKVETKVSVELHREEQGSHRGEYPPDQESGGAARLASSQPPEQRK
GILKNKVTYPPPLTLTEQTLKGRLREKLADCEQSPTSSRTSSLGSGGPDCAITVKSPGREPGRDHLNGVAMNVRTGS
AQADGSDSEKP

Transmembrane domains.
amino acids 4-24, 2235-2255, 2470-2490, 2504-2524, 2530-2550, 2571-2591, 2611-2631, 2651-2671, 2686-2706

N-glycosylation sites.
amino acids 403-406, 546-549, 634-637, 778-781, 1114-1117, 1139-1142, 1213-1216, 1249-1252, 1259-1262, 1287-1290, 1576-1579, 1623-1626, 1640-1643, 1979-1982, 2103-2106, 2122-2125, 2257-2260, 2415-2418, 2437-2440, 2523-2526, 2741-2744

Glycosaminoglycan attachment sites.
amino acids 80-83, 238-241

FIGURE 107B cAMP- and cGMP-dependent protein kinase phosphorylation sites.
amino acids 77-80, 234-237, 2304-2307

Tyrosine kinase phosphorylation sites.
amino acids 363-370, 1379-1385, 1569-1577

N-myristoylation sites.
amino acids 25-30, 37-42, 47-52, 124-129, 137-142, 138-143, 206-211, 303-308, 407-412, 473-478, 489-494, 501-506, 613-618, 727-732, 741-746, 805-810, 842-847, 933-938, 948-953, 1015-1020, 1122-1127, 1125-1130, 1268-1273, 1383-1388, 1410-1415, 1416-1421, 1424-1429, 1521-1526, 1575-1580, 1583-1588, 1587-1592, 1601-1606, 1619-1624, 1641-1646, 1662-1667, 1680-1685, 1734-1739, 1766-1771, 1801-1806, 1811-1816, 1839-1844, 1843-1848, 1847-1852, 1848-1853, 1927-1932, 1959-1964, 1983-1988, 2020-2025, 2054-2059, 2071-2076, 2081-2086, 2146-2151, 2421-2426, 2424-2429, 2521-2526, 2587-2592, 2714-2719, 2775-2780, 2779-2784, 2844-2849, 2898-2903, 2927-2932, 2972-2977, 2994-2999, 3002-3007

Amidation sites.
amino acids 74-77, 1654-1657, 2302-2305, 2645-2648, 2717-2720

Aspartic acid and asparagine hydroxylation sites.
amino acids 1664-1675, 1887-1898

EGF-like domain cysteine pattern signature.
amino acids 1349-1360, 1387-1398, 1673-1684, 1896-1907, 1934-1945, 2022-2033

Cadherins extracellular repeated domain signature.
amino acids 341-351, 447-457, 553-563, 675-685, 880-890, 987-997, 1089-1099

Cadherin domains.
amino acids 250-344, 358-450, 464-556, 570-678, 692-780, 794-883, 897-990, 1004-1092, 1110-1198

7 transmembrane receptor.
amino acids 2465-2708, 2470-2710

EGF-like domains.
amino acids 1876-1907, 1911-1945, 1653-1684, 1407-1440, 1307-1360, 1367-1398

Laminin G domains.
amino acids 1470-1532, 1579-1632, 1719-1780, 1833-1852, 2003-2048

Latrophilin/CL-1-like GPS domain.
amino acids 2407-2460

Hormone receptor domain.
amino acids 2052-2109

FIGURE 108

MVDVKCLSDCKLQNQLEKLGFSPGPILPSTRKLYEKKLVQLLVSPPCAPPVMNGPRELDGAQDSDDSEELNIILQGN
IILSTEKSKKLKKWPEASTTKRKAVDTYCLDYKPSKGRRWAARAPSTRITYGTITKERDYCAEDQTIESWREEGFPV
GLKLAVLGIFIIVVFVYLTVENKSLFG

Transmembrane domain.

amino acids 154-174

N-glycosylation site.

amino acids 176-179

N-myristoylation sites.

amino acids 60-65, 155-160

Amidation site.

amino acids 113-116

LEM domain.

amino acids 1-44

FIGURE 109

MSKSKCSVGLMSSVVAPAKEPNAVGPKEVELILVKEQNGVQLTSSTLTNPRQSPVEAQDRETWGKKIDFLLSVIGFA
VDLANVWRFPYLCYKNGGGAFLVPYLLFMVIAGMPLFYMELALGQFNREGAAGVWKICPILKGVGFTVILISLYVGF
FYNVIIAWALHYLFSSFTTELPWIHCNNSWNSPNCSDAHPGDSSGDSSGLNDTFGTTPAAEYFERGVLHLHQSHGID
DLGPPRWQLTACLVLVIVLLYFSLWKGVKTSGKVVWITATMPYVVLTALLLRGVTLPGAIDGIRAYLSVDFYRLCEA
SVWIDAATQVCFSLGVGFGVLIAFSSYNKFTNNCYRDAIVTTSINSLTSFSSGFVVFSFLGYMAQKHSVPIGDVAKD
GPGLIFIIYPEAIATLPLSSAWAVVFFIMLLTLGIDSAMGGMESVITGLIDEFQLLHRHRELFTLFIVLATFLLSLF
CVTNGGIYVFTLLDHFAAGTSILFGVLIEAIGVAWFYGVGQFSDDIQQMTGQRPSLYWRLCWKLVSPCFLLFVVVVS
IVTFRPPHYGAYIFPDWANALGWVIATSSMAMVPIYAAYKFCSLPGSFREKLAYAIAPEKDRELVDRGEVRQFTLRH
WLKV

Transmembrane domains.
amino acids 65-85, 98-118, 133-153, 149-169, 236-256, 272-292, 310-330, 350-370, 393-413, 409-429, 445-465, 481-501, 520-540, 560-580

N-glycosylation sites.
amino acids 181-184, 188-191, 205-208

N-myristoylation sites.
amino acids 9-14, 39-44, 140-145, 203-208, 209-214, 258-263, 289-294, 323-328, 327-332, 419-424, 425-430, 513-518

Amidation site.
amino acids 63-66

Leucine zipper pattern.
amino acids 440-461

Sodium:neurotransmitter symporter family signature 1.
amino acids 84-98

Sodium:neurotransmitter symporter family signature 2.
amino acids 166-186

FIGURE 110

MGLAMEHGGSYARAGGSSRGCWYYLRYFFLFVSLIQFLIILGLVLFMVYGNVHVSTESNLQATERRAEGLYSQLLGL
TASQSNLTKELNFTTRAKDAIMQMWLNARRDLDRINASFRQCQGDRVIYTNNQRYMAAIILSEKQCRDQFKDMNKSC
DALLFMLNQKVKTLEVEIAKEKTICTKDKESVLLNKRVAEEQLVECVKTRELQHQERQLAKEQLQKVQALCLPLDKD
KFEMDLRNLWRDSIIPRSLDNLGYNLYHPLGSELASIRRACDHMPSLMSSKVEELARSLRADIERVARENSDLQRQK
LEAQQGLRASQEAKQKVEKEAQAREAKLQAECSRQTQLALEEKAVLRKERDNLAKELEEKKREAEQLRMELAIRNSA
LDTCIKTKSQPMMPVSRPMGPVPNPQPIDPASLEEFKRKILESQRPPAGIPVAPSSG

Transmembrane domain.

amino acids 28-48

N-glycosylation sites.

amino acids 83-86, 89-92, 113-116, 151-154

Tyrosine kinase phosphorylation sites.

amino acids 65-71, 248-255

N-myristoylation sites.

amino acids 8-13, 16-21, 76-81, 262-267, 314-319

FIGURE 111

MMAGMKIQLVCMLLLAFSSWSLCSDSEEEMKALEADFLTNMHTSKISKAHVPSWKMTLLNVCSLVNNLNSPAEETGE
VHEEELVARRKLPTALDGFSLEAMLTIYQLHKICHSRAFQHWELIQEDILDTGNDKNGKEEVIKRKIPYILKRQLYE
NKPRRPYILKRDSYYY

Signal sequence.
amino acids 1-23 cAMP- and cGMP-dependent protein kinase phosphorylation site.
amino acids 164-167

N-myristoylation site.
amino acids 130-135

FIGURE 112

MLLRSAGKLNVGTKKEDGESTAPTPRPKVLRCKCHHHCPEDSVNNICSTDGYCFTMIEEDDSGLPVVTSGCLGLEGS
DFQCRDTPIPHQRRSIECCTERNECNKDLHPTLPPLKNRDFVDGPIHHRALLISVTVCSLLLVLIILFCYFRYKRQE
TRPRYSIGLEQDETYIPPGESLRDLIEQSQSSGSGSGLPLLVQRTIAKQIQMVKQIGKGRYGEVWMGKWRGEKVAVK
VFFTTEEASWFRETEIYQTVLMRHENILGFIAADIKGTGSWTQLYLITDYHENGSLYDYLKSTTLDAKSMLKLAYSS
VSGLCHLHTEIFSTQGKPAIAHRDLKSKNILVKKNGTCCIADLGLAVKFISDTNEVDIPPNTRVGTKRYMPPEVLDE
SLNRNHFQSYIMADMYSFGLILWEVARRCVSGGIVEEYQLPYHDLVPSDPSYEDMREIVCIKKLRPSFPNRWSSDEC
LRQMGKLMTECWAHNPASRLTALRVKKTLAKMSESQDIKL

Transmembrane domain.
amino acids 126-146

N-glycosylation sites.
amino acids 284-287, 343-346

Glycosaminoglycan attachment sites.
amino acids 186-189, 188-191

N-myristoylation sites.
amino acids 73-78, 187-192

Serine/Threonine protein kinases active-site signature.
amino acids 328-340

Mitochondrial energy transfer proteins signature.
amino acids 172-180

Protein kinase domain.
amino acids 204-491

Activin types I and II receptor domain.
amino acids 17-110

FIGURE 113

TTGAAGTGCATTGCTGCAGCTGGTAGCATGAGTGGTGGCCACCACCTGCAGCTGGCTGCCCTCTGGCCCTGGCTGCT
GATGGCTACCCTGCAGGCAGGCTTTGGACGCACAGGACTGGTACTGGCAGCAGCGGTGGAGTCTGAAAGATCAGCAG
AACAGAAAGCTGTTATCAGAGTGATCCCCTTGAAAATGGACCCCACAGGAAAACTGAATCTCACTTTGGAAGGTGTG
TTTGCTGGTGTTGCTGAAATAACTCCAGCAGAAGGAAAATTAATGCAGTCCCACCCGCTGTACCTGTGCAATGCCAG
TGATGACGACAATCTGGAGCCTGGATTCATCAGCATCGTCAAGCTGGAGAGTCCTCGACGGGCCCCCCACCCCTGCC
TGTCACTGGCTAGCAAGGCTCGGATGGCGGGTGAGCGAGGAGCCAGTGCTGTCCTCTTTGACATCACTGAGGATCGA
GCTGCTGCTGAGCAGCTGCAGCAGCCGCTGGGGCTGACCTGGCCAGTGGTGTTGATCTGGGGTAATGACGCTGAGAA
GCTGATGGAGTTTGTGTACAAGAACCAAAAGGCCCATGTGAGGATTGAGCTGAAGGAGCCCCCGGCCTGGCCAGATT
ATGATGTGTGGATCCTAATGACAGTGGTGGGCACCATCTTTGTGATCATCCTGGCTTCGGTGCTGCGCATCCGGTGC
CGCCCCCGCCACAGCAGGCCGGATCCGCTTCAGCAGAGAACAGCCTGGGCCATCAGCCAGCTGGCCACCAGGAGGTA
CCAGGCCAGCTGCAGGCAGGCCCGGGGTGAGTGGCCAGACTCAGGGAGCAGCTGCAGCTCAGCCCCTGTGTGTGCCA
TCTGTCTGGAGGAGTTCTCTGAGGGGCAGGAGCTACGGGTCATTTCCTGCCTCCATGAGTTCCATCGTAACTGTGTG
GACCCCTGGTTACATCAGCATCGGACTTGCCCCCTCTGCATGTTCAACATCACAGAGGGAGATTCATTTTCCCAGTC
CCTGGGACCCTCTCGATCTTACCAAGAACCAGGTCGAAGACTCCACCTCATTCGCCAGCATCCCGGCCATGCCCACT
ACCACCTCCCTGCTGCCTACCTGTTGGGCCCTTCCCGGAGTGCAGTGGCTCGGCCCCCACGACCTGGTCCCTTCCTG
CCATCCCAGGAGCCAGGCATGGGCCCTCGGCATCACCGCTTCCCCAGAGCTACACATCCCCGGGCTCCAGGAGAGCA
GCAGCGCCTGGCAGGAGCCCAGCACCCCTATGCACAAGGCTGGGGACTGAGCCACCTCCAATCCACCTCACAGCACC
CTGCTGCTTGCCCAGTGCCCCTACGCCGGGCCAGGCCCCCTGACAGCAGTGGATCTGGAGAAAGCTATTGCACAGAA
CGCAGTGGGTACCTGGCAGATGGGCCAGCCAGTGACTCCAGCTCAGGGCCCTGTCATGGCTCTTCCAGTGACTCTGT
GGTCAACTGCACGGACATCAGCCTACAGGGGGTCCATGGCAGCAGTTCTACTTTCTGCAGCTCCCTAAGCAGTGACT
TTGACCCCCTAGTGTACTGCAGCCCTAAAGGGGATCCCCAGCGAGTGGACATGCAGCCTAGTGTGACCTCTCGGCCT
CGTTCCTTGGACTCGGTGGTGCCCACAGGGGAAACCCAGGTTTCCAGCCATGTCCACTACCACCGCCACCGGCACCA
CCACTACAAAAAGCGGTTCCAGTGGCATGGCAGGAAGCCTGGCCCAGAAACCGGAGTCCCCCAGTCCAGGCCTCCTA
TTCCTCGGACACAGCCCCAGCCAGAGCCACCTTCTCCTGATCAGCAAGTCACCAGATCCAACTCAGCAGCCCCTTCG
GGGCGGCTCTCTAACCCACAGTGCCCCAGGGCCCTCCCTGAGCCAGCCCCTGGCCCAGTTGACGCCTCCAGCATCTG
CCCCAGTACCAGCAGTCTGTTCAACTTGCAAAAATCCAGCCTCTCTGCCCGACACCCACAGAGGAAAAGGCGGGGGG
GTCCCTCCGAGCCCACCCCTGGCTCTCGGCCCCAGGATGCAACTGTGCACCCAGCTTGCCAGATTTTTCCCCATTAC
ACCCCCAGTGTGGCATATCCTTGGTCCCCAGAGGCACACCCCTTGATCTGTGGACCTCCAGGCCTGGACAAGAGGCT
GCTACCAGAAACCCCAGGCCCCTGTTACTCAAATTCACAGCCAGTGTGGTTGTGCCTGACTCCTCGCCAGCCCCTGG
AACCACATCCACCTGGGGAGGGGCCTTCTGAATGGAGTTCTGACACCGCAGAGGGCAGGCCATGCCCTTATCCGCAC
TGCCAGGTGCTGTCGGCCCAGCCTGGCTCAGAGGAGGAACTCGAGGAGCTGTGTGAACAGGCTGTGTGAGATGTTCA
GGCCTAGCTCCAACCA

FIGURE 114

MSGGHHLQLAALWPWLLMATLQAGFGRTGLVLAAAVESERSAEQKAVIRVIPLKMDPTGKLNLTLEGVFAGVAEITP
AEGKLMQSHPLYLCNASDDDNLEPGFISIVKLESPRRAPHPCLSLASKARMAGERGASAVLFDITEDRAAAEQLQQP
LGLTWPVVLIWGNDAEKLMEFVYKNQKAHVRIELKEPPAWPDYDVWILMTVVGTIFVIILASVLRIRCRPRHSRPDP
LQQRTAWAISQLATRRYQASCRQARGEWPDSGSSCSSAPVCAICLEEFSEGQELRVISCLHEFHRNCVDPWLHQHRT
CPLCMFNITEGDSFSQSLGPSRSYQEPGRRLHLIRQHPGHAHYHLPAAYLLGPSRSAVARPPRPGPFLPSQEPGMGP
RHHRFPRATHPRAPGEQQRLAGAQHPYAQGWGLSHLQSTSQHPAACPVPLRRARPPDSSGSGESYCTERSGYLADGP
ASDSSSGPCHGSSSDSVVNCTDISLQGVHGSSSTFCSSLSSDFDPLVYCSPKGDPQRVDMQPSVTSRPRSLDSVVPT
GETQVSSHVHYHRHRHHHYKKRFQWHGRKPGPETGVPQSRPPIPRTQPQPEPPSPDQQVTRSNSAAPSGRLSNPQCP
RALPEPAPGPVDASSICPSTSSLFNLQKSSLSARHPQRKRRGGPSEPTPGSRPQDATVHPACQIFPHYTPSVAYPWS
PEAHPLICGPPGLDKRLLPETPGPCYSNSQPVWLCLTPRQPLEPHPPGEGPSEWSSDTAEGRPCPYPHCQVLSAQPG
SEEELEELCEQAV

Signal sequence.

amino acids 1-26

Transmembrane domain.

amino acids 198-218

N-glycosylation sites.

amino acids 62-65, 92-95, 315-318, 481-484

Glycosaminoglycan attachment site.

amino acids 444-447

Tyrosine kinase phosphorylation site.

amino acids 171-177

N-myristoylation sites.

amino acids 29-34, 67-72, 263-268, 445-450, 489-494, 492-497, 574-579

Amidation sites.

amino acids 335-338, 565-568

Zinc finger, C3HC4 type (RING finger).

amino acids 272-312

FIGURE 115

CCCTTTGAAGTGCATTGCTGCAGCTGGTAGCATGAGTGGTGGCCACCAGCTGCAGCTGGCTGCCCTCTGGCCCTGGC
TGCTGATGGCTACCCTGCAGGCAGGCTTTGGACGCACAGGACTGGTACTGGCAGCAGCGGTGGAGTCTGAAAGATCA
GCAGAACAGAAAGCTGTTATCAGAGTGATCCCCTTGAAAATGGACCCCACAGGAAAACTGAATCTCACTTTGGAAGG
TGTGTTTGCTGGTGTTGCTGAAATAACTCCAGCAGAAGGAAAATTAATGCAGTCCCACCCGCTGTACCTGTGCAATG
CCAGTGATGACGACAATCTGGAGCCTGGATTCATCAGCATCGTCAAGCTGGAGAGTCCTCGACGGGCCCCCCGCCCC
TGCCTGTCACTGGCTAGCAAGGCTCGGATGGCGGGTGAGCGAGGAGCCAGTGCTGTCCTCTTTGACATCACTGAGGA
TCGAGCTGCTGCTGAGCAGCTGCAGCAGCCGCTGGGGCTGACCTGGCCAGTGGTGTTGATCTGGGGTAATGACGCTG
AGAAGCTGATGGAGTTTGTGTACAAGAACCAAAAGGCCCATGTGAGGATTGAGCTGAAGGAGCCCCCGGCCTGGCCA
GATTATGATGTGTGGATCCTAATGACAGTGGTGGGCACCATCTTTGTGATCATCCTGGCTTCGGTGCTGCGCATCCA
GTGCCGCCCCCGCCACAGCAGGCCGGATCCGCTTCAGCAGAGAACAGCCTGGGCCATCAGCCAGCTGGCCACCAGGA
GGTACCAGGCCAGCTGCAGGCAGGCCCGGGGTGAGTGGCCAGACTCAGGGAGCAGCTGCAGCTCAGCCCCTGTGTGT
GCCATCTGTCTGGAGGAGTTCTCTGAGGGGCAGGAGCTACGGGTCATTTCCTGCCTCCATGAGTTCCATCGTAACTG
TGTGGACCCCTGGTTACATCAGCATCGGACTTGCCCCCTCTGCATGTTCAACATCACAGAGGGAGATTCATTTTCCC
AGTCCCTGGGACCCTCTCGATCTTACCAAGAACCAGGTCGAAGACTCCACCTCATTCGCCAGCATCCCGGCCATGCC
CACTACCACCTCCCTGCTGCCTACCTGTTGGGCCCTTCCCGGAGTGCAGTGGCTCGGCCCCCACGACCTGGTCCCTT
CCTGCCATCCCAGGAGCCAGGCATGGCCCTCGGCATCACCGCTTCCCCAGAGCTGCACATCCCCGGGCTCCAGGAG
AGCAGCAGCGCCTGGCAGGAGCCCAGCACCCCTATGCACAAGGCTGGGGACTGAGCCACCTCCAATCCACCTCACAG
CACCCTGCTGCTTGCCCAGTGCCCCTACGCCGGGCCAGGCCCCCTGACAGCAGTGGATCTGGAGAAAGCTATTGCAC
AGAACGCAGTGGGTACCTGGCAGATGGGCCAGCCAGTGACTCCAGCTCAGGGCCCTGTCATGGCTCTTCCAGTGACT
CTGTGGTCAACTGCACGGACATCAGCCTACAGGGGGTCCATGGCAGCAGTTCTACTTTCTGCAGCTCCCTAAGCAGT
GACTTTGACCCCCTAGTGTACTGCAGCCCTAAAGGGGATCCCCAGCGAGTGGACATGCAGCCTAGTGTGACCTCTCG
GCCTCGTTCCTTGGACTCGGTGGTGCCCACAGGGGAAACCCAGGTTTCCAGCCATGTCCACTACCACCGCCACCGGC
ACCACCACTACAAAAAGCGGTTCCAGTGGCATGGCAGGAAGCCTGGCCCAGAAACCGGAGTCCCCCAGTCCAGGCCT
CCTATTCCTCGGACACAGCCCCAGCCAGAGCCACCTTCTCCTGATCAGCAAGTCACCAGATCCAACTCAGCAGCCCC
TTCGGGGCGGCTCTCTAACCCACAGTGCCCCAGGGCCCTCCCTGAGCCAGCCCCTGGCCCAGTTGACGCCTCCAGCA
TCTGCCCCAGTACCAGCAGTCTGTTCAACTTGCAAAAATCCAGCCTCTCTGCCCGACACCCACAGAGGAAAAGGCGG
GGGGGTCCCTCCGAGCCCACCCCTGGCTCTCGGCCCCAGGATGCAACTGTGCACCCAGCTTGCCAGATTTTTCCCCA
TTACACCCCCAGTGTGGCATATCCTTGGTCCCCAGAGGCACACCCCTTGATCTGTGGACCTCCAGGCCTGGACAAGA
GGCTGCTACCAGAAACCCCAGGCCCCTGTTACTCAAATTCACAGCCAGTGTGGTTGTGCCTGACTCCTCGCCAGCCC
CTGGAACCACATCCACCTGGGGAGGGGCCTTCTGAATGGAGTTCTGACACCGCAGAGGGCAGGCCATGCCCTTGTCC
GCACTGCCAGGTGCTGTCGGCCCAGCCTGGCTCAGAGGAGGAACTCGAGGAGCTGTGTGAACAGGCTGTGTGAGATG
TTCAGGCCTAGCTCCAACCA

FIGURE 116

MSGGHQLQLAALWPWLLMATLQAGFGRTGLVLAAAVESERSAEQKAVIRVIPLKMDPTGKLNLTLEGVFAGVAEITP
AEGKLMQSHPLYLCNASDDDNLEPGFISIVKLESPRRAPRPCLSLASKARMAGERGASAVLFDITEDRAAAEQLQQP
LGLTWPVVLIWGNDAEKLMEFVYKNQKAHVRIELKEPPAWPDYDVWILMTVVGTIFVIILASVLRIQCRPRHSRPDP
LQQRTAWAISQLATRRYQASCRQARGEWPDSGSSCSSAPVCAICLEEFSEGQELRVISCLHEFHRNCVDPWLHQHRT
CPLCMFNITEGDSFSQSLGPSRSYQEPGRRLHLIRQHPGHAHYHLPAAYLLGPSRSAVARPPRPGPFLPSQEPGMGP
RHHRFPRAAHPRAPGEQQRLAGAQHPYAQGWGLSHLQSTSQHPAACPVPLRRARPPDSSGSGESYCTERSGYLADGP
ASDSSSGPCHGSSSDSVVNCTDISLQGVHGSSSTFCSSLSSDFDPLVYCSPKGDPQRVDMQPSVTSRPRSLDSVVPT
GETQVSSHVHYHRHRHHHYKKRFQWHGRKPGPETGVPQSRPPIPRTQPQPEPPSPDQQVTRSNSAAPSGRLSNPQCP
RALPEPAPGPVDASSICPSTSSLFNLQKSSLSARHPQRKRRGGPSEPTPGSRPQDATVHPACQIFPHYTPSVAYPWS
PEAHPLICGPPGLDKRLLPETPGPCYSNSQPVWLCLTPRQPLEPHPPGEGPSEWSSDTAEGRPCPCPHCQVLSAQPG
SEEELEELCEQAV

Signal sequence.
amino acids 1-26

Transmembrane domain.
amino acids 198-218

N-glycosylation sites.
amino acids 62-65, 92-95, 315-318, 481-484

Glycosaminoglycan attachment site.
amino acids 444-447

Tyrosine kinase phosphorylation site.
amino acids 171-177

N-myristoylation sites.
amino acids 29-34, 67-72, 263-268, 445-450, 489-494, 492-497, 574-579

Amidation sites.
amino acids 335-338, 565-568

Zinc finger, C3HC4 type (RING finger)
amino acids 272-312

FIGURE 117

TTGAAGTGCATTGCTGCAGCTGGTAGCATGAGTGGTGGCCACCACCTGCAGCTGGCTGCCCTCTGGCCCTGGCTGCT
GATGGCTACCCTGCAGGCAGGCTTTGGACGCACAGGACTGGTACTGGCAGCAGCGGTGGAGTCTGAAAGATCAGCAG
AACAGAAAGCTGTTATCAGAGTGATCCCCTTGAAAATGGACCCCACAGGAAAACTGAATCTCACTTTGGAAGGTGTG
TTTGCTGGTGTTGCTGAAATAACTCCAGCAGAAGGAAAATTAATGCAGTCCCACCCGCTGTACCTGTGCAATGCCAG
TGATGACGACAATCTGGAGCCTGGATTCATCAGCATCGTCAAGCTGGAGAGTCCTCGACGGGCCCCCCACCCCTGCC
TGTCACTGGCTAGCAAGGCTCGGATGGCGGGTGAGCGAGGAGCCAGTGCTGTCCTCTTTGACATCACTGAGGATCGA
GCTGCTGCTGAGCAGCTGCAGCAGCCGCTGGGGCTGACCTGGCCAGTGGTGTTGATCTGGGGTAATGACGCTGAGAA
GCTGATGGAGTTTGTGTACAAGAACCAAAAGGCCCATGTGAGGATTGAGCTGAAGGAGCCCCCGGCCTGGCCAGATT
ATGATGTGTGGATCCTAATGACAGTGGTGGGCACCATCTTTGTGATCATCCTGGCTTCGGTGCTGCGCATCCGGTGC
CGCCCCCGCCACAGCAGGCCGGATCCGCTTCAGCAGAGAACAGCCTGGGCCATCAGCCAGCTGGCCACCAGGAGGTA
CCAGGCCAGCTGCAGGCAGGCCCGGGGTGAGTGGCCAGACTCAGGGAGCAGCTGCAGCTCAGCCCCTGTGTGTGCCA
TCTGTCTGGAGGAGTTCTCTGAGGGGCAGGAGCTACGGGTCATTTCCTGCCTCCATGAGTTCCATCGTAACTGTGTG
GACCCCTGGTTACATCAGCATCGGACTTGCCCCCTCTGCATGTTCAACATCACAGAGGGAGATTCATTTTCCCAGTC
CCTGGGACCCTCTCGATCTTACCAAGAACCAGGTCGAAGACTCCACCTCATTCGCCAGCATCCCGGCCATGCCCACT
ACCACCTCCCTGCTGCCTACCTGTTGGGCCCTTCCCGGAGTGCAGTGGCTCGGCCCCCACGACCTGGTCCCTTCCTG
CCATCCCAGGAGCCAGGCATGGGCCCTCGGCATCACCGCTTCCCCAGAGCTGCACATCCCCGGGCTCCAGGAGAGCA
GCAGCGCCTGGCAGGAGCCCAGCACCCCTATGCACAAGGCTGGGGAATGAGCCACCTCCAATCCACCTCACAGCACC
CTGCTGCTTGCCCAGTGCCCCTACGCCGGGCCAGGCCCCCTGACAGCAGTGGATCTGGAGAAAGCTATTGCACAGAA
CGCAGTGGGTACCTGGCAGATGGGCCAGCCAGTGACTCCAGCTCAGGGCCCTGTCATGGCTCTTCCAGTGACTCTGT
GGTCAACTGCACGGACATCAGCCTACAGGGGGTCCATGGCAGCAGTTCTACTTTCTGCAGCTCCCTAAGCAGTGACT
TTGACCCCCTAGTGTACTGCAGCCCTAAAGGGGATCCCCAGCGAGTGGACATGCAGCCTAGTGTGACCTCTCGGCCT
CGTTCCTTGGACTCGGTGGTGCCCACAGGGGAAACCCAGGTTTCCAGCCATGTCCACTACCACCGCCACCGGCACCA
CCACTACAAAAAGCGGTTCCAGTGGCATGGCAGGAAGCCTGGCCCAGAAACCGGAGTCCCCCAGTCCAGGCCTCCTA
TTCCTCGGACACAGCCCCAGCCAGAGCCACCTTCTCCTGATCAGCAAGTCACCAGATCCAACTCAGCAGCCCCTTCG
GGGCGGCTCTCTAACCCACAGTGCCCCAGGGCCCTCCCTGAGCCAGCCCCTGGCCCAGTTGACGCCTCCAGCATCTG
CCCCAGTACCAGCAGTCTGTTCAACTTGCAAAAATCCAGCCTCTCTGCCCGACACCCACAGAGGAAAAGGCGGGGGG
GTCCCTCCGAGCCCACCCCTGGCTCTCGGCCCCAGGATGCAACTGTGCACCCAGCTTGCCAGATTTTTCCCCATTAC
ACCCCCAGTGTGGCATATCCTTGGTCCCCAGAGGCACACCCCTTGATCTGTGGACCTCCAGGCCTGGACAAGAGGCT
GCTACCAGAAACCCCAGGCCCCTGTTACTCAAATTCACAGCCAGTGTGGTTGTGCCTGACTCCTCGCCAGCCCCTGG
AACCACATCCACCTGGGGAGGGGCCTTCTGAATGGAGTTCTGACACCGCAGAGGGCAGGCCATGCCCTTATCCGCAC
TGCCAGGTGCTGTCGGCCCAGCCTGGCTCAGAGGAGGAACTCGAGGAGCTGTGTGAACAGGCTGTGTGAGATGTTCA
GGCCTAGCTCCAACCA

FIGURE 118

MSGGHHLQLAALWPWLLMATLQAGFGRTGLVLAAAVESERSAEQKAVIRVIPLKMDPTGKLNLTLEGVFAGVAEITP
AEGKLMQSHPLYLCNASDDDNLEPGFISIVKLESPRRAPHPCLSLASKARMAGERGASAVLFDITEDRAAAEQLQQP
LGLTWPVVLIWGNDAEKLMEFVYKNQKAHVRIELKEPPAWPDYDVWILMTVVGTIFVIILASVLRIRCRPRHSRPDP
LQQRTAWAISQLATRRYQASCRQARGEWPDSGSSCSSAPVCAICLEEFSEGQELRVISCLHEFHRNCVDPWLHQHRT
CPLCMFNITEGDSFSQSLGPSRSYQEPGRRLHLIRQHPGHAHYHLPAAYLLGPSRSAVARPPRPGPFLPSQEPGMGP
RHHRFPRAAHPRAPGEQQRLAGAQHPYAQGWGMSHLQSTSQHPAACPVPLRRARPPDSSGSGESYCTERSGYLADGP
ASDSSSGPCHGSSSDSVVNCTDISLQGVHGSSSTFCSSLSSDFDPLVYCSPKGDPQRVDMQPSVTSRPRSLDSVVPT
GETQVSSHVHYHRHRHHHYKKRFQWHGRKPGPETGVPQSRPPIPRTQPQPEPPSPDQQVTRSNSAAPSGRLSNPQCP
RALPEPAPGPVDASSICPSTSSLFNLQKSSLSARHPQRKRRGGPSEPTPGSRPQDATVHPACQIFPHYTPSVAYPWS
PEAHPLICGPPGLDKRLLPETPGPCYSNSQPVWLCLTPRQPLEPHPPGEGPSEWSSDTAEGRPCPYPHCQVLSAQPG
SEEELEELCEQAV

Signal sequence.
amino acids 1-26

Transmembrane domain.
amino acids 198-218

N-glycosylation sites.
amino acids 62-65, 92-95, 315-318, 481-484

Glycosaminoglycan attachment site.
amino acids 444-447

Tyrosine kinase phosphorylation site.
amino acids 171-177

N-myristoylation sites.
amino acids 29-34, 67-72, 263-268, 445-450, 489-494, 492-497, 574-579

Amidation sites.
amino acids 335-338, 565-568

Zinc finger, C3HC4 type (RING finger).
amino acids 272-312

FIGURE 119A

GGAAAGCTAGCGGCAGAGGCTCAGCCCCGGCGGCAGCGCGCGCCCCGCTGCCAGCCCATTTTCCGGACGCCACCCGC
GGGCACTGCCGACGCCCCCGGGGCTGCCGAGGGGAGGCCGGGGGGCGCAGCGGAGCGCGGTCCCGCGCACTGAGCC
CCGCGGCGCCCCGGGAACTTGGCGGCGACCCGAGCCCGGCGAGCCGGGGCGCGCCTCCCCCGCCGCGCGCCTCCTGC
ATGCGGGGCCCCAGCTCCGGGCGCCGGCCGGAGCCCCCCCCGGCCGCCCCCGAGCCCCCCGCGCCCCGCGCCGCGCC
GCCGCGCCGTCCATGCACCGCTTGATGGGGGTCAACAGCACCGCCGCCGCCGCCGCCGGGCAGCCCAATGTCTCCTG
CACGTGCAACTGCAAACGCTCTTTGTTCCAGAGCATGGAGATCACGGAGCTGGAGTTTGTTCAGATCATCATCATCG
TGGTGGTGATGATGGTGATGGTGGTGGTGATCACGTGCCTGCTGAGCCACTACAAGCTGTCTGCACGGTCCTTCATC
AGCCGGCACAGCCAGGGGCGGAGGAGAGAAGATGCCCTGTCCTCAGAAGGATGCCTGTGGCCCTCGGAGAGCACAGT
GTCAGGCAACGGAATCCCAGAGCCGCAGGTCTACGCCCCGCCTCGGCCCACCGACCGCCTGGCCGTGCCGCCCTTCG
CCCAGCGGGAGCGCTTCCACCGCTTCCAGCCCACCTATCCGTACCTGCAGCACGAGATCGACCTGCCACCCACCATC
TCGCTGTCAGACGGGGAGGAGCCCCCACCCTACCAGGGCCCCTGCACCCTCCAGCTTCGGGACCCCGAGCAGCAGCT
GGAACTGAACCGGGAGTCGGTGCGCGCACCCCCAAACAGAACCATCTTCGACAGTGACCTGATGGATAGTGCCAGGC
TGGGCGGCCCCTGCCCCCCCAGCAGTAACTCGGGCATCAGCGCCACGTGCTACGGCAGCGGCGGGCGCATGGAGGGG
CCGCCGCCCACCTACAGCGAGGTCATCGGCCACTACCCGGGGTCCTCCTTCCAGCACCAGCAGAGCAGTGGGCCGCC
CTCCTTGCTGGAGGGGACCCGGCTCCACCACACACACATCGCGCCCCTAGAGAGCGCAGCCATCTGGAGCAAAGAGA
AGGATAAACAGAAAGGACACCCTCTCTAGGGTCCCCAGGGGGGCCGGGCTGGGGCTGCGTAGGTGAAAAGGCAGAAC
ACTCCGCGCTTCTTAGAAGAGGAGTGAGAGGAAGGCGGGGGGCGCAGCAACGCATCGTGTGGCCCTCCCCTCCCACC
TCCCTGTGTATAAATATTTACATGTGATGTCTGGTCTGAATGCACAAGCTAAGAGAGCTTGCAAAAAAAAAAAGAAA
AAAGAAAAAAAAAAAACCACGTTTCTTTGTTGAGCTGTGTCTTGAAGGCAAAAGAAAAAAAATTTCTACAGTAGTCTT
TCTTGTTTCTAGTTGAGCTGCGTGCGTGAATGCTTATTTTCTTTTGTTTATGATAATTTCACTTAACTTTAAAGACA
TATTTGCACAAAACCTTTGTTTAAAGATCTGCAATATTATATATATAAATATATATAAGATAAGAGAAACTGTATGT
GCGAGGGCAGGAGTATTTTTGTATTAGAAGAGGCCTATTAAAAAAAAAAGTTGTTTTCTGAACTAGAAGAGGAAAAA
AATGGCAATTTTTGAGTGCCAAGTCAGAAAGTGTGTATTACCTTGTAAAGAAAAAAATTACAAAGCAGGGGTTTAGA
GTTATTTATATAAATGTTGAGATTTTGCACTATTTTTTAATATAAATATGTCAGTGCTTGCTTGATGGAAACTTCTC
TTGTGTCTGTTGAGACTTTAAGGGAGAAATGTCGGAATTTCAGAGTCGCCTGACGGCAGAGGGTGAGCCCCCGTGGA
GTCTGCAGAGAGGCCTTGGCCAGGAGCGGCGGGCTTTCCCGAGGGGCCACTGTCCCTGCAGAGTGGATGCTTCTGCC
TAGTGACAGGTTATCACCACGTTATATATTCCCTACCGAAGGAGACACCTTTTCCCCCCTGACCCAGAACAGCCTTT
AAATCACAAGCAAAATAGGAAAGTTAACCACGGAGGCACCGAGTTCCAGGTAGTGGTTTTGCCTTTCCCAAAAATGA
AAATAAACTGTTACCGAAGGAATTAGTTTTTCCTCTTCTTTTTTCCAACTGTGAAGGTCCCCGTGGGGTGGAGCATG
GTGCCCCTCACAAGCCGCAGCGGCTGGTGCCCGGGCTACCAGGGACATGCCAGAGGGCTCGATGACTTGTCTCTGCA
GGGCGCTTTGGTGGTTGTTCAGCTGGCTAAAGGTTCACCGGTGAAGGCAGGTGCGGTAACTGCCGCACTGGACCCTA
GGAAGCCCCAGGTATTCGCAATCTGACCTCCTCCTGTCTGTTTCCCTTCACGGATCAATTCTCACTTAAGAGGCCAA
TAAACAACCCAACATGAAAAGGTGACAAGCCTGGGTTTCTCCCAGGATAGGTGAAAGGGTTAAAATGAGTAAAGCAG
TTGAGCAAACACCAACCCGAGCTTCGGGCGCAGAATTCTTCACCTTCTCTTCCCCTTTCCATCTCCTTTCCCCGCGG
AAACAACGCTTCCCTTCTGGTGTGTCTGTTGATCTGTGTTTTCATTTACATCTCTCTTAGACTCCGCTCTTGTTCTC
CAGGTTTTCACCAGATAGATTTGGGGTTGGCGGGACCTGCTGGTGACGTGCAGGTGAAGGACAGGAAGGGGCATGTG
AGCGTAAATAGAGGTGACCAGAGGAGAGCATGAGGGGTGGGGCTTTGGGACCCACCGGGGCCAGTGGCTGGAGCTTG
ACGTCTTTCCTCCCCATGGGGGTGGAGGGCCCCCAGCTGGAAGAGCAGACTCCCAGCTGCTACCCCCCTCCCTTCCC
ATGGGAGTGGCTTTCCATTTTGGGCAGAATGCTGACTAGTAGACTAACATAAAAGATATAAAAGGCAATAACTATTG
TTTGTGAGCAACTTTTTTATAACTTCCAAAACAAAAACCTGAGCACAGTTTTGAAGTTCTAGCCACTCGAGCTCATG
CATGTGAAACGTGTGCTTTACGAAGGTGGCAGCTGACAGACGTGGGCTCTGCATGCCGCCAGCCTAGTAGAAAGTTC
TCGTTCATTGGCAACAGCAGAACCTGCCTCTCCGTGAAGTCGTCAGCCTAAAATTTGTTTCTCTCTTGAAGAGGATT
CTTTGAAAAGGTCCTGCAGAGAAATCAGTACAGGTTATCCCGAAAGGTACAAGGACGCACTTGTAAAGATGATTAAA
ACGTATCTTTCCTTTATGTGACGCGTCTCTAGTGCCTTACTGAAGAAGCAGTGACACTCCCGTCGCTCGGTGAGGAC
GTTCCCGGACAGTGCCTCACTCACCTGGGACTGGTATCCCCTCCCAGGGTCCACCAAGGGCTCCTGCTTTTCAGACA
CCCCATCATCCTCGCGCGTCCTCACCCTGTCTCTACCAGGGAGGTGCCTAGCTTGGTGAGGTTACTCCTGCTCCTCC
AACCTTTTTTTGCCAAGGTTTGTACACGACTCCCATCTAGGCTGAAAACCTAGAAGTGGACCTTGTGTGTGTGCATG
GTGTCAGCCCAAAGCCAGGCTGAGACAGTCCTCATATCCTCTTGAGCCAAACTGTTTGGGTCTCGTTGCTTCATGGT
ATGGTCTGGATTTGTGGGAATGGCTTTGCGTGAGAAAGGGGAGGAGAGTGGTTGCTGCCCTCAGCCGGCTTGAGGAC
AGAGCCTGTCCCTCTCATGACAACTCAGTGTTGAAGCCCAGTGTCCTCAGCTTCATGTCCAGTGGATGGCAGAAGTT
CATGGGGTAGTGGCCTCTCAAAGGCTGGGCGCATCCCAAGACAGCCAGCAGGTTGTCTCTGGAAACGACCAGAGTTA
AGCTCTCGGCTTCTCTGCTGAGGGTGCACCCTTTCCTCTAGATGGTAGTTGTCACGTTATCTTTGAAAA

FIGURE 119B

CTCTTGGACTGCTCCTGAGGAGGCCCTCTTTTCCAGTAGGAAGTTAGATGGGGGTTCTCAGAAGTGGCTGATTGGAA
GGGGACAAGCTTCGTTTCAGGGGTCTGCCGTTCCATCCTGGTTCAGAGAAGGCCGAGCGTGGCTTTCTCTAGCCTTG
TCACTGTCTCCCTGCCTGTCAATCACCACCTTTCCTCCAGAGGAGGAAAATTATCTCCCCTGCAAAGCCCGGTTCTA
CACAGATTTCACAAATTGTGCTAAGAACCGTCCGTGTTCTCAGAAAGCCCAGTGTTTTTGCAAAGAATGAAAAGGGA
CCCCATATGTAGCAAAAATCAGGGCTGGGGGAGAGCCGGGTTCATTCCCTGTCCTCATTGGTCGTCCCTATGAATTG
TACGTTTCAGAGAAATTTTTTTTCCTATGTGCAACACGAAGCTTCCAGAACCATAAAATATCCCGTCGATAAGGAAA
GAAAATGTCGTTGTTGTTGTTTTTCTGGAAACTGCTTGAAATCTTGCTGTACTATAGAGCTCAGAAGGACACAGCCC
GTCCTCCCCTGCCTGCCTGATTCCATGGCTGTTGTGCTGATTCCAATGCTTTCACGTTGGTTCCTGGCGTGGGAACT
GCTCTCCTTTGCAGCCCCATTTCCCAAGCTCTGTTCAAGTTAAACTTATGTAAGCTTTCCGTGGCATGCGGGGCGCG
CACCCACGTCCCCGCTGCGTAAGACTCTGTATTTGGATGCCAATCCACAGGCCTGAAGAAACTGCTTGTTGTGTATC
AGTAATCATTAGTGGCAATGATGACATTCTGAAAAGCTGCAATACTTATACAATAAATTTTACAATTCTTTGG

FIGURE 120

MHRLMGVNSTAAAAAGQPNVSCTCNCKRSLFQSMEITELEFVQIIIIVVVMMVMVVVITCLLSHYKLSARSFISRHS
QGRRREDALSSEGCLWPSESTVSGNGIPEPQVYAPPRPTDRLAVPPFAQRERFHRFQPTYPYLQHEIDLPPTISLSD
GEEPPPYQGPCTLQLRDPEQQLELNRESVRAPPNRTIFDSDLMDSARLGGPCPPSSNSGISATCYGSGGRMEGPPPT
YSEVIGHYPGSSFQHQQSSGPPSLLEGTRLHHTHIAPLESAAIWSKEKDKQKGHPL

Signal sequence.

amino acids 1-16

Transmembrane domain.

amino acids 41-61

N-glycosylation sites.

amino acids 8-11, 19-22, 188-191

Glycosaminoglycan attachment site.

amino acids 100-103

N-myristoylation sites.

amino acids 6-11, 213-218

Amidation site.

amino acids 78-81

SEQUENCE LISTING

<160> NUMBER OF SEQ ID NOS: 120

<210> SEQ ID NO 1
<211> LENGTH: 3781
<212> TYPE: DNA
<213> ORGANISM: Homo Sapien

<400> SEQUENCE: 1

```
ctccgggtcc ccaggggctg cgccgggccg gcctggcaag ggggacgagt      50
cagtggacac tccaggaaga gcggccccgc ggggggcgat gaccgtgcgc     100
tgaccctgac tcactccagg tccggaggcg ggggcccccg gggcgactcg     150
ggggcggacc gcggggcgga gctgccgccc gtgagtccgg ccgagccacc     200
tgagcccgag ccgcgggaca ccgtcgctcc tgctctccga atgctgcgca     250
ccgcgatggg cctgaggagc tggctcgccg ccccatgggg cgcgctgccg     300
cctcggccac cgctgctgct gctcctgctg ctgctgctcc tgctgcagcc     350
gccgcctccg acctgggcgc tcagcccccg gatcagcctg cctctgggct     400
ctgaagagcg gccattcctc agattcgaag ctgaacacat ctccaactac     450
acagcccttc tgctgagcag ggatggcagg accctgtacg tgggtgctcg     500
agaggccctc tttgcactca gtagcaacct cagcttcctg ccaggcgggg     550
agtaccagga gctgctttgg ggtgcagacg cagagaagaa acagcagtgc     600
agcttcaagg gcaaggaccc acagcgcgac tgtcaaaact acatcaagat     650
cctcctgccg ctcagcggca gtcacctgtt cacctgtggc acagcagcct     700
tcagccccat gtgtacctac atcaacatgg agaacttcac cctggcaagg     750
gacgagaagg ggaatgtcct cctggaagat ggcaagggcc gttgtccctt     800
cgacccgaat ttcaagtcca ctgccctggt ggttgatggc gagctctaca     850
ctggaacagt cagcagcttc caagggaatg acccggccat ctcgcggagc     900
caaagccttc gccccaccaa gaccgagagc tccctcaact ggctgcaaga     950
cccagctttt gtggcctcag cctacattcc tgagagcctg ggcagcttgc    1000
aaggcgatga tgacaagatc tacttttttct tcagcgagac tggccaggaa    1050
tttgagttct ttgagaacac cattgtgtcc cgcattgccc gcatctgcaa    1100
gggcgatgag ggtggagagc gggtgctaca gcagcgctgg acctccttcc    1150
tcaaggccca gctgctgtgc tcacggcccg acgatggctt ccccttcaac    1200
gtgctgcagg atgtcttcac gctgagcccc agcccccagg actggcgtga    1250
cacccttttc tatggggtct tcacttccca gtggcacagg ggaactacag    1300
aaggctctgc cgtctgtgtc ttcacaatga aggatgtgca gagagtcttc    1350
agcggcctct acaaggaggt gaaccgtgag acacagcagt ggtacaccgt    1400
gacccacccg gtgcccacac cccggcctgg agcgtgcatc accaacagtg    1450
cccgggaaag gaagatcaac tcatccctgc agctcccaga ccgcgtgctg    1500
aacttcctca aggaccactt cctgatggac gggcaggtcc gaagccgcat    1550
gctgctgctg cagccccagg ctcgctacca gcgcgtggct gtacaccgcg    1600
tccctggcct gcaccacacc tacgatgtcc tcttcctggg cactggtgac    1650
ggccggctcc acaaggcagt gagcgtgggc ccccgggtgc acatcattga    1700
```

-continued

```
ggagctgcag atcttctcat cgggacagcc cgtgcagaat ctgctcctgg     1750
acacccacag gggctgctg tatgcggcct cacactcggg cgtagtccag      1800
gtgcccatgg ccaactgcag cctgtaccgg agctgtgggg actgcctcct     1850
cgcccgggac ccctactgtg cttggagcgg ctccagctgc aagcacgtca     1900
gcctctacca gcctcagctg gccaccaggc cgtggatcca ggacatcgag     1950
ggagccagcg ccaaggacct ttgcagcgcg tcttcggttg tgtccccgtc     2000
ttttgtacca acaggggaga agccatgtga gcaagtccag ttccagccca     2050
acacagtgaa cactttggcc tgcccgctcc tctccaacct ggcgacccga     2100
ctctggctac gcaacggggc cccgtcaat gcctcggcct cctgccacgt      2150
gctacccact ggggacctgc tgctggtggg cacccaacag ctgggggagt     2200
tccagtgctg gtcactagag gagggcttcc agcagctggt agccagctac     2250
tgcccagagg tggtggagga cggggtggca gaccaaacag atgagggtgg     2300
cagtgtaccc gtcattatca gcacatcgcg tgtgagtgca ccagctggtg     2350
gcaaggccag ctggggtgca gacaggtcct actggaagga gttcctggtg     2400
atgtgcacgc tctttgtgct ggccgtgctg ctcccagttt tattcttgct     2450
ctaccggcac cggaacagca tgaaagtctt cctgaagcag ggggaatgtg     2500
ccagcgtgca ccccaagacc tgccctgtgg tgctgccccc tgagacccgc     2550
ccactcaacg gcctagggcc ccctagcacc ccgctcgatc accgagggta     2600
ccagtccctg tcagacagcc ccccgggggc ccgagtcttc actgagtcag     2650
agaagaggcc actcagcatc caagacagct tcgtggaggt atccccagtg     2700
tgcccccggc cccgggtccg ccttggctcg gagatccgtg actctgtggt     2750
gtgagagctg acttccagag gacgctgccc tggcttcagg ggctgtgaat     2800
gctcggagag ggtcaactgg acctcccctc cgctctgctc ttcgtggaac     2850
acgaccgtgg tgcccggccc ttgggagcct tggagccagc tggcctgctg     2900
ctctccagtc aagtagcgaa gctcctacca cccagacacc caaacagccg     2950
tggccccaga ggtcctggcc aaatatgggg gcctgcctag gttggtggaa     3000
cagtgctcct tatgtaaact gagccctttg tttaaaaaac aattccaaat     3050
gtgaaactag aatgagaggg aagagatagc atggcatgca gcacacacgg     3100
ctgctccagt tcatggcctc ccaggggtgc tggggatgca tccaaagtgg     3150
ttgtctgaga cagagttgga aaccctcacc aactggcctc ttcaccttcc     3200
acattatccc gctgccaccg gctgccctgt ctcactgcag attcaggacc     3250
agcttgggct gcgtgcgttc tgccttgcca gtcagccgag gatgtagttg     3300
ttgctgccgt cgtcccacca cctcagggac cagagggcta ggttggcact     3350
gcggccctca ccaggtcctg ggctcggacc caactcctgg acctttccag     3400
cctgtatcag gctgtggcca cacgagagga cagcgcgagc tcaggagaga     3450
tttcgtgaca atgtacgcct ttccctcaga attcagggaa gagactgtcg     3500
cctgccttcc tccgttgttg cgtgagaacc cgtgtgcccc ttcccaccat     3550
atccaccctc gctccatctt tgaactcaaa cacgaggaac taactgcacc     3600
ctggtcctct ccccagtccc cagttcaccc tccatccctc accttcctcc     3650
actctaaggg atatcaacac tgcccagcac aggggccctg aatttatgtg     3700
```

-continued gtttttatac atttttaat aagatgcact ttatgtcatt ttttaataaa 3750
gtctgaagaa ttactgttta aaaaaaaaaa a 3781

<210> SEQ ID NO 2
<211> LENGTH: 2010
<212> TYPE: DNA
<213> ORGANISM: Homo Sapien

<400> SEQUENCE: 2
ggaaaggctg agtctccagc tcaaggtcaa aacgtccaag gccgaaagcc 50
ctccagtttc ccctggacgc cttgctcctg cttctgctac gaccttctgg 100
ggaaaacgaa tttctcattt tcttcttaaa ttgccatttt cgctttagga 150
gatgaatgtt ttcctttggc tgttttggca atgactctga attaaagcga 200
tgctaacgcc tcttttcccc ctaattgtta aaagctatgg actgcaggaa 250
gatggcccgc ttctcttaca gtgtgatttg gatcatggcc atttctaaag 300
tctttgaact gggattagtt gccgggctgg gccatcagga atttgctcgt 350
ccatctcggg gatacctggc cttcagagat gacagcattt ggccccagga 400
ggagcctgca attcggcctc ggtcttccca gcgtgtgccg cccatgggga 450
tacagcacag taaggagcta aacagaacct gctgcctgaa tgggggaacc 500
tgcatgctgg ggtccttttg tgcctgccct ccctccttct acggacggaa 550
ctgtgagcac gatgtgcgca aagagaactg tgggtctgtg ccccatgaca 600
cctggctgcc caagaagtgt tccctgtgta aatgctggca cggtcagctc 650
cgctgctttc ctcaggcatt tctacccggc tgtgatggcc ttgtgatgga 700
tgagcacctc gtggcttcca ggactccaga actaccaccg tctgcacgta 750
ctaccacttt tatgctagtt ggcatctgcc tttctataca aagctactat 800
taatcgacat tgacctattt ccagaaatac aattttagat atcatgcaaa 850
tttcatgacc agtaaaggct gctgctacaa tgtcctaact gaaagatgat 900
catttgtagt tgccttaaaa taatgaatac atttccaaaa tggtctctaa 950
catttcctta cagaactact tcttacttct ttgccctgcc ctctcccaaa 1000
aaactacttc ttttttcaaa agaaagtcag ccatatctcc attgtgccta 1050
agtccagtgt ttcttttttt tttttttttg agacggagtc tcactctgtc 1100
acccaggctg gactgcaatg acgcgatctt ggttcactgc aacctccgca 1150
tccggggttc aagccattct cctgcctcag cctcccaagt aactgggatt 1200
acaggcatgt gtcaccatgc ccagctaatt tttttgtatt tttagtagag 1250
atgggggttt caccatattg gccagtctgg tctcgaactc ctgaccttgt 1300
gatccactcg cctcagcctc tcgaagtgct gagattacac acgtgagcaa 1350
ctgtgcaagg cctggtgttt cttgatacat gtaattctac caaggtcttc 1400
ttaatatgtt cttttaaatg attgaattat atgttcagat tattggagac 1450
taattctaat gtggacctta gaatacagtt ttgagtagag ttgatcaaaa 1500
tcaattaaaa tagtctcttt aaaaggaaag aaaacatctt taaggggagg 1550
aaccagagtg ctgaaggaat ggaagtccat ctgcgtgtgt gcagggagac 1600
tgggtaggaa agaggaagca aatagaagag agaggttgaa aaacaaaatg 1650
ggttacttga ttggtgatta ggtggtggta gagaagcaag taaaaaggct 1700

-continued

```
aaatggaagg gcaagtttcc atcatctata gaaagctata taagacaaga      1750

actccccttt ttttcccaaa ggcattataa aaagaatgaa gcctccttag      1800

aaaaaaaatt atacctcaat gtccccaaca agattgctta ataaattgtg      1850

tttcctccaa gctattcaat tcttttaact gttgtagaag acaaaatgtt      1900

cacaatatat ttagttgtaa accaagtgat caaactacat attgtaaagc      1950

ccatttttaa aatacattgt atatatgtgt atgcacagta aaaatggaaa      2000

ctatattgaa                                                  2010
```

<210> SEQ ID NO 3
<211> LENGTH: 549
<212> TYPE: DNA
<213> ORGANISM: Homo Sapien

<400> SEQUENCE: 3

```
gccaggaggg agagccttcc ccaagcaaac aatccagagc agctgtgcaa        50

acaacggtgc ataaatgagg cctcctggac catgaagcga gtcctgagct       100

gcgtcccgga gcccacggtg gtcatggctg ccagagcgct ctgcatgctg       150

gggctggtcc tggccttgct gtcctccagc tctgctgagg agtacgtggg       200

cctgtctgca aaccagtgtg ccgtgccagc caaggacagg gtggactgcg       250

gctacccca tgtcaccccc aaggagtgca acaaccgggg ctgctgcttt       300

gactccagga tccctggagt gccttggtgt ttcaagcccc tgcaggaagc       350

agaatgcacc ttctgaggca cctccagctg cccccggccg gggggatgcga       400

ggctcggagc acccttgccc ggctgtgatt gctgccaggc actgttcatc       450

tcagcttttc tgtccctttg ctcccggcaa gcgcttctgc tgaaagttca       500

tatctggagc ctgatgtctt aacgaataaa ggtcccatgc tccacccga        549
```

<210> SEQ ID NO 4
<211> LENGTH: 1424
<212> TYPE: DNA
<213> ORGANISM: Homo Sapien

<400> SEQUENCE: 4

```
gaccagactc gtctcaggcc agttgcagcc ttctcagcca aacgccgacc        50

aaggaaaact cactaccatg agaattgcag tgatttgctt ttgcctccta       100

ggcatcacct gtgccatacc agttaaacag gctgattctg gaagttctga       150

ggaaaagcag ctttacaaca aatacccaga tgctgtggcc acatggctaa       200

accctgaccc atctcagaag cagaatctcc tagccccaca gaatgctgtg       250

tcctctgaag aaaccaatga ctttaaacaa gagacccttc caagtaagtc       300

caacgaaagc catgaccaca tggatgatat ggatgatgaa gatgatgatg       350

accatgtgga cagccaggac tccattgact cgaacgactc tgatgatgta       400

gatgacactg atgattctca ccagtctgat gagtctcacc attctgatga       450

atctgatgaa ctggtcactg attttcccac ggacctgcca gcaaccgaag       500

ttttcactcc agttgtcccc acagtagaca catatgatgg ccgaggtgat       550

agtgtggttt atggactgag gtcaaaatct aagaagtttc gcagacctga       600

catccagtac cctgatgcta cagacgagga catcacctca cacatggaaa       650

gcgaggagtt gaatggtgca tacaaggcca tccccgttgc ccaggacctg       700
```

aacgcgcctt ctgattggga cagccgtggg aaggacagtt atgaaacgag 750
tcagctggat gaccagagtg ctgaaaccca cagccacaag cagtccagat 800
tatataagcg gaaagccaat gatgagagca atgagcattc cgatgtgatt 850
gatagtcagg aactttccaa agtcagccgt gaattccaca gccatgaatt 900
tcacagccat gaagatatgc tggttgtaga ccccaaaagt aaggaagaag 950
ataaacacct gaaatttcgt atttctcatg aattagatag tgcatcttct 1000
gaggtcaatt aaaaggagaa aaaatacaat ttctcacttt gcatttagtc 1050
aaaagaaaaa atgctttata gcaaaatgaa agagaacatg aaatgcttct 1100
ttctcagttt attggttgaa tgtgtatcta tttgagtctg gaaataacta 1150
atgtgtttga taattagttt agtttgtggc ttcatggaaa ctccctgtaa 1200
actaaaagct tcagggttat gtctatgttc attctataga agaaatgcaa 1250
actatcactg tattttaata tttgttattc tctcatgaat agaaatttat 1300
gtagaagcaa acaaaatact tttacccact taaaaagaga atataacatt 1350
ttatgtcact ataatctttt gtttttaag ttagtgtata ttttgttgtg 1400
attatctttt tgtggtgtga ataa 1424

<210> SEQ ID NO 5
<211> LENGTH: 1166
<212> TYPE: DNA
<213> ORGANISM: Homo Sapien
<220> FEATURE:
<221> NAME/KEY: unsure
<222> LOCATION: 721-761
<223> OTHER INFORMATION: unknown base

<400> SEQUENCE: 5
cggacgcgtg ggcggaggga agaggaccgc aaaccaaccc aggacccgct 50
cagttccacg cgcggcagcc ctccgtgcgc gcaggctcgg tatgagccgc 100
acagcctaca cggtgggagc cctgcttctc ctcttgggga ccctgctgcc 150
ggctgctgaa gggaaaaaga aagggtccca aggtgccatc cccccgccag 200
acaaggccca gcacaatgac tcagagcaga ctcagtcgcc ccagcagcct 250
ggctccagga accgggggcg gggccaaggg cggggcactg ccatgcccgg 300
ggaggaggtg ctggagtcca gccaagaggc cctgcatgtg acggagcgca 350
aatacctgaa gcgagactgg tgcaaaaccc agccgcttaa gcagaccatc 400
cacgaggaag gctgcaacag tcgcaccatc atcaaccgct tctgttacgg 450
ccagtgcaac tctttctaca tccccaggca catccggaag gaggaaggtt 500
cctttcagtc ctgctccttc tgcaagccca agaaattcac taccatgatg 550
gtcacactca actgccctga actacagcca cctaccaaga agaagagagt 600
cacacgtgtg aagcagtgtc gttgcatatc catcgatttg gattaagcca 650
aatccaggtg cacccagcat gtcctaggaa tgcagcccca ggaagtccca 700
gacctaaaac aaccagattc nnnnnnnnnn nnnnnnnnnn nnnnnnnnnn 750
nnnnnnnnnn nagacttacg atgcatgtat acaaacgaat agcagataat 800
gatgactagt tcacacataa agtcctttta aggagaaaat ctaaaatgaa 850
aagtggataa acagaacatt tataagtgat cagttaatgc ctaagagtga 900
aagtagttct attgacattc ctcaagatat ttaatatcaa ctgcattatg 950

-continued tattatgtct gcttaaatca tttaaaaacg gcaaagaatt atatagacta 1000
tgaggtacct tgctgtgtag gaggatgaaa ggggagttga tagtctcata 1050
aaactaattt ggcttcaagt ttcatgaatc tgtaactaga atttaatttt 1100
caccccaata atgttctata tagcctttgc taaagagcaa ctaataaatt 1150
aaacctattc tttcaa 1166

<210> SEQ ID NO 6
<211> LENGTH: 2279
<212> TYPE: DNA
<213> ORGANISM: Homo Sapien

<400> SEQUENCE: 6
cggacctgaa cccctaaaag cggaaccgcc tcccgccctc gccatcgcgg 50
agctgagtcg ccggcggcgg tggctgctgc cagacccgga gtttcctctt 100
tcactggatg gagctgaact ttgggcggcc agagcagcac agctgtccgg 150
ggatcgctgc atgctgagct ccctcggcaa gacccagcgg cggctcggga 200
ttttttgggg ggggcgggga ccagccccgc gccggcacca tgttcctggc 250
gaccctgtac ttcgcgctgc cgctcttgga cttgctcctg tcggccgaag 300
tgagcggcgg agaccgcctg gattgcgtga aagccagtga tcagtgcctg 350
aaggagcaga gctgcagcac caagtaccgc acgctaaggc agtgcgtggc 400
gggcaaggag accaacttca gcctggcatc cggcctggag gccaaggatg 450
agtgccgcag cgccatggag gccctgaagc agaagtcgct ctacaactgc 500
cgctgcaagc ggggtatgaa gaaggagaag aactgcctgc gcatttactg 550
gagcatgtac cagagcctgc agggaaatga tctgctggag gattccccat 600
atgaaccagt taacagcaga ttgtcagata tattccgggt ggtcccattc 650
atatcagtgg agcacattcc caaagggaac aactgcctgg atgcagcgaa 700
ggcctgcaac ctcgacgaca tttgcaagaa gtacaggtcg gcgtacatca 750
ccccgtgcac caccagcgtg tccaatgatg tctgcaaccg ccgcaagtgc 800
cacaaggccc tccggcagtt ctttgacaag gtcccggcca agcacagcta 850
cggaatgctc ttctgctcct gccgggacat cgcctgcaca gagcggaggc 900
gacagaccat cgtgcctgtg tgctcctatg aagagaggga gaagcccaac 950
tgtttgaatt tgcaggactc ctgcaagacg aattacatct gcagatctcg 1000
ccttgcggat ttttttacca actgccagcc agagtcaagg tctgtcagca 1050
gctgtctaaa ggaaaactac gctgactgcc tcctcgccta ctcggggctt 1100
attggcacag tcatgacccc caactacata gactccagta gcctcagtgt 1150
ggccccatgg tgtgactgca gcaacagtgg gaacgaccta gaagagtgct 1200
tgaaattttt gaatttcttc aaggacaata catgtcttaa aaatgcaatt 1250
caagcctttg gcaatggctc cgatgtgacc gtgtggcagc cagccttccc 1300
agtacagacc accactgcca ctaccaccac tgccctccgg gttaagaaca 1350
agcccctggg gccagcaggg tctgagaatg aaattcccac tcatgttttg 1400
ccaccgtgtg caaatttaca ggcacagaag ctgaaatcca atgtgtcggg 1450
caatacacac ctctgtattt ccaatggtaa ttatgaaaaa gaaggtctcg 1500
gtgcttccag ccacataacc acaaaatcaa tggctgctcc tccaagctgt 1550

```
ggtctgagcc cactgctggt cctggtggta accgctctgt ccaccctatt      1600

atctttaaca gaaacatcat agctgcatta aaaaaataca atatggacat      1650

gtaaaaagac aaaaaccaag ttatctgttt cctgttctct tgtatagctg      1700

aaattccagt ttaggagctc agttgagaaa cagttccatt caactggaac      1750

attttttttt tttcctttta agaaagcttc ttgtgatcct tcggggcttc      1800

tgtgaaaaac ctgatgcagt gctccatcca aactcagaag gctttgggat      1850

atgctgtatt ttaaagggac agtttgtaac ttgggctgta aagcaaactg      1900

gggctgtgtt ttcgatgatg atgatgatca tgatgatgat catcatgatc      1950

atgatgatga tcatcatgat catgatgatg attttaacag ttttacttct      2000

ggcctttcct agctagagaa ggagttaata tttctaaggt aactcccata      2050

tctcctttaa tgacattgat ttctaatgat ataaatttca gcctacattg      2100

atgccaagct tttttgccac aaagaagatt cttaccaaga gtgggctttg      2150

tggaaacagc tggtactgat gttcaccttt atatatgtac tagcattttc      2200

cacgctgatg tttatgtact gtaaacagtt ctgcactctt gtacaaaaga      2250

aaaaacacct gtcacatcca aatataaaa                             2279


<210> SEQ ID NO 7
<211> LENGTH: 562
<212> TYPE: DNA
<213> ORGANISM: Homo Sapien

<400> SEQUENCE: 7

atgcagcacc gaggcttcct cctcctcacc ctcctcgccc tgctggcgct        50

cacctccgcg gtcgccaaaa agaaagataa ggtgaagaag ggcggcccgg       100

ggagcgagtg cgctgagtgg gcctgggggc cctgcacccc cagcagcaag       150

gattgcggcg tgggtttccg cgagggcacc tgcggggccc agacccagcg       200

catccggtgc agggtgccct gcaactggaa gaaggagttt ggagccgact       250

gcaagtacaa gtttgagaac tggggtgcgt gtgatggggg cacaggcacc       300

aaagtccgcc aaggcaccct gaagaaggcg cgctacaatg ctcagtgcca       350

ggagaccatc cgcgtcacca agccctgcac ccccaagacc aaagcaaagg       400

ccaaagccaa gaaagggaag ggaaaggact agacgccaag cctggatgcc       450

aaggagcccc tggtgtcaca tggggcctgg cccacgccct ccctctccca       500

ggcccgagat gtgacccacc agtgccttct gtctgctcgt tagctttaat       550

caatcatgcc cc                                                562


<210> SEQ ID NO 8
<211> LENGTH: 1524
<212> TYPE: DNA
<213> ORGANISM: Homo Sapien

<400> SEQUENCE: 8

gcggcagcag cgcgggcccc agcagcctcg gcagccacag ccgctgcagc        50

cggggcagcc tccgctgctg tcgcctcctc tgatgcgctt gccctctccc       100

ggccccggga ctccgggaga atgtgggtcc taggcatcgc ggcaactttt       150

tgcggattgt tcttgcttcc aggctttgcg ctgcaaatcc agtgctacca       200

gtgtgaagaa ttccagctga acaacgactg ctcctccccc gagttcattg       250
```

-continued

```
tgaattgcac ggtgaacgtt caagacatgt gtcagaaaga agtgatggag      300
caaagtgccg ggatcatgta ccgcaagtcc tgtgcatcat cagcggcctg      350
tctcatcgcc tctgccgggt accagtcctt ctgctcccca gggaaactga      400
actcagtttg catcagctgc tgcaacaccc ctctttgtaa cgggccaagg      450
cccaagaaaa ggggaagttc tgcctcggcc ctcaggccag ggctccgcac      500
caccatcctg ttcctcaaat tagccctctt ctcggcacac tgctgaagct      550
gaaggagatg ccacccccctc ctgcattgtt cttccagccc tcgcccccaa     600
ccccccacct ccctgagtga gtttcttctg ggtgtccttt tattctgggt      650
agggagcggg agtccgtgtt ctcttttgtt cctgtgcaaa taatgaaaga      700
gctcggtaaa gcattctgaa taaattcagc ctgactgaat tttcagtatg      750
tacttgaagg aaggaggtgg agtgaaagtt cacccccatg tctgtgtaac      800
cggagtcaag gccaggctgg cagagtcagt ccttagaagt cactgaggtg      850
ggcatctgcc ttttgtaaag cctccagtgt ccattccatc cctgatgggg      900
gcatagtttg agactgcaga gtgagagtga cgttttctta gggctggagg      950
gccagttccc actcaaggct ccctcgcttg acattcaaac ttcatgctcc     1000
tgaaaaccat tctctgcagc agaattggct ggtttcgcgc ctgagttggg     1050
ctctagtgac tcgagactca atgactggga cttagactgg ggctcggcct     1100
cgctctgaaa agtgcttaag aaaatcttct cagttctcct tgcagaggac     1150
tggcgccggg acgcgaagag caacgggcgc tgcacaaagc gggcgctgtc     1200
ggtggtggag tgcgcatgta cgcgcaggcg cttctcgtgg ttggcgtgct     1250
gcagcgacag gcggcagcac agcacctgca cgaacacccg ccgaaactgc     1300
tgcgaggaca ccgtgtacag gagcgggttg atgaccgagc tgaggtagaa     1350
aaacgtctcc gagaagggga ggaggatcat gtacgcccgg aagtaggacc     1400
tcgtccagtc gtgcttgggt ttggccgcag ccatgatcct ccgaatctgg     1450
ttgggcatcc agcatacggc caatgtcaca acaatcagcc ctgggcagac     1500
acgagcagga gggagagaca gaga                                 1524
```

<210> SEQ ID NO 9
<211> LENGTH: 1253
<212> TYPE: DNA
<213> ORGANISM: Homo Sapien

<400> SEQUENCE: 9

```
caccctccgt ggcaaggcga ggccccgggg gcgggccggg gtcaccacgc       50
ctgccccagg gaaccgcaca gacggtactc acccttcttg cgatgatgtg      100
agatgataaa atgcctacat gatgagatga agtgagatga aaaacatagg      150
ccttgtgatg gaatgggaaa ttccagagat aatttgcacg tgcgctaagc      200
tgcggctacc cccgcaagca accttccaag tccttcgtgg caatggtgct      250
tccgtgggga ccgtgctcat gttccgctgc ccctccaacc accagatggt      300
ggggtctggg ctcctcacct gcacctggaa ggggagcatc gctgagtggt      350
cttcagggtc cccagtgtgc aaactggtgc caccacacga gacctttggc      400
ttcaaggtgg ccgtgatcgc ctccattgtg agctgtgcca tcatcctgct      450
catgtccatg gccttcctca cctgctgcct cctcaagtgc gtgaagaaga      500
```

gcaagcggcg gcgctccaac aggtcagccc agctgtggtc ccagctgaaa 550
gatgaggact tggagacggt gcaggccgca taccttggcc tcaagcactt 600
caacaaaccc gtgagcgggc ccagccaggc gcacgacaac cacagcttca 650
ccacagacca tggtgagagc accagcaagc tggccagtgt gacccgcagc 700
gtggacaagg accctgggat ccccagagct ctaagcctca gtggctcctc 750
cagctcaccc caagcccagg tgatggtgca catggcaaac cccagacagc 800
ccctgcctgc ctctgggctg gccacaggaa tgccacaaca gcccgcagca 850
tatgccctag ggtgaccacg cagtgaggct ggtgcccatg ctccacactg 900
ggaggccagg ctgaccccac cagccagtca gctacaactc cacatcaact 950
ccacatgcgc ccagctcgag actgatgagt ggaatcagct tccaggtgta 1000
gggacccctt gaggggccga gctgacatcc aaggctgagg accccagtgg 1050
ggagtgttct gttccggcat atcctggccg taacgatttt tatagttatg 1100
gactacttga aaccactact gagggtaatt tactagctgt ggcctcccac 1150
taactagcat tcctttaaag agactgggaa atgttttaag caaatctagt 1200
tttgtataat aaaataagaa aatagcaata aacttctttt cagcaactac 1250
aaa 1253

<210> SEQ ID NO 10
<211> LENGTH: 5542
<212> TYPE: DNA
<213> ORGANISM: Homo Sapien

<400> SEQUENCE: 10
ctgactgcac tggtgatggt ccctggcaat ccaacctggc accatcgcag 50
ttggagtact atgcatcttc accagatgaa aaggctctag tagaagctgc 100
tgcaaggatt ggtattgtgt ttattggcaa ttctgaagaa actatggagg 150
ttaaaactct tggaaaactg gaacggtaca aactgcttca tattctggaa 200
tttgattcag atcgtaggag aatgagtgta attgttcagg caccttcagg 250
tgagaagtta ttatttgcta aaggagctga gtcatcaatt ctccctaaat 300
gtataggtgg agaaatagaa aaaaccagaa ttcatgtaga tgaatttgct 350
ttgaaagggc taagaactct gtgtatagca tatagaaaat ttacatcaaa 400
agagtatgag gaaatagata aacgcatatt tgaagccagg actgccttgc 450
agcagcggga agagaaattg gcagctgttt tccagttcat agagaaagac 500
ctgatattac ttggagccac agcagtagaa gacagactac aagataaagt 550
tcgagaaact attgaagcat tgagaatggc tggtatcaaa gtatgggtac 600
ttactgggga taaacatgaa acagctgtta gtgtgagttt atcatgtggc 650
cattttcata gaaccatgaa catccttgaa cttataaacc agaaatcaga 700
cagcgagtgt gctgaacaat tgaggcagct tgccagaaga attacagagg 750
atcatgtgat tcagcatggg ctggtagtgg atgggaccag cctatctctt 800
gcactcaggg agcatgaaaa actatttatg gaagtttgca gaaattgttc 850
agctgtatta tgctgtcgta tggctccact gcagaaagca aaagtaataa 900
gactaataaa aatatcacct gagaaaccta taacattggc tgttggtgat 950
ggtgctaatg acgtaagcat gatacaagaa gcccatgttg gcataggaat 1000

-continued

```
catgggtaaa gaaggaagac aggctgcaag aaacagtgac tatgcaatag        1050
ccagatttaa gttcctctcc aaattgcttt ttgttcatgg tcatttttat        1100
tatattagaa tagctaccct tgtacagtat ttttttata agaatgtgtg        1150
ctttatcaca ccccagtttt tatatcagtt ctactgtttg ttttctcagc        1200
aaacattgta tgacagcgtg tacctgactt tatacaatat ttgttttact        1250
tccctaccta ttctgatata tagtcttttg gaacagcatg tagaccctca        1300
tgtgttacaa aataagccca ccctttatcg agacattagt aaaaaccgcc        1350
tcttaagtat taaaacattt ctttattgga ccatcctggg cttcagtcat        1400
gcctttattt tctttttgg atcctattta ctaataggga aagatacatc        1450
tctgcttgga aatggccaga tgtttggaaa ctggacattt ggcactttgg        1500
tcttcacagt catggttatt acagtcacag taaagatggc tctggaaact        1550
catttttgga cttggatcaa ccatctcgtt acctggggat ctattatatt        1600
ttattttgta ttttccttgt tttatggagg gattctctgg ccatttttgg        1650
gctcccagaa tatgtatttt gtgtttattc agctcctgtc aagtggttct        1700
gcttggtttg ccataatcct catggttgtt acatgtctat ttcttgatat        1750
cataaagaag gtctttgacc gacacctcca ccctacaagt actgaaaagg        1800
cacagcttac tgaaacaaat gcaggtatca agtgcttgga ctccatgtgc        1850
tgtttcccgg aaggagaagc agcgtgtgca tctgttggaa gaatgctgga        1900
acgagttata ggaagatgta gtccaaccca catcagcaga tcatggagtg        1950
catcggatcc tttctatacc aacgacagga gcatcttgac tctctccaca        2000
atggactcat ctacttgtta aaggggcagt agtactttgt gggagccagt        2050
tcacctcctt tcctaaaatt cagtgtgatc accctgttaa tggccacact        2100
agctctgaaa ttaatttcca aaatctttgt agtagttcat acccactcag        2150
agttataatg gcaaacaaac agaaagcatt agtacaagcc cctcccaaca        2200
cccttaattt gaatctgaac atgttaaaat ttgagaataa agagacattt        2250
ttcatctctt tgtctggttt gtcccttgtg cttatgggac tcctaatggc        2300
atttcagtct gttgctgagg ccattatatt ttaatataaa tgtagaaaaa        2350
agagagaaat cttagtaaag agtatttttt agtattagct tgattattga        2400
ctcttctatt taaatctgct tctgtaaatt atgctgaaag tttgccttga        2450
gaactctatt tttttattag agttatattt aaagcttttc atgggaaaag        2500
ttaatgtgaa tactgaggaa ttttggtccc tcagtgacct gtgttgttaa        2550
ttcattaatg cattctgagt tcacagagca aattaggaga atcatttcca        2600
accattattt actgcagtat ggggagtaaa tttataccaa ttcctctaac        2650
tgtactgtaa cacagcctgt aaagttagcc atataaatgc aagggtatat        2700
catatataca aatcaggaat caggtccgtt caccgaactt caaattgatg        2750
tttactaata tttttgtgac agagtataaa gaccctatag tgggtaaatt        2800
agatactatt agcatattat taatttaatg tctttatcat tggatctttt        2850
gcatgcttta atctggttaa catatttaaa tttgcttttt ttctctttac        2900
ctgaaggctc tgtgtatagt atttcatgac atcgttgtac agtttaacta        2950
tcaataaaaa gtttggacag tatttaaata ttgcaaatat gtttaattat        3000
```

-continued

```
acaaatcaga atagtatggg taattaaatg aatacaaaaa gaagagcctc      3050
tttctgcagc cgacttagac atgctcttcc ctttctataa gctagatttt      3100
agaataaagg gtttcagtta ataatcttat tttcaggtta tgtcatctaa      3150
cttatagcaa actaccacaa tacagtgagt tctgccagtg tcccagtaca      3200
aggcatattt caggtgtggc tgtggaatgt aaaaatgctc aacttgtatc      3250
aggtaatgtt agcaataaat taaatgctaa gaatgattaa tcgggtacat      3300
gttactgtaa ttaactcatt gcacttcaaa acctaacttc catcctgaat      3350
ttatcaagta gttcagtatt gtcatttgtt tttgttttat tgaaaagtaa      3400
tgttgtctta agatttagaa gtgattatta gcttgagaac tattacccag      3450
ctctaagcaa ataatgattg tatacatatt aagataatgg ttaaatgcgg      3500
ttttaccaag ttttcccttg aaaatgtaat tcctttatgg agatttattg      3550
tgcagcccta agcttccttc ccatttcatg aatataaggc ttctagaatt      3600
ggactggcag gggaaagaat ggtagagaca gaaattaaga ctttatcctt      3650
gtttgcttgt aaactattat tttcttgcta atgtaacatt tgtctgttcc      3700
agtgatgtaa ggatattaag ttattaagct aaatattaat tttcaaaaat      3750
agtccttctt taacttagat atttcatagc tggatttagg aagatctgtt      3800
attctggaag tactaaaaag aataatacaa cgtacaatgt ctgcattcac      3850
taattcatgt tccagaagag gaaataatga agatatactc agtagagtac      3900
taggtgggag gatatggaaa tttgctcata aaatctctta taaaacgtgc      3950
atataacaaa atgacaccca gtaggcctgc attacattta catgaccgtg      4000
tttatttgcc atcaaataaa ctgagtactg acaccagaca aagactccaa      4050
agtcataaaa tagcctatga ccaactgcag caagacagga ggtcagctcg      4100
cctataatgg tgcttaaagt gtgattgatg taattttctg tactcaccat      4150
ttgaagttag ttaaggagaa ctttattttt ttaaaaaaag taaatggcaa      4200
ccactagtgt gctcatcctg aactgttact ccaaatccac tccgttttta      4250
aagcaaaatt atcttgtgat tttaagaaaa gagttttcta tttatttaag      4300
aaagtaacaa tgcagtctgc aagctttcag tagttttcta gtgctatatt      4350
catcctgtaa aactcttact acgtaaccag taatcacaag gaaagtgtcc      4400
cctttgcata tttctttaaa attctttctt tggaaagtat gatgttgata      4450
attaacttac ccttatctgc caaaaccaga gcaaaatgct aaatacgtta      4500
ttgctaatca gtggtctcaa atcgatttgc ctccctttgc ctcgtctgag      4550
ggctgtaagc ctgaagatag tggcaagcac caagtcagtt tccaaaattg      4600
cccctcagct gctttaagtg actcagcacc ctgcctcagc ttcagcaggc      4650
gtaggctcac cctgggcgga gcaaagtatg ggccagggag aactacagct      4700
acgaagacct gctgtcgagt tgagaaaagg ggagaattta tggtctgaat      4750
tttctaactg tcctctttct tgggtctaaa gctcataata cacaaaggct      4800
tccagacctg agccacaccc aggccctatc ctgaacagga gactaaacag      4850
aggcaaatca accctaggaa atacttgcat tctgccctac ggttagtacc      4900
aggactgagg tcatttctac tggaaaagat tgtgagattg aacttatctg      4950
atcgcttgag actcctaata ggcaggagtc aaggccacta gaaaattgac      5000
```

-continued agttaagagc caaaagtttt taaaatatgc tactctgaaa aatctcgtga 5050
aggctgtagg aaaagggaga atcttccatg ttggtgtttt tcctgtaaag 5100
atcagtttgg ggtatgatat aagcaggtat taataaaaat aacacaccaa 5150
agagttacgt aaaacatgtt ttattaattt tggtccccac gtacagacat 5200
tttatttcta ttttgaaatg agttatctat tttcataaaa gtaaaacact 5250
attaaagtgc tgttttatgt gaaataactt gaatgttgtt cctataaaaa 5300
atagatcata actcatgata tgtttgtaat catggtaatt tagattttta 5350
tgaggaatga gtatctggaa atattgtagc aatacttggt ttaaaatttt 5400
ggacctgaga cactgtggct gtctaatgta atcctttaaa aattctctgc 5450
attgtcagta aatgtagtat attattgtac agctactcat aatttttttaa 5500 agtttatgaa gttatattta tcaaataaaa actttcctat at 5542

<210> SEQ ID NO 11
<211> LENGTH: 6155
<212> TYPE: DNA
<213> ORGANISM: Homo Sapien

<400> SEQUENCE: 11
atgtgggaag aagaagacat tgctattctg ttcaataaag aaccaggaaa 50
aacagagaat attgaaaata atctaagttc caaccataga agaagctgca 100
gaagaagtga agaaagtgat gatgatttgg attttgatat tggtttagaa 150
aacacaggag gagaccctca aattctgaga tttatttcag acttccttgc 200
ttttttggtt ctctacaatt tcatcattcc aatttcatta tatgtgacag 250
tcgaaatgca gaaatttctt ggatcatttt ttattggctg ggatcttgat 300
ctgtatcatg aagaatcaga tcagaaagct caagtcaata cttccgatct 350
gaatgaagag cttggacagg tagagtacgt gtttacagat aaaactggta 400
cactgacaga aaatgagatg cagtttcggg aatgttcaat taatggcatg 450
aaataccaag aaattaatgg tagacttgta cccgaaggac caacaccaga 500
ctcttcagaa ggaaacttat cttatcttag tagtttatcc catcttaaca 550
acttatccca tcttacaacc agttcctctt tcagaaccag tcctgaaaat 600
gaaactgaac taattaaaga acatgatctc ttctttaaag cagtcagtct 650
ctgtcacact gtacagatta gcaatgttca aactgactgc actggtgatg 700
gtccctggca atccaacctg gcaccatcgc agttggagta ctatgcatct 750
tcaccagatg aaaaggctct agtagaagct gctgcaaggt acaaactgct 800
tcatattctg gaatttgatt cagatcgtag gagaatgagt gtaattgttc 850
aggcaccttc aggtgagaag ttattatttg ctaaaggagc tgagtcatca 900
attctcccta aatgtatagg tggagaaata gaaaaaacca gaattcatgt 950
agatgaattt gctttgaaag ggctaagaac tctgtgtata gcatatagaa 1000
aatttacatc aaaagagtat gaggaaatag ataaacgcat atttgaagcc 1050
aggactgcct tgcagcagcg ggaagagaaa ttggcagctg ttttccagtt 1100
catagagaaa gacctgatat tacttggagc cacagcagta gaagacagac 1150
tacaagataa agttcgagaa actattgaag cattgagaat ggctggtatc 1200
aaagtatggg tacttactgg ggataaacat gaaacagctg ttagtgtgag 1250

-continued

```
tttatcatgt ggccattttc atagaaccat gaacatcctt gaacttataa      1300
accagaaatc agacagcgag tgtgctgaac aattgaggca gcttgccaga      1350
agaattacag aggatcatgt gattcagcat gggctggtag tggatgggac      1400
cagcctatct cttgcactca gggagcatga aaaactattt atggaagttt      1450
gcagaaattg ttcagctgta ttatgctgtc gtatggctcc actgcagaaa      1500
gcaaaagtaa taagactaat aaaaatatca cctgagaaac ctataacatt      1550
ggctgttggt gatggtgcta atgacgtaag catgatacaa gaagcccatg      1600
ttggcatagg aatcatgggt aaagaaggaa gacaggctgc aagaaacagt      1650
gactatgcaa tagccagatt taagttcctc tccaaattgc tttttgttca      1700
tggtcatttt tattatatta gaatagctac ccttgtacag tatttttttt      1750
ataagaatgt gtgctttatc acaccccagt tttatatca gttctactgt       1800
ttgttttctc agcaaacatt gtatgacagc gtgtacctga ctttatacaa      1850
tatttgtttt acttccctac ctattctgat atatagtctt ttggaacagc      1900
atgtagaccc tcatgtgtta caaaataagc ccacccttta tcgagacatt      1950
agtaaaaacc gcctcttaag tattaaaaca tttctttatt ggaccatcct      2000
gggcttcagt catgccttta ttttcttttt tggatcctat ttactaatag      2050
ggaaagatac atctctgctt ggaaatggcc agatgtttgg aaactggaca      2100
tttggcactt tggtcttcac agtcatggtt attacagtca cagtaaagat      2150
ggctctggaa actcattttt ggacttggat caaccatctc gttacctggg      2200
gatctattat attttatttt gtattttcct tgttttatgg agggattctc      2250
tggccatttt tgggctccca gaatatgtat tttgtgttta ttcagctcct      2300
gtcaagtggt tctgcttggt ttgccataat cctcatggtt gttacatgtc      2350
tatttcttga tatcataaag aaggtctttg accgacacct ccaccctaca      2400
agtactgaaa aggcacagct tactgaaaca aatgcaggta tcaagtgctt      2450
ggactccatg tgctgtttcc cggaaggaga agcagcgtgt gcatctgttg      2500
gaagaatgct ggaacgagtt ataggaagat gtagtccaac ccacatcagc      2550
agatcatgga gtgcatcgga tcctttctat accaacgaca ggagcatctt      2600
gactctctcc acaatggact catctacttg ttaaaggggc agtagtactt      2650
tgtgggagcc agttcacctc ctttcctaaa attcagtgtg atcaccctgt      2700
taatggccac actagctctg aaattaattt ccaaaatctt tgtagtagtt      2750
catacccact cagagttata atggcaaaca aacagaaagc attagtacaa      2800
gcccctccca acacccttaa tttgaatctg aacatgttaa aatttgagaa      2850
taaagagaca tttttcatct ctttgtctgg tttgtccctt gtgcttatgg      2900
gactcctaat ggcatttcag tctgttgctg aggccattat attttaatat      2950
aaatgtagaa aaaagagaga aatcttagta aagagtattt tttagtatta      3000
gcttgattat tgactcttct atttaaatct gcttctgtaa attatgctga      3050
aagtttgcct tgagaactct atttttttat tagagttata tttaaagctt      3100
ttcatgggaa aagttaatgt gaatactgag gaattttggt ccctcagtga      3150
cctgtgttgt taattcatta atgcattctg agttcacaga gcaaattagg      3200
agaatcattt ccaaccatta tttactgcag tatggggagt aaatttatac      3250
```

-continued

```
caattcctct aactgtactg taacacagcc tgtaaagtta gccatataaa        3300
tgcaagggta tatcatatat acaaatcagg aatcaggtcc gttcaccgaa        3350
cttcaaattg atgtttacta atatttttgt gacagagtat aaagacccta        3400
tagtgggtaa attagatact attagcatat tattaattta atgtctttat        3450
cattggatct tttgcatgct ttaatctggt taacatattt aaatttgctt        3500
tttttctctt tacctgaagg ctctgtgtat agtatttcat gacatcgttg        3550
tacagtttaa ctatcaataa aaagtttgga cagtatttaa atattgcaaa        3600
tatgtttaat tatacaaatc agaatagtat gggtaattaa atgaatacaa        3650
aaagaagagc ctctttctgc agccgactta gacatgctct tccctttcta        3700
taagctagat tttagaataa agggtttcag ttaataatct tattttcagg        3750
ttatgtcatc taacttatag caaactacca caatacagtg agttctgcca        3800
gtgtcccagt acaaggcata tttcaggtgt ggctgtggaa tgtaaaaatg        3850
ctcaacttgt atcaggtaat gttagcaata aattaaatgc taagaatgat        3900
taatcgggta catgttactg taattaactc attgcacttc aaaacctaac        3950
ttccatcctg aatttatcaa gtagttcagt attgtcattt gtttttgttt        4000
tattgaaaag taatgttgtc ttaagattta gaagtgatta ttagcttgag        4050
aactattacc cagctctaag caaataatga ttgtatacat attaagataa        4100
tggttaaatg cggttttacc aagttttccc ttgaaaatgt aattccttta        4150
tggagattta ttgtgcagcc ctaagcttcc ttcccatttc atgaatataa        4200
ggcttctaga attggactgg caggggaaag aatggtagag acagaaatta        4250
agactttatc cttgtttgct tgtaaactat tattttcttg ctaatgtaac        4300
atttgtctgt tccagtgatg taaggatatt aagttattaa gctaaatatt        4350
aattttcaaa aatagtcctt ctttaactta gatatttcat agctggattt        4400
aggaagatct gttattctgg aagtactaaa aagaataata caacgtacaa        4450
tgtctgcatt cactaattca tgttccagaa gaggaaataa tgaagatata        4500
ctcagtagag tactaggtgg gaggatatgg aaatttgctc ataaaatctc        4550
ttataaaacg tgcatataac aaaatgacac ccagtaggcc tgcattacat        4600
ttacatgacc gtgtttattt gccatcaaat aaactgagta ctgacaccag        4650
acaaagactc caaagtcata aaatagccta tgaccaactg cagcaagaca        4700
ggaggtcagc tcgcctataa tggtgcttaa agtgtgattg atgtaatttt        4750
ctgtactcac catttgaagt tagttaagga gaactttatt tttttaaaaa        4800
aagtaaatgg caaccactag tgtgctcatc ctgaactgtt actccaaatc        4850
cactccgttt ttaaagcaaa attatcttgt gattttaaga aaagagtttt        4900
ctatttattt aagaaagtaa caatgcagtc tgcaagcttt cagtagtttt        4950
ctagtgctat attcatcctg taaaactctt actacgtaac cagtaatcac        5000
aaggaaagtg tccccttttgc atatttcttt aaaattcttt ctttggaaag       5050
tatgatgttg ataattaact tacccttatc tgccaaaacc agagcaaaat        5100
gctaaatacg ttattgctaa tcagtggtct caaatcgatt tgcctccctt        5150
tgcctcgtct gagggctgta agcctgaaga tagtggcaag caccaagtca        5200
gtttccaaaa ttgcccctca gctgctttaa gtgactcagc accctgcctc        5250
```

-continued agcttcagca ggcgtaggct caccctgggc ggagcaaagt atgggccagg 5300
gagaactaca gctacgaaga cctgctgtcg agttgagaaa aggggagaat 5350
ttatggtctg aatttctaa ctgtcctctt tcttgggtct aaagctcata 5400
atacacaaag gcttccagac ctgagccaca cccaggccct atcctgaaca 5450
ggagactaaa cagaggcaaa tcaaccctag gaaatacttg cattctgccc 5500
tacggttagt accaggactg aggtcatttc tactggaaaa gattgtgaga 5550
ttgaacttat ctgatcgctt gagactccta ataggcagga gtcaaggcca 5600
ctagaaaatt gacagttaag agccaaaagt ttttaaaata tgctactctg 5650
aaaaatctcg tgaaggctgt aggaaaaggg agaatcttcc atgttggtgt 5700
ttttcctgta aagatcagtt tggggtatga tataagcagg tattaataaa 5750
aataacacac caaagagtta cgtaaaacat gttttattaa ttttggtccc 5800
cacgtacaga cattttattt ctattttgaa atgagttatc tattttcata 5850
aaagtaaaac actattaaag tgctgtttta tgtgaaataa cttgaatgtt 5900
gttcctataa aaaatagatc ataactcatg atatgtttgt aatcatggta 5950
atttagattt ttatgaggaa tgagtatctg gaaatattgt agcaatactt 6000
ggtttaaaat tttggacctg agacactgtg gctgtctaat gtaatccttt 6050
aaaaattctc tgcattgtca gtaaatgtag tatattattg tacagctact 6100
cataattttt taaagtttat gaagttatat ttatcaaata aaaactttcc 6150
tatat 6155

<210> SEQ ID NO 12
<211> LENGTH: 1372
<212> TYPE: DNA
<213> ORGANISM: Homo Sapien

<400> SEQUENCE: 12
gcacgagggc gcttttgtct ccggtgagtt ttgtggcggg aagcttctgc 50
gctggtgctt agtaaccgac tttcctccgg actcctgcac gacctgctcc 100
tacagccggc gatccactcc cggctgttcc cccggagggt ccagaggcct 150
ttcagaagga gaaggcagct ctgtttctct gcagaggagt agggtccttt 200
cagccatgaa gcatgtgttg aacctctacc tgttaggtgt ggtactgacc 250
ctactctcca tcttcgttag agtgatggag tccctagaag gcttactaga 300
gagcccatcg cctgggacct cctggaccac cagaagccaa ctagccaaca 350
cagagcccac caagggcctt ccagaccatc catccagaag catgtgataa 400
gacctccttc catactggcc atattttgga acactgacct agacatgtcc 450
agatgggagt cccattccta gcagacaagc tgagcaccgt tgtaaccaga 500
gaactattac taggccttga agaacctgtc taactggatg ctcattgcct 550
gggcaaggcc tgtttaggcc ggttgcggtg gctcatgcct gtaatcctag 600
cactttggga ggctgaggtg ggtggatcac ctgaggtcag gagttcgaga 650
ccagcctcgc caacatggcg aaaccccatc tctactaaaa atacaaaagt 700
tagctgggtg tggtggcaga ggcctgtaat cccagttcct tgggaggctg 750
aggcgggaga attgcttgaa cccggggacg gaggttgcag tgaaccgaga 800
tcgcactgct gtacccagcc tgggccacag tgcaagactc catctcaaaa 850

-continued aaaaaaagaa aagaaaaagc ctgtttaatg cacaggtgtg agtggattgc 900
ttatggctat gagataggtt gatctcgccc ttaccccggg gtctggtgta 950
tgctgtgctt tcctcagcag tatggctctg acatctctta gatgtcccaa 1000
cttcagctgt tgggagatgg tgatattttc aaccctactt cctaaacatc 1050
tgtctggggt tcctttagtc ttgaatgtct tatgctcaat tatttggtgt 1100
tgagcctctc ttccacaaga gctcctccat gtttggatag cagttgaaga 1150
ggttgtgtgg gtgggctgtt gggagtgagg atggagtgtt cagtgcccat 1200
ttctcatttt acattttaaa gtcgttcctc caacatagtg tgtattggtc 1250
tgaagggggt ggtgggatgc caaagcctgc tcaagttatg gacattgtgg 1300
ccaccatgtg gcttaaatga ttttttctaa ctaataaagt ggaatatata 1350
tttcaaaaaa aaaaaaaaaa aa 1372

<210> SEQ ID NO 13
<211> LENGTH: 770
<212> TYPE: DNA
<213> ORGANISM: Homo Sapien
<220> FEATURE:
<221> NAME/KEY: unsure
<222> LOCATION: 45, 611, 715
<223> OTHER INFORMATION: unknown base

<400> SEQUENCE: 13
atacgactca ctatagggcg aattgggtac cgggcccccc ctcgngtcga 50
cggtatcgat aagcttgata tcgaattcgg ccacactggc cggatcctct 100
agagatccct cgacctcgac ccacgcgtcc gcccacgcgt ccgatgtgcc 150
tctgggcaaa gaagcagagc taacgaggaa agggatttaa agagtttttc 200
ttgggtgttt gtcaaacttt tattccctgt ctgtgtgcag aggggattca 250
acttcaattt ttctgcagtg gctctgagtc cagcccctta cttaaagatc 300
tggaaagcat gaagactggg cttttttttcc tatgtctctt gggaactgca 350
gctgcaatcc cgacaaatgc aagattatta tctgatcatt ccaaaccaac 400
tgctgaaacg gtagcacccg acaacactgc aatccccagt ttaagggctg 450
aagatgaaga aaatgaaaaa gaaacagcag tatccacaga agacgattcc 500
caccataagg ctgaaaaatc atcagtacta aagtcaaaag aggaaagcca 550
tgaacagtca gcagaacagg gcaagagttc tagccaagag ctgggattga 600
aggatcaaga ngacagtgat ggtgacttaa gtgtgaattt ggagtatgca 650
ccaactgaag gtacattgga cataaaagaa gatatgagtg agcctcagga 700
gaaaaactct caganacact gattttttgg ctcctggggt agttccttcc 750
agattctacc acagaagttt 770

<210> SEQ ID NO 14
<211> LENGTH: 1187
<212> TYPE: DNA
<213> ORGANISM: Homo Sapien

<400> SEQUENCE: 14
cgcgggccat ggctccctgg gcggaggccg agcactcggc gctgaacccg 50
ctgcgcgcgg tgtggctcac gctgaccgcc gccttcctgc tgaccctact 100
gctgcagctc ctgccgcccg gcctgctccc gggctgcgcg atcttccagg 150
acctgatccg ctatgggaaa accaagtgtg gggagccgtc gcgccccgcc 200
gcctgccgag cctttgatgt ccccaagaga tatttttccc acttttatat 250
catctcagtg ctgtggaatg gcttcctgct ttggtgcctt actcaatctc 300
tgttcctggg agcacctttt ccaagctggc ttcatggttt gctcagaatt 350
ctcggggcgg cacagttcca gggaggggag ctggcactgt ctgcattctt 400
agtgctagta tttctgtggc tgcacagctt acgaagactc ttcgagtgcc 450
tctacgtcag tgtcttctcc aatgtcatga ttcacgtcgt gcagtactgt 500
tttggacttg tctattatgt ccttgttggc ctaactgtgc tgagccaagt 550
gccaatggat ggcaggaatg cctacataac agggaaaaat ctattgatgc 600
aagcacggtg gttccatatt cttgggatga tgatgttcat ctggtcatct 650
gcccatcagt ataagtgcca tgttattctc ggcaatctca ggaaaaataa 700
agcaggagtg gtcattcact gtaaccacag gatcccattt ggagactggt 750
ttgaatatgt ttcttcccct aactacttag cagagctgat gatctacgtt 800
tccatggccg tcacctttgg gttccacaac ttaacttggt ggctagtggt 850
gacaaatgtc ttctttaatc aggccctgtc tgcctttctc agccaccaat 900
tctacaaaag caaatttgtc tcttacccga agcataggaa agctttccta 950
ccatttttgt tttaagttaa cctcagtcat gaagaatgca aaccaggtga 1000
tggtttcaat gcctaaggac agtgaagtct ggagcccaaa gtacagtttc 1050
agcaaagctg tttgaaactc tccattccat ttctataccc cacaagtttt 1100
cactgaatga gcatggcagt gccactcaat aaaatgaatc tccaaagtat 1150
cttcaaagaa taaatactaa tggcaaaaaa aaaaaaa 1187

<210> SEQ ID NO 15
<211> LENGTH: 1840
<212> TYPE: DNA
<213> ORGANISM: Homo Sapien

<400> SEQUENCE: 15
tccacacaca caaaaaacct gcgcgtgagg ggggaggaaa agcagggcct 50
ttaaaaaggc aatcacaaca acttttgctg ccaggatgcc cttgctttgg 100
ctgagaggat ttctgttggc aagttgctgg attatagtga ggagttcccc 150
caccccagga tccgaggggc acagcgcggc ccccgactgt ccgtcctgtg 200
cgctggccgc cctcccaaag gatgtaccca actctcagcc agagatggtg 250
gaggccgtca agaagcacat tttaaacatg ctgcacttga agaagagacc 300
cgatgtcacc cagccggtac ccaaggcggc gcttctgaac gcgatcagaa 350
agcttcatgt gggcaaagtc ggggagaacg ggtatgtgga gatagaggat 400
gacattggaa ggagggcaga aatgaatgaa cttatggagc agacctcgga 450
gatcatcacg tttgccgagt caggaacagc caggaagacg ctgcacttcg 500
agatttccaa ggaaggcagt gacctgtcag tggtggagcg tgcagaagtc 550
tggctcttcc taaaagtccc caaggccaac aggaccagga ccaaagtcac 600
catccgcctc ttccagcagc agaagcaccc gcagggcagc ttggacacag 650
gggaagaggc cgaggaagtg ggcttaaagg gggagaggag tgaactgttg 700
ctctctgaaa aagtagtaga cgctcggaag agcacctggc atgtcttccc 750

-continued

```
tgtctccagc agcatccagc ggttgctgga ccagggcaag agctccctgg            800

acgttcggat tgcctgtgag cagtgccagg agagtggcgc cagcttggtt            850

ctcctgggca agaagaagaa gaaagaagag gaggggaag ggaaaaagaa            900

gggcggaggt gaaggtgggg caggagcaga tgaggaaaag gagcagtcgc            950

acagaccttt cctcatgctg caggcccggc agtctgaaga ccaccctcat           1000

cgccggcgtc ggcggggctt ggagtgtgat ggcaaggtca acatctgctg           1050

taagaaacag ttctttgtca gtttcaagga catcggctgg aatgactgga           1100

tcattgctcc ctctggctat catgccaact actgcgaggg tgagtgcccg           1150

agccatatag caggcacgtc cgggtcctca ctgtccttcc actcaacagt           1200

catcaaccac taccgcatgc ggggccatag cccctttgcc aacctcaaat           1250

cgtgctgtgt gcccaccaag ctgagaccca tgtccatgtt gtactatgat           1300

gatggtcaaa acatcatcaa aaaggacatt cagaacatga tcgtggagga           1350

gtgtgggtgc tcatagagtt gcccagccca gggggaaagg gagcaagagt           1400

tgtccagaga agacagtggc aaaatgaaga aatttttaag gtttctgagt           1450

taaccagaaa aatagaaatt aaaaacaaaa caaaacaaaa aaaaaaacaa           1500

aaaaaaacaa aagtaaatta aaaacaaacc tgatgaaaca gatgaaacag           1550

atgaaggaag atgtggaaat cttagcctgc cttagccagg gctcagagat           1600

gaagcagtga agagacagat tgggagggaa agggagaatg gtgtaccctt           1650

tatttcttct gaaatcacac tgatgacatc agttgtttaa acggggtatt           1700

gtcctttccc cccttgaggt tcccttgtga gcttgaatca accaatctga           1750

tctgcagtag tgtggactag aacaacccaa atagcatcta gaaagccatg           1800

agtttgaaag ggcccatcac aggcactttc ctagcctaat                      1840
```

<210> SEQ ID NO 16
<211> LENGTH: 1771
<212> TYPE: DNA
<213> ORGANISM: Homo Sapien

<400> SEQUENCE: 16

```
gcggagaagc cgggagcgcg gggctcagtc ggggggcggc ggcggcggcg             50

gctccgggga tggcggcggc tccgctgctg ctgctgctgc tgctcgtgcc            100

cgtgccgctg ctgccgctgc tggcccaagg gcccggaggg gcgctgggaa            150

accggcatgc ggtgtactgg aacagctcca accagcacct gcggcgagag            200

ggctacaccg tgcaggtgaa cgtgaacgac tatctggata tttactgccc            250

gcactacaac agctcggggg tgggccccgg ggcgggaccg gggcccggag            300

gcggggcaga gcagtacgtg ctgtacatgg tgagccgcaa cggctaccgc            350

acctgcaacg ccagccaggg cttcaagcgc tgggagtgca accggccgca            400

cgccccgcac agccccatca agttctcgga gaagttccag cgctacagcg            450

ccttctctct gggctacgag ttccacgccg gccacgagta ctactacatc            500

tccacgccca ctcacaacct gcactggaag tgtctgagga tgaaggtgtt            550

cgtctgctgc gcctccacat cgcactccgg ggagaagccg gtccccactc            600

tcccccagtt caccatgggc cccaatgtga agatcaacgt gctggaagac            650

tttgagggag agaaccctca ggtgcccaag cttgagaaga gcatcagcgg            700
```

gaccagcccc aaacgggaac acctgcccct ggccgtgggc atcgccttct 750
tcctcatgac gttcttggcc tcctagctct gccccctccc ctgggggggg 800
agagatgggg cggggcttgg aaggagcagg gagcctttgg cctctccaag 850
ggaagcctag tgggcctaga cccctcctcc catggctaga agtggggcct 900
gcaccataca tctgtgtccg ccccctctac cccttccccc cacgtagggc 950
actgtagtgg accaagcacg gggacagcca tgggtcccgg gcggccttgt 1000
ggctctggta atgtttggta ccaaacttgg gggccaaaaa gggcagtgct 1050
caggactccc tggcccctgg tacctttccc tgactcctgg tgccctctcc 1100
ctttgtcccc ccagagagac atatgccccc agagagagca aatcgaagcg 1150
tgggaggcac ccccattgct ctcctccagg ggcagaacat ggggaggggga 1200 ctagatgggc aaggggcagc actgcctgct gcttccttcc cctgtttaca 1250
gcaataaagc acgtcctcct cccccactcc cacttccagg attgtggttt 1300
ggattgaaac caagtttaca agtagacacc cctggggggg cgggcagtgg 1350
acaaggatgg caaggggtgg gcattggggt gccaggcagg catgtacaga 1400
ctctatatct ctatatataa tgtacagaca gacagagtcc cttccctctt 1450
taaccccctg acctttcttg acttcccctt cagcttcaga ccccttcccc 1500
accaggctta ggcccccccca caccttgggg ggaccccccct ggcccctctt 1550 ttgtcttctg tgaagacagg acctatgcaa cgcacagaca cttttggaga 1600
ccgtaaaaca acagcgcccc ctcccttcca gccctgagcc gggaaccatc 1650
tcccaggacc ttgccctgct caccctatgt ggtcccacct atcctcctgg 1700
gcctttttca agtgctttgg ctgtgacttt catactctgc tcttagtcta 1750
aaaaaaataa actggagata a 1771

<210> SEQ ID NO 17
<211> LENGTH: 4126
<212> TYPE: DNA
<213> ORGANISM: Homo sapien

<400> SEQUENCE: 17
cgctcgccat gggccactcc ccacctgtcc tgcctttgtg tgcctctgtg 50
tctttgctgg gtggcctgac ctttggttat gaactggcag tcatatcagg 100
tgccctgctg ccactgcagc ttgactttgg gctaagctgc ttggagcagg 150
agttcctggt gggcagcctg ctcctggggg ctctcctcgc ctccctggtt 200
ggtggcttcc tcattgactg ctatggcagg aagcaagcca tcctcgggag 250
caacttggtg ctgctggcag gcagcctgac cctgggcctg gctggttccc 300
tggcctggct ggtcctgggc cgcgctgtgg ttggcttcgc catttccctc 350
tcctccatgg cttgctgtat ctacgtgtca gagctggtgg ggccacggca 400
gcggggagtg ctggtgtccc tctatgaggc aggcatcacc gtgggcatcc 450
tgctctccta tgccctcaac tatgcactgg ctggtacccc ctggggatgg 500
aggcacatgt tcggctgggc cactgcacct gctgtcctgc aatccctcag 550
cctcctcttc ctccctgctg gtacagatga gactgcaaca cacaaggacc 600
tcatcccact ccagggaggt gaggccccca agctgggccc ggggaggcca 650
cggtactcct ttctggacct cttcagggca cgcgataaca tgcgaggccg 700

-continued

```
gaccacagtg ggcctggggc tggtgctctt ccagcaacta acagggcagc       750
ccaacgtgct gtgctatgcc tccaccatct tcagctccgt tggtttccat       800
gggggatcct cagccgtgct ggcctctgtg gggcttggcg cagtgaaggt       850
ggcagctacc ctgaccgcca tggggctggt ggaccgtgca ggccgcaggg       900
ctctgttgct agctggctgt gccctcatgg ccctgtccgt cagtggcata       950
ggcctcgtca gctttgccgt gcccatggac tcaggcccaa gctgtctggc      1000
tgtgcccaat gccaccgggc agacaggcct ccctggagac tctggcctgc      1050
tgcaggactc ctctctacct cccattccaa ggaccaatga ggaccaaagg      1100
gagccaatct tgtccactgc taagaaaacc aagccccatc ccagatctgg      1150
agacccctca gcccctcctc ggctggccct gagctctgcc ctccctgggc      1200
cccctctgcc cgctcggggg catgcactgc tgcgctggac cgcactgctg      1250
tgcctgatgg tctttgtcag tgccttctcc tttgggtttg ggccagtgac      1300
ctggcttgtc ctcagcgaga tctaccctgt ggagatacga ggaagagcct      1350
tcgccttctg caacagcttc aactgggcgg ccaacctctt catcagcctc      1400
tccttcctcg atctcattgg caccatcggc ttgtcctgga ccttcctgct      1450
ctacggactg accgctgtcc tcggcctggg cttcatctat ttatttgttc      1500
ctgaaacaaa aggccagtcg ttggcagaga tagaccagca gttccagaag      1550
agacggttca ccctgagctt tggccacagg cagaactcca ctggcatccc      1600
gtacagccgc atcgagatct ctgcggcctc ctgaggaatc cgtctgcctg      1650
gaaattctgg aactgtggct ttggcagacc atctccagca tcctgcttcc      1700
taggccccag agcacaagtt ccagctggtc ttttgggagt ggcccctgcc      1750
cccaaaggtg gtctgctttt gctggggtaa aaaggatgaa agtctgagaa      1800
tgcccaactc ttcattttga gtctcaggcc ctgaaggttc ctgaggatct      1850
agcttcatgc ctcagtttcc ccattgactt gcacatctct gcagtattta      1900
taagaagaat attctatgaa gtctttgttg caccatggac ttttctcaaa      1950
gaatctcaag ggtaccaatc ctggcaggaa gtctctcccg atatcacccc      2000
taaatccaaa tgaggatatc atcttttcta atctcttttt tcaactggct      2050
gggacatttt cggaaggggg aagtctcttt ttttactctt atcatttttt      2100
ttttttgagg tggagtctca ttctgttgcc caggctggcc tgatcttggc      2150
tcactgcaac ctccacctcc tgagttcaag cgattcttgt gcctcagcct      2200
cctaagcagc tgggactaca ggcgcatgca accataccca gctaatttat      2250
ttttagcaga gatggggttt cactgtgttg gccaggctgg tcgtgaactc      2300
ctgagctcaa gtgatccacc cacctcagcc tcccagagtg ctaggattac      2350
aggcctttttg actcttttat ctgagtttta ttgacccctc taattctctt      2400
acccagaata tttatccttc accagcaact ctgactcttt gacgggaggc      2450
ctcagttcta gtccttggtc tgctggtgtc attgctgtag gaatgaccac      2500
gggcctcagt ttccccattt gtataatggg aagcctgtac caggtcattc      2550
ttaagatttc tcctgactcc agtgagctgg aattctaaat gctggtctag      2600
gagctgtctc caggatggtg caggatggct ttgcggaaag gagatgggtt      2650
tggaggccaa caaacctgct tgtcaatatt gcctttgcct cttggcagcc      2700
```

cttgaacttg agtaaataac aactccctga acctcagttt cctcatctgc 2750
agaatgggga taattatgtc ccaggggtat atttagaccc tgtttccttt 2800
caggagggtc cccagctggt ccagggcctg ggaaatttct acttatcctc 2850
attacccagg tccctccttt ggaccctgta aagggtcagg gtgaatcaga 2900
tgggggactg agcaagtagc tatgactgca gatcatgtaa ggaagggact 2950
gacaagaagc tcccagatgc tggggagaat gaagagctaa aatagatcct 3000
aggtgctgga tgctttgtca tccatgcgtg cacatatggg tgctggcaga 3050
gcccccaagg actctggcct ctcgagttct cctatcttct ccattctaga 3100
tgcttccctt gtatccagtg atgtgctgga gctggctttg ccaagcttgt 3150
gagagctggt tgctacattt tcaggatttt tacaagttgg taaacacagc 3200
cattataaaa aattaaatga tttaaattta taattaagta aattacatta 3250
aaacaaaaaa attatactca aaattcatta cttaatttta ctacctgtta 3300
ctattatctg tgcttttgag gctatttcta catagtaact cttatggaga 3350
cctaggggag acaccgcgca tctcttcctg attccccact caatgacatc 3400
atgttagtct ttggttgctt aactggctgt ggggagtgtt tttgtatcac 3450
aaagattaga gaggactaca catcagggct tgatttattg tttgttgatt 3500
ttctagactt cagaacatgc tggataaaat gtcagtaatg caaattaaac 3550
tttaaagtat gtcttgtttg tagccaatac atggtgtata gcaccaaaaa 3600
atggagggat tattcttcca gtagttgaac actgtcatcc gtttcagctg 3650
acagctgctc aaatcattta agaaggagtt ctgacattca ttttcattgt 3700
tttacttttg tcttcctcac tagtgtaaac aaaaatttca accagcattc 3750
atgccgaacc tatacccatt cttcagtgcc tagctgtaca gttatcaggg 3800
atttttattt gtagtctaat tttgtcaaat catggccaaa tcgcagtgat 3850
agttgacttt ggatacaagg tttggcaaaa aaaaaaatat taacaaaata 3900
ttctgtaaga atcaattgtc tatatggaat ttaggataaa gaatatttac 3950
aataaagaat atttacaata aagagtttat tattatttgt aagttgtgtg 4000
caacaaacat accctttatc tctgtaaaat ttatacacac aaaaattaac 4050
aaaagattct gtaagaatta attggctata tggaatttag gatagaatat 4100
ttacaataaa gagtatttac aataaa 4126

<210> SEQ ID NO 18
<211> LENGTH: 5615
<212> TYPE: DNA
<213> ORGANISM: Homo Sapien
<220> FEATURE:
<221> NAME/KEY: unsure
<222> LOCATION: 429
<223> OTHER INFORMATION: unknown base

<400> SEQUENCE: 18
gcttcagtcc cgcgaccgaa gcagggcgcg cagcagcgct gagtgccccg 50
gaacgtgcgt cgcgccccca gtgtccgtcg cgtccgccgc gccccgggcg 100
gggatggggc ggccagactg agcgccgcac ccgccatcca gacccgccgg 150
ccctagccgc agtccctcca gccgtggccc cagcgcgcac gggcgatggc 200
gaaggcgacg tccggtgccg cggggctgcg tctgctgttg ctgctgctgc 250

-continued

```
tgccgctgct aggcaaagtg gcattgggcc tctacttctc gagggatgct         300

tactgggaga agctgtatgt ggaccaggcg gccggcacgc ccttgctgta         350

cgtccatgcc ctgcgggacg cccctgagga ggtgcccagc ttccgcctgg         400

gccagcatct ctacggcacg taccgcacnc ggctgcatga gaacaactgg         450

atctgcatcc aggaggacac cggcctcctc taccttaacc ggagcctgga         500

ccatagctcc tgggagaagc tcagtgtccg caaccgcggc tttcccctgc         550

tcaccgtcta cctcaaggtc ttcctgtcac ccacatccct tcgtgagggc         600

gagtgccagt ggccaggctg tgcccgcgta tacttctcct tcttcaacac         650

ctcctttcca gcctgcagct ccctcaagcc ccgggagctc tgcttcccag         700

agacaaggcc ctccttccgc attcgggaga accgaccccc aggcaccttc         750

caccagttcc gcctgctgcc tgtgcagttc ttgtgcccca acatcagcgt         800

ggcctacagg ctcctggagg gtgagggtct gcccttccgc tgcgccccgg         850

acagcctgga ggtgagcacg cgctgggccc tggaccgcga gcagcgggag         900

aagtacgagc tggtggccgt gtgcaccgtg cacgccggcg cgcgcgagga         950

ggtggtgatg gtgcccttcc cggtgaccgt gtacgacgag gacgactcgg        1000

cgcccacctt ccccgcgggc gtcgacaccg ccagcgccgt ggtggagttc        1050

aagcggaagg aggacaccgt ggtggccacg ctgcgtgtct tcgatgcaga        1100

cgtggtacct gcatcagggg agctggtgag gcggtacaca agcacgctgc        1150

tccccgggga cacctgggcc cagcagacct tccgggtgga acactggccc        1200

aacgagacct cggtccaggc caacggcagc ttcgtgcggg cgaccgtaca        1250

tgactatagg ctggttctca accggaacct ctccatctcg gagaaccgca        1300

ccatgcagct ggcggtgctg gtcaatgact cagacttcca gggcccagga        1350

gcgggcgtcc tcttgctcca cttcaacgtg tcggtgctgc cggtcagcct        1400

gcacctgccc agtacctact ccctctccgt gagcaggagg gctcgccgat        1450

ttgcccagat cgggaaagtc tgtgtggaaa actgccaggc gttcagtggc        1500

atcaacgtcc agtacaagct gcattcctct ggtgccaact gcagcacgct        1550

aggggtggtc acctcagccg aggacacctc ggggatcctg tttgtgaatg        1600

acaccaaggc cctgcggcgg cccaagtgtg ccgaacttca ctacatggtg        1650

gtggccaccg accagcagac ctctaggcag gcccaggccc agctgcttgt        1700

aacagtggag gggtcatatg tggccgagga ggcgggctgc cccctgtcct        1750

gtgcagtcag caagagacgg ctggagtgtg aggagtgtgg cggcctgggc        1800

tccccaacag gcaggtgtga gtggaggcaa ggagatggca aagggatcac        1850

caggaacttc tccacctgct ctcccagcac caagacctgc cccgacggcc        1900

actgcgatgt tgtggagacc caagacatca acatttgccc tcaggactgc        1950

ctccggggca gcattgttgg gggacacgag cctggggagc cccgggggat        2000

taaagctggc tatggcacct gcaactgctt ccctgaggag gagaagtgct        2050

tctgcgagcc cgaagacatc caggatccac tgtgcgacga gctgtgccgc        2100

acggtgatcg cagccgctgt cctcttctcc ttcatcgtct cggtgctgct        2150

gtctgccttc tgcatccact gctaccacaa gtttgcccac aagccaccca        2200

tctcctcagc tgagatgacc ttccggaggc ccgcccaggc cttcccggtc        2250
```

-continued

```
agctactcct cttccggtgc ccgccggccc tcgctggact ccatggagaa    2300

ccaggtctcc gtggatgcct tcaagatcct ggaggatcca aagtgggaat    2350

tccctcggaa gaacttggtt cttggaaaaa ctctaggaga aggcgaattt    2400

ggaaaagtgg tcaaggcaac ggccttccat ctgaaaggca gagcagggta    2450

caccacggtg gccgtgaaga tgctgaaaga gaacgcctcc ccgagtgagc    2500

ttcgagacct gctgtcagag ttcaacgtcc tgaagcaggt caaccaccca    2550

catgtcatca aattgtatgg ggcctgcagc caggatggcc cgctcctcct    2600

catcgtggag tacgccaaat acggctccct gcggggcttc ctccgcgaga    2650

gccgcaaagt ggggcctggc tacctgggca gtggaggcag ccgcaactcc    2700

agctccctgg accacccgga tgagcgggcc ctcaccatgg gcgacctcat    2750

ctcatttgcc tggcagatct cacaggggat gcagtatctg gccgagatga    2800

agctcgttca tcgggacttg gcagccagaa acatcctggt agctgagggg    2850

cggaagatga agatttcgga tttcggcttg tcccgagatg tttatgaaga    2900

ggattcctac gtgaagagga gccagggtcg gattccagtt aaatggatgg    2950

caattgaatc cctttttgat catatctaca ccacgcaaag tgatgtatgg    3000

tcttttggtg tcctgctgtg ggagatcgtg accctagggg gaaaccccta    3050

tcctgggatt cctcctgagc ggctcttcaa ccttctgaag accggccacc    3100

ggatggagag gccagacaac tgcagcgagg agatgtaccg cctgatgctg    3150

caatgctgga agcaggagcc ggacaaaagg ccggtgtttg cggacatcag    3200

caaagacctg gagaagatga tggttaagag gagagactac ttggaccttg    3250

cggcgtccac tccatctgac tccctgattt atgacgacgg cctctcagag    3300

gaggagacac cgctggtgga ctgtaataat gcccccctcc ctcgagccct    3350

cccttccaca tggattgaaa acaaactcta tggcatgtca gacccgaact    3400

ggcctggaga gagtcctgta ccactcacga gagctgatgg cactaacact    3450

gggtttccaa gatatccaaa tgatagtgta tatgctaact ggatgctttc    3500

accctcagcg gcaaaattaa tggacacgtt tgatagttaa catttctttg    3550

tgaaaggtaa tggactcaca aggggaagaa acatgctgag aatggaaagt    3600

ctaccggccc tttctttgtg aacgtcacat tggccgagcc gtgttcagtt    3650

cccaggtggc agactcgttt ttggtagttt gttttaactt ccaaggtggt    3700

tttacttctg atagccggtg attttccctc ctagcagaca tgccacaccg    3750

ggtaagagct ctgagtctta gtggttaagc attcctttct cttcagtgcc    3800

cagcagcacc cagtgttggt ctgtgtccat cagtgaccac caacattctg    3850

tgttcacatg tgtgggtcca acacttacta cctggtgtat gaaattggac    3900

ctgaactgtt ggatttttct agttgccgcc aaacaaggca aaaaaattta    3950

aacatgaagc acacacacaa aaaaggcagt aggaaaaatg ctggccctga    4000

tgacctgtcc ttattcagaa tgagagactg cggggggggc ctgggggtag    4050

tgtcaatgcc cctccagggc tggaggggaa gaggggcccc gaggatgggc    4100

ctgggctcag cattcgagat cttgagaatg atttttttta aatcatgcaa    4150

cctttcctta ggaagacatt tggttttcat catgattaag atgattccta    4200

gatttagcac aatggagaga ttccatgcca tctttactat gtggatggtg    4250
```

-continued gtatcaggga agagggctca caagacacat ttgtcccccg ggcccaccac 4300
atcatcctca cgtgttcggt actgagcagc cactacccct gatgagaaca 4350
gtatgaagaa agggggctgt tggagtccca gaattgctga cagcagaggc 4400
tttgctgctg tgaatcccac ctgccaccag cctgcagcac accccacagc 4450
caagtagagg cgaaacgagt ggctcatcct acctgttagg agcaggtagg 4500
gcttgtactc actttaattt gaatcttatc aacttactca taaagggaca 4550
ggctagctag ctgtgtcaga agtagcaatg acaatgacca aggactgcta 4600
cacctctgat tacaattctg atgtgaaaaa gatggtgttt ggctcttata 4650
gagcctgtgt gaaaggccca tggatcagct cttcctgtgt ttgtaattta 4700
atgctgctac aagatgtttc tgtttcttag attctgacca tgactcataa 4750
gcttcttgtc attcttcatt gcttgtttgt ggtcacagat gcacaacact 4800
cctccagtct tgtgggggca gcttttggga agtctcagca gctcttctgg 4850
ctgtgttgtc agcactgtaa cttcgcagaa aagagtcgga ttaccaaaac 4900
actgcctgct cttcagactt aaagcactga taggacttaa aatagtctca 4950
ttcaaatact gtattttata taggcatttc acaaaaacag caaaattgtg 5000
gcattttgtg aggccaaggc ttggatgcgt gtgtaataga gccttatggt 5050
gtgtgcgcac acacccagag gagagtttga aaaatgctta ttggacacgt 5100
aacctggctc taatttgggc tgtttttcag atacactgtg ataagttctt 5150
ttacaaatat ctatagacat ggtaaacttt tggttttcag atatgcttaa 5200
tgatagtctt actaaatgca gaaataagaa taaactttct caaattatta 5250
aaaatgccta cacagtaagt gtgaattgct gcaacaggtt tgttctcagg 5300
agggtaagaa ctccaggtct aaacagctga cccagtgatg gggaatttat 5350
ccttgaccaa tttatccttg accaataacc taattgtcta ttcctgagtt 5400
ataaaggtcc ccatccttat tagctctact ggaattttca tacacgtaaa 5450
tgcagaagtt actaagtatt aagtattact gagtattaag tagtaatctg 5500
tcagttatta aaatttgtaa aatctattta tgaaaggtca ttaaaccaga 5550
tcatgttcct ttttttgtaa tcaaggtgac taagaaaatc agttgtgtaa 5600
ataaaatcat gtatc 5615

<210> SEQ ID NO 19
<211> LENGTH: 4315
<212> TYPE: DNA
<213> ORGANISM: Homo Sapien

<400> SEQUENCE: 19
tgagagccaa gcaaagaaca ttaaggaagg aaggaggaat gaggctggat 50
acggtgcagt gaaaaaggca cttccaagag tggggcactc actacgcaca 100
gactcgacgg tgccatcagc atgagaactt accgctactt cttgctgctc 150
ttttgggtgg gccagcccta cccaactctc tcaactccac tatcaaagag 200
gactagtggt ttcccagcaa agaaaagggc cctggagctc tctggaaaca 250
gcaaaaatga gctgaaccgt tcaaaaagga gctggatgtg gaatcagttc 300
tttctcctgg aggaatacac aggatccgat tatcagtatg tgggcaagtt 350
acattcagac caggatagag gagatggatc acttaaatat atcctttcag 400

-continued

```
gagatggagc aggagatctc ttcattatta atgaaaacac aggcgacata        450
caggccacca agaggctgga cagggaagaa aaacccgttt acatccttcg        500
agctcaagct ataaacagaa ggacagggag acccgtggag cccgagtctg        550
aattcatcat caagatccat gacatcaatg acaatgaacc aatattcacc        600
aaggaggttt acacagccac tgtccctgaa atgtctgatg tcggtacatt        650
tgttgtccaa gtcactgcga cggatgcaga tgatccaaca tatgggaaca        700
gtgctaaagt tgtctacagt attctacagg gacagcccta tttttcagtt        750
gaatcagaaa caggtattat caagacagct ttgctcaaca tggatcgaga        800
aaacagggag cagtaccaag tggtgattca agccaaggat atgggcggcc        850
agatgggagg attatctggg accaccaccg tgaacatcac actgactgat        900
gtcaacgaca accctccccg attcccccag agtacatacc agtttaaaac        950
tcctgaatct tctccaccgg ggacaccaat tggcagaatc aaagccagcg       1000
acgctgatgt gggagaaaat gctgaaattg agtacagcat cacagacggt       1050
gaggggctgg atatgtttga tgtcatcacc gaccaggaaa cccaggaagg       1100
gattataact gtcaaaaagc tcttggactt tgaaaagaag aaagtgtata       1150
cccttaaagt ggaagcctcc aatccttatg ttgagccacg atttctctac       1200
ttggggcctt tcaaagattc agccacggtt agaattgtgg tggaggatgt       1250
agatgagcca cctgtcttca gcaaactggc ctacatctta caaataagag       1300
aagatgctca gataaacacc acaataggct ccgtcacagc ccaagatcca       1350
gatgctgcca ggaatcctgt caagtactct gtagatcgac acacagatat       1400
ggacagaata ttcaacattg attctggaaa tggttcgatt tttacatcga       1450
aacttcttga ccgagaaaca ctgctatggc acaacattac agtgatagca       1500
acagagatca ataatccaaa gcaaagtagt cgagtacctc tatatattaa       1550
agttctagat gtcaatgaca acgccccaga atttgctgag ttctatgaaa       1600
cttttgtctg tgaaaaagca aaggcagatc agttgattca gaccctgcat       1650
gctgttgaca aggatgaccc ttatagtgga caccaatttt cgttttcctt       1700
ggcccctgaa gcagccagtg gctcaaactt taccattcaa gacaacaaag       1750
acaacacggc gggaatctta actcggaaaa atggctataa tagacacgag       1800
atgagcacct atctcttgcc tgtggtcatt tcagacaacg actacccagt       1850
tcaaagcagc actgggacag tgactgtccg ggtctgtgca tgtgaccacc       1900
acgggaacat gcaatcctgc catgcggagg cgctcatcca ccccacggga       1950
ctgagcacgg gggctctggt tgccatcctt ctgtgcatcg tgatcctact       2000
agtgacagtg gtgctgtttg cagctctgag gcggcagcga aaaaaagagc       2050
ctttgatcat ttccaaagag gacatcagag ataacattgt cagttacaac       2100
gacgaaggtg gtggagagga ggacacccag gcttttgata tcggcaccct       2150
gaggaatcct gaagccatag aggacaacaa attacgaagg gacattgtgc       2200
ccgaagccct tttcctaccc cgacggactc caacagctcg cgacaacacc       2250
gatgtcagag atttcattaa ccaaaggtta aaggaaaatg acacggaccc       2300
cactgccccg ccatacgact ccttggccac ttacgcctat gaaggcactg       2350
gctccgtggc ggattccctg agctcgctgg agtcagtgac cacggatgca       2400
```

-continued

```
gatcaagact atgattacct tagtgactgg ggacctcgat tcaaaaagct           2450
tgcagatatg tatggaggag tggacagtga caaagactcc taatctgttg           2500
ccttttcat tttccaatac gacactgaaa tatgtgaagt ggctatttct            2550
ttatatttat ccactactcc gtgaaggctt ctctgttcta cccgttccaa           2600
aagccaatgg ctgcagtccg tgtggatcca atgttagaga ctttttcta            2650
gtacactttt atgagcttcc aaggggcaaa tttttatttt ttagtgcatc           2700
cagttaacca agtcagccca acaggcaggt gccggagggg aggacaggga           2750
acagtatttc cacttgttct cagggcagcg tgcccgcttc cgctgtcctg           2800
gtgttttact acactccatg tcaggtcagc caactgccct aactgtacat           2850
ttcacaggct aatgggataa aggactgtgc tttaaagata aaaatatcat           2900
catagtaaaa gaaatgaggg catatcggct cacaaagaga taaactacat           2950
aggggtgttt atttgtgtca caaagaattt aaaataacac ttgcccatgc           3000
tatttgttct tcaagaactt tctctgccat caactactat tcaaaacctc           3050
aaatccaccc atatgttaaa attctcatta ctcttaagga atagaagcaa           3100
attaaacggt aacatccaaa agcaaccaca aacctagtac gacttcattc           3150
cttccactaa ctcatagttt gttatatcct agactagaca tgcgaaagtt           3200
tgcctttgta ccatataaag ggggagggaa atagctaata atgttaacca           3250
aggaaatata ttttaccata catttaaagt tttggccacc acatgtatca           3300
cgggtcactt gaaattcttt cagctatcag taggctaatg tcaaaattgt           3350
ttaaaaattc ttgaaagaat tttcctgaga caaattttaa cttcttgtct           3400
atagttgtca gtattattct actatactgt acatgaaagt agcagtgtga           3450
agtacaataa ttcatattct tcatatcctt cttacacgac taagttgaat           3500
tagtaaagtt agattaaata aaacttaaat ctcactctag gagttcagtg           3550
gagaggttag agccagccac acttgaacct aataccctgc ccttgacatc           3600
tggaaacctc tacatattta tataacgtga tacatttgga taaacaacat           3650
tgagattatg atgaaaacct acatattcca tgtttggaag acccttggaa           3700
gaggaaaatt ggattccctt aaacaaaagt gtttaagatt gtaattaaaa           3750
tgatagttga ttttcaaaag cattaatttt ttttcattgt ttttaacttt           3800
gctttcatga ccatcctgcc atccttgact ttgaactaat gataaagtaa           3850
tgatctcaaa ctatgacaga aaagtaatgt aaaatccatc caatctatta           3900
tttctctaat tatgcaatta gcctcatagt tattatccag aggacccaac           3950
tgaactgaac taatccttct ggcagattca aatcgtttat ttcacacgct           4000
gttctaatgg cacttatcat tagaatctta ccttgtgcag tcatcagaaa           4050
ttccagcgta ctataatgaa aacatccttg ttttgaaaac ctaaaagaca           4100
ggctctgtat atatatatac ttaagaatat gctgacttca cttattagtc           4150
ttagggattt attttcaatt aatattaatt ttctacaaat aattttagtg           4200
tcatttccat ttggggatat tgtcatatca gcacatattt tctgtttgga           4250
aacacactgt tgtttagtta agttttaaat aggtgtatta cccaagaagt           4300
aaagatggaa acgtt                                                 4315
```

<210> SEQ ID NO 20

<211> LENGTH: 2521
<212> TYPE: DNA
<213> ORGANISM: Homo Sapien

<400> SEQUENCE: 20
cggtggaggc cacagacacc tcaaacctgg attccacaat tctacgttaa 50
gtgttggagt ttttattact ctgctgtagg aaagcctttg ccaatgctta 100
caaggaactg tttatccctg cttctctggg ttctgtttga tggaggtctc 150
ctaacaccac tacaaccaca gccacagcag actttagcca cagagccaag 200
agaaaatgtt atccatctgc caggacaacg gtcacatttc caacgtgtta 250
aacgtggctg ggtatggaat caatttttg tgctggaaga atacgtgggc 300
tccgagcctc agtatgtggg aaagctccat tccgacttag acaagggaga 350
gggcactgtg aaatacaccc tctcaggaga tggcgctggc accgttttta 400
ccattgatga aaccacaggg gacattcatg caataaggag cctagataga 450
gaagagaaac ctttctacac tcttcgtgct caggctgtgg acatagaaac 500
cagaaagccc ctggagcctg aatcagaatt catcatcaaa gtgcaggata 550
ttaatgataa tgagccaaag tttttggatg gaccttatgt tgctactgtt 600
ccagaaatgt ctcctgtggg tgcatatgta ctccaggtca aggccacaga 650
tgcagatgac ccgacctatg gaaacagtgc cagagtcgtt tacagcattc 700
ttcagggaca accttatttc tctattgatc ccaagacagg tgttattaga 750
acagctttgc caaacatgga cagagaagtc aaagaacaat atcaagtact 800
catccaagcc aaggatatgg gaggacagct tggaggatta gccggaacaa 850
caatagtcaa catcactctc accgatgtca atgacaatcc acctcgattc 900
cccaaaagca tcttccactt gaaagttcct gagtcttccc ctattggttc 950
agctattgga agaataagag ctgtggatcc tgattttgga caaaatgcag 1000
aaattgaata caatattgtt ccaggagatg ggggaaattt gtttgacatc 1050
gtcacagatg aggatacaca agagggagtc atcaaattga aaaagccttt 1100
agattttgaa acaaagaagg catacacttt caaagttgag gcttccaacc 1150
ttcaccttga ccaccggttt cactcggcgg gccctttcaa agacacagct 1200
acggtgaaga tcagcgtgct ggacgtagat gagccaccgg ttttcagcaa 1250
gccgctctac accatggagg tttatgaaga cactccggta gggaccatca 1300
ttggcgctgt cactgctcaa gacctggatg taggcagcgg tgctgttagg 1350
tacttcatag attggaagag tgatggggac agctacttta caatagatgg 1400
aaatgaagga accatcgcca ctaatgaatt actagacaga gaaagcactg 1450
cgcagtataa tttctccata attgcgagta aagttagtaa ccctttattg 1500
accagcaaag tcaatatact gattaatgtc ttagatgtaa atgaatttcc 1550
tccagaaata tctgtgccat atgagacagc cgtgtgtgaa aatgccaagc 1600
caggacagat aattcagata gtcagtgctg cagaccgaga tctttcacct 1650
gctgggcaac aattctcctt tagattatca cctgaggctg ctatcaaacc 1700
aaattttaca gttcgtgact tcagaaacaa cacagcgggg attgaaaccc 1750
gaagaaatgg atacagccgc aggcagcaag agttgtattt cctccctgtt 1800
gtaatagaag acagcagcta ccctgtccag agcagcacaa acacaatgac 1850

-continued tattcgagtc tgtagatgtg actctgatgg caccatcctg tcttgtaatg 1900
tggaagcaat ttttctacct gtaggactta gcactggggc gttgattgca 1950
attctactat gcattgttat actcttagcc atagttgtac tgtatgtagc 2000
actgcgaagg cagaagaaaa agcacaccct gatgacctct aaagaagaca 2050
tcagagacaa cgtcatccat tacgatgatg aaggaggtgg ggaggaagat 2100
acccaggctt tcgacatcgg ggctctgaga aacccaaaag tgattgagga 2150
gaacaaaatt cgcagggata taaaaccaga ctctctctgt ttacctcgtc 2200
agagaccacc catggaagat aacacagaca taagggattt cattcatcaa 2250
aggctacagg aaaatgatgt agatccaact gccccaccaa tcgattcact 2300
ggccacatat gcctacgaag ggagtgggtc cgtggcagag tccctcagct 2350
ctatagactc tctcaccaca gaagccgacc aggactatga ctatctgaca 2400
gactggggac cccgctttaa agtcttggca gacatgtttg gcgaagaaga 2450
gagttataac cctgataaag tcacttaagg gagtcgtgga ggctaaaata 2500
caaccgagag gggagatttt t 2521

<210> SEQ ID NO 21
<211> LENGTH: 736
<212> TYPE: DNA
<213> ORGANISM: Homo Sapien

<400> SEQUENCE: 21
ggctctcacc ctcctctcct gcagctccag ctctgtgctc tgcctctgag 50
gagaccatgg cccggcctct gtgtaccctg ctactcctga tggctaccct 100
ggctggggct ctggcctcga gctccaagga ggagaatagg ataatcccag 150
gtggcatcta tgatgcagac ctcaatgatg agtgggtaca gcgtgccctt 200
cacttcgcca tcagcgagta caacaaggcc accgaagatg agtactacag 250
acgcccgctg caggtgctgc gagccaggga gcagaccttt ggggggggtga 300 attacttctt cgacgtagag gtgggccgca ccatatgtac caagtcccag 350
cccaacttgg acacctgtgc cttccatgaa cagccagaac tgcagaagaa 400
acagttatgc tctttcgaga tctacgaagt tccctgggag gacagaatgt 450
ccctggtgaa ttccaggtgt caagaagcct aggggtctgt gccaggccag 500
tcacaccgac caccacccac tcccaccccc tgtagtgctc ccacccctgg 550
actggtggcc cccaccctgc gggaggcctc cccatgtgcc tgtgccaaga 600
gacagacaga gaaggctgca ggagtccttt gttgctcagc agggcgctct 650
gccctccctc cttccttctt gcttctaata gacctggtac atggtacaca 700
cacccccacc tcctgcaatt aaacagtagc atcgcc 736

<210> SEQ ID NO 22
<211> LENGTH: 2025
<212> TYPE: DNA
<213> ORGANISM: Homo Sapien

<400> SEQUENCE: 22
ggcagcggtg gcaggggctg caggagcaag tgaccaggag caggactggg 50
gacaggcctg atcgcccctg cacgaaccag acccttcgcc gccctcacga 100
tgactacctc tccgatcctg cagctgctgc tgcggctctc actgtgcggg 150

```
ctgctgctcc agagggcgga gacaggctct aaggggcaga cggcggggga     200

gctgtaccag cgctgggaac ggtaccgcag ggagtgccag gagaccttgg     250

cagccgcgga accgccttca ggcctcgcct gtaacgggtc cttcgatatg     300

tacgtctgct gggactatgc tgcacccaat gccactgccc gtgcgtcctg     350

cccctggtac ctgccctggc accaccatgt ggctgcaggt ttcgtcctcc     400

gccagtgtgg cagtgatggc caatggggac tttggagaga ccatacacaa     450

tgtgagaacc cagagaagaa tgaggccttt ctggaccaaa ggctcatctt     500

ggagcggttg caggtcatgt acactgtcgg ctactccctg tctctcgcca     550

cactgctgct agccctgctc atcttgagtt tgttcaggcg gctacattgc     600

actagaaact atatccacat caacctgttc acgtctttca tgctgcgagc     650

tgcggccatt ctcagccgag accgtctgct acctcgacct ggcccctacc     700

ttggggacca ggcccttgcg ctgtggaacc aggccctcgc tgcctgccgc     750

acggcccaga tcgtgaccca gtactgcgtg ggtgccaact acacgtggct     800

gctggtggag ggcgtctacc tgcacagtct cctggtgctc gtgggaggct     850

ccgaggaggg ccacttccgc tactacctgc tcctcggctg gggggccccc     900

gcgcttttcg tcattccctg ggtgatcgtc aggtacctgt acgagaacac     950

gcagtgctgg gagcgcaacg aagtcaaggc catttggtgg attatacgga    1000

cccccatcct catgaccatc ttgattaatt tcctcatttt tatccgcatt    1050

cttggcattc tcctgtccaa gctgaggaca cggcaaatgc gctgccggga    1100

ttaccggctg aggctggctc gctccacgct gacgctggtg cccctgctgg    1150

gtgtccacga ggtggtgttt gctcccgtga cagaggaaca ggcccggggc    1200

gccctgcgct tcgccaagct cggctttgag atcttcctca gctccttcca    1250

gggcttcctg gtcagcgtcc tctactgctt catcaacaag gaggtgcagt    1300

cggagatccg ccgtggctgg caccactgcc gcctgcgccg cagcctgggc    1350

gaggagcaac gccagctccc ggagcgcgcc ttccgggccc tgccctccgg    1400

ctccggcccg ggcgaggtcc ccaccagccg cggcttgtcc tcggggaccc    1450

tcccagggcc tgggaatgag gccagccggg agttggaaag ttactgctag    1500

ggggcgggat ccccgtgtct gttcagttag catggattta ttgagtgcca    1550

actgcgtgcc aggcccagta cggaggacgc tggggaaatg gtgaaggaaa    1600

cagaaaaaag gtccctgccc ttctggagat gacaactgag tggggaaaac    1650

agaccgtgaa cacaaaacat caagttccac acacgctatg gaatggttat    1700

gaagggaagc gagaaggggg cctagggtgg tctgggaggc gtctccaagg    1750

aggtgacact taagccatcc ccgaaagagg tgaaagagat cactttgggg    1800

agagctggag aacaggattc taggcggaag cgatagcata ggcaaaggcc    1850

cttgggcagg aaggcgctca gccttggctg gagtagaatt aagtcagagc    1900

caacaggttg gggagagaca gagaagtggg caggggcacc caagttggga    1950

tttcatttca ggtgcattgg agattcttag gagtgtctct tgggggtaat    2000

attttatttt ttaaaaaatg aggat                               2025
```

<210> SEQ ID NO 23
<211> LENGTH: 3168
<212> TYPE: DNA

<213> ORGANISM: Homo Sapien

<400> SEQUENCE: 23
gccagagcgt gagccgcgac ctccgcgcag gtggtcgcgc cggtctccgc 50
ggaaatgttg tccaaagttc ttccagtcct cctaggcatc ttattgatcc 100
tccagtcgag ggtcgaggga cctcagactg aatcaaagaa tgaagcctct 150
tcccgtgatg ttgtctatgg cccccagccc cagcctctgg aaaatcagct 200
cctctctgag gaaacaaagt caactgagac tgagactggg agcagagttg 250
gcaaactgcc agaagcctct cgcatcctga acactatcct gagtaattat 300
gaccacaaac tgcgccctgg cattggagag aagcccactg tggtcactgt 350
tgagatcgcc gtcaacagcc ttggtcctct ctctatccta gacatggaat 400
acaccattga catcatcttc tcccagacct ggtacgacga acgcctctgt 450
tacaacgaca cctttgagtc tcttgttctg aatggcaatg tggtgagcca 500
gctatggatc ccggacacct tttttaggaa ttctaagagg acccacgagc 550
atgagatcac catgcccaac cagatggtcc gcatctacaa ggatggcaag 600
gtgttgtaca caattaggat gaccattgat gccggatgct cactccacat 650
gctcagattt ccaatggatt ctcactcttg ccctctatct ttctctagct 700
tttcctatcc tgagaatgag atgatctaca agtgggaaaa tttcaagctt 750
gaaatcaatg agaagaactc ctggaagctc ttccagtttg attttacagg 800
agtgagcaac aaaactgaaa taatcacaac cccagttggt gacttcatgg 850
tcatgacgat ttcttcaat gtgagcaggc ggtttggcta tgttgccttt 900
caaaactatg tcccttcttc cgtgaccacg atgctctcct gggtttcctt 950
ttggatcaag acagagtctg ctccagcccg gacctctcta gggatcacct 1000
ctgttctgac catgaccacg ttgggcacct tttctcgtaa gaatttcccg 1050
cgtgtctcct atatcacagc cttggatttc tatatcgcca tctgcttcgt 1100
cttctgcttc tgcgctctgt tggagtttgc tgtgctcaac ttcctgatct 1150
acaaccagac aaaagcccat gcttctccta aactccgcca tcctcgtatc 1200
aatagccgtg cccatgcccg tacccgtgca cgttcccgag cctgtgcccg 1250
ccaacatcag gaagcttttg tgtgccagat tgtcaccact gagggaagtg 1300
atggagagga gcgcccgtct tgctcagccc agcagccccc tagcccaggt 1350
agccctgagg gtccccgcag cctctgctcc aagctggcct gctgtgagtg 1400
gtgcaagcgt tttaagaagt acttctgcat ggtccccgat tgtgagggca 1450
gtacctggca gcagggccgc ctctgcatcc atgtctaccg cctggataac 1500
tactcgagag ttgttttccc agtgactttc ttcttcttca atgtgctcta 1550
ctggcttgtt tgccttaact tgtaggtacc agctggtacc ctgtggggca 1600
acctctccag ttccccagga ggtccaagcc ccttgccaag ggagttgggg 1650
gaaagcagca gcagcagcag gagcgactag agtttttcct gccccattcc 1700
ccaaacagaa gcttgcagag ggtttgtctt tgctgcccct ctcccctacc 1750
tggcccattc actgagtctt ctcagcagac catttcaaat tattaataaa 1800
tgggccacct ccctcttctt caaggagcat ccgtgatgct cagtgttcaa 1850
aaccacagcc acttagtgat cagctcccta aaaccatgcc taagtacagg 1900

-continued

```
cggattagct atcttccaac aatgctgacc accagacaat tactgcattt     1950

ttccagaagc ccactattgc ctttgtagtg ctttcggccc agttctggcc     2000

tcagcctcaa agtgcaccga ctagttgctt gcctatacct ggcacctcat     2050

taagatgctg ggcagcagta taacaggagg aagagatccc tctcctttgg     2100

tcagattatt atgttctcag ttctctctcc ctgctacccc tttctctgca     2150

gatagataga cactggcatt atccctttag gaagaggggg gggcagcaag     2200

agagcctatt tgggacagca ttcctctctc tctgctgctg tgacatctcc     2250

ctctccttgc tggctccatc tttcgtctgc actaccaatt caatgccctt     2300

catccaatgg gtatctattt ttgtgtgtga ttatagtaac tactccctgc     2350

tttatatgcc accctcttcc ttctctttga cccctgtgac tctttctgta     2400

actttcccag tgacttcccc tagccctgac ccaggcacta ggccttggtg     2450

acttcctggg gccaagaaac taaggaaact cggctttgca acaggcatta     2500

ctcgccattg attggtgccc acccagggca cactgtcgga gttctatcac     2550

ttgcttgacc cctggaccca taaaccagtc cactgttata cccggggcac     2600

tctaaccatc acaatcaatc aatcaaattc ccttaaattt gtatggcact     2650

ggaactttgg caaagcactt ttgacaagtt gtgtctgatt ggagcttcat     2700

gatagccttg tgacatcttt agggcaggat tcttatcccc attttgcaga     2750

tgaaaaccct gagtcacaga tttctgtggg actgtggatc tcactggaag     2800

ctatccaaga gcccactgtc accttctaga ccacatgata gggctagaca     2850

gctcagttca ccatgattct cttctgtcac ctctgctggc acaccagtgg     2900

caaggcccag aatggcgacc tctctttagc tcaatttctg ggcctgaggt     2950

gctcagactg cccccaagat caaatctctc ctggctgtag taacccagtg     3000

gaatgaattt ggacatgccc caatgcttct atatgctaag tgaaatctgt     3050

gtctgtaatt tgttgggggg tggatagggt ggggtctcca tctacttttt     3100

gtcaccatca tctgaaatgg ggaaatatgt aaataaatat atcagcaaag     3150

caaaaagaaa aaaaaaaa                                        3168
```

```
<210> SEQ ID NO 24
<211> LENGTH: 2837
<212> TYPE: DNA
<213> ORGANISM: Homo Sapien

<400> SEQUENCE: 24

tatcacagga ttgtctactt cagcaatagc aactaatgga tttgtaagag       50

gaggaggagc atattattta atatctagaa gtctagggcc agaatttggt      100

ggtgcaattg gtctaatctt cgcctttgcc aacgctgttg cagttgctat      150

gtatgtggtt ggatttgcag aaaccgtggt ggagttgctt aaggaacatt      200

ccatacttat gatagatgaa atcaatgata tccgaattat tggagccatt      250

acagtcgtga ttcttttagg tatctcagta gctggaatgg agtgggaagc      300

aaaagctcag attgttcttt tggtgatcct acttcttgct attggtgatt      350

tcgtcatagg aacatttatc ccactggaga gcaagaagcc aaaagggttt      400

tttggttata aatctgaaat atttaatgag aactttgggc ccgattttcg      450

agaggaagag actttctttt ctgtatttgc catctttttt cctgctgcaa      500
```

-continued

```
ctggtattct ggctggagca aatatctcag gtgatcttgc agatcctcag       550

tcagccatac ccaaaggaac actcctagcc attttaatta ctacattggt       600

ttacgtagga attgcagtat ctgtaggttc ttgtgttgtt cgagatgcca       650

ctggaaacgt taatgacact atcgtaacag agctaacaaa ctgtacttct       700

gcagcctgca aattaaactt tgatttttca tcttgtgaaa gcagtccttg       750

ttcctatggc ctaatgaaca acttccaggt aatgagtatg gtgtcaggat       800

ttacaccact aatttctgca ggtatatttt cagccactct ttcttcagca       850

ttagcatccc tagtgagtgc tcccaaaata tttcaggctc tatgtaagga       900

caacatctac ccagctttcc agatgtttgc taaaggttat gggaaaaata       950

atgaacctct tcgtggctac atcttaacat tcttaattgc acttggattc      1000

atcttaattg ctgaactgaa tgttattgca ccaattatct caaacttctt      1050

ccttgcatca tatgcattga tcaatttttc agtattccat gcatcacttg      1100

caaaatctcc aggatggcgt cctgcattca aatactacaa catgtggata      1150

tcacttcttg gagcaattct ttgttgcata gtaatgttcg tcattaactg      1200

gtgggctgca ttgctaacat atgtgatagt ccttgggctg tatatttatg      1250

ttacctacaa aaaaccagat gtgaattggg gatcctctac acaagccctg      1300

acttacctga atgcactgca gcattcaatt cgtctttctg gagtggaaga      1350

ccacgtgaaa aactttaggc cacagtgtct tgttatgaca ggtgctccaa      1400

actcacgtcc agctttactt catcttgttc atgatttcac aaaaaatgtt      1450

ggtttgatga tctgtggcca tgtacatatg ggtcctcgaa gacaagccat      1500

gaaagagatg tccatcgatc aagccaaata tcagcgatgg cttattaaga      1550

acaaaatgaa ggcattttat gctccagtac atgcagatga cttgagagaa      1600

ggtgcacagt atttgatgca ggctgctggt cttggtcgta tgaagccaaa      1650

cacacttgtc cttggattta agaaagattg gttgcaagca gatatgaggg      1700

atgtggatat gtatataaac ttatttcatg atgcttttga catacaatat      1750

ggagtagtgg ttattcgcct aaaagaaggt ctggatatat ctcatcttca      1800

aggacaagaa gaattattgt catcacaaga gaaatctcct ggcaccaagg      1850

atgtggtagt aagtgtggaa tatagtaaaa agtccgattt agatacttcc      1900

aaaccactca gtgaaaaacc aattacacac aaagttgagg aagaggatgg      1950

caagactgca actcaaccac tgttgaaaaa agaatccaaa ggccctattg      2000

tgcctttaaa tgtagctgac caaaagcttc ttgaagctag tacacagttt      2050

cagaaaaaac aaggaaagaa tactattgat gtctggtggc tttttgatga      2100

tggaggtttg accttattga taccttacct tctgacgacc aagaaaaaat      2150

ggaaagactg taagatcaga gtattcattg gtggaaagat aaacagaata      2200

gaccatgacc ggagagcgat ggctactttg cttagcaagt tccggataga      2250

cttttctgat atcatggttc taggagatat caataccaaa ccaaagaaag      2300

aaaatattat agcttttgag gaaatcattg agccatacag acttcatgaa      2350

gatgataaag agcaagatat tgcagataaa atgaaagaag atgaaccatg      2400

gcgaataaca gataatgagc ttgaacttta taagaccaag acataccggc      2450

agatcaggtt aaatgagtta ttaaaggaac attcaagcac agctaatatt      2500
```

attgtcatga gtctcccagt tgcacgaaaa ggtgctgtgt ctagtgctct 2550
ctacatggca tggttagaag ctctatctaa ggacctacca ccaatcctcc 2600
tagttcgtgg gaatcatcag agtgtcctta ccttctattc ataaatgttc 2650
tatacagtgg acagccctcc agaatggtac ttcagtgcct agtgtagtaa 2700
cctgaaatct tcaatgacac attaacatca caatggcgaa tggtgacttt 2750
tctttcacga tttcattaat ttgaaagcac acaggaaagc ttgctccatt 2800
gataacgtgt atggagactt cggttttagt caattcc 2837

<210> SEQ ID NO 25
<211> LENGTH: 4709
<212> TYPE: DNA
<213> ORGANISM: Homo Sapien

<400> SEQUENCE: 25
gagcttgtcc agacgaagcc tcgcagggat gggttggagc ctgggccgtg 50
cttcgctcag gcagcgtttg aggcagaccc agcagggtcc tcctggggcc 100
ttcctgcctt tgaactgcgg tggcgggcgg gcgcacggtc tcctgtacgc 150
cctagactag gggccgccat ctccatggcc acggccgtga gccggccctg 200
cgccggcagg tcgcgggaca tactgtggcg cgttttgggc tggaggatag 250
ttgcaagtat tgtttggtca gtgctatttc tacccatctg caccacagta 300
tttataattt tcagcaggat tgatttgttt catcctatac agtggctgtc 350
tgattctttc agtgacctgt atagttccta tgtaatcttt tacttcctgc 400
tgctgtcagt ggtaataata ataataagta ttttcaatgt ggagttctat 450
gcagttgtgc cttctattcc ttgctccaga ctagctctga tagggaagat 500
cattcatcct cagcaactca tgcactcatt tattcatgct gcaatgggaa 550
tggtgatggc ctggtgtgct gcagtgataa cccagggcca gtacagcttt 600
cttgtggttc cctgcactgg tactaacagc tttggtagcc ctgctgcgca 650
aacctgctta aatgaatatc atcttttttt cctactgact ggagcattta 700
tgggctatag ctatagcctc ctgtattttg ttaacaacat gaactatctt 750
ccatttccca tcatacagca atacaagttc ttgcgtttta ggagatctct 800
gctcttatta gttaaacaca gttgtgtgga atcactgttc ctggttagaa 850
atttctgcat tttatattat tttcttggct atattcccaa agcttggatt 900
agcactgcta tgaaccttca catagatgag caggttcata ggccacttga 950
cacagtgagt ggcctcttaa atctctcgtt actctaccat gtctggctgt 1000
gtggtgtctt tctcctgacg acttggtatg tctcatggat actcttcaaa 1050
atctatgcca cagaggctca tgtgtttcct gttcaaccac catttgcaga 1100
agggtcagat gagtgccttc caaaagtgtt aaatagcaat cctcccccca 1150
tcataaagta tttagccttg caggacctga tgttgctttc tcaatattct 1200
ccttcacgaa gacaagaagt tttcagcctc agccaaccag gtggacatcc 1250
ccacaattgg acagccattt caagggagtg tttgaatctt ttaaatggta 1300
tgactcagaa actgattctc tatcaagaag ctgctgctac gaatgggaga 1350
gtgtcttcat cttacccagt ggaacctaag aaattaaatt ctccagaaga 1400
aactgctttt cagacaccaa aatctagcca gatgcctcgg ccttcagtgc 1450

-continued

```
caccattagt taaaacatca ctgttttctt caaaattatc tacacctgat      1500
gttgtgagcc catttgggac cccatttggc tctagtgtaa tgaatcggat      1550
ggctggaatt tttgatgtaa acacctgcta tgggtcaccg caaagtcctc      1600
agctaataag aagggggcca agattgtgga catcagcttc tgatcagcaa      1650
atgactgaat tttctaatcc ttctccatct acctctatta gtgctgaggg      1700
taagacaatg agacaaccca gtgtgattta ttcatggatt cagaataaac      1750
gtgaacagat taagaatttc ttgtcaaaac gggtgctgat aatgtatttt      1800
ttcagtaagc acccagaggc ctccattcag gctgtttttt cagatgccca      1850
aatgcatatt tgggcattag aaggtctgtc gcacttagta gcagcatcat      1900
ttacagagga tagatttgga gttgtccaga cgacactacc agctatcctt      1950
aatactttgt tgacactgca agaggcagtc gacaagtact ttaagcttcc      2000
tcatgcttcc agtaaaccac cccggatttc aggaagcctt gtggacactt      2050
catataaaac attaagattt gcattcagag catcactgaa aactgccatc      2100
tatcgaataa ctactacatt tggtgaacat ctgaatgctg tgcaagcatc      2150
tgcagaacat cagaaaagac ttcaacagtt cttggagttc aaagaatagt      2200
taagtaatat aaactgtgtt cattacactg ctgatacaac tacagatggg      2250
acagtaaatg ttcagcattc ttggatcaga agaaaacgga ctaattagat      2300
gcttcctttg tcgtggtggt tgctttgaaa actatacttt aatgggagaa      2350
atcatggaaa gaaattctca acagaataac tgaaaactgc cttttctgta      2400
ccgattgctt tttgtgtgtg tggtataata aaatctttat tcaattttac      2450
agaagcattg atggcagtcg aaatgtctct agctcatata acttaatagt      2500
aataactaaa aaactttag aatttacttt tgaaaggagg gaagccagtt      2550
ctgaaatgag tataggttga tttcatagtc ttcttaatta agagtttagc      2600
tctttgtaaa ctcaaaatac ataaactttt taagtgtagt ttcatttact      2650
gaaggataaa aatggtaaca gtgcagcaat attcacaaaa aatattgtct      2700
aacggacata ttttgttaat ctgttaggtt gggtttttgt ttccagggac      2750
aaattaaatt tgtatgatta cccaaaaaag ggtctcagtt tacagatgct      2800
aactctatat aaaggaatgt ggaaaaactc agttcttaag ttacaagatt      2850
aaaaattcac atttggtctt taagaaacaa ttgactgaca tctatgaatt      2900
tattttgtat catgctagta aacacgaagt attaatgtat gggtattttc      2950
ccagctagtt ttgctttctt tttctggagc aaaacattaa gtgattgcag      3000
agtttttcaa gcaagagaaa aaggtttgca aaaaaaccca ggaaatgttc      3050
ccttttttcc ccaccattca tcttcattag atcaaattct gtgaaacttg      3100
tctggtctct caaagggagc agcctctgta gtgttaaatg gctaattaaa      3150
ataggaagat ctttatagcc agaaacaact tagtcatcaa atagcaagtg      3200
aaaccaaaac gtcagaggga ttactgtact tggaagtatg ttgtgtgtcc      3250
caaatgtgaa cgaagtattg ttagaattta ttagatcagc ttctttggag      3300
atcaaagatt ggaaatccta gtcatagata ttcactggac tggctttgga      3350
ctgaaatgct cctttgtaat tcttttccta ttgtcttttc cttctagtgt      3400
cccaaaatat tttctttaaa gtcagcacag tactgtatat gaatctttaa      3450
```

tgtggtatca tatatgtcta cttttgtctg attcatcgat gtattatatc 3500
tttataattg aatattttag ctccgggtcc tgttgcccct tcaagcagta 3550
catgccaaat tataaatagg tgctactggc cttgagcata tcactgtggg 3600
acagttcccc aattgtcaag tgtttagata tgtagactat tgccatttgt 3650
ttttttgttt tggttttgct ttgtgtctga agctgaattg atttcttttt 3700
tttgaatgtg aaagttgaat ttcaaacgta gtcatttctt acagatggcc 3750
aagacagaaa attgtggcta ggttgactga gaactgttgt cttccatgta 3800
ttaacacaat taagcttttt atattccact ctctgtgctg accctggctg 3850
aggcattttg ggagacaagg actctgaatc ttctgcttcc attaaagaag 3900
aactgtgata ttcaacattg gatttctgag aataaagata ggatgattcc 3950
tttgaacttt gacttacttg tataaaatgt ccagctaggt taggtttttg 4000
ccatttccta tatactttgg gtaaagctac atttgatgag caatgtgaat 4050
gtttctgaga atgttcattc ctgttttctc ttaagagaat gtgctgtgta 4100
ctaaatacag gccacatagt gtctgcctgt tgaagatctg gaaactgcct 4150
ccccagatct gtattgtatt tggtaggtaa gggggtcagt ttcttttttct 4200 cattgtgtgt tgataatcta cacaccatct gttggaacca gggtgttatt 4250
atggggaact cctcctgtgt actaggagga ggaccttagg gagaccaaga 4300
ggagagaagc atttcctttg atgaagtcac atcctgtcta tgagcccact 4350
aatgctgtaa cattggcctg aaagagagtg ttctttaaaa gcctttctcg 4400
gctgttagta taaaaacatg atggtatcag ctcttagcat gtttgcttga 4450
cccttatgga aggtataaat ccacagaact tccttcccag agaactggga 4500
aattgtccta gaaataaacc ttgtacagtt gagtggacat ggataagcaa 4550
caatttgtta ctttgcagga tttgttcctt ggtaattgtt tggtgtgtca 4600
tcctgtaaat attcatgata gtctgtttat atccttttgt atatcgttga 4650
tactggattg ggtagaaaaa taaattggca atttaaaaaa atggaacagt 4700
taattgaaa 4709

<210> SEQ ID NO 26
<211> LENGTH: 6310
<212> TYPE: DNA
<213> ORGANISM: Homo Sapien

<400> SEQUENCE: 26
gatgggggcc ccgtttgtct gggccttggg ccttttgatg ctgcagatgc 50
tgctctttgt ggctggggaa cagggcacac aggatatcac cgatgccagc 100
gaaagggggc tccacatgca gaagctgggg tctgggtcag tgcaggctgc 150
gctggcggag ctggtggccc tgccctgtct ctttaccctg cagccacggc 200
caagcgcagc ccgagatgcc cctcggataa agtggaccaa ggtgcggact 250
gcgtcgggcc agcgacagga cttgcccatc ctggtggcca aggacaatgt 300
cgtgagggtg gccaaaagct ggcagggacg agtgtcactg ccttcctacc 350
cccggcgccg agccaacgcc acgctacttc tggggccact gagggccagt 400
gactctgggc tgtaccgctg ccaggtggtg aggggcatcg aggatgagca 450
ggacctggtg cccttggagg tgacaggtgt tgtgttccac taccgatcag 500

-continued

```
cccgggaccg ctatgcactg accttcgctg aggcccagga ggcctgccgt     550
ctcagctcag ccatcattgc agcccctcgg catctacagg ctgcctttga     600
ggatggcttt gacaactgtg atgctggctg gctctctgac cgcactgttc     650
ggtatcctat cacccagtcc cgtcctggtt gctatggcga ccgtagcagc     700
cttccagggg ttcggagcta tgggaggcgc aacccacagg aactctacga     750
tgtgtattgc tttgcccggg agctgggggg cgaggtcttc tacgtgggcc     800
cggcccgccg cctgacactg gccggcgcgc gtgcacagtg ccgccgccag     850
ggtgccgcgc tggcctcggt gggacagctg cacctggcct ggcatgaggg     900
cctggaccag tgcgacccgg gctggctggc cgacggcagc gtgcgctacc     950
cgatccagac gccgcgccgg cgctgcgggg gcccagcccc gggcgtgcgc    1000
accgtctacc gcttcgctaa ccggaccggc ttcccctcac ccgccgagcg    1050
cttcgacgcc tactgcttcc gagctcatca ccccacgtca caacatggag    1100
acctagagac cccatcctct ggggatgagg gggagattct gtcagcagag    1150
gggcccccag ttagagaact ggagcccacc ctggaggagg aagaggtggt    1200
cacccctgac ttccaggagc ctctggtgtc cagtggggaa gaagaaaccc    1250
tgattttgga ggagaagcag gagtctcaac agaccctcag ccctacccct    1300
ggggacccca tgctggcctc atggcccact ggggaagtgt ggctaagcac    1350
ggtggccccc agccctagcg acatgggggc aggcactgca gcaagttcac    1400
acacggaggt ggccccaact gaccctatgc ctaggagaag gggggcgcttc   1450
aaagggttga atgggcgcta cttccagcag caggaaccgg agccggggct    1500
gcaagggggg atggaggcca gcgcccagcc ccccacctca gaggctgcag    1550
tgaaccaaat ggagcctccg ttggccatgg cagtcacaga gatgttgggc    1600
agtggccaga gccggagccc ctgggctgat ctgaccaatg aggtggatat    1650
gcctggagct ggttctgctg gtggcaagag ctccccagag ccctggctgt    1700
ggcccccctac catggtccca cccagcatct caggccacag cagggcccct   1750
gtcctggagc tagagaaagc cgagggcccc agtgccaggc cagccacccc    1800
agacctgttt tggtccccct tggaggccac tgtctcagct cccagccctg    1850
ccccctggga ggcattccct gtggccacct ccccagatct ccctatgatg    1900
gccatgctgc gtggtcccaa agagtggatg ctaccacacc ccaccccccat   1950
ctccaccgag gccaatagag ttgaggcaca tggtgaggcc accgccacgg    2000
ctccaccctc ccctgctgca gagaccaagg tgtattccct gcctctctct    2050
ttgaccccaa caggacaggg tggagaggcc atgcccacaa cacctgagtc    2100
ccccagggca gacttcagag aaactgggga gaccagccct gctcaggtca    2150
acaaagctga gcactccagc tccagcccat ggccttctgt aaacaggaat    2200
gtggctgtag gttttgtccc cactgagact gccactgagc caacgggcct    2250
caggggtatc ccggggtctg agtctggggt cttcgacaca gcagaaagcc    2300
ccacttctgg cttgcaggcc actgtagatg aggtgcagga cccctggccc    2350
tcagtgtaca gcaaagggct ggatgcaagt tccccatctg ccccccctggg   2400
gagccctgga gtcttcttgg tacccaaagt caccccaaat ttggagcctt    2450
gggttgctac agatgaagga cccactgtga atcccatgga ttccacagtc    2500
```

-continued

```
acgccggccc ccagtgatgc tagtggaatt tgggaacctg gatcccaggt      2550
gtttgaagaa gccgaaagca ccaccttgag ccctcaggtg gccctggata      2600
caagcattgt gacgcccctc acgaccctgg agcaggggga caaggttgga      2650
gttccagcca tgtctacact gggctcctca agctcccaac cccacccaga      2700
gccagaggat caggtggaga cccagggaac atcaggagct tcagtgcctc      2750
cgcatcagag cagtccccta gggaaaccgg ctgttcctcc tgggacaccg      2800
actgcagcca gtgtgggcga gtctgcctca gtttcctcag gggagcctac      2850
ggtaccgtgg gacccctcca gcaccctgct gcctgtcacc ctgggcatag      2900
aggacttcga actggaggtc ctggcaggga gcccgggtgt agagagcttc      2950
tgggaggagg tggcaagtgg agaggagcca gccctgccag ggacccctat      3000
gaatgcaggt gcggaggagg tgcactcaga tccctgtgag aacaaccctt      3050
gtcttcatgg agggacatgt aatgccaatg gcaccatgta tggctgtagc      3100
tgtgatcagg gcttcgccgg ggagaactgt gagattgaca ttgatgactg      3150
cctctgcagc cctgtgaga atggaggcac ctgtattgat gaggtcaatg      3200
gctttgtctg cctttgcctc cccagctatg gggcagctt ttgtgagaaa       3250
gacaccgagg gctgtgaccg cggctggcat aagttccagg gccactgtta      3300
ccgctatttt gcccaccgga gggcatggga agatgccgag aaggactgcc      3350
gccgccgctc cggccacctg accagcgtcc actcaccgga ggaacacagc      3400
ttcattaata gctttgggca tgaaaacacg tggatcggcc tgaacgacag      3450
gatcgtggag agagatttcc agtggacgga caacaccggg ctgcaatttg      3500
agaactggcg agagaaccag ccggacaatt tcttcgcggg tggcgaggac      3550
tgtgtggtga tggtggcgca tgaaagcggg cgctggaacg atgtcccctg      3600
caactacaac ctaccctatg tctgcaagaa gggcacagtg ctctgtggtc      3650
cccctccggc agtggagaat gcctcactca tcggtgcccg caaggccaag      3700
aacaatgtcc atgccactgt aaggtaccag tgcaatgaag gatttgccca      3750
gcaccatgtg gtcaccattc gatgccggag caatggcaag tgggacaggc      3800
cccaaattgt ctgcaccaaa cccagacgtt cacatcggat gcggggacac      3850
caccaccacc accaacacca ccaccagcat caccaccaca aatcccgcaa      3900
ggagcgcaga aaacacaaga aacacccaac ggaggactgg gagaaggacg      3950
aagggaattt ttgctgaaga accagaaaaa agaaagcaca acacctttcc      4000
catgcctcct ctggagcctt cgcctgggga gacagaaccc agagagaaac      4050
aagagagtcc agaagtccct gaaccccaaa ctgttctcgc aaaaaaaata      4100
ttcctttgaa caaaggtctt cttttccttt ttttacatac acaagatctt      4150
cttggcaggt ggagccaggt gtctgaaaag ttcattctcg tctggctgaa      4200
ctctgggagt gtgtcccagc tgagggaagc acaagtagca aagctcattg      4250
gtctggtctc ttgtttgcca ggctgattga agcaggcctt gatgagggtg      4300
catgagtgta tgtttgcatt cacatgaagg aattgctttt cacaccagaa      4350
attcagactt agtcaatgtt ggctgaattc ctaaatccag gaagaagcct      4400
ggacgtaggg tcattagctt tgggaataga aggctacaca gaagcacact      4450
gtttttgaac ttgacaacag ctctcccttt accctggact tcagcccaag      4500
```

-continued

```
ttccgtcttt ggtcttggtg gataaacaca cagtgtggag atcccacgta      4550
ctgcatttta gggatgtttt taggacaacc tccctccatg ccttcagagt      4600
taggagtgag aatgatcaaa gcaatatgta ggtgatggag ggagagtgta      4650
ttgctaaccc ttccaggtct agtccagcgc tgagatttgg tggttctgca      4700
tgtgtgatga atctctttca cacaaataga cgagaggata tttagggcta      4750
gatgagccca gatttcttcc ccctccatct ctcagggaga caaagaacct      4800
ccttcctgga ccaaggaggt gctgccaagt tttctagccc agtgcacata      4850
cccagtcctt aagcagacat tggtagtgcc cctgccctgg gtcccactcc      4900
tgccccaccc cacccttgtc cctggccatt gcctggtggt ctagaaacac      4950
ttaaaacttg aagtagtgac acctacctgc ggtcatattg tagagagatg      5000
ctcagtgtta aaactgaaac acacaaacac acacacacac acatttttct      5050
cttgtagatt ttaatttttt aagtgggaaa gaactcacct tgccttcctc      5100
ccccaaatgt gcaacctgta aaaggtctct ccacaccagg ggccaggatc      5150
cagttccctc atctctggca ggaaagatcc acagcttttc ctccatgtct      5200
gttactcact ttcagcagtc cgggtaaaat ctgtggatca gggttaaaaa      5250
agcaccgtgg agaatggccc tcttcaggaa agaaaaataa gcaaatgaat      5300
ggtccaccta ggggttcagt aaagaaagaa atgtgttaac tgagcctgaa      5350
tcccttctgg gaagtaataa tgaccattga caactaagaa gtagacacca      5400
tgctaaagac ttacatacaa tctccttgaa tcttctcaat agcccattga      5450
cttagaaact gttactttcc cattttacac acagtgaaac tgaggctcag      5500
atataaagga aaggtactgg cttgaagtca caaccacgac aggagtaagg      5550
atttggaata aggatttggt cctgttttct ggaccaaatc cttactctgg      5600
ctctgcttac actttctctc catcaccaaa tccttactcc aaatccagaa      5650
gtcagagcca actcccatct tggttctgac ccaaatcctg ctctggactc      5700
tggagaggag attgaaatat aattgcaccc tcatacacat ttaggaaatg      5750
gttaagaagt gtaaactgaa cccttatcct tgtcttcaat cttcctccct      5800
gtagacatct atcttattat ggttattatt cagaaaaccc agggatacag      5850
gtttgtcttc ttactttgat aactcttctt agtttaaaat aataataata      5900
acacatcttt ggtcatctat gtcacacaaa aattttcctt tgtttgcggg      5950
gggctgggga tgcagtgttt tttggggggt cttggtttat gctccctgcc      6000
cttgagcccc tcagccgttt gccctgcccc cacctcggct ccatggtggg      6050
agggggctct ggtcttttct aaagtgggcg gtttgtcttt tgatctttcc      6100
cttttggatg tgcgtgtgtg tctgcgtgtg ccatgtgcgt ggcacgcata      6150
tgagtgtgtg tgcgtgtgaa cggctttggg tcctgctggt tttgctgtga      6200
gctgcagtgt tctgtgggtc tgtggtatct gacactgtgg acattaatgt      6250
acttcttgga cattttaata aatttttaa cagttcaaaa aaaaaaaaaa       6300
aaaaaaaaaa                                                  6310
```

<210> SEQ ID NO 27
<211> LENGTH: 4577
<212> TYPE: DNA
<213> ORGANISM: Homo Sapien

<400> SEQUENCE: 27

```
actagagatg gcgggcgggc tgctctgaag agacctcggc ggcggcggag      50
gaggagagaa gcgcagcgcc gcgccgcgcc ggggcccatg tggggaggag     100
tcggagtcgc tgttgccgcc gccgcctgta gctgctggac ccgagtggga     150
gtgaggggga aacggcagga tgaagttcgc cgagcacctc tccgcgcaca     200
tcactcccga gtggaggaag caatacatcc agtatgaggc tttcaaggat     250
atgctgtatt cagctcagga ccaggcacct tctgtggaag ttacagatga     300
ggacacagta aagaggtatt ttgccaagtt tgaagagaag tttttccaaa     350
cctgtgaaaa agaacttgcc aaaatcaaca cattttattc agagaagctc     400
gcagaggctc agcgcaggtt tgctacactt cagaatgagc ttcagtcatc     450
actggatgca cagaaagaaa gcactggtgt tactacgctg cgacaacgca     500
gaaagccagt cttccacttg tcccatgagg aacgtgtcca acatagaaat     550
attaaagacc ttaaactggc cttcagtgag ttctacctca gtctaatcct     600
gctgcagaac tatcagaatc tgaattttac agggtttcga aaaatcctga     650
aaaagcatga caagatcctg gaaacatctc gtggagcaga ttggcgagtg     700
gctcacgtag aggtggcccc attttataca tgcaagaaaa tcaaccagct     750
tatctctgaa actgaggctg tagtgaccaa tgaacttgaa gatggtgaca     800
gacaaaaggc tatgaagcgt ttacgtgtcc cccctttggg agctgctcag     850
cctgcaccag catggactac ttttagagtt ggcctatttt gtggaatatt     900
cattgtactg aatattaccc ttgtgcttgc cgctgtattt aaacttgaaa     950
cagatagaag tatatggccc ttgataagaa tctatcgggg tggctttctt    1000
ctgattgaat tcctttttct actgggcatc aacacgtatg gttggagaca    1050
ggctggagta aaccatgtac tcatctttga acttaatccg agaagcaatt    1100
tgtctcatca acatctcttt gagattgctg gattcctcgg gatattgtgg    1150
tgcctgagcc ttctggcatg cttctttgct ccaattagtg tcatccccac    1200
atatgtgtat ccacttgccc tttatggatt tatggttttc ttccttatca    1250
accccaccaa aactttctac tataaatccc ggttttggct gcttaaactg    1300
ctgtttcgag tatttacagc cccccttccat aaggtaggct ttgctgattt    1350
ctggctggcg gatcagctga acagcctgtc agtgatactg atggacctgg    1400
aatatatgat ctgcttctac agtttggagc tcaaatggga tgaaagtaag    1450
ggcctgttgc caaataattc agaagaatca ggaatttgcc acaaatatac    1500
atatggtgtg cgggccattg ttcagtgcat tcctgcttgg cttcgcttca    1550
tccagtgcct gcgccgatat cgagacacaa aaagggcctt tcctcattta    1600
gttaatgctg gcaagtactc cacaactttc ttcatggtgg cgtttgcagc    1650
cctttacagc actcacaaag aacgaggtca ctcggacact atggtgttct    1700
tttacctgtg gattgtcttt tatatcatca gttcctgcta taccctcatc    1750
tgggatctca agatggactg gggtctcttc gataagaatg ctggagagaa    1800
cactttcctc cgggaagaga ttgtataccc ccaaaaagcc tactactact    1850
gtgccataat agaggatgtg attctgcgct ttgcttggac tatccaaatc    1900
tcgattacct ctacaacttt gttgcctcat tctggggaca tcattgctac    1950
```

-continued

```
tgtctttgcc ccacttgagg ttttccggcg atttgtgtgg aacttcttcc      2000
gcctggagaa tgaacatctg aataactgtg gtgaattccg tgctgtgcgg      2050
gacatctctg tggcccccct gaacgcagat gatcagactc tcctagaaca      2100
gatgatggac caggatgatg gggtacgaaa ccgccagaag aatcggtcat      2150
ggaagtacaa ccagagcata tccctgcgcc ggcctcgcct cgcttctcaa      2200
tccaaggctc gtgacactaa ggtattgata gaagacacag atgatgaagc      2250
taacacttga attttctgaa gtctagctta acatctttgg ttttcctact      2300
ctacaatcct ttcctcgacc aacgcaacct ctagtacctt tccagccgaa      2350
aacaggagaa aacacataac acattttccg agctcttccg gatcggatcc      2400
tatggactcc aaacaagctc actgtgtttc ttttcttttc ttctggttta      2450
attttaattt tctattttca aaacaagtat ttacttcatt tgccaatcag      2500
aggatgtttt aagaaacaaa acatagtatc ttatggattg tttacaatca      2550
caaggacata gatacctatc aggatgaaga acaggcattg caaggaccct      2600
ctgatgggac ggtactgaga tatctcggct tccgctcagc ccggttttga      2650
atggttgaaa ccggacattg gtttttaaat tttttgtcag tttatgtgga      2700
gaattttttt ctttccttca tacccagcgc aaaggcactg gccgcacttg      2750
caggaaaagt gcaacttaaa gcagtacctt cattcatgaa gctacttttt      2800
aatttgatgt aacttttctt attttgggaa gggttgctgg gtgggtggga      2850
aatatgatgt atttgttaca catagtttc tcattattta tgaaacttaa       2900
ccatacagaa tgatataact cctgtgcaat gaaggtgata acagtaaaag      2950
tgatataact cctgtgcaat gaaggtgata acagtaaaag aaggcagggg      3000
aaacttacgt tggatgacat ttatgagggt cagtcccaca tacctctttc      3050
aggagacaac ttgcaccagt ttgacctttt cttttctttg tttttatttt      3100
aagccaaagt ttcattgcta acttcttaag ttgctgctgc tttagagtcc      3150
tgagcatatc tctcataaca aggaatccca cacttcacac caccggctga      3200
atttcatgga agaggttctg ataatttttt taacttttta aggaacagat      3250
gtggaataca ctggcccata tttcaacctt aacagctgaa gctatgcctt      3300
attatgcatc cacatgtatg gtccctgtag cgtgaccttt actagctctg      3350
aatcagaaga cagagctatt tcagaggctc tgtgtgccct cactagatag      3400
tttttcttct gggttcaacc actttagcca gaatttgatc aaattaaaag      3450
tctgtcatgg ggaaactata tttttgagca catggaacaa attatacttc      3500
ctcattcata ttatgttgat acaaaagacc ttggcagcca tttctcccag      3550
cagttttaaa ggatgaacat tggatttcat gccatcccat agaaaacctg      3600
ttttaaaatt ttagggatct ttacttggtc atacatgaaa agtacactgc      3650
ttagaaatta tagactatta tgatctgtcc acagtgccca ttgtcacttc      3700
tttgtctcat ttcttccctt tgttccttag tcatccaaat aagcctgaaa      3750
accataagag atattacttt attgaatatg gttggcatta aatttagcat      3800
ttcattatct aacaaaatta atataaattc caggacatgg taaaatgtgt      3850
tttaataacc cccagaccca aatgaaaatt tcaaagtcaa taccagcaga      3900
ttcatgaaag taaatttagt cctataattt tcagcttaat tataaacaaa      3950
```

-continued

```
ggaacaaata agtggaaggg cagctattac cattcgctta gtcaaaacat      4000

tcggttactg ccctttaata cactcctatc atcagcactt ccaccatgta      4050

ttacaagtct tgacccatcc ctgtcgtaac tccagtaaaa gttactgtta      4100

ctagaaaatt tttatcaatt aactgacaaa tagtttcttt ttaaagtagt      4150

ttcttccatc tttattctga ctagcttcca aaatgtgttc ccttttttgaa      4200

tcgaggtttt tttgttttgt tttgttttct gaaaaaatca tacaactttg      4250

tgcttctatt gctttttttgt gttttgttaa gcatgtccct tggcccaaat      4300

ggaagaggaa atgtttaatt aatgcttttt agtttaaata aattgaatca      4350

tttataataa tcagtgttaa caatttagtg acccttggta ggttaaaggt      4400

tgcattattt atacttgaga tttttttccc ctaactattc tgttttttgt      4450

actttaaaac tatgggggaa atatcactgg tctgtcaaga aacagcagta      4500

attattactg agttaaattg aaaagtccag tggaccaggc atttcttata      4550

taaataaaat tggtggtact aatgtgt                               4577
```

<210> SEQ ID NO 28
<211> LENGTH: 2203
<212> TYPE: DNA
<213> ORGANISM: Homo Sapien

<400> SEQUENCE: 28

```
cccttgctgg acccgagtgg gagtgagggg gaaacggcag gatgaagttc        50

gccgagcacc tctccgcgca catcactccc gagtggagga agcaatacat       100

ccagtatgag gctttcaagg atatgctgta ttcagctcag gaccaggcac       150

cttctgtgga agttacagat gaggacacag taaagaggta ttttgccaag       200

tttgaagaga agtttttcca aacctgtgaa aaagaacttg ccaaaatcaa       250

cacattttat tcagagaagc tcgcagaggc tcagcgcagg tttgctacac       300

ttcagaatga gcttcagtca tcactggatg cacagaaaga aagcactggt       350

gttactacgc tgcgacaacg cagaaagcca gtcttccact tgtcccatga       400

ggaacgtgtc caacatagaa atattaaaga ccttaaactg gccttcagtg       450

agttctacct cagtctaatc ctgctgcaga actatcagaa tctgaatttt       500

acagggtttc gaaaaatcct gaaaaagcat gacaagatcc tggaaacatc       550

tcgtggagca gattggcgag tggctcacgt agaggtggcc ccattttata       600

catgcaagaa aatcaaccag cttatctctg aaactgaggc tgtagtgacc       650

aatgaacttg aagatggtga cagacaaaag gctatgaagc gtttacgtgt       700

ccccccctttg ggagctgctc agcctgcacc agcatggact acttttagag       750

ttggcctatt ttgtggaata ttcattgtac tgaatattac ccttgtgctt       800

gccgctgtat ttaaacttga aacagataga agtatatggc ccttgataag       850

aatctatcgg ggtggctttc ttctgattga attccttttt ctactgggca       900

tcaacacgta tggttggaga caggctggag taaaccatgt actcatcttt       950

gaacttaatc cgagaagcaa tttgtctcat caacatctct ttgagattgc      1000

tggattcctc gggatattgt ggtgcctgag ccttctggca tgcttctttg      1050

ctccaattag tgtcatcccc acatatgtgt atccacttgc cctttatgga      1100

tttatggttt tcttccttat caaccccacc aaaactttct actataaatc      1150
```

```
ccggttttgg ctgcttaaac tgctgtttcg agtatttaca gccccccttcc   1200

ataaggtagg ctttgctgat ttctggctgg cggatcagct gaacagcctg   1250

tcagtgatac tgatggacct ggaatatatg atctgcttct acagtttgga   1300

gctcaaatgg gatgaaagta agggcctgtt gccaaataat tcagaagaat   1350

caggaatttg ccacaaatat acatatggtg tgcgggccat tgttcagtgc   1400

attcctgctt ggcttcgctt catccagtgc ctgcgccgat atcgagacac   1450

aaaaagggcc tttcctcatt tagttaatgc tggcaaatac tccacaactt   1500

tcttcatggt gacgtttgca gccctttaca gcactcacaa agaacgaggt   1550

cactcggaca ctatggtgtt cttttacctg tggattgtct tttatatcat   1600

cagttcctgc tataccctca tctgggatct caagatggac tggggtctct   1650

tcgataagaa tgctggagag aacactttcc tccgggaaga gattgtatac   1700

ccccaaaaag cctactacta ctgtgccata atagaggatg tgattctgcg   1750

ctttgcttgg actatccaaa tctcgattac ctctacaact ttgttgcctc   1800

attctgggga catcattgct actgtctttg ccccacttga ggttttccgg   1850

cgatttgtgt ggaacttctt ccgcctggag aatgaacatc tgaataactg   1900

tggtgaattc cgtgctgtgc gggacatctc tgtggccccc ctgaacgcag   1950

atgatcagac tctcctagaa cagatgatgg accaggatga tggggtacga   2000

aaccgccaga agaatcggtc atggaagtac aaccagagca tatccctgcg   2050

ccggcctcgc ctcgcttctc aatccaaggc tcgtgacact aaggtattga   2100

tagaagacac agatgatgaa gctaacactt gaattttctg aagtctagct   2150

taacatcttt ggttttccta ctctacaatc ctttcctcga ccaacgcaag   2200

ggc                                                       2203
```

```
<210> SEQ ID NO 29
<211> LENGTH: 3162
<212> TYPE: DNA
<213> ORGANISM: Homo Sapien

<400> SEQUENCE: 29

gcgccctagc cctctttcgg ggatactggc cgaccccctc ttccttttcc     50

cctttagtga aggcctcccc cgtcgccgcg cggcttcccg gagccgactg    100

cagactccct cagcccggtg ttccccgcgt ccggacgccg aggtcgcggc    150

ttcgcagaaa ctcgggcccc tccatccgcc ctcagaaaag ggagcgatgt    200

tgatctcagg aagcacaaag ggaccttcct agctctgact gaaccacgga    250

gctcaccctg gacagtatca ctccgtggag gaagactgtg agactgtggc    300

tggaagccag attgtagcca cacatccgcc cctgccctac cccagagccc    350

tggagcagca actggctgca gatcacagac acagtgagga tatgagtgta    400

ggggtgagca cctcagcccc tctttcccca acctcgggca caagcgtggg    450

catgtctacc ttctccatca tggactatgt ggtgttcgtc ctgctgctgg    500

ttctctctct tgccattggg ctctaccatg cttgtcgtgg ctggggccgg    550

catactgttg gtgagctgct gatggcggac cgcaaaatgg gctgccttcc    600

ggtggcactg tccctgctgg ccaccttcca gtcagccgtg gccatcctgg    650

gtgtgccgtc agagatctac cgatttggga cccaatattg gttcctgggc    700
```

-continued

```
tgctgctact ttctggggct gctgatacct gcacacatct tcatccccgt        750
tttctaccgc ctgcatctca ccagtgccta tgagtacctg gagcttcgat        800
tcaataaaac tgtgcgagtg tgtggaactg tgaccttcat ctttcagatg        850
gtgatctaca tgggagttgt gctctatgct ccgtcattgg ctctcaatgc        900
agtgactggc tttgatctgt ggctgtccgt gctggccctg ggcattgtct        950
gtaccgtcta tacagctctg ggtgggctga aggccgtcat ctggacagat       1000
gtgttccaga cactggtcat gttcctcggg cagctggcag ttatcatcgt       1050
ggggtcagcc aaggtgggcg gcttggggcg tgtgtgggcc gtggcttccc       1100
agcacggccg catctctggg tttgagctgg atccagaccc ctttgtgcgg       1150
cacaccttct ggaccttggc cttcgggggt gtcttcatga tgctctcctt       1200
atacggggtg aaccaggctc aggtgcagcg gtacctcagt tcccgcacgg       1250
agaaggctgc tgtgctctcc tgttatgcag tgttcccctt ccagcaggtg       1300
tccctctgcg tgggctgcct cattggcctg gtcatgttcg cgtattacca       1350
ggagtatccc atgagcattc agcaggctca ggcagcccca gaccagttcg       1400
tcctgtactt tgtgatggat ctcctgaagg gcctgccagg cctgccaggg       1450
ctcttcattg cctgcctctt cagcggctct ctcagcacta tatcctctgc       1500
ttttaattca ttggcaactg ttacgatgga agacctgatt cgaccttggt       1550
tccctgagtt ctctgaagcc cgggccatca tgctttccag aggccttgcc       1600
tttggctatg ggctgctttg tctaggaatg gcctatattt cctcccagat       1650
gggacctgtg ctgcaggcag caatcagcat ctttggcatg gttgggggac       1700
cgctgctggg actcttctgc cttggaatgt tctttccatg tgctaaccct       1750
cctggtgctg ttgtgggcct gttggctggg ctcgtcatgg ccttctggat       1800
tggcatcggg agcatcgtga ccagcatggg cttcagcatg ccaccctctc       1850
cctctaatgg gtccagcttc tccctgccca ccaatctaac cgttgccact       1900
gtgaccacac tgatgccctt gactaccttc tccaagccca cagggctgca       1950
gcggttctat tccttgtctt acttatggta cagtgctcac aactccacca       2000
cagtgattgt ggtgggcctg attgtcagtc tactcactgg gagaatgcga       2050
ggccggtccc tgaaccctgc aaccatttac ccagtgttgc caaagctcct       2100
gtccctcctt ccgttgtcct gtcagaagcg gctccactgc aggagctacg       2150
gccaggacca cctcgacact ggcctgtttc ctgagaagcc gaggaatggt       2200
gtgctggggg acagcagaga caaggaggcc atggccctgg atggcacagc       2250
ctatcagggg agcagctcca cctgcatcct ccaggagacc tccctgtgat       2300
gttgactcag gaccccgcct ctgtcctcac tgtgccaggc catagccaga       2350
ggccaccctg tagtacaggg atgagtcttg gtgtgttctg cagggacagg       2400
cctggatgat ctagctcata ccaaaggacc ttgttctgag aggttcttgc       2450
ctgcaggaga agctgtcaca tctcaagcat gtgaggcacc gtttttctcg       2500
tcgcttgcca atctgttttt taaaggatca ggctcgtagg gagcaggatc       2550
atgccagaaa tagggatgga agtgcatcct ctgggaaaaa gataatggct       2600
tctgattcaa catagccata gtcctttgaa gtaagtggct agaaacagca       2650
ctctggttat aattgcccca gggcctgatt caggactgac tctccaccat       2700
```

-continued aaaactggaa gctgcttccc ctgtagtccc catttcagta ccagttctgc 2750
cagccacagt gagcccctat tattactttc agattgtctg tgacactcaa 2800
gcccctctca tttttatctg tctacctcca ttctgaagag ggaggttttg 2850
gtgtccctgg tcctctggga atagaagatc catttgtctt tgtgtagagc 2900
aagcacgttt tccacctcac tgtctccatc ctccacctct gagatggaca 2950
cttaagagac ggggcaaatg tggatccaag aaaccagggc catgaccagg 3000
tccactgtgg agcagccatc tatctacctg actcctgagc caggctgccg 3050
tggtgtcatt tctgtcatcc gtgctctgtt tccttttgga gtttcttctc 3100
cacattatct ttgttcctgg ggaataaaaa ctaccattgg acctaaaaaa 3150
aaaaaaaaaa aa 3162

<210> SEQ ID NO 30
<211> LENGTH: 1432
<212> TYPE: DNA
<213> ORGANISM: Homo Sapien

<400> SEQUENCE: 30
gcgggcgccc agtgcaccgg aggaggtgag cgccaggtcg ccttcgcggc 50
ccggggacac aggcagggac gcgggagctg atgcggctgg accggccggg 100
gaaacagtat tttctggaag gggcccctc tgaagcggtc caggatcctg 150
cacatggcgc tgaccggggc ctcagacccc tctgcagagg cagaggccaa 200
cggggagaag ccctttctgc tgcgggcatt gcagatcgcg ctggtggtct 250
ccctctactg ggtcacctcc atctccatgg tgttccttaa taagtacctg 300
ctggacagcc cctccctgcg gctggacacc cccatcttcg tcaccttcta 350
ccagtgcctg gtgaccacgc tgctgtgcaa aggcctcagc gctctggccg 400
cctgctgccc tggtgccgtg gacttcccca gcttgcgcct ggacctcagg 450
gtggcccgca gcgtcctgcc cctgtcggtg gtcttcatcg gcatgatcac 500
cttcaataac ctctgcctca agtacgtcgg tgtggccttc tacaatgtgg 550
gccgctcact caccaccgtc ttcaacgtgc tgctctccta cctgctgctc 600
aagcagacca cctccttcta tgccctgctc acctgcggta tcatcatcgg 650
gggcttctgg cttggtgtgg accaggaggg ggcagaaggc accctgtcgt 700
ggctgggcac cgtcttcggc gtgctggcta gcctctgtgt ctcgctcaac 750
gccatctaca ccacgaaggt gctcccggcg gtggacggca gcatctggcg 800
cctgactttc tacaacaacg tcaacgcctg catcctcttc ctgcccctgc 850
tcctgctgct cggggagctt caggccctgc gtgaccttgc ccagctgggc 900
agtgcccact tctgggggat gatgacgctg ggcggcctgt ttggctttgc 950
catcggctac gtgacaggac tgcagatcaa gttcaccagt ccgctgaccc 1000
acaatgtgtc gggcacggcc aaggcctgtg cccagacagt gctggccgtg 1050
ctctactacg aggagaccaa gagcttcctc tggtggacga gcaacatgat 1100
ggtgctgggc ggctcctccg cctacacctg ggtcaggggc tgggagatga 1150
agaagactcc ggaggagccc agccccaaag acagcgagaa gagcgccatg 1200
ggggtgtgag caccacaggc accctggatg gcccggcccc ggggcccgta 1250
cacaggcggg gccagcacag tagtgaaggc ggtctcctgg accccagaag 1300
cgtgctgtgg tgtggactgg gtgctactta tagacccaat cagaatacgg 1350
tggttgagaa ggaaccagtg tttacaagta atatcagaaa gttgaaggaa 1400
ccagtgttta caagtaatac cagaaagttg cc 1432

<210> SEQ ID NO 31
<211> LENGTH: 1094
<212> TYPE: DNA
<213> ORGANISM: Homo Sapien

<400> SEQUENCE: 31
gcccttatcc tgcacatggc gctgaccggg gcctcagacc cctctgcaga 50
ggcagaggcc aacggggaga agccctttct gctgcgggca ttgcagatcg 100
cgctggtggt ctccctctac tggtcacct ccatctccat ggtgttcctt 150
aataagtacc tgctggacag cccctccctg cggctggaca cccccatctt 200
cgtcaccttc taccagtgcc tggtgaccac gctgctgtgc aaaggcctca 250
gcgctctggc cgcctgctgc cctggtgccg tggacttccc cagcttgcgc 300
ctggacctca gggtggcccg cagcgtcctg cccctgtcgg tggtcttcat 350
cggcatgatc accttcaata acctctgcct caagtacgtc ggtgtggcct 400
tctacaatgt gggccgctca ctcaccaccg tcttcaacgt gctgctctcc 450
tacctgctgc tcaagcagac cacctccttc tatgccctgc tcacctgcgg 500
tatcatcatc gggggcttct ggcttggtgt ggaccaggag gggggcagaag 550 gcaccctgtc gtggctgggc accgtcttcg gcgtgctggc tagcctctgt 600
gtctcgctca acgccatcta caccacgaag gtgctcccgg cggtggacgg 650
cagcatctgg cgcctgactt tctacaacaa cgtcaacgcc tgcatcctct 700
tcctgcccct gctcctgctg ctcggggagc ttcaggccct gcgtgacttt 750
gcccagctgg gcagtgccca cttctggggg atgatgacgc tgggcggcct 800
gtttggcttt gccatcggct acgtgacagg actgcagatc aagttcacca 850
gtccgctgac ccacaatgtg tcgggcacgg ccaaggcctg tgcccagaca 900
gtgctggccg tgctctacta cgaggagacc aagagcttcc tctggtggac 950
gagcaacatg atggtgctgg gcggctcctc cgcctacacc tgggtcaggg 1000
gctgggagat gaagaagact ccggaggagc ccagccccaa agacagcgag 1050
aagagcgcca tgggggtgtg agcaccacag gcaccctgaa gggc 1094

<210> SEQ ID NO 32
<211> LENGTH: 900
<212> TYPE: DNA
<213> ORGANISM: Homo Sapien

<400> SEQUENCE: 32
ccgagcgcgg ggcaccgggg gcctcctgta taggcgggca ccatgggctc 50
ctgctccggc cgctgcgcgc tcgtcgtcct ctgcgctttt cagctggtcg 100
ccgccctgga gaggcaggtg tttgacttcc tgggctacca gtgggcgccc 150
atcctggcca actttgtcca catcatcatc gtcatcctgg gactcttcgg 200
caccatccag taccggctgc gctacgtcat ggtgtacacg ctgtgggcag 250
ccgtctgggt cacctggaac gtcttcatca tctgcttcta cctggaagtc 300
ggtggcctct tacaggacag cgagctactg accttcagcc tctcccggca 350

```
tcgctcctgg tggcgtgagc gctggccagg ctgtctgcat gaggaggtgc        400

cagcagtggg cctcggggcc ccccatggcc aggccctggt gtcaggtgct        450

ggctgtgccc tggagcccag ctatgtggag gccctacaca gtggcctgca        500

gatcctgatc gcgcttctgg gctttgtctg tggctgccag gtggtcagcg        550

tgtttacgga ggaagaggac agctttgatt tcattggtgg atttgatcca        600

tttcctctct accatgtcaa tgaaaagcca tccagtctct tgtccaagca        650

ggtgtacttg cctgcgtaag tgaggaaaca gctgatcctg ctcctgtggc        700

ctccagcctc agcgaccgac cagtgacaat gacaggagct cccaggcctt        750

gggacgcgcc cccacccagc accccccagg cggccggcag cacctgccct        800

gggttctaag tactggacac cagccagggc ggcagggcag tgccacggct        850

ggctgcagcg tcaagagagt ttgtaatttc ctttctctta aaaaaaaaaa        900


<210> SEQ ID NO 33
<211> LENGTH: 666
<212> TYPE: DNA
<213> ORGANISM: Homo Sapien

<400> SEQUENCE: 33

ctcctgtata ggcgggcacc atgggctcct gctccggccg ctgcgcgctc         50

gtcgtcctct gcgcttttca gctggtcgcc gccctggaga ggcaggtgtt        100

tgacttcctg ggctaccagt gggcgcccat cctggccaac tttgtccaca        150

tcatcatcgt catcctggga ctcttcggca ccatccagta ccggctgcgc        200

tatgtcatgg tgtacacgct gtgggcagcc gtctgggtca cctggaacgt        250

cttcatcatc tgcttctacc tggaagtcgg tggcctctta aaggacagcg        300

agctactgac cttcagcctc tcccggcatc gctcctggtg gcgtgagcgc        350

tggccaggct gtctgcatga ggaggtgcca gcagtgggcc tcggggcccc        400

ccatggccag gccctggtgt caggtgctgg ctgtgccctg gagcccagct        450

atgtggaggc cctacacagt tgcctgcaga tcctgatcgc gcttctgggc        500

tttgtctgtg gctgccaggt ggtcagcgtg tttacggagg aagaggacag        550

ctttgatttc attggtggat ttgatccatt tcctctctac catgtcaatg        600

aaaagccatc cagtctcttg tccaagcagg tgtacttgcc tgcgtaagtg        650

aggaaacagc tgatcc                                             666


<210> SEQ ID NO 34
<211> LENGTH: 582
<212> TYPE: DNA
<213> ORGANISM: Homo sapien

<400> SEQUENCE: 34

ctcctgtata ggcgggcacc atgggctcct gctccggccg ctgcgcgctc         50

gtcgtcctct gcgcttttca gctggtcgcc gccctggaga ggcaggtgtt        100

tgacttcctg ggctaccagt gggcgcccat cctggccaac tttgtccaca        150

tcatcatcgt catcctggga ctcttcggca ccatccagta ccggctgcgc        200

tatgtcatgg tgtacacgct gtgggcagcc gtctgggtca cctggaacgt        250

cttcatcatc tgcttctacc tggaagtcgg tggcctctta aaggacagcg        300

agctactgac cttcagcctc tcccggcatc gctcctggtg gcgtgagcgc        350
```

tggccaggct gtctgcatga ggaggtgcca gcagtgggcc tcggggcccc 400
ccatggccag gccctggtgt caggtgctgg ctgtgccctg gagcccagct 450
atgtggaggc cctacacagt tgcctgcaga tcctgatcgc gcttctgggc 500
tttgtctgtg gctgccaggt ggtcagcgtg tttacggagg aagaggacag 550
ctgcctgcgt aagtgaggaa acagctgatc ca 582

<210> SEQ ID NO 35
<211> LENGTH: 582
<212> TYPE: DNA
<213> ORGANISM: Homo Sapien

<400> SEQUENCE: 35
ctcctgtata ggcgggcacc atgggctcct gctccggccg ctgcgcgctc 50
gtcgtcctct gcgcttttca gctggtcgcc gccctggaga ggcaggtgtt 100
tgacttcctg ggctaccagt gggcgcccat cctggccaac tttgtccaca 150
tcatcatcgt catcctggga ctcttcggca ccatccagta ccggctgcgc 200
tacgtcatgg tgtacacgct gtgggcagcc gtctgggtca cctggaacgt 250
cttcatcatc tgcttctacc tggaagtcgg tggcctctta caggacagcg 300
agctactgac cttcagcctc tcccggcatc gctcctggtg gcgtgagcgc 350
tggccaggct gtctgcatga ggaggtgcca gcagtgggcc tcggggcccc 400
ccatggccag gccctggtgt caggtgctgg ctgtgccctg gagcccagct 450
atgtggaggc cctacacagt ggcctgcaga tcctgatcgc gcttctgggc 500
tttgtctgtg gctgccaggt ggtcagcgtg tttacggagg aagaggacag 550
ctgcctgcgt aagtgaggaa acagctgatc ca 582

<210> SEQ ID NO 36
<211> LENGTH: 1546
<212> TYPE: DNA
<213> ORGANISM: Homo sapien

<400> SEQUENCE: 36
gcatggaaag tctttatttg agccccttag ctgatgtgga atcagaagag 50
caaaaaggtc atcttcagag tggcctgggc tgggtccttt tctctccagg 100
atagaaaagt ggtggtcact ttatccctag tagacatgct gctgggcttt 150
atcgccccag cattcccatc ccctccagag ccccttgtca ctccagacca 200
gcgagtgtgg gcctttatct ggactctgct tcctccctgg ggacaccagg 250
tcttggagca agagaacttg gcaggctctc cccatggcag tcttattcct 300
cctcctgttc ctatgtggaa ctccccaggc tgcagacaac atgcaggcca 350
tctatgtggc cttgggggag gcagtagagc tgccatgtcc ctcaccacct 400
actctacatg gggacgaaca cctgtcatgg ttctgcagcc ctgcagcagg 450
ctccttcacc accctggtag cccaagtcca agtgggcagg ccagccccag 500
accctggaaa accaggaagg gaatccaggc tcagactgct ggggaactat 550
tctttgtggt tggagggatc caaagaggaa gatgccgggc ggtactggtg 600
cgctgtgcta ggtcagcacc acaactacca gaactggagg gtgtacgacg 650
tcttggtgct caaaggatcc cagttatctg caagggctgc agatggatcc 700
ccctgcaatg tcctcctgtg ctctgtggtc cccagcagac gcatggactc 750

-continued tgtgacctgg caggaaggga agggtcccgt gaggggccgt gttcagtcct 800
tctggggcag tgaggctgcc ctgctcttgg tgtgtcctgg ggaggggctt 850
tctgagccca ggagccgaag accaagaatc atccgctgcc tcatgactca 900
caacaaaggg gtcagcttta gcctggcagc ctccatcgat gcttctcctg 950
ccctctgtgc cccttccacg ggctgggaca tgccttggat tctgatgctg 1000
ctgctcacaa tgggccaggg agttgtcatc ctggccctca gcatcgtgct 1050
ctggaggcag agggtccgtg gggctccagg cagaggaaac cgaatgcggt 1100
gctacaactg tggtggaagc cccagcagtt cttgcaaaga ggccgtgacc 1150
acctgtggcg agggcagacc ccagccaggc ctggaacaga tcaagctacc 1200
tggaaacccc ccagtgacct tgattcacca acatccagcc tgcgtcgcag 1250
cccatcattg caatcaagtg gagacagagt cggtgggaga cgtgacttat 1300
ccagcccaca gggactgcta cctgggagac ctgtgcaaca gcgccgtggc 1350
aagccatgtg gcccctgcag gcattttggc tgcagcagct accgccctga 1400
cctgtctctt gccaggactg tggagcggat agggggagta ggagtagaga 1450
agggaacaag ggagcaaggg aacaagggac atctgaacat ctaatgtgag 1500
aagagaaaca tccttctgtg agtcattaaa atctatgaac cactct 1546

<210> SEQ ID NO 37
<211> LENGTH: 4619
<212> TYPE: DNA
<213> ORGANISM: Homo Sapien

<400> SEQUENCE: 37
ctttagagaa aggaagggcc aaaactacga cttggctttc tgaaacggaa 50
gcataaatgt tcttttcctc catttgtctg gatctgagaa cctgcatttg 100
gtattagcta gtggaagcag tatgtatggt tgaagtgcat tgctgcagct 150
ggtagcatga gtggtggcca ccagctgcag ctggctgccc tctggccctg 200
gctgctgatg gctaccctgc aggcaggctt tggacgcaca ggactggtac 250
tggcagcagc ggtggagtct gaaagatcag cagaacagaa agctgttatc 300
agagtgatcc ccttgaaaat ggaccccaca ggaaaactga atctcacttt 350
ggaaggtgtg tttgctggtg ttgctgaaat aactccagca gaaggaaaat 400
taatgcagtc ccacccactg tacctgtgca atgccagtga tgacgacaat 450
ctggagcctg gattcatcag catcgtcaag ctggagagtc ctcgacgggc 500
cccccgcccc tgcctgtcac tggctagcaa ggctcggatg gcgggtgagc 550
gaggagccag tgctgtcctc tttgacatca ctgaggatcg agctgctgct 600
gagcagctgc agcagccgct ggggctgacc tggccagtgg tgttgatctg 650 ggtaatgac gctgagaagc tgatggagtt tgtgtacaag aaccaaaagg 700
cccatgtgag gattgagctg aaggagcccc cggcctggcc agattatgat 750
gtgtggatcc taatgacagt ggtgggcacc atctttgtga tcatcctggc 800
ttcggtgctg cgcatccggt gccgcccccg ccacagcagg ccggatccgc 850
ttcagcagag aacagcctgg gccatcagcc agctggccac caggaggtac 900
caggccagct gcaggcaggc ccggggtgag tggccagact cagggagcag 950
ctgcagctca gcccctgtgt gtgccatctg tctggaggag ttctctgagg 1000

-continued

```
ggcaggagct acgggtcatt tcctgcctcc atgagttcca tcgtaactgt    1050
gtggacccct ggttacatca gcatcggact tgccccctct gcgtgttcaa    1100
catcacagag ggagattcat tttcccagtc cctgggaccc tctcgatctt    1150
accaagaacc aggtcgaaga ctccacctca ttcgccagca tcccggccat    1200
gcccactacc acctccctgc tgcctacctg ttgggccctt cccggagtgc    1250
agtggctcgg cccccacgac ctggtccctt cctgccatcc caggagccag    1300
gcatgggccc tcggcatcac cgcttcccca gagctgcaca tccccgggct    1350
ccaggagagc agcagcgcct ggcaggagcc cagcacccct atgcacaagg    1400
ctggggaatg agccacctcc aatccacctc acagcaccct gctgcttgcc    1450
cagtgcccct acgccgggcc aggccccctg acagcagtgg atctggagaa    1500
agctattgca cagaacgcag tgggtacctg gcagatgggc cagccagtga    1550
ctccagctca gggccctgtc atggctcttc cagtgactct gtggtcaact    1600
gcacggacat cagcctacag gggtccatg gcagcagttc tactttctgc     1650
agctccctaa gcagtgactt tgacccccta gtgtactgca gccctaaagg    1700
ggatccccag cgagtggaca tgcagcctag tgtgacctct cggcctcgtt    1750
ccttggactc ggtggtgccc acaggggaaa cccaggtttc cagccatgtc    1800
cactaccacc gccaccggca ccaccactac aaaaagcggt tccagtggca    1850
tggcaggaag cctggcccag aaaccggagt cccccagtcc aggcctccta    1900
ttcctcggac acagccccag ccagagccac cttctcctga tcagcaagtc    1950
accggatcca actcagcagc cccttcgggg cggctctcta acccacagtg    2000
ccccagggcc ctccctgagc cagcccctgg cccagttgac gcctccagca    2050
tctgccccag taccagcagt ctgttcaact tgcaaaaatc cagcctctct    2100
gcccgacacc cacagaggaa aaggcggggg ggtccctccg agcccacccc    2150
tggctctcgg ccccaggatg caactgtgca cccagcttgc cagatttttc    2200
cccattacac ccccagtgtg gcatatcctt ggtccccaga ggcacacccc    2250
ttgatctgtg gacctccagg cctggacaag aggctgctac cagaaacccc    2300
aggcccctgt tactcaaatt cacagccagt gtggttgtgc ctgactcctc    2350
gccagcccct ggaaccacat ccacctgggg aggggccttc tgaatggagt    2400
tctgacaccg cagagggcag gccatgccct tatccgcact gccaggtgct    2450
gtcggcccag cctggctcag aggaggaact cgaggagctg tgtgaacagg    2500
ctgtgtgaga tgttcaggcc tagctccaac caagagtgtg ctccagatgt    2550
gtttgggccc tacctggcac agagtcctgc tcctgggaaa ggaaaggacc    2600
acagcaaaca ccattctttt tgccgtactt cctagaagca ctggaagagg    2650
actggtgatg gtggagggtg agagggtgcc gtttcctgct ccagctccag    2700
accttgtctg cagaaaacat ctgcagtgca gcaaatccat gtccagccag    2750
gcaaccagct gctgcctgtg gcgtgtgtgg gctggatccc ttgaaggctg    2800
agtttttgag ggcagaaagc tagctatggg tagccaggtg ttacaaaggt    2850
gctgctcctt ctccaacccc tacttggttt ccctcacccc aagcctcatg    2900
ttcataccag ccagtgggtt cagcagaacg catgacacct tatcacctcc    2950
ctccttgggt gagctctgaa caccagcttt ggcccctcca cagtaaggct    3000
```

gctacatcag gggcaaccct ggctctatca ttttcctttt ttgccaaaag 3050
gaccagtagc ataggtgagc cctgagcact aaaaggaggg gtccctgaag 3100
ctttcccact atagtgtgga gttctgtccc tgaggtgggt acagcagcct 3150
tggttcctct gggggttgag aataagaata gtggggaggg aaaaactcct 3200
ccttgaagat ttcctgtctc agagtcccag agaggtagaa aggaggaatt 3250
tctgctggac ttcatctggg cagaggaagg atggaatgaa ggtagaaaag 3300
gcagaattac agctgagcgg ggacaacaaa gagttcttct ctgggaaaag 3350
ttttgtctta gagcaaggat ggaaaatggg gacaacaaag gaaaagcaaa 3400
gtgtgaccct tgggtttgga cagcccagag gcccagctcc ccagtataag 3450
ccatacaggc cagggaccca caggagagtg gattagagca caagtctggc 3500
ctcactgagt ggacaagagc tgatgggcct catcagggtg acattcaccc 3550
cagggcagcc tgaccactct tggcccctca ggcattatcc catttggaat 3600
gtgaatgtgg tggcaaagtg ggcagaggac cccacctggg aacctttttc 3650
cctcagttag tggggagact agcacctagg tacccacatg ggtatttata 3700
tctgaaccag acagacgctt gaatcaggca ctatgttaag aaatatattt 3750
atttgctaat atatttatcc acaaatgtgg tctggtcttg tggttttgtt 3800
ctgtcgtgac tgtcactcag ggtaacaacg tcatctcttt ctacatcaag 3850
agaagtaaat tatttatgtt atcagaggct aggctccgat tcatgaaagg 3900
atagggtaga gtagagggct tggcaataag aactggtttg taagccccta 3950
aaagtgtggc ttagtgagat cagggaagga gaaagcatga ctggattctt 4000
actgtgcttc agtcattatt attatactgt tcacttcaca cattatcata 4050
cttcagtgac tyagaccttg ggcaaatact ctgtgcctcg ctttttcagt 4100
ccataaaatg ggcctactta atagttgttg caggacttac atgagataat 4150
agagtgtaga aaatatgttc caaagtggaa agttttattc agtgatagaa 4200
aacatccaaa cctgtcacag agcccatctg aacacagcat gggaccgcca 4250
acaagaagaa agcccgcccg gaagcagctc aatcaggagg ctgggctgga 4300
atgacagcgc agcggggcct gaaactattt atatcccaaa gctcctctca 4350
gataaacaca aatgactgcg ttctgcctgc actcgggcta ttgcgaggac 4400
agagagctgg tgctccattg gcgtgaagtc tccagggcca gaaggggcct 4450
ttgtcgcttc ctcacaaggc acaagttccc cttctgcttc cccgagaaag 4500
gtttggtagg ggtggtggtt tagtgcctat agaacaaggc atttcgcttc 4550
ctagacggtg aaatgaaagg gaaaaaaagg acacctaatc tcctacaaat 4600
ggtctttagt aaaggaacc 4619

<210> SEQ ID NO 38
<211> LENGTH: 3510
<212> TYPE: DNA
<213> ORGANISM: Homo Sapien

<400> SEQUENCE: 38
gcagctctgg gggagctcgg agctcccgat cacggcttct tgggggtagc 50
tacggctggg tgtgtagaac ggggccgggg ctggggctgg gtcccctagt 100
ggagacccaa gtgcgagagg caagaactct gcagcttcct gccttctggg 150

-continued

```
tcagttcctt attcaagtct gcagccggct cccagggaga tctcggtgga        200
acttcagaaa cgctgggcag tctgcctttc aaccatgccc ctgtccctgg        250
gagccgagat gtgggggcct gaggcctggc tgctgctgct gctactgctg        300
gcatcattta caggccggtg ccccgcgggt gagctggaga cctcagacgt        350
ggtaactgtg gtgctgggcc aggacgcaaa actgccctgc ttctaccgag        400
gggactccgg cgagcaagtg gggcaagtgg catgggctcg ggtggacgcg        450
ggcgaaggcg cccaggaact agcgctactg cactccaaat acgggcttca        500
tgtgagcccg gcttacgagg gccgcgtgga gcagccgccg cccccacgca        550
acccccctgga cggctcagtg ctcctgcgca acgcagtgca ggcggatgag       600
ggcgagtacg agtgccgggt cagcaccttc cccgccggca gcttccaggc        650
gcggctgcgg ctccgagtgc tggtgcctcc cctgccctca ctgaatcctg        700
gtccagcact agaagagggc cagggcctga ccctggcagc ctcctgcaca        750
gctgagggca gcccagcccc cagcgtgacc tgggacacgg aggtcaaagg        800
cacaacgtcc agccgttcct tcaagcactc ccgctctgct gccgtcacct        850
cagagttcca cttggtgcct agccgcagca tgaatgggca gccactgact        900
tgtgtggtgt cccatcctgg cctgctccag gaccaaagga tcacccacat        950
cctccacgtg tccttccttg ctgaggcctc tgtgaggggc cttgaagacc       1000
aaaatctgtg gcacattggc agagaaggag ctatgctcaa gtgcctgagt       1050
gaagggcagc cccctccctc atacaactgg acacggctgg atgggcctct       1100
gcccagtggg gtacgagtgg atggggacac tttgggcttt cccccactga       1150
ccactgagca cagcggcatc tacgtctgcc atgtcagcaa tgagttctcc       1200
tcaagggatt ctcaggtcac tgtggatgtt cttgaccccc aggaagactc       1250
tgggaagcag gtggacctag tgtcagcctc ggtggtggtg gtgggtgtga       1300
tcgccgcact cttgttctgc cttctggtgg tggtggtggt gctcatgtcc       1350
cgataccatc ggcgcaaggc ccagcagatg acccagaaat atgaggagga       1400
gctgaccctg accagggaga actccatccg gaggctgcat tcccatcaca       1450
cggaccccag gagccagccg gaggagagtg tagggctgag agccgagggc       1500
caccctgata gtctcaagga caacagtagc tgctctgtga tgagtgaaga       1550
gcccgagggc cgcagttact ccacgctgac cacggtgagg gagatagaaa       1600
cacagactga actgctgtct ccaggctctg ggcgggccga ggaggaggaa       1650
gatcaggatg aaggcatcaa acaggccatg aaccattttg ttcaggagaa       1700
tgggacccta cgggccaagc ccacgggcaa tggcatctac atcaatgggc       1750
ggggacacct ggtctgaccc aggcctgcct cccttcccta ggcctggctc       1800
cttctgttga catgggagat tttagctcat cttgggggcc tccttaaaca       1850
cccccatttc ttgcggaaga tgctccccat cccactgact gcttgacctt       1900
tacctccaac ccttctgttc atcgggaggg ctccaccaat tgagtctctc       1950
ccaccatgca tgcaggtcac tgtgtgtgtg catgtgtgcc tgtgtgagtg       2000
ttgactgact gtgtgtgtgt ggaggggtga ctgtccgtgg aggggtgact       2050
gtgtccgtgg tgtgtattat gctgtcatat cagagtcaag tgaactgtgg       2100
tgtatgtgcc acgggatttg agtggttgcg tgggcaacac tgtcagggtt       2150
```

```
tggcgtgtgt gtcatgtggc tgtgtgtgac ctctgcctga aaaagcaggt      2200

attttctcag accccagagc agtattaatg atgcagaggt tggaggagag      2250

aggtggagac tgtggctcag acccaggtgt gcgggcatag ctggagctgg      2300

aatctgcctc cggtgtgagg gaacctgtct cctaccactt cggagccatg      2350

ggggcaagtg tgaagcagcc agtccctggg tcagccagag gcttgaactg      2400

ttacagaagc cctctgccct ctggtggcct ctgggcctgc tgcatgtaca      2450

tattttctgt aaatatacat gcgccgggag cttcttgcag gaatactgct      2500

ccgaatcact tttaattttt ttcttttttt tttcttgccc tttccattag      2550

ttgtattttt tatttatttt tatttttatt ttttttaga gatggagtct      2600

cactatgttg ctcaggctgg ccttgaactc ctgggctcaa gcaatcctcc      2650

tgcctcagcc tccctagtag ctgggacttt aagtgtacac cactgtgcct      2700

gctttgaatc ctttacgaag agaaaaaaaa aattaaagaa agcctttaga      2750

tttatccaat gtttactact gggattgctt aaagtgaggc ccctccaaca      2800

ccaggggggtt aattcctgtg attgtgaaag gggctacttc caaggcatct      2850

tcatgcaggc agccccttgg gagggcacct gagagctggt agagtctgaa      2900

attagggatg tgagcctcgt ggttactgag taaggtaaaa ttgcatccac      2950

cattgtttgt gataccttag ggaattgctt ggacctggtg acaagggctc      3000

ctgttcaata gtggtgttgg ggagagagag agcagtgatt atagaccgag      3050

agagtaggag ttgaggtgag gtgaaggagg tgctgggggt gagaatgtcg      3100

cctttccccc tgggttttgg atcactaatt caaggctctt ctggatgttt      3150

ctctgggttg gggctggagt tcaatgaggt ttatttttag ctggcccacc      3200

cagatacact cagccagaat acctagattt agtacccaaa ctcttcttag      3250

tctgaaatct gctggatttc tggcctaagg gagaggctcc catccttcgt      3300

tccccagcca gcctaggact tcgaatgtgg agcctgaaga tctaagatcc      3350

taacatgtac attttatgta aatatgtgca tatttgtaca taaaatgata      3400

ttctgttttt aaataaacag acaaaacttg aaaaaaaaaa aaaaaaaaaa      3450

aaaaaaaaaa aaaaaaaaaa aaaaaaaaaa aaaaaaaaaa aaaaaaaaaa      3500

aaaaaaaaaa                                                  3510
```

<210> SEQ ID NO 39
<211> LENGTH: 2211
<212> TYPE: DNA
<213> ORGANISM: Homo sapien

<400> SEQUENCE: 39

```
ttgggggttt attctcttcc cttctaactt gacagggtct tgctctgtca        50

ttcaggcaag agtgcagtag tgtgatcact tcttactgcc gcctcaagct       100

tccagcctca actcaagcaa tcctcccacc tcagccaccc aagtggctgg       150

gactacagat taagaatgac ccaaaataaa ttaaagcttt gttccaaagc       200

caatgtgtat actgaagtgc ctgatggagg atggggctgg gcggtagctg       250

tttcattttt cttcgttgaa gtcttcacct acggcatcat caagacattt       300

ggtgtcttct ttaatgactt aatggacagt tttaatgaat ccaatagcag       350

gatctcatgg ataatctcaa tctgtgtgtt tgtcttaaca ttttcagctc       400
```

-continued

```
ccctcgccac agtcctgagc aatcgtttcg gacaccgtct ggtagtgatg         450
ttgggggggc tacttgtcag caccgggatg gtggccgcct ccttctcaca         500
agaggtttct catatgtacg tcgccatcgg catcatctct ggtctgggat         550
actgctttag ttttctccca actgtaacca tcctatcaca atattttggc         600
aaaagacgtt ccatagtcac tgcagttgct tccacaggag aatgtttcgc         650
tgtgtttgct ttcgcaccag caatcatggc tctgaaggag cgcattggct         700
ggagatacag cctcctcttc gtgggcctac tacagttaaa cattgtcatc         750
ttcggagcac tgctcagacc catcattatc agaggaccag cgtcaccgaa         800
aatagtcatc caggaaaatc ggaaagaagc gcagtatatg cttgaaaatg         850
agaaaacacg aacctcaata gactccattg actcaggagt agaactaact         900
acctcaccta aaaatgtgcc tactcacact aacctggaac tggagccgaa         950
ggccgacatg cagcaggtcc tggtgaagac cagccccagg ccaagcgaaa        1000
agaaagcccc gctattagac ttctccattt tgaaagagaa aagttttatt        1050
tgttatgcat tatttggtct ctttgcaaca ctgggattct ttgcaccttc        1100
cttgtacatc attcctctgg gcattagtct gggcattgac caggaccgcg        1150
ctgctttttt attatctacg atggccattg cagaagtttt cggaaggatc        1200
ggagctggtt ttgtcctcaa cagggagccc attcgtaaga tttacattga        1250
gctcatctgc gtcatcttat tgactgtgtc tctgtttgcc tttacttttg        1300
ctactgaatt ctggggtcta atgtcatgca gcatattttt tgggtttatg        1350
gttggaacaa taggaggact cacattccac tgcttgctga agatgatgtc        1400
gtgggcattg cagaagatgt cttctgcagc tggggtctac atcttcattc        1450
agagcatagc aggactggct ggaccgcccc ttgcaggttt gttggtggac        1500
caaagtaaga tctacagcag ggccttctac tcctgcgcag ctggcatggc        1550
cctggctgct gtgtgcctcg ccctggtgag accgtgtaag atgggactgt        1600
gccagcgtca tcactcaggt gaaacaaagg tagtgagcca tcgtgggaag        1650
actttacagg acatacctga agactttctg gaaatggatc ttgcaaaaaa        1700
tgagcacaga gttcacgtgc aaatggagcc ggtatgacac actttcttac        1750
aacaacagcc actgtgttgg ctggagaggg atggggtggg cccaacgggg        1800
acacaaggag gcagaggagc taacccctct actccacttt caaaactaca        1850
ttttaaaggg aatgtgtatg tgaagagcac taccaacatc gcttttgttt        1900
tgttttgttt tgttttaagc tttttttttt tgcttgtttt taaagccaaa        1950
acaaaaaaca accaagcact cttccatata taaatctggc tgtattcagt        2000
agcaatacaa gagatatgta gaaagactct ttggttcaca ttccgatatt        2050
aaaatagtga catgaactgg caaagtggtt ttaaaagctt tcacgtggga        2100
taaatgattt tcttttttc ttttctttct tcctatggtc ttgtctgaat         2150
aaactactct cctgaataaa acaacatcca acccaggtca ttgaaatgaa        2200
attggccagt c                                                  2211
```

<210> SEQ ID NO 40
<211> LENGTH: 685
<212> TYPE: DNA
<213> ORGANISM: Homo Sapien

<400> SEQUENCE: 40

```
gatgtgctcc ttggagctgg tgtgcagtgt cctgactgta agatcaagtc     50
caaacctgtt ttggaattga ggaaacttct cttttgatct cagcccttgg    100
tggtccaggt cttcatgctg ctgtgggtga tattactggt cctggctcct    150
gtcagtggac agtttgcaag gacacccagg cccattattt tcctccagcc    200
tccatggacc acagtcttcc aaggagagag agtgaccctc acttgcaagg    250
gatttcgctt ctactcacca cagaaaacaa aatggtacca tcggtacctt    300
gggaaagaaa tactaagaga aaccccagac aatatccttg aggttcagga    350
atctggagag tacagatgcc aggcccaggg ctcccctctc agtagccctg    400
tgcacttgga tttttcttca gagatgggat ttcctcatgc tgcccaggct    450
aatgttgaac tcctgggctc aagtgatctg ctcacctagg cctctcaaag    500
cgctgggatt acagcttcgc tgatcctgca agctccactt tctgtgtttg    550
aaggagactc tgtggttctg aggtgccggg caaaggcgga agtaacactg    600
aataatacta tttacaagaa tgataatgtc ctggcattcc ttaataaaag    650
aactgacttc caaaaaaaaa aaaaaaaaaa aaaaa                    685
```

<210> SEQ ID NO 41
<211> LENGTH: 5392
<212> TYPE: DNA
<213> ORGANISM: Homo Sapien

<400> SEQUENCE: 41

```
aattcactaa tgcattctgc tctttttgag agcacagctt ctcagatgtg     50
ctccttggag ctggtgtgca gtgtcctgac tgtaagatca agtccaaacc    100
tgttttggaa ttgaggaaac ttctcttttg atctcagccc ttggtggtcc    150
aggtcttcat gctgctgtgg gtgatattac tggtcctggc tcctgtcagt    200
ggacagtttg caaggacacc caggcccatt attttcctcc agcctccatg    250
gaccacagtc ttccaaggag agagagtgac cctcacttgc aagggatttc    300
gcttctactc accacagaaa acaaaatggt accatcggta cctcgggaaa    350
gaaatactaa gagaaacccc agacaatatc cttgaggttc aggaatctgg    400
agagtacaga tgccaggccc agggctcccc tctcagtagc cctgtgcact    450
tggatttttc ttcagcttcg ctgatcctgc aagctccact ttctgtgttt    500
gaaggagact ctgtggttct gaggtgccgg gcaaaggcgg aagtaacact    550
gaataatact atttacaaga atgataatgt cctggcattc cttaataaaa    600
gaactgactt ccatattcct catgcatgtc tcaaggacaa tggtgcatat    650
cgctgtactg gatataagga aagttgttgc cctgtttctt ccaatacagt    700
caaaatccaa gtccaagagc catttacacg tccagtgctg agagccagct    750
ccttccagcc catcagcggg aacccagtga ccctgacctg tgagacccag    800
ctctctctag agaggtcaga tgtcccgctc cggttccgct tcttcagaga    850
tgaccagacc ctgggattag gctggagtct ctccccgaat ttccagatta    900
ctgccatgtg gagtaaagat tcagggttct actggtgtaa ggcagcaaca    950
atgcctcaca gcgtcatatc tgacagcccg agatcctgga tacaggtgca   1000
gatccctgca tctcatcctg tcctcactct cagccctgaa aaggctctga   1050
```

```
attttgaggg aaccaaggtg acacttcact gtgaaaccca ggaagattct    1100
ctgcgcactt tgtacaggtt ttatcatgag ggtgtccccc tgaggcacaa    1150
gtcagtccgc tgtgaaaggg gagcatccat cagcttctca ctgactacag    1200
agaattcagg gaactactac tgcacagctg acaatggcct tggcgccaag    1250
cccagtaagg ctgtgagcct ctcagtcact gttcccgtgt ctcatcctgt    1300
cctcaacctc agctctcctg aggacctgat tttgaggga gccaaggtga     1350
cacttcactg tgaagcccag agaggttcac tccccatcct gtaccagttt    1400
catcatgagg atgctgccct ggagcgtagg tcggccaact ctgcaggagg    1450
agtggccatc agcttctctc tgactgcaga gcattcaggg aactactact    1500
gcacagctga caatggcttt ggcccccagc gcagtaaggc ggtgagcctc    1550
tccatcactg tccctgtgtc tcatcctgtc ctcaccctca gctctgctga    1600
ggccctgact tttgaaggag ccactgtgac acttcactgt gaagtccaga    1650
gaggttcccc acaaatccta taccagtttt atcatgagga catgcccctg    1700
tggagcagct caacaccctc tgtgggaaga gtgtccttca gcttctctct    1750
gactgaagga cattcaggga attactactg cacagctgac aatggctttg    1800
gtccccagcg cagtgaagtg gtgagccttt ttgtcactgt tccagtgtct    1850
cgccccatcc tcaccctcag ggttcccagg gcccaggctg tggtgggga     1900
cctgctggag cttcactgtg aggccccgag aggctctccc ccaatcctgt    1950
actggtttta tcatgaggat gtcaccctgg ggagcagctc agccccctct    2000
ggaggagaag cttctttcaa cctctctctg actgcagaac attctggaaa    2050
ctactcatgt gaggccaaca atggcctagt ggcccagcac agtgacacaa    2100
tatcactcag tgttatagtt ccagtatctc gtcccatcct caccttcagg    2150
gctcccaggg cccaggctgt ggtgggggac ctgctggagc ttcactgtga    2200
ggccctgaga ggctcctccc caatcctgta ctggttttat catgaagatg    2250
tcaccctggg taagatctca gccccctctg gaggaggggc ctccttcaac    2300
ctctctctga ctacagaaca ttctggaatc tactcctgtg aggcagacaa    2350
tggtccggag gcccagcgca gtgagatggt gacactgaaa gttgcagttc    2400
cggtgtctcg cccggtcctc accctcaggg ctcccgggac ccatgctgcg    2450
gtgggggacc tgctggagct tcactgtgag gccctgagag gctctcccct    2500
gatcctgtac cggtttttc atgaggatgt caccctagga aataggtcgt     2550
cccctctgg aggagcgtcc ttaaacctct ctctgactgc agagcactct     2600
ggaaactact cctgtgaggc cgacaatggc ctcggggccc agcgcagtga    2650
gacagtgaca ctttatatca cagggctgac cgcgaacaga agtggccctt    2700
ttgccacagg agtcgccggg ggcctgctca gcatagcagg ccttgctgcg    2750
ggggcactgc tgctctactg ctggctctcg agaaaagcag ggagaaagcc    2800
tgcctctgac cccgccagga gccctccaga ctcggactcc caagagccca    2850
cctatcacaa tgtaccagcc tgggaagagc tgcaaccagt gtacactaat    2900
gcaaatccta gaggagaaaa tgtggtttac tcagaagtac ggatcatcca    2950
agagaaaaag aaacatgcag tggcctctga ccccaggcat ctcaggaaca    3000
agggttcccc tatcatctac tctgaagtta aggtggcgtc aaccccggtt    3050
```

-continued

```
tccggatccc tgttcttggc ttcctcagct cctcacagat gagtccacac    3100

gtctctccaa ctgctgtttc agcctctgca ccccaaagtt ccccttgggg    3150

gagaagcagc attgaagtgg gaagatttag gctgccccag accatatcta    3200

ctggcctttg tttcacatgt cctcattctc agtctgacca gaatgcaggg    3250

ccctgctgga ctgtcacctg tttcccagtt aaagccctga ctggcaggtt    3300

ttttaatcca gtggcaaggt gctcccactc cagggcccag cacatctcct    3350

ggattcctta gtgggcttca gctgtgattg ctgttctgag tactgctctc    3400

atcacacccc cacagagggg gtcttaccac acaaagggag agtgggcctt    3450

caggagatgc cgggctggcc taacagctca ggtgctccta aactccgaca    3500

cagagttcct gctttgggtg gatgcatttc tcaattgtca tcagcctggt    3550

ggggctactg cagtgtgctg ccaaatggga cagcacacag cctgtgcaca    3600

tgggacatgt gatgggtctc cccacggggg ctgcatttca cactcctcca    3650

cctgtctcaa actctaaggt cggcacttga caccaaggta acttctctcc    3700

tgctcatgtg tcagtgtcta cctgcccaag taagtggctt tcatacacca    3750

agtcccaagt tcttcccatc ctaacagaag taacccagca agtcaaggcc    3800

aggaggacca ggggtgcaga cagaacacat actggaacac aggaggtgct    3850

caattactat ttgactgact gactgaatga atgaatgaat gaggaagaaa    3900

actgtgggta atcaaactgg cataaaatcc agtgcactcc ctaggaaatc    3950

cgggaggtat tctggcttcc ctaagaaaca acggaagaga aggagcttgg    4000

atgaggaaac tgttcagcaa gaggaagggc ttctcacact ttcatgtgct    4050

tgtggatcac ctgaggatcc tgtgaaaata cagatactga ttcagtgggt    4100

ctgtgtagag cctgagactg ccattctaac atgttcccag gggatgctga    4150

tgctgctggc cctgggactg cactgcatgc atgtgaagcc ctataggtct    4200

cagcagaggc ccatggagag ggaatgtgtg gctctggctg cccagggccc    4250

aactcggttc acacggatcg tgctgctccc tggccagcct ttggccacag    4300

caccaccagc tgctgttgct gagagagctt cttctctgtg acatgttggc    4350

tttcatcagc caccctggga agcggaaagt agctgccact atctttgttt    4400

ccccacctca ggcctcacac tttcccatga aaagggtgaa tgtatataac    4450

ctgagccctc tccattcaga gttgttctcc catctctgag caatgggatg    4500

ttctgttccg cttttatgat atccatcaca tcttatcttg atctttgctc    4550

ccagtggatt gtacagtgat gacttttaag ccccacggcc ctgaaataaa    4600

atccttccaa gggcattgga agctctctcc acctgaacca tggcttttca    4650

tgcttccaag tgtcagggcc ttgcccagat agacagggct gactctgctg    4700

ccccaacctt tcaaggagga aaccagacac ctgagacagg agcctgtatg    4750

cagcccagtg cagccttgca gaggacaagg ctggaggcat ttgtcatcac    4800

tacagatatg caactaaaat agacgtggag caagagaaat gcattcccac    4850

cgaggccgct tttttaggcc tagttgaaag tcaagaagga cagcagcaag    4900

cataggctca ggattaaaga aaaaaatctg ctcacagttt gttctggagg    4950

tcacatcacc aacaaagctc acgccctatg cagttctgag aaggtggagg    5000

caccaggctc aaaagaggaa atttagaatt tctcattggg agagtaaggt    5050
```

-continued acccccatcc cagaatgata actgcacagt ggcagaacaa actccaccct 5100
aatgtgggtg gaccccatcc agtctgttga aggcctgagt gtaacaaaag 5150
ggcttattct tcctcaagta agggggaact cctgctttgg gctgggacat 5200
aagtttttct gctttcagac gcaaactgaa aaatggctct tcttgggtct 5250
tgagcttgct ggcatatgga ctgaaagaaa ctatgctatt ggatctcctg 5300
gatctccagc ttgctgactg cagatcttga gatatgtcag cctctacagt 5350
cacaagagct aattcattct aataaaccaa tctttctgta aa 5392

<210> SEQ ID NO 42
<211> LENGTH: 626
<212> TYPE: DNA
<213> ORGANISM: Homo Sapien

<400> SEQUENCE: 42
ggacctggga aggagcatag gacagggcaa ggcgggataa ggaggggcac 50
cacagccctt aaggcacgag ggaacctcac tgcgcatgct cctttggtgc 100
ccacctcagt gcgcatgttc actgggcgtc ttcccatcgg ccccttcgcc 150
agtgtgggga acgcggcgga gctgtgagcc ggcgactcgg gtccctgagg 200
tctggattct ttctccgcta ctgagacacg gcggacacac acaaacacag 250
aaccacacag ccagtcccag gagcccagta atggagagcc ccaaaaagaa 300
gaaccagcag ctgaaagtcg ggatcctaca cctgggcagc agacagaaga 350
agatcaggat acagctgaga tcccagtgcg cgacatggaa ggtgatctgc 400
aagagctgca tcagtcaaac accggggata aatctggatt tgggttccgg 450
cgtcaaggtg aagataatac ctaaagagga acactgtaaa atgccagaag 500
caggtgaaga gcaaccacaa gtttaaatga agacaagctg aaacaacgca 550
agctggtttt atattagata tttgacttaa actatctcaa taaagttttg 600
cagctttcac caaaaaaaaa aaaaaa 626

<210> SEQ ID NO 43
<211> LENGTH: 1505
<212> TYPE: DNA
<213> ORGANISM: Homo Sapien

<400> SEQUENCE: 43
agcggctggc gagccggcgc cggccgagct gcgggagccg cggagagcac 50
cagctgtcgc cgcgggagct gctccggccg caccatgcgg gagctggcca 100
ttgagatcgg ggtgcgagcc ctgctcttcg gagtcttcgt ttttacagag 150
tttttggatc cgttccagag agtcatccag ccagaagaga tctggctcta 200
taaaaatcct ttggtgcaat cagataacat acctacccgc ctcatgtttg 250
caatttcttt cctcacaccc ctggctgtta tttgtgtggt gaaaattatc 300
cggcgaacag acaagactga aattaaggaa gccttcttag cggtgtcctt 350
ggctcttgct ttgaatggag tctgcacaaa cactattaaa ttaatagtgg 400
gaagacctcg cgccgatttc ttttaccgct gctttccaga tggagtgatg 450
aactcggaaa tgcattgcac aggtgacccc gatctggtgt ccgagggccg 500
caaaagcttc cccagcatcc attcctcctt tgccttttcg ggccttggct 550
tcacgacgtt ctacttggcg ggcaagctgc actgcttcac cgagagtggg 600

```
cggggaaaga gctggcggct ctgtgctgcc atcctgccct tgtactgcgc        650

catgatgatt gccctgtccc gcatgtgcga ctacaagcat cactggcaag        700

attcctttgt gggtggagtc atcgcgctca tttttgcata catttgctac        750

agacagcact atcctcctct gggccaacac agcttgccat aaaccctacg        800

ttagtctgcg agtttgccat aaaccctacg ttagtctgcg agtcccagcc        850

tcactgaaga aagaggagag gcccacagct gacagcgcac ccagcttgcc        900

tctggagggg atcaccgaag gcccggtatg accagtgtcc tgggaggatg        950

gacactaagc cctgggcaca tctgccaccc tgacatcata acacaataga       1000

aatggttttc tgtagtgtat ttttcatcag ttgtttctca aagtcatcgt       1050

acttctgctt ctgtttcact gatggtgttc ctgctacttt aaatgtctac       1100

ttccaacatc cttgaatttg caagtgaagg acaacaatct ctgagagacg       1150

tgtggaagag gctgcgaagg tggggtttgg ggagcttcgc cgattcgtct       1200

atctgaaatg tttgctgtaa cagccacctt cctatgtttt catggttagt       1250

aaacataata aaacctccca tcgggaaaaa atacaaaatt cattgattta       1300

ggaatatata tataatattc acatgtgtaa ttccccccct ccctttagtg       1350

agggtaattc aagatccttc tcaactgctt tgtgcgactt agactttatg       1400

ttgcagcaga ctttttttatt ttacttatag cgcggaatcc gtgtttcctc      1450

agaatcaggg aatccgcccg aaaatctgtt acaaaggccg ccaagtgaca       1500

taact                                                        1505


<210> SEQ ID NO 44
<211> LENGTH: 1850
<212> TYPE: DNA
<213> ORGANISM: Homo Sapien

<400> SEQUENCE: 44

tccttgggtt cgggtgaaag cgcctggggg ttcgtggcca tgatccccga         50

gctgctggag aactgaaggc ggacagtctc ctgcgaaacc aggcaatggc        100

ggagctggag tttgttcaga tcatcatcat cgtggtggtg atgatggtga        150

tggtggtggt gatcacgtgc ctgctgagcc actacaagct gtctgcacgg        200

tccttcatca gccggcacag ccaggggcgg aggagagaag atgccctgtc        250

ctcagaagga tgcctgtggc cctcggagag cacagtgtca ggcaacggaa        300

tcccagagcc gcaggtctac gccccgcctc ggcccaccga ccgcctggcc        350

gtgccgccct tcgcccagcg ggagcgcttc caccgcttcc agcccaccta        400

tccgtacctg cagcacgaga tcgacctgcc acccaccatc tcgctgtcag        450

acggggagga gcccccaccc taccagggcc cctgcaccct ccagcttcgg        500

gaccccgagc agcagctgga actgaaccgg gagtcggtgc gcgcaccccc        550

aaacagaacc atcttcgaca gtgacctgat ggatagtgcc aggctgggcg        600

gcccctgccc ccccagcagt aactcgggca tcagcgccac gtgctacggc        650

agcggcgggc gcatggaggg gccgccgccc acctacagcg aggtcatcgg        700

ccactacccg gggtcctcct tccagcacca gcagagcagt gggccgccct        750

ccttgctgga ggggacccgg ctccaccaca cacacatcgc gcccctagag        800

agcgcagcca tctggagcaa agagaaggat aaacagaaag gacaccctct        850
```

-continued

```
ctagggtccc caggggggcc gggctggggc tgcgtaggtg aaaaggcaga        900

acactccgcg cttcttagaa gaggagtgag aggaaggcgg ggggcgcagc        950

aacgcatcgt gtggccctcc cctcccacct ccctgtgtat aaatatttac       1000

atgtgatgtc tggtctgaat gcacaagcta agagagcttg caaaaaaaaa       1050

aagaaaaaag aaaaaaaaaa accacgtttc tttgttgagc tgtgtcttga       1100

aggcaaaaga aaaaaaattt ctacagtagt ctttcttgtt tctagttgag       1150

ctgcgtgcgt gaatgcttat tttcttttgt ttatgataat ttcacttaac       1200

tttaaagaca tatttgcaca aaacctttgt ttaaagatct gcaatattat       1250

atatataaat atatataaga taagagaaac tgtatgtgcg agggcaggag       1300

tatttttgta ttagaagagg cctattaaaa aaaaaagttg ttttctgaac       1350

tagaagagga aaaaaatggc aatttttgag tgccaagtca gaaagtgtgt       1400

attaccttgt aaagaaaaaa attacaaagc aggggtttag agttatttat       1450

ataaatgttg agattttgca ctattttta atataaatat gtcagtgctt        1500

gcttgatgga aacttctctt gtgtctgttg agactttaag ggagaaatgt       1550

cggaatttca gagtcgcctg acggcagagg gtgagccccc gtggagtctg       1600

cagagaggcc ttggccagga gcggcgggct ttcccgaggg gccactgtcc       1650

ctgcagagtg gatgcttctg cctagtgaca ggttatcacc acgttatata       1700

ttccctaccg aaggagacac cttttccccc ctgacccaga acagccttta       1750

aatcacaagc aaaataggaa agttaaccac ggaggcaccg agttccaggt       1800

agtggttttg cctttcccaa aaatgaaaat aaactgttac cgaaggaatt       1850
```

```
<210> SEQ ID NO 45
<211> LENGTH: 806
<212> TYPE: DNA
<213> ORGANISM: Homo Sapien

<400> SEQUENCE: 45

gcccttcgga cagtctcctg cgaaaccagg caatggcgga gctggagttt         50

gttcagatca tcatcatcgt ggtggtgatg atggtgatgg tggtggtgat        100

cacgtgcctg ctgagccact acaagctgtc tgcacggtcc ttcatcagcc        150

ggcacagcca ggggcggagg agagaagatg ccctgtcctc agaaggatgc        200

ctgtggccct cggagagcac agtgtcaggc aacggaatcc cagagccgca        250

ggtctacgcc ccgcctcggc ccaccgaccg cctggccgtg ccgcccttcg        300

cccagcggga gcgcttccac cgcttccagc ccacctatcc gtacctgcag        350

cacgagatcg acctgccgcc caccatctcg ctgtcagacg gggaggagcc        400

cccaccctac cagggcccct gcaccctcca gcttcgggac cccgagcagc        450

agctggaact gaaccgggag tcggtgcgcg cacccccaaa cagaaccatc        500

ttcgacagtg acctgatgga tagtgccagg ctgggcggcc cctgcccccc        550

cagcagtaac tcgggcatca gcgccacgtg ctacggcagc ggcgggcgca        600

tggaggggcc gccgcccacc tacagcgagg tcatcggcca ctacccgggg        650

tcctccttcc agcaccagca gagcagtggg ccgccctcct tgctggaggg        700

gacccggctc caccacacac acatcgcgcc cctagagagc gcagccatct        750

ggagcaaaga gaaggataaa cagaaaggac accctctcta gggtccccag        800
```

aagggc 806

<210> SEQ ID NO 46
<211> LENGTH: 1982
<212> TYPE: DNA
<213> ORGANISM: Homo Sapien

<400> SEQUENCE: 46
ggcgagaggc gggctgaggc ggcccagcgg cggcaggtga ggcggaacca 50
accctcctgg ccatgggagg ggccgtggtg gacgagggcc ccacaggcgt 100
caaggcccct gacggcggct ggggctgggc cgtgctcttc ggctgtttcg 150
tcatcactgg cttctcctac gccttcccca aggccgtcag tgtcttcttc 200
aaggagctca tacaggagtt tgggatcggc tacagcgaca cagcctggat 250
ctcctccatc ctgctggcca tgctctacgg gacaggtccg ctctgcagtg 300
tgtgcgtgaa ccgctttggc tgccggcccg tcatgcttgt ggggggtctc 350
tttgcgtcgc tgggcatggt ggctgcgtcc ttttgccgga gcatcatcca 400
ggtctacctc accactgggg tcatcacggg gttgggtttg gcactcaact 450
tccagccctc gctcatcatg ctgaaccgct acttcagcaa gcggcgcccc 500
atggccaacg ggctggcggc agcaggtagc cctgtcttcc tgtgtgccct 550
gagcccgctg gggcagctgc tgcaggaccg ctacggctgg cggggcggct 600
tcctcatcct gggcggcctg ctgctcaact gctgcgtgtg tgccgcactc 650
atgaggcccc tggtggtcac ggcccagccg ggctcggggc cgccgcgacc 700
ctcccggcgc ctgctagacc tgagcgtctt ccgggaccgc ggctttgtgc 750
tttacgccgt ggccgcctcg gtcatggtgc tggggctctt cgtcccgccc 800
gtgttcgtgg tgagctacgc caaggacctg ggcgtgcccg acaccaaggc 850
cgccttcctg ctcaccatcc tgggcttcat tgacatcttc gcgcggccgg 900
ccgcgggctt cgtggcgggg cttgggaagg tgcggcccta ctccgtctac 950
ctcttcagct tctccatgtt cttcaacggc ctcgcggacc tggcgggctc 1000
tacggcgggc gactacggcg gcctcgtggt cttctgcatc ttctttggca 1050
tctcctacgg catggtgggg gccctgcagt tcgaggtgct catggccatc 1100
gtgggcaccc acaagttctc cagtgccatt ggcctggtgc tgctgatgga 1150
ggcggtggcc gtgctcgtcg ggccccccttc gggaggcaaa ctcctggatg 1200
cgacccacgt ctacatgtac gtgttcatcc tggcgggggc cgaggtgctc 1250
acctcctccc tgattttgct gctgggcaac ttcttctgca ttaggaagaa 1300
gcccaaagag ccacagcctg aggtggcggc cgcggaggag gagaagctcc 1350
acaagcctcc tgcagactcg gggtggactt tgcgggaggt ggagcatttc 1400
ctgaaggctg agcctgagaa aaacggggag gtggttcaca ccccggaaac 1450
aagtgtctga gtggctgggc ggggccggca ggcacaggga ggaggtacag 1500
aagccggcaa cgcttgctat ttattttaca aactggactg gctcaggcag 1550
ggccacggct gggctccagc tgccggccca gcggatcgtc gcccgatcag 1600
tgttttgagg gggaaggtgg cggggtggga accgtgtcat tccagagtgg 1650
atctgcggtg aagccaagcc gcaaggttac aaggcatcct caccaggggc 1700
cccgcctgct gctcccaggt ggcctgcggc cactgctatg ctcaaggacc 1750
tggaaaccca tgcttcgaga caacgtgact ttaatgggag ggtgggtggg 1800
ccgcagacag gctggcaggg caggtgctgc gtggggccct ctccagcccg 1850
tcctaccctg ggctcacatg gggcctgtgc ccacccctct tgagtgtctt 1900
ggggacagct ctttccaccc ctggaagatg gaaataaacc tgcgtgtggg 1950
tggagtgttc tcgtgccgaa ttcaaaaagc tt 1982

<210> SEQ ID NO 47
<211> LENGTH: 2171
<212> TYPE: DNA
<213> ORGANISM: Homo Sapien

<400> SEQUENCE: 47
cccacgcgtc cgcccacgcg tccgccgggt cctgcgcgct ccggactgag 50
gtggcgtccc tgggccggac ggcggtgtcc cggcgtggcg ggaagccggc 100
actggagcgg gagcgcactg ggcgcgggac cgggaggcgc agggaccgga 150
cggctcccga gtcgcccacc tgacggtacc gagagggcgg cgcccctccg 200
agcagagccg tcccggccac tcccctggga tctgacttgg ctcttgcggt 250
cgcgggcacc gtgaagccct ggggtgtgcg tggctcctcc tggtaggcgc 300
cctttcccgg cgtccggctt ggggtggtgg tggcgttgac tccagccccg 350
cctctccctg gagaggaggg ctccactcgc tccttcggcc tcctcccctg 400
gggccgcagc gactcgggcc ggcttcctgc ttccctgcct gccggcggtc 450
ccgctggcta gaagaagtct tcacttccca ggagagccaa agcgtgtctg 500
gccctaggtg ggaaaagaac tggctgtgac ctttgccctg acctggaagg 550
gcccagcctt gggctgaatg gcagcaccca cgcccgcccg tccggtgctg 600
acccacctgc tggtggctct cttcggcatg ggctcctggg ctgcggtcaa 650
tgggatctgg gtggagctac ctgtggtggt caaagagctt ccagagggtt 700
ggagcctccc ctcttacgtc tctgtgcttg tggctctggg gaacctgggt 750
ctgctggtgg tgaccctctg gaggaggctg gccccaggaa aggacgagca 800
ggtccccatc cgggtggtgc aggtgctggg catggtgggc acagccctgc 850
tggcctctct gtggcaccat gtggccccag tggcaggaca gttgcattct 900
gtggccttct tagcactggc ctttgtgctg gcactggcat gctgtgcctc 950
gaatgtcact ttcctgccct tcttgagcca cctgccacct cgcttcttac 1000
ggtcattctt cctgggtcaa ggcctgagtg ccctgctgcc ctgcgtgctg 1050
gccctagtgc agggtgtggg ccgcctcgag tgcccgccag cccccatcaa 1100
cggcacccct ggccccccgc tcgacttcct tgagcgtttt cccgccagca 1150
ccttcttctg ggcactgact gcccttctgg tcgcttcagc tgctgccttc 1200
cagggtcttc tgctgctgtt gccgccacca ccatctgtac ccacagggga 1250
gttaggatca ggcctccagg tgggagcccc aggagcagag gaagaggtgg 1300
aagagtcctc accactgcaa gagccaccaa gccaggcagc aggcaccacc 1350
cctggtccag accctaaggc ctatcagctt ctatcagccc gcagtgcctg 1400
cctgctgggc ctgttggccg ccaccaacgc gctgaccaat ggcgtgctgc 1450
ctgccgtgca gagcttttcc tgcttaccct acgggcgtct ggcctaccac 1500
ctggctgtgg tgctgggcag tgctgccaat cccctggcct gcttcctggc 1550

-continued catgggtgtg ctgtgcaggt ccttggcagg gctgggcggc ctctctctgc 1600
tgggcgtgtt ctgtgggggc tacctgatgg cgctggcagt cctgagcccc 1650
tgcccgcccc tggtgggcac ctcggcgggg gtggtcctcg tggtgctgtc 1700
gtgggtgctg tgtcttggcg tgttctccta cgtgaaggtg gcagccagct 1750
ccctgctgca tggcgggggc cggccggcat tgctggcagc cggcgtggcc 1800
atccaggtgg gctctctgct cggcgctgtt gctatgttcc ccccgaccag 1850
catctatcac gtgttccaca gcagaaagga ctgtgcagac ccctgtgact 1900
cctgagcctg ggcaggtggg gaccccgctc cccaacacct gtctttccct 1950
caatgctgcc accatgcctg agtgcctgca gcccaggagg cccgcacacc 2000
ggtacactcg tggacaccta cacactccat aggagatcct ggctttccag 2050
ggtgggcaag ggcaaggagc aggcttggag ccagggacca gtgggggctg 2100
tagggtaagc ccctgagcct gggacctaca tgtggtttgc gtaataaaac 2150
atttgtattt aaaaaaaaaa a 2171

<210> SEQ ID NO 48
<211> LENGTH: 1617
<212> TYPE: DNA
<213> ORGANISM: Homo Sapien

<400> SEQUENCE: 48
gccagcacag ctgccctctg gaccctgcgg accccagccg agccccttcc 50
tgagttccac aggcgcagcc cccgggcggt cgggcggagg ggtccccggg 100
gcggtgccag gcgcaatcct ggagggcggc cgggaggagg aggtgcgcgc 150
ggccatgcac accgtggcta cgtccggacc caacgcgtcc tggggggcac 200
cggccaacgc ctccggctgc ccgggctgtg gcgccaacgc ctcggacggc 250
ccagtccctt cgccgcgggc cgtggacgcc tggctcgtgc cgctcttctt 300
cgcggcgctg atgctgctgg gcctggtggg gaactcgctg gtcatctacg 350
tcatctgccg ccacaagccg atgcggaccg tgaccaactt ctacatcgcc 400
aacctggcgg ccacggacgt gaccttcctc ctgtgctgcg tccccttcac 450
ggccctgctg tacccgctgc ccggctgggt gctgggcgac ttcatgtgca 500
agttcgtcaa ctacatccag caggtctcgg tgcaggccac gtgtgccact 550
ctgaccgcca tgagtgtgga ccgctggtac gtgacggtgt tcccgttgcg 600
cgccctgcac cgccgcacgc cccgcctggc gctggctgtc agcctcagca 650
tctgggtagg ctctgcggcg gtgtctgcgc cggtgctcgc cctgcaccgc 700
ctgtcacccg ggccgcgcgc ctactgcagt gaggccttcc ccagccgcgc 750
cctggagcgc gccttcgcac tgtacaacct gctggcgctg tacctgctgc 800
cgctgctcgc cacctgcgcc tgctatgcgg ccatgctgcg ccacctgggc 850
cgggtcgccg tgcgccccgc gcccgccgat agcgccctgc aggggcaggt 900
gctggcagag cgcgcaggcg ccgtgcgggc caaggtctcg cggctggtgg 950
cggccgtggt cctgctcttc gccgcctgct ggggccccat ccagctgttc 1000
ctggtgctgc aggcgctggg ccccgcgggc tcctggcacc cacgcagcta 1050
cgccgcctac gcgcttaaga cctgggctca ctgcatgtcc tacagcaact 1100
ccgcgctgaa cccgctgctc tacgccttcc tgggctcgca cttccgacag 1150

```
gccttccgcc gcgtctgccc ctgcgcgccg cgccgccccc gccgccccg        1200

ccggcccgga ccctcggacc ccgcagcccc acacgcggag ctgcaccgcc       1250

tggggtccca cccggccccc gccagggcgc agaagccagg gagcagtggg       1300

ctggccgcgc gcgggctgtg cgtcctgggg gaggacaacg cccctcttg        1350

agcggacccg gtgggaatcc gagcggctcc ctcgggagcg gggactgctg       1400

gaacagcggc tattcttctg ttattagtat tttttttact gtccaagatc       1450

aactgtggaa atattttggt ctcttgtgac gttcggtgca gtttcgttgt       1500

gaagtttgct attgatattg aaattatgac ttctgtgttt cctgaaatta       1550

aacatgtgtc aacacaggac tttttggatc attccagaaa gtgtcagacg       1600

tttaaaaaaa aaaaaaa                                           1617
```

<210> SEQ ID NO 49
<211> LENGTH: 3095
<212> TYPE: DNA
<213> ORGANISM: Homo Sapien

<400> SEQUENCE: 49

```
ggcgcggggc gccatggcac accgagcggc tccgtcttct gctcctcaga         50

gagcccggct ggcggcctgg gatgacaaga tgtctggact gcaatcctgc        100

acagttttga gagggagatg acttgagtgg ttggctttta tctccacaac        150

aatgtccatg aacaattcca aacagctagt gtctcctgca gctgcgcttc        200

tttcaaacac aacctgccag acggaaaacc ggctttccgt attttttca         250

gtaatcttca tgacagtggg aatcttgtca aacagccttg ccatcgccat        300

tctcatgaag gcatatcaga gatttagaca gaagtccaag gcatcgtttc        350

tgcttttggc cagcggcctg gtaatcactg atttctttgg ccatctcatc        400

aatggagcca tagcagtatt tgtatatgct tctgataaag aatggatccg        450

ctttgaccaa tcaaatgtcc tttgcagtat ttttggtatc tgcatggtgt        500

tttctggtct gtgcccactt cttctaggca gtgtgatggc cattgagcgg        550

tgtattggag tcacaaaacc aatatttcat tctacgaaaa ttacatccaa        600

acatgtgaaa atgatgttaa gtggtgtgtg cttgtttgct gttttcatag        650

ctttgctgcc catccttgga catcgagact ataaaattca ggcgtcgagg        700

acctggtgtt tctacaacac agaagacatc aaagactggg aagatagatt        750

ttatcttcta cttttttctt ttctggggct cttagccctt ggtgtttcat        800

tgttgtgcaa tgcaatcaca ggaattacac ttttaagagt taaatttaaa        850

agtcagcagc acagacaagg cagatctcat catttggaaa tggtaatcca        900

gctcctggcg ataatgtgtg tctcctgtat ttgttggagc ccatttctgg        950

ttacaatggc caacattgga ataaatggaa atcattctct ggaaacctgt       1000

gaaacaacac tttttgctct ccgaatggca acatggaatc aaatcttaga       1050

tccttgggta tatattcttc tacgaaaggc tgtccttaag aatctctata       1100

agcttgccag tcaatgctgt ggagtgcatg tcatcagctt acatatttgg       1150

gagcttagtt ccattaaaaa ttccttaaag gttgctgcta tttctgagtc       1200

accagttgca gagaaatcag caagcaccta gcttaatagg acagtaaatc       1250

tgtgtggggc tagaacaaaa attaagacat gtttggcaat atttcagtta       1300
```

-continued gttaaatacc tgtagcctaa ctggaaaatt caggcttcat catgtagttt 1350
gaagatacta ttgtcagatt caggttttga aatttgtcaa ataaacagga 1400
taactgtaca ttttcaactt gtttttgcca atgggaggta gacacaataa 1450
aataatgcca tgggagtcac actgaaagca attttgagct tatctgtctt 1500
atttatgctt tgagtgaatc atctgttgag gtctaatgcc tctacttggc 1550
ctatttgcca gagaacatct taatgcagcc tgcatagtga aatggttatt 1600
ttgagatcac cgctctgtag ctaaccctta taaactaggc tcagtaaaat 1650
aaagcactct tattttttga tctggcctat tttgcccctc attgtgtagc 1700
ctcaattaac acatgcatgg tcatgacacc cagaattcat gatggtttgt 1750
tataacaacc tctgcatatt ccaggtctgg cagacaggtt gcctgaccct 1800
gcaatcctat ctagaatggg cccattcttg tcacatttga caaataggac 1850
tgcctacatt tattattatg aaggtcgatt gttgttggaa gtgtttttc 1900 atgtcataga ttagcaattt tcaaataatt atttttctc tgaaaatttt 1950 gtgtgtgatt gcacaataaa taatttttag agaaacaaag gctctttctc 2000
agcacattga tgggcaacta gaattacagc agtttcaaac tctaccatgg 2050
ataatgcaaa caaaccgaag ctacatgcca atgataggtg caaagaatat 2100
tggcaaaagg tgctttacct tgagccatta tttgtgtcag agaacaaaag 2150
aaacagaatc aatatataaa ttcaaagact atctgcagct agtgtgtttc 2200
ttctttacac acatatacac acagacatca gaaaattctg ttgagagcag 2250
gttcattaaa tttgtaagat ggcatattct aaagcctgtg ctaccagtac 2300
taagagggga agactggcaa tttgccaagc acttggggat tattataaca 2350
attaactagg agatcaagag ataataatct ctccccaaat tttccaataa 2400
taattgagac tttttctttg cttgtttgtg taattcaacc aaaagaattt 2450
caatacccat tcaaattgtc ctaggtctat cagaaattag ggaaggtagt 2500
cctgctttat aataggaaaa tgtatttctg tataagattt ctttgctttc 2550
attaaaaatg ggattcattt aaaaattaat ctttccctgt taggctgatt 2600
tcagattctc taggaaatct ggtgaagtaa ccagaagact ttcagatggt 2650
ttatttgctt tcagcagaga atttatttca tacagttact taagagtgtt 2700
gatgtcttgt gaacagagat ataaggaacc attctccatc cttccttatc 2750
atgctgggta caatgcttct atgaatattt ccatgtattt tgactgggga 2800
gaggcatgga gaagaaactc tcattcaggg gctccaggat ccttctcctt 2850
gaggcttcta aataaatggc agaattcttg ctgtattgcc atgatgtcac 2900
cctggccatg tgtactgact tgaggagatc ttgcaacatg gccatgtgca 2950
aggctttaag gagtgagaga gatgtgtaca tatcttagga gggttatcta 3000
tgttatctga gtatatgttt gggtaaccaa attggtctta aaaatgatgt 3050
taacccaaga agtagacatc aaaaattaaa aaaaaaaaaa aaaaa 3095

<210> SEQ ID NO 50
<211> LENGTH: 6476
<212> TYPE: DNA
<213> ORGANISM: Homo Sapien

<400> SEQUENCE: 50

-continued

```
atgtcacgca tgagccggca tccagacaag gacctggccc agggtccctt      50
caacacctgc tgtggctgca ccttaatggc tagtcctgct aatctccctc     100
cgaacactca agcagctgca gaaagggccc tttcccagag caggtggaag     150
agggtgcaag tgcccgcccc ggcatccctg tccccttttcc cactggccat    200
ggcttcagtt gccttctgga tcagcatcct gattggctgc gaggaacaga     250
ctctctgcag aggctggcgt agcccagtcg gggatggctg tgctcatgtg     300
cctccccagg agcgagcgac cgcagaggca gaccctccag ggcggtgcag     350
cacctccacg gcgtcgtcta ccatctgtgg cctgtggcat ttgtccccac     400
ggctgcagct cctcccacct ctgcattcca ggcagggaga agagtcgggc     450
aaaactgaga aggtgcttct ctggggaaga gagggcctcc atgtgtggaa     500
acccggagtc ctgcagcccg atgtccacgg cacctccaac ctggggaact     550
gctccttcct gcacggcctg gttacggctc cctcttgtcc acggcgggcg     600
ggcgccgagc tgctgaattc tttaggaagt cagtttgcca ttagcctttt     650
tgaagttcag agtggaactg agcccagcat tacaggtgtg gccacgtcag     700
ggcagtgcag ggctatgcca ctgaagcatt atctcctttt gctggtgggc     750
tgccaagcct ggggtgcagg gttggcctac catggctgcc ctagcgagtg     800
tacctgctcc agggcctccc aggtggagtg caccggggca cgcattgtgg     850
cggtgcccac ccctctgccc tggaacgcca tgagcctgca gatcctcaac     900
acgcacatca ctgaactcaa tgagtccccg ttcctcaata tttcagccct     950
catcgccctg aggattgaga agaatgagct gtcgcgcatc acgcctgggg    1000
ccttccgaaa cctgggctcg ctgcgctatc tcagcctcgc caacaacaag    1050
ctgcaggttc tgcccatcgg cctcttccag ggcctggaca gccttgagtc    1100
tctccttctg tccagtaacc agctgttgca gatccagccg gcccacttct    1150
cccagtgcag caacctcaag gagctgcagt tgcacggcaa ccacctggaa    1200
tacatccctg acggagcctt cgaccacctg gtaggactca cgaagctcaa    1250
tctgggcaag aatagcctca cccacatctc acccagggtc ttccagcacc    1300
tgggcaatct ccaggtcctc cggctgtatg agaacaggct cacggatatc    1350
cccatgggca cttttgatgg gcttgttaac ctgcaggaac tggctctaca    1400
gcagaaccag attggactgc tctcccctgg tctcttccac aacaaccaca    1450
acctccagag actctacctg tccaacaacc acatctccca gctgccaccc    1500
agcatcttca tgcagctgcc ccagctcaac cgtcttactc tctttgggaa    1550
ttccctgaag gagctctctc tggggatctt cgggcccatg cccaacctgc    1600
gggagctttg gctctatgac aaccacatct cttctctacc cgacaatgtc    1650
ttcagcaacc tccgccagtt gcaggtcctg attcttagcc gcaatcagat    1700
cagcttcatc tccccgggtg ccttcaacgg gctaacggag cttcgggagc    1750
tgtccctcca caccaacgca ctgcaggacc tggacgggaa tgtcttccgc    1800
atgttggcca acctgcagaa catctccctg cagaacaatc gcctcagaca    1850
gctcccaggg aatatcttcg ccaacgtcaa tggcctcatg gccatccagc    1900
tgcagaacaa ccagctggag aacttgcccc tcggcatctt cgatcacctg    1950
gggaaactgt gtgagctgcg gctgtatgac aatccctgga ggtgtgactc    2000
```

-continued

```
agacatcctt ccgctccgca actggctcct gctcaaccag cctaggttag        2050
ggacggacac tgtacctgtg tgtttcagcc cagccaatgt ccgaggccag        2100
tccctcatta tcatcaatgt caacgttgct gttccaagcg tccatgtacc        2150
tgaggtgcct agttacccag aaacaccatg gtacccagac acacccagtt        2200
accctgacac cacatccgtc tcttctacca ctgagctaac cagccctgtg        2250
gaagactaca ctgatctgac taccattcag gtcactgatg accgcagcgt        2300
ttggggcatg acccatgccc atagcgggct ggccattgcc gccattgtaa        2350
ttggcattgt cgccctggcc tgctccctgg ctgcctgcgt cggctgttgc        2400
tgctgcaaga agaggagcca agctgtcctg atgcagatga aggcacccaa        2450
tgagtgttaa agaggcaggc tggagcaggg ctggggaatg atgggactgg        2500
aggacctggg aatttcatct ttctgcctcc acccctgggt ccatggagct        2550
ttcccgtgat tgctctttct ggccctagat aaaggtgtgc ctacctcttc        2600
ctgacttgcc tgattctccc gtagagaagc aggtcgtgcc ggaccttcct        2650
acaatcagga agatagatcc aactggccat ggcaaaagcc ctggggattt        2700
ccgattcata cccctgggct tccttcgaga gggctcttcc tccaaatcct        2750
ccccacctgt cctccaagaa cagccttccc tgcgcccagg ccccctccgg        2800
gcctctgtag actcagttag tccacagcct gctcacttcg tgggaatagt        2850
tctccgctga gatagcccct ctcgcctaag tattatgtaa gttgatttcc        2900
cttcttttgt ttctcttgtt tgtgctatgg cttgacccag catgtcccct        2950
caaatgaaag ttctcccctt gattttctgc tcctgaaggc agggtgagtt        3000
ctctcctcaa agaagacttc aaaccattta actggtttct taagagccgt        3050
caatcagcct ggttttgggg atgctatgaa agagagaagg aaaatcatgc        3100
cgctcagttc ctggagacag aagagccgtc atcagtgtct cacttgtgat        3150
ttttatctgg aaaaggaaga aacaccccag cacagcaagc tcagcctttt        3200
agagaaggat atttccaaac tgcaaacttt gctttgaaaa gtttagccct        3250
ttaaggaatg aaatcatgta gaattttgga cttctaaaaa cattaaaatc        3300
agcttattaa tacgggatag agaaagaaat ctggtgcctg ggggtccctg        3350
tgttcacccc tagagtttgt tttaaaattt ttaattgaag catgtgaagt        3400
gtacctgcag aaaagtggga acatgatagt gtatggcttg gtggattttc        3450
acaaactgaa catacctgtg taatcagcat ctagacccag acccagagcg        3500
tcacaaatat cccccatcct gggcttttcc cagaggagat gggggcttct        3550
gaagatggac ttacctggga cctgcccccc atgagccagg acggtccccc        3600
cacagtcagc ctgtgcaaag gccccgtggc caggggtgga ggagaatatg        3650
tgggtgtgga caggatggga gactgtggcc tgaacaggag attttattat        3700
atctggagac cctgagagac cctgagacct ggggcaccct ggctggccag        3750
gtcagaagca tcctgactgc agaggtccgt gcagccacac cctcttccct        3800
gccagcaagc tgtctgcggc tcatcggagg cccctccgcc tggagccttc        3850
tatggacgtg atatgcctgt atctgttttt aattttcatt cttcacttag        3900
gggaagtgaa atcgctcaga gatgagatcc tttaattgaa aacgaagtgt        3950
aacggaatct agtgtctttc taatgtggta aaattctcca tcaacatcac        4000
```

-continued

```
agtcagctgg cagctgaact tcagaatctc acttacagca ggcgacacgg      4050
gggtacaccg atgggtcaca ctgggtctgg gggctccctg gagctcctcc      4100
tgcgtgtggt ctggttagga gttgagttgt ttgctccagg gttattctcc      4150
tcctcgagtc acagtcacac gaatacctgc cttctctggc tttcctgcta      4200
tacacatatt cacatggcgc tcaagaagtt aggctcatgg caacgtgtgt      4250
ctttctctgg acaactggcc cagtttacag tgaaatggag aatttcaggt      4300
ctccacgtct gcccaggaaa gaacttcagc tgactccacg ggatctgga       4350
aatccacgac caatcccgat cggctcttat tagctccccg ctccacaaga      4400
cacctgtgct ttggaaatcc accaccaatc ccgatcggct cttattagct      4450
ccccgctcca caagacacct gtgatctgga aatctaccac caatcccgat      4500
cggctcttat tagctccccg ctccacaaga cacctgtgac atcctccagg      4550
gccacaggag cacgtgctga ccagttttcc cttccagttc ctgcacaaaa      4600
agtgtccaga gggctgtttg caaacactag tgcactttgt agcttttcac      4650
cctctgtccc agggaatcta ggagagatga ggcccgtcag agtcaagaga      4700
tgtcatcccc ccagggtctc caaggcattt ccacactatt ggtggcacct      4750
ggaggacatg caccaaggct tgccagagcc aacaggaagt gagcccagag      4800
catggcacat gagcatcacc cgctgatggt ggcctgctgt gcctggtgcc      4850
aacaggggca tcccggccca taccccctcca gacaggaagc atgggtttgc     4900
ccacagacct gtcgggtgct cctgtgagtg gcctccagat gtctttgtgc      4950
ataggcacaa gtgggccagg gctggaggga ggtgggaaac ctcatcatcc      5000
ggtgggccct gccaatctta acccagaacc cttaggtatt cctggcagta      5050
gccatgacat tggagcacct tcctctccag ccagaggctg acctgagggc      5100
cactgtcctc agatgacacc acccaggagc accctaggtg aggggtgagg      5150
gcccccttat gtgaacctct tgcctcttcc tttctcccat cagagtggtt      5200
ggatggagcc attggcctcc ttttcttcag cgggcccttc aacctctctg      5250
caccatgttg tctggctgag gagctactag aaaagctgag tggagtctcc      5300
tttccaacag gatgatgcat ttgctcaatt ctcagggctg gaatgagccg      5350
gctggtcccc cagaaagctg gagtggggta cagagttcag ttttcctctc      5400
tgtttacagc tccttgacag tcccacgccc atctggagtg ggagctggga      5450
gtcagtgttg gagaagaaac aacaaaagcc aattagaacc actattttta      5500
aaaagtgctt actgtgcaca gatactcttc aagcactgga cgtggattct      5550
ctctctagcc ctcagcaccc ctgcggtagg agtgccgcct ctacccactt      5600
gtgatggggt acagaggcac ttgctcttct gcatggtgtt caataggctg      5650
ggagttttat ttatctcttc aaactttgta caagagctca tggcttgtct      5700
tgggctttcg tcattaaacc aaaggaaatg gaagccattc ccctgttgct      5750
ctccttagtc ttggtcatca gaacctcact tggtaccata tagatcaaaa      5800
gctttgtaac cacaggaaaa aataaactct tccatccctt aaagaataga      5850
atagtttgtc cctctcatgg gaattgggct gtatgtatat tgttcttcct      5900
ccttagaatt tagagataca agagttctac ttagaacttt tcatggacac      5950
aatttccaca acctttcaga tgctgatgta gagctattgg gaaagaactt      6000
```

ccaaactcag gaagtttgca gagagcagac agctagagat aactcgggac 6050
ccagagttgg tcgacagatg ttagatgtat cctagctttt agctataaac 6100
cactcaaaga ttcagccccc agatcccaca gtcagaactg aatctgcgtt 6150
gttgggaagc cagcagtggc cttgggaagg aagccatggc tgtggttcag 6200
agagggtggg ctggcaagcc acttccgggg aaaactcctt ccgccccagg 6250
tttcttcttc tcttaaggag agattattct caccaacccg ctgccttcat 6300
gctgccttca aagctagatc atgtttgcct tgcttagaga attactgcaa 6350
atcagcccca gtgcttggcg atgcatttac agatttctag gccctcaggg 6400
ttttgtagag tgtgagccct ggtgggcagg gttgggggt ctgtcttctg 6450 ctggatgctg cttgtaatcc atttgg 6476

<210> SEQ ID NO 51
<211> LENGTH: 11389
<212> TYPE: DNA
<213> ORGANISM: Homo sapien

<400> SEQUENCE: 51
atggcgccgc cgccgccgcc cgtgctgccc gtgctgctgc tcctggccgc 50
cgccgccgcc ctgccggcga tggggctgcg agcggccgcc tgggagccgc 100
gcgtacccgg cgggacccgc gccttcgccc tccggcccgg ctgtacctac 150
gcggtgggcg ccgcttgcac gccccgggcg ccgcgggagc tgctggacgt 200
gggccgcgat gggcggctgg caggacgtcg gcgcgtctcg ggcgcggggc 250
gcccgctgcc gctgcaagtc cgcttggtgg cccgcagtgc cccgacggcg 300
ctgagccgcc gcctgcgggc gcgcacgcac cttcccggct gcggagcccg 350
tgcccggctc tgcggaaccg gtgcccggct ctgcggggcg ctctgcttcc 400
ccgtccccgg cggctgcgcg gccgcgcagc attcggcgct cgcagctccg 450
accaccttac ccgcctgccg ctgcccgccg cgccccaggc cccgctgtcc 500
cggccgtccc atctgcctgc cgccgggcgg ctcggtccgc ctgcgtctgc 550
tgtgcgccct gcggcgcgcg gctggcgccg tccgggtggg actggcgctg 600
gaggccgcca ccgcggggac gccctccgcg tcgccatccc catcgccgcc 650
cctgccgccg aacttgcccg aagcccgggc ggggccggcg cgacgggccc 700
ggcggggcac gagcggcaga gggagcctga agtttccgat gcccaactac 750
caggtggcgt tgtttgagaa cgaaccggcg ggcaccctca tcctccagct 800
gcacgcgcac tacaccatcg agggcgagga ggagcgcgtg agctattaca 850
tggaggggct gttcgacgag cgctcccggg gctacttccg aatcgactct 900
gccacgggcg ccgtgagcac ggacagcgta ctggaccgcg agaccaagga 950
gacgcacgtc ctcagggtga aagccgtgga ctacagtacg ccgccgcgct 1000
cggccaccac ctacatcact gtcttggtca aagacaccaa cgaccacagc 1050
ccggtcttcg agcagtcgga gtaccgcgag cgcgtgcggg agaacctgga 1100
ggtgggctac gaggtgctga ccatccgcgc cagcgaccgc gactcgccca 1150
tcaacgccaa cttgcgttac cgcgtgttgg ggggcgcgtg ggacgtcttc 1200
cagctcaacg agagctctgg cgtggtgagc acacgggcgg tgctggaccg 1250
ggaggaggcg gccgagtacc agctcctggt ggaggccaac gaccaggggc 1300

```
gcaatccggg cccgctcagt gccacggcca ccgtgtacat cgaggtggag    1350
gacgagaacg acaactaccc ccagttcagc gagcagaact acgtggtcca    1400
ggtgccccgag gacgtggggc tcaacacggc tgtgctgcga gtgcaggcca    1450
cggaccggga ccagggccag aacgcggcca ttcactacag catcctcagc    1500
gggaacgtgg ccggccagtt ctacctgcac tcgctgagcg ggatcctgga    1550
tgtgatcaac cccttggatt tcgaggatgt ccagaaatac tcgctgagca    1600
ttaaggccca ggatgggggc cggcccccgc tcatcaattc ttcaggggtg    1650
gtgtctgtgc aggtgctgga tgtcaacgac aacgagccta tctttgtgag    1700
cagccccttc caggccacgg tgctggagaa tgtgcccctg ggctaccccg    1750
tggtgcacat tcaggcggtg gacgcggact ctggagagaa cgcccggctg    1800
cactatcgcc tggtggacac ggcctccacc tttctggggg gcggcagcgc    1850
tgggcctaag aatcctgccc ccacccctga cttccccttc cagatccaca    1900
acagctccgg ttggatcaca gtgtgtgccg agctggaccg cgaggaggtg    1950
gagcactaca gcttcggggt ggaggcggtg gaccacggct cgccccccat    2000
gagctcctcc accagcgtgt ccatcacggt gctggacgtg aatgacaacg    2050
acccggtgtt cacgcagccc acctacgagc ttcgtctgaa tgaggatgcg    2100
gccgtgggga gcagcgtgct gaccctgcag gcccgcgacc gtgacgccaa    2150
cagtgtgatt acctaccagc tcacaggcgg caacacccgg aaccgctttg    2200
cactcagcag ccagagaggg ggcggcctca tcaccctggc gctacctctg    2250
gactacaagc aggagcagca gtacgtgctg gcggtgacag catccgacgg    2300
cacacggtcg cacactgcgc atgtcctaat caacgtcact gatgccaaca    2350
cccacaggcc tgtctttcag agctcccatt acacagtgag tgtcagtgag    2400
gacaggcctg tgggcacctc cattgctacc ctcagtgcca acgatgagga    2450
cacaggagag aatgcccgca tcacctacgt gattcaggac cccgtgccgc    2500
agttccgcat tgaccccgac agtggcacca tgtacaccat gatggagctg    2550
gactatgaga accaggtcgc ctacacgctg accatcatgg cccaggacaa    2600
cggcatcccg cagaaatcag acaccaccac cctagagatc ctcatcctcg    2650
atgccaatga caatgcaccc cagttcctgt gggatttcta ccagggttcc    2700
atctttgagg atgctccacc ctcgaccagc atcctccagg tctctgccac    2750
ggaccgggac tcaggtccca atgggcgtct gctgtacacc ttccagggtg    2800
gggacgacgg cgatggggac ttctacatcg agcccacgtc cggtgtgatt    2850
cgcacccagc gccggctgga ccgggagaat gtggccgtgt acaacctttg    2900
ggctctggct gtggatcggg gcagtcccac tccccttagc gcctcggtag    2950
aaatccaggt gaccatcttg gacattaatg acaatgcccc catgtttgag    3000
aaggacgaac tggagctgtt tgttgaggag aacaacccag tggggtcggt    3050
ggtggcaaag attcgtgcta acgaccctga tgaaggccct aatgcccaga    3100
tcatgtatca gattgtggaa ggggacatgc ggcatttctt ccagctggac    3150
ctgctcaacg gggacctgcg tgccatggtg gagctggact ttgaggtccg    3200
gcgggagtat gtgctggtgg tgcaggccac gtcggctccg ctggtgagcc    3250
gagccacggt gcacatcctt ctcgtggacc agaatgacaa cccgcctgtg    3300
```

-continued

```
ctgcccgact tccagatcct cttcaacaac tatgtcacca acaagtccaa          3350
cagtttcccc accggcgtga tcggctgcat cccggcccat gaccccgacg          3400
tgtcagacag cctcaactac accttcgtgc agggcaacga gctgcgcctg          3450
ttgctgctgg accccgccac gggcgaactg cagctcagcc gcgacctgga          3500
caacaaccgg ccgctggagg cgctcatgga ggtgtctgtg tctgatggca          3550
tccacagcgt cacggccttc tgcaccctgc gtgtcaccat catcacggac          3600
gacatgctga ccaacagcat cactgtccgc ctggagaaca tgtcccagga          3650
gaagttcctg tccccgctgc tggccctctt cgtggagggg gtggccgccg          3700
tgctgtccac caccaaggac gacgtcttcg tcttcaacgt ccagaacgac          3750
accgacgtca gctccaacat cctgaacgtg accttctcgg cgctgctgcc          3800
tggcggcgtc cgcggccagt tcttcccgtc ggaggacctg caggagcaga          3850
tctacctgaa tcggacgctg ctgaccacca tctccacgca gcgcgtgctg          3900
cccttcgacg acaacatctg cctgcgcgag ccctgcgaga actacatgaa          3950
gtgcgtgtcc gttctgcgat tcgacagctc cgcgcccttc ctcagctcca          4000
ccaccgtgct cttccggccc atccacccca tcaacggcct gcgctgccgc          4050
tgcccgcccg gcttcaccgg cgactactgc gagacggaga tcgacctctg          4100
ctactccgac ccgtgcggcg ccaacggccg ctgccgcagc cgcgagggcg          4150
gctacacctg cgagtgcttc gaggacttca ctggagagca ctgtgaggtg          4200
gatgcccgct caggccgctg tgccaacggg gtgtgcaaga acgggggcac          4250
ctgcgtgaac ctgctcatcg gcggcttcca ctgcgtgtgt cctcctggcg          4300
agtatgagag gccctactgt gaggtgacca ccaggagctt cccgccccag          4350
tccttcgtca ccttccgggg cctgagacag cgcttccact tcaccatctc          4400
cctcacgttt gccactcagg aaaggaacgg cttgcttctc tacaacggcc          4450
gcttcaatga gaagcacgac ttcatcgccc tggagatcgt ggacgagcag          4500
gtgcagctca ccttctctgc aggcgagaca acaacgaccg tggcaccgaa          4550
ggttcccagt ggtgtgagtg acgggcggtg gcactctgtg caggtgcagt          4600
actacaacaa gcccaatatt ggccacctgg gcctgcccca tgggccgtcc          4650
ggggaaaaga tggccgtggt gacagtggat gattgtgaca caaccatggc          4700
tgtgcgcttt ggaaaggaca tcgggaacta cagctgcgct gcccagggca          4750
ctcagaccgg ctccaagaag tccctggatc tgaccggccc tctactcctg          4800
gggggtgtcc ccaacctgcc agaagacttc ccagtgcaca accggcagtt          4850
cgtgggctgc atgcggaacc tgtcagtcga cggcaaaaat gtggacatgg          4900
ccggattcat cgccaacaat ggcacccggg aaggctgcgc tgctcggagg          4950
aacttctgcg atgggaggcg gtgtcagaat ggaggcacct gtgtcaacag          5000
gtggaatatg tatctgtgtg agtgtccact ccgattcggc gggaagaact          5050
gtgagcaagc catgcctcac ccccagctct tcagcggtga gagcgtcgtg          5100
tcctggagtg acctgaacat catcatctct gtgccctggt acctggggct          5150
catgttccgg acccggaagg aggacagcgt tctgatggag gccaccagtg          5200
gtgggcccac cagctttcgc ctccagatcc tgaacaacta cctccagttt          5250
gaggtgtccc acggcccctc cgatgtggag tccgtgatgc tgtccgggtt          5300
```

gcgggtgacc gacggggagt ggcaccacct gctgatcgag ctgaagaatg 5350
ttaaggagga cagtgagatg aagcacctgg tcaccatgac cttggactat 5400
gggatggacc agaacaaggc agatatcggg ggcatgcttc ccgggctgac 5450
ggtaaggagc gtggtggtcg gaggcgcctc tgaagacaag gtctccgtgc 5500
gccgtggatt ccgaggctgc atgcagggag tgaggatggg ggggacgccc 5550
accaacgtcg ccaccctgaa catgaacaac gcactcaagg tcagggtgaa 5600
ggacggctgt gatgtggacg acccctgtac ctcgagcccc tgtcccccca 5650
atagccgctg ccacgacgcc tgggaggact acagctgcgt ctgtgacaaa 5700
gggtaccttg gaataaactg tgtggatgcc tgtcacctga acccctgcga 5750
gaacatgggg gcctgcgtgc gctcccccgg ctccccgcag ggctacgtgt 5800
gcgagtgtgg gcccagtcac tacgggccgt actgtgagaa caaactcgac 5850
cttccgtgcc ccagaggctg gtgggggaac cccgtctgtg gaccctgcca 5900
ctgtgccgtc agcaaaggct ttgatcccga ctgtaataag accaacggcc 5950
agtgccaatg caaggagaat tactacaagc tcctagccca ggacacctgt 6000
ctgccctgcg actgcttccc ccatggctcc cacagccgca cttgcgacat 6050
ggccaccggg cagtgtgcct gcaagcccgg cgtcatcggc cgccagtgca 6100
accgctgcga caacccgttt gccgaggtca ccacgctcgg ctgtgaagtg 6150
atctacaatg gctgtcccaa agcatttgag gccggcatct ggtggccaca 6200
gaccaagttc gggcagccgg ctgcggtgcc atgccctaag ggatccgttg 6250
gaaatgcggt ccgacactgc agcgggggaga agggctggct gcccccagag 6300
ctctttaact gtaccaccat ctccttcgtg gacctcaggg ccatgaatga 6350
gaagctgagc cgcaatgaga cgcaggtgga cggcgccagg gccctgcagc 6400
tggtgagggc gctgcgcagt gctacacagc acacgggcac gctctttggc 6450
aatgacgtgc gcacggccta ccagctgctg ggccacgtcc ttcagcacga 6500
gagctggcag cagggcttcg acctggcagc cacgcaggac gccgactttc 6550
acgaggacgt catccactcg ggcagcgccc tcctggcccc agccaccagg 6600
gcggcgtggg agcagatcca gcggagcgag ggcggcacgg cacagctgct 6650
ccggcgcctc gagggctact tcagcaacgt ggcacgcaac gtgcggcgga 6700
cgtacctgcg gcccttcgtc atcgtcaccg ccaacatgat tcttgctgtc 6750
gacatctttg acaagttcaa ctttacggga gccagggtcc cgcgattcga 6800
caccatccat gaagagttcc ccagggagct ggagtcctcc gtctccttcc 6850
cagccgactt cttcagacca cctgaagaaa aagaaggccc cctgctgagg 6900
ccggctggcc ggaggaccac cccgcagacc acgcgcccgg ggcctggcac 6950
cgagagggag gccccgatca gcaggcggag gcgacaccct gatgacgctg 7000
gccagttcgc cgtcgctctg gtcatcattt accgcaccct ggggcagctc 7050
ctgcccgagc gctacgaccc cgaccgtcgc agcctccggt tgcctcaccg 7100
gcccatcatt aataccccga tggtgagcac gctggtgtac agcgaggggg 7150
ctccgctccc gagacccctg gagaggcccg tcctggtgga gttcgccctg 7200
ctggaggtgg aggagcgaac caagcctgtc tgcgtgttct ggaaccactc 7250
cctggccgtt ggtgggacgg gagggtggtc tgcccggggc tgcgagctcc 7300

-continued

```
tgtccaggaa ccggacacat gtcgcctgcc agtgcagcca cacagccagc       7350
tttgcggtgc tcatggatat ctccaggcgt gagaacgggg aggtcctgcc       7400
tctgaagatt gtcacctatg ccgctgtgtc cttgtcactg gcagccctgc       7450
tggtggcctt cgtcctcctg agcctggtcc gcatgctgcg ctccaacctg       7500
cacagcattc acaagcacct cgccgtggcg ctcttcctct ctcagctggt       7550
gttcgtgatt gggatcaacc agacggaaaa cccgtttctg tgcacagtgg       7600
ttgccatcct cctccactac atctacatga gcacctttgc ctggaccctc       7650
gtggagagcc tgcatgtcta ccgcatgctg accgaggtgc gcaacatcga       7700
cacggggccc atgcggttct actacgtcgt gggctggggc atcccggcca       7750
ttgtcacagg actggcggtc ggcctggacc cccagggcta cgggaacccc       7800
gacttctgct ggctgtcgct tcaagacacc ctgatttgga gctttgcggg       7850
gcccatcgga gctgttataa tcatcaacac agtcacttct gtcctatctg       7900
caaaggtttc ctgccaaaga aagcaccatt attatgggaa aaaagggatc       7950
gtctccctgc tgaggaccgc attcctcctg ctgctgctca tcagcgccac       8000
ctggctgctg gggctgctgg ctgtgaaccg cgatgcactg agctttcact       8050
acctcttcgc catcttcagc ggcttacagg gccccttcgt cctccttttc       8100
cactgcgtgc tcaaccagga ggtccggaag cacctgaagg gcgtgctcgg       8150
cgggaggaag ctgcacctgg aggactccgc caccaccagg gccaccctgc       8200
tgacgcgctc cctcaactgc aacaccacct tcggtgacgg gcctgacatg       8250
ctgcgcacag acttgggcga gtccaccgcc tcgctggaca gcatcgtcag       8300
ggatgaaggg atccagaagc tcggcgtgtc ctctgggctg gtgaggggca       8350
gccacggaga gccagacgcg tccctcatgc ccaggagctg caaggatccc       8400
cctggccacg attccgactc agatagcgag ctgtccctgg atgagcagag       8450
cagctcttac gcctcctcac actcgtcaga cagcgaggac gatggggtgg       8500
gagctgagga aaaatgggac ccggccaggg gcgccgtcca cagcaccccc       8550
aaaggggacg ctgtggccaa ccacgttccg gccggctggc ccgaccagag       8600
cctggctgag agtgacagtg aggaccccag cggcaagccc cgcctgaagg       8650
tggagaccaa ggtcagcgtg gagctgcacc gcgaggagca gggcagtcac       8700
cgtggagagt acccccccgga ccaggagagc gggggcgcag ccaggcttgc       8750
tagcagccag cccccagagc agaggaaagg catcttgaaa aataaagtca       8800
cctacccgcc gccgctgacg ctgacggagc agacgctgaa gggccggctc       8850
cgggagaagc tggccgactg tgagcagagc cccacatcct cgcgcacgtc       8900
ttccctgggc tctggcggcc ccgactgcgc catcacagtc aagagccctg       8950
ggagggagcc ggggcgtgac cacctcaacg ggtggccat gaatgtgcgc        9000
actgggagcg cccaggccga tggctccgac tctgagaaac cgtgaggcaa       9050
gcccgtcacc ccacacaggc tgcggcatca ccctcagacc ttggagccca       9100
aggggccact gcccttgaag tggagtgggc ccagagtgtg gcggtcccca       9150
tggtggcagc cccccgactg atcatccaga cacaaaggtc ttggttctcc       9200
caggagctca gggcctgtca gacctggtga caagtgccaa aggccacagg       9250
catgagggag gcgtggacca ctgggccagc accgctgagt cctaagactg       9300
```

-continued

```
cagtcaaagc cagaactgag aggggacccc agactgggcc cagaggctgg      9350
ccagagttca ggaacgccgg gcacagacca aagaccgcgg tccagccccg      9400
cccaggcggg catctcatgg cagtgcggac ccgtggctgg cagcccgggc      9450
agtcctttgc aaaggcaccc cttgtcttaa aatcacttcg ctatgtggga      9500
aaggtggaga tacttttata tatttgtatg ggactctgag gaggtgcaac      9550
ctgtatatat attgcattcg tgctgacttt gttatcccga gagatccatg      9600
caatgatctc ttgctgtctt ctctgtcaag attgcacagt tgtacttgaa      9650
tctggcatgt gttgacgaaa ctggtgcccc agcagatcaa aggtgggaaa      9700
tacgtcagca gtggggctaa aaccaagcgg ctagaagccc tacagctgcc      9750
ttcggccagg aagtgaggat ggtgtgggcc ctccccgccg gccccctggg      9800
tccccagtgt tcgctgtgtg tgcgtttgtc ctctgctgcc atctgccccg      9850
gctgtgtgaa ttcaagacag ggcagtgcag cactaggcag gtgtgaggag      9900
ccctgctgag gtcactgtgg ggcacggttg ccacacggct gtcatttttc      9950
acctggtcat tctgtgacca ccaccccctc ccctcaccgc ctcccaggtg     10000
gcccgggagc tgcaggtggg gatggctttg tcctttgctc ctgctccccg     10050
tgggacctgg gaccttaaag cgttgcaggt tcctgatttg gacagaggtg     10100
tggggccttc caggccgtta catacctcct gccaattctc taactctctg     10150
agactgcgag gatctccagg cagggttctc ccctctggag tctgaccaat     10200
tacttcattt tgcttcaaat ggccaattgt gcagagggac aaagccacag     10250
ccacactctt caacggttac caaactgttt ttggaaattc acaccaaggt     10300
cgggcccact gcaggcagct ggcacagcgt ggcccgaggg gctgtggaac     10350
gggtcccgga actgtcagac atgtttgatt ttagcgtttc ctttgttctt     10400
caaatcaggt gcccaaataa gtgatcagca cagctgcttc caaataggag     10450
aaaccataaa ataggatgaa aatcaagtaa aatgcaaaga tgtccacact     10500
gttttaaact tgaccctgat gaaaatgtga gcactgttag cagatgccta     10550
tgggagagga aaagcgtatc tgaaaatggt ccaggacagg aggatgaaat     10600
gagatcccag agtcctcaca cctgaatgaa ttatacatgt gccttaccag     10650
gtgagtggtc tttcgaagat aaaaaactct agtcccttta aacgtttgcc     10700
cctggcgttt cctaagtacg aaaaggtttt taagtcttcg aacagtctcc     10750
tttcatgact ttaacaggat tctgccccct gaggtgtaat ttttttgttc     10800
tatttttttc cacgtactcc acagccaaca tcacgaggtg taatttttaa     10850
tttgatcaga actgttacca aaaaacaact gtcagtttta ttgagatggg     10900
aaaaatgtaa acctattttt attacttaag actttatggg agagattaga     10950
cactggaggt ttttaacaga acgtgtattt attaatgttc aaaacactgg     11000
aattacaaat gagaagagtc tacaataaat taagattttt gaatttgtac     11050
ttctgcggtg ctggtttttc tccacaaaca cccccgcccc tccccatgcc     11100
cagggtggcc gtggaaggga cggtttacgg acgtgcagct gagctgtccg     11150
tgtcccatgc tccctcagcc agtggaacgt gccggaactt tttgtccatt     11200
ccctagtagg cctgccacag cctagatggg cagtttttgt ctttcaccaa     11250
atttgaggac ttttttttt tgccattatt tcttcagttt tcttttcttg     11300
```

cactgatctt tctcctctcc ttctgtgact ccagtgactc agacgttaga 11350
cctcttgatg ttttcccact ggtccctgag gctctgttc 11389

<210> SEQ ID NO 52
<211> LENGTH: 1107
<212> TYPE: DNA
<213> ORGANISM: Homo Sapien
<220> FEATURE:
<221> NAME/KEY: unsure
<222> LOCATION: 170-208
<223> OTHER INFORMATION: unknown base

<400> SEQUENCE: 52
cggcctaagg tagcgacggg actggccggg ggcggcagga cccgaaggcg 50
ctaggcggat tcaccggatg ggagttgaat cgcgtcccgg tctttctagc 100
tgtgcccgga aatcgggcgt gcgggcagct acagcagaga atcggacaag 150
gagggaagaa agagatggtn nnnnnnnnnn nnnnnnnnnn nnnnnnnnnn 200
nnnnnnnnga agtgagtgca agaggagccg gcttagcatc taaactgatt 250
ctaccatcag aaaagaggcc aaacttctat catcatggtg gatgtgaagt 300
gtctgagtga ctgtaaattg cagaaccaac ttgagaagct tggattttca 350
cctggcccaa tactaccttc caccagaaag ttgtatgaaa aaaagttagt 400
acagttgttg gtctcacctc cctgtgcacc acctgtgatg aatggaccca 450
gagagctgga tggagcgcag gacagtgatg acagcgaaga gcttaatatc 500
attttgcaag gaaatatcat actctcaaca gaaaaaagca agaaactcaa 550
aaaatggcct gaggcttcca ccactaaacg caaagctgta gatacctatt 600
gcttggatta taagccttcc aagggaagaa ggtgggctgc aagagcacca 650
agcaccagaa tcacatatgg gactatcacc aaagagagag actactgcgc 700
ggaagaccag actatcgaga gctggagaga agaaggtttc ccagtgggct 750
tgaagcttgc tgtgcttggt attttcatca ttgtggtgtt tgtctacctg 800
actgtggaaa ataagtcgct gtttggttaa gtaatttagg agcaaagcaa 850
tgctccaagc gaggcctcct gcttcaggaa agaaccaaaa cactaccctg 900
aagggccagc ctagcctgca gccctccctt gcagggagcc ttcccttgca 950
ctgtgctgct ctcacagatc ggtgtctggg ctcagccagg tggaaggaac 1000
ctgcctaacc aggcacctgt gttaagagca tgatggttag gaaatccccc 1050
aagtcatgtc aactctcatt aaaggtgctt ccatatttga gcaggcgtca 1100
aacaagg 1107

<210> SEQ ID NO 53
<211> LENGTH: 3946
<212> TYPE: DNA
<213> ORGANISM: Homo Sapien

<400> SEQUENCE: 53
accgctccgg agcgggaggg gaggcttcgc ggaacgctct cggcgccagg 50
actcgcgtgc aaagcccagg cccgggcggc cagaccaaga gggaagaagc 100
acagaattcc tcaactccca gtgtgcccat gagtaagagc aaatgctccg 150
tgggactcat gtcttccgtg gtggccccgg ctaaggagcc caatgccgtg 200
ggcccgaagg aggtggagct catccttgtc aaggagcaga acggagtgca 250

-continued

```
gctcaccagc tccaccctca ccaacccgcg gcagagcccc gtggaggccc        300
aggatcggga gacctggggc aagaagatcg actttctcct gtccgtcatt        350
ggctttgctg tggacctggc caacgtctgg cggttcccct acctgtgcta        400
caaaaatggt ggcggtgcct tcctggtccc ctacctgctc ttcatggtca        450
ttgctgggat gccacttttc tacatggagc tggccctcgg ccagttcaac        500
agggaagggg ccgctggtgt ctggaagatc tgccccatac tgaaaggtgt        550
gggcttcacg gtcatcctca tctcactgta tgtcggcttc ttctacaacg        600
tcatcatcgc ctgggcgctg cactatctct tctcctcctt caccacggag        650
ctcccctgga tccactgcaa caactcctgg aacagcccca actgctcgga        700
tgcccatcct ggtgactcca gtggagacag ctcgggcctc aacgacactt        750
ttgggaccac acctgctgcc gagtactttg aacgtggcgt gctgcacctc        800
caccagagcc atggcatcga cgacctgggg cctccgcggt ggcagctcac        850
agcctgcctg gtgctggtca tcgtgctgct ctacttcagc ctctggaagg        900
gcgtgaagac ctcagggaag gtggtatgga tcacagccac catgccatac        950
gtggtcctca ctgccctgct cctgcgtggg gtcaccctcc ctggagccat       1000
agacggcatc agagcatacc tgagcgttga cttctaccgg ctctgcgagg       1050
cgtctgtttg gattgacgcg gccacccagg tgtgcttctc cctgggcgtg       1100
gggttcgggg tgctgatcgc cttctccagc tacaacaagt tcaccaacaa       1150
ctgctacagg gacgcgattg tcaccacctc catcaactcc ctgacgagct       1200
tctcctccgg cttcgtcgtc ttctccttcc tggggtacat ggcacagaag       1250
cacagtgtgc ccatcgggga cgtggccaag gacgggccag ggctgatctt       1300
catcatctac ccggaagcca tcgccacgct ccctctgtcc tcagcctggg       1350
ccgtggtctt cttcatcatg ctgctcaccc tgggtatcga cagcgccatg       1400
ggtggtatgg agtcagtgat caccgggctc atcgatgagt tccagctgct       1450
gcacagacac cgtgagctct tcacgctctt catcgtcctg gcgaccttcc       1500
tcctgtccct gttctgcgtc accaacggtg gcatctacgt cttcacgctc       1550
ctggaccatt ttgcagccgg cacgtccatc ctctttggag tgctcatcga       1600
agccatcgga gtggcctggt tctatggtgt tgggcagttc agcgacgaca       1650
tccagcagat gaccgggcag cggcccagcc tgtactggcg gctgtgctgg       1700
aagctggtca gcccctgctt tctcctgttc gtggtcgtgg tcagcattgt       1750
gaccttcaga cccccccact acggagccta catcttcccc gactgggcca       1800
acgcgctggg ctgggtcatc gccacatcct ccatggccat ggtgcccatc       1850
tatgcggcct acaagttctg cagcctgcct gggtcctttc gagagaaact       1900
ggcctacgcc attgcacccg agaaggaccg tgagctggtg gacagagggg       1950
aggtgcgcca gttcacgctc cgccactggc tcaaggtgta gagggagcag       2000
agacgaagac cccaggaagt catcctgcaa tgggagagac acgaacaaac       2050
caaggaaatc taagtttcga gagaaaggag ggcaacttct actcttcaac       2100
ctctactgaa aacacaaaca acaaagcaga agactcctct cttctgactg       2150
tttacacctt tccgtgccgg gagcgcacct cgccgtgtct tgtgttgctg       2200
taataacgac gtagatctgt gcagcgaggt ccaccccgtt gttgtccctg       2250
```

cagggcagaa aaacgtctaa cttcatgctg tctgtgtgag gctccctccc 2300
tccctgctcc ctgctcccgg ctctgaggct gccccagggg cactgtgttc 2350
tcaggcgggg atcacgatcc ttgtagacgc acctgctgag aatccccgtg 2400
ctcacagtag cttcctagac catttacttt gcccatatta aaaagccaag 2450
tgtcctgctt ggtttagctg tgcagaaggt gaaatggagg aaaccacaaa 2500
ttcatgcaaa gtcctttccc gatgcgtggc tcccagcaga ggccgtaaat 2550
tgagcgttca gttgacacat tgcacacaca gtctgttcag aggcattgga 2600
ggatgggggt cctggtatgt ctcaccagga aattctgttt atgttcttgc 2650
agcagagaga aataaaactc cttgaaacca gctcaggcta ctgccactca 2700
ggcagcctgt gggtccttgt ggtgtaggga acggcctgag aggagcgtgt 2750
cctatccccg gacgcatgca gggcccccac aggagcgtgt cctatccccg 2800
gacgcatgca gggcccccac aggagcatgt cctatccctg gacgcatgca 2850
gggcccccac aggagcgtgt actaccccag aacgcatgca gggcccccac 2900
aggagcgtgt actaccccag gacgcatgca gggcccccac tggagcgtgt 2950
actaccccag gacgcatgca gggcccccac aggagcgtgt cctatccccg 3000
gaccggacgc atgcagggcc cccacaggag cgtgtactac cccaggacgc 3050
atgcagggcc cccacaggag cgtgtactac cccaggatgc atgcagggcc 3100
cccacaggag cgtgtactac cccaggacgc atgcagggcc cccatgcagg 3150
cagcctgcag accaacactc tgcctggcct tgagccgtga cctccaggaa 3200
gggaccccac tggaatttta tttctctcag gtgcgtgcca catcaataac 3250
aacagttttt atgtttgcga atggcttttt aaaatcatat ttacctgtga 3300
atcaaaacaa attcaagaat gcagtatccg cgagcctgct tgctgatatt 3350
gcagtttttg tttacaagaa taattagcaa tactgagtga aggatgttgg 3400
ccaaaagctg ctttccatgg cacactgccc tctgccactg acaggaaagt 3450
ggatgccata gtttgaattc atgcctcaag tcggtgggcc tgcctacgtg 3500
ctgcccgagg gcaggggccg tgcagggcca gtcatggctg tcccctgcaa 3550
gtggacgtgg gctccaggga ctggagtgta atgctcggtg ggagccgtca 3600
gcctgtgaac tgccaggcag ctgcagttag cacagaggat ggcttcccca 3650
ttgccttctg gggagggaca cagaggacgg cttccccatc gccttctggc 3700
cgctgcagtc agcacagaga gcggcttccc cattgccttc tggggaggga 3750
cacagaggac agtttcccca tcgccttctg gttgttgaag acagcacaga 3800
gagcggcttc cccatcgcct tctggggagg ggctccgtgt agcaacccag 3850
gtgttgtccg tgtctgttga ccaatctcta ttcagcatcg tgtgggtccc 3900
taagcacaat aaaagacatc cacaatggaa aaaaaaaaag gaattc 3946

<210> SEQ ID NO 54
<211> LENGTH: 2317
<212> TYPE: DNA
<213> ORGANISM: Homo Sapien

<400> SEQUENCE: 54
cggacgcgtg ggtgagcagg gacggtgcac cggacggcgg gatcgagcaa 50
atgggtctgg ccatggagca cggagggtcc tacgctcggg cgggggcag 100

-continued

```
ctctcggggc tgctggtatt acctgcgcta cttcttcctc ttcgtctccc      150
tcatccaatt cctcatcatc ctggggctcg tgctcttcat ggtctatggc      200
aacgtgcacg tgagcacaga gtccaacctg caggccaccg agcgccgagc      250
cgagggccta tacagtcagc tcctagggct cacggcctcc cagtccaact      300
tgaccaagga gctcaacttc accacccgcg ccaaggatgc catcatgcag      350
atgtggctga atgctcgccg cgacctggac cgcatcaatg ccagcttccg      400
ccagtgccag ggtgaccggg tcatctacac gaacaatcag aggtacatgg      450
ctgccatcat cttgagtgag aagcaatgca gagatcaatt caaggacatg      500
aacaagagct gcgatgcctt gctcttcatg ctgaatcaga aggtgaagac      550
gctggaggtg gagatagcca aggagaagac catttgcact aaggataagg      600
aaagcgtgct gctgaacaaa cgcgtggcgg aggaacagct ggttgaatgc      650
gtgaaaaccc gggagctgca gcaccaagag cgccagctgg ccaaggagca      700
actgcaaaag gtgcaagccc tctgcctgcc cctggacaag gacaagtttg      750
agatggacct tcgtaacctg tggagggact ccattatccc acgcagcctg      800
gacaacctgg gttacaacct ctaccatccc ctgggctcgg aattggcctc      850
catccgcaga gcctgcgacc acatgcccag cctcatgagc tccaaggtgg      900
aggagctggc ccggagcctc cgggcggata tcgaacgcgt ggcccgcgag      950
aactcagacc tccaacgcca gaagctggaa gcccagcagg gcctgcgggc     1000
cagtcaggag gcgaaacaga aggtggagaa ggaggctcag gcccgggagg     1050
ccaagctcca agctgaatgc tcccggcaga cccagctagc gctggaggag     1100
aaggcggtgc tgcggaagga acgagacaac ctggccaagg agctggaaga     1150
gaagaagagg gaggcggagc agctcaggat ggagctggcc atcagaaact     1200
cagccctgga cacctgcatc aagaccaagt cgcagccgat gatgccagtg     1250
tcaaggccca tgggccctgt ccccaacccc cagcccatcg acccagctag     1300
cctggaggag ttcaagagga agatcctgga gtcccagagg cccccctgcag     1350
gcatccctgt agccccatcc agtggctgag gaggctccag gcctgaggac     1400
caagggatgg cccgactcgg cggtttgcgg aggatgcagg gatatgctca     1450
cagcgcccga cacaaccccc tcccgccgcc cccaaccacc cagggccacc     1500
atcagacaac tccctgcatg caaaccccta gtaccctctc acacccgcac     1550
ccgcgcctca cgatccctca cccagagcac acggccgcgg agatgacgtc     1600
acgcaagcaa cggcgctgac gtcacatatc accgtggtga tggcgtcacg     1650
tggccatgta gacgtcacga agagatatag cgatggcgtc gtgcagatgc     1700
agcacgtcgc acacagacat ggggaacttg gcatgacgtc acaccgagat     1750
gcagcaacga cgtcacgggc catgtcgacg tcacacatat taatgtcaca     1800
cagacgcggc gatggcatca cacagacggt gatgatgtca cacacagaca     1850
cagtgacaac acacaccatg acaacgacac ctatagatat ggcaccaaca     1900
tcacatgcac gcatgccctt tcacacacac tttctaccca attctcacct     1950
agtgtcacgt tcccccgacc ctggcacacg ggccaaggta cccacaggat     2000
cccatcccct cccgcacagc cctgggcccc agcacctccc ctcctccagc     2050
ttcctggcct cccagccact tcctcacccc cagtgcctgg acccggaggt     2100
```

-continued gagaacagga agccattcac ctccgctcct tgagcgtgag tgtttccagg 2150
accccctcgg ggccctgagc cgggggtgag ggtcacctgt tgtcgggagg 2200
ggagccactc cttctccccc aactcccagc cctgcctgtg gcccgttgaa 2250
atgttggtgg cacttaataa atattagtaa atccttaaaa aaaaaaaaaa 2300
aaaaaaaaaa aaaaaaa 2317

<210> SEQ ID NO 55
<211> LENGTH: 756
<212> TYPE: DNA
<213> ORGANISM: Homo Sapien

<400> SEQUENCE: 55
cggacttggc ttgttagaag gctgaaagat gatggcagga atgaaaatcc 50
agcttgtatg catgctactc ctggctttca gctcctggag tctgtgctca 100
gattcagaag aggaaatgaa agcattagaa gcagatttct tgaccaatat 150
gcatacatca aagattagta aagcacatgt tccctcttgg aagatgactc 200
tgctaaatgt ttgcagtctt gtaaataatt tgaacagccc agctgaggaa 250
acaggagaag ttcatgaaga ggagcttgtt gcaagaagga aacttcctac 300
tgctttagat ggctttagct tggaagcaat gttgacaata taccagctcc 350
acaaaatctg tcacagcagg gcttttcaac actgggagtt aatccaggaa 400
gatattcttg atactggaaa tgacaaaaat ggaaaggaag aagtcataaa 450
gagaaaaatt ccttatattc tgaaacggca gctgtatgag aataaaccca 500
gaagacccta catactcaaa agagattctt actattactg agagaataaa 550
tcatttattt acatgtgatt gtgattcatc atcccttaat taaatatcaa 600
attatatttg tgtgaaaatg tgacaaacac acttatctgt ctcttctaca 650
attgtggttt attgaatgtg tttttctgca ctaatagaaa ttagactaag 700
tgttttcaaa taaatctaaa tcttcaaaaa aaaaaaaaaa aaatggggcc 750
gcaatt 756

<210> SEQ ID NO 56
<211> LENGTH: 3722
<212> TYPE: DNA
<213> ORGANISM: Homo Sapien

<400> SEQUENCE: 56
cgcggggcgc ggagtcggcg gggcctcgcg ggacgcgggc agtgcggaga 50
ccgcggcgct gaggacgcgg gagccgggag cgcacgcgcg gggtggagtt 100
cagcctactc tttcttagat gtgaaaggaa aggaagatca tttcatgcct 150
tgttgataaa ggttcagact tctgctgatt cataaccatt tggctctgag 200
ctatgacaag agaggaaaca aaaagttaaa cttacaagcc tgccataagt 250
gagaagcaaa cttccttgat aacatgcttt tgcgaagtgc aggaaaatta 300
aatgtgggca ccaagaaaga ggatggtgag agtacagccc ccaccccccg 350
tccaaaggtc ttgcgttgta aatgccacca ccattgtcca gaagactcag 400
tcaacaatat ttgcagcaca gacggatatt gtttcacgat gatagaagag 450
gatgactctg ggttgcctgt ggtcacttct ggttgcctag gactagaagg 500
ctcagatttt cagtgtcggg acactcccat tcctcatcaa agaagatcaa 550

-continued

```
ttgaatgctg cacagaaagg aacgaatgta ataaagacct acaccctaca      600
ctgcctccat tgaaaaacag agattttgtt gatggaccta tacaccacag      650
ggctttactt atatctgtga ctgtctgtag tttgctcttg gtccttatca      700
tattattttg ttacttccgg tataaaagac aagaaaccag acctcgatac      750
agcattgggt tagaacagga tgaaacttac attcctcctg gagaatccct      800
gagagactta attgagcagt ctcagagctc aggaagtgga tcaggcctcc      850
ctctgctggt ccaaaggact atagctaagc agattcagat ggtgaaacag      900
attggaaaag gtcgctatgg ggaagtttgg atgggaaagt ggcgtggcga      950
aaaggtagct gtgaaagtgt tcttcaccac agaggaagcc agctggttca     1000
gagagacaga aatatatcag acagtgttga tgaggcatga aaacattttg     1050
ggtttcattg ctgcagatat caaagggaca gggtcctgga cccagttgta     1100
cctaatcaca gactatcatg aaaatggttc cctttatgat tatctgaagt     1150
ccaccaccct agacgctaaa tcaatgctga agttagccta ctcttctgtc     1200
agtggcttat gtcatttaca cacagaaatc tttagtactc aaggcaaacc     1250
agcaattgcc catcgagatc tgaaaagtaa aaacattctg gtgaagaaaa     1300
atggaacttg ctgtattgct gacctgggcc tggctgttaa atttattagt     1350
gatacaaatg aagttgacat accacctaac actcgagttg gcaccaaacg     1400
ctatatgcct ccagaagtgt tggacgagag cttgaacaga aatcacttcc     1450
agtcttacat catggctgac atgtatagtt ttggcctcat cctttgggag     1500
gttgctagga gatgtgtatc aggaggtata gtggaagaat accagcttcc     1550
ttatcatgac ctagtgccca gtgacccctc ttatgaggac atgagggaga     1600
ttgtgtgcat caagaagtta cgcccctcat tcccaaaccg gtggagcagt     1650
gatgagtgtc taaggcagat gggaaaactc atgacagaat gctgggctca     1700
caatcctgca tcaaggctga cagccctgcg ggttaagaaa acacttgcca     1750
aaatgtcaga gtcccaggac attaaactct gataggagag gaaaagtaag     1800
catctctgca gaaagccaac aggtactctt ctgtttgtgg gcagagcaaa     1850
agacatcaaa taagcatcca cagtacaagc cttgaacatc gtcctgcttc     1900
ccagtgggtt cagacctcac ctttcaggga gcgacctggg caaagacaga     1950
gaagctccca gaaggagaga ttgatccatg tctgtttgta ggacggagaa     2000
accgcttggg taacttgttc aagatatgat gcatgttgct ttctaagaaa     2050
gccctgtatt ttgtgattgc cttttttttt ttttaagatg ctttcatttt     2100
gccaaaataa aacagataat gtggatggtt taagggttat agtattatag     2150
tttaaataat aacaacaaaa ttcttcccag gaactctgct ggaaggtaaa     2200
ttaaaatact tgtttttcca ttggtaaaat attgttgcac tctgtgaacc     2250
aaaagacagt ctaagttgga ggacatagaa cggaactcat cttaaacata     2300
ctccccaccc cgtcttggcc tcctcagacc actttggcca tccctgcatt     2350
tggggccgct atggtaatgt gaatgcactg ggtacaaaca ccgcctgtct     2400
aggaccacat ttggaattcc tgcaggtggc cttttgcagc ttcaggcaat     2450
atggaacaaa tgaaggttta tgtgactcta atagaagtaa ttgttgatag     2500
gtgtttttca gatccacttc tgtttctgat tgagttaggc atctctttca     2550
```

```
tggtaaaacc cttttcatta aacacaaaaa aagctttttt tttttttttt      2600
tttttttttt ttttttaatg tgcagaggat tgacctgtgc atgcttttga      2650
tctctcattc aaaggatcaa tattaaataa aattgtcatg agctgtgttg      2700
aagacagggt gctttcaaat agaggtaatt tgctcttgtg ttgtaagagg      2750
aacatgtcaa caaagatagg aaatgagggt gatcgtgcag atggcttgta      2800
tcttatatat gcaaaggagc caatctcaga agcacaaaga aaaaagtgtg      2850
cataccttat tttgtacaga taaagatgat gtctttttgt tattgtctgt      2900
ctgttttgta tgtgtctgag ataagggata gagaggaaac atccgtcagg      2950
ctaatttaac tacattttat tttaaaaata gagaaacata acctctagat      3000
gggacagcag aggacagtta gtagaggcca caaactgtta tgggctgctg      3050
tgttttgttc taaaatcaat atggttggag catgtatatc ttaggtgatc      3100
atttcacatc ttaggaatgc ctactcattt tattttattc tagtgatgct      3150
caattcacta tttaatttat tatattttct cttctgtggc acttatacaa      3200
aatatctctt cacctactta gttctacagg gttttaactt tggagcaaca      3250
tgaataaaat catcgagaag gccaatattg tttagcaaca tgaatacaat      3300
acagtttaaa gttgtacaca tcctgctcaa ctttattcat atacatttcc      3350
tttctgtggt tttcttttgc ttcttagaaa ttctgttagt ggttagtaaa      3400
gaatttgaaa gtactttctc cttgctgttt tttttttttt ttaagacatt      3450
cctcccagaa tactccaggg ggcagtgttt tataacacat tttccccact      3500
gggtgattga aggatggagg atttttgaaa atttgacagc tacatgaaac      3550
atgagaaaac attttcctca cttctgaagt cggtttgcag ctggtaactt      3600
gttcatccag aaaacattct aaagcaatga gactttgtga gctgtgctta      3650
cagtttggga gaatcatgaa gattctttct atattttgca tttacttccc      3700
agtgcttcat agctgcattt tg                                    3722

<210> SEQ ID NO 57
<211> LENGTH: 837
<212> TYPE: PRT
<213> ORGANISM: Homo Sapien

<400> SEQUENCE: 57

Met Leu Arg Thr Ala Met Gly Leu Arg Ser Trp Leu Ala Ala Pro
1               5                   10                  15

Trp Gly Ala Leu Pro Pro Arg Pro Pro Leu Leu Leu Leu Leu Leu
                20                  25                  30

Leu Leu Leu Leu Leu Gln Pro Pro Pro Pro Thr Trp Ala Leu Ser
                35                  40                  45

Pro Arg Ile Ser Leu Pro Leu Gly Ser Glu Glu Arg Pro Phe Leu
                50                  55                  60

Arg Phe Glu Ala Glu His Ile Ser Asn Tyr Thr Ala Leu Leu Leu
                65                  70                  75

Ser Arg Asp Gly Arg Thr Leu Tyr Val Gly Ala Arg Glu Ala Leu
                80                  85                  90

Phe Ala Leu Ser Ser Asn Leu Ser Phe Leu Pro Gly Gly Glu Tyr
                95                  100                 105

Gln Glu Leu Leu Trp Gly Ala Asp Ala Glu Lys Lys Gln Gln Cys
                110                 115                 120
```

-continued

```
Ser Phe Lys Gly Lys Asp Pro Gln Arg Asp Cys Gln Asn Tyr Ile
                125                 130                 135

Lys Ile Leu Leu Pro Leu Ser Gly Ser His Leu Phe Thr Cys Gly
                140                 145                 150

Thr Ala Ala Phe Ser Pro Met Cys Thr Tyr Ile Asn Met Glu Asn
                155                 160                 165

Phe Thr Leu Ala Arg Asp Glu Lys Gly Asn Val Leu Leu Glu Asp
                170                 175                 180

Gly Lys Gly Arg Cys Pro Phe Asp Pro Asn Phe Lys Ser Thr Ala
                185                 190                 195

Leu Val Val Asp Gly Glu Leu Tyr Thr Gly Thr Val Ser Ser Phe
                200                 205                 210

Gln Gly Asn Asp Pro Ala Ile Ser Arg Ser Gln Ser Leu Arg Pro
                215                 220                 225

Thr Lys Thr Glu Ser Ser Leu Asn Trp Leu Gln Asp Pro Ala Phe
                230                 235                 240

Val Ala Ser Ala Tyr Ile Pro Glu Ser Leu Gly Ser Leu Gln Gly
                245                 250                 255

Asp Asp Asp Lys Ile Tyr Phe Phe Phe Ser Glu Thr Gly Gln Glu
                260                 265                 270

Phe Glu Phe Phe Glu Asn Thr Ile Val Ser Arg Ile Ala Arg Ile
                275                 280                 285

Cys Lys Gly Asp Glu Gly Gly Glu Arg Val Leu Gln Gln Arg Trp
                290                 295                 300

Thr Ser Phe Leu Lys Ala Gln Leu Leu Cys Ser Arg Pro Asp Asp
                305                 310                 315

Gly Phe Pro Phe Asn Val Leu Gln Asp Val Phe Thr Leu Ser Pro
                320                 325                 330

Ser Pro Gln Asp Trp Arg Asp Thr Leu Phe Tyr Gly Val Phe Thr
                335                 340                 345

Ser Gln Trp His Arg Gly Thr Thr Glu Gly Ser Ala Val Cys Val
                350                 355                 360

Phe Thr Met Lys Asp Val Gln Arg Val Phe Ser Gly Leu Tyr Lys
                365                 370                 375

Glu Val Asn Arg Glu Thr Gln Gln Trp Tyr Thr Val Thr His Pro
                380                 385                 390

Val Pro Thr Pro Arg Pro Gly Ala Cys Ile Thr Asn Ser Ala Arg
                395                 400                 405

Glu Arg Lys Ile Asn Ser Ser Leu Gln Leu Pro Asp Arg Val Leu
                410                 415                 420

Asn Phe Leu Lys Asp His Phe Leu Met Asp Gly Gln Val Arg Ser
                425                 430                 435

Arg Met Leu Leu Leu Gln Pro Gln Ala Arg Tyr Gln Arg Val Ala
                440                 445                 450

Val His Arg Val Pro Gly Leu His His Thr Tyr Asp Val Leu Phe
                455                 460                 465

Leu Gly Thr Gly Asp Gly Arg Leu His Lys Ala Val Ser Val Gly
                470                 475                 480

Pro Arg Val His Ile Ile Glu Glu Leu Gln Ile Phe Ser Ser Gly
                485                 490                 495

Gln Pro Val Gln Asn Leu Leu Leu Asp Thr His Arg Gly Leu Leu
                500                 505                 510

Tyr Ala Ala Ser His Ser Gly Val Val Gln Val Pro Met Ala Asn
                515                 520                 525
```

Cys Ser Leu Tyr Arg Ser Cys Gly Asp Cys Leu Leu Ala Arg Asp
530 535 540

Pro Tyr Cys Ala Trp Ser Gly Ser Ser Cys Lys His Val Ser Leu
545 550 555

Tyr Gln Pro Gln Leu Ala Thr Arg Pro Trp Ile Gln Asp Ile Glu
560 565 570

Gly Ala Ser Ala Lys Asp Leu Cys Ser Ala Ser Ser Val Val Ser
575 580 585

Pro Ser Phe Val Pro Thr Gly Glu Lys Pro Cys Glu Gln Val Gln
590 595 600

Phe Gln Pro Asn Thr Val Asn Thr Leu Ala Cys Pro Leu Leu Ser
605 610 615

Asn Leu Ala Thr Arg Leu Trp Leu Arg Asn Gly Ala Pro Val Asn
620 625 630

Ala Ser Ala Ser Cys His Val Leu Pro Thr Gly Asp Leu Leu Leu
635 640 645

Val Gly Thr Gln Gln Leu Gly Glu Phe Gln Cys Trp Ser Leu Glu
650 655 660

Glu Gly Phe Gln Gln Leu Val Ala Ser Tyr Cys Pro Glu Val Val
665 670 675

Glu Asp Gly Val Ala Asp Gln Thr Asp Glu Gly Gly Ser Val Pro
680 685 690

Val Ile Ile Ser Thr Ser Arg Val Ser Ala Pro Ala Gly Gly Lys
695 700 705

Ala Ser Trp Gly Ala Asp Arg Ser Tyr Trp Lys Glu Phe Leu Val
710 715 720

Met Cys Thr Leu Phe Val Leu Ala Val Leu Leu Pro Val Leu Phe
725 730 735

Leu Leu Tyr Arg His Arg Asn Ser Met Lys Val Phe Leu Lys Gln
740 745 750

Gly Glu Cys Ala Ser Val His Pro Lys Thr Cys Pro Val Val Leu
755 760 765

Pro Pro Glu Thr Arg Pro Leu Asn Gly Leu Gly Pro Pro Ser Thr
770 775 780

Pro Leu Asp His Arg Gly Tyr Gln Ser Leu Ser Asp Ser Pro Pro
785 790 795

Gly Ala Arg Val Phe Thr Glu Ser Glu Lys Arg Pro Leu Ser Ile
800 805 810

Gln Asp Ser Phe Val Glu Val Ser Pro Val Cys Pro Arg Pro Arg
815 820 825

Val Arg Leu Gly Ser Glu Ile Arg Asp Ser Val Val
830 835

<210> SEQ ID NO 58
<211> LENGTH: 188
<212> TYPE: PRT
<213> ORGANISM: Homo Sapien

<400> SEQUENCE: 58

Met Asp Cys Arg Lys Met Ala Arg Phe Ser Tyr Ser Val Ile Trp
1 5 10 15

Ile Met Ala Ile Ser Lys Val Phe Glu Leu Gly Leu Val Ala Gly
20 25 30

Leu Gly His Gln Glu Phe Ala Arg Pro Ser Arg Gly Tyr Leu Ala
35 40 45

```
Phe Arg Asp Asp Ser Ile Trp Pro Gln Glu Glu Pro Ala Ile Arg
                50                  55                  60

Pro Arg Ser Ser Gln Arg Val Pro Pro Met Gly Ile Gln His Ser
                65                  70                  75

Lys Glu Leu Asn Arg Thr Cys Cys Leu Asn Gly Gly Thr Cys Met
                80                  85                  90

Leu Gly Ser Phe Cys Ala Cys Pro Pro Ser Phe Tyr Gly Arg Asn
                95                 100                 105

Cys Glu His Asp Val Arg Lys Glu Asn Cys Gly Ser Val Pro His
               110                 115                 120

Asp Thr Trp Leu Pro Lys Lys Cys Ser Leu Cys Lys Cys Trp His
               125                 130                 135

Gly Gln Leu Arg Cys Phe Pro Gln Ala Phe Leu Pro Gly Cys Asp
               140                 145                 150

Gly Leu Val Met Asp Glu His Leu Val Ala Ser Arg Thr Pro Glu
               155                 160                 165

Leu Pro Pro Ser Ala Arg Thr Thr Thr Phe Met Leu Val Gly Ile
               170                 175                 180

Cys Leu Ser Ile Gln Ser Tyr Tyr
               185


<210> SEQ ID NO 59
<211> LENGTH: 80
<212> TYPE: PRT
<213> ORGANISM: Homo Sapien

<400> SEQUENCE: 59

Met Ala Ala Arg Ala Leu Cys Met Leu Gly Leu Val Leu Ala Leu
  1               5                  10                  15

Leu Ser Ser Ser Ser Ala Glu Glu Tyr Val Gly Leu Ser Ala Asn
                20                  25                  30

Gln Cys Ala Val Pro Ala Lys Asp Arg Val Asp Cys Gly Tyr Pro
                35                  40                  45

His Val Thr Pro Lys Glu Cys Asn Asn Arg Gly Cys Cys Phe Asp
                50                  55                  60

Ser Arg Ile Pro Gly Val Pro Trp Cys Phe Lys Pro Leu Gln Glu
                65                  70                  75

Ala Glu Cys Thr Phe
                80


<210> SEQ ID NO 60
<211> LENGTH: 314
<212> TYPE: PRT
<213> ORGANISM: Homo Sapien

<400> SEQUENCE: 60

Met Arg Ile Ala Val Ile Cys Phe Cys Leu Leu Gly Ile Thr Cys
  1               5                  10                  15

Ala Ile Pro Val Lys Gln Ala Asp Ser Gly Ser Ser Glu Glu Lys
                20                  25                  30

Gln Leu Tyr Asn Lys Tyr Pro Asp Ala Val Ala Thr Trp Leu Asn
                35                  40                  45

Pro Asp Pro Ser Gln Lys Gln Asn Leu Leu Ala Pro Gln Asn Ala
                50                  55                  60

Val Ser Ser Glu Glu Thr Asn Asp Phe Lys Gln Glu Thr Leu Pro
                65                  70                  75
```

-continued

```
Ser Lys Ser Asn Glu Ser His Asp His Met Asp Asp Met Asp Asp
                 80                  85                  90

Glu Asp Asp Asp Asp His Val Asp Ser Gln Asp Ser Ile Asp Ser
                 95                 100                 105

Asn Asp Ser Asp Asp Val Asp Asp Thr Asp Asp Ser His Gln Ser
                110                 115                 120

Asp Glu Ser His His Ser Asp Glu Ser Asp Glu Leu Val Thr Asp
                125                 130                 135

Phe Pro Thr Asp Leu Pro Ala Thr Glu Val Phe Thr Pro Val Val
                140                 145                 150

Pro Thr Val Asp Thr Tyr Asp Gly Arg Gly Asp Ser Val Val Tyr
                155                 160                 165

Gly Leu Arg Ser Lys Ser Lys Lys Phe Arg Arg Pro Asp Ile Gln
                170                 175                 180

Tyr Pro Asp Ala Thr Asp Glu Asp Ile Thr Ser His Met Glu Ser
                185                 190                 195

Glu Glu Leu Asn Gly Ala Tyr Lys Ala Ile Pro Val Ala Gln Asp
                200                 205                 210

Leu Asn Ala Pro Ser Asp Trp Asp Ser Arg Gly Lys Asp Ser Tyr
                215                 220                 225

Glu Thr Ser Gln Leu Asp Asp Gln Ser Ala Glu Thr His Ser His
                230                 235                 240

Lys Gln Ser Arg Leu Tyr Lys Arg Lys Ala Asn Asp Glu Ser Asn
                245                 250                 255

Glu His Ser Asp Val Ile Asp Ser Gln Glu Leu Ser Lys Val Ser
                260                 265                 270

Arg Glu Phe His Ser His Glu Phe His Ser His Glu Asp Met Leu
                275                 280                 285

Val Val Asp Pro Lys Ser Lys Glu Glu Asp Lys His Leu Lys Phe
                290                 295                 300

Arg Ile Ser His Glu Leu Asp Ser Ala Ser Ser Glu Val Asn
                305                 310


<210> SEQ ID NO 61
<211> LENGTH: 184
<212> TYPE: PRT
<213> ORGANISM: Homo Sapien

<400> SEQUENCE: 61

Met Ser Arg Thr Ala Tyr Thr Val Gly Ala Leu Leu Leu Leu Leu
  1               5                  10                  15

Gly Thr Leu Leu Pro Ala Ala Glu Gly Lys Lys Lys Gly Ser Gln
                 20                  25                  30

Gly Ala Ile Pro Pro Pro Asp Lys Ala Gln His Asn Asp Ser Glu
                 35                  40                  45

Gln Thr Gln Ser Pro Gln Gln Pro Gly Ser Arg Asn Arg Gly Arg
                 50                  55                  60

Gly Gln Gly Arg Gly Thr Ala Met Pro Gly Glu Glu Val Leu Glu
                 65                  70                  75

Ser Ser Gln Glu Ala Leu His Val Thr Glu Arg Lys Tyr Leu Lys
                 80                  85                  90

Arg Asp Trp Cys Lys Thr Gln Pro Leu Lys Gln Thr Ile His Glu
                 95                 100                 105

Glu Gly Cys Asn Ser Arg Thr Ile Ile Asn Arg Phe Cys Tyr Gly
                110                 115                 120
```

```
Gln Cys Asn Ser Phe Tyr Ile Pro Arg His Ile Arg Lys Glu Glu
                125                 130                 135

Gly Ser Phe Gln Ser Cys Ser Phe Cys Lys Pro Lys Lys Phe Thr
                140                 145                 150

Thr Met Met Val Thr Leu Asn Cys Pro Glu Leu Gln Pro Pro Thr
                155                 160                 165

Lys Lys Lys Arg Val Thr Arg Val Lys Gln Cys Arg Cys Ile Ser
                170                 175                 180

Ile Asp Leu Asp


<210> SEQ ID NO 62
<211> LENGTH: 460
<212> TYPE: PRT
<213> ORGANISM: Homo Sapien

<400> SEQUENCE: 62

Met Phe Leu Ala Thr Leu Tyr Phe Ala Leu Pro Leu Leu Asp Leu
  1               5                  10                  15

Leu Leu Ser Ala Glu Val Ser Gly Gly Asp Arg Leu Asp Cys Val
                 20                  25                  30

Lys Ala Ser Asp Gln Cys Leu Lys Glu Gln Ser Cys Ser Thr Lys
                 35                  40                  45

Tyr Arg Thr Leu Arg Gln Cys Val Ala Gly Lys Glu Thr Asn Phe
                 50                  55                  60

Ser Leu Ala Ser Gly Leu Glu Ala Lys Asp Glu Cys Arg Ser Ala
                 65                  70                  75

Met Glu Ala Leu Lys Gln Lys Ser Leu Tyr Asn Cys Arg Cys Lys
                 80                  85                  90

Arg Gly Met Lys Lys Glu Lys Asn Cys Leu Arg Ile Tyr Trp Ser
                 95                 100                 105

Met Tyr Gln Ser Leu Gln Gly Asn Asp Leu Leu Glu Asp Ser Pro
                110                 115                 120

Tyr Glu Pro Val Asn Ser Arg Leu Ser Asp Ile Phe Arg Val Val
                125                 130                 135

Pro Phe Ile Ser Val Glu His Ile Pro Lys Gly Asn Asn Cys Leu
                140                 145                 150

Asp Ala Ala Lys Ala Cys Asn Leu Asp Asp Ile Cys Lys Lys Tyr
                155                 160                 165

Arg Ser Ala Tyr Ile Thr Pro Cys Thr Thr Ser Val Ser Asn Asp
                170                 175                 180

Val Cys Asn Arg Arg Lys Cys His Lys Ala Leu Arg Gln Phe Phe
                185                 190                 195

Asp Lys Val Pro Ala Lys His Ser Tyr Gly Met Leu Phe Cys Ser
                200                 205                 210

Cys Arg Asp Ile Ala Cys Thr Glu Arg Arg Arg Gln Thr Ile Val
                215                 220                 225

Pro Val Cys Ser Tyr Glu Glu Arg Glu Lys Pro Asn Cys Leu Asn
                230                 235                 240

Leu Gln Asp Ser Cys Lys Thr Asn Tyr Ile Cys Arg Ser Arg Leu
                245                 250                 255

Ala Asp Phe Phe Thr Asn Cys Gln Pro Glu Ser Arg Ser Val Ser
                260                 265                 270

Ser Cys Leu Lys Glu Asn Tyr Ala Asp Cys Leu Leu Ala Tyr Ser
                275                 280                 285

Gly Leu Ile Gly Thr Val Met Thr Pro Asn Tyr Ile Asp Ser Ser
```

```
                290                 295                 300

Ser Leu Ser Val Ala Pro Trp Cys Asp Cys Ser Asn Ser Gly Asn
                305                 310                 315

Asp Leu Glu Glu Cys Leu Lys Phe Leu Asn Phe Phe Lys Asp Asn
                320                 325                 330

Thr Cys Leu Lys Asn Ala Ile Gln Ala Phe Gly Asn Gly Ser Asp
                335                 340                 345

Val Thr Val Trp Gln Pro Ala Phe Pro Val Gln Thr Thr Thr Ala
                350                 355                 360

Thr Thr Thr Thr Ala Leu Arg Val Lys Asn Lys Pro Leu Gly Pro
                365                 370                 375

Ala Gly Ser Glu Asn Glu Ile Pro Thr His Val Leu Pro Pro Cys
                380                 385                 390

Ala Asn Leu Gln Ala Gln Lys Leu Lys Ser Asn Val Ser Gly Asn
                395                 400                 405

Thr His Leu Cys Ile Ser Asn Gly Asn Tyr Glu Lys Glu Gly Leu
                410                 415                 420

Gly Ala Ser Ser His Ile Thr Thr Lys Ser Met Ala Ala Pro Pro
                425                 430                 435

Ser Cys Gly Leu Ser Pro Leu Leu Val Leu Val Val Thr Ala Leu
                440                 445                 450

Ser Thr Leu Leu Ser Leu Thr Glu Thr Ser
                455                 460


<210> SEQ ID NO 63
<211> LENGTH: 143
<212> TYPE: PRT
<213> ORGANISM: Homo Sapien

<400> SEQUENCE: 63

Met Gln His Arg Gly Phe Leu Leu Leu Thr Leu Leu Ala Leu Leu
  1               5                  10                  15

Ala Leu Thr Ser Ala Val Ala Lys Lys Lys Asp Lys Val Lys Lys
                 20                  25                  30

Gly Gly Pro Gly Ser Glu Cys Ala Glu Trp Ala Trp Gly Pro Cys
                 35                  40                  45

Thr Pro Ser Ser Lys Asp Cys Gly Val Gly Phe Arg Glu Gly Thr
                 50                  55                  60

Cys Gly Ala Gln Thr Gln Arg Ile Arg Cys Arg Val Pro Cys Asn
                 65                  70                  75

Trp Lys Lys Glu Phe Gly Ala Asp Cys Lys Tyr Lys Phe Glu Asn
                 80                  85                  90

Trp Gly Ala Cys Asp Gly Gly Thr Gly Thr Lys Val Arg Gln Gly
                 95                 100                 105

Thr Leu Lys Lys Ala Arg Tyr Asn Ala Gln Cys Gln Glu Thr Ile
                110                 115                 120

Arg Val Thr Lys Pro Cys Thr Pro Lys Thr Lys Ala Lys Ala Lys
                125                 130                 135

Ala Lys Lys Gly Lys Gly Lys Asp
                140


<210> SEQ ID NO 64
<211> LENGTH: 141
<212> TYPE: PRT
<213> ORGANISM: Homo sapien

<400> SEQUENCE: 64
```

```
Met Trp Val Leu Gly Ile Ala Ala Thr Phe Cys Gly Leu Phe Leu
  1               5                  10                  15

Leu Pro Gly Phe Ala Leu Gln Ile Gln Cys Tyr Gln Cys Glu Glu
                 20                  25                  30

Phe Gln Leu Asn Asn Asp Cys Ser Ser Pro Glu Phe Ile Val Asn
                 35                  40                  45

Cys Thr Val Asn Val Gln Asp Met Cys Gln Lys Glu Val Met Glu
                 50                  55                  60

Gln Ser Ala Gly Ile Met Tyr Arg Lys Ser Cys Ala Ser Ser Ala
                 65                  70                  75

Ala Cys Leu Ile Ala Ser Ala Gly Tyr Gln Ser Phe Cys Ser Pro
                 80                  85                  90

Gly Lys Leu Asn Ser Val Cys Ile Ser Cys Cys Asn Thr Pro Leu
                 95                 100                 105

Cys Asn Gly Pro Arg Pro Lys Lys Arg Gly Ser Ser Ala Ser Ala
                110                 115                 120

Leu Arg Pro Gly Leu Arg Thr Thr Ile Leu Phe Leu Lys Leu Ala
                125                 130                 135

Leu Phe Ser Ala His Cys
                140


<210> SEQ ID NO 65
<211> LENGTH: 242
<212> TYPE: PRT
<213> ORGANISM: Homo Sapien

<400> SEQUENCE: 65

Met Lys Asn Ile Gly Leu Val Met Glu Trp Glu Ile Pro Glu Ile
  1               5                  10                  15

Ile Cys Thr Cys Ala Lys Leu Arg Leu Pro Pro Gln Ala Thr Phe
                 20                  25                  30

Gln Val Leu Arg Gly Asn Gly Ala Ser Val Gly Thr Val Leu Met
                 35                  40                  45

Phe Arg Cys Pro Ser Asn His Gln Met Val Gly Ser Gly Leu Leu
                 50                  55                  60

Thr Cys Thr Trp Lys Gly Ser Ile Ala Glu Trp Ser Ser Gly Ser
                 65                  70                  75

Pro Val Cys Lys Leu Val Pro Pro His Glu Thr Phe Gly Phe Lys
                 80                  85                  90

Val Ala Val Ile Ala Ser Ile Val Ser Cys Ala Ile Ile Leu Leu
                 95                 100                 105

Met Ser Met Ala Phe Leu Thr Cys Cys Leu Leu Lys Cys Val Lys
                110                 115                 120

Lys Ser Lys Arg Arg Arg Ser Asn Arg Ser Ala Gln Leu Trp Ser
                125                 130                 135

Gln Leu Lys Asp Glu Asp Leu Glu Thr Val Gln Ala Ala Tyr Leu
                140                 145                 150

Gly Leu Lys His Phe Asn Lys Pro Val Ser Gly Pro Ser Gln Ala
                155                 160                 165

His Asp Asn His Ser Phe Thr Thr Asp His Gly Glu Ser Thr Ser
                170                 175                 180

Lys Leu Ala Ser Val Thr Arg Ser Val Asp Lys Asp Pro Gly Ile
                185                 190                 195

Pro Arg Ala Leu Ser Leu Ser Gly Ser Ser Ser Ser Pro Gln Ala
                200                 205                 210
```

Gln Val Met Val His Met Ala Asn Pro Arg Gln Pro Leu Pro Ala
215 220 225

Ser Gly Leu Ala Thr Gly Met Pro Gln Gln Pro Ala Ala Tyr Ala
230 235 240

Leu Gly

<210> SEQ ID NO 66
<211> LENGTH: 672
<212> TYPE: PRT
<213> ORGANISM: Homo sapien

<400> SEQUENCE: 66

Asp Cys Thr Gly Asp Gly Pro Trp Gln Ser Asn Leu Ala Pro Ser
1 5 10 15

Gln Leu Glu Tyr Tyr Ala Ser Ser Pro Asp Glu Lys Ala Leu Val
20 25 30

Glu Ala Ala Ala Arg Ile Gly Ile Val Phe Ile Gly Asn Ser Glu
35 40 45

Glu Thr Met Glu Val Lys Thr Leu Gly Lys Leu Glu Arg Tyr Lys
50 55 60

Leu Leu His Ile Leu Glu Phe Asp Ser Asp Arg Arg Arg Met Ser
65 70 75

Val Ile Val Gln Ala Pro Ser Gly Glu Lys Leu Leu Phe Ala Lys
80 85 90

Gly Ala Glu Ser Ser Ile Leu Pro Lys Cys Ile Gly Gly Glu Ile
95 100 105

Glu Lys Thr Arg Ile His Val Asp Glu Phe Ala Leu Lys Gly Leu
110 115 120

Arg Thr Leu Cys Ile Ala Tyr Arg Lys Phe Thr Ser Lys Glu Tyr
125 130 135

Glu Glu Ile Asp Lys Arg Ile Phe Glu Ala Arg Thr Ala Leu Gln
140 145 150

Gln Arg Glu Glu Lys Leu Ala Ala Val Phe Gln Phe Ile Glu Lys
155 160 165

Asp Leu Ile Leu Leu Gly Ala Thr Ala Val Glu Asp Arg Leu Gln
170 175 180

Asp Lys Val Arg Glu Thr Ile Glu Ala Leu Arg Met Ala Gly Ile
185 190 195

Lys Val Trp Val Leu Thr Gly Asp Lys His Glu Thr Ala Val Ser
200 205 210

Val Ser Leu Ser Cys Gly His Phe His Arg Thr Met Asn Ile Leu
215 220 225

Glu Leu Ile Asn Gln Lys Ser Asp Ser Glu Cys Ala Glu Gln Leu
230 235 240

Arg Gln Leu Ala Arg Arg Ile Thr Glu Asp His Val Ile Gln His
245 250 255

Gly Leu Val Val Asp Gly Thr Ser Leu Ser Leu Ala Leu Arg Glu
260 265 270

His Glu Lys Leu Phe Met Glu Val Cys Arg Asn Cys Ser Ala Val
275 280 285

Leu Cys Cys Arg Met Ala Pro Leu Gln Lys Ala Lys Val Ile Arg
290 295 300

Leu Ile Lys Ile Ser Pro Glu Lys Pro Ile Thr Leu Ala Val Gly
305 310 315

```
Asp Gly Ala Asn Asp Val Ser Met Ile Gln Glu Ala His Val Gly
                320                 325                 330

Ile Gly Ile Met Gly Lys Glu Gly Arg Gln Ala Ala Arg Asn Ser
                335                 340                 345

Asp Tyr Ala Ile Ala Arg Phe Lys Phe Leu Ser Lys Leu Leu Phe
                350                 355                 360

Val His Gly His Phe Tyr Tyr Ile Arg Ile Ala Thr Leu Val Gln
                365                 370                 375

Tyr Phe Phe Tyr Lys Asn Val Cys Phe Ile Thr Pro Gln Phe Leu
                380                 385                 390

Tyr Gln Phe Tyr Cys Leu Phe Ser Gln Gln Thr Leu Tyr Asp Ser
                395                 400                 405

Val Tyr Leu Thr Leu Tyr Asn Ile Cys Phe Thr Ser Leu Pro Ile
                410                 415                 420

Leu Ile Tyr Ser Leu Leu Glu Gln His Val Asp Pro His Val Leu
                425                 430                 435

Gln Asn Lys Pro Thr Leu Tyr Arg Asp Ile Ser Lys Asn Arg Leu
                440                 445                 450

Leu Ser Ile Lys Thr Phe Leu Tyr Trp Thr Ile Leu Gly Phe Ser
                455                 460                 465

His Ala Phe Ile Phe Phe Phe Gly Ser Tyr Leu Leu Ile Gly Lys
                470                 475                 480

Asp Thr Ser Leu Leu Gly Asn Gly Gln Met Phe Gly Asn Trp Thr
                485                 490                 495

Phe Gly Thr Leu Val Phe Thr Val Met Val Ile Thr Val Thr Val
                500                 505                 510

Lys Met Ala Leu Glu Thr His Phe Trp Thr Trp Ile Asn His Leu
                515                 520                 525

Val Thr Trp Gly Ser Ile Ile Phe Tyr Phe Val Phe Ser Leu Phe
                530                 535                 540

Tyr Gly Gly Ile Leu Trp Pro Phe Leu Gly Ser Gln Asn Met Tyr
                545                 550                 555

Phe Val Phe Ile Gln Leu Leu Ser Ser Gly Ser Ala Trp Phe Ala
                560                 565                 570

Ile Ile Leu Met Val Val Thr Cys Leu Phe Leu Asp Ile Ile Lys
                575                 580                 585

Lys Val Phe Asp Arg His Leu His Pro Thr Ser Thr Glu Lys Ala
                590                 595                 600

Gln Leu Thr Glu Thr Asn Ala Gly Ile Lys Cys Leu Asp Ser Met
                605                 610                 615

Cys Cys Phe Pro Glu Gly Glu Ala Ala Cys Ala Ser Val Gly Arg
                620                 625                 630

Met Leu Glu Arg Val Ile Gly Arg Cys Ser Pro Thr His Ile Ser
                635                 640                 645

Arg Ser Trp Ser Ala Ser Asp Pro Phe Tyr Thr Asn Asp Arg Ser
                650                 655                 660

Ile Leu Thr Leu Ser Thr Met Asp Ser Ser Thr Cys
                665                 670
```

<210> SEQ ID NO 67
<211> LENGTH: 877
<212> TYPE: PRT
<213> ORGANISM: Homo Sapien

<400> SEQUENCE: 67

-continued

```
Met Trp Glu Glu Glu Asp Ile Ala Ile Leu Phe Asn Lys Glu Pro
  1               5                  10                  15

Gly Lys Thr Glu Asn Ile Glu Asn Asn Leu Ser Ser Asn His Arg
                 20                  25                  30

Arg Ser Cys Arg Arg Ser Glu Glu Ser Asp Asp Asp Leu Asp Phe
                 35                  40                  45

Asp Ile Gly Leu Glu Asn Thr Gly Gly Asp Pro Gln Ile Leu Arg
                 50                  55                  60

Phe Ile Ser Asp Phe Leu Ala Phe Leu Val Leu Tyr Asn Phe Ile
                 65                  70                  75

Ile Pro Ile Ser Leu Tyr Val Thr Val Glu Met Gln Lys Phe Leu
                 80                  85                  90

Gly Ser Phe Phe Ile Gly Trp Asp Leu Asp Leu Tyr His Glu Glu
                 95                 100                 105

Ser Asp Gln Lys Ala Gln Val Asn Thr Ser Asp Leu Asn Glu Glu
                110                 115                 120

Leu Gly Gln Val Glu Tyr Val Phe Thr Asp Lys Thr Gly Thr Leu
                125                 130                 135

Thr Glu Asn Glu Met Gln Phe Arg Glu Cys Ser Ile Asn Gly Met
                140                 145                 150

Lys Tyr Gln Glu Ile Asn Gly Arg Leu Val Pro Glu Gly Pro Thr
                155                 160                 165

Pro Asp Ser Ser Glu Gly Asn Leu Ser Tyr Leu Ser Ser Leu Ser
                170                 175                 180

His Leu Asn Asn Leu Ser His Leu Thr Thr Ser Ser Ser Phe Arg
                185                 190                 195

Thr Ser Pro Glu Asn Glu Thr Glu Leu Ile Lys Glu His Asp Leu
                200                 205                 210

Phe Phe Lys Ala Val Ser Leu Cys His Thr Val Gln Ile Ser Asn
                215                 220                 225

Val Gln Thr Asp Cys Thr Gly Asp Gly Pro Trp Gln Ser Asn Leu
                230                 235                 240

Ala Pro Ser Gln Leu Glu Tyr Tyr Ala Ser Ser Pro Asp Glu Lys
                245                 250                 255

Ala Leu Val Glu Ala Ala Ala Arg Tyr Lys Leu Leu His Ile Leu
                260                 265                 270

Glu Phe Asp Ser Asp Arg Arg Arg Met Ser Val Ile Val Gln Ala
                275                 280                 285

Pro Ser Gly Glu Lys Leu Leu Phe Ala Lys Gly Ala Glu Ser Ser
                290                 295                 300

Ile Leu Pro Lys Cys Ile Gly Gly Glu Ile Glu Lys Thr Arg Ile
                305                 310                 315

His Val Asp Glu Phe Ala Leu Lys Gly Leu Arg Thr Leu Cys Ile
                320                 325                 330

Ala Tyr Arg Lys Phe Thr Ser Lys Glu Tyr Glu Glu Ile Asp Lys
                335                 340                 345

Arg Ile Phe Glu Ala Arg Thr Ala Leu Gln Gln Arg Glu Glu Lys
                350                 355                 360

Leu Ala Ala Val Phe Gln Phe Ile Glu Lys Asp Leu Ile Leu Leu
                365                 370                 375

Gly Ala Thr Ala Val Glu Asp Arg Leu Gln Asp Lys Val Arg Glu
                380                 385                 390

Thr Ile Glu Ala Leu Arg Met Ala Gly Ile Lys Val Trp Val Leu
                395                 400                 405
```

```
Thr Gly Asp Lys His Glu Thr Ala Val Ser Val Ser Leu Ser Cys
                410                 415                 420

Gly His Phe His Arg Thr Met Asn Ile Leu Glu Leu Ile Asn Gln
                425                 430                 435

Lys Ser Asp Ser Glu Cys Ala Glu Gln Leu Arg Gln Leu Ala Arg
                440                 445                 450

Arg Ile Thr Glu Asp His Val Ile Gln His Gly Leu Val Val Asp
                455                 460                 465

Gly Thr Ser Leu Ser Leu Ala Leu Arg Glu His Glu Lys Leu Phe
                470                 475                 480

Met Glu Val Cys Arg Asn Cys Ser Ala Val Leu Cys Cys Arg Met
                485                 490                 495

Ala Pro Leu Gln Lys Ala Lys Val Ile Arg Leu Ile Lys Ile Ser
                500                 505                 510

Pro Glu Lys Pro Ile Thr Leu Ala Val Gly Asp Gly Ala Asn Asp
                515                 520                 525

Val Ser Met Ile Gln Glu Ala His Val Gly Ile Gly Ile Met Gly
                530                 535                 540

Lys Glu Gly Arg Gln Ala Ala Arg Asn Ser Asp Tyr Ala Ile Ala
                545                 550                 555

Arg Phe Lys Phe Leu Ser Lys Leu Leu Phe Val His Gly His Phe
                560                 565                 570

Tyr Tyr Ile Arg Ile Ala Thr Leu Val Gln Tyr Phe Phe Tyr Lys
                575                 580                 585

Asn Val Cys Phe Ile Thr Pro Gln Phe Leu Tyr Gln Phe Tyr Cys
                590                 595                 600

Leu Phe Ser Gln Gln Thr Leu Tyr Asp Ser Val Tyr Leu Thr Leu
                605                 610                 615

Tyr Asn Ile Cys Phe Thr Ser Leu Pro Ile Leu Ile Tyr Ser Leu
                620                 625                 630

Leu Glu Gln His Val Asp Pro His Val Leu Gln Asn Lys Pro Thr
                635                 640                 645

Leu Tyr Arg Asp Ile Ser Lys Asn Arg Leu Leu Ser Ile Lys Thr
                650                 655                 660

Phe Leu Tyr Trp Thr Ile Leu Gly Phe Ser His Ala Phe Ile Phe
                665                 670                 675

Phe Phe Gly Ser Tyr Leu Leu Ile Gly Lys Asp Thr Ser Leu Leu
                680                 685                 690

Gly Asn Gly Gln Met Phe Gly Asn Trp Thr Phe Gly Thr Leu Val
                695                 700                 705

Phe Thr Val Met Val Ile Thr Val Thr Val Lys Met Ala Leu Glu
                710                 715                 720

Thr His Phe Trp Thr Trp Ile Asn His Leu Val Thr Trp Gly Ser
                725                 730                 735

Ile Ile Phe Tyr Phe Val Phe Ser Leu Phe Tyr Gly Gly Ile Leu
                740                 745                 750

Trp Pro Phe Leu Gly Ser Gln Asn Met Tyr Phe Val Phe Ile Gln
                755                 760                 765

Leu Leu Ser Ser Gly Ser Ala Trp Phe Ala Ile Ile Leu Met Val
                770                 775                 780

Val Thr Cys Leu Phe Leu Asp Ile Ile Lys Lys Val Phe Asp Arg
                785                 790                 795

His Leu His Pro Thr Ser Thr Glu Lys Ala Gln Leu Thr Glu Thr
```

```
                800                 805                 810

Asn Ala Gly Ile Lys Cys Leu Asp Ser Met Cys Cys Phe Pro Glu
                815                 820                 825

Gly Glu Ala Ala Cys Ala Ser Val Gly Arg Met Leu Glu Arg Val
                830                 835                 840

Ile Gly Arg Cys Ser Pro Thr His Ile Ser Arg Ser Trp Ser Ala
                845                 850                 855

Ser Asp Pro Phe Tyr Thr Asn Asp Arg Ser Ile Leu Thr Leu Ser
                860                 865                 870

Thr Met Asp Ser Ser Thr Cys
                875


<210> SEQ ID NO 68
<211> LENGTH: 63
<212> TYPE: PRT
<213> ORGANISM: Homo Sapien

<400> SEQUENCE: 68

Met Lys His Val Leu Asn Leu Tyr Leu Leu Gly Val Val Leu Thr
  1               5                  10                  15

Leu Leu Ser Ile Phe Val Arg Val Met Glu Ser Leu Glu Gly Leu
                 20                  25                  30

Leu Glu Ser Pro Ser Pro Gly Thr Ser Trp Thr Thr Arg Ser Gln
                 35                  40                  45

Leu Ala Asn Thr Glu Pro Thr Lys Gly Leu Pro Asp His Pro Ser
                 50                  55                  60

Arg Ser Met


<210> SEQ ID NO 69
<211> LENGTH: 137
<212> TYPE: PRT
<213> ORGANISM: Homo Sapien
<220> FEATURE:
<221> NAME/KEY: unsure
<222> LOCATION: 101, 136
<223> OTHER INFORMATION: unknown amino acid

<400> SEQUENCE: 69

Met Lys Thr Gly Leu Phe Phe Leu Cys Leu Leu Gly Thr Ala Ala
  1               5                  10                  15

Ala Ile Pro Thr Asn Ala Arg Leu Leu Ser Asp His Ser Lys Pro
                 20                  25                  30

Thr Ala Glu Thr Val Ala Pro Asp Asn Thr Ala Ile Pro Ser Leu
                 35                  40                  45

Arg Ala Glu Asp Glu Glu Asn Glu Lys Glu Thr Ala Val Ser Thr
                 50                  55                  60

Glu Asp Asp Ser His His Lys Ala Glu Lys Ser Ser Val Leu Lys
                 65                  70                  75

Ser Lys Glu Glu Ser His Glu Gln Ser Ala Glu Gln Gly Lys Ser
                 80                  85                  90

Ser Ser Gln Glu Leu Gly Leu Lys Asp Gln Xaa Asp Ser Asp Gly
                 95                 100                 105

Asp Leu Ser Val Asn Leu Glu Tyr Ala Pro Thr Glu Gly Thr Leu
                110                 115                 120

Asp Ile Lys Glu Asp Met Ser Glu Pro Gln Glu Lys Asn Ser Gln
                125                 130                 135

Xaa His
```

<210> SEQ ID NO 70
<211> LENGTH: 318
<212> TYPE: PRT
<213> ORGANISM: Homo Sapien

<400> SEQUENCE: 70

```
Met Ala Pro Trp Ala Glu Ala Glu His Ser Ala Leu Asn Pro Leu
  1               5                  10                  15

Arg Ala Val Trp Leu Thr Leu Thr Ala Ala Phe Leu Leu Thr Leu
                 20                  25                  30

Leu Leu Gln Leu Leu Pro Pro Gly Leu Leu Pro Gly Cys Ala Ile
                 35                  40                  45

Phe Gln Asp Leu Ile Arg Tyr Gly Lys Thr Lys Cys Gly Glu Pro
                 50                  55                  60

Ser Arg Pro Ala Ala Cys Arg Ala Phe Asp Val Pro Lys Arg Tyr
                 65                  70                  75

Phe Ser His Phe Tyr Ile Ile Ser Val Leu Trp Asn Gly Phe Leu
                 80                  85                  90

Leu Trp Cys Leu Thr Gln Ser Leu Phe Leu Gly Ala Pro Phe Pro
                 95                 100                 105

Ser Trp Leu His Gly Leu Leu Arg Ile Leu Gly Ala Ala Gln Phe
                110                 115                 120

Gln Gly Gly Glu Leu Ala Leu Ser Ala Phe Leu Val Leu Val Phe
                125                 130                 135

Leu Trp Leu His Ser Leu Arg Arg Leu Phe Glu Cys Leu Tyr Val
                140                 145                 150

Ser Val Phe Ser Asn Val Met Ile His Val Val Gln Tyr Cys Phe
                155                 160                 165

Gly Leu Val Tyr Tyr Val Leu Val Gly Leu Thr Val Leu Ser Gln
                170                 175                 180

Val Pro Met Asp Gly Arg Asn Ala Tyr Ile Thr Gly Lys Asn Leu
                185                 190                 195

Leu Met Gln Ala Arg Trp Phe His Ile Leu Gly Met Met Met Phe
                200                 205                 210

Ile Trp Ser Ser Ala His Gln Tyr Lys Cys His Val Ile Leu Gly
                215                 220                 225

Asn Leu Arg Lys Asn Lys Ala Gly Val Val Ile His Cys Asn His
                230                 235                 240

Arg Ile Pro Phe Gly Asp Trp Phe Glu Tyr Val Ser Ser Pro Asn
                245                 250                 255

Tyr Leu Ala Glu Leu Met Ile Tyr Val Ser Met Ala Val Thr Phe
                260                 265                 270

Gly Phe His Asn Leu Thr Trp Trp Leu Val Val Thr Asn Val Phe
                275                 280                 285

Phe Asn Gln Ala Leu Ser Ala Phe Leu Ser His Gln Phe Tyr Lys
                290                 295                 300

Ser Lys Phe Val Ser Tyr Pro Lys His Arg Lys Ala Phe Leu Pro
                305                 310                 315

Phe Leu Phe
```

<210> SEQ ID NO 71
<211> LENGTH: 426
<212> TYPE: PRT
<213> ORGANISM: Homo sapien

<400> SEQUENCE: 71

-continued

```
Met Pro Leu Leu Trp Leu Arg Gly Phe Leu Leu Ala Ser Cys Trp
  1               5                  10                  15

Ile Ile Val Arg Ser Ser Pro Thr Pro Gly Ser Glu Gly His Ser
                 20                  25                  30

Ala Ala Pro Asp Cys Pro Ser Cys Ala Leu Ala Ala Leu Pro Lys
                 35                  40                  45

Asp Val Pro Asn Ser Gln Pro Glu Met Val Glu Ala Val Lys Lys
                 50                  55                  60

His Ile Leu Asn Met Leu His Leu Lys Lys Arg Pro Asp Val Thr
                 65                  70                  75

Gln Pro Val Pro Lys Ala Ala Leu Leu Asn Ala Ile Arg Lys Leu
                 80                  85                  90

His Val Gly Lys Val Gly Glu Asn Gly Tyr Val Glu Ile Glu Asp
                 95                 100                 105

Asp Ile Gly Arg Arg Ala Glu Met Asn Glu Leu Met Glu Gln Thr
                110                 115                 120

Ser Glu Ile Ile Thr Phe Ala Glu Ser Gly Thr Ala Arg Lys Thr
                125                 130                 135

Leu His Phe Glu Ile Ser Lys Glu Gly Ser Asp Leu Ser Val Val
                140                 145                 150

Glu Arg Ala Glu Val Trp Leu Phe Leu Lys Val Pro Lys Ala Asn
                155                 160                 165

Arg Thr Arg Thr Lys Val Thr Ile Arg Leu Phe Gln Gln Gln Lys
                170                 175                 180

His Pro Gln Gly Ser Leu Asp Thr Gly Glu Glu Ala Glu Glu Val
                185                 190                 195

Gly Leu Lys Gly Glu Arg Ser Glu Leu Leu Leu Ser Glu Lys Val
                200                 205                 210

Val Asp Ala Arg Lys Ser Thr Trp His Val Phe Pro Val Ser Ser
                215                 220                 225

Ser Ile Gln Arg Leu Leu Asp Gln Gly Lys Ser Ser Leu Asp Val
                230                 235                 240

Arg Ile Ala Cys Glu Gln Cys Gln Glu Ser Gly Ala Ser Leu Val
                245                 250                 255

Leu Leu Gly Lys Lys Lys Lys Lys Glu Glu Glu Gly Glu Gly Lys
                260                 265                 270

Lys Lys Gly Gly Gly Glu Gly Gly Ala Gly Ala Asp Glu Glu Lys
                275                 280                 285

Glu Gln Ser His Arg Pro Phe Leu Met Leu Gln Ala Arg Gln Ser
                290                 295                 300

Glu Asp His Pro His Arg Arg Arg Arg Arg Gly Leu Glu Cys Asp
                305                 310                 315

Gly Lys Val Asn Ile Cys Cys Lys Lys Gln Phe Phe Val Ser Phe
                320                 325                 330

Lys Asp Ile Gly Trp Asn Asp Trp Ile Ile Ala Pro Ser Gly Tyr
                335                 340                 345

His Ala Asn Tyr Cys Glu Gly Glu Cys Pro Ser His Ile Ala Gly
                350                 355                 360

Thr Ser Gly Ser Ser Leu Ser Phe His Ser Thr Val Ile Asn His
                365                 370                 375

Tyr Arg Met Arg Gly His Ser Pro Phe Ala Asn Leu Lys Ser Cys
                380                 385                 390

Cys Val Pro Thr Lys Leu Arg Pro Met Ser Met Leu Tyr Tyr Asp
```

395                 400                 405

Asp Gly Gln Asn Ile Ile Lys Lys Asp Ile Gln Asn Met Ile Val
                410                 415                 420

Glu Glu Cys Gly Cys Ser
                425

<210> SEQ ID NO 72
<211> LENGTH: 238
<212> TYPE: PRT
<213> ORGANISM: Homo Sapien

<400> SEQUENCE: 72

Met Ala Ala Ala Pro Leu Leu Leu Leu Leu Leu Leu Val Pro Val
  1               5                  10                  15

Pro Leu Leu Pro Leu Leu Ala Gln Gly Pro Gly Gly Ala Leu Gly
                 20                  25                  30

Asn Arg His Ala Val Tyr Trp Asn Ser Ser Asn Gln His Leu Arg
                 35                  40                  45

Arg Glu Gly Tyr Thr Val Gln Val Asn Val Asn Asp Tyr Leu Asp
                 50                  55                  60

Ile Tyr Cys Pro His Tyr Asn Ser Ser Gly Val Gly Pro Gly Ala
                 65                  70                  75

Gly Pro Gly Pro Gly Gly Gly Ala Glu Gln Tyr Val Leu Tyr Met
                 80                  85                  90

Val Ser Arg Asn Gly Tyr Arg Thr Cys Asn Ala Ser Gln Gly Phe
                 95                 100                 105

Lys Arg Trp Glu Cys Asn Arg Pro His Ala Pro His Ser Pro Ile
                110                 115                 120

Lys Phe Ser Glu Lys Phe Gln Arg Tyr Ser Ala Phe Ser Leu Gly
                125                 130                 135

Tyr Glu Phe His Ala Gly His Glu Tyr Tyr Tyr Ile Ser Thr Pro
                140                 145                 150

Thr His Asn Leu His Trp Lys Cys Leu Arg Met Lys Val Phe Val
                155                 160                 165

Cys Cys Ala Ser Thr Ser His Ser Gly Glu Lys Pro Val Pro Thr
                170                 175                 180

Leu Pro Gln Phe Thr Met Gly Pro Asn Val Lys Ile Asn Val Leu
                185                 190                 195

Glu Asp Phe Glu Gly Glu Asn Pro Gln Val Pro Lys Leu Glu Lys
                200                 205                 210

Ser Ile Ser Gly Thr Ser Pro Lys Arg Glu His Leu Pro Leu Ala
                215                 220                 225

Val Gly Ile Ala Phe Phe Leu Met Thr Phe Leu Ala Ser
                230                 235

<210> SEQ ID NO 73
<211> LENGTH: 541
<212> TYPE: PRT
<213> ORGANISM: Homo Sapien

<400> SEQUENCE: 73

Met Gly His Ser Pro Pro Val Leu Pro Leu Cys Ala Ser Val Ser
  1               5                  10                  15

Leu Leu Gly Gly Leu Thr Phe Gly Tyr Glu Leu Ala Val Ile Ser
                 20                  25                  30

Gly Ala Leu Leu Pro Leu Gln Leu Asp Phe Gly Leu Ser Cys Leu
                 35                  40                  45

```
Glu Gln Glu Phe Leu Val Gly Ser Leu Leu Leu Gly Ala Leu Leu
                50                  55                  60

Ala Ser Leu Val Gly Gly Phe Leu Ile Asp Cys Tyr Gly Arg Lys
                65                  70                  75

Gln Ala Ile Leu Gly Ser Asn Leu Val Leu Leu Ala Gly Ser Leu
                80                  85                  90

Thr Leu Gly Leu Ala Gly Ser Leu Ala Trp Leu Val Leu Gly Arg
                95                 100                 105

Ala Val Val Gly Phe Ala Ile Ser Leu Ser Ser Met Ala Cys Cys
               110                 115                 120

Ile Tyr Val Ser Glu Leu Val Gly Pro Arg Gln Arg Gly Val Leu
               125                 130                 135

Val Ser Leu Tyr Glu Ala Gly Ile Thr Val Gly Ile Leu Leu Ser
               140                 145                 150

Tyr Ala Leu Asn Tyr Ala Leu Ala Gly Thr Pro Trp Gly Trp Arg
               155                 160                 165

His Met Phe Gly Trp Ala Thr Ala Pro Ala Val Leu Gln Ser Leu
               170                 175                 180

Ser Leu Leu Phe Leu Pro Ala Gly Thr Asp Glu Thr Ala Thr His
               185                 190                 195

Lys Asp Leu Ile Pro Leu Gln Gly Gly Glu Ala Pro Lys Leu Gly
               200                 205                 210

Pro Gly Arg Pro Arg Tyr Ser Phe Leu Asp Leu Phe Arg Ala Arg
               215                 220                 225

Asp Asn Met Arg Gly Arg Thr Thr Val Gly Leu Gly Leu Val Leu
               230                 235                 240

Phe Gln Gln Leu Thr Gly Gln Pro Asn Val Leu Cys Tyr Ala Ser
               245                 250                 255

Thr Ile Phe Ser Ser Val Gly Phe His Gly Gly Ser Ser Ala Val
               260                 265                 270

Leu Ala Ser Val Gly Leu Gly Ala Val Lys Val Ala Ala Thr Leu
               275                 280                 285

Thr Ala Met Gly Leu Val Asp Arg Ala Gly Arg Arg Ala Leu Leu
               290                 295                 300

Leu Ala Gly Cys Ala Leu Met Ala Leu Ser Val Ser Gly Ile Gly
               305                 310                 315

Leu Val Ser Phe Ala Val Pro Met Asp Ser Gly Pro Ser Cys Leu
               320                 325                 330

Ala Val Pro Asn Ala Thr Gly Gln Thr Gly Leu Pro Gly Asp Ser
               335                 340                 345

Gly Leu Leu Gln Asp Ser Ser Leu Pro Pro Ile Pro Arg Thr Asn
               350                 355                 360

Glu Asp Gln Arg Glu Pro Ile Leu Ser Thr Ala Lys Lys Thr Lys
               365                 370                 375

Pro His Pro Arg Ser Gly Asp Pro Ser Ala Pro Pro Arg Leu Ala
               380                 385                 390

Leu Ser Ser Ala Leu Pro Gly Pro Pro Leu Pro Ala Arg Gly His
               395                 400                 405

Ala Leu Leu Arg Trp Thr Ala Leu Leu Cys Leu Met Val Phe Val
               410                 415                 420

Ser Ala Phe Ser Phe Gly Phe Gly Pro Val Thr Trp Leu Val Leu
               425                 430                 435

Ser Glu Ile Tyr Pro Val Glu Ile Arg Gly Arg Ala Phe Ala Phe
```

```
                440                 445                 450

Cys Asn Ser Phe Asn Trp Ala Ala Asn Leu Phe Ile Ser Leu Ser
                455                 460                 465

Phe Leu Asp Leu Ile Gly Thr Ile Gly Leu Ser Trp Thr Phe Leu
                470                 475                 480

Leu Tyr Gly Leu Thr Ala Val Leu Gly Leu Gly Phe Ile Tyr Leu
                485                 490                 495

Phe Val Pro Glu Thr Lys Gly Gln Ser Leu Ala Glu Ile Asp Gln
                500                 505                 510

Gln Phe Gln Lys Arg Arg Phe Thr Leu Ser Phe Gly His Arg Gln
                515                 520                 525

Asn Ser Thr Gly Ile Pro Tyr Ser Arg Ile Glu Ile Ser Ala Ala
                530                 535                 540

Ser


<210> SEQ ID NO 74
<211> LENGTH: 1114
<212> TYPE: PRT
<213> ORGANISM: Homo Sapien

<400> SEQUENCE: 74

Met Ala Lys Ala Thr Ser Gly Ala Ala Gly Leu Arg Leu Leu Leu
  1               5                  10                  15

Leu Leu Leu Leu Pro Leu Leu Gly Lys Val Ala Leu Gly Leu Tyr
                 20                  25                  30

Phe Ser Arg Asp Ala Tyr Trp Glu Lys Leu Tyr Val Asp Gln Ala
                 35                  40                  45

Ala Gly Thr Pro Leu Leu Tyr Val His Ala Leu Arg Asp Ala Pro
                 50                  55                  60

Glu Glu Val Pro Ser Phe Arg Leu Gly Gln His Leu Tyr Gly Thr
                 65                  70                  75

Tyr Arg Thr Arg Leu His Glu Asn Asn Trp Ile Cys Ile Gln Glu
                 80                  85                  90

Asp Thr Gly Leu Leu Tyr Leu Asn Arg Ser Leu Asp His Ser Ser
                 95                 100                 105

Trp Glu Lys Leu Ser Val Arg Asn Arg Gly Phe Pro Leu Leu Thr
                110                 115                 120

Val Tyr Leu Lys Val Phe Leu Ser Pro Thr Ser Leu Arg Glu Gly
                125                 130                 135

Glu Cys Gln Trp Pro Gly Cys Ala Arg Val Tyr Phe Ser Phe Phe
                140                 145                 150

Asn Thr Ser Phe Pro Ala Cys Ser Ser Leu Lys Pro Arg Glu Leu
                155                 160                 165

Cys Phe Pro Glu Thr Arg Pro Ser Phe Arg Ile Arg Glu Asn Arg
                170                 175                 180

Pro Pro Gly Thr Phe His Gln Phe Arg Leu Leu Pro Val Gln Phe
                185                 190                 195

Leu Cys Pro Asn Ile Ser Val Ala Tyr Arg Leu Leu Glu Gly Glu
                200                 205                 210

Gly Leu Pro Phe Arg Cys Ala Pro Asp Ser Leu Glu Val Ser Thr
                215                 220                 225

Arg Trp Ala Leu Asp Arg Glu Gln Arg Glu Lys Tyr Glu Leu Val
                230                 235                 240

Ala Val Cys Thr Val His Ala Gly Ala Arg Glu Glu Val Val Met
                245                 250                 255
```

-continued

```
Val Pro Phe Pro Val Thr Val Tyr Asp Glu Asp Asp Ser Ala Pro
                260                 265                 270

Thr Phe Pro Ala Gly Val Asp Thr Ala Ser Ala Val Val Glu Phe
                275                 280                 285

Lys Arg Lys Glu Asp Thr Val Val Ala Thr Leu Arg Val Phe Asp
                290                 295                 300

Ala Asp Val Val Pro Ala Ser Gly Glu Leu Val Arg Arg Tyr Thr
                305                 310                 315

Ser Thr Leu Leu Pro Gly Asp Thr Trp Ala Gln Gln Thr Phe Arg
                320                 325                 330

Val Glu His Trp Pro Asn Glu Thr Ser Val Gln Ala Asn Gly Ser
                335                 340                 345

Phe Val Arg Ala Thr Val His Asp Tyr Arg Leu Val Leu Asn Arg
                350                 355                 360

Asn Leu Ser Ile Ser Glu Asn Arg Thr Met Gln Leu Ala Val Leu
                365                 370                 375

Val Asn Asp Ser Asp Phe Gln Gly Pro Gly Ala Gly Val Leu Leu
                380                 385                 390

Leu His Phe Asn Val Ser Val Leu Pro Val Ser Leu His Leu Pro
                395                 400                 405

Ser Thr Tyr Ser Leu Ser Val Ser Arg Arg Ala Arg Arg Phe Ala
                410                 415                 420

Gln Ile Gly Lys Val Cys Val Glu Asn Cys Gln Ala Phe Ser Gly
                425                 430                 435

Ile Asn Val Gln Tyr Lys Leu His Ser Ser Gly Ala Asn Cys Ser
                440                 445                 450

Thr Leu Gly Val Val Thr Ser Ala Glu Asp Thr Ser Gly Ile Leu
                455                 460                 465

Phe Val Asn Asp Thr Lys Ala Leu Arg Arg Pro Lys Cys Ala Glu
                470                 475                 480

Leu His Tyr Met Val Val Ala Thr Asp Gln Gln Thr Ser Arg Gln
                485                 490                 495

Ala Gln Ala Gln Leu Leu Val Thr Val Glu Gly Ser Tyr Val Ala
                500                 505                 510

Glu Glu Ala Gly Cys Pro Leu Ser Cys Ala Val Ser Lys Arg Arg
                515                 520                 525

Leu Glu Cys Glu Glu Cys Gly Gly Leu Gly Ser Pro Thr Gly Arg
                530                 535                 540

Cys Glu Trp Arg Gln Gly Asp Gly Lys Gly Ile Thr Arg Asn Phe
                545                 550                 555

Ser Thr Cys Ser Pro Ser Thr Lys Thr Cys Pro Asp Gly His Cys
                560                 565                 570

Asp Val Val Glu Thr Gln Asp Ile Asn Ile Cys Pro Gln Asp Cys
                575                 580                 585

Leu Arg Gly Ser Ile Val Gly Gly His Glu Pro Gly Glu Pro Arg
                590                 595                 600

Gly Ile Lys Ala Gly Tyr Gly Thr Cys Asn Cys Phe Pro Glu Glu
                605                 610                 615

Glu Lys Cys Phe Cys Glu Pro Glu Asp Ile Gln Asp Pro Leu Cys
                620                 625                 630

Asp Glu Leu Cys Arg Thr Val Ile Ala Ala Ala Val Leu Phe Ser
                635                 640                 645

Phe Ile Val Ser Val Leu Leu Ser Ala Phe Cys Ile His Cys Tyr
```

-continued

```
                650                 655                 660

His Lys Phe Ala His Lys Pro Pro Ile Ser Ser Ala Glu Met Thr
                665                 670                 675

Phe Arg Arg Pro Ala Gln Ala Phe Pro Val Ser Tyr Ser Ser Ser
                680                 685                 690

Gly Ala Arg Arg Pro Ser Leu Asp Ser Met Glu Asn Gln Val Ser
                695                 700                 705

Val Asp Ala Phe Lys Ile Leu Glu Asp Pro Lys Trp Glu Phe Pro
                710                 715                 720

Arg Lys Asn Leu Val Leu Gly Lys Thr Leu Gly Glu Gly Glu Phe
                725                 730                 735

Gly Lys Val Val Lys Ala Thr Ala Phe His Leu Lys Gly Arg Ala
                740                 745                 750

Gly Tyr Thr Thr Val Ala Val Lys Met Leu Lys Glu Asn Ala Ser
                755                 760                 765

Pro Ser Glu Leu Arg Asp Leu Leu Ser Glu Phe Asn Val Leu Lys
                770                 775                 780

Gln Val Asn His Pro His Val Ile Lys Leu Tyr Gly Ala Cys Ser
                785                 790                 795

Gln Asp Gly Pro Leu Leu Leu Ile Val Glu Tyr Ala Lys Tyr Gly
                800                 805                 810

Ser Leu Arg Gly Phe Leu Arg Glu Ser Arg Lys Val Gly Pro Gly
                815                 820                 825

Tyr Leu Gly Ser Gly Gly Ser Arg Asn Ser Ser Ser Leu Asp His
                830                 835                 840

Pro Asp Glu Arg Ala Leu Thr Met Gly Asp Leu Ile Ser Phe Ala
                845                 850                 855

Trp Gln Ile Ser Gln Gly Met Gln Tyr Leu Ala Glu Met Lys Leu
                860                 865                 870

Val His Arg Asp Leu Ala Ala Arg Asn Ile Leu Val Ala Glu Gly
                875                 880                 885

Arg Lys Met Lys Ile Ser Asp Phe Gly Leu Ser Arg Asp Val Tyr
                890                 895                 900

Glu Glu Asp Ser Tyr Val Lys Arg Ser Gln Gly Arg Ile Pro Val
                905                 910                 915

Lys Trp Met Ala Ile Glu Ser Leu Phe Asp His Ile Tyr Thr Thr
                920                 925                 930

Gln Ser Asp Val Trp Ser Phe Gly Val Leu Leu Trp Glu Ile Val
                935                 940                 945

Thr Leu Gly Gly Asn Pro Tyr Pro Gly Ile Pro Pro Glu Arg Leu
                950                 955                 960

Phe Asn Leu Leu Lys Thr Gly His Arg Met Glu Arg Pro Asp Asn
                965                 970                 975

Cys Ser Glu Glu Met Tyr Arg Leu Met Leu Gln Cys Trp Lys Gln
                980                 985                 990

Glu Pro Asp Lys Arg Pro Val Phe Ala Asp Ile Ser Lys Asp Leu
                995                1000                1005

Glu Lys Met Met Val Lys Arg Arg Asp Tyr Leu Asp Leu Ala Ala
               1010                1015                1020

Ser Thr Pro Ser Asp Ser Leu Ile Tyr Asp Asp Gly Leu Ser Glu
               1025                1030                1035

Glu Glu Thr Pro Leu Val Asp Cys Asn Asn Ala Pro Leu Pro Arg
               1040                1045                1050
```

```
Ala Leu Pro Ser Thr Trp Ile Glu Asn Lys Leu Tyr Gly Met Ser
                1055                1060                1065

Asp Pro Asn Trp Pro Gly Glu Ser Pro Val Pro Leu Thr Arg Ala
                1070                1075                1080

Asp Gly Thr Asn Thr Gly Phe Pro Arg Tyr Pro Asn Asp Ser Val
                1085                1090                1095

Tyr Ala Asn Trp Met Leu Ser Pro Ser Ala Ala Lys Leu Met Asp
                1100                1105                1110

Thr Phe Asp Ser


<210> SEQ ID NO 75
<211> LENGTH: 790
<212> TYPE: PRT
<213> ORGANISM: Homo Sapien

<400> SEQUENCE: 75

Met Arg Thr Tyr Arg Tyr Phe Leu Leu Leu Phe Trp Val Gly Gln
  1               5                  10                  15

Pro Tyr Pro Thr Leu Ser Thr Pro Leu Ser Lys Arg Thr Ser Gly
                 20                  25                  30

Phe Pro Ala Lys Lys Arg Ala Leu Glu Leu Ser Gly Asn Ser Lys
                 35                  40                  45

Asn Glu Leu Asn Arg Ser Lys Arg Ser Trp Met Trp Asn Gln Phe
                 50                  55                  60

Phe Leu Leu Glu Glu Tyr Thr Gly Ser Asp Tyr Gln Tyr Val Gly
                 65                  70                  75

Lys Leu His Ser Asp Gln Asp Arg Gly Asp Gly Ser Leu Lys Tyr
                 80                  85                  90

Ile Leu Ser Gly Asp Gly Ala Gly Asp Leu Phe Ile Ile Asn Glu
                 95                 100                 105

Asn Thr Gly Asp Ile Gln Ala Thr Lys Arg Leu Asp Arg Glu Glu
                110                 115                 120

Lys Pro Val Tyr Ile Leu Arg Ala Gln Ala Ile Asn Arg Arg Thr
                125                 130                 135

Gly Arg Pro Val Glu Pro Glu Ser Glu Phe Ile Ile Lys Ile His
                140                 145                 150

Asp Ile Asn Asp Asn Glu Pro Ile Phe Thr Lys Glu Val Tyr Thr
                155                 160                 165

Ala Thr Val Pro Glu Met Ser Asp Val Gly Thr Phe Val Val Gln
                170                 175                 180

Val Thr Ala Thr Asp Ala Asp Asp Pro Thr Tyr Gly Asn Ser Ala
                185                 190                 195

Lys Val Val Tyr Ser Ile Leu Gln Gly Gln Pro Tyr Phe Ser Val
                200                 205                 210

Glu Ser Glu Thr Gly Ile Ile Lys Thr Ala Leu Leu Asn Met Asp
                215                 220                 225

Arg Glu Asn Arg Glu Gln Tyr Gln Val Val Ile Gln Ala Lys Asp
                230                 235                 240

Met Gly Gly Gln Met Gly Gly Leu Ser Gly Thr Thr Thr Val Asn
                245                 250                 255

Ile Thr Leu Thr Asp Val Asn Asp Asn Pro Pro Arg Phe Pro Gln
                260                 265                 270

Ser Thr Tyr Gln Phe Lys Thr Pro Glu Ser Ser Pro Pro Gly Thr
                275                 280                 285

Pro Ile Gly Arg Ile Lys Ala Ser Asp Ala Asp Val Gly Glu Asn
```

```
                290                 295                 300

Ala Glu Ile Glu Tyr Ser Ile Thr Asp Gly Glu Gly Leu Asp Met
                305                 310                 315

Phe Asp Val Ile Thr Asp Gln Glu Thr Gln Glu Gly Ile Ile Thr
                320                 325                 330

Val Lys Lys Leu Leu Asp Phe Glu Lys Lys Lys Val Tyr Thr Leu
                335                 340                 345

Lys Val Glu Ala Ser Asn Pro Tyr Val Glu Pro Arg Phe Leu Tyr
                350                 355                 360

Leu Gly Pro Phe Lys Asp Ser Ala Thr Val Arg Ile Val Val Glu
                365                 370                 375

Asp Val Asp Glu Pro Pro Val Phe Ser Lys Leu Ala Tyr Ile Leu
                380                 385                 390

Gln Ile Arg Glu Asp Ala Gln Ile Asn Thr Thr Ile Gly Ser Val
                395                 400                 405

Thr Ala Gln Asp Pro Asp Ala Ala Arg Asn Pro Val Lys Tyr Ser
                410                 415                 420

Val Asp Arg His Thr Asp Met Asp Arg Ile Phe Asn Ile Asp Ser
                425                 430                 435

Gly Asn Gly Ser Ile Phe Thr Ser Lys Leu Leu Asp Arg Glu Thr
                440                 445                 450

Leu Leu Trp His Asn Ile Thr Val Ile Ala Thr Glu Ile Asn Asn
                455                 460                 465

Pro Lys Gln Ser Ser Arg Val Pro Leu Tyr Ile Lys Val Leu Asp
                470                 475                 480

Val Asn Asp Asn Ala Pro Glu Phe Ala Glu Phe Tyr Glu Thr Phe
                485                 490                 495

Val Cys Glu Lys Ala Lys Ala Asp Gln Leu Ile Gln Thr Leu His
                500                 505                 510

Ala Val Asp Lys Asp Asp Pro Tyr Ser Gly His Gln Phe Ser Phe
                515                 520                 525

Ser Leu Ala Pro Glu Ala Ala Ser Gly Ser Asn Phe Thr Ile Gln
                530                 535                 540

Asp Asn Lys Asp Asn Thr Ala Gly Ile Leu Thr Arg Lys Asn Gly
                545                 550                 555

Tyr Asn Arg His Glu Met Ser Thr Tyr Leu Leu Pro Val Val Ile
                560                 565                 570

Ser Asp Asn Asp Tyr Pro Val Gln Ser Ser Thr Gly Thr Val Thr
                575                 580                 585

Val Arg Val Cys Ala Cys Asp His His Gly Asn Met Gln Ser Cys
                590                 595                 600

His Ala Glu Ala Leu Ile His Pro Thr Gly Leu Ser Thr Gly Ala
                605                 610                 615

Leu Val Ala Ile Leu Leu Cys Ile Val Ile Leu Leu Val Thr Val
                620                 625                 630

Val Leu Phe Ala Ala Leu Arg Arg Gln Arg Lys Lys Glu Pro Leu
                635                 640                 645

Ile Ile Ser Lys Glu Asp Ile Arg Asp Asn Ile Val Ser Tyr Asn
                650                 655                 660

Asp Glu Gly Gly Gly Glu Glu Asp Thr Gln Ala Phe Asp Ile Gly
                665                 670                 675

Thr Leu Arg Asn Pro Glu Ala Ile Glu Asp Asn Lys Leu Arg Arg
                680                 685                 690
```

```
Asp Ile Val Pro Glu Ala Leu Phe Leu Pro Arg Arg Thr Pro Thr
                695                 700                 705

Ala Arg Asp Asn Thr Asp Val Arg Asp Phe Ile Asn Gln Arg Leu
                710                 715                 720

Lys Glu Asn Asp Thr Asp Pro Thr Ala Pro Pro Tyr Asp Ser Leu
                725                 730                 735

Ala Thr Tyr Ala Tyr Glu Gly Thr Gly Ser Val Ala Asp Ser Leu
                740                 745                 750

Ser Ser Leu Glu Ser Val Thr Thr Asp Ala Asp Gln Asp Tyr Asp
                755                 760                 765

Tyr Leu Ser Asp Trp Gly Pro Arg Phe Lys Lys Leu Ala Asp Met
                770                 775                 780

Tyr Gly Gly Val Asp Ser Asp Lys Asp Ser
                785                 790


<210> SEQ ID NO 76
<211> LENGTH: 794
<212> TYPE: PRT
<213> ORGANISM: Homo Sapien

<400> SEQUENCE: 76

Met Leu Thr Arg Asn Cys Leu Ser Leu Leu Leu Trp Val Leu Phe
  1               5                  10                  15

Asp Gly Gly Leu Leu Thr Pro Leu Gln Pro Gln Pro Gln Gln Thr
                 20                  25                  30

Leu Ala Thr Glu Pro Arg Glu Asn Val Ile His Leu Pro Gly Gln
                 35                  40                  45

Arg Ser His Phe Gln Arg Val Lys Arg Gly Trp Val Trp Asn Gln
                 50                  55                  60

Phe Phe Val Leu Glu Glu Tyr Val Gly Ser Glu Pro Gln Tyr Val
                 65                  70                  75

Gly Lys Leu His Ser Asp Leu Asp Lys Gly Glu Gly Thr Val Lys
                 80                  85                  90

Tyr Thr Leu Ser Gly Asp Gly Ala Gly Thr Val Phe Thr Ile Asp
                 95                 100                 105

Glu Thr Thr Gly Asp Ile His Ala Ile Arg Ser Leu Asp Arg Glu
                110                 115                 120

Glu Lys Pro Phe Tyr Thr Leu Arg Ala Gln Ala Val Asp Ile Glu
                125                 130                 135

Thr Arg Lys Pro Leu Glu Pro Glu Ser Glu Phe Ile Ile Lys Val
                140                 145                 150

Gln Asp Ile Asn Asp Asn Glu Pro Lys Phe Leu Asp Gly Pro Tyr
                155                 160                 165

Val Ala Thr Val Pro Glu Met Ser Pro Val Gly Ala Tyr Val Leu
                170                 175                 180

Gln Val Lys Ala Thr Asp Ala Asp Asp Pro Thr Tyr Gly Asn Ser
                185                 190                 195

Ala Arg Val Val Tyr Ser Ile Leu Gln Gly Gln Pro Tyr Phe Ser
                200                 205                 210

Ile Asp Pro Lys Thr Gly Val Ile Arg Thr Ala Leu Pro Asn Met
                215                 220                 225

Asp Arg Glu Val Lys Glu Gln Tyr Gln Val Leu Ile Gln Ala Lys
                230                 235                 240

Asp Met Gly Gly Gln Leu Gly Gly Leu Ala Gly Thr Thr Ile Val
                245                 250                 255
```

-continued

```
Asn Ile Thr Leu Thr Asp Val Asn Asp Asn Pro Pro Arg Phe Pro
                260                 265                 270

Lys Ser Ile Phe His Leu Lys Val Pro Glu Ser Ser Pro Ile Gly
                275                 280                 285

Ser Ala Ile Gly Arg Ile Arg Ala Val Asp Pro Asp Phe Gly Gln
                290                 295                 300

Asn Ala Glu Ile Glu Tyr Asn Ile Val Pro Gly Asp Gly Gly Asn
                305                 310                 315

Leu Phe Asp Ile Val Thr Asp Glu Asp Thr Gln Glu Gly Val Ile
                320                 325                 330

Lys Leu Lys Lys Pro Leu Asp Phe Glu Thr Lys Lys Ala Tyr Thr
                335                 340                 345

Phe Lys Val Glu Ala Ser Asn Leu His Leu Asp His Arg Phe His
                350                 355                 360

Ser Ala Gly Pro Phe Lys Asp Thr Ala Thr Val Lys Ile Ser Val
                365                 370                 375

Leu Asp Val Asp Glu Pro Pro Val Phe Ser Lys Pro Leu Tyr Thr
                380                 385                 390

Met Glu Val Tyr Glu Asp Thr Pro Val Gly Thr Ile Ile Gly Ala
                395                 400                 405

Val Thr Ala Gln Asp Leu Asp Val Gly Ser Gly Ala Val Arg Tyr
                410                 415                 420

Phe Ile Asp Trp Lys Ser Asp Gly Asp Ser Tyr Phe Thr Ile Asp
                425                 430                 435

Gly Asn Glu Gly Thr Ile Ala Thr Asn Glu Leu Leu Asp Arg Glu
                440                 445                 450

Ser Thr Ala Gln Tyr Asn Phe Ser Ile Ile Ala Ser Lys Val Ser
                455                 460                 465

Asn Pro Leu Leu Thr Ser Lys Val Asn Ile Leu Ile Asn Val Leu
                470                 475                 480

Asp Val Asn Glu Phe Pro Pro Glu Ile Ser Val Pro Tyr Glu Thr
                485                 490                 495

Ala Val Cys Glu Asn Ala Lys Pro Gly Gln Ile Ile Gln Ile Val
                500                 505                 510

Ser Ala Ala Asp Arg Asp Leu Ser Pro Ala Gly Gln Gln Phe Ser
                515                 520                 525

Phe Arg Leu Ser Pro Glu Ala Ala Ile Lys Pro Asn Phe Thr Val
                530                 535                 540

Arg Asp Phe Arg Asn Asn Thr Ala Gly Ile Glu Thr Arg Arg Asn
                545                 550                 555

Gly Tyr Ser Arg Arg Gln Gln Glu Leu Tyr Phe Leu Pro Val Val
                560                 565                 570

Ile Glu Asp Ser Ser Tyr Pro Val Gln Ser Ser Thr Asn Thr Met
                575                 580                 585

Thr Ile Arg Val Cys Arg Cys Asp Ser Asp Gly Thr Ile Leu Ser
                590                 595                 600

Cys Asn Val Glu Ala Ile Phe Leu Pro Val Gly Leu Ser Thr Gly
                605                 610                 615

Ala Leu Ile Ala Ile Leu Leu Cys Ile Val Ile Leu Leu Ala Ile
                620                 625                 630

Val Val Leu Tyr Val Ala Leu Arg Arg Gln Lys Lys Lys His Thr
                635                 640                 645

Leu Met Thr Ser Lys Glu Asp Ile Arg Asp Asn Val Ile His Tyr
                650                 655                 660
```

```
Asp Asp Glu Gly Gly Gly Glu Glu Asp Thr Gln Ala Phe Asp Ile
                665                 670                 675

Gly Ala Leu Arg Asn Pro Lys Val Ile Glu Glu Asn Lys Ile Arg
                680                 685                 690

Arg Asp Ile Lys Pro Asp Ser Leu Cys Leu Pro Arg Gln Arg Pro
                695                 700                 705

Pro Met Glu Asp Asn Thr Asp Ile Arg Asp Phe Ile His Gln Arg
                710                 715                 720

Leu Gln Glu Asn Asp Val Asp Pro Thr Ala Pro Pro Ile Asp Ser
                725                 730                 735

Leu Ala Thr Tyr Ala Tyr Glu Gly Ser Gly Ser Val Ala Glu Ser
                740                 745                 750

Leu Ser Ser Ile Asp Ser Leu Thr Thr Glu Ala Asp Gln Asp Tyr
                755                 760                 765

Asp Tyr Leu Thr Asp Trp Gly Pro Arg Phe Lys Val Leu Ala Asp
                770                 775                 780

Met Phe Gly Glu Glu Glu Ser Tyr Asn Pro Asp Lys Val Thr
                785                 790


<210> SEQ ID NO 77
<211> LENGTH: 141
<212> TYPE: PRT
<213> ORGANISM: Homo Sapien

<400> SEQUENCE: 77

Met Ala Arg Pro Leu Cys Thr Leu Leu Leu Leu Met Ala Thr Leu
  1               5                  10                  15

Ala Gly Ala Leu Ala Ser Ser Ser Lys Glu Glu Asn Arg Ile Ile
                 20                  25                  30

Pro Gly Gly Ile Tyr Asp Ala Asp Leu Asn Asp Glu Trp Val Gln
                 35                  40                  45

Arg Ala Leu His Phe Ala Ile Ser Glu Tyr Asn Lys Ala Thr Glu
                 50                  55                  60

Asp Glu Tyr Tyr Arg Arg Pro Leu Gln Val Leu Arg Ala Arg Glu
                 65                  70                  75

Gln Thr Phe Gly Gly Val Asn Tyr Phe Phe Asp Val Glu Val Gly
                 80                  85                  90

Arg Thr Ile Cys Thr Lys Ser Gln Pro Asn Leu Asp Thr Cys Ala
                 95                 100                 105

Phe His Glu Gln Pro Glu Leu Gln Lys Lys Gln Leu Cys Ser Phe
                110                 115                 120

Glu Ile Tyr Glu Val Pro Trp Glu Asp Arg Met Ser Leu Val Asn
                125                 130                 135

Ser Arg Cys Gln Glu Ala
                140


<210> SEQ ID NO 78
<211> LENGTH: 466
<212> TYPE: PRT
<213> ORGANISM: Homo Sapien

<400> SEQUENCE: 78

Met Thr Thr Ser Pro Ile Leu Gln Leu Leu Leu Arg Leu Ser Leu
  1               5                  10                  15

Cys Gly Leu Leu Leu Gln Arg Ala Glu Thr Gly Ser Lys Gly Gln
                 20                  25                  30
```

-continued

```
Thr Ala Gly Glu Leu Tyr Gln Arg Trp Glu Arg Tyr Arg Arg Glu
                35                  40                  45

Cys Gln Glu Thr Leu Ala Ala Ala Glu Pro Pro Ser Gly Leu Ala
                50                  55                  60

Cys Asn Gly Ser Phe Asp Met Tyr Val Cys Trp Asp Tyr Ala Ala
                65                  70                  75

Pro Asn Ala Thr Ala Arg Ala Ser Cys Pro Trp Tyr Leu Pro Trp
                80                  85                  90

His His His Val Ala Ala Gly Phe Val Leu Arg Gln Cys Gly Ser
                95                  100                 105

Asp Gly Gln Trp Gly Leu Trp Arg Asp His Thr Gln Cys Glu Asn
                110                 115                 120

Pro Glu Lys Asn Glu Ala Phe Leu Asp Gln Arg Leu Ile Leu Glu
                125                 130                 135

Arg Leu Gln Val Met Tyr Thr Val Gly Tyr Ser Leu Ser Leu Ala
                140                 145                 150

Thr Leu Leu Leu Ala Leu Leu Ile Leu Ser Leu Phe Arg Arg Leu
                155                 160                 165

His Cys Thr Arg Asn Tyr Ile His Ile Asn Leu Phe Thr Ser Phe
                170                 175                 180

Met Leu Arg Ala Ala Ala Ile Leu Ser Arg Asp Arg Leu Leu Pro
                185                 190                 195

Arg Pro Gly Pro Tyr Leu Gly Asp Gln Ala Leu Ala Leu Trp Asn
                200                 205                 210

Gln Ala Leu Ala Ala Cys Arg Thr Ala Gln Ile Val Thr Gln Tyr
                215                 220                 225

Cys Val Gly Ala Asn Tyr Thr Trp Leu Leu Val Glu Gly Val Tyr
                230                 235                 240

Leu His Ser Leu Leu Val Leu Val Gly Gly Ser Glu Glu Gly His
                245                 250                 255

Phe Arg Tyr Tyr Leu Leu Leu Gly Trp Gly Ala Pro Ala Leu Phe
                260                 265                 270

Val Ile Pro Trp Val Ile Val Arg Tyr Leu Tyr Glu Asn Thr Gln
                275                 280                 285

Cys Trp Glu Arg Asn Glu Val Lys Ala Ile Trp Trp Ile Ile Arg
                290                 295                 300

Thr Pro Ile Leu Met Thr Ile Leu Ile Asn Phe Leu Ile Phe Ile
                305                 310                 315

Arg Ile Leu Gly Ile Leu Leu Ser Lys Leu Arg Thr Arg Gln Met
                320                 325                 330

Arg Cys Arg Asp Tyr Arg Leu Arg Leu Ala Arg Ser Thr Leu Thr
                335                 340                 345

Leu Val Pro Leu Leu Gly Val His Glu Val Val Phe Ala Pro Val
                350                 355                 360

Thr Glu Glu Gln Ala Arg Gly Ala Leu Arg Phe Ala Lys Leu Gly
                365                 370                 375

Phe Glu Ile Phe Leu Ser Ser Phe Gln Gly Phe Leu Val Ser Val
                380                 385                 390

Leu Tyr Cys Phe Ile Asn Lys Glu Val Gln Ser Glu Ile Arg Arg
                395                 400                 405

Gly Trp His His Cys Arg Leu Arg Arg Ser Leu Gly Glu Glu Gln
                410                 415                 420

Arg Gln Leu Pro Glu Arg Ala Phe Arg Ala Leu Pro Ser Gly Ser
                425                 430                 435
```

Gly Pro Gly Glu Val Pro Thr Ser Arg Gly Leu Ser Ser Gly Thr
440 445 450

Leu Pro Gly Pro Gly Asn Glu Ala Ser Arg Glu Leu Glu Ser Tyr
455 460 465

Cys

<210> SEQ ID NO 79
<211> LENGTH: 506
<212> TYPE: PRT
<213> ORGANISM: Homo Sapien

<400> SEQUENCE: 79

Met Leu Ser Lys Val Leu Pro Val Leu Leu Gly Ile Leu Leu Ile
1 5 10 15

Leu Gln Ser Arg Val Glu Gly Pro Gln Thr Glu Ser Lys Asn Glu
20 25 30

Ala Ser Ser Arg Asp Val Val Tyr Gly Pro Gln Pro Gln Pro Leu
35 40 45

Glu Asn Gln Leu Leu Ser Glu Glu Thr Lys Ser Thr Glu Thr Glu
50 55 60

Thr Gly Ser Arg Val Gly Lys Leu Pro Glu Ala Ser Arg Ile Leu
65 70 75

Asn Thr Ile Leu Ser Asn Tyr Asp His Lys Leu Arg Pro Gly Ile
80 85 90

Gly Glu Lys Pro Thr Val Val Thr Val Glu Ile Ala Val Asn Ser
95 100 105

Leu Gly Pro Leu Ser Ile Leu Asp Met Glu Tyr Thr Ile Asp Ile
110 115 120

Ile Phe Ser Gln Thr Trp Tyr Asp Glu Arg Leu Cys Tyr Asn Asp
125 130 135

Thr Phe Glu Ser Leu Val Leu Asn Gly Asn Val Val Ser Gln Leu
140 145 150

Trp Ile Pro Asp Thr Phe Phe Arg Asn Ser Lys Arg Thr His Glu
155 160 165

His Glu Ile Thr Met Pro Asn Gln Met Val Arg Ile Tyr Lys Asp
170 175 180

Gly Lys Val Leu Tyr Thr Ile Arg Met Thr Ile Asp Ala Gly Cys
185 190 195

Ser Leu His Met Leu Arg Phe Pro Met Asp Ser His Ser Cys Pro
200 205 210

Leu Ser Phe Ser Ser Phe Ser Tyr Pro Glu Asn Glu Met Ile Tyr
215 220 225

Lys Trp Glu Asn Phe Lys Leu Glu Ile Asn Glu Lys Asn Ser Trp
230 235 240

Lys Leu Phe Gln Phe Asp Phe Thr Gly Val Ser Asn Lys Thr Glu
245 250 255

Ile Ile Thr Thr Pro Val Gly Asp Phe Met Val Met Thr Ile Phe
260 265 270

Phe Asn Val Ser Arg Arg Phe Gly Tyr Val Ala Phe Gln Asn Tyr
275 280 285

Val Pro Ser Ser Val Thr Thr Met Leu Ser Trp Val Ser Phe Trp
290 295 300

Ile Lys Thr Glu Ser Ala Pro Ala Arg Thr Ser Leu Gly Ile Thr
305 310 315

-continued

Ser Val Leu Thr Met Thr Thr Leu Gly Thr Phe Ser Arg Lys Asn
320 325 330

Phe Pro Arg Val Ser Tyr Ile Thr Ala Leu Asp Phe Tyr Ile Ala
335 340 345

Ile Cys Phe Val Phe Cys Phe Cys Ala Leu Leu Glu Phe Ala Val
350 355 360

Leu Asn Phe Leu Ile Tyr Asn Gln Thr Lys Ala His Ala Ser Pro
365 370 375

Lys Leu Arg His Pro Arg Ile Asn Ser Arg Ala His Ala Arg Thr
380 385 390

Arg Ala Arg Ser Arg Ala Cys Ala Arg Gln His Gln Glu Ala Phe
395 400 405

Val Cys Gln Ile Val Thr Thr Glu Gly Ser Asp Gly Glu Glu Arg
410 415 420

Pro Ser Cys Ser Ala Gln Gln Pro Pro Ser Pro Gly Ser Pro Glu
425 430 435

Gly Pro Arg Ser Leu Cys Ser Lys Leu Ala Cys Cys Glu Trp Cys
440 445 450

Lys Arg Phe Lys Lys Tyr Phe Cys Met Val Pro Asp Cys Glu Gly
455 460 465

Ser Thr Trp Gln Gln Gly Arg Leu Cys Ile His Val Tyr Arg Leu
470 475 480

Asp Asn Tyr Ser Arg Val Val Phe Pro Val Thr Phe Phe Phe Phe
485 490 495

Asn Val Leu Tyr Trp Leu Val Cys Leu Asn Leu
500 505

<210> SEQ ID NO 80
<211> LENGTH: 1212
<212> TYPE: PRT
<213> ORGANISM: Homo Sapien

<400> SEQUENCE: 80

Met Glu Pro Arg Pro Thr Ala Pro Ser Ser Gly Ala Pro Gly Leu
1 5 10 15

Ala Gly Val Gly Glu Thr Pro Ser Ala Ala Ala Leu Ala Ala Ala
20 25 30

Arg Val Glu Leu Pro Gly Thr Ala Val Pro Ser Val Pro Glu Asp
35 40 45

Ala Ala Pro Ala Ser Arg Asp Gly Gly Gly Val Arg Asp Glu Gly
50 55 60

Pro Ala Ala Ala Gly Asp Gly Leu Gly Arg Pro Leu Gly Pro Thr
65 70 75

Pro Ser Gln Ser Arg Phe Gln Val Asp Leu Val Ser Glu Asn Ala
80 85 90

Gly Arg Ala Ala Ala Ala Ala Ala Ala Ala Ala Ala Ala Ala Ala
95 100 105

Ala Ala Gly Ala Gly Ala Gly Ala Lys Gln Thr Pro Ala Asp Gly
110 115 120

Glu Ala Ser Gly Glu Ser Glu Pro Ala Lys Gly Ser Glu Glu Ala
125 130 135

Lys Gly Arg Phe Arg Val Asn Phe Val Asp Pro Ala Ala Ser Ser
140 145 150

Ser Ala Glu Asp Ser Leu Ser Asp Ala Ala Gly Val Gly Val Asp
155 160 165

-continued

```
Gly Pro Asn Val Ser Phe Gln Asn Gly Gly Asp Thr Val Leu Ser
                170                 175                 180

Glu Gly Ser Ser Leu His Ser Gly Gly Gly Gly Gly Ser Gly His
                185                 190                 195

His Gln His Tyr Tyr Tyr Asp Thr His Thr Asn Thr Tyr Tyr Leu
                200                 205                 210

Arg Thr Phe Gly His Asn Thr Met Asp Ala Val Pro Arg Ile Asp
                215                 220                 225

His Tyr Arg His Thr Ala Ala Gln Leu Gly Glu Lys Leu Leu Arg
                230                 235                 240

Pro Ser Leu Ala Glu Leu His Asp Glu Leu Glu Lys Glu Pro Phe
                245                 250                 255

Glu Asp Gly Phe Ala Asn Gly Glu Glu Ser Thr Pro Thr Arg Asp
                260                 265                 270

Ala Val Val Thr Tyr Thr Ala Glu Ser Lys Gly Val Val Lys Phe
                275                 280                 285

Gly Trp Ile Lys Gly Val Leu Val Arg Cys Met Leu Asn Ile Trp
                290                 295                 300

Gly Val Met Leu Phe Ile Arg Leu Ser Trp Ile Val Gly Gln Ala
                305                 310                 315

Gly Ile Gly Leu Ser Val Leu Val Ile Met Met Ala Thr Val Val
                320                 325                 330

Thr Thr Ile Thr Gly Leu Ser Thr Ser Ala Ile Ala Thr Asn Gly
                335                 340                 345

Phe Val Arg Gly Gly Gly Ala Tyr Tyr Leu Ile Ser Arg Ser Leu
                350                 355                 360

Gly Pro Glu Phe Gly Gly Ala Ile Gly Leu Ile Phe Ala Phe Ala
                365                 370                 375

Asn Ala Val Ala Val Ala Met Tyr Val Val Gly Phe Ala Glu Thr
                380                 385                 390

Val Val Glu Leu Leu Lys Glu His Ser Ile Leu Met Ile Asp Glu
                395                 400                 405

Ile Asn Asp Ile Arg Ile Ile Gly Ala Ile Thr Val Val Ile Leu
                410                 415                 420

Leu Gly Ile Ser Val Ala Gly Met Glu Trp Glu Ala Lys Ala Gln
                425                 430                 435

Ile Val Leu Leu Val Ile Leu Leu Leu Ala Ile Gly Asp Phe Val
                440                 445                 450

Ile Gly Thr Phe Ile Pro Leu Glu Ser Lys Lys Pro Lys Gly Phe
                455                 460                 465

Phe Gly Tyr Lys Ser Glu Ile Phe Asn Glu Asn Phe Gly Pro Asp
                470                 475                 480

Phe Arg Glu Glu Glu Thr Phe Phe Ser Val Phe Ala Ile Phe Phe
                485                 490                 495

Pro Ala Ala Thr Gly Ile Leu Ala Gly Ala Asn Ile Ser Gly Asp
                500                 505                 510

Leu Ala Asp Pro Gln Ser Ala Ile Pro Lys Gly Thr Leu Leu Ala
                515                 520                 525

Ile Leu Ile Thr Thr Leu Val Tyr Val Gly Ile Ala Val Ser Val
                530                 535                 540

Gly Ser Cys Val Val Arg Asp Ala Thr Gly Asn Val Asn Asp Thr
                545                 550                 555

Ile Val Thr Glu Leu Thr Asn Cys Thr Ser Ala Ala Cys Lys Leu
                560                 565                 570
```

Asn Phe Asp Phe Ser Ser Cys Glu Ser Ser Pro Cys Ser Tyr Gly
575 580 585

Leu Met Asn Asn Phe Gln Val Met Ser Met Val Ser Gly Phe Thr
590 595 600

Pro Leu Ile Ser Ala Gly Ile Phe Ser Ala Thr Leu Ser Ser Ala
605 610 615

Leu Ala Ser Leu Val Ser Ala Pro Lys Ile Phe Gln Ala Leu Cys
620 625 630

Lys Asp Asn Ile Tyr Pro Ala Phe Gln Met Phe Ala Lys Gly Tyr
635 640 645

Gly Lys Asn Asn Glu Pro Leu Arg Gly Tyr Ile Leu Thr Phe Leu
650 655 660

Ile Ala Leu Gly Phe Ile Leu Ile Ala Glu Leu Asn Val Ile Ala
665 670 675

Pro Ile Ile Ser Asn Phe Phe Leu Ala Ser Tyr Ala Leu Ile Asn
680 685 690

Phe Ser Val Phe His Ala Ser Leu Ala Lys Ser Pro Gly Trp Arg
695 700 705

Pro Ala Phe Lys Tyr Tyr Asn Met Trp Ile Ser Leu Leu Gly Ala
710 715 720

Ile Leu Cys Cys Ile Val Met Phe Val Ile Asn Trp Trp Ala Ala
725 730 735

Leu Leu Thr Tyr Val Ile Val Leu Gly Leu Tyr Ile Tyr Val Thr
740 745 750

Tyr Lys Lys Pro Asp Val Asn Trp Gly Ser Ser Thr Gln Ala Leu
755 760 765

Thr Tyr Leu Asn Ala Leu Gln His Ser Ile Arg Leu Ser Gly Val
770 775 780

Glu Asp His Val Lys Asn Phe Arg Pro Gln Cys Leu Val Met Thr
785 790 795

Gly Ala Pro Asn Ser Arg Pro Ala Leu Leu His Leu Val His Asp
800 805 810

Phe Thr Lys Asn Val Gly Leu Met Ile Cys Gly His Val His Met
815 820 825

Gly Pro Arg Arg Gln Ala Met Lys Glu Met Ser Ile Asp Gln Ala
830 835 840

Lys Tyr Gln Arg Trp Leu Ile Lys Asn Lys Met Lys Ala Phe Tyr
845 850 855

Ala Pro Val His Ala Asp Asp Leu Arg Glu Gly Ala Gln Tyr Leu
860 865 870

Met Gln Ala Ala Gly Leu Gly Arg Met Lys Pro Asn Thr Leu Val
875 880 885

Leu Gly Phe Lys Lys Asp Trp Leu Gln Ala Asp Met Arg Asp Val
890 895 900

Asp Met Tyr Ile Asn Leu Phe His Asp Ala Phe Asp Ile Gln Tyr
905 910 915

Gly Val Val Val Ile Arg Leu Lys Glu Gly Leu Asp Ile Ser His
920 925 930

Leu Gln Gly Gln Glu Glu Leu Leu Ser Ser Gln Glu Lys Ser Pro
935 940 945

Gly Thr Lys Asp Val Val Val Ser Val Glu Tyr Ser Lys Lys Ser
950 955 960

Asp Leu Asp Thr Ser Lys Pro Leu Ser Glu Lys Pro Ile Thr His

```
                965                 970                 975

Lys Val Glu Glu Glu Asp Gly Lys Thr Ala Thr Gln Pro Leu Leu
                980                 985                 990

Lys Lys Glu Ser Lys Gly Pro Ile Val Pro Leu Asn Val Ala Asp
                995                 1000                1005

Gln Lys Leu Leu Glu Ala Ser Thr Gln Phe Gln Lys Lys Gln Gly
                1010                1015                1020

Lys Asn Thr Ile Asp Val Trp Trp Leu Phe Asp Asp Gly Gly Leu
                1025                1030                1035

Thr Leu Leu Ile Pro Tyr Leu Leu Thr Thr Lys Lys Lys Trp Lys
                1040                1045                1050

Asp Cys Lys Ile Arg Val Phe Ile Gly Gly Lys Ile Asn Arg Ile
                1055                1060                1065

Asp His Asp Arg Arg Ala Met Ala Thr Leu Leu Ser Lys Phe Arg
                1070                1075                1080

Ile Asp Phe Ser Asp Ile Met Val Leu Gly Asp Ile Asn Thr Lys
                1085                1090                1095

Pro Lys Lys Glu Asn Ile Ile Ala Phe Glu Glu Ile Ile Glu Pro
                1100                1105                1110

Tyr Arg Leu His Glu Asp Asp Lys Glu Gln Asp Ile Ala Asp Lys
                1115                1120                1125

Met Lys Glu Asp Glu Pro Trp Arg Ile Thr Asp Asn Glu Leu Glu
                1130                1135                1140

Leu Tyr Lys Thr Lys Thr Tyr Arg Gln Ile Arg Leu Asn Glu Leu
                1145                1150                1155

Leu Lys Glu His Ser Ser Thr Ala Asn Ile Ile Val Met Ser Leu
                1160                1165                1170

Pro Val Ala Arg Lys Gly Ala Val Ser Ser Ala Leu Tyr Met Ala
                1175                1180                1185

Trp Leu Glu Ala Leu Ser Lys Asp Leu Pro Pro Ile Leu Leu Val
                1190                1195                1200

Arg Gly Asn His Gln Ser Val Leu Thr Phe Tyr Ser
                1205                1210


<210> SEQ ID NO 81
<211> LENGTH: 674
<212> TYPE: PRT
<213> ORGANISM: Homo Sapien

<400> SEQUENCE: 81

Met Ala Thr Ala Val Ser Arg Pro Cys Ala Gly Arg Ser Arg Asp
  1               5                  10                  15

Ile Leu Trp Arg Val Leu Gly Trp Arg Ile Val Ala Ser Ile Val
                 20                  25                  30

Trp Ser Val Leu Phe Leu Pro Ile Cys Thr Thr Val Phe Ile Ile
                 35                  40                  45

Phe Ser Arg Ile Asp Leu Phe His Pro Ile Gln Trp Leu Ser Asp
                 50                  55                  60

Ser Phe Ser Asp Leu Tyr Ser Ser Tyr Val Ile Phe Tyr Phe Leu
                 65                  70                  75

Leu Leu Ser Val Val Ile Ile Ile Ile Ser Ile Phe Asn Val Glu
                 80                  85                  90

Phe Tyr Ala Val Val Pro Ser Ile Pro Cys Ser Arg Leu Ala Leu
                 95                 100                 105

Ile Gly Lys Ile Ile His Pro Gln Gln Leu Met His Ser Phe Ile
```

-continued

```
                110                 115                 120

His Ala Ala Met Gly Met Val Met Ala Trp Cys Ala Ala Val Ile
                125                 130                 135

Thr Gln Gly Gln Tyr Ser Phe Leu Val Val Pro Cys Thr Gly Thr
                140                 145                 150

Asn Ser Phe Gly Ser Pro Ala Ala Gln Thr Cys Leu Asn Glu Tyr
                155                 160                 165

His Leu Phe Phe Leu Leu Thr Gly Ala Phe Met Gly Tyr Ser Tyr
                170                 175                 180

Ser Leu Leu Tyr Phe Val Asn Asn Met Asn Tyr Leu Pro Phe Pro
                185                 190                 195

Ile Ile Gln Gln Tyr Lys Phe Leu Arg Phe Arg Arg Ser Leu Leu
                200                 205                 210

Leu Leu Val Lys His Ser Cys Val Glu Ser Leu Phe Leu Val Arg
                215                 220                 225

Asn Phe Cys Ile Leu Tyr Tyr Phe Leu Gly Tyr Ile Pro Lys Ala
                230                 235                 240

Trp Ile Ser Thr Ala Met Asn Leu His Ile Asp Glu Gln Val His
                245                 250                 255

Arg Pro Leu Asp Thr Val Ser Gly Leu Leu Asn Leu Ser Leu Leu
                260                 265                 270

Tyr His Val Trp Leu Cys Gly Val Phe Leu Leu Thr Thr Trp Tyr
                275                 280                 285

Val Ser Trp Ile Leu Phe Lys Ile Tyr Ala Thr Glu Ala His Val
                290                 295                 300

Phe Pro Val Gln Pro Pro Phe Ala Glu Gly Ser Asp Glu Cys Leu
                305                 310                 315

Pro Lys Val Leu Asn Ser Asn Pro Pro Pro Ile Ile Lys Tyr Leu
                320                 325                 330

Ala Leu Gln Asp Leu Met Leu Leu Ser Gln Tyr Ser Pro Ser Arg
                335                 340                 345

Arg Gln Glu Val Phe Ser Leu Ser Gln Pro Gly Gly His Pro His
                350                 355                 360

Asn Trp Thr Ala Ile Ser Arg Glu Cys Leu Asn Leu Leu Asn Gly
                365                 370                 375

Met Thr Gln Lys Leu Ile Leu Tyr Gln Glu Ala Ala Ala Thr Asn
                380                 385                 390

Gly Arg Val Ser Ser Ser Tyr Pro Val Glu Pro Lys Lys Leu Asn
                395                 400                 405

Ser Pro Glu Glu Thr Ala Phe Gln Thr Pro Lys Ser Ser Gln Met
                410                 415                 420

Pro Arg Pro Ser Val Pro Pro Leu Val Lys Thr Ser Leu Phe Ser
                425                 430                 435

Ser Lys Leu Ser Thr Pro Asp Val Val Ser Pro Phe Gly Thr Pro
                440                 445                 450

Phe Gly Ser Ser Val Met Asn Arg Met Ala Gly Ile Phe Asp Val
                455                 460                 465

Asn Thr Cys Tyr Gly Ser Pro Gln Ser Pro Gln Leu Ile Arg Arg
                470                 475                 480

Gly Pro Arg Leu Trp Thr Ser Ala Ser Asp Gln Gln Met Thr Glu
                485                 490                 495

Phe Ser Asn Pro Ser Pro Ser Thr Ser Ile Ser Ala Glu Gly Lys
                500                 505                 510
```

```
Thr Met Arg Gln Pro Ser Val Ile Tyr Ser Trp Ile Gln Asn Lys
                515                 520                 525

Arg Glu Gln Ile Lys Asn Phe Leu Ser Lys Arg Val Leu Ile Met
                530                 535                 540

Tyr Phe Phe Ser Lys His Pro Glu Ala Ser Ile Gln Ala Val Phe
                545                 550                 555

Ser Asp Ala Gln Met His Ile Trp Ala Leu Glu Gly Leu Ser His
                560                 565                 570

Leu Val Ala Ala Ser Phe Thr Glu Asp Arg Phe Gly Val Val Gln
                575                 580                 585

Thr Thr Leu Pro Ala Ile Leu Asn Thr Leu Leu Thr Leu Gln Glu
                590                 595                 600

Ala Val Asp Lys Tyr Phe Lys Leu Pro His Ala Ser Ser Lys Pro
                605                 610                 615

Pro Arg Ile Ser Gly Ser Leu Val Asp Thr Ser Tyr Lys Thr Leu
                620                 625                 630

Arg Phe Ala Phe Arg Ala Ser Leu Lys Thr Ala Ile Tyr Arg Ile
                635                 640                 645

Thr Thr Thr Phe Gly Glu His Leu Asn Ala Val Gln Ala Ser Ala
                650                 655                 660

Glu His Gln Lys Arg Leu Gln Gln Phe Leu Glu Phe Lys Glu
                665                 670


<210> SEQ ID NO 82
<211> LENGTH: 1321
<212> TYPE: PRT
<213> ORGANISM: Homo Sapien

<400> SEQUENCE: 82

Met Gly Ala Pro Phe Val Trp Ala Leu Gly Leu Leu Met Leu Gln
  1               5                  10                  15

Met Leu Leu Phe Val Ala Gly Glu Gln Gly Thr Gln Asp Ile Thr
                 20                  25                  30

Asp Ala Ser Glu Arg Gly Leu His Met Gln Lys Leu Gly Ser Gly
                 35                  40                  45

Ser Val Gln Ala Ala Leu Ala Glu Leu Val Ala Leu Pro Cys Leu
                 50                  55                  60

Phe Thr Leu Gln Pro Arg Pro Ser Ala Ala Arg Asp Ala Pro Arg
                 65                  70                  75

Ile Lys Trp Thr Lys Val Arg Thr Ala Ser Gly Gln Arg Gln Asp
                 80                  85                  90

Leu Pro Ile Leu Val Ala Lys Asp Asn Val Val Arg Val Ala Lys
                 95                 100                 105

Ser Trp Gln Gly Arg Val Ser Leu Pro Ser Tyr Pro Arg Arg Arg
                110                 115                 120

Ala Asn Ala Thr Leu Leu Leu Gly Pro Leu Arg Ala Ser Asp Ser
                125                 130                 135

Gly Leu Tyr Arg Cys Gln Val Val Arg Gly Ile Glu Asp Glu Gln
                140                 145                 150

Asp Leu Val Pro Leu Glu Val Thr Gly Val Val Phe His Tyr Arg
                155                 160                 165

Ser Ala Arg Asp Arg Tyr Ala Leu Thr Phe Ala Glu Ala Gln Glu
                170                 175                 180

Ala Cys Arg Leu Ser Ser Ala Ile Ile Ala Ala Pro Arg His Leu
                185                 190                 195
```

```
Gln Ala Ala Phe Glu Asp Gly Phe Asp Asn Cys Asp Ala Gly Trp
                200                 205                 210

Leu Ser Asp Arg Thr Val Arg Tyr Pro Ile Thr Gln Ser Arg Pro
                215                 220                 225

Gly Cys Tyr Gly Asp Arg Ser Ser Leu Pro Gly Val Arg Ser Tyr
                230                 235                 240

Gly Arg Arg Asn Pro Gln Glu Leu Tyr Asp Val Tyr Cys Phe Ala
                245                 250                 255

Arg Glu Leu Gly Gly Glu Val Phe Tyr Val Gly Pro Ala Arg Arg
                260                 265                 270

Leu Thr Leu Ala Gly Ala Arg Ala Gln Cys Arg Arg Gln Gly Ala
                275                 280                 285

Ala Leu Ala Ser Val Gly Gln Leu His Leu Ala Trp His Glu Gly
                290                 295                 300

Leu Asp Gln Cys Asp Pro Gly Trp Leu Ala Asp Gly Ser Val Arg
                305                 310                 315

Tyr Pro Ile Gln Thr Pro Arg Arg Arg Cys Gly Gly Pro Ala Pro
                320                 325                 330

Gly Val Arg Thr Val Tyr Arg Phe Ala Asn Arg Thr Gly Phe Pro
                335                 340                 345

Ser Pro Ala Glu Arg Phe Asp Ala Tyr Cys Phe Arg Ala His His
                350                 355                 360

Pro Thr Ser Gln His Gly Asp Leu Glu Thr Pro Ser Ser Gly Asp
                365                 370                 375

Glu Gly Glu Ile Leu Ser Ala Glu Gly Pro Pro Val Arg Glu Leu
                380                 385                 390

Glu Pro Thr Leu Glu Glu Glu Glu Val Val Thr Pro Asp Phe Gln
                395                 400                 405

Glu Pro Leu Val Ser Ser Gly Glu Glu Glu Thr Leu Ile Leu Glu
                410                 415                 420

Glu Lys Gln Glu Ser Gln Gln Thr Leu Ser Pro Thr Pro Gly Asp
                425                 430                 435

Pro Met Leu Ala Ser Trp Pro Thr Gly Glu Val Trp Leu Ser Thr
                440                 445                 450

Val Ala Pro Ser Pro Ser Asp Met Gly Ala Gly Thr Ala Ala Ser
                455                 460                 465

Ser His Thr Glu Val Ala Pro Thr Asp Pro Met Pro Arg Arg Arg
                470                 475                 480

Gly Arg Phe Lys Gly Leu Asn Gly Arg Tyr Phe Gln Gln Gln Glu
                485                 490                 495

Pro Glu Pro Gly Leu Gln Gly Gly Met Glu Ala Ser Ala Gln Pro
                500                 505                 510

Pro Thr Ser Glu Ala Ala Val Asn Gln Met Glu Pro Pro Leu Ala
                515                 520                 525

Met Ala Val Thr Glu Met Leu Gly Ser Gly Gln Ser Arg Ser Pro
                530                 535                 540

Trp Ala Asp Leu Thr Asn Glu Val Asp Met Pro Gly Ala Gly Ser
                545                 550                 555

Ala Gly Gly Lys Ser Ser Pro Glu Pro Trp Leu Trp Pro Pro Thr
                560                 565                 570

Met Val Pro Pro Ser Ile Ser Gly His Ser Arg Ala Pro Val Leu
                575                 580                 585

Glu Leu Glu Lys Ala Glu Gly Pro Ser Ala Arg Pro Ala Thr Pro
                590                 595                 600
```

-continued

```
Asp Leu Phe Trp Ser Pro Leu Glu Ala Thr Val Ser Ala Pro Ser
                605                 610                 615

Pro Ala Pro Trp Glu Ala Phe Pro Val Ala Thr Ser Pro Asp Leu
                620                 625                 630

Pro Met Met Ala Met Leu Arg Gly Pro Lys Glu Trp Met Leu Pro
                635                 640                 645

His Pro Thr Pro Ile Ser Thr Glu Ala Asn Arg Val Glu Ala His
                650                 655                 660

Gly Glu Ala Thr Ala Thr Ala Pro Pro Ser Pro Ala Ala Glu Thr
                665                 670                 675

Lys Val Tyr Ser Leu Pro Leu Ser Leu Thr Pro Thr Gly Gln Gly
                680                 685                 690

Gly Glu Ala Met Pro Thr Thr Pro Glu Ser Pro Arg Ala Asp Phe
                695                 700                 705

Arg Glu Thr Gly Glu Thr Ser Pro Ala Gln Val Asn Lys Ala Glu
                710                 715                 720

His Ser Ser Ser Ser Pro Trp Pro Ser Val Asn Arg Asn Val Ala
                725                 730                 735

Val Gly Phe Val Pro Thr Glu Thr Ala Thr Glu Pro Thr Gly Leu
                740                 745                 750

Arg Gly Ile Pro Gly Ser Glu Ser Gly Val Phe Asp Thr Ala Glu
                755                 760                 765

Ser Pro Thr Ser Gly Leu Gln Ala Thr Val Asp Glu Val Gln Asp
                770                 775                 780

Pro Trp Pro Ser Val Tyr Ser Lys Gly Leu Asp Ala Ser Ser Pro
                785                 790                 795

Ser Ala Pro Leu Gly Ser Pro Gly Val Phe Leu Val Pro Lys Val
                800                 805                 810

Thr Pro Asn Leu Glu Pro Trp Val Ala Thr Asp Glu Gly Pro Thr
                815                 820                 825

Val Asn Pro Met Asp Ser Thr Val Thr Pro Ala Pro Ser Asp Ala
                830                 835                 840

Ser Gly Ile Trp Glu Pro Gly Ser Gln Val Phe Glu Glu Ala Glu
                845                 850                 855

Ser Thr Thr Leu Ser Pro Gln Val Ala Leu Asp Thr Ser Ile Val
                860                 865                 870

Thr Pro Leu Thr Thr Leu Glu Gln Gly Asp Lys Val Gly Val Pro
                875                 880                 885

Ala Met Ser Thr Leu Gly Ser Ser Ser Ser Gln Pro His Pro Glu
                890                 895                 900

Pro Glu Asp Gln Val Glu Thr Gln Gly Thr Ser Gly Ala Ser Val
                905                 910                 915

Pro Pro His Gln Ser Ser Pro Leu Gly Lys Pro Ala Val Pro Pro
                920                 925                 930

Gly Thr Pro Thr Ala Ala Ser Val Gly Glu Ser Ala Ser Val Ser
                935                 940                 945

Ser Gly Glu Pro Thr Val Pro Trp Asp Pro Ser Ser Thr Leu Leu
                950                 955                 960

Pro Val Thr Leu Gly Ile Glu Asp Phe Glu Leu Glu Val Leu Ala
                965                 970                 975

Gly Ser Pro Gly Val Glu Ser Phe Trp Glu Glu Val Ala Ser Gly
                980                 985                 990

Glu Glu Pro Ala Leu Pro Gly Thr Pro Met Asn Ala Gly Ala Glu
```

995 1000 1005

Glu Val His Ser Asp Pro Cys Glu Asn Asn Pro Cys Leu His Gly
1010 1015 1020

Gly Thr Cys Asn Ala Asn Gly Thr Met Tyr Gly Cys Ser Cys Asp
1025 1030 1035

Gln Gly Phe Ala Gly Glu Asn Cys Glu Ile Asp Ile Asp Asp Cys
1040 1045 1050

Leu Cys Ser Pro Cys Glu Asn Gly Gly Thr Cys Ile Asp Glu Val
1055 1060 1065

Asn Gly Phe Val Cys Leu Cys Leu Pro Ser Tyr Gly Gly Ser Phe
1070 1075 1080

Cys Glu Lys Asp Thr Glu Gly Cys Asp Arg Gly Trp His Lys Phe
1085 1090 1095

Gln Gly His Cys Tyr Arg Tyr Phe Ala His Arg Arg Ala Trp Glu
1100 1105 1110

Asp Ala Glu Lys Asp Cys Arg Arg Arg Ser Gly His Leu Thr Ser
1115 1120 1125

Val His Ser Pro Glu Glu His Ser Phe Ile Asn Ser Phe Gly His
1130 1135 1140

Glu Asn Thr Trp Ile Gly Leu Asn Asp Arg Ile Val Glu Arg Asp
1145 1150 1155

Phe Gln Trp Thr Asp Asn Thr Gly Leu Gln Phe Glu Asn Trp Arg
1160 1165 1170

Glu Asn Gln Pro Asp Asn Phe Phe Ala Gly Gly Glu Asp Cys Val
1175 1180 1185

Val Met Val Ala His Glu Ser Gly Arg Trp Asn Asp Val Pro Cys
1190 1195 1200

Asn Tyr Asn Leu Pro Tyr Val Cys Lys Lys Gly Thr Val Leu Cys
1205 1210 1215

Gly Pro Pro Pro Ala Val Glu Asn Ala Ser Leu Ile Gly Ala Arg
1220 1225 1230

Lys Ala Lys Asn Asn Val His Ala Thr Val Arg Tyr Gln Cys Asn
1235 1240 1245

Glu Gly Phe Ala Gln His His Val Val Thr Ile Arg Cys Arg Ser
1250 1255 1260

Asn Gly Lys Trp Asp Arg Pro Gln Ile Val Cys Thr Lys Pro Arg
1265 1270 1275

Arg Ser His Arg Met Arg Gly His His His His His Gln His His
1280 1285 1290

His Gln His His His His Lys Ser Arg Lys Glu Arg Arg Lys His
1295 1300 1305

Lys Lys His Pro Thr Glu Asp Trp Glu Lys Asp Glu Gly Asn Phe
1310 1315 1320

Cys

<210> SEQ ID NO 83
<211> LENGTH: 696
<212> TYPE: PRT
<213> ORGANISM: Homo Sapien

<400> SEQUENCE: 83

Met Lys Phe Ala Glu His Leu Ser Ala His Ile Thr Pro Glu Trp
1 5 10 15

Arg Lys Gln Tyr Ile Gln Tyr Glu Ala Phe Lys Asp Met Leu Tyr
20 25 30

```
Ser Ala Gln Asp Gln Ala Pro Ser Val Glu Val Thr Asp Glu Asp
                35                  40                  45

Thr Val Lys Arg Tyr Phe Ala Lys Phe Glu Glu Lys Phe Phe Gln
                50                  55                  60

Thr Cys Glu Lys Glu Leu Ala Lys Ile Asn Thr Phe Tyr Ser Glu
                65                  70                  75

Lys Leu Ala Glu Ala Gln Arg Arg Phe Ala Thr Leu Gln Asn Glu
                80                  85                  90

Leu Gln Ser Ser Leu Asp Ala Gln Lys Glu Ser Thr Gly Val Thr
                95                 100                 105

Thr Leu Arg Gln Arg Arg Lys Pro Val Phe His Leu Ser His Glu
               110                 115                 120

Glu Arg Val Gln His Arg Asn Ile Lys Asp Leu Lys Leu Ala Phe
               125                 130                 135

Ser Glu Phe Tyr Leu Ser Leu Ile Leu Leu Gln Asn Tyr Gln Asn
               140                 145                 150

Leu Asn Phe Thr Gly Phe Arg Lys Ile Leu Lys Lys His Asp Lys
               155                 160                 165

Ile Leu Glu Thr Ser Arg Gly Ala Asp Trp Arg Val Ala His Val
               170                 175                 180

Glu Val Ala Pro Phe Tyr Thr Cys Lys Lys Ile Asn Gln Leu Ile
               185                 190                 195

Ser Glu Thr Glu Ala Val Val Thr Asn Glu Leu Glu Asp Gly Asp
               200                 205                 210

Arg Gln Lys Ala Met Lys Arg Leu Arg Val Pro Pro Leu Gly Ala
               215                 220                 225

Ala Gln Pro Ala Pro Ala Trp Thr Thr Phe Arg Val Gly Leu Phe
               230                 235                 240

Cys Gly Ile Phe Ile Val Leu Asn Ile Thr Leu Val Leu Ala Ala
               245                 250                 255

Val Phe Lys Leu Glu Thr Asp Arg Ser Ile Trp Pro Leu Ile Arg
               260                 265                 270

Ile Tyr Arg Gly Gly Phe Leu Leu Ile Glu Phe Leu Phe Leu Leu
               275                 280                 285

Gly Ile Asn Thr Tyr Gly Trp Arg Gln Ala Gly Val Asn His Val
               290                 295                 300

Leu Ile Phe Glu Leu Asn Pro Arg Ser Asn Leu Ser His Gln His
               305                 310                 315

Leu Phe Glu Ile Ala Gly Phe Leu Gly Ile Leu Trp Cys Leu Ser
               320                 325                 330

Leu Leu Ala Cys Phe Phe Ala Pro Ile Ser Val Ile Pro Thr Tyr
               335                 340                 345

Val Tyr Pro Leu Ala Leu Tyr Gly Phe Met Val Phe Phe Leu Ile
               350                 355                 360

Asn Pro Thr Lys Thr Phe Tyr Tyr Lys Ser Arg Phe Trp Leu Leu
               365                 370                 375

Lys Leu Leu Phe Arg Val Phe Thr Ala Pro Phe His Lys Val Gly
               380                 385                 390

Phe Ala Asp Phe Trp Leu Ala Asp Gln Leu Asn Ser Leu Ser Val
               395                 400                 405

Ile Leu Met Asp Leu Glu Tyr Met Ile Cys Phe Tyr Ser Leu Glu
               410                 415                 420

Leu Lys Trp Asp Glu Ser Lys Gly Leu Leu Pro Asn Asn Ser Glu
```

```
                425                 430                 435

Glu Ser Gly Ile Cys His Lys Tyr Thr Tyr Gly Val Arg Ala Ile
                440                 445                 450

Val Gln Cys Ile Pro Ala Trp Leu Arg Phe Ile Gln Cys Leu Arg
                455                 460                 465

Arg Tyr Arg Asp Thr Lys Arg Ala Phe Pro His Leu Val Asn Ala
                470                 475                 480

Gly Lys Tyr Ser Thr Thr Phe Phe Met Val Ala Phe Ala Ala Leu
                485                 490                 495

Tyr Ser Thr His Lys Glu Arg Gly His Ser Asp Thr Met Val Phe
                500                 505                 510

Phe Tyr Leu Trp Ile Val Phe Tyr Ile Ile Ser Ser Cys Tyr Thr
                515                 520                 525

Leu Ile Trp Asp Leu Lys Met Asp Trp Gly Leu Phe Asp Lys Asn
                530                 535                 540

Ala Gly Glu Asn Thr Phe Leu Arg Glu Glu Ile Val Tyr Pro Gln
                545                 550                 555

Lys Ala Tyr Tyr Tyr Cys Ala Ile Ile Glu Asp Val Ile Leu Arg
                560                 565                 570

Phe Ala Trp Thr Ile Gln Ile Ser Ile Thr Ser Thr Thr Leu Leu
                575                 580                 585

Pro His Ser Gly Asp Ile Ile Ala Thr Val Phe Ala Pro Leu Glu
                590                 595                 600

Val Phe Arg Arg Phe Val Trp Asn Phe Phe Arg Leu Glu Asn Glu
                605                 610                 615

His Leu Asn Asn Cys Gly Glu Phe Arg Ala Val Arg Asp Ile Ser
                620                 625                 630

Val Ala Pro Leu Asn Ala Asp Asp Gln Thr Leu Leu Glu Gln Met
                635                 640                 645

Met Asp Gln Asp Asp Gly Val Arg Asn Arg Gln Lys Asn Arg Ser
                650                 655                 660

Trp Lys Tyr Asn Gln Ser Ile Ser Leu Arg Arg Pro Arg Leu Ala
                665                 670                 675

Ser Gln Ser Lys Ala Arg Asp Thr Lys Val Leu Ile Glu Asp Thr
                680                 685                 690

Asp Asp Glu Ala Asn Thr
                695


<210> SEQ ID NO 84
<211> LENGTH: 696
<212> TYPE: PRT
<213> ORGANISM: Homo Sapien

<400> SEQUENCE: 84

Met Lys Phe Ala Glu His Leu Ser Ala His Ile Thr Pro Glu Trp
  1               5                  10                  15

Arg Lys Gln Tyr Ile Gln Tyr Glu Ala Phe Lys Asp Met Leu Tyr
                 20                  25                  30

Ser Ala Gln Asp Gln Ala Pro Ser Val Glu Val Thr Asp Glu Asp
                 35                  40                  45

Thr Val Lys Arg Tyr Phe Ala Lys Phe Glu Glu Lys Phe Phe Gln
                 50                  55                  60

Thr Cys Glu Lys Glu Leu Ala Lys Ile Asn Thr Phe Tyr Ser Glu
                 65                  70                  75

Lys Leu Ala Glu Ala Gln Arg Arg Phe Ala Thr Leu Gln Asn Glu
```

-continued

```
                80                  85                  90

Leu Gln Ser Ser Leu Asp Ala Gln Lys Glu Ser Thr Gly Val Thr
                95                  100                 105

Thr Leu Arg Gln Arg Arg Lys Pro Val Phe His Leu Ser His Glu
                110                 115                 120

Glu Arg Val Gln His Arg Asn Ile Lys Asp Leu Lys Leu Ala Phe
                125                 130                 135

Ser Glu Phe Tyr Leu Ser Leu Ile Leu Leu Gln Asn Tyr Gln Asn
                140                 145                 150

Leu Asn Phe Thr Gly Phe Arg Lys Ile Leu Lys Lys His Asp Lys
                155                 160                 165

Ile Leu Glu Thr Ser Arg Gly Ala Asp Trp Arg Val Ala His Val
                170                 175                 180

Glu Val Ala Pro Phe Tyr Thr Cys Lys Lys Ile Asn Gln Leu Ile
                185                 190                 195

Ser Glu Thr Glu Ala Val Val Thr Asn Glu Leu Glu Asp Gly Asp
                200                 205                 210

Arg Gln Lys Ala Met Lys Arg Leu Arg Val Pro Pro Leu Gly Ala
                215                 220                 225

Ala Gln Pro Ala Pro Ala Trp Thr Thr Phe Arg Val Gly Leu Phe
                230                 235                 240

Cys Gly Ile Phe Ile Val Leu Asn Ile Thr Leu Val Leu Ala Ala
                245                 250                 255

Val Phe Lys Leu Glu Thr Asp Arg Ser Ile Trp Pro Leu Ile Arg
                260                 265                 270

Ile Tyr Arg Gly Gly Phe Leu Leu Ile Glu Phe Leu Phe Leu Leu
                275                 280                 285

Gly Ile Asn Thr Tyr Gly Trp Arg Gln Ala Gly Val Asn His Val
                290                 295                 300

Leu Ile Phe Glu Leu Asn Pro Arg Ser Asn Leu Ser His Gln His
                305                 310                 315

Leu Phe Glu Ile Ala Gly Phe Leu Gly Ile Leu Trp Cys Leu Ser
                320                 325                 330

Leu Leu Ala Cys Phe Phe Ala Pro Ile Ser Val Ile Pro Thr Tyr
                335                 340                 345

Val Tyr Pro Leu Ala Leu Tyr Gly Phe Met Val Phe Phe Leu Ile
                350                 355                 360

Asn Pro Thr Lys Thr Phe Tyr Tyr Lys Ser Arg Phe Trp Leu Leu
                365                 370                 375

Lys Leu Leu Phe Arg Val Phe Thr Ala Pro Phe His Lys Val Gly
                380                 385                 390

Phe Ala Asp Phe Trp Leu Ala Asp Gln Leu Asn Ser Leu Ser Val
                395                 400                 405

Ile Leu Met Asp Leu Glu Tyr Met Ile Cys Phe Tyr Ser Leu Glu
                410                 415                 420

Leu Lys Trp Asp Glu Ser Lys Gly Leu Leu Pro Asn Asn Ser Glu
                425                 430                 435

Glu Ser Gly Ile Cys His Lys Tyr Thr Tyr Gly Val Arg Ala Ile
                440                 445                 450

Val Gln Cys Ile Pro Ala Trp Leu Arg Phe Ile Gln Cys Leu Arg
                455                 460                 465

Arg Tyr Arg Asp Thr Lys Arg Ala Phe Pro His Leu Val Asn Ala
                470                 475                 480
```

```
Gly Lys Tyr Ser Thr Thr Phe Phe Met Val Thr Phe Ala Ala Leu
                485                 490                 495

Tyr Ser Thr His Lys Glu Arg Gly His Ser Asp Thr Met Val Phe
                500                 505                 510

Phe Tyr Leu Trp Ile Val Phe Tyr Ile Ile Ser Ser Cys Tyr Thr
                515                 520                 525

Leu Ile Trp Asp Leu Lys Met Asp Trp Gly Leu Phe Asp Lys Asn
                530                 535                 540

Ala Gly Glu Asn Thr Phe Leu Arg Glu Glu Ile Val Tyr Pro Gln
                545                 550                 555

Lys Ala Tyr Tyr Tyr Cys Ala Ile Ile Glu Asp Val Ile Leu Arg
                560                 565                 570

Phe Ala Trp Thr Ile Gln Ile Ser Ile Thr Ser Thr Thr Leu Leu
                575                 580                 585

Pro His Ser Gly Asp Ile Ile Ala Thr Val Phe Ala Pro Leu Glu
                590                 595                 600

Val Phe Arg Arg Phe Val Trp Asn Phe Phe Arg Leu Glu Asn Glu
                605                 610                 615

His Leu Asn Asn Cys Gly Glu Phe Arg Ala Val Arg Asp Ile Ser
                620                 625                 630

Val Ala Pro Leu Asn Ala Asp Asp Gln Thr Leu Leu Glu Gln Met
                635                 640                 645

Met Asp Gln Asp Asp Gly Val Arg Asn Arg Gln Lys Asn Arg Ser
                650                 655                 660

Trp Lys Tyr Asn Gln Ser Ile Ser Leu Arg Arg Pro Arg Leu Ala
                665                 670                 675

Ser Gln Ser Lys Ala Arg Asp Thr Lys Val Leu Ile Glu Asp Thr
                680                 685                 690

Asp Asp Glu Ala Asn Thr
                695
```

<210> SEQ ID NO 85
<211> LENGTH: 635
<212> TYPE: PRT
<213> ORGANISM: Homo Sapien

<400> SEQUENCE: 85

```
Met Ser Val Gly Val Ser Thr Ser Ala Pro Leu Ser Pro Thr Ser
  1               5                  10                  15

Gly Thr Ser Val Gly Met Ser Thr Phe Ser Ile Met Asp Tyr Val
                 20                  25                  30

Val Phe Val Leu Leu Leu Val Leu Ser Leu Ala Ile Gly Leu Tyr
                 35                  40                  45

His Ala Cys Arg Gly Trp Gly Arg His Thr Val Gly Glu Leu Leu
                 50                  55                  60

Met Ala Asp Arg Lys Met Gly Cys Leu Pro Val Ala Leu Ser Leu
                 65                  70                  75

Leu Ala Thr Phe Gln Ser Ala Val Ala Ile Leu Gly Val Pro Ser
                 80                  85                  90

Glu Ile Tyr Arg Phe Gly Thr Gln Tyr Trp Phe Leu Gly Cys Cys
                 95                 100                 105

Tyr Phe Leu Gly Leu Leu Ile Pro Ala His Ile Phe Ile Pro Val
                110                 115                 120

Phe Tyr Arg Leu His Leu Thr Ser Ala Tyr Glu Tyr Leu Glu Leu
                125                 130                 135
```

-continued

```
Arg Phe Asn Lys Thr Val Arg Val Cys Gly Thr Val Thr Phe Ile
                140                 145                 150

Phe Gln Met Val Ile Tyr Met Gly Val Val Leu Tyr Ala Pro Ser
                155                 160                 165

Leu Ala Leu Asn Ala Val Thr Gly Phe Asp Leu Trp Leu Ser Val
                170                 175                 180

Leu Ala Leu Gly Ile Val Cys Thr Val Tyr Thr Ala Leu Gly Gly
                185                 190                 195

Leu Lys Ala Val Ile Trp Thr Asp Val Phe Gln Thr Leu Val Met
                200                 205                 210

Phe Leu Gly Gln Leu Ala Val Ile Ile Val Gly Ser Ala Lys Val
                215                 220                 225

Gly Gly Leu Gly Arg Val Trp Ala Val Ala Ser Gln His Gly Arg
                230                 235                 240

Ile Ser Gly Phe Glu Leu Asp Pro Asp Pro Phe Val Arg His Thr
                245                 250                 255

Phe Trp Thr Leu Ala Phe Gly Gly Val Phe Met Met Leu Ser Leu
                260                 265                 270

Tyr Gly Val Asn Gln Ala Gln Val Gln Arg Tyr Leu Ser Ser Arg
                275                 280                 285

Thr Glu Lys Ala Ala Val Leu Ser Cys Tyr Ala Val Phe Pro Phe
                290                 295                 300

Gln Gln Val Ser Leu Cys Val Gly Cys Leu Ile Gly Leu Val Met
                305                 310                 315

Phe Ala Tyr Tyr Gln Glu Tyr Pro Met Ser Ile Gln Gln Ala Gln
                320                 325                 330

Ala Ala Pro Asp Gln Phe Val Leu Tyr Phe Val Met Asp Leu Leu
                335                 340                 345

Lys Gly Leu Pro Gly Leu Pro Gly Leu Phe Ile Ala Cys Leu Phe
                350                 355                 360

Ser Gly Ser Leu Ser Thr Ile Ser Ser Ala Phe Asn Ser Leu Ala
                365                 370                 375

Thr Val Thr Met Glu Asp Leu Ile Arg Pro Trp Phe Pro Glu Phe
                380                 385                 390

Ser Glu Ala Arg Ala Ile Met Leu Ser Arg Gly Leu Ala Phe Gly
                395                 400                 405

Tyr Gly Leu Leu Cys Leu Gly Met Ala Tyr Ile Ser Ser Gln Met
                410                 415                 420

Gly Pro Val Leu Gln Ala Ala Ile Ser Ile Phe Gly Met Val Gly
                425                 430                 435

Gly Pro Leu Leu Gly Leu Phe Cys Leu Gly Met Phe Phe Pro Cys
                440                 445                 450

Ala Asn Pro Pro Gly Ala Val Val Gly Leu Leu Ala Gly Leu Val
                455                 460                 465

Met Ala Phe Trp Ile Gly Ile Gly Ser Ile Val Thr Ser Met Gly
                470                 475                 480

Phe Ser Met Pro Pro Ser Pro Ser Asn Gly Ser Ser Phe Ser Leu
                485                 490                 495

Pro Thr Asn Leu Thr Val Ala Thr Val Thr Thr Leu Met Pro Leu
                500                 505                 510

Thr Thr Phe Ser Lys Pro Thr Gly Leu Gln Arg Phe Tyr Ser Leu
                515                 520                 525

Ser Tyr Leu Trp Tyr Ser Ala His Asn Ser Thr Thr Val Ile Val
                530                 535                 540
```

```
Val Gly Leu Ile Val Ser Leu Leu Thr Gly Arg Met Arg Gly Arg
                545                 550                 555

Ser Leu Asn Pro Ala Thr Ile Tyr Pro Val Leu Pro Lys Leu Leu
                560                 565                 570

Ser Leu Leu Pro Leu Ser Cys Gln Lys Arg Leu His Cys Arg Ser
                575                 580                 585

Tyr Gly Gln Asp His Leu Asp Thr Gly Leu Phe Pro Glu Lys Pro
                590                 595                 600

Arg Asn Gly Val Leu Gly Asp Ser Arg Asp Lys Glu Ala Met Ala
                605                 610                 615

Leu Asp Gly Thr Ala Tyr Gln Gly Ser Ser Ser Thr Cys Ile Leu
                620                 625                 630

Gln Glu Thr Ser Leu
                635


<210> SEQ ID NO 86
<211> LENGTH: 351
<212> TYPE: PRT
<213> ORGANISM: Homo Sapien

<400> SEQUENCE: 86

Met Ala Leu Thr Gly Ala Ser Asp Pro Ser Ala Glu Ala Glu Ala
  1               5                  10                  15

Asn Gly Glu Lys Pro Phe Leu Leu Arg Ala Leu Gln Ile Ala Leu
                 20                  25                  30

Val Val Ser Leu Tyr Trp Val Thr Ser Ile Ser Met Val Phe Leu
                 35                  40                  45

Asn Lys Tyr Leu Leu Asp Ser Pro Ser Leu Arg Leu Asp Thr Pro
                 50                  55                  60

Ile Phe Val Thr Phe Tyr Gln Cys Leu Val Thr Thr Leu Leu Cys
                 65                  70                  75

Lys Gly Leu Ser Ala Leu Ala Ala Cys Cys Pro Gly Ala Val Asp
                 80                  85                  90

Phe Pro Ser Leu Arg Leu Asp Leu Arg Val Ala Arg Ser Val Leu
                 95                 100                 105

Pro Leu Ser Val Val Phe Ile Gly Met Ile Thr Phe Asn Asn Leu
                110                 115                 120

Cys Leu Lys Tyr Val Gly Val Ala Phe Tyr Asn Val Gly Arg Ser
                125                 130                 135

Leu Thr Thr Val Phe Asn Val Leu Leu Ser Tyr Leu Leu Leu Lys
                140                 145                 150

Gln Thr Thr Ser Phe Tyr Ala Leu Leu Thr Cys Gly Ile Ile Ile
                155                 160                 165

Gly Gly Phe Trp Leu Gly Val Asp Gln Glu Gly Ala Glu Gly Thr
                170                 175                 180

Leu Ser Trp Leu Gly Thr Val Phe Gly Val Leu Ala Ser Leu Cys
                185                 190                 195

Val Ser Leu Asn Ala Ile Tyr Thr Thr Lys Val Leu Pro Ala Val
                200                 205                 210

Asp Gly Ser Ile Trp Arg Leu Thr Phe Tyr Asn Asn Val Asn Ala
                215                 220                 225

Cys Ile Leu Phe Leu Pro Leu Leu Leu Leu Leu Gly Glu Leu Gln
                230                 235                 240

Ala Leu Arg Asp Leu Ala Gln Leu Gly Ser Ala His Phe Trp Gly
                245                 250                 255
```

```
Met Met Thr Leu Gly Gly Leu Phe Gly Phe Ala Ile Gly Tyr Val
                260                 265                 270

Thr Gly Leu Gln Ile Lys Phe Thr Ser Pro Leu Thr His Asn Val
                275                 280                 285

Ser Gly Thr Ala Lys Ala Cys Ala Gln Thr Val Leu Ala Val Leu
                290                 295                 300

Tyr Tyr Glu Glu Thr Lys Ser Phe Leu Trp Trp Thr Ser Asn Met
                305                 310                 315

Met Val Leu Gly Gly Ser Ser Ala Tyr Thr Trp Val Arg Gly Trp
                320                 325                 330

Glu Met Lys Lys Thr Pro Glu Glu Pro Ser Pro Lys Asp Ser Glu
                335                 340                 345

Lys Ser Ala Met Gly Val
                350


<210> SEQ ID NO 87
<211> LENGTH: 351
<212> TYPE: PRT
<213> ORGANISM: Homo Sapien

<400> SEQUENCE: 87

Met Ala Leu Thr Gly Ala Ser Asp Pro Ser Ala Glu Ala Glu Ala
  1               5                  10                  15

Asn Gly Glu Lys Pro Phe Leu Leu Arg Ala Leu Gln Ile Ala Leu
                 20                  25                  30

Val Val Ser Leu Tyr Trp Val Thr Ser Ile Ser Met Val Phe Leu
                 35                  40                  45

Asn Lys Tyr Leu Leu Asp Ser Pro Ser Leu Arg Leu Asp Thr Pro
                 50                  55                  60

Ile Phe Val Thr Phe Tyr Gln Cys Leu Val Thr Thr Leu Leu Cys
                 65                  70                  75

Lys Gly Leu Ser Ala Leu Ala Ala Cys Cys Pro Gly Ala Val Asp
                 80                  85                  90

Phe Pro Ser Leu Arg Leu Asp Leu Arg Val Ala Arg Ser Val Leu
                 95                 100                 105

Pro Leu Ser Val Val Phe Ile Gly Met Ile Thr Phe Asn Asn Leu
                110                 115                 120

Cys Leu Lys Tyr Val Gly Val Ala Phe Tyr Asn Val Gly Arg Ser
                125                 130                 135

Leu Thr Thr Val Phe Asn Val Leu Leu Ser Tyr Leu Leu Leu Lys
                140                 145                 150

Gln Thr Thr Ser Phe Tyr Ala Leu Leu Thr Cys Gly Ile Ile Ile
                155                 160                 165

Gly Gly Phe Trp Leu Gly Val Asp Gln Glu Gly Ala Glu Gly Thr
                170                 175                 180

Leu Ser Trp Leu Gly Thr Val Phe Gly Val Leu Ala Ser Leu Cys
                185                 190                 195

Val Ser Leu Asn Ala Ile Tyr Thr Thr Lys Val Leu Pro Ala Val
                200                 205                 210

Asp Gly Ser Ile Trp Arg Leu Thr Phe Tyr Asn Asn Val Asn Ala
                215                 220                 225

Cys Ile Leu Phe Leu Pro Leu Leu Leu Leu Leu Gly Glu Leu Gln
                230                 235                 240

Ala Leu Arg Asp Phe Ala Gln Leu Gly Ser Ala His Phe Trp Gly
                245                 250                 255
```

```
Met Met Thr Leu Gly Gly Leu Phe Gly Phe Ala Ile Gly Tyr Val
                260                 265                 270

Thr Gly Leu Gln Ile Lys Phe Thr Ser Pro Leu Thr His Asn Val
                275                 280                 285

Ser Gly Thr Ala Lys Ala Cys Ala Gln Thr Val Leu Ala Val Leu
                290                 295                 300

Tyr Tyr Glu Glu Thr Lys Ser Phe Leu Trp Trp Thr Ser Asn Met
                305                 310                 315

Met Val Leu Gly Gly Ser Ser Ala Tyr Thr Trp Val Arg Gly Trp
                320                 325                 330

Glu Met Lys Lys Thr Pro Glu Glu Pro Ser Pro Lys Asp Ser Glu
                335                 340                 345

Lys Ser Ala Met Gly Val
                350


<210> SEQ ID NO 88
<211> LENGTH: 208
<212> TYPE: PRT
<213> ORGANISM: Homo Sapien

<400> SEQUENCE: 88

Met Gly Ser Cys Ser Gly Arg Cys Ala Leu Val Val Leu Cys Ala
  1               5                  10                  15

Phe Gln Leu Val Ala Ala Leu Glu Arg Gln Val Phe Asp Phe Leu
                 20                  25                  30

Gly Tyr Gln Trp Ala Pro Ile Leu Ala Asn Phe Val His Ile Ile
                 35                  40                  45

Ile Val Ile Leu Gly Leu Phe Gly Thr Ile Gln Tyr Arg Leu Arg
                 50                  55                  60

Tyr Val Met Val Tyr Thr Leu Trp Ala Ala Val Trp Val Thr Trp
                 65                  70                  75

Asn Val Phe Ile Ile Cys Phe Tyr Leu Glu Val Gly Gly Leu Leu
                 80                  85                  90

Gln Asp Ser Glu Leu Leu Thr Phe Ser Leu Ser Arg His Arg Ser
                 95                 100                 105

Trp Trp Arg Glu Arg Trp Pro Gly Cys Leu His Glu Glu Val Pro
                110                 115                 120

Ala Val Gly Leu Gly Ala Pro His Gly Gln Ala Leu Val Ser Gly
                125                 130                 135

Ala Gly Cys Ala Leu Glu Pro Ser Tyr Val Glu Ala Leu His Ser
                140                 145                 150

Gly Leu Gln Ile Leu Ile Ala Leu Leu Gly Phe Val Cys Gly Cys
                155                 160                 165

Gln Val Val Ser Val Phe Thr Glu Glu Glu Asp Ser Phe Asp Phe
                170                 175                 180

Ile Gly Gly Phe Asp Pro Phe Pro Leu Tyr His Val Asn Glu Lys
                185                 190                 195

Pro Ser Ser Leu Leu Ser Lys Gln Val Tyr Leu Pro Ala
                200                 205


<210> SEQ ID NO 89
<211> LENGTH: 208
<212> TYPE: PRT
<213> ORGANISM: Homo Sapien

<400> SEQUENCE: 89
```

```
Met Gly Ser Cys Ser Gly Arg Cys Ala Leu Val Val Leu Cys Ala
  1               5                  10                  15

Phe Gln Leu Val Ala Ala Leu Glu Arg Gln Val Phe Asp Phe Leu
                 20                  25                  30

Gly Tyr Gln Trp Ala Pro Ile Leu Ala Asn Phe Val His Ile Ile
                 35                  40                  45

Ile Val Ile Leu Gly Leu Phe Gly Thr Ile Gln Tyr Arg Leu Arg
                 50                  55                  60

Tyr Val Met Val Tyr Thr Leu Trp Ala Ala Val Trp Val Thr Trp
                 65                  70                  75

Asn Val Phe Ile Ile Cys Phe Tyr Leu Glu Val Gly Gly Leu Leu
                 80                  85                  90

Lys Asp Ser Glu Leu Leu Thr Phe Ser Leu Ser Arg His Arg Ser
                 95                 100                 105

Trp Trp Arg Glu Arg Trp Pro Gly Cys Leu His Glu Glu Val Pro
                110                 115                 120

Ala Val Gly Leu Gly Ala Pro His Gly Gln Ala Leu Val Ser Gly
                125                 130                 135

Ala Gly Cys Ala Leu Glu Pro Ser Tyr Val Glu Ala Leu His Ser
                140                 145                 150

Cys Leu Gln Ile Leu Ile Ala Leu Leu Gly Phe Val Cys Gly Cys
                155                 160                 165

Gln Val Val Ser Val Phe Thr Glu Glu Glu Asp Ser Phe Asp Phe
                170                 175                 180

Ile Gly Gly Phe Asp Pro Phe Pro Leu Tyr His Val Asn Glu Lys
                185                 190                 195

Pro Ser Ser Leu Leu Ser Lys Gln Val Tyr Leu Pro Ala
                200                 205
```

<210> SEQ ID NO 90
<211> LENGTH: 181
<212> TYPE: PRT
<213> ORGANISM: Homo Sapien

<400> SEQUENCE: 90

```
Met Gly Ser Cys Ser Gly Arg Cys Ala Leu Val Val Leu Cys Ala
  1               5                  10                  15

Phe Gln Leu Val Ala Ala Leu Glu Arg Gln Val Phe Asp Phe Leu
                 20                  25                  30

Gly Tyr Gln Trp Ala Pro Ile Leu Ala Asn Phe Val His Ile Ile
                 35                  40                  45

Ile Val Ile Leu Gly Leu Phe Gly Thr Ile Gln Tyr Arg Leu Arg
                 50                  55                  60

Tyr Val Met Val Tyr Thr Leu Trp Ala Ala Val Trp Val Thr Trp
                 65                  70                  75

Asn Val Phe Ile Ile Cys Phe Tyr Leu Glu Val Gly Gly Leu Leu
                 80                  85                  90

Lys Asp Ser Glu Leu Leu Thr Phe Ser Leu Ser Arg His Arg Ser
                 95                 100                 105

Trp Trp Arg Glu Arg Trp Pro Gly Cys Leu His Glu Glu Val Pro
                110                 115                 120

Ala Val Gly Leu Gly Ala Pro His Gly Gln Ala Leu Val Ser Gly
                125                 130                 135

Ala Gly Cys Ala Leu Glu Pro Ser Tyr Val Glu Ala Leu His Ser
                140                 145                 150
```

Cys Leu Gln Ile Leu Ile Ala Leu Leu Gly Phe Val Cys Gly Cys
155 160 165

Gln Val Val Ser Val Phe Thr Glu Glu Glu Asp Ser Cys Leu Arg
170 175 180

Lys

<210> SEQ ID NO 91
<211> LENGTH: 181
<212> TYPE: PRT
<213> ORGANISM: Homo Sapien

<400> SEQUENCE: 91

Met Gly Ser Cys Ser Gly Arg Cys Ala Leu Val Val Leu Cys Ala
1 5 10 15

Phe Gln Leu Val Ala Ala Leu Glu Arg Gln Val Phe Asp Phe Leu
20 25 30

Gly Tyr Gln Trp Ala Pro Ile Leu Ala Asn Phe Val His Ile Ile
35 40 45

Ile Val Ile Leu Gly Leu Phe Gly Thr Ile Gln Tyr Arg Leu Arg
50 55 60

Tyr Val Met Val Tyr Thr Leu Trp Ala Ala Val Trp Val Thr Trp
65 70 75

Asn Val Phe Ile Ile Cys Phe Tyr Leu Glu Val Gly Gly Leu Leu
80 85 90

Gln Asp Ser Glu Leu Leu Thr Phe Ser Leu Ser Arg His Arg Ser
95 100 105

Trp Trp Arg Glu Arg Trp Pro Gly Cys Leu His Glu Glu Val Pro
110 115 120

Ala Val Gly Leu Gly Ala Pro His Gly Gln Ala Leu Val Ser Gly
125 130 135

Ala Gly Cys Ala Leu Glu Pro Ser Tyr Val Glu Ala Leu His Ser
140 145 150

Gly Leu Gln Ile Leu Ile Ala Leu Leu Gly Phe Val Cys Gly Cys
155 160 165

Gln Val Val Ser Val Phe Thr Glu Glu Glu Asp Ser Cys Leu Arg
170 175 180

Lys

<210> SEQ ID NO 92
<211> LENGTH: 382
<212> TYPE: PRT
<213> ORGANISM: Homo Sapien

<400> SEQUENCE: 92

Met Ala Val Leu Phe Leu Leu Leu Phe Leu Cys Gly Thr Pro Gln
1 5 10 15

Ala Ala Asp Asn Met Gln Ala Ile Tyr Val Ala Leu Gly Glu Ala
20 25 30

Val Glu Leu Pro Cys Pro Ser Pro Pro Thr Leu His Gly Asp Glu
35 40 45

His Leu Ser Trp Phe Cys Ser Pro Ala Ala Gly Ser Phe Thr Thr
50 55 60

Leu Val Ala Gln Val Gln Val Gly Arg Pro Ala Pro Asp Pro Gly
65 70 75

Lys Pro Gly Arg Glu Ser Arg Leu Arg Leu Leu Gly Asn Tyr Ser
80 85 90

Leu Trp Leu Glu Gly Ser Lys Glu Glu Asp Ala Gly Arg Tyr Trp
95 100 105

Cys Ala Val Leu Gly Gln His His Asn Tyr Gln Asn Trp Arg Val
110 115 120

Tyr Asp Val Leu Val Leu Lys Gly Ser Gln Leu Ser Ala Arg Ala
125 130 135

Ala Asp Gly Ser Pro Cys Asn Val Leu Leu Cys Ser Val Val Pro
140 145 150

Ser Arg Arg Met Asp Ser Val Thr Trp Gln Glu Gly Lys Gly Pro
155 160 165

Val Arg Gly Arg Val Gln Ser Phe Trp Gly Ser Glu Ala Ala Leu
170 175 180

Leu Leu Val Cys Pro Gly Glu Gly Leu Ser Glu Pro Arg Ser Arg
185 190 195

Arg Pro Arg Ile Ile Arg Cys Leu Met Thr His Asn Lys Gly Val
200 205 210

Ser Phe Ser Leu Ala Ala Ser Ile Asp Ala Ser Pro Ala Leu Cys
215 220 225

Ala Pro Ser Thr Gly Trp Asp Met Pro Trp Ile Leu Met Leu Leu
230 235 240

Leu Thr Met Gly Gln Gly Val Val Ile Leu Ala Leu Ser Ile Val
245 250 255

Leu Trp Arg Gln Arg Val Arg Gly Ala Pro Gly Arg Gly Asn Arg
260 265 270

Met Arg Cys Tyr Asn Cys Gly Gly Ser Pro Ser Ser Ser Cys Lys
275 280 285

Glu Ala Val Thr Thr Cys Gly Glu Gly Arg Pro Gln Pro Gly Leu
290 295 300

Glu Gln Ile Lys Leu Pro Gly Asn Pro Pro Val Thr Leu Ile His
305 310 315

Gln His Pro Ala Cys Val Ala Ala His His Cys Asn Gln Val Glu
320 325 330

Thr Glu Ser Val Gly Asp Val Thr Tyr Pro Ala His Arg Asp Cys
335 340 345

Tyr Leu Gly Asp Leu Cys Asn Ser Ala Val Ala Ser His Val Ala
350 355 360

Pro Ala Gly Ile Leu Ala Ala Ala Ala Thr Ala Leu Thr Cys Leu
365 370 375

Leu Pro Gly Leu Trp Ser Gly
380

<210> SEQ ID NO 93
<211> LENGTH: 783
<212> TYPE: PRT
<213> ORGANISM: Homo Sapien

<400> SEQUENCE: 93

Met Ser Gly Gly His Gln Leu Gln Leu Ala Ala Leu Trp Pro Trp
1 5 10 15

Leu Leu Met Ala Thr Leu Gln Ala Gly Phe Gly Arg Thr Gly Leu
20 25 30

Val Leu Ala Ala Ala Val Glu Ser Glu Arg Ser Ala Glu Gln Lys
35 40 45

Ala Val Ile Arg Val Ile Pro Leu Lys Met Asp Pro Thr Gly Lys
50 55 60

-continued

```
Leu Asn Leu Thr Leu Glu Gly Val Phe Ala Gly Val Ala Glu Ile
                65                  70                  75

Thr Pro Ala Glu Gly Lys Leu Met Gln Ser His Pro Leu Tyr Leu
                80                  85                  90

Cys Asn Ala Ser Asp Asp Asp Asn Leu Glu Pro Gly Phe Ile Ser
                95                  100                 105

Ile Val Lys Leu Glu Ser Pro Arg Arg Ala Pro Arg Pro Cys Leu
                110                 115                 120

Ser Leu Ala Ser Lys Ala Arg Met Ala Gly Glu Arg Gly Ala Ser
                125                 130                 135

Ala Val Leu Phe Asp Ile Thr Glu Asp Arg Ala Ala Ala Glu Gln
                140                 145                 150

Leu Gln Gln Pro Leu Gly Leu Thr Trp Pro Val Val Leu Ile Trp
                155                 160                 165

Gly Asn Asp Ala Glu Lys Leu Met Glu Phe Val Tyr Lys Asn Gln
                170                 175                 180

Lys Ala His Val Arg Ile Glu Leu Lys Glu Pro Pro Ala Trp Pro
                185                 190                 195

Asp Tyr Asp Val Trp Ile Leu Met Thr Val Val Gly Thr Ile Phe
                200                 205                 210

Val Ile Ile Leu Ala Ser Val Leu Arg Ile Arg Cys Arg Pro Arg
                215                 220                 225

His Ser Arg Pro Asp Pro Leu Gln Gln Arg Thr Ala Trp Ala Ile
                230                 235                 240

Ser Gln Leu Ala Thr Arg Arg Tyr Gln Ala Ser Cys Arg Gln Ala
                245                 250                 255

Arg Gly Glu Trp Pro Asp Ser Gly Ser Ser Cys Ser Ser Ala Pro
                260                 265                 270

Val Cys Ala Ile Cys Leu Glu Glu Phe Ser Glu Gly Gln Glu Leu
                275                 280                 285

Arg Val Ile Ser Cys Leu His Glu Phe His Arg Asn Cys Val Asp
                290                 295                 300

Pro Trp Leu His Gln His Arg Thr Cys Pro Leu Cys Val Phe Asn
                305                 310                 315

Ile Thr Glu Gly Asp Ser Phe Ser Gln Ser Leu Gly Pro Ser Arg
                320                 325                 330

Ser Tyr Gln Glu Pro Gly Arg Arg Leu His Leu Ile Arg Gln His
                335                 340                 345

Pro Gly His Ala His Tyr His Leu Pro Ala Ala Tyr Leu Leu Gly
                350                 355                 360

Pro Ser Arg Ser Ala Val Ala Arg Pro Pro Arg Pro Gly Pro Phe
                365                 370                 375

Leu Pro Ser Gln Glu Pro Gly Met Gly Pro Arg His His Arg Phe
                380                 385                 390

Pro Arg Ala Ala His Pro Arg Ala Pro Gly Glu Gln Gln Arg Leu
                395                 400                 405

Ala Gly Ala Gln His Pro Tyr Ala Gln Gly Trp Gly Met Ser His
                410                 415                 420

Leu Gln Ser Thr Ser Gln His Pro Ala Ala Cys Pro Val Pro Leu
                425                 430                 435

Arg Arg Ala Arg Pro Pro Asp Ser Ser Gly Ser Gly Glu Ser Tyr
                440                 445                 450

Cys Thr Glu Arg Ser Gly Tyr Leu Ala Asp Gly Pro Ala Ser Asp
                455                 460                 465
```

```
Ser Ser Ser Gly Pro Cys His Gly Ser Ser Ser Asp Ser Val Val
                470                 475                 480

Asn Cys Thr Asp Ile Ser Leu Gln Gly Val His Gly Ser Ser Ser
                485                 490                 495

Thr Phe Cys Ser Ser Leu Ser Ser Asp Phe Asp Pro Leu Val Tyr
                500                 505                 510

Cys Ser Pro Lys Gly Asp Pro Gln Arg Val Asp Met Gln Pro Ser
                515                 520                 525

Val Thr Ser Arg Pro Arg Ser Leu Asp Ser Val Val Pro Thr Gly
                530                 535                 540

Glu Thr Gln Val Ser Ser His Val His Tyr His Arg His Arg His
                545                 550                 555

His His Tyr Lys Lys Arg Phe Gln Trp His Gly Arg Lys Pro Gly
                560                 565                 570

Pro Glu Thr Gly Val Pro Gln Ser Arg Pro Pro Ile Pro Arg Thr
                575                 580                 585

Gln Pro Gln Pro Glu Pro Pro Ser Pro Asp Gln Gln Val Thr Gly
                590                 595                 600

Ser Asn Ser Ala Ala Pro Ser Gly Arg Leu Ser Asn Pro Gln Cys
                605                 610                 615

Pro Arg Ala Leu Pro Glu Pro Ala Pro Gly Pro Val Asp Ala Ser
                620                 625                 630

Ser Ile Cys Pro Ser Thr Ser Ser Leu Phe Asn Leu Gln Lys Ser
                635                 640                 645

Ser Leu Ser Ala Arg His Pro Gln Arg Lys Arg Arg Gly Gly Pro
                650                 655                 660

Ser Glu Pro Thr Pro Gly Ser Arg Pro Gln Asp Ala Thr Val His
                665                 670                 675

Pro Ala Cys Gln Ile Phe Pro His Tyr Thr Pro Ser Val Ala Tyr
                680                 685                 690

Pro Trp Ser Pro Glu Ala His Pro Leu Ile Cys Gly Pro Pro Gly
                695                 700                 705

Leu Asp Lys Arg Leu Leu Pro Glu Thr Pro Gly Pro Cys Tyr Ser
                710                 715                 720

Asn Ser Gln Pro Val Trp Leu Cys Leu Thr Pro Arg Gln Pro Leu
                725                 730                 735

Glu Pro His Pro Pro Gly Glu Gly Pro Ser Glu Trp Ser Ser Asp
                740                 745                 750

Thr Ala Glu Gly Arg Pro Cys Pro Tyr Pro His Cys Gln Val Leu
                755                 760                 765

Ser Ala Gln Pro Gly Ser Glu Glu Glu Leu Glu Glu Leu Cys Glu
                770                 775                 780

Gln Ala Val


<210> SEQ ID NO 94
<211> LENGTH: 510
<212> TYPE: PRT
<213> ORGANISM: Homo Sapien

<400> SEQUENCE: 94

Met Pro Leu Ser Leu Gly Ala Glu Met Trp Gly Pro Glu Ala Trp
  1               5                  10                  15

Leu Leu Leu Leu Leu Leu Leu Ala Ser Phe Thr Gly Arg Cys Pro
                 20                  25                  30
```

```
Ala Gly Glu Leu Glu Thr Ser Asp Val Val Thr Val Val Leu Gly
                35                  40                  45

Gln Asp Ala Lys Leu Pro Cys Phe Tyr Arg Gly Asp Ser Gly Glu
                50                  55                  60

Gln Val Gly Gln Val Ala Trp Ala Arg Val Asp Ala Gly Glu Gly
                65                  70                  75

Ala Gln Glu Leu Ala Leu Leu His Ser Lys Tyr Gly Leu His Val
                80                  85                  90

Ser Pro Ala Tyr Glu Gly Arg Val Glu Gln Pro Pro Pro Pro Arg
                95                 100                 105

Asn Pro Leu Asp Gly Ser Val Leu Leu Arg Asn Ala Val Gln Ala
               110                 115                 120

Asp Glu Gly Glu Tyr Glu Cys Arg Val Ser Thr Phe Pro Ala Gly
               125                 130                 135

Ser Phe Gln Ala Arg Leu Arg Leu Arg Val Leu Val Pro Pro Leu
               140                 145                 150

Pro Ser Leu Asn Pro Gly Pro Ala Leu Glu Glu Gly Gln Gly Leu
               155                 160                 165

Thr Leu Ala Ala Ser Cys Thr Ala Glu Gly Ser Pro Ala Pro Ser
               170                 175                 180

Val Thr Trp Asp Thr Glu Val Lys Gly Thr Thr Ser Ser Arg Ser
               185                 190                 195

Phe Lys His Ser Arg Ser Ala Ala Val Thr Ser Glu Phe His Leu
               200                 205                 210

Val Pro Ser Arg Ser Met Asn Gly Gln Pro Leu Thr Cys Val Val
               215                 220                 225

Ser His Pro Gly Leu Leu Gln Asp Gln Arg Ile Thr His Ile Leu
               230                 235                 240

His Val Ser Phe Leu Ala Glu Ala Ser Val Arg Gly Leu Glu Asp
               245                 250                 255

Gln Asn Leu Trp His Ile Gly Arg Glu Gly Ala Met Leu Lys Cys
               260                 265                 270

Leu Ser Glu Gly Gln Pro Pro Pro Ser Tyr Asn Trp Thr Arg Leu
               275                 280                 285

Asp Gly Pro Leu Pro Ser Gly Val Arg Val Asp Gly Asp Thr Leu
               290                 295                 300

Gly Phe Pro Pro Leu Thr Thr Glu His Ser Gly Ile Tyr Val Cys
               305                 310                 315

His Val Ser Asn Glu Phe Ser Ser Arg Asp Ser Gln Val Thr Val
               320                 325                 330

Asp Val Leu Asp Pro Gln Glu Asp Ser Gly Lys Gln Val Asp Leu
               335                 340                 345

Val Ser Ala Ser Val Val Val Val Gly Val Ile Ala Ala Leu Leu
               350                 355                 360

Phe Cys Leu Leu Val Val Val Val Val Leu Met Ser Arg Tyr His
               365                 370                 375

Arg Arg Lys Ala Gln Gln Met Thr Gln Lys Tyr Glu Glu Glu Leu
               380                 385                 390

Thr Leu Thr Arg Glu Asn Ser Ile Arg Arg Leu His Ser His His
               395                 400                 405

Thr Asp Pro Arg Ser Gln Pro Glu Glu Ser Val Gly Leu Arg Ala
               410                 415                 420

Glu Gly His Pro Asp Ser Leu Lys Asp Asn Ser Ser Cys Ser Val
               425                 430                 435
```

```
Met Ser Glu Glu Pro Glu Gly Arg Ser Tyr Ser Thr Leu Thr Thr
                440                 445                 450

Val Arg Glu Ile Glu Thr Gln Thr Glu Leu Leu Ser Pro Gly Ser
                455                 460                 465

Gly Arg Ala Glu Glu Glu Glu Asp Gln Asp Glu Gly Ile Lys Gln
                470                 475                 480

Ala Met Asn His Phe Val Gln Glu Asn Gly Thr Leu Arg Ala Lys
                485                 490                 495

Pro Thr Gly Asn Gly Ile Tyr Ile Asn Gly Arg Gly His Leu Val
                500                 505                 510


<210> SEQ ID NO 95
<211> LENGTH: 523
<212> TYPE: PRT
<213> ORGANISM: Homo Sapien

<400> SEQUENCE: 95

Met Thr Gln Asn Lys Leu Lys Leu Cys Ser Lys Ala Asn Val Tyr
  1               5                  10                  15

Thr Glu Val Pro Asp Gly Gly Trp Gly Trp Ala Val Ala Val Ser
                 20                  25                  30

Phe Phe Phe Val Glu Val Phe Thr Tyr Gly Ile Ile Lys Thr Phe
                 35                  40                  45

Gly Val Phe Phe Asn Asp Leu Met Asp Ser Phe Asn Glu Ser Asn
                 50                  55                  60

Ser Arg Ile Ser Trp Ile Ile Ser Ile Cys Val Phe Val Leu Thr
                 65                  70                  75

Phe Ser Ala Pro Leu Ala Thr Val Leu Ser Asn Arg Phe Gly His
                 80                  85                  90

Arg Leu Val Val Met Leu Gly Gly Leu Leu Val Ser Thr Gly Met
                 95                 100                 105

Val Ala Ala Ser Phe Ser Gln Glu Val Ser His Met Tyr Val Ala
                110                 115                 120

Ile Gly Ile Ile Ser Gly Leu Gly Tyr Cys Phe Ser Phe Leu Pro
                125                 130                 135

Thr Val Thr Ile Leu Ser Gln Tyr Phe Gly Lys Arg Arg Ser Ile
                140                 145                 150

Val Thr Ala Val Ala Ser Thr Gly Glu Cys Phe Ala Val Phe Ala
                155                 160                 165

Phe Ala Pro Ala Ile Met Ala Leu Lys Glu Arg Ile Gly Trp Arg
                170                 175                 180

Tyr Ser Leu Leu Phe Val Gly Leu Leu Gln Leu Asn Ile Val Ile
                185                 190                 195

Phe Gly Ala Leu Leu Arg Pro Ile Ile Ile Arg Gly Pro Ala Ser
                200                 205                 210

Pro Lys Ile Val Ile Gln Glu Asn Arg Lys Glu Ala Gln Tyr Met
                215                 220                 225

Leu Glu Asn Glu Lys Thr Arg Thr Ser Ile Asp Ser Ile Asp Ser
                230                 235                 240

Gly Val Glu Leu Thr Thr Ser Pro Lys Asn Val Pro Thr His Thr
                245                 250                 255

Asn Leu Glu Leu Glu Pro Lys Ala Asp Met Gln Gln Val Leu Val
                260                 265                 270

Lys Thr Ser Pro Arg Pro Ser Glu Lys Lys Ala Pro Leu Leu Asp
                275                 280                 285
```

```
Phe Ser Ile Leu Lys Glu Lys Ser Phe Ile Cys Tyr Ala Leu Phe
                290                 295                 300

Gly Leu Phe Ala Thr Leu Gly Phe Phe Ala Pro Ser Leu Tyr Ile
                305                 310                 315

Ile Pro Leu Gly Ile Ser Leu Gly Ile Asp Gln Asp Arg Ala Ala
                320                 325                 330

Phe Leu Leu Ser Thr Met Ala Ile Ala Glu Val Phe Gly Arg Ile
                335                 340                 345

Gly Ala Gly Phe Val Leu Asn Arg Glu Pro Ile Arg Lys Ile Tyr
                350                 355                 360

Ile Glu Leu Ile Cys Val Ile Leu Leu Thr Val Ser Leu Phe Ala
                365                 370                 375

Phe Thr Phe Ala Thr Glu Phe Trp Gly Leu Met Ser Cys Ser Ile
                380                 385                 390

Phe Phe Gly Phe Met Val Gly Thr Ile Gly Gly Leu Thr Phe His
                395                 400                 405

Cys Leu Leu Lys Met Met Ser Trp Ala Leu Gln Lys Met Ser Ser
                410                 415                 420

Ala Ala Gly Val Tyr Ile Phe Ile Gln Ser Ile Ala Gly Leu Ala
                425                 430                 435

Gly Pro Pro Leu Ala Gly Leu Leu Val Asp Gln Ser Lys Ile Tyr
                440                 445                 450

Ser Arg Ala Phe Tyr Ser Cys Ala Ala Gly Met Ala Leu Ala Ala
                455                 460                 465

Val Cys Leu Ala Leu Val Arg Pro Cys Lys Met Gly Leu Cys Gln
                470                 475                 480

Arg His His Ser Gly Glu Thr Lys Val Val Ser His Arg Gly Lys
                485                 490                 495

Thr Leu Gln Asp Ile Pro Glu Asp Phe Leu Glu Met Asp Leu Ala
                500                 505                 510

Lys Asn Glu His Arg Val His Val Gln Met Glu Pro Val
                515                 520


<210> SEQ ID NO 96
<211> LENGTH: 124
<212> TYPE: PRT
<213> ORGANISM: Homo Sapien

<400> SEQUENCE: 96

Met Leu Leu Trp Val Ile Leu Leu Val Leu Ala Pro Val Ser Gly
  1               5                  10                  15

Gln Phe Ala Arg Thr Pro Arg Pro Ile Ile Phe Leu Gln Pro Pro
                 20                  25                  30

Trp Thr Thr Val Phe Gln Gly Glu Arg Val Thr Leu Thr Cys Lys
                 35                  40                  45

Gly Phe Arg Phe Tyr Ser Pro Gln Lys Thr Lys Trp Tyr His Arg
                 50                  55                  60

Tyr Leu Gly Lys Glu Ile Leu Arg Glu Thr Pro Asp Asn Ile Leu
                 65                  70                  75

Glu Val Gln Glu Ser Gly Glu Tyr Arg Cys Gln Ala Gln Gly Ser
                 80                  85                  90

Pro Leu Ser Ser Pro Val His Leu Asp Phe Ser Ser Glu Met Gly
                 95                 100                 105

Phe Pro His Ala Ala Gln Ala Asn Val Glu Leu Leu Gly Ser Ser
                110                 115                 120
```

Asp Leu Leu Thr

<210> SEQ ID NO 97
<211> LENGTH: 977
<212> TYPE: PRT
<213> ORGANISM: Homo Sapien

<400> SEQUENCE: 97

```
Met Leu Leu Trp Val Ile Leu Leu Val Leu Ala Pro Val Ser Gly
  1               5                  10                  15

Gln Phe Ala Arg Thr Pro Arg Pro Ile Ile Phe Leu Gln Pro Pro
                 20                  25                  30

Trp Thr Thr Val Phe Gln Gly Glu Arg Val Thr Leu Thr Cys Lys
                 35                  40                  45

Gly Phe Arg Phe Tyr Ser Pro Gln Lys Thr Lys Trp Tyr His Arg
                 50                  55                  60

Tyr Leu Gly Lys Glu Ile Leu Arg Glu Thr Pro Asp Asn Ile Leu
                 65                  70                  75

Glu Val Gln Glu Ser Gly Glu Tyr Arg Cys Gln Ala Gln Gly Ser
                 80                  85                  90

Pro Leu Ser Ser Pro Val His Leu Asp Phe Ser Ser Ala Ser Leu
                 95                 100                 105

Ile Leu Gln Ala Pro Leu Ser Val Phe Glu Gly Asp Ser Val Val
                110                 115                 120

Leu Arg Cys Arg Ala Lys Ala Glu Val Thr Leu Asn Asn Thr Ile
                125                 130                 135

Tyr Lys Asn Asp Asn Val Leu Ala Phe Leu Asn Lys Arg Thr Asp
                140                 145                 150

Phe His Ile Pro His Ala Cys Leu Lys Asp Asn Gly Ala Tyr Arg
                155                 160                 165

Cys Thr Gly Tyr Lys Glu Ser Cys Cys Pro Val Ser Ser Asn Thr
                170                 175                 180

Val Lys Ile Gln Val Gln Glu Pro Phe Thr Arg Pro Val Leu Arg
                185                 190                 195

Ala Ser Ser Phe Gln Pro Ile Ser Gly Asn Pro Val Thr Leu Thr
                200                 205                 210

Cys Glu Thr Gln Leu Ser Leu Glu Arg Ser Asp Val Pro Leu Arg
                215                 220                 225

Phe Arg Phe Phe Arg Asp Asp Gln Thr Leu Gly Leu Gly Trp Ser
                230                 235                 240

Leu Ser Pro Asn Phe Gln Ile Thr Ala Met Trp Ser Lys Asp Ser
                245                 250                 255

Gly Phe Tyr Trp Cys Lys Ala Ala Thr Met Pro His Ser Val Ile
                260                 265                 270

Ser Asp Ser Pro Arg Ser Trp Ile Gln Val Gln Ile Pro Ala Ser
                275                 280                 285

His Pro Val Leu Thr Leu Ser Pro Glu Lys Ala Leu Asn Phe Glu
                290                 295                 300

Gly Thr Lys Val Thr Leu His Cys Glu Thr Gln Glu Asp Ser Leu
                305                 310                 315

Arg Thr Leu Tyr Arg Phe Tyr His Glu Gly Val Pro Leu Arg His
                320                 325                 330

Lys Ser Val Arg Cys Glu Arg Gly Ala Ser Ile Ser Phe Ser Leu
                335                 340                 345
```

```
Thr Thr Glu Asn Ser Gly Asn Tyr Tyr Cys Thr Ala Asp Asn Gly
                350                 355                 360

Leu Gly Ala Lys Pro Ser Lys Ala Val Ser Leu Ser Val Thr Val
                365                 370                 375

Pro Val Ser His Pro Val Leu Asn Leu Ser Ser Pro Glu Asp Leu
                380                 385                 390

Ile Phe Glu Gly Ala Lys Val Thr Leu His Cys Glu Ala Gln Arg
                395                 400                 405

Gly Ser Leu Pro Ile Leu Tyr Gln Phe His His Glu Asp Ala Ala
                410                 415                 420

Leu Glu Arg Arg Ser Ala Asn Ser Ala Gly Gly Val Ala Ile Ser
                425                 430                 435

Phe Ser Leu Thr Ala Glu His Ser Gly Asn Tyr Tyr Cys Thr Ala
                440                 445                 450

Asp Asn Gly Phe Gly Pro Gln Arg Ser Lys Ala Val Ser Leu Ser
                455                 460                 465

Ile Thr Val Pro Val Ser His Pro Val Leu Thr Leu Ser Ser Ala
                470                 475                 480

Glu Ala Leu Thr Phe Glu Gly Ala Thr Val Thr Leu His Cys Glu
                485                 490                 495

Val Gln Arg Gly Ser Pro Gln Ile Leu Tyr Gln Phe Tyr His Glu
                500                 505                 510

Asp Met Pro Leu Trp Ser Ser Ser Thr Pro Ser Val Gly Arg Val
                515                 520                 525

Ser Phe Ser Phe Ser Leu Thr Glu Gly His Ser Gly Asn Tyr Tyr
                530                 535                 540

Cys Thr Ala Asp Asn Gly Phe Gly Pro Gln Arg Ser Glu Val Val
                545                 550                 555

Ser Leu Phe Val Thr Val Pro Val Ser Arg Pro Ile Leu Thr Leu
                560                 565                 570

Arg Val Pro Arg Ala Gln Ala Val Val Gly Asp Leu Leu Glu Leu
                575                 580                 585

His Cys Glu Ala Pro Arg Gly Ser Pro Pro Ile Leu Tyr Trp Phe
                590                 595                 600

Tyr His Glu Asp Val Thr Leu Gly Ser Ser Ser Ala Pro Ser Gly
                605                 610                 615

Gly Glu Ala Ser Phe Asn Leu Ser Leu Thr Ala Glu His Ser Gly
                620                 625                 630

Asn Tyr Ser Cys Glu Ala Asn Asn Gly Leu Val Ala Gln His Ser
                635                 640                 645

Asp Thr Ile Ser Leu Ser Val Ile Val Pro Val Ser Arg Pro Ile
                650                 655                 660

Leu Thr Phe Arg Ala Pro Arg Ala Gln Ala Val Val Gly Asp Leu
                665                 670                 675

Leu Glu Leu His Cys Glu Ala Leu Arg Gly Ser Ser Pro Ile Leu
                680                 685                 690

Tyr Trp Phe Tyr His Glu Asp Val Thr Leu Gly Lys Ile Ser Ala
                695                 700                 705

Pro Ser Gly Gly Gly Ala Ser Phe Asn Leu Ser Leu Thr Thr Glu
                710                 715                 720

His Ser Gly Ile Tyr Ser Cys Glu Ala Asp Asn Gly Pro Glu Ala
                725                 730                 735

Gln Arg Ser Glu Met Val Thr Leu Lys Val Ala Val Pro Val Ser
                740                 745                 750
```

Arg Pro Val Leu Thr Leu Arg Ala Pro Gly Thr His Ala Ala Val
755 760 765

Gly Asp Leu Leu Glu Leu His Cys Glu Ala Leu Arg Gly Ser Pro
770 775 780

Leu Ile Leu Tyr Arg Phe Phe His Glu Asp Val Thr Leu Gly Asn
785 790 795

Arg Ser Ser Pro Ser Gly Gly Ala Ser Leu Asn Leu Ser Leu Thr
800 805 810

Ala Glu His Ser Gly Asn Tyr Ser Cys Glu Ala Asp Asn Gly Leu
815 820 825

Gly Ala Gln Arg Ser Glu Thr Val Thr Leu Tyr Ile Thr Gly Leu
830 835 840

Thr Ala Asn Arg Ser Gly Pro Phe Ala Thr Gly Val Ala Gly Gly
845 850 855

Leu Leu Ser Ile Ala Gly Leu Ala Ala Gly Ala Leu Leu Leu Tyr
860 865 870

Cys Trp Leu Ser Arg Lys Ala Gly Arg Lys Pro Ala Ser Asp Pro
875 880 885

Ala Arg Ser Pro Pro Asp Ser Asp Ser Gln Glu Pro Thr Tyr His
890 895 900

Asn Val Pro Ala Trp Glu Glu Leu Gln Pro Val Tyr Thr Asn Ala
905 910 915

Asn Pro Arg Gly Glu Asn Val Val Tyr Ser Glu Val Arg Ile Ile
920 925 930

Gln Glu Lys Lys Lys His Ala Val Ala Ser Asp Pro Arg His Leu
935 940 945

Arg Asn Lys Gly Ser Pro Ile Ile Tyr Ser Glu Val Lys Val Ala
950 955 960

Ser Thr Pro Val Ser Gly Ser Leu Phe Leu Ala Ser Ser Ala Pro
965 970 975

His Arg

<210> SEQ ID NO 98
<211> LENGTH: 146
<212> TYPE: PRT
<213> ORGANISM: Homo Sapien

<400> SEQUENCE: 98

Met Leu Leu Trp Cys Pro Pro Gln Cys Ala Cys Ser Leu Gly Val
1 5 10 15

Phe Pro Ser Ala Pro Ser Pro Val Trp Gly Thr Arg Arg Ser Cys
20 25 30

Glu Pro Ala Thr Arg Val Pro Glu Val Trp Ile Leu Ser Pro Leu
35 40 45

Leu Arg His Gly Gly His Thr Gln Thr Gln Asn His Thr Ala Ser
50 55 60

Pro Arg Ser Pro Val Met Glu Ser Pro Lys Lys Lys Asn Gln Gln
65 70 75

Leu Lys Val Gly Ile Leu His Leu Gly Ser Arg Gln Lys Lys Ile
80 85 90

Arg Ile Gln Leu Arg Ser Gln Cys Ala Thr Trp Lys Val Ile Cys
95 100 105

Lys Ser Cys Ile Ser Gln Thr Pro Gly Ile Asn Leu Asp Leu Gly
110 115 120

```
Ser Gly Val Lys Val Lys Ile Ile Pro Lys Glu Glu His Cys Lys
                125                 130                 135

Met Pro Glu Ala Gly Glu Glu Gln Pro Gln Val
                140                 145


<210> SEQ ID NO 99
<211> LENGTH: 235
<212> TYPE: PRT
<213> ORGANISM: Homo Sapien

<400> SEQUENCE: 99

Met Arg Glu Leu Ala Ile Glu Ile Gly Val Arg Ala Leu Leu Phe
  1               5                  10                  15

Gly Val Phe Val Phe Thr Glu Phe Leu Asp Pro Phe Gln Arg Val
                 20                  25                  30

Ile Gln Pro Glu Glu Ile Trp Leu Tyr Lys Asn Pro Leu Val Gln
                 35                  40                  45

Ser Asp Asn Ile Pro Thr Arg Leu Met Phe Ala Ile Ser Phe Leu
                 50                  55                  60

Thr Pro Leu Ala Val Ile Cys Val Val Lys Ile Ile Arg Arg Thr
                 65                  70                  75

Asp Lys Thr Glu Ile Lys Glu Ala Phe Leu Ala Val Ser Leu Ala
                 80                  85                  90

Leu Ala Leu Asn Gly Val Cys Thr Asn Thr Ile Lys Leu Ile Val
                 95                 100                 105

Gly Arg Pro Arg Ala Asp Phe Phe Tyr Arg Cys Phe Pro Asp Gly
                110                 115                 120

Val Met Asn Ser Glu Met His Cys Thr Gly Asp Pro Asp Leu Val
                125                 130                 135

Ser Glu Gly Arg Lys Ser Phe Pro Ser Ile His Ser Ser Phe Ala
                140                 145                 150

Phe Ser Gly Leu Gly Phe Thr Thr Phe Tyr Leu Ala Gly Lys Leu
                155                 160                 165

His Cys Phe Thr Glu Ser Gly Arg Gly Lys Ser Trp Arg Leu Cys
                170                 175                 180

Ala Ala Ile Leu Pro Leu Tyr Cys Ala Met Met Ile Ala Leu Ser
                185                 190                 195

Arg Met Cys Asp Tyr Lys His His Trp Gln Asp Ser Phe Val Gly
                200                 205                 210

Gly Val Ile Ala Leu Ile Phe Ala Tyr Ile Cys Tyr Arg Gln His
                215                 220                 225

Tyr Pro Pro Leu Gly Gln His Ser Leu Pro
                230                 235


4<210> SEQ ID NO 100
<211> LENGTH: 252
<212> TYPE: PRT
<213> ORGANISM: Homo Sapien

<400> SEQUENCE: 100

Met Ala Glu Leu Glu Phe Val Gln Ile Ile Ile Ile Val Val Val
  1               5                  10                  15

Met Met Val Met Val Val Val Ile Thr Cys Leu Leu Ser His Tyr
                 20                  25                  30

Lys Leu Ser Ala Arg Ser Phe Ile Ser Arg His Ser Gln Gly Arg
                 35                  40                  45

Arg Arg Glu Asp Ala Leu Ser Ser Glu Gly Cys Leu Trp Pro Ser
```

```
                50                  55                  60

Glu Ser Thr Val Ser Gly Asn Gly Ile Pro Glu Pro Gln Val Tyr
                65                  70                  75

Ala Pro Pro Arg Pro Thr Asp Arg Leu Ala Val Pro Pro Phe Ala
                80                  85                  90

Gln Arg Glu Arg Phe His Arg Phe Gln Pro Thr Tyr Pro Tyr Leu
                95                  100                 105

Gln His Glu Ile Asp Leu Pro Pro Thr Ile Ser Leu Ser Asp Gly
                110                 115                 120

Glu Glu Pro Pro Pro Tyr Gln Gly Pro Cys Thr Leu Gln Leu Arg
                125                 130                 135

Asp Pro Glu Gln Gln Leu Glu Leu Asn Arg Glu Ser Val Arg Ala
                140                 145                 150

Pro Pro Asn Arg Thr Ile Phe Asp Ser Asp Leu Met Asp Ser Ala
                155                 160                 165

Arg Leu Gly Gly Pro Cys Pro Pro Ser Ser Asn Ser Gly Ile Ser
                170                 175                 180

Ala Thr Cys Tyr Gly Ser Gly Gly Arg Met Glu Gly Pro Pro Pro
                185                 190                 195

Thr Tyr Ser Glu Val Ile Gly His Tyr Pro Gly Ser Ser Phe Gln
                200                 205                 210

His Gln Gln Ser Ser Gly Pro Pro Ser Leu Leu Glu Gly Thr Arg
                215                 220                 225

Leu His His Thr His Ile Ala Pro Leu Glu Ser Ala Ala Ile Trp
                230                 235                 240

Ser Lys Glu Lys Asp Lys Gln Lys Gly His Pro Leu
                245                 250


<210> SEQ ID NO 101
<211> LENGTH: 252
<212> TYPE: PRT
<213> ORGANISM: Homo Sapien

<400> SEQUENCE: 101

Met Ala Glu Leu Glu Phe Val Gln Ile Ile Ile Ile Val Val Val
  1               5                   10                  15

Met Met Val Met Val Val Val Ile Thr Cys Leu Leu Ser His Tyr
                20                  25                  30

Lys Leu Ser Ala Arg Ser Phe Ile Ser Arg His Ser Gln Gly Arg
                35                  40                  45

Arg Arg Glu Asp Ala Leu Ser Ser Glu Gly Cys Leu Trp Pro Ser
                50                  55                  60

Glu Ser Thr Val Ser Gly Asn Gly Ile Pro Glu Pro Gln Val Tyr
                65                  70                  75

Ala Pro Pro Arg Pro Thr Asp Arg Leu Ala Val Pro Pro Phe Ala
                80                  85                  90

Gln Arg Glu Arg Phe His Arg Phe Gln Pro Thr Tyr Pro Tyr Leu
                95                  100                 105

Gln His Glu Ile Asp Leu Pro Pro Thr Ile Ser Leu Ser Asp Gly
                110                 115                 120

Glu Glu Pro Pro Pro Tyr Gln Gly Pro Cys Thr Leu Gln Leu Arg
                125                 130                 135

Asp Pro Glu Gln Gln Leu Glu Leu Asn Arg Glu Ser Val Arg Ala
                140                 145                 150

Pro Pro Asn Arg Thr Ile Phe Asp Ser Asp Leu Met Asp Ser Ala
```

```
                155                 160                 165

Arg Leu Gly Gly Pro Cys Pro Pro Ser Ser Asn Ser Gly Ile Ser
                170                 175                 180

Ala Thr Cys Tyr Gly Ser Gly Gly Arg Met Glu Gly Pro Pro Pro
                185                 190                 195

Thr Tyr Ser Glu Val Ile Gly His Tyr Pro Gly Ser Ser Phe Gln
                200                 205                 210

His Gln Gln Ser Ser Gly Pro Pro Ser Leu Leu Glu Gly Thr Arg
                215                 220                 225

Leu His His Thr His Ile Ala Pro Leu Glu Ser Ala Ala Ile Trp
                230                 235                 240

Ser Lys Glu Lys Asp Lys Gln Lys Gly His Pro Leu
                245                 250


<210> SEQ ID NO 102
<211> LENGTH: 465
<212> TYPE: PRT
<213> ORGANISM: Homo Sapien

<400> SEQUENCE: 102

Met Gly Gly Ala Val Val Asp Glu Gly Pro Thr Gly Val Lys Ala
  1               5                  10                  15

Pro Asp Gly Gly Trp Gly Trp Ala Val Leu Phe Gly Cys Phe Val
                 20                  25                  30

Ile Thr Gly Phe Ser Tyr Ala Phe Pro Lys Ala Val Ser Val Phe
                 35                  40                  45

Phe Lys Glu Leu Ile Gln Glu Phe Gly Ile Gly Tyr Ser Asp Thr
                 50                  55                  60

Ala Trp Ile Ser Ser Ile Leu Leu Ala Met Leu Tyr Gly Thr Gly
                 65                  70                  75

Pro Leu Cys Ser Val Cys Val Asn Arg Phe Gly Cys Arg Pro Val
                 80                  85                  90

Met Leu Val Gly Gly Leu Phe Ala Ser Leu Gly Met Val Ala Ala
                 95                 100                 105

Ser Phe Cys Arg Ser Ile Ile Gln Val Tyr Leu Thr Thr Gly Val
                110                 115                 120

Ile Thr Gly Leu Gly Leu Ala Leu Asn Phe Gln Pro Ser Leu Ile
                125                 130                 135

Met Leu Asn Arg Tyr Phe Ser Lys Arg Arg Pro Met Ala Asn Gly
                140                 145                 150

Leu Ala Ala Ala Gly Ser Pro Val Phe Leu Cys Ala Leu Ser Pro
                155                 160                 165

Leu Gly Gln Leu Leu Gln Asp Arg Tyr Gly Trp Arg Gly Gly Phe
                170                 175                 180

Leu Ile Leu Gly Gly Leu Leu Leu Asn Cys Cys Val Cys Ala Ala
                185                 190                 195

Leu Met Arg Pro Leu Val Val Thr Ala Gln Pro Gly Ser Gly Pro
                200                 205                 210

Pro Arg Pro Ser Arg Arg Leu Leu Asp Leu Ser Val Phe Arg Asp
                215                 220                 225

Arg Gly Phe Val Leu Tyr Ala Val Ala Ala Ser Val Met Val Leu
                230                 235                 240

Gly Leu Phe Val Pro Pro Val Phe Val Val Ser Tyr Ala Lys Asp
                245                 250                 255

Leu Gly Val Pro Asp Thr Lys Ala Ala Phe Leu Leu Thr Ile Leu
```

260 265 270

Gly Phe Ile Asp Ile Phe Ala Arg Pro Ala Ala Gly Phe Val Ala
275 280 285

Gly Leu Gly Lys Val Arg Pro Tyr Ser Val Tyr Leu Phe Ser Phe
290 295 300

Ser Met Phe Phe Asn Gly Leu Ala Asp Leu Ala Gly Ser Thr Ala
305 310 315

Gly Asp Tyr Gly Gly Leu Val Val Phe Cys Ile Phe Phe Gly Ile
320 325 330

Ser Tyr Gly Met Val Gly Ala Leu Gln Phe Glu Val Leu Met Ala
335 340 345

Ile Val Gly Thr His Lys Phe Ser Ser Ala Ile Gly Leu Val Leu
350 355 360

Leu Met Glu Ala Val Ala Val Leu Val Gly Pro Pro Ser Gly Gly
365 370 375

Lys Leu Leu Asp Ala Thr His Val Tyr Met Tyr Val Phe Ile Leu
380 385 390

Ala Gly Ala Glu Val Leu Thr Ser Ser Leu Ile Leu Leu Leu Gly
395 400 405

Asn Phe Phe Cys Ile Arg Lys Lys Pro Lys Glu Pro Gln Pro Glu
410 415 420

Val Ala Ala Ala Glu Glu Glu Lys Leu His Lys Pro Pro Ala Asp
425 430 435

Ser Gly Val Asp Leu Arg Glu Val Glu His Phe Leu Lys Ala Glu
440 445 450

Pro Glu Lys Asn Gly Glu Val Val His Thr Pro Glu Thr Ser Val
455 460 465

<210> SEQ ID NO 103
<211> LENGTH: 445
<212> TYPE: PRT
<213> ORGANISM: Homo Sapien

<400> SEQUENCE: 103

Met Ala Ala Pro Thr Pro Ala Arg Pro Val Leu Thr His Leu Leu
1 5 10 15

Val Ala Leu Phe Gly Met Gly Ser Trp Ala Ala Val Asn Gly Ile
20 25 30

Trp Val Glu Leu Pro Val Val Val Lys Glu Leu Pro Glu Gly Trp
35 40 45

Ser Leu Pro Ser Tyr Val Ser Val Leu Val Ala Leu Gly Asn Leu
50 55 60

Gly Leu Leu Val Val Thr Leu Trp Arg Arg Leu Ala Pro Gly Lys
65 70 75

Asp Glu Gln Val Pro Ile Arg Val Val Gln Val Leu Gly Met Val
80 85 90

Gly Thr Ala Leu Leu Ala Ser Leu Trp His His Val Ala Pro Val
95 100 105

Ala Gly Gln Leu His Ser Val Ala Phe Leu Ala Leu Ala Phe Val
110 115 120

Leu Ala Leu Ala Cys Cys Ala Ser Asn Val Thr Phe Leu Pro Phe
125 130 135

Leu Ser His Leu Pro Pro Arg Phe Leu Arg Ser Phe Phe Leu Gly
140 145 150

Gln Gly Leu Ser Ala Leu Leu Pro Cys Val Leu Ala Leu Val Gln

```
                155                 160                 165

Gly Val Gly Arg Leu Glu Cys Pro Pro Ala Pro Ile Asn Gly Thr
                170                 175                 180

Pro Gly Pro Pro Leu Asp Phe Leu Glu Arg Phe Pro Ala Ser Thr
                185                 190                 195

Phe Phe Trp Ala Leu Thr Ala Leu Leu Val Ala Ser Ala Ala Ala
                200                 205                 210

Phe Gln Gly Leu Leu Leu Leu Leu Pro Pro Pro Pro Ser Val Pro
                215                 220                 225

Thr Gly Glu Leu Gly Ser Gly Leu Gln Val Gly Ala Pro Gly Ala
                230                 235                 240

Glu Glu Glu Val Glu Glu Ser Ser Pro Leu Gln Glu Pro Pro Ser
                245                 250                 255

Gln Ala Ala Gly Thr Thr Pro Gly Pro Asp Pro Lys Ala Tyr Gln
                260                 265                 270

Leu Leu Ser Ala Arg Ser Ala Cys Leu Leu Gly Leu Leu Ala Ala
                275                 280                 285

Thr Asn Ala Leu Thr Asn Gly Val Leu Pro Ala Val Gln Ser Phe
                290                 295                 300

Ser Cys Leu Pro Tyr Gly Arg Leu Ala Tyr His Leu Ala Val Val
                305                 310                 315

Leu Gly Ser Ala Ala Asn Pro Leu Ala Cys Phe Leu Ala Met Gly
                320                 325                 330

Val Leu Cys Arg Ser Leu Ala Gly Leu Gly Gly Leu Ser Leu Leu
                335                 340                 345

Gly Val Phe Cys Gly Gly Tyr Leu Met Ala Leu Ala Val Leu Ser
                350                 355                 360

Pro Cys Pro Pro Leu Val Gly Thr Ser Ala Gly Val Val Leu Val
                365                 370                 375

Val Leu Ser Trp Val Leu Cys Leu Gly Val Phe Ser Tyr Val Lys
                380                 385                 390

Val Ala Ala Ser Ser Leu Leu His Gly Gly Gly Arg Pro Ala Leu
                395                 400                 405

Leu Ala Ala Gly Val Ala Ile Gln Val Gly Ser Leu Leu Gly Ala
                410                 415                 420

Val Ala Met Phe Pro Pro Thr Ser Ile Tyr His Val Phe His Ser
                425                 430                 435

Arg Lys Asp Cys Ala Asp Pro Cys Asp Ser
                440                 445


<210> SEQ ID NO 104
<211> LENGTH: 398
<212> TYPE: PRT
<213> ORGANISM: Homo Sapien

<400> SEQUENCE: 104

Met His Thr Val Ala Thr Ser Gly Pro Asn Ala Ser Trp Gly Ala
  1               5                  10                  15

Pro Ala Asn Ala Ser Gly Cys Pro Gly Cys Gly Ala Asn Ala Ser
                 20                  25                  30

Asp Gly Pro Val Pro Ser Pro Arg Ala Val Asp Ala Trp Leu Val
                 35                  40                  45

Pro Leu Phe Phe Ala Ala Leu Met Leu Leu Gly Leu Val Gly Asn
                 50                  55                  60

Ser Leu Val Ile Tyr Val Ile Cys Arg His Lys Pro Met Arg Thr
```

```
                65                  70                  75

Val Thr Asn Phe Tyr Ile Ala Asn Leu Ala Ala Thr Asp Val Thr
                80                  85                  90

Phe Leu Leu Cys Cys Val Pro Phe Thr Ala Leu Leu Tyr Pro Leu
                95                  100                 105

Pro Gly Trp Val Leu Gly Asp Phe Met Cys Lys Phe Val Asn Tyr
                110                 115                 120

Ile Gln Gln Val Ser Val Gln Ala Thr Cys Ala Thr Leu Thr Ala
                125                 130                 135

Met Ser Val Asp Arg Trp Tyr Val Thr Val Phe Pro Leu Arg Ala
                140                 145                 150

Leu His Arg Arg Thr Pro Arg Leu Ala Leu Ala Val Ser Leu Ser
                155                 160                 165

Ile Trp Val Gly Ser Ala Ala Val Ser Ala Pro Val Leu Ala Leu
                170                 175                 180

His Arg Leu Ser Pro Gly Pro Arg Ala Tyr Cys Ser Glu Ala Phe
                185                 190                 195

Pro Ser Arg Ala Leu Glu Arg Ala Phe Ala Leu Tyr Asn Leu Leu
                200                 205                 210

Ala Leu Tyr Leu Leu Pro Leu Leu Ala Thr Cys Ala Cys Tyr Ala
                215                 220                 225

Ala Met Leu Arg His Leu Gly Arg Val Ala Val Arg Pro Ala Pro
                230                 235                 240

Ala Asp Ser Ala Leu Gln Gly Gln Val Leu Ala Glu Arg Ala Gly
                245                 250                 255

Ala Val Arg Ala Lys Val Ser Arg Leu Val Ala Ala Val Val Leu
                260                 265                 270

Leu Phe Ala Ala Cys Trp Gly Pro Ile Gln Leu Phe Leu Val Leu
                275                 280                 285

Gln Ala Leu Gly Pro Ala Gly Ser Trp His Pro Arg Ser Tyr Ala
                290                 295                 300

Ala Tyr Ala Leu Lys Thr Trp Ala His Cys Met Ser Tyr Ser Asn
                305                 310                 315

Ser Ala Leu Asn Pro Leu Leu Tyr Ala Phe Leu Gly Ser His Phe
                320                 325                 330

Arg Gln Ala Phe Arg Arg Val Cys Pro Cys Ala Pro Arg Arg Pro
                335                 340                 345

Arg Arg Pro Arg Arg Pro Gly Pro Ser Asp Pro Ala Ala Pro His
                350                 355                 360

Ala Glu Leu His Arg Leu Gly Ser His Pro Ala Pro Ala Arg Ala
                365                 370                 375

Gln Lys Pro Gly Ser Ser Gly Leu Ala Ala Arg Gly Leu Cys Val
                380                 385                 390

Leu Gly Glu Asp Asn Ala Pro Leu
                395


<210> SEQ ID NO 105
<211> LENGTH: 359
<212> TYPE: PRT
<213> ORGANISM: Homo Sapien

<400> SEQUENCE: 105

Met Ser Met Asn Asn Ser Lys Gln Leu Val Ser Pro Ala Ala Ala
  1               5                  10                  15

Leu Leu Ser Asn Thr Thr Cys Gln Thr Glu Asn Arg Leu Ser Val
```

```
                20                  25                  30

Phe Phe Ser Val Ile Phe Met Thr Val Gly Ile Leu Ser Asn Ser
                35                  40                  45

Leu Ala Ile Ala Ile Leu Met Lys Ala Tyr Gln Arg Phe Arg Gln
                50                  55                  60

Lys Ser Lys Ala Ser Phe Leu Leu Leu Ala Ser Gly Leu Val Ile
                65                  70                  75

Thr Asp Phe Phe Gly His Leu Ile Asn Gly Ala Ile Ala Val Phe
                80                  85                  90

Val Tyr Ala Ser Asp Lys Glu Trp Ile Arg Phe Asp Gln Ser Asn
                95                  100                 105

Val Leu Cys Ser Ile Phe Gly Ile Cys Met Val Phe Ser Gly Leu
                110                 115                 120

Cys Pro Leu Leu Leu Gly Ser Val Met Ala Ile Glu Arg Cys Ile
                125                 130                 135

Gly Val Thr Lys Pro Ile Phe His Ser Thr Lys Ile Thr Ser Lys
                140                 145                 150

His Val Lys Met Met Leu Ser Gly Val Cys Leu Phe Ala Val Phe
                155                 160                 165

Ile Ala Leu Leu Pro Ile Leu Gly His Arg Asp Tyr Lys Ile Gln
                170                 175                 180

Ala Ser Arg Thr Trp Cys Phe Tyr Asn Thr Glu Asp Ile Lys Asp
                185                 190                 195

Trp Glu Asp Arg Phe Tyr Leu Leu Leu Phe Ser Phe Leu Gly Leu
                200                 205                 210

Leu Ala Leu Gly Val Ser Leu Leu Cys Asn Ala Ile Thr Gly Ile
                215                 220                 225

Thr Leu Leu Arg Val Lys Phe Lys Ser Gln Gln His Arg Gln Gly
                230                 235                 240

Arg Ser His His Leu Glu Met Val Ile Gln Leu Leu Ala Ile Met
                245                 250                 255

Cys Val Ser Cys Ile Cys Trp Ser Pro Phe Leu Val Thr Met Ala
                260                 265                 270

Asn Ile Gly Ile Asn Gly Asn His Ser Leu Glu Thr Cys Glu Thr
                275                 280                 285

Thr Leu Phe Ala Leu Arg Met Ala Thr Trp Asn Gln Ile Leu Asp
                290                 295                 300

Pro Trp Val Tyr Ile Leu Leu Arg Lys Ala Val Leu Lys Asn Leu
                305                 310                 315

Tyr Lys Leu Ala Ser Gln Cys Cys Gly Val His Val Ile Ser Leu
                320                 325                 330

His Ile Trp Glu Leu Ser Ser Ile Lys Asn Ser Leu Lys Val Ala
                335                 340                 345

Ala Ile Ser Glu Ser Pro Val Ala Glu Lys Ser Ala Ser Thr
                350                 355


<210> SEQ ID NO 106
<211> LENGTH: 819
<212> TYPE: PRT
<213> ORGANISM: Homo Sapien

<400> SEQUENCE: 106

Met Ser Arg Met Ser Arg His Pro Asp Lys Asp Leu Ala Gln Gly
  1               5                  10                  15

Pro Phe Asn Thr Cys Cys Gly Cys Thr Leu Met Ala Ser Pro Ala
```

-continued

```
                20                  25                  30

Asn Leu Pro Pro Asn Thr Gln Ala Ala Ala Glu Arg Ala Leu Ser
                35                  40                  45

Gln Ser Arg Trp Lys Arg Val Gln Val Pro Ala Pro Ala Ser Leu
                50                  55                  60

Ser Pro Phe Pro Leu Ala Met Ala Ser Val Ala Phe Trp Ile Ser
                65                  70                  75

Ile Leu Ile Gly Cys Glu Glu Gln Thr Leu Cys Arg Gly Trp Arg
                80                  85                  90

Ser Pro Val Gly Asp Gly Cys Ala His Val Pro Pro Gln Glu Arg
                95                  100                 105

Ala Thr Ala Glu Ala Asp Pro Pro Gly Arg Cys Ser Thr Ser Thr
                110                 115                 120

Ala Ser Ser Thr Ile Cys Gly Leu Trp His Leu Ser Pro Arg Leu
                125                 130                 135

Gln Leu Leu Pro Pro Leu His Ser Arg Gln Gly Glu Glu Ser Gly
                140                 145                 150

Lys Thr Glu Lys Val Leu Leu Trp Gly Arg Glu Gly Leu His Val
                155                 160                 165

Trp Lys Pro Gly Val Leu Gln Pro Asp Val His Gly Thr Ser Asn
                170                 175                 180

Leu Gly Asn Cys Ser Phe Leu His Gly Leu Val Thr Ala Pro Ser
                185                 190                 195

Cys Pro Arg Arg Ala Gly Ala Glu Leu Leu Asn Ser Leu Gly Ser
                200                 205                 210

Gln Phe Ala Ile Ser Leu Phe Glu Val Gln Ser Gly Thr Glu Pro
                215                 220                 225

Ser Ile Thr Gly Val Ala Thr Ser Gly Gln Cys Arg Ala Met Pro
                230                 235                 240

Leu Lys His Tyr Leu Leu Leu Leu Val Gly Cys Gln Ala Trp Gly
                245                 250                 255

Ala Gly Leu Ala Tyr His Gly Cys Pro Ser Glu Cys Thr Cys Ser
                260                 265                 270

Arg Ala Ser Gln Val Glu Cys Thr Gly Ala Arg Ile Val Ala Val
                275                 280                 285

Pro Thr Pro Leu Pro Trp Asn Ala Met Ser Leu Gln Ile Leu Asn
                290                 295                 300

Thr His Ile Thr Glu Leu Asn Glu Ser Pro Phe Leu Asn Ile Ser
                305                 310                 315

Ala Leu Ile Ala Leu Arg Ile Glu Lys Asn Glu Leu Ser Arg Ile
                320                 325                 330

Thr Pro Gly Ala Phe Arg Asn Leu Gly Ser Leu Arg Tyr Leu Ser
                335                 340                 345

Leu Ala Asn Asn Lys Leu Gln Val Leu Pro Ile Gly Leu Phe Gln
                350                 355                 360

Gly Leu Asp Ser Leu Glu Ser Leu Leu Leu Ser Ser Asn Gln Leu
                365                 370                 375

Leu Gln Ile Gln Pro Ala His Phe Ser Gln Cys Ser Asn Leu Lys
                380                 385                 390

Glu Leu Gln Leu His Gly Asn His Leu Glu Tyr Ile Pro Asp Gly
                395                 400                 405

Ala Phe Asp His Leu Val Gly Leu Thr Lys Leu Asn Leu Gly Lys
                410                 415                 420
```

-continued

```
Asn Ser Leu Thr His Ile Ser Pro Arg Val Phe Gln His Leu Gly
                425                 430                 435

Asn Leu Gln Val Leu Arg Leu Tyr Glu Asn Arg Leu Thr Asp Ile
                440                 445                 450

Pro Met Gly Thr Phe Asp Gly Leu Val Asn Leu Gln Glu Leu Ala
                455                 460                 465

Leu Gln Gln Asn Gln Ile Gly Leu Leu Ser Pro Gly Leu Phe His
                470                 475                 480

Asn Asn His Asn Leu Gln Arg Leu Tyr Leu Ser Asn Asn His Ile
                485                 490                 495

Ser Gln Leu Pro Pro Ser Ile Phe Met Gln Leu Pro Gln Leu Asn
                500                 505                 510

Arg Leu Thr Leu Phe Gly Asn Ser Leu Lys Glu Leu Ser Leu Gly
                515                 520                 525

Ile Phe Gly Pro Met Pro Asn Leu Arg Glu Leu Trp Leu Tyr Asp
                530                 535                 540

Asn His Ile Ser Ser Leu Pro Asp Asn Val Phe Ser Asn Leu Arg
                545                 550                 555

Gln Leu Gln Val Leu Ile Leu Ser Arg Asn Gln Ile Ser Phe Ile
                560                 565                 570

Ser Pro Gly Ala Phe Asn Gly Leu Thr Glu Leu Arg Glu Leu Ser
                575                 580                 585

Leu His Thr Asn Ala Leu Gln Asp Leu Asp Gly Asn Val Phe Arg
                590                 595                 600

Met Leu Ala Asn Leu Gln Asn Ile Ser Leu Gln Asn Asn Arg Leu
                605                 610                 615

Arg Gln Leu Pro Gly Asn Ile Phe Ala Asn Val Asn Gly Leu Met
                620                 625                 630

Ala Ile Gln Leu Gln Asn Asn Gln Leu Glu Asn Leu Pro Leu Gly
                635                 640                 645

Ile Phe Asp His Leu Gly Lys Leu Cys Glu Leu Arg Leu Tyr Asp
                650                 655                 660

Asn Pro Trp Arg Cys Asp Ser Asp Ile Leu Pro Leu Arg Asn Trp
                665                 670                 675

Leu Leu Leu Asn Gln Pro Arg Leu Gly Thr Asp Thr Val Pro Val
                680                 685                 690

Cys Phe Ser Pro Ala Asn Val Arg Gly Gln Ser Leu Ile Ile Ile
                695                 700                 705

Asn Val Asn Val Ala Val Pro Ser Val His Val Pro Glu Val Pro
                710                 715                 720

Ser Tyr Pro Glu Thr Pro Trp Tyr Pro Asp Thr Pro Ser Tyr Pro
                725                 730                 735

Asp Thr Thr Ser Val Ser Ser Thr Thr Glu Leu Thr Ser Pro Val
                740                 745                 750

Glu Asp Tyr Thr Asp Leu Thr Thr Ile Gln Val Thr Asp Asp Arg
                755                 760                 765

Ser Val Trp Gly Met Thr His Ala His Ser Gly Leu Ala Ile Ala
                770                 775                 780

Ala Ile Val Ile Gly Ile Val Ala Leu Ala Cys Ser Leu Ala Ala
                785                 790                 795

Cys Val Gly Cys Cys Cys Cys Lys Lys Arg Ser Gln Ala Val Leu
                800                 805                 810

Met Gln Met Lys Ala Pro Asn Glu Cys
                815
```

<210> SEQ ID NO 107
<211> LENGTH: 3014
<212> TYPE: PRT
<213> ORGANISM: Homo Sapien

<400> SEQUENCE: 107

Met Ala Pro Pro Pro Pro Pro Val Leu Pro Val Leu Leu Leu Leu
1 5 10 15

Ala Ala Ala Ala Ala Leu Pro Ala Met Gly Leu Arg Ala Ala Ala
20 25 30

Trp Glu Pro Arg Val Pro Gly Gly Thr Arg Ala Phe Ala Leu Arg
35 40 45

Pro Gly Cys Thr Tyr Ala Val Gly Ala Ala Cys Thr Pro Arg Ala
50 55 60

Pro Arg Glu Leu Leu Asp Val Gly Arg Asp Gly Arg Leu Ala Gly
65 70 75

Arg Arg Arg Val Ser Gly Ala Gly Arg Pro Leu Pro Leu Gln Val
80 85 90

Arg Leu Val Ala Arg Ser Ala Pro Thr Ala Leu Ser Arg Arg Leu
95 100 105

Arg Ala Arg Thr His Leu Pro Gly Cys Gly Ala Arg Ala Arg Leu
110 115 120

Cys Gly Thr Gly Ala Arg Leu Cys Gly Ala Leu Cys Phe Pro Val
125 130 135

Pro Gly Gly Cys Ala Ala Ala Gln His Ser Ala Leu Ala Ala Pro
140 145 150

Thr Thr Leu Pro Ala Cys Arg Cys Pro Pro Arg Pro Arg Pro Arg
155 160 165

Cys Pro Gly Arg Pro Ile Cys Leu Pro Pro Gly Gly Ser Val Arg
170 175 180

Leu Arg Leu Leu Cys Ala Leu Arg Arg Ala Ala Gly Ala Val Arg
185 190 195

Val Gly Leu Ala Leu Glu Ala Ala Thr Ala Gly Thr Pro Ser Ala
200 205 210

Ser Pro Ser Pro Ser Pro Pro Leu Pro Pro Asn Leu Pro Glu Ala
215 220 225

Arg Ala Gly Pro Ala Arg Arg Ala Arg Arg Gly Thr Ser Gly Arg
230 235 240

Gly Ser Leu Lys Phe Pro Met Pro Asn Tyr Gln Val Ala Leu Phe
245 250 255

Glu Asn Glu Pro Ala Gly Thr Leu Ile Leu Gln Leu His Ala His
260 265 270

Tyr Thr Ile Glu Gly Glu Glu Glu Arg Val Ser Tyr Tyr Met Glu
275 280 285

Gly Leu Phe Asp Glu Arg Ser Arg Gly Tyr Phe Arg Ile Asp Ser
290 295 300

Ala Thr Gly Ala Val Ser Thr Asp Ser Val Leu Asp Arg Glu Thr
305 310 315

Lys Glu Thr His Val Leu Arg Val Lys Ala Val Asp Tyr Ser Thr
320 325 330

Pro Pro Arg Ser Ala Thr Thr Tyr Ile Thr Val Leu Val Lys Asp
335 340 345

Thr Asn Asp His Ser Pro Val Phe Glu Gln Ser Glu Tyr Arg Glu
350 355 360

```
Arg Val Arg Glu Asn Leu Glu Val Gly Tyr Glu Val Leu Thr Ile
                365                 370                 375

Arg Ala Ser Asp Arg Asp Ser Pro Ile Asn Ala Asn Leu Arg Tyr
                380                 385                 390

Arg Val Leu Gly Gly Ala Trp Asp Val Phe Gln Leu Asn Glu Ser
                395                 400                 405

Ser Gly Val Val Ser Thr Arg Ala Val Leu Asp Arg Glu Glu Ala
                410                 415                 420

Ala Glu Tyr Gln Leu Leu Val Glu Ala Asn Asp Gln Gly Arg Asn
                425                 430                 435

Pro Gly Pro Leu Ser Ala Thr Ala Thr Val Tyr Ile Glu Val Glu
                440                 445                 450

Asp Glu Asn Asp Asn Tyr Pro Gln Phe Ser Glu Gln Asn Tyr Val
                455                 460                 465

Val Gln Val Pro Glu Asp Val Gly Leu Asn Thr Ala Val Leu Arg
                470                 475                 480

Val Gln Ala Thr Asp Arg Asp Gln Gly Gln Asn Ala Ala Ile His
                485                 490                 495

Tyr Ser Ile Leu Ser Gly Asn Val Ala Gly Gln Phe Tyr Leu His
                500                 505                 510

Ser Leu Ser Gly Ile Leu Asp Val Ile Asn Pro Leu Asp Phe Glu
                515                 520                 525

Asp Val Gln Lys Tyr Ser Leu Ser Ile Lys Ala Gln Asp Gly Gly
                530                 535                 540

Arg Pro Pro Leu Ile Asn Ser Ser Gly Val Val Ser Val Gln Val
                545                 550                 555

Leu Asp Val Asn Asp Asn Glu Pro Ile Phe Val Ser Ser Pro Phe
                560                 565                 570

Gln Ala Thr Val Leu Glu Asn Val Pro Leu Gly Tyr Pro Val Val
                575                 580                 585

His Ile Gln Ala Val Asp Ala Asp Ser Gly Glu Asn Ala Arg Leu
                590                 595                 600

His Tyr Arg Leu Val Asp Thr Ala Ser Thr Phe Leu Gly Gly Gly
                605                 610                 615

Ser Ala Gly Pro Lys Asn Pro Ala Pro Thr Pro Asp Phe Pro Phe
                620                 625                 630

Gln Ile His Asn Ser Ser Gly Trp Ile Thr Val Cys Ala Glu Leu
                635                 640                 645

Asp Arg Glu Glu Val Glu His Tyr Ser Phe Gly Val Glu Ala Val
                650                 655                 660

Asp His Gly Ser Pro Pro Met Ser Ser Ser Thr Ser Val Ser Ile
                665                 670                 675

Thr Val Leu Asp Val Asn Asp Asn Asp Pro Val Phe Thr Gln Pro
                680                 685                 690

Thr Tyr Glu Leu Arg Leu Asn Glu Asp Ala Ala Val Gly Ser Ser
                695                 700                 705

Val Leu Thr Leu Gln Ala Arg Asp Arg Asp Ala Asn Ser Val Ile
                710                 715                 720

Thr Tyr Gln Leu Thr Gly Gly Asn Thr Arg Asn Arg Phe Ala Leu
                725                 730                 735

Ser Ser Gln Arg Gly Gly Gly Leu Ile Thr Leu Ala Leu Pro Leu
                740                 745                 750

Asp Tyr Lys Gln Glu Gln Gln Tyr Val Leu Ala Val Thr Ala Ser
```

-continued

```
                755                 760                 765

Asp Gly Thr Arg Ser His Thr Ala His Val Leu Ile Asn Val Thr
                770                 775                 780

Asp Ala Asn Thr His Arg Pro Val Phe Gln Ser Ser His Tyr Thr
                785                 790                 795

Val Ser Val Ser Glu Asp Arg Pro Val Gly Thr Ser Ile Ala Thr
                800                 805                 810

Leu Ser Ala Asn Asp Glu Asp Thr Gly Glu Asn Ala Arg Ile Thr
                815                 820                 825

Tyr Val Ile Gln Asp Pro Val Pro Gln Phe Arg Ile Asp Pro Asp
                830                 835                 840

Ser Gly Thr Met Tyr Thr Met Met Glu Leu Asp Tyr Glu Asn Gln
                845                 850                 855

Val Ala Tyr Thr Leu Thr Ile Met Ala Gln Asp Asn Gly Ile Pro
                860                 865                 870

Gln Lys Ser Asp Thr Thr Thr Leu Glu Ile Leu Ile Leu Asp Ala
                875                 880                 885

Asn Asp Asn Ala Pro Gln Phe Leu Trp Asp Phe Tyr Gln Gly Ser
                890                 895                 900

Ile Phe Glu Asp Ala Pro Pro Ser Thr Ser Ile Leu Gln Val Ser
                905                 910                 915

Ala Thr Asp Arg Asp Ser Gly Pro Asn Gly Arg Leu Leu Tyr Thr
                920                 925                 930

Phe Gln Gly Gly Asp Asp Gly Asp Gly Asp Phe Tyr Ile Glu Pro
                935                 940                 945

Thr Ser Gly Val Ile Arg Thr Gln Arg Arg Leu Asp Arg Glu Asn
                950                 955                 960

Val Ala Val Tyr Asn Leu Trp Ala Leu Ala Val Asp Arg Gly Ser
                965                 970                 975

Pro Thr Pro Leu Ser Ala Ser Val Glu Ile Gln Val Thr Ile Leu
                980                 985                 990

Asp Ile Asn Asp Asn Ala Pro Met Phe Glu Lys Asp Glu Leu Glu
                995                 1000                1005

Leu Phe Val Glu Glu Asn Asn Pro Val Gly Ser Val Val Ala Lys
                1010                1015                1020

Ile Arg Ala Asn Asp Pro Asp Glu Gly Pro Asn Ala Gln Ile Met
                1025                1030                1035

Tyr Gln Ile Val Glu Gly Asp Met Arg His Phe Phe Gln Leu Asp
                1040                1045                1050

Leu Leu Asn Gly Asp Leu Arg Ala Met Val Glu Leu Asp Phe Glu
                1055                1060                1065

Val Arg Arg Glu Tyr Val Leu Val Val Gln Ala Thr Ser Ala Pro
                1070                1075                1080

Leu Val Ser Arg Ala Thr Val His Ile Leu Leu Val Asp Gln Asn
                1085                1090                1095

Asp Asn Pro Pro Val Leu Pro Asp Phe Gln Ile Leu Phe Asn Asn
                1100                1105                1110

Tyr Val Thr Asn Lys Ser Asn Ser Phe Pro Thr Gly Val Ile Gly
                1115                1120                1125

Cys Ile Pro Ala His Asp Pro Asp Val Ser Asp Ser Leu Asn Tyr
                1130                1135                1140

Thr Phe Val Gln Gly Asn Glu Leu Arg Leu Leu Leu Leu Asp Pro
                1145                1150                1155
```

-continued

Ala Thr Gly Glu Leu Gln Leu Ser Arg Asp Leu Asp Asn Asn Arg
1160 1165 1170

Pro Leu Glu Ala Leu Met Glu Val Ser Val Ser Asp Gly Ile His
1175 1180 1185

Ser Val Thr Ala Phe Cys Thr Leu Arg Val Thr Ile Ile Thr Asp
1190 1195 1200

Asp Met Leu Thr Asn Ser Ile Thr Val Arg Leu Glu Asn Met Ser
1205 1210 1215

Gln Glu Lys Phe Leu Ser Pro Leu Leu Ala Leu Phe Val Glu Gly
1220 1225 1230

Val Ala Ala Val Leu Ser Thr Thr Lys Asp Asp Val Phe Val Phe
1235 1240 1245

Asn Val Gln Asn Asp Thr Asp Val Ser Ser Asn Ile Leu Asn Val
1250 1255 1260

Thr Phe Ser Ala Leu Leu Pro Gly Gly Val Arg Gly Gln Phe Phe
1265 1270 1275

Pro Ser Glu Asp Leu Gln Glu Gln Ile Tyr Leu Asn Arg Thr Leu
1280 1285 1290

Leu Thr Thr Ile Ser Thr Gln Arg Val Leu Pro Phe Asp Asp Asn
1295 1300 1305

Ile Cys Leu Arg Glu Pro Cys Glu Asn Tyr Met Lys Cys Val Ser
1310 1315 1320

Val Leu Arg Phe Asp Ser Ser Ala Pro Phe Leu Ser Ser Thr Thr
1325 1330 1335

Val Leu Phe Arg Pro Ile His Pro Ile Asn Gly Leu Arg Cys Arg
1340 1345 1350

Cys Pro Pro Gly Phe Thr Gly Asp Tyr Cys Glu Thr Glu Ile Asp
1355 1360 1365

Leu Cys Tyr Ser Asp Pro Cys Gly Ala Asn Gly Arg Cys Arg Ser
1370 1375 1380

Arg Glu Gly Gly Tyr Thr Cys Glu Cys Phe Glu Asp Phe Thr Gly
1385 1390 1395

Glu His Cys Glu Val Asp Ala Arg Ser Gly Arg Cys Ala Asn Gly
1400 1405 1410

Val Cys Lys Asn Gly Gly Thr Cys Val Asn Leu Leu Ile Gly Gly
1415 1420 1425

Phe His Cys Val Cys Pro Pro Gly Glu Tyr Glu Arg Pro Tyr Cys
1430 1435 1440

Glu Val Thr Thr Arg Ser Phe Pro Pro Gln Ser Phe Val Thr Phe
1445 1450 1455

Arg Gly Leu Arg Gln Arg Phe His Phe Thr Ile Ser Leu Thr Phe
1460 1465 1470

Ala Thr Gln Glu Arg Asn Gly Leu Leu Leu Tyr Asn Gly Arg Phe
1475 1480 1485

Asn Glu Lys His Asp Phe Ile Ala Leu Glu Ile Val Asp Glu Gln
1490 1495 1500

Val Gln Leu Thr Phe Ser Ala Gly Glu Thr Thr Thr Thr Val Ala
1505 1510 1515

Pro Lys Val Pro Ser Gly Val Ser Asp Gly Arg Trp His Ser Val
1520 1525 1530

Gln Val Gln Tyr Tyr Asn Lys Pro Asn Ile Gly His Leu Gly Leu
1535 1540 1545

Pro His Gly Pro Ser Gly Glu Lys Met Ala Val Val Thr Val Asp
1550 1555 1560

```
Asp Cys Asp Thr Thr Met Ala Val Arg Phe Gly Lys Asp Ile Gly
                1565                1570                1575

Asn Tyr Ser Cys Ala Ala Gln Gly Thr Gln Thr Gly Ser Lys Lys
                1580                1585                1590

Ser Leu Asp Leu Thr Gly Pro Leu Leu Leu Gly Gly Val Pro Asn
                1595                1600                1605

Leu Pro Glu Asp Phe Pro Val His Asn Arg Gln Phe Val Gly Cys
                1610                1615                1620

Met Arg Asn Leu Ser Val Asp Gly Lys Asn Val Asp Met Ala Gly
                1625                1630                1635

Phe Ile Ala Asn Asn Gly Thr Arg Glu Gly Cys Ala Ala Arg Arg
                1640                1645                1650

Asn Phe Cys Asp Gly Arg Arg Cys Gln Asn Gly Gly Thr Cys Val
                1655                1660                1665

Asn Arg Trp Asn Met Tyr Leu Cys Glu Cys Pro Leu Arg Phe Gly
                1670                1675                1680

Gly Lys Asn Cys Glu Gln Ala Met Pro His Pro Gln Leu Phe Ser
                1685                1690                1695

Gly Glu Ser Val Val Ser Trp Ser Asp Leu Asn Ile Ile Ile Ser
                1700                1705                1710

Val Pro Trp Tyr Leu Gly Leu Met Phe Arg Thr Arg Lys Glu Asp
                1715                1720                1725

Ser Val Leu Met Glu Ala Thr Ser Gly Gly Pro Thr Ser Phe Arg
                1730                1735                1740

Leu Gln Ile Leu Asn Asn Tyr Leu Gln Phe Glu Val Ser His Gly
                1745                1750                1755

Pro Ser Asp Val Glu Ser Val Met Leu Ser Gly Leu Arg Val Thr
                1760                1765                1770

Asp Gly Glu Trp His His Leu Leu Ile Glu Leu Lys Asn Val Lys
                1775                1780                1785

Glu Asp Ser Glu Met Lys His Leu Val Thr Met Thr Leu Asp Tyr
                1790                1795                1800

Gly Met Asp Gln Asn Lys Ala Asp Ile Gly Gly Met Leu Pro Gly
                1805                1810                1815

Leu Thr Val Arg Ser Val Val Val Gly Gly Ala Ser Glu Asp Lys
                1820                1825                1830

Val Ser Val Arg Arg Gly Phe Arg Gly Cys Met Gln Gly Val Arg
                1835                1840                1845

Met Gly Gly Thr Pro Thr Asn Val Ala Thr Leu Asn Met Asn Asn
                1850                1855                1860

Ala Leu Lys Val Arg Val Lys Asp Gly Cys Asp Val Asp Asp Pro
                1865                1870                1875

Cys Thr Ser Ser Pro Cys Pro Pro Asn Ser Arg Cys His Asp Ala
                1880                1885                1890

Trp Glu Asp Tyr Ser Cys Val Cys Asp Lys Gly Tyr Leu Gly Ile
                1895                1900                1905

Asn Cys Val Asp Ala Cys His Leu Asn Pro Cys Glu Asn Met Gly
                1910                1915                1920

Ala Cys Val Arg Ser Pro Gly Ser Pro Gln Gly Tyr Val Cys Glu
                1925                1930                1935

Cys Gly Pro Ser His Tyr Gly Pro Tyr Cys Glu Asn Lys Leu Asp
                1940                1945                1950

Leu Pro Cys Pro Arg Gly Trp Trp Gly Asn Pro Val Cys Gly Pro
```

```
                1955                1960                1965

Cys His Cys Ala Val Ser Lys Gly Phe Asp Pro Asp Cys Asn Lys
                1970                1975                1980

Thr Asn Gly Gln Cys Gln Cys Lys Glu Asn Tyr Tyr Lys Leu Leu
                1985                1990                1995

Ala Gln Asp Thr Cys Leu Pro Cys Asp Cys Phe Pro His Gly Ser
                2000                2005                2010

His Ser Arg Thr Cys Asp Met Ala Thr Gly Gln Cys Ala Cys Lys
                2015                2020                2025

Pro Gly Val Ile Gly Arg Gln Cys Asn Arg Cys Asp Asn Pro Phe
                2030                2035                2040

Ala Glu Val Thr Thr Leu Gly Cys Glu Val Ile Tyr Asn Gly Cys
                2045                2050                2055

Pro Lys Ala Phe Glu Ala Gly Ile Trp Trp Pro Gln Thr Lys Phe
                2060                2065                2070

Gly Gln Pro Ala Ala Val Pro Cys Pro Lys Gly Ser Val Gly Asn
                2075                2080                2085

Ala Val Arg His Cys Ser Gly Glu Lys Gly Trp Leu Pro Pro Glu
                2090                2095                2100

Leu Phe Asn Cys Thr Thr Ile Ser Phe Val Asp Leu Arg Ala Met
                2105                2110                2115

Asn Glu Lys Leu Ser Arg Asn Glu Thr Gln Val Asp Gly Ala Arg
                2120                2125                2130

Ala Leu Gln Leu Val Arg Ala Leu Arg Ser Ala Thr Gln His Thr
                2135                2140                2145

Gly Thr Leu Phe Gly Asn Asp Val Arg Thr Ala Tyr Gln Leu Leu
                2150                2155                2160

Gly His Val Leu Gln His Glu Ser Trp Gln Gln Gly Phe Asp Leu
                2165                2170                2175

Ala Ala Thr Gln Asp Ala Asp Phe His Glu Asp Val Ile His Ser
                2180                2185                2190

Gly Ser Ala Leu Leu Ala Pro Ala Thr Arg Ala Ala Trp Glu Gln
                2195                2200                2205

Ile Gln Arg Ser Glu Gly Gly Thr Ala Gln Leu Leu Arg Arg Leu
                2210                2215                2220

Glu Gly Tyr Phe Ser Asn Val Ala Arg Asn Val Arg Arg Thr Tyr
                2225                2230                2235

Leu Arg Pro Phe Val Ile Val Thr Ala Asn Met Ile Leu Ala Val
                2240                2245                2250

Asp Ile Phe Asp Lys Phe Asn Phe Thr Gly Ala Arg Val Pro Arg
                2255                2260                2265

Phe Asp Thr Ile His Glu Glu Phe Pro Arg Glu Leu Glu Ser Ser
                2270                2275                2280

Val Ser Phe Pro Ala Asp Phe Phe Arg Pro Pro Glu Glu Lys Glu
                2285                2290                2295

Gly Pro Leu Leu Arg Pro Ala Gly Arg Arg Thr Thr Pro Gln Thr
                2300                2305                2310

Thr Arg Pro Gly Pro Gly Thr Glu Arg Glu Ala Pro Ile Ser Arg
                2315                2320                2325

Arg Arg Arg His Pro Asp Asp Ala Gly Gln Phe Ala Val Ala Leu
                2330                2335                2340

Val Ile Ile Tyr Arg Thr Leu Gly Gln Leu Leu Pro Glu Arg Tyr
                2345                2350                2355
```

-continued

```
Asp Pro Asp Arg Arg Ser Leu Arg Leu Pro His Arg Pro Ile Ile
                2360                2365                2370

Asn Thr Pro Met Val Ser Thr Leu Val Tyr Ser Glu Gly Ala Pro
                2375                2380                2385

Leu Pro Arg Pro Leu Glu Arg Pro Val Leu Val Glu Phe Ala Leu
                2390                2395                2400

Leu Glu Val Glu Glu Arg Thr Lys Pro Val Cys Val Phe Trp Asn
                2405                2410                2415

His Ser Leu Ala Val Gly Gly Thr Gly Gly Trp Ser Ala Arg Gly
                2420                2425                2430

Cys Glu Leu Leu Ser Arg Asn Arg Thr His Val Ala Cys Gln Cys
                2435                2440                2445

Ser His Thr Ala Ser Phe Ala Val Leu Met Asp Ile Ser Arg Arg
                2450                2455                2460

Glu Asn Gly Glu Val Leu Pro Leu Lys Ile Val Thr Tyr Ala Ala
                2465                2470                2475

Val Ser Leu Ser Leu Ala Ala Leu Leu Val Ala Phe Val Leu Leu
                2480                2485                2490

Ser Leu Val Arg Met Leu Arg Ser Asn Leu His Ser Ile His Lys
                2495                2500                2505

His Leu Ala Val Ala Leu Phe Leu Ser Gln Leu Val Phe Val Ile
                2510                2515                2520

Gly Ile Asn Gln Thr Glu Asn Pro Phe Leu Cys Thr Val Val Ala
                2525                2530                2535

Ile Leu Leu His Tyr Ile Tyr Met Ser Thr Phe Ala Trp Thr Leu
                2540                2545                2550

Val Glu Ser Leu His Val Tyr Arg Met Leu Thr Glu Val Arg Asn
                2555                2560                2565

Ile Asp Thr Gly Pro Met Arg Phe Tyr Tyr Val Val Gly Trp Gly
                2570                2575                2580

Ile Pro Ala Ile Val Thr Gly Leu Ala Val Gly Leu Asp Pro Gln
                2585                2590                2595

Gly Tyr Gly Asn Pro Asp Phe Cys Trp Leu Ser Leu Gln Asp Thr
                2600                2605                2610

Leu Ile Trp Ser Phe Ala Gly Pro Ile Gly Ala Val Ile Ile Ile
                2615                2620                2625

Asn Thr Val Thr Ser Val Leu Ser Ala Lys Val Ser Cys Gln Arg
                2630                2635                2640

Lys His His Tyr Tyr Gly Lys Lys Gly Ile Val Ser Leu Leu Arg
                2645                2650                2655

Thr Ala Phe Leu Leu Leu Leu Leu Ile Ser Ala Thr Trp Leu Leu
                2660                2665                2670

Gly Leu Leu Ala Val Asn Arg Asp Ala Leu Ser Phe His Tyr Leu
                2675                2680                2685

Phe Ala Ile Phe Ser Gly Leu Gln Gly Pro Phe Val Leu Leu Phe
                2690                2695                2700

His Cys Val Leu Asn Gln Glu Val Arg Lys His Leu Lys Gly Val
                2705                2710                2715

Leu Gly Gly Arg Lys Leu His Leu Glu Asp Ser Ala Thr Thr Arg
                2720                2725                2730

Ala Thr Leu Leu Thr Arg Ser Leu Asn Cys Asn Thr Thr Phe Gly
                2735                2740                2745

Asp Gly Pro Asp Met Leu Arg Thr Asp Leu Gly Glu Ser Thr Ala
                2750                2755                2760
```

```
Ser Leu Asp Ser Ile Val Arg Asp Glu Gly Ile Gln Lys Leu Gly
                2765                2770                2775

Val Ser Ser Gly Leu Val Arg Gly Ser His Gly Glu Pro Asp Ala
                2780                2785                2790

Ser Leu Met Pro Arg Ser Cys Lys Asp Pro Pro Gly His Asp Ser
                2795                2800                2805

Asp Ser Asp Ser Glu Leu Ser Leu Asp Glu Gln Ser Ser Ser Tyr
                2810                2815                2820

Ala Ser Ser His Ser Ser Asp Ser Glu Asp Asp Gly Val Gly Ala
                2825                2830                2835

Glu Glu Lys Trp Asp Pro Ala Arg Gly Ala Val His Ser Thr Pro
                2840                2845                2850

Lys Gly Asp Ala Val Ala Asn His Val Pro Ala Gly Trp Pro Asp
                2855                2860                2865

Gln Ser Leu Ala Glu Ser Asp Ser Glu Asp Pro Ser Gly Lys Pro
                2870                2875                2880

Arg Leu Lys Val Glu Thr Lys Val Ser Val Glu Leu His Arg Glu
                2885                2890                2895

Glu Gln Gly Ser His Arg Gly Glu Tyr Pro Pro Asp Gln Glu Ser
                2900                2905                2910

Gly Gly Ala Ala Arg Leu Ala Ser Ser Gln Pro Pro Glu Gln Arg
                2915                2920                2925

Lys Gly Ile Leu Lys Asn Lys Val Thr Tyr Pro Pro Pro Leu Thr
                2930                2935                2940

Leu Thr Glu Gln Thr Leu Lys Gly Arg Leu Arg Glu Lys Leu Ala
                2945                2950                2955

Asp Cys Glu Gln Ser Pro Thr Ser Ser Arg Thr Ser Ser Leu Gly
                2960                2965                2970

Ser Gly Gly Pro Asp Cys Ala Ile Thr Val Lys Ser Pro Gly Arg
                2975                2980                2985

Glu Pro Gly Arg Asp His Leu Asn Gly Val Ala Met Asn Val Arg
                2990                2995                3000

Thr Gly Ser Ala Gln Ala Asp Gly Ser Asp Ser Glu Lys Pro
                3005                3010


<210> SEQ ID NO 108
<211> LENGTH: 181
<212> TYPE: PRT
<213> ORGANISM: Homo Sapien

<400> SEQUENCE: 108

Met Val Asp Val Lys Cys Leu Ser Asp Cys Lys Leu Gln Asn Gln
  1               5                  10                  15

Leu Glu Lys Leu Gly Phe Ser Pro Gly Pro Ile Leu Pro Ser Thr
                 20                  25                  30

Arg Lys Leu Tyr Glu Lys Lys Leu Val Gln Leu Leu Val Ser Pro
                 35                  40                  45

Pro Cys Ala Pro Pro Val Met Asn Gly Pro Arg Glu Leu Asp Gly
                 50                  55                  60

Ala Gln Asp Ser Asp Asp Ser Glu Glu Leu Asn Ile Ile Leu Gln
                 65                  70                  75

Gly Asn Ile Ile Leu Ser Thr Glu Lys Ser Lys Lys Leu Lys Lys
                 80                  85                  90

Trp Pro Glu Ala Ser Thr Thr Lys Arg Lys Ala Val Asp Thr Tyr
                 95                 100                 105
```

```
Cys Leu Asp Tyr Lys Pro Ser Lys Gly Arg Arg Trp Ala Ala Arg
                110                 115                 120

Ala Pro Ser Thr Arg Ile Thr Tyr Gly Thr Ile Thr Lys Glu Arg
                125                 130                 135

Asp Tyr Cys Ala Glu Asp Gln Thr Ile Glu Ser Trp Arg Glu Glu
                140                 145                 150

Gly Phe Pro Val Gly Leu Lys Leu Ala Val Leu Gly Ile Phe Ile
                155                 160                 165

Ile Val Val Phe Val Tyr Leu Thr Val Glu Asn Lys Ser Leu Phe
                170                 175                 180

Gly


<210> SEQ ID NO 109
<211> LENGTH: 620
<212> TYPE: PRT
<213> ORGANISM: Homo Sapien

<400> SEQUENCE: 109

Met Ser Lys Ser Lys Cys Ser Val Gly Leu Met Ser Ser Val Val
  1               5                  10                  15

Ala Pro Ala Lys Glu Pro Asn Ala Val Gly Pro Lys Glu Val Glu
                 20                  25                  30

Leu Ile Leu Val Lys Glu Gln Asn Gly Val Gln Leu Thr Ser Ser
                 35                  40                  45

Thr Leu Thr Asn Pro Arg Gln Ser Pro Val Glu Ala Gln Asp Arg
                 50                  55                  60

Glu Thr Trp Gly Lys Lys Ile Asp Phe Leu Leu Ser Val Ile Gly
                 65                  70                  75

Phe Ala Val Asp Leu Ala Asn Val Trp Arg Phe Pro Tyr Leu Cys
                 80                  85                  90

Tyr Lys Asn Gly Gly Gly Ala Phe Leu Val Pro Tyr Leu Leu Phe
                 95                 100                 105

Met Val Ile Ala Gly Met Pro Leu Phe Tyr Met Glu Leu Ala Leu
                110                 115                 120

Gly Gln Phe Asn Arg Glu Gly Ala Ala Gly Val Trp Lys Ile Cys
                125                 130                 135

Pro Ile Leu Lys Gly Val Gly Phe Thr Val Ile Leu Ile Ser Leu
                140                 145                 150

Tyr Val Gly Phe Phe Tyr Asn Val Ile Ile Ala Trp Ala Leu His
                155                 160                 165

Tyr Leu Phe Ser Ser Phe Thr Thr Glu Leu Pro Trp Ile His Cys
                170                 175                 180

Asn Asn Ser Trp Asn Ser Pro Asn Cys Ser Asp Ala His Pro Gly
                185                 190                 195

Asp Ser Ser Gly Asp Ser Ser Gly Leu Asn Asp Thr Phe Gly Thr
                200                 205                 210

Thr Pro Ala Ala Glu Tyr Phe Glu Arg Gly Val Leu His Leu His
                215                 220                 225

Gln Ser His Gly Ile Asp Asp Leu Gly Pro Pro Arg Trp Gln Leu
                230                 235                 240

Thr Ala Cys Leu Val Leu Val Ile Val Leu Leu Tyr Phe Ser Leu
                245                 250                 255

Trp Lys Gly Val Lys Thr Ser Gly Lys Val Val Trp Ile Thr Ala
                260                 265                 270
```

-continued

```
Thr Met Pro Tyr Val Val Leu Thr Ala Leu Leu Leu Arg Gly Val
                275                 280                 285

Thr Leu Pro Gly Ala Ile Asp Gly Ile Arg Ala Tyr Leu Ser Val
                290                 295                 300

Asp Phe Tyr Arg Leu Cys Glu Ala Ser Val Trp Ile Asp Ala Ala
                305                 310                 315

Thr Gln Val Cys Phe Ser Leu Gly Val Gly Phe Gly Val Leu Ile
                320                 325                 330

Ala Phe Ser Ser Tyr Asn Lys Phe Thr Asn Asn Cys Tyr Arg Asp
                335                 340                 345

Ala Ile Val Thr Thr Ser Ile Asn Ser Leu Thr Ser Phe Ser Ser
                350                 355                 360

Gly Phe Val Val Phe Ser Phe Leu Gly Tyr Met Ala Gln Lys His
                365                 370                 375

Ser Val Pro Ile Gly Asp Val Ala Lys Asp Gly Pro Gly Leu Ile
                380                 385                 390

Phe Ile Ile Tyr Pro Glu Ala Ile Ala Thr Leu Pro Leu Ser Ser
                395                 400                 405

Ala Trp Ala Val Val Phe Phe Ile Met Leu Leu Thr Leu Gly Ile
                410                 415                 420

Asp Ser Ala Met Gly Gly Met Glu Ser Val Ile Thr Gly Leu Ile
                425                 430                 435

Asp Glu Phe Gln Leu Leu His Arg His Arg Glu Leu Phe Thr Leu
                440                 445                 450

Phe Ile Val Leu Ala Thr Phe Leu Leu Ser Leu Phe Cys Val Thr
                455                 460                 465

Asn Gly Gly Ile Tyr Val Phe Thr Leu Leu Asp His Phe Ala Ala
                470                 475                 480

Gly Thr Ser Ile Leu Phe Gly Val Leu Ile Glu Ala Ile Gly Val
                485                 490                 495

Ala Trp Phe Tyr Gly Val Gly Gln Phe Ser Asp Asp Ile Gln Gln
                500                 505                 510

Met Thr Gly Gln Arg Pro Ser Leu Tyr Trp Arg Leu Cys Trp Lys
                515                 520                 525

Leu Val Ser Pro Cys Phe Leu Leu Phe Val Val Val Val Ser Ile
                530                 535                 540

Val Thr Phe Arg Pro Pro His Tyr Gly Ala Tyr Ile Phe Pro Asp
                545                 550                 555

Trp Ala Asn Ala Leu Gly Trp Val Ile Ala Thr Ser Ser Met Ala
                560                 565                 570

Met Val Pro Ile Tyr Ala Ala Tyr Lys Phe Cys Ser Leu Pro Gly
                575                 580                 585

Ser Phe Arg Glu Lys Leu Ala Tyr Ala Ile Ala Pro Glu Lys Asp
                590                 595                 600

Arg Glu Leu Val Asp Arg Gly Glu Val Arg Gln Phe Thr Leu Arg
                605                 610                 615

His Trp Leu Lys Val
                620
```

<210> SEQ ID NO 110
<211> LENGTH: 442
<212> TYPE: PRT
<213> ORGANISM: Homo Sapien

<400> SEQUENCE: 110

```
Met Gly Leu Ala Met Glu His Gly Gly Ser Tyr Ala Arg Ala Gly
  1               5                  10                  15

Gly Ser Ser Arg Gly Cys Trp Tyr Tyr Leu Arg Tyr Phe Phe Leu
                 20                  25                  30

Phe Val Ser Leu Ile Gln Phe Leu Ile Ile Leu Gly Leu Val Leu
                 35                  40                  45

Phe Met Val Tyr Gly Asn Val His Val Ser Thr Glu Ser Asn Leu
                 50                  55                  60

Gln Ala Thr Glu Arg Arg Ala Glu Gly Leu Tyr Ser Gln Leu Leu
                 65                  70                  75

Gly Leu Thr Ala Ser Gln Ser Asn Leu Thr Lys Glu Leu Asn Phe
                 80                  85                  90

Thr Thr Arg Ala Lys Asp Ala Ile Met Gln Met Trp Leu Asn Ala
                 95                 100                 105

Arg Arg Asp Leu Asp Arg Ile Asn Ala Ser Phe Arg Gln Cys Gln
                110                 115                 120

Gly Asp Arg Val Ile Tyr Thr Asn Asn Gln Arg Tyr Met Ala Ala
                125                 130                 135

Ile Ile Leu Ser Glu Lys Gln Cys Arg Asp Gln Phe Lys Asp Met
                140                 145                 150

Asn Lys Ser Cys Asp Ala Leu Leu Phe Met Leu Asn Gln Lys Val
                155                 160                 165

Lys Thr Leu Glu Val Glu Ile Ala Lys Glu Lys Thr Ile Cys Thr
                170                 175                 180

Lys Asp Lys Glu Ser Val Leu Leu Asn Lys Arg Val Ala Glu Glu
                185                 190                 195

Gln Leu Val Glu Cys Val Lys Thr Arg Glu Leu Gln His Gln Glu
                200                 205                 210

Arg Gln Leu Ala Lys Glu Gln Leu Gln Lys Val Gln Ala Leu Cys
                215                 220                 225

Leu Pro Leu Asp Lys Asp Lys Phe Glu Met Asp Leu Arg Asn Leu
                230                 235                 240

Trp Arg Asp Ser Ile Ile Pro Arg Ser Leu Asp Asn Leu Gly Tyr
                245                 250                 255

Asn Leu Tyr His Pro Leu Gly Ser Glu Leu Ala Ser Ile Arg Arg
                260                 265                 270

Ala Cys Asp His Met Pro Ser Leu Met Ser Ser Lys Val Glu Glu
                275                 280                 285

Leu Ala Arg Ser Leu Arg Ala Asp Ile Glu Arg Val Ala Arg Glu
                290                 295                 300

Asn Ser Asp Leu Gln Arg Gln Lys Leu Glu Ala Gln Gln Gly Leu
                305                 310                 315

Arg Ala Ser Gln Glu Ala Lys Gln Lys Val Glu Lys Glu Ala Gln
                320                 325                 330

Ala Arg Glu Ala Lys Leu Gln Ala Glu Cys Ser Arg Gln Thr Gln
                335                 340                 345

Leu Ala Leu Glu Glu Lys Ala Val Leu Arg Lys Glu Arg Asp Asn
                350                 355                 360

Leu Ala Lys Glu Leu Glu Glu Lys Lys Arg Glu Ala Glu Gln Leu
                365                 370                 375

Arg Met Glu Leu Ala Ile Arg Asn Ser Ala Leu Asp Thr Cys Ile
                380                 385                 390

Lys Thr Lys Ser Gln Pro Met Met Pro Val Ser Arg Pro Met Gly
                395                 400                 405
```

```
Pro Val Pro Asn Pro Gln Pro Ile Asp Pro Ala Ser Leu Glu Glu
                410                 415                 420

Phe Lys Arg Lys Ile Leu Glu Ser Gln Arg Pro Pro Ala Gly Ile
                425                 430                 435

Pro Val Ala Pro Ser Ser Gly
                440


<210> SEQ ID NO 111
<211> LENGTH: 170
<212> TYPE: PRT
<213> ORGANISM: Homo Sapien

<400> SEQUENCE: 111

Met Met Ala Gly Met Lys Ile Gln Leu Val Cys Met Leu Leu Leu
  1               5                  10                  15

Ala Phe Ser Ser Trp Ser Leu Cys Ser Asp Ser Glu Glu Glu Met
                 20                  25                  30

Lys Ala Leu Glu Ala Asp Phe Leu Thr Asn Met His Thr Ser Lys
                 35                  40                  45

Ile Ser Lys Ala His Val Pro Ser Trp Lys Met Thr Leu Leu Asn
                 50                  55                  60

Val Cys Ser Leu Val Asn Asn Leu Asn Ser Pro Ala Glu Glu Thr
                 65                  70                  75

Gly Glu Val His Glu Glu Glu Leu Val Ala Arg Arg Lys Leu Pro
                 80                  85                  90

Thr Ala Leu Asp Gly Phe Ser Leu Glu Ala Met Leu Thr Ile Tyr
                 95                 100                 105

Gln Leu His Lys Ile Cys His Ser Arg Ala Phe Gln His Trp Glu
                110                 115                 120

Leu Ile Gln Glu Asp Ile Leu Asp Thr Gly Asn Asp Lys Asn Gly
                125                 130                 135

Lys Glu Glu Val Ile Lys Arg Lys Ile Pro Tyr Ile Leu Lys Arg
                140                 145                 150

Gln Leu Tyr Glu Asn Lys Pro Arg Arg Pro Tyr Ile Leu Lys Arg
                155                 160                 165

Asp Ser Tyr Tyr Tyr
                170


<210> SEQ ID NO 112
<211> LENGTH: 502
<212> TYPE: PRT
<213> ORGANISM: Homo Sapien

<400> SEQUENCE: 112

Met Leu Leu Arg Ser Ala Gly Lys Leu Asn Val Gly Thr Lys Lys
  1               5                  10                  15

Glu Asp Gly Glu Ser Thr Ala Pro Thr Pro Arg Pro Lys Val Leu
                 20                  25                  30

Arg Cys Lys Cys His His His Cys Pro Glu Asp Ser Val Asn Asn
                 35                  40                  45

Ile Cys Ser Thr Asp Gly Tyr Cys Phe Thr Met Ile Glu Glu Asp
                 50                  55                  60

Asp Ser Gly Leu Pro Val Val Thr Ser Gly Cys Leu Gly Leu Glu
                 65                  70                  75

Gly Ser Asp Phe Gln Cys Arg Asp Thr Pro Ile Pro His Gln Arg
                 80                  85                  90
```

-continued

```
Arg Ser Ile Glu Cys Cys Thr Glu Arg Asn Glu Cys Asn Lys Asp
                95                  100                 105

Leu His Pro Thr Leu Pro Pro Leu Lys Asn Arg Asp Phe Val Asp
                110                 115                 120

Gly Pro Ile His His Arg Ala Leu Leu Ile Ser Val Thr Val Cys
                125                 130                 135

Ser Leu Leu Leu Val Leu Ile Ile Leu Phe Cys Tyr Phe Arg Tyr
                140                 145                 150

Lys Arg Gln Glu Thr Arg Pro Arg Tyr Ser Ile Gly Leu Glu Gln
                155                 160                 165

Asp Glu Thr Tyr Ile Pro Pro Gly Glu Ser Leu Arg Asp Leu Ile
                170                 175                 180

Glu Gln Ser Gln Ser Ser Gly Ser Gly Ser Gly Leu Pro Leu Leu
                185                 190                 195

Val Gln Arg Thr Ile Ala Lys Gln Ile Gln Met Val Lys Gln Ile
                200                 205                 210

Gly Lys Gly Arg Tyr Gly Glu Val Trp Met Gly Lys Trp Arg Gly
                215                 220                 225

Glu Lys Val Ala Val Lys Val Phe Phe Thr Thr Glu Glu Ala Ser
                230                 235                 240

Trp Phe Arg Glu Thr Glu Ile Tyr Gln Thr Val Leu Met Arg His
                245                 250                 255

Glu Asn Ile Leu Gly Phe Ile Ala Ala Asp Ile Lys Gly Thr Gly
                260                 265                 270

Ser Trp Thr Gln Leu Tyr Leu Ile Thr Asp Tyr His Glu Asn Gly
                275                 280                 285

Ser Leu Tyr Asp Tyr Leu Lys Ser Thr Thr Leu Asp Ala Lys Ser
                290                 295                 300

Met Leu Lys Leu Ala Tyr Ser Ser Val Ser Gly Leu Cys His Leu
                305                 310                 315

His Thr Glu Ile Phe Ser Thr Gln Gly Lys Pro Ala Ile Ala His
                320                 325                 330

Arg Asp Leu Lys Ser Lys Asn Ile Leu Val Lys Lys Asn Gly Thr
                335                 340                 345

Cys Cys Ile Ala Asp Leu Gly Leu Ala Val Lys Phe Ile Ser Asp
                350                 355                 360

Thr Asn Glu Val Asp Ile Pro Pro Asn Thr Arg Val Gly Thr Lys
                365                 370                 375

Arg Tyr Met Pro Pro Glu Val Leu Asp Glu Ser Leu Asn Arg Asn
                380                 385                 390

His Phe Gln Ser Tyr Ile Met Ala Asp Met Tyr Ser Phe Gly Leu
                395                 400                 405

Ile Leu Trp Glu Val Ala Arg Arg Cys Val Ser Gly Gly Ile Val
                410                 415                 420

Glu Glu Tyr Gln Leu Pro Tyr His Asp Leu Val Pro Ser Asp Pro
                425                 430                 435

Ser Tyr Glu Asp Met Arg Glu Ile Val Cys Ile Lys Lys Leu Arg
                440                 445                 450

Pro Ser Phe Pro Asn Arg Trp Ser Ser Asp Glu Cys Leu Arg Gln
                455                 460                 465

Met Gly Lys Leu Met Thr Glu Cys Trp Ala His Asn Pro Ala Ser
                470                 475                 480

Arg Leu Thr Ala Leu Arg Val Lys Lys Thr Leu Ala Lys Met Ser
                485                 490                 495
```

Glu Ser Gln Asp Ile Lys Leu
500

<210> SEQ ID NO 113
<211> LENGTH: 2403
<212> TYPE: DNA
<213> ORGANISM: Homo Sapien

<400> SEQUENCE: 113
ttgaagtgca ttgctgcagc tggtagcatg agtggtggcc accacctgca 50
gctggctgcc ctctggccct ggctgctgat ggctaccctg caggcaggct 100
ttggacgcac aggactggta ctggcagcag cggtggagtc tgaaagatca 150
gcagaacaga aagctgttat cagagtgatc cccttgaaaa tggaccccac 200
aggaaaactg aatctcactt tggaaggtgt gtttgctggt gttgctgaaa 250
taactccagc agaaggaaaa ttaatgcagt cccacccgct gtacctgtgc 300
aatgccagtg atgacgacaa tctggagcct ggattcatca gcatcgtcaa 350
gctggagagt cctcgacggg ccccccaccc ctgcctgtca ctggctagca 400
aggctcggat ggcgggtgag cgaggagcca gtgctgtcct ctttgacatc 450
actgaggatc gagctgctgc tgagcagctg cagcagccgc tggggctgac 500
ctggccagtg gtgttgatct ggggtaatga cgctgagaag ctgatggagt 550
ttgtgtacaa gaaccaaaag gcccatgtga ggattgagct gaaggagccc 600
ccggcctggc cagattatga tgtgtggatc ctaatgacag tggtgggcac 650
catctttgtg atcatcctgg cttcggtgct gcgcatccgg tgccgccccc 700
gccacagcag gccggatccg cttcagcaga gaacagcctg ggccatcagc 750
cagctggcca ccaggaggta ccaggccagc tgcaggcagg cccggggtga 800
gtggccagac tcagggagca gctgcagctc agcccctgtg tgtgccatct 850
gtctggagga gttctctgag gggcaggagc tacgggtcat ttcctgcctc 900
catgagttcc atcgtaactg tgtggacccc tggttacatc agcatcggac 950
ttgccccctc tgcatgttca acatcacaga gggagattca ttttcccagt 1000
ccctgggacc ctctcgatct taccaagaac caggtcgaag actccacctc 1050
attcgccagc atcccggcca tgcccactac cacctccctg ctgcctacct 1100
gttgggccct tcccggagtg cagtggctcg gcccccacga cctggtccct 1150
tcctgccatc ccaggagcca ggcatgggcc ctcggcatca ccgcttcccc 1200
agagctacac atccccgggc tccaggagag cagcagcgcc tggcaggagc 1250
ccagcacccc tatgcacaag gctggggact gagccacctc caatccacct 1300
cacagcaccc tgctgcttgc ccagtgcccc tacgccgggc caggccccct 1350
gacagcagtg gatctggaga aagctattgc acagaacgca gtgggtacct 1400
ggcagatggg ccagccagtg actccagctc agggccctgt catggctctt 1450
ccagtgactc tgtggtcaac tgcacggaca tcagcctaca gggggtccat 1500
ggcagcagtt ctactttctg cagctcccta agcagtgact ttgacccccct 1550 agtgtactgc agccctaaag gggatcccca gcgagtggac atgcagccta 1600
gtgtgacctc tcggcctcgt tccttggact cggtggtgcc cacaggggaa 1650
acccaggttt ccagccatgt ccactaccac cgccaccggc accaccacta 1700

-continued caaaaagcgg ttccagtggc atggcaggaa gcctggccca gaaaccggag 1750
tcccccagtc caggcctcct attcctcgga cacagcccca gccagagcca 1800
ccttctcctg atcagcaagt caccagatcc aactcagcag ccccttcggg 1850
gcggctctct aacccacagt gccccagggc cctccctgag ccagcccctg 1900
gcccagttga cgcctccagc atctgcccca gtaccagcag tctgttcaac 1950
ttgcaaaaat ccagcctctc tgcccgacac ccacagagga aaaggcgggg 2000
gggtccctcc gagcccaccc ctggctctcg gccccaggat gcaactgtgc 2050
acccagcttg ccagattttt ccccattaca cccccagtgt ggcatatcct 2100
tggtccccag aggcacaccc cttgatctgt ggacctccag gcctggacaa 2150
gaggctgcta ccagaaaccc caggccccctg ttactcaaat tcacagccag 2200
tgtggttgtg cctgactcct cgccagcccc tggaaccaca tccacctggg 2250
gaggggcctt ctgaatggag ttctgacacc gcagagggca ggccatgccc 2300
ttatccgcac tgccaggtgc tgtcggccca gcctggctca gaggaggaac 2350
tcgaggagct gtgtgaacag gctgtgtgag atgttcaggc ctagctccaa 2400
cca 2403

<210> SEQ ID NO 114
<211> LENGTH: 783
<212> TYPE: PRT
<213> ORGANISM: Homo Sapien

<400> SEQUENCE: 114

Met Ser Gly Gly His His Leu Gln Leu Ala Ala Leu Trp Pro Trp
1 5 10 15

Leu Leu Met Ala Thr Leu Gln Ala Gly Phe Gly Arg Thr Gly Leu
20 25 30

Val Leu Ala Ala Ala Val Glu Ser Glu Arg Ser Ala Glu Gln Lys
35 40 45

Ala Val Ile Arg Val Ile Pro Leu Lys Met Asp Pro Thr Gly Lys
50 55 60

Leu Asn Leu Thr Leu Glu Gly Val Phe Ala Gly Val Ala Glu Ile
65 70 75

Thr Pro Ala Glu Gly Lys Leu Met Gln Ser His Pro Leu Tyr Leu
80 85 90

Cys Asn Ala Ser Asp Asp Asp Asn Leu Glu Pro Gly Phe Ile Ser
95 100 105

Ile Val Lys Leu Glu Ser Pro Arg Arg Ala Pro His Pro Cys Leu
110 115 120

Ser Leu Ala Ser Lys Ala Arg Met Ala Gly Glu Arg Gly Ala Ser
125 130 135

Ala Val Leu Phe Asp Ile Thr Glu Asp Arg Ala Ala Ala Glu Gln
140 145 150

Leu Gln Gln Pro Leu Gly Leu Thr Trp Pro Val Val Leu Ile Trp
155 160 165

Gly Asn Asp Ala Glu Lys Leu Met Glu Phe Val Tyr Lys Asn Gln
170 175 180

Lys Ala His Val Arg Ile Glu Leu Lys Glu Pro Pro Ala Trp Pro
185 190 195

Asp Tyr Asp Val Trp Ile Leu Met Thr Val Val Gly Thr Ile Phe
200 205 210

-continued

```
Val Ile Ile Leu Ala Ser Val Leu Arg Ile Arg Cys Arg Pro Arg
                215                 220                 225

His Ser Arg Pro Asp Pro Leu Gln Gln Arg Thr Ala Trp Ala Ile
                230                 235                 240

Ser Gln Leu Ala Thr Arg Arg Tyr Gln Ala Ser Cys Arg Gln Ala
                245                 250                 255

Arg Gly Glu Trp Pro Asp Ser Gly Ser Ser Cys Ser Ser Ala Pro
                260                 265                 270

Val Cys Ala Ile Cys Leu Glu Glu Phe Ser Glu Gly Gln Glu Leu
                275                 280                 285

Arg Val Ile Ser Cys Leu His Glu Phe His Arg Asn Cys Val Asp
                290                 295                 300

Pro Trp Leu His Gln His Arg Thr Cys Pro Leu Cys Met Phe Asn
                305                 310                 315

Ile Thr Glu Gly Asp Ser Phe Ser Gln Ser Leu Gly Pro Ser Arg
                320                 325                 330

Ser Tyr Gln Glu Pro Gly Arg Arg Leu His Leu Ile Arg Gln His
                335                 340                 345

Pro Gly His Ala His Tyr His Leu Pro Ala Ala Tyr Leu Leu Gly
                350                 355                 360

Pro Ser Arg Ser Ala Val Ala Arg Pro Pro Arg Pro Gly Pro Phe
                365                 370                 375

Leu Pro Ser Gln Glu Pro Gly Met Gly Pro Arg His His Arg Phe
                380                 385                 390

Pro Arg Ala Thr His Pro Arg Ala Pro Gly Glu Gln Gln Arg Leu
                395                 400                 405

Ala Gly Ala Gln His Pro Tyr Ala Gln Gly Trp Gly Leu Ser His
                410                 415                 420

Leu Gln Ser Thr Ser Gln His Pro Ala Ala Cys Pro Val Pro Leu
                425                 430                 435

Arg Arg Ala Arg Pro Pro Asp Ser Ser Gly Ser Gly Glu Ser Tyr
                440                 445                 450

Cys Thr Glu Arg Ser Gly Tyr Leu Ala Asp Gly Pro Ala Ser Asp
                455                 460                 465

Ser Ser Ser Gly Pro Cys His Gly Ser Ser Ser Asp Ser Val Val
                470                 475                 480

Asn Cys Thr Asp Ile Ser Leu Gln Gly Val His Gly Ser Ser Ser
                485                 490                 495

Thr Phe Cys Ser Ser Leu Ser Ser Asp Phe Asp Pro Leu Val Tyr
                500                 505                 510

Cys Ser Pro Lys Gly Asp Pro Gln Arg Val Asp Met Gln Pro Ser
                515                 520                 525

Val Thr Ser Arg Pro Arg Ser Leu Asp Ser Val Val Pro Thr Gly
                530                 535                 540

Glu Thr Gln Val Ser Ser His Val His Tyr His Arg His Arg His
                545                 550                 555

His His Tyr Lys Lys Arg Phe Gln Trp His Gly Arg Lys Pro Gly
                560                 565                 570

Pro Glu Thr Gly Val Pro Gln Ser Arg Pro Pro Ile Pro Arg Thr
                575                 580                 585

Gln Pro Gln Pro Glu Pro Pro Ser Pro Asp Gln Gln Val Thr Arg
                590                 595                 600

Ser Asn Ser Ala Ala Pro Ser Gly Arg Leu Ser Asn Pro Gln Cys
                605                 610                 615
```

```
Pro Arg Ala Leu Pro Glu Pro Ala Pro Gly Pro Val Asp Ala Ser
                620                 625                 630

Ser Ile Cys Pro Ser Thr Ser Ser Leu Phe Asn Leu Gln Lys Ser
                635                 640                 645

Ser Leu Ser Ala Arg His Pro Gln Arg Lys Arg Arg Gly Gly Pro
                650                 655                 660

Ser Glu Pro Thr Pro Gly Ser Arg Pro Gln Asp Ala Thr Val His
                665                 670                 675

Pro Ala Cys Gln Ile Phe Pro His Tyr Thr Pro Ser Val Ala Tyr
                680                 685                 690

Pro Trp Ser Pro Glu Ala His Pro Leu Ile Cys Gly Pro Pro Gly
                695                 700                 705

Leu Asp Lys Arg Leu Leu Pro Glu Thr Pro Gly Pro Cys Tyr Ser
                710                 715                 720

Asn Ser Gln Pro Val Trp Leu Cys Leu Thr Pro Arg Gln Pro Leu
                725                 730                 735

Glu Pro His Pro Pro Gly Glu Gly Pro Ser Glu Trp Ser Ser Asp
                740                 745                 750

Thr Ala Glu Gly Arg Pro Cys Pro Tyr Pro His Cys Gln Val Leu
                755                 760                 765

Ser Ala Gln Pro Gly Ser Glu Glu Glu Leu Glu Glu Leu Cys Glu
                770                 775                 780

Gln Ala Val


<210> SEQ ID NO 115
<211> LENGTH: 2407
<212> TYPE: DNA
<213> ORGANISM: Homo Sapien

<400> SEQUENCE: 115

ccctttgaag tgcattgctg cagctggtag catgagtggt ggccaccagc        50

tgcagctggc tgccctctgg ccctggctgc tgatggctac cctgcaggca       100

ggctttggac gcacaggact ggtactggca gcagcggtgg agtctgaaag       150

atcagcagaa cagaaagctg ttatcagagt gatccccttg aaaatggacc       200

ccacaggaaa actgaatctc actttggaag gtgtgtttgc tggtgttgct       250

gaaataactc cagcagaagg aaaattaatg cagtcccacc cgctgtacct       300

gtgcaatgcc agtgatgacg acaatctgga gcctggattc atcagcatcg       350

tcaagctgga gagtcctcga cgggcccccc gcccctgcct gtcactggct       400

agcaaggctc ggatggcggg tgagcgagga gccagtgctg tcctctttga       450

catcactgag gatcgagctg ctgctgagca gctgcagcag ccgctggggc       500

tgacctggcc agtggtgttg atctggggta atgacgctga gaagctgatg       550

gagtttgtgt acaagaacca aaaggcccat gtgaggattg agctgaagga       600

gccccccggcc tggccagatt atgatgtgtg gatcctaatg acagtggtgg       650

gcaccatctt tgtgatcatc ctggcttcgg tgctgcgcat ccagtgccgc       700

cccgcgccaca gcaggccgga tccgcttcag cagagaacag cctgggccat       750

cagccagctg gccaccagga ggtaccaggc cagctgcagg caggcccggg       800

gtgagtggcc agactcaggg agcagctgca gctcagcccc tgtgtgtgcc       850

atctgtctgg aggagttctc tgaggggcag gagctacggg tcatttcctg       900
```

cctccatgag ttccatcgta actgtgtgga cccctggtta catcagcatc 950
ggacttgccc cctctgcatg ttcaacatca cagagggaga ttcattttcc 1000
cagtccctgg gaccctctcg atcttaccaa gaaccaggtc gaagactcca 1050
cctcattcgc cagcatcccg gccatgccca ctaccacctc cctgctgcct 1100
acctgttggg cccttcccgg agtgcagtgg ctcggccccc acgacctggt 1150
cccttcctgc catcccagga gccaggcatg ggccctcggc atcaccgctt 1200
ccccagagct gcacatcccc gggctccagg agagcagcag cgcctggcag 1250
gagcccagca cccctatgca caaggctggg gactgagcca cctccaatcc 1300
acctcacagc accctgctgc ttgcccagtg cccctacgcc gggccaggcc 1350
ccctgacagc agtggatctg gagaaagcta ttgcacagaa cgcagtgggt 1400
acctggcaga tgggccagcc agtgactcca gctcagggcc ctgtcatggc 1450
tcttccagtg actctgtggt caactgcacg gacatcagcc tacagggggt 1500
ccatggcagc agttctactt tctgcagctc cctaagcagt gactttgacc 1550
ccctagtgta ctgcagccct aaaggggatc cccagcgagt ggacatgcag 1600
cctagtgtga cctctcggcc tcgttccttg gactcggtgg tgcccacagg 1650
ggaaacccag gtttccagcc atgtccacta ccaccgccac cggcaccacc 1700
actacaaaaa gcggttccag tggcatggca ggaagcctgg cccagaaacc 1750
ggagtccccc agtccaggcc tcctattcct cggacacagc cccagccaga 1800
gccaccttct cctgatcagc aagtcaccag atccaactca gcagcccctt 1850
cggggcggct ctctaaccca cagtgcccca gggccctccc tgagccagcc 1900
cctggcccag ttgacgcctc cagcatctgc cccagtacca gcagtctgtt 1950
caacttgcaa aaatccagcc tctctgcccg acacccacag aggaaaaggc 2000
ggggggatcc ctccgagccc accccctggct ctcggcccca ggatgcaact 2050
gtgcacccag cttgccagat tttccccat tacaccccca gtgtggcata 2100
tccttggtcc ccagaggcac accccttgat ctgtggacct ccaggcctgg 2150
acaagaggct gctaccagaa accccaggcc cctgttactc aaattcacag 2200
ccagtgtggt tgtgcctgac tcctcgccag cccctggaac cacatccacc 2250
tggggagggg ccttctgaat ggagttctga caccgcagag ggcaggccat 2300
gcccttgtcc gcactgccag gtgctgtcgg cccagcctgg ctcagaggag 2350
gaactcgagg agctgtgtga acaggctgtg tgagatgttc aggcctagct 2400
ccaacca 2407

<210> SEQ ID NO 116
<211> LENGTH: 783
<212> TYPE: PRT
<213> ORGANISM: Homo Sapien

<400> SEQUENCE: 116

Met Ser Gly Gly His Gln Leu Gln Leu Ala Ala Leu Trp Pro Trp
1 5 10 15

Leu Leu Met Ala Thr Leu Gln Ala Gly Phe Gly Arg Thr Gly Leu
20 25 30

Val Leu Ala Ala Ala Val Glu Ser Glu Arg Ser Ala Glu Gln Lys
35 40 45

Ala Val Ile Arg Val Ile Pro Leu Lys Met Asp Pro Thr Gly Lys

-continued

```
                50                  55                  60

Leu Asn Leu Thr Leu Glu Gly Val Phe Ala Gly Val Ala Glu Ile
                65                  70                  75

Thr Pro Ala Glu Gly Lys Leu Met Gln Ser His Pro Leu Tyr Leu
                80                  85                  90

Cys Asn Ala Ser Asp Asp Asp Asn Leu Glu Pro Gly Phe Ile Ser
                95                  100                 105

Ile Val Lys Leu Glu Ser Pro Arg Arg Ala Pro Arg Pro Cys Leu
                110                 115                 120

Ser Leu Ala Ser Lys Ala Arg Met Ala Gly Glu Arg Gly Ala Ser
                125                 130                 135

Ala Val Leu Phe Asp Ile Thr Glu Asp Arg Ala Ala Ala Glu Gln
                140                 145                 150

Leu Gln Gln Pro Leu Gly Leu Thr Trp Pro Val Val Leu Ile Trp
                155                 160                 165

Gly Asn Asp Ala Glu Lys Leu Met Glu Phe Val Tyr Lys Asn Gln
                170                 175                 180

Lys Ala His Val Arg Ile Glu Leu Lys Glu Pro Pro Ala Trp Pro
                185                 190                 195

Asp Tyr Asp Val Trp Ile Leu Met Thr Val Val Gly Thr Ile Phe
                200                 205                 210

Val Ile Ile Leu Ala Ser Val Leu Arg Ile Gln Cys Arg Pro Arg
                215                 220                 225

His Ser Arg Pro Asp Pro Leu Gln Gln Arg Thr Ala Trp Ala Ile
                230                 235                 240

Ser Gln Leu Ala Thr Arg Arg Tyr Gln Ala Ser Cys Arg Gln Ala
                245                 250                 255

Arg Gly Glu Trp Pro Asp Ser Gly Ser Ser Cys Ser Ser Ala Pro
                260                 265                 270

Val Cys Ala Ile Cys Leu Glu Glu Phe Ser Glu Gly Gln Glu Leu
                275                 280                 285

Arg Val Ile Ser Cys Leu His Glu Phe His Arg Asn Cys Val Asp
                290                 295                 300

Pro Trp Leu His Gln His Arg Thr Cys Pro Leu Cys Met Phe Asn
                305                 310                 315

Ile Thr Glu Gly Asp Ser Phe Ser Gln Ser Leu Gly Pro Ser Arg
                320                 325                 330

Ser Tyr Gln Glu Pro Gly Arg Arg Leu His Leu Ile Arg Gln His
                335                 340                 345

Pro Gly His Ala His Tyr His Leu Pro Ala Ala Tyr Leu Leu Gly
                350                 355                 360

Pro Ser Arg Ser Ala Val Ala Arg Pro Pro Arg Pro Gly Pro Phe
                365                 370                 375

Leu Pro Ser Gln Glu Pro Gly Met Gly Pro Arg His His Arg Phe
                380                 385                 390

Pro Arg Ala Ala His Pro Arg Ala Pro Gly Glu Gln Gln Arg Leu
                395                 400                 405

Ala Gly Ala Gln His Pro Tyr Ala Gln Gly Trp Gly Leu Ser His
                410                 415                 420

Leu Gln Ser Thr Ser Gln His Pro Ala Ala Cys Pro Val Pro Leu
                425                 430                 435

Arg Arg Ala Arg Pro Pro Asp Ser Ser Gly Ser Gly Glu Ser Tyr
                440                 445                 450
```

```
Cys Thr Glu Arg Ser Gly Tyr Leu Ala Asp Gly Pro Ala Ser Asp
                455                 460                 465

Ser Ser Ser Gly Pro Cys His Gly Ser Ser Ser Asp Ser Val Val
                470                 475                 480

Asn Cys Thr Asp Ile Ser Leu Gln Gly Val His Gly Ser Ser Ser
                485                 490                 495

Thr Phe Cys Ser Ser Leu Ser Ser Asp Phe Asp Pro Leu Val Tyr
                500                 505                 510

Cys Ser Pro Lys Gly Asp Pro Gln Arg Val Asp Met Gln Pro Ser
                515                 520                 525

Val Thr Ser Arg Pro Arg Ser Leu Asp Ser Val Val Pro Thr Gly
                530                 535                 540

Glu Thr Gln Val Ser Ser His Val His Tyr His Arg His Arg His
                545                 550                 555

His His Tyr Lys Lys Arg Phe Gln Trp His Gly Arg Lys Pro Gly
                560                 565                 570

Pro Glu Thr Gly Val Pro Gln Ser Arg Pro Pro Ile Pro Arg Thr
                575                 580                 585

Gln Pro Gln Pro Glu Pro Pro Ser Pro Asp Gln Gln Val Thr Arg
                590                 595                 600

Ser Asn Ser Ala Ala Pro Ser Gly Arg Leu Ser Asn Pro Gln Cys
                605                 610                 615

Pro Arg Ala Leu Pro Glu Pro Ala Pro Gly Pro Val Asp Ala Ser
                620                 625                 630

Ser Ile Cys Pro Ser Thr Ser Ser Leu Phe Asn Leu Gln Lys Ser
                635                 640                 645

Ser Leu Ser Ala Arg His Pro Gln Arg Lys Arg Arg Gly Gly Pro
                650                 655                 660

Ser Glu Pro Thr Pro Gly Ser Arg Pro Gln Asp Ala Thr Val His
                665                 670                 675

Pro Ala Cys Gln Ile Phe Pro His Tyr Thr Pro Ser Val Ala Tyr
                680                 685                 690

Pro Trp Ser Pro Glu Ala His Pro Leu Ile Cys Gly Pro Pro Gly
                695                 700                 705

Leu Asp Lys Arg Leu Leu Pro Glu Thr Pro Gly Pro Cys Tyr Ser
                710                 715                 720

Asn Ser Gln Pro Val Trp Leu Cys Leu Thr Pro Arg Gln Pro Leu
                725                 730                 735

Glu Pro His Pro Pro Gly Glu Gly Pro Ser Glu Trp Ser Ser Asp
                740                 745                 750

Thr Ala Glu Gly Arg Pro Cys Pro Cys Pro His Cys Gln Val Leu
                755                 760                 765

Ser Ala Gln Pro Gly Ser Glu Glu Glu Leu Glu Glu Leu Cys Glu
                770                 775                 780

Gln Ala Val
```

<210> SEQ ID NO 117
<211> LENGTH: 2403
<212> TYPE: DNA
<213> ORGANISM: Homo Sapien

<400> SEQUENCE: 117

```
ttgaagtgca ttgctgcagc tggtagcatg agtggtggcc accacctgca        50

gctggctgcc ctctggccct ggctgctgat ggctaccctg caggcaggct       100
```

-continued

```
ttggacgcac aggactggta ctggcagcag cggtggagtc tgaaagatca      150
gcagaacaga aagctgttat cagagtgatc cccttgaaaa tggaccccac      200
aggaaaactg aatctcactt tggaaggtgt gtttgctggt gttgctgaaa      250
taactccagc agaaggaaaa ttaatgcagt cccacccgct gtacctgtgc      300
aatgccagtg atgacgacaa tctggagcct ggattcatca gcatcgtcaa      350
gctggagagt cctcgacggg ccccccaccc ctgcctgtca ctggctagca      400
aggctcggat ggcgggtgag cgaggagcca gtgctgtcct ctttgacatc      450
actgaggatc gagctgctgc tgagcagctg cagcagccgc tggggctgac      500
ctggccagtg gtgttgatct ggggtaatga cgctgagaag ctgatggagt      550
ttgtgtacaa gaaccaaaag gcccatgtga ggattgagct gaaggagccc      600
ccggcctggc cagattatga tgtgtggatc ctaatgacag tggtgggcac      650
catctttgtg atcatcctgg cttcggtgct gcgcatccgg tgccgccccc      700
gccacagcag gccggatccg cttcagcaga gaacagcctg ggccatcagc      750
cagctggcca ccaggaggta ccaggccagc tgcaggcagg cccggggtga      800
gtggccagac tcagggagca gctgcagctc agcccctgtg tgtgccatct      850
gtctggagga gttctctgag gggcaggagc tacgggtcat ttcctgcctc      900
catgagttcc atcgtaactg tgtggacccc tggttacatc agcatcggac      950
ttgccccctc tgcatgttca acatcacaga gggagattca ttttcccagt     1000
ccctgggacc ctctcgatct taccaagaac caggtcgaag actccacctc     1050
attcgccagc atcccggcca tgcccactac cacctccctg ctgcctacct     1100
gttgggccct tcccggagtg cagtggctcg gcccccacga cctggtccct     1150
tcctgccatc ccaggagcca ggcatgggcc ctcggcatca ccgcttcccc     1200
agagctgcac atccccgggc tccaggagag cagcagcgcc tggcaggagc     1250
ccagcacccc tatgcacaag gctggggaat gagccacctc caatccacct     1300
cacagcaccc tgctgcttgc ccagtgcccc tacgccgggc caggccccct     1350
gacagcagtg gatctggaga aagctattgc acagaacgca gtgggtacct     1400
ggcagatggg ccagccagtg actccagctc agggccctgt catggctctt     1450
ccagtgactc tgtggtcaac tgcacggaca tcagcctaca gggggtccat     1500
ggcagcagtt ctactttctg cagctcccta agcagtgact ttgaccccct     1550
agtgtactgc agccctaaag gggatcccca gcgagtggac atgcagccta     1600
gtgtgacctc tcggcctcgt tccttggact cggtggtgcc cacaggggaa     1650
acccaggttt ccagccatgt ccactaccac cgccaccggc accaccacta     1700
caaaaagcgg ttccagtggc atggcaggaa gcctggccca gaaaccggag     1750
tcccccagtc caggcctcct attcctcgga cacagcccca gccagagcca     1800
ccttctcctg atcagcaagt caccagatcc aactcagcag ccccttcggg     1850
gcggctctct aacccacagt gccccagggc cctccctgag ccagcccctg     1900
gcccagttga cgcctccagc atctgcccca gtaccagcag tctgttcaac     1950
ttgcaaaaat ccagcctctc tgcccgacac ccacagagga aaaggcgggg     2000
gggtccctcc gagcccaccc ctggctctcg gccccaggat gcaactgtgc     2050
acccagcttg ccagattttt ccccattaca cccccagtgt ggcatatcct     2100
```

tggtccccag aggcacaccc cttgatctgt ggacctccag gcctggacaa 2150
gaggctgcta ccagaaaccc caggcccctg ttactcaaat tcacagccag 2200
tgtggttgtg cctgactcct cgccagcccc tggaaccaca tccacctggg 2250
gaggggcctt ctgaatggag ttctgacacc gcagagggca ggccatgccc 2300
ttatccgcac tgccaggtgc tgtcggccca gcctggctca gaggaggaac 2350
tcgaggagct gtgtgaacag gctgtgtgag atgttcaggc ctagctccaa 2400
cca 2403

<210> SEQ ID NO 118
<211> LENGTH: 783
<212> TYPE: PRT
<213> ORGANISM: Homo Sapien

<400> SEQUENCE: 118

Met Ser Gly Gly His His Leu Gln Leu Ala Ala Leu Trp Pro Trp
1 5 10 15

Leu Leu Met Ala Thr Leu Gln Ala Gly Phe Gly Arg Thr Gly Leu
20 25 30

Val Leu Ala Ala Ala Val Glu Ser Glu Arg Ser Ala Glu Gln Lys
35 40 45

Ala Val Ile Arg Val Ile Pro Leu Lys Met Asp Pro Thr Gly Lys
50 55 60

Leu Asn Leu Thr Leu Glu Gly Val Phe Ala Gly Val Ala Glu Ile
65 70 75

Thr Pro Ala Glu Gly Lys Leu Met Gln Ser His Pro Leu Tyr Leu
80 85 90

Cys Asn Ala Ser Asp Asp Asp Asn Leu Glu Pro Gly Phe Ile Ser
95 100 105

Ile Val Lys Leu Glu Ser Pro Arg Arg Ala Pro His Pro Cys Leu
110 115 120

Ser Leu Ala Ser Lys Ala Arg Met Ala Gly Glu Arg Gly Ala Ser
125 130 135

Ala Val Leu Phe Asp Ile Thr Glu Asp Arg Ala Ala Ala Glu Gln
140 145 150

Leu Gln Gln Pro Leu Gly Leu Thr Trp Pro Val Val Leu Ile Trp
155 160 165

Gly Asn Asp Ala Glu Lys Leu Met Glu Phe Val Tyr Lys Asn Gln
170 175 180

Lys Ala His Val Arg Ile Glu Leu Lys Glu Pro Pro Ala Trp Pro
185 190 195

Asp Tyr Asp Val Trp Ile Leu Met Thr Val Val Gly Thr Ile Phe
200 205 210

Val Ile Ile Leu Ala Ser Val Leu Arg Ile Arg Cys Arg Pro Arg
215 220 225

His Ser Arg Pro Asp Pro Leu Gln Gln Arg Thr Ala Trp Ala Ile
230 235 240

Ser Gln Leu Ala Thr Arg Arg Tyr Gln Ala Ser Cys Arg Gln Ala
245 250 255

Arg Gly Glu Trp Pro Asp Ser Gly Ser Ser Cys Ser Ser Ala Pro
260 265 270

Val Cys Ala Ile Cys Leu Glu Glu Phe Ser Glu Gly Gln Glu Leu
275 280 285

Arg Val Ile Ser Cys Leu His Glu Phe His Arg Asn Cys Val Asp

-continued

```
                290                 295                 300

Pro Trp Leu His Gln His Arg Thr Cys Pro Leu Cys Met Phe Asn
                305                 310                 315

Ile Thr Glu Gly Asp Ser Phe Ser Gln Ser Leu Gly Pro Ser Arg
                320                 325                 330

Ser Tyr Gln Glu Pro Gly Arg Arg Leu His Leu Ile Arg Gln His
                335                 340                 345

Pro Gly His Ala His Tyr His Leu Pro Ala Ala Tyr Leu Leu Gly
                350                 355                 360

Pro Ser Arg Ser Ala Val Ala Arg Pro Pro Arg Pro Gly Pro Phe
                365                 370                 375

Leu Pro Ser Gln Glu Pro Gly Met Gly Pro Arg His His Arg Phe
                380                 385                 390

Pro Arg Ala Ala His Pro Arg Ala Pro Gly Glu Gln Gln Arg Leu
                395                 400                 405

Ala Gly Ala Gln His Pro Tyr Ala Gln Gly Trp Gly Met Ser His
                410                 415                 420

Leu Gln Ser Thr Ser Gln His Pro Ala Ala Cys Pro Val Pro Leu
                425                 430                 435

Arg Arg Ala Arg Pro Pro Asp Ser Ser Gly Ser Gly Glu Ser Tyr
                440                 445                 450

Cys Thr Glu Arg Ser Gly Tyr Leu Ala Asp Gly Pro Ala Ser Asp
                455                 460                 465

Ser Ser Ser Gly Pro Cys His Gly Ser Ser Ser Asp Ser Val Val
                470                 475                 480

Asn Cys Thr Asp Ile Ser Leu Gln Gly Val His Gly Ser Ser Ser
                485                 490                 495

Thr Phe Cys Ser Ser Leu Ser Ser Asp Phe Asp Pro Leu Val Tyr
                500                 505                 510

Cys Ser Pro Lys Gly Asp Pro Gln Arg Val Asp Met Gln Pro Ser
                515                 520                 525

Val Thr Ser Arg Pro Arg Ser Leu Asp Ser Val Val Pro Thr Gly
                530                 535                 540

Glu Thr Gln Val Ser Ser His Val His Tyr His Arg His Arg His
                545                 550                 555

His His Tyr Lys Lys Arg Phe Gln Trp His Gly Arg Lys Pro Gly
                560                 565                 570

Pro Glu Thr Gly Val Pro Gln Ser Arg Pro Pro Ile Pro Arg Thr
                575                 580                 585

Gln Pro Gln Pro Glu Pro Pro Ser Pro Asp Gln Gln Val Thr Arg
                590                 595                 600

Ser Asn Ser Ala Ala Pro Ser Gly Arg Leu Ser Asn Pro Gln Cys
                605                 610                 615

Pro Arg Ala Leu Pro Glu Pro Ala Pro Gly Pro Val Asp Ala Ser
                620                 625                 630

Ser Ile Cys Pro Ser Thr Ser Ser Leu Phe Asn Leu Gln Lys Ser
                635                 640                 645

Ser Leu Ser Ala Arg His Pro Gln Arg Lys Arg Arg Gly Gly Pro
                650                 655                 660

Ser Glu Pro Thr Pro Gly Ser Arg Pro Gln Asp Ala Thr Val His
                665                 670                 675

Pro Ala Cys Gln Ile Phe Pro His Tyr Thr Pro Ser Val Ala Tyr
                680                 685                 690
```

Pro Trp Ser Pro Glu Ala His Pro Leu Ile Cys Gly Pro Pro Gly
695 700 705

Leu Asp Lys Arg Leu Leu Pro Glu Thr Pro Gly Pro Cys Tyr Ser
710 715 720

Asn Ser Gln Pro Val Trp Leu Cys Leu Thr Pro Arg Gln Pro Leu
725 730 735

Glu Pro His Pro Pro Gly Glu Gly Pro Ser Glu Trp Ser Ser Asp
740 745 750

Thr Ala Glu Gly Arg Pro Cys Pro Tyr Pro His Cys Gln Val Leu
755 760 765

Ser Ala Gln Pro Gly Ser Glu Glu Glu Leu Glu Glu Leu Cys Glu
770 775 780

Gln Ala Val

<210> SEQ ID NO 119
<211> LENGTH: 4839
<212> TYPE: DNA
<213> ORGANISM: Homo Sapien

<400> SEQUENCE: 119
ggaaagctag cggcagaggc tcagccccgg cggcagcgcg cgccccgctg 50
ccagcccatt ttccggacgc cacccgcggg cactgccgac gcccccgggg 100
ctgccgaggg gaggccgggg gggcgcagcg gagcgcggtc ccgcgcactg 150
agccccgcgg cgccccggga acttggcggc gacccgagcc cggcgagccg 200
gggcgcgcct cccccgccgc gcgcctcctg catgcggggc cccagctccg 250
ggcgccggcc ggagcccccc ccggccgccc ccgagccccc cgcgccccgc 300
gccgcgccgc cgcgccgtcc atgcaccgct tgatgggggt caacagcacc 350
gccgccgccg ccgccgggca gcccaatgtc tcctgcacgt gcaactgcaa 400
acgctctttg ttccagagca tggagatcac ggagctggag tttgttcaga 450
tcatcatcat cgtggtggtg atgatggtga tggtggtggt gatcacgtgc 500
ctgctgagcc actacaagct gtctgcacgg tccttcatca gccggcacag 550
ccaggggcgg aggagagaag atgccctgtc ctcagaagga tgcctgtggc 600
cctcggagag cacagtgtca ggcaacggaa tcccagagcc gcaggtctac 650
gccccgcctc ggcccaccga ccgcctggcc gtgccgccct tcgcccagcg 700
ggagcgcttc caccgcttcc agcccaccta tccgtacctg cagcacgaga 750
tcgacctgcc acccaccatc tcgctgtcag acggggagga gcccccaccc 800
taccagggcc cctgcaccct ccagcttcgg gacccccgagc agcagctgga 850 actgaaccgg gagtcggtgc gcgcaccccc aaacagaacc atcttcgaca 900
gtgacctgat ggatagtgcc aggctgggcg gcccctgccc ccccagcagt 950
aactcgggca tcagcgccac gtgctacggc agcggcgggc gcatggaggg 1000
gccgccgccc acctacagcg aggtcatcgg ccactacccg gggtcctcct 1050
tccagcacca gcagagcagt gggccgccct ccttgctgga ggggacccgg 1100
ctccaccaca cacacatcgc gcccctagag agcgcagcca tctggagcaa 1150
agagaaggat aaacagaaag gacaccctct ctagggtccc caggggggcc 1200
gggctggggc tgcgtaggtg aaaaggcaga acactccgcg cttcttagaa 1250
gaggagtgag aggaaggcgg ggggcgcagc aacgcatcgt gtggccctcc 1300

-continued

```
cctcccacct ccctgtgtat aaatatttac atgtgatgtc tggtctgaat     1350
gcacaagcta agagagcttg caaaaaaaaa aagaaaaaag aaaaaaaaaa     1400
accacgtttc tttgttgagc tgtgtcttga aggcaaaaga aaaaaaattt     1450
ctacagtagt ctttcttgtt tctagttgag ctgcgtgcgt gaatgcttat     1500
tttcttttgt ttatgataat ttcacttaac tttaaagaca tatttgcaca     1550
aaacctttgt ttaaagatct gcaatattat atatataaat atatataaga     1600
taagagaaac tgtatgtgcg agggcaggag tatttttgta ttagaagagg     1650
cctattaaaa aaaaaagttg ttttctgaac tagaagagga aaaaaatggc     1700
aatttttgag tgccaagtca gaaagtgtgt attaccttgt aaagaaaaaa     1750
attacaaagc aggggtttag agttatttat ataaatgttg agattttgca     1800
ctatttttta atataaatat gtcagtgctt gcttgatgga aacttctctt     1850
gtgtctgttg agactttaag ggagaaatgt cggaatttca gagtcgcctg     1900
acggcagagg gtgagccccc gtggagtctg cagagaggcc ttggccagga     1950
gcggcgggct ttcccgaggg gccactgtcc ctgcagagtg gatgcttctg     2000
cctagtgaca ggttatcacc acgttatata ttccctaccg aaggagacac     2050
cttttccccc ctgacccaga acagccttta aatcacaagc aaaataggaa     2100
agttaaccac ggaggcaccg agttccaggt agtggttttg cctttcccaa     2150
aaatgaaaat aaactgttac cgaaggaatt agtttttcct cttctttttt     2200
ccaactgtga aggtccccgt ggggtggagc atggtgcccc tcacaagccg     2250
cagcggctgg tgcccgggct accagggaca tgccagaggg ctcgatgact     2300
tgtctctgca gggcgctttg gtggttgttc agctggctaa aggttcaccg     2350
gtgaaggcag gtgcggtaac tgccgcactg gaccctagga agccccaggt     2400
attcgcaatc tgacctcctc ctgtctgttt cccttcacgg atcaattctc     2450
acttaagagg ccaataaaca acccaacatg aaaaggtgac aagcctgggt     2500
ttctcccagg ataggtgaaa gggttaaaat gagtaaagca gttgagcaaa     2550
caccaacccg agcttcgggc gcagaattct tcaccttctc ttccccttc      2600
catctccttt ccccgcggaa acaacgcttc ccttctggtg tgtctgttga     2650
tctgtgtttt catttacatc tctcttagac tccgctcttg ttctccaggt     2700
tttcaccaga tagatttggg gttggcggga cctgctggtg acgtgcaggt     2750
gaaggacagg aaggggcatg tgagcgtaaa tagaggtgac cagaggagag     2800
catgaggggt ggggctttgg gacccaccgg ggccagtggc tggagcttga     2850
cgtctttcct ccccatgggg gtgggagggc ccccagctgg aagagcagac     2900
tcccagctgc taccccctcc cttcccatgg gagtggcttt ccattttggg     2950
cagaatgctg actagtagac taacataaaa gatataaaag gcaataacta     3000
ttgtttgtga gcaacttttt tataacttcc aaaacaaaaa cctgagcaca     3050
gttttgaagt tctagccact cgagctcatg catgtgaaac gtgtgcttta     3100
cgaaggtggc agctgacaga cgtgggctct gcatgccgcc agcctagtag     3150
aaagttctcg ttcattggca acagcagaac ctgcctctcc gtgaagtcgt     3200
cagcctaaaa tttgtttctc tcttgaagag gattctttga aaaggtcctg     3250
cagagaaatc agtacaggtt atcccgaaag gtacaaggac gcacttgtaa     3300
```

```
agatgattaa aacgtatctt tcctttatgt gacgcgtctc tagtgcctta           3350

ctgaagaagc agtgacactc ccgtcgctcg gtgaggacgt tcccggacag           3400

tgcctcactc acctgggact ggtatcccct cccagggtcc accaagggct           3450

cctgcttttc agacacccca tcatcctcgc gcgtcctcac cctgtctcta           3500

ccagggaggt gcctagcttg gtgaggttac tcctgctcct ccaacctttt           3550

tttgccaagg tttgtacacg actcccatct aggctgaaaa cctagaagtg           3600

gaccttgtgt gtgtgcatgg tgtcagccca aagccaggct gagacagtcc           3650

tcatatcctc ttgagccaaa ctgtttgggt ctcgttgctt catggtatgg           3700

tctggatttg tgggaatggc tttgcgtgag aaaggggagg agagtggttg           3750

ctgccctcag ccggcttgag gacagagcct gtccctctca tgacaactca           3800

gtgttgaagc ccagtgtcct cagcttcatg tccagtggat ggcagaagtt           3850

catggggtag tggcctctca aaggctgggc gcatcccaag acagccagca           3900

ggttgtctct ggaaacgacc agagttaagc tctcggcttc tctgctgagg           3950

gtgcaccctt tcctctagat ggtagttgtc acgttatctt tgaaaactct           4000

tggactgctc ctgaggaggc cctcttttcc agtaggaagt tagatggggg           4050

ttctcagaag tggctgattg gaaggggaca agcttcgttt caggggtctg           4100

ccgttccatc ctggttcaga gaaggccgag cgtggctttc tctagccttg           4150

tcactgtctc cctgcctgtc aatcaccacc tttcctccag aggaggaaaa           4200

ttatctcccc tgcaaagccc ggttctacac agatttcaca aattgtgcta           4250

agaaccgtcc gtgttctcag aaagcccagt gtttttgcaa agaatgaaaa           4300

gggaccccat atgtagcaaa aatcagggct gggggagagc cgggttcatt           4350

ccctgtcctc attggtcgtc cctatgaatt gtacgtttca gagaaatttt           4400

ttttcctatg tgcaacacga agcttccaga accataaaat atcccgtcga           4450

taaggaaaga aaatgtcgtt gttgttgttt ttctggaaac tgcttgaaat           4500

cttgctgtac tatagagctc agaaggacac agcccgtcct cccctgcctg           4550

cctgattcca tggctgttgt gctgattcca atgctttcac gttggttcct           4600

ggcgtgggaa ctgctctcct ttgcagcccc atttcccaag ctctgttcaa           4650

gttaaactta tgtaagcttt ccgtggcatg cggggcgcgc acccacgtcc           4700

ccgctgcgta agactctgta tttggatgcc aatccacagg cctgaagaaa           4750

ctgcttgttg tgtatcagta atcattagtg gcaatgatga cattctgaaa           4800

agctgcaata cttatacaat aaattttaca attctttgg                       4839
```

<210> SEQ ID NO 120
<211> LENGTH: 287
<212> TYPE: PRT
<213> ORGANISM: Homo Sapien

<400> SEQUENCE: 120

```
Met His Arg Leu Met Gly Val Asn Ser Thr Ala Ala Ala Ala Ala
  1               5                  10                  15

Gly Gln Pro Asn Val Ser Cys Thr Cys Asn Cys Lys Arg Ser Leu
                 20                  25                  30

Phe Gln Ser Met Glu Ile Thr Glu Leu Glu Phe Val Gln Ile Ile
                 35                  40                  45

Ile Ile Val Val Val Met Met Val Met Val Val Val Ile Thr Cys
```

-continued

```
                50                  55                  60

Leu Leu Ser His Tyr Lys Leu Ser Ala Arg Ser Phe Ile Ser Arg
                65                  70                  75

His Ser Gln Gly Arg Arg Arg Glu Asp Ala Leu Ser Ser Glu Gly
                80                  85                  90

Cys Leu Trp Pro Ser Glu Ser Thr Val Ser Gly Asn Gly Ile Pro
                95                  100                 105

Glu Pro Gln Val Tyr Ala Pro Pro Arg Pro Thr Asp Arg Leu Ala
                110                 115                 120

Val Pro Pro Phe Ala Gln Arg Glu Arg Phe His Arg Phe Gln Pro
                125                 130                 135

Thr Tyr Pro Tyr Leu Gln His Glu Ile Asp Leu Pro Pro Thr Ile
                140                 145                 150

Ser Leu Ser Asp Gly Glu Glu Pro Pro Pro Tyr Gln Gly Pro Cys
                155                 160                 165

Thr Leu Gln Leu Arg Asp Pro Glu Gln Gln Leu Glu Leu Asn Arg
                170                 175                 180

Glu Ser Val Arg Ala Pro Pro Asn Arg Thr Ile Phe Asp Ser Asp
                185                 190                 195

Leu Met Asp Ser Ala Arg Leu Gly Gly Pro Cys Pro Pro Ser Ser
                200                 205                 210

Asn Ser Gly Ile Ser Ala Thr Cys Tyr Gly Ser Gly Gly Arg Met
                215                 220                 225

Glu Gly Pro Pro Pro Thr Tyr Ser Glu Val Ile Gly His Tyr Pro
                230                 235                 240

Gly Ser Ser Phe Gln His Gln Gln Ser Ser Gly Pro Pro Ser Leu
                245                 250                 255

Leu Glu Gly Thr Arg Leu His His Thr His Ile Ala Pro Leu Glu
                260                 265                 270

Ser Ala Ala Ile Trp Ser Lys Glu Lys Asp Lys Gln Lys Gly His
                275                 280                 285

Pro Leu
```

COMPOSITIONS AND METHODS FOR THE DIAGNOSIS AND TREATMENT OF TUMOR

RELATED APPLICATIONS

This application is a continuation of U.S. patent application Ser. No. 11/804,045, filed May 15, 2007, which is a continuation of U.S. patent application Ser. No. 10/872,972, filed Jun. 21, 2004, now abandoned, which is a continuation of U.S. patent application Ser. No. 10/241,220 filed Sep. 11, 2002, now abandoned, the benefit of all of which applications is claimed under 35 U.S.C. §120, and which claims the benefit under 35 U.S.C. §119 to U.S. Provisional Patent Application Nos. 60/323,268, filed Sep. 18, 2001, 60/339,227, filed Oct. 19, 2001, 60/336,827, filed Nov. 7, 2001, 60/331,906, filed Nov. 20, 2001, 60/345,444, filed Jan. 2, 2002, 60/369,724, filed Apr. 3, 2002 and 60/404,809, filed Aug. 19, 2002, the entirety of all of which non-provisional and provisional applications are hereby incorporated herein by reference.

FIELD OF THE INVENTION

The present invention is directed to compositions of matter useful for the diagnosis and treatment of tumor in mammals and to methods of using those compositions of matter for the same.

BACKGROUND OF THE INVENTION

Malignant tumors (cancers) are the second leading cause of death in the United States, after heart disease (Boring et al., *CA Cancel J. Clin.* 43:7 (1993)). Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites via a process called metastasis. In a cancerous state, a cell proliferates under conditions in which normal cells would not grow. Cancer manifests itself in a wide variety of forms, characterized by different degrees of invasiveness and aggressiveness.

In attempts to discover effective cellular targets for cancer diagnosis and therapy, researchers have sought to identify transmembrane or otherwise membrane-associated polypeptides that are specifically expressed on the surface of one or more particular type(s) of cancer cell as compared to on one or more normal non-cancerous cell(s). Often, such membrane-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies. In this regard, it is noted that antibody-based therapy has proved very effective in the treatment of certain cancers. For example, HERCEPTIN® and RITUXAN® (both from Genentech Inc., South San Francisco, Calif.) are antibodies that have been used successfully to treat breast cancer and non-Hodgkin's lymphoma, respectively. More specifically, HERCEPTIN® is a recombinant DNA-derived humanized monoclonal antibody that selectively binds to the extracellular domain of the human epidermal growth factor receptor 2 (HER2) proto-oncogene. HER2 protein overexpression is observed in 25-30% of primary breast cancers. RITUXAN® is a genetically engineered chimeric murine/human monoclonal antibody directed against the CD20 antigen found on the surface of normal and malignant B lymphocytes. Both these antibodies are recombinantly produced in CHO cells.

In other attempts to discover effective cellular targets for cancer diagnosis and therapy, researchers have sought to identify (1) non-membrane-associated polypeptides that are specifically produced by one or more particular type(s) of cancer cell(s) as compared to by one or more particular type(s) of non-cancerous normal cell(s), (2) polypeptides that are produced by cancer cells at an expression level that is significantly higher than that of one or more normal non-cancerous cell(s), or (3) polypeptides whose expression is specifically limited to only a single (or very limited number of different) tissue type(s) in both the cancerous and non-cancerous state (e.g., normal prostate and prostate tumor tissue). Such polypeptides may remain intracellularly located or may be secreted by the cancer cell. Moreover, such polypeptides may be expressed not by the cancer cell itself, but rather by cells which produce and/or secrete polypeptides having a potentiating or growth-enhancing effect on cancer cells. Such secreted polypeptides are often proteins that provide cancer cells with a growth advantage over normal cells and include such things as, for example, angiogenic factors, cellular adhesion factors, growth factors, and the like. Identification of antagonists of such non-membrane associated polypeptides would be expected to serve as effective therapeutic agents for the treatment of such cancers. Furthermore, identification of the expression pattern of such polypeptides would be useful for the diagnosis of particular cancers in mammals.

Despite the above identified advances in mammalian cancer therapy, there is a great need for additional diagnostic and therapeutic agents capable of detecting the presence of tumor in a mammal and for effectively inhibiting neoplastic cell growth, respectively. Accordingly, it is an objective of the present invention to identify: (1) cell membrane-associated polypeptides that are more abundantly expressed on one or more type(s) of cancer cell(s) as compared to on normal cells or on other different cancer cells, (2) non-membrane-associated polypeptides that are specifically produced by one or more particular type(s) of cancer cell(s) (or by other cells that produce polypeptides having a potentiating effect on the growth of cancer cells) as compared to by one or more particular type(s) of non-cancerous normal cell(s), (3) non-membrane-associated polypeptides that are produced by cancer cells at an expression level that is significantly higher than that of one or more normal non-cancerous cell(s), or (4) polypeptides whose expression is specifically limited to only a single (or very limited number of different) tissue type(s) in both a cancerous and non-cancerous state (e.g., normal prostate and prostate tumor tissue), and to use those polypeptides, and their encoding nucleic acids, to produce compositions of matter useful in the therapeutic treatment and diagnostic detection of cancer in mammals. It is also an objective of the present invention to identify cell membrane-associated, secreted or intracellular polypeptides whose expression is limited to a single or very limited number of tissues, and to use those polypeptides, and their encoding nucleic acids, to produce compositions of matter useful in the therapeutic treatment and diagnostic detection of cancer in mammals.

SUMMARY OF THE INVENTION

A. Embodiments

In the present specification, Applicants describe for the first time the identification of various cellular polypeptides (and their encoding nucleic acids or fragments thereof) which are expressed to a greater degree on the surface of or by one or more types of cancer cell(s) as compared to on the surface of or by one or more types of normal non-cancer cells. Alternatively, such polypeptides are expressed by cells which produce and/or secrete polypeptides having a potentiating or growth-enhancing effect on cancer cells. Again alternatively, such polypeptides may not be overexpressed by tumor cells as compared to normal cells of the same tissue type, but rather may be specifically expressed by both tumor cells and normal cells of only a single or very limited number of tissue types (preferably tissues which are not essential for life, e.g., prostate, etc.). All of the above polypeptides are herein referred to as Tumor-associated Antigenic Target polypeptides ("TAT" polypeptides) and are expected to serve as effective targets for cancer therapy and diagnosis in mammals.

Accordingly, in one embodiment of the present invention, the invention provides an isolated nucleic acid molecule having a nucleotide sequence that encodes a tumor-associated antigenic target polypeptide or fragment thereof (a "TAT" polypeptide).

In certain aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule encoding a full-length TAT polypeptide having an amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule comprising the coding sequence of a full-length TAT polypeptide cDNA as disclosed herein, the coding sequence of a TAT polypeptide lacking the signal peptide as disclosed herein, the coding sequence of an extracellular domain of a transmembrane TAT polypeptide, with or without the signal peptide, as disclosed herein or the coding sequence of any other specifically defined fragment of the full-length TAT polypeptide amino acid sequence as disclosed herein, or (b) the complement of the DNA molecule of (a).

In further aspects, the invention concerns an isolated nucleic acid molecule comprising a nucleotide sequence having at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% nucleic acid sequence identity, to (a) a DNA molecule that encodes the same mature polypeptide encoded by the full-length coding region of any of the human protein cDNAs deposited with the ATCC as disclosed herein, or (b) the complement of the DNA molecule of (a).

Another aspect of the invention provides an isolated nucleic acid molecule comprising a nucleotide sequence encoding a TAT polypeptide which is either transmembrane domain-deleted or transmembrane domain-inactivated, or is complementary to such encoding nucleotide sequence, wherein the transmembrane domain(s) of such polypeptide(s) are disclosed herein. Therefore, soluble extracellular domains of the herein described TAT polypeptides are contemplated.

In other aspects, the present invention is directed to isolated nucleic acid molecules which hybridize to (a) a nucleotide sequence encoding a TAT polypeptide having a full-length amino acid sequence as disclosed herein, a TAT polypeptide amino acid sequence lacking the signal peptide as disclosed herein, an extracellular domain of a transmembrane TAT polypeptide, with or without the signal peptide, as disclosed herein or any other specifically defined fragment of a full-length TAT polypeptide amino acid sequence as disclosed herein, or (b) the complement of the nucleotide sequence of (a). In this regard, an embodiment of the present invention is directed to fragments of a full-length TAT polypeptide coding sequence, or the complement thereof, as disclosed herein, that may find use as, for example, hybridization probes useful as, for example, diagnostic probes, antisense oligonucleotide probes, or for encoding fragments of a full-length TAT polypeptide that may optionally encode a polypeptide comprising a binding site for an anti-TAT polypeptide antibody, a TAT binding oligopeptide or other small organic molecule that binds to a TAT polypeptide. Such nucleic acid fragments are usually at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length. It is noted that novel fragments of a TAT polypeptide-encoding nucleotide sequence may be determined in a routine manner by aligning the TAT polypeptide-encoding nucleotide sequence with other known nucleotide sequences using any of a number of well known sequence alignment programs and determining which TAT polypeptide-encoding nucleotide sequence fragment(s) are novel. All of such novel fragments of TAT polypeptide-encoding nucleotide sequences are contemplated herein. Also contemplated are the TAT polypeptide fragments encoded by these nucleotide molecule fragments, preferably those TAT polypeptide fragments that comprise a binding site for an anti-TAT antibody, a TAT binding oligopeptide or other small organic molecule that binds to a TAT polypeptide.

In another embodiment, the invention provides isolated TAT polypeptides encoded by any of the isolated nucleic acid sequences hereinabove identified.

In a certain aspect, the invention concerns an isolated TAT polypeptide, comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, 99% or 100% amino acid sequence identity, to a TAT polypeptide having a full-length amino acid sequence as disclosed herein, a TAT polypeptide amino acid sequence lacking the signal peptide as disclosed herein, an extracellular domain of a transmembrane TAT polypeptide protein, with or without the signal peptide, as disclosed herein, an amino acid sequence encoded by any of the nucleic acid sequences disclosed herein or any other specifically defined fragment of a full-length TAT polypeptide amino acid sequence as disclosed herein.

In a further aspect, the invention concerns an isolated TAT polypeptide comprising an amino acid sequence having at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to an amino acid sequence encoded by any of the human protein cDNAs deposited with the ATCC as disclosed herein.

In a specific aspect, the invention provides an isolated TAT polypeptide without the N-terminal signal sequence and/or without the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

Another aspect of the invention provides an isolated TAT polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the TAT polypeptide and recovering the TAT polypeptide from the cell culture.

In other embodiments of the present invention, the invention provides vectors comprising DNA encoding any of the herein described polypeptides. Host cells comprising any such vector are also provided. By way of example, the host cells may be CHO cells, *E. coli* cells, or yeast cells. A process for producing any of the herein described polypeptides is further provided and comprises culturing host cells under conditions suitable for expression of the desired polypeptide and recovering the desired polypeptide from the cell culture.

In other embodiments, the invention provides isolated chimeric polypeptides comprising any of the herein described TAT polypeptides fused to a heterologous (non-TAT) polypeptide. Example of such chimeric molecules comprise any of the herein described TAT polypeptides fused to a heterologous polypeptide such as, for example, an epitope tag sequence or a Fc region of an immunoglobulin.

In another embodiment, the invention provides an antibody which binds, preferably specifically, to any of the above or below described polypeptides. Optionally, the antibody is a monoclonal antibody, antibody fragment, chimeric antibody, humanized antibody, single-chain antibody or antibody that competitively inhibits the binding of an anti-TAT polypeptide antibody to its respective antigenic epitope. Antibodies of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies of the present invention may optionally be produced in CHO cells or bacterial cells and preferably induce death of a cell to which they bind. For diagnostic purposes, the antibodies of the present invention may be detectably labeled, attached to a solid support, or the like.

In other embodiments of the present invention, the invention provides vectors comprising DNA encoding any of the herein described antibodies. Host cell comprising any such vector are also provided. By way of example, the host cells may be CHO cells, *E. coli* cells, or yeast cells. A process for producing any of the herein described antibodies is further provided and comprises culturing host cells under conditions suitable for expression of the desired antibody and recovering the desired antibody from the cell culture.

In another embodiment, the invention provides oligopeptides ("TAT binding oligopeptides") which bind, preferably specifically, to any of the above or below described TAT polypeptides. Optionally, the TAT binding oligopeptides of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAT binding oligopeptides of the present invention may optionally be produced in CHO cells or bacterial cells and preferably induce death of a cell to which they bind. For diagnostic purposes, the TAT binding oligopeptides of the present invention may be detectably labeled, attached to a solid support, or the like.

In other embodiments of the present invention, the invention provides vectors comprising DNA encoding any of the herein described TAT binding oligopeptides. Host cell comprising any such vector are also provided. By way of example, the host cells may be CHO cells, *E. coli* cells, or yeast cells. A process for producing any of the herein described TAT binding oligopeptides is further provided and comprises culturing host cells under conditions suitable for expression of the desired oligopeptide and recovering the desired oligopeptide from the cell culture.

In another embodiment, the invention provides small organic molecules ("TAT binding organic molecules") which bind, preferably specifically, to any of the above or below described TAT polypeptides. Optionally, the TAT binding organic molecules of the present invention may be conjugated to a growth inhibitory agent or cytotoxic agent such as a toxin, including, for example, a maytansinoid or calicheamicin, an antibiotic, a radioactive isotope, a nucleolytic enzyme, or the like. The TAT binding organic molecules of the present invention preferably induce death of a cell to which they bind. For diagnostic purposes, the TAT binding organic molecules of the present invention may be detectably labeled, attached to a solid support, or the like.

In a still further embodiment, the invention concerns a composition of matter comprising a TAT polypeptide as described herein, a chimeric TAT polypeptide as described herein, an anti-TAT antibody as described herein, a TAT binding oligopeptide as described herein, or a TAT binding organic molecule as described herein, in combination with a carrier. Optionally, the carrier is a pharmaceutically acceptable carrier.

In yet another embodiment, the invention concerns an article of manufacture comprising a container and a composition of matter contained within the container, wherein the composition of matter may comprise a TAT polypeptide as described herein, a chimeric TAT polypeptide as described herein, an anti-TAT antibody as described herein, a TAT binding oligopeptide as described herein, or a TAT binding organic molecule as described herein. The article may further optionally comprise a label affixed to the container, or a package insert included with the container, that refers to the use of the composition of matter for the therapeutic treatment or diagnostic detection of a tumor.

Another embodiment of the present invention is directed to the use of a TAT polypeptide as described herein, a chimeric TAT polypeptide as described herein, an anti-TAT polypeptide antibody as described herein, a TAT binding oligopeptide as described herein, or a TAT binding organic molecule as described herein, for the preparation of a medicament useful in the treatment of a condition which is responsive to the TAT polypeptide, chimeric TAT polypeptide, anti-TAT polypeptide antibody, TAT binding oligopeptide, or TAT binding organic molecule.

B. Additional Embodiments

Another embodiment of the present invention is directed to a method for inhibiting the growth of a cell that expresses a TAT polypeptide, wherein the method comprises contacting the cell with an antibody, an oligopeptide or a small organic molecule that binds to the TAT polypeptide, and wherein the binding of the antibody, oligopeptide or organic molecule to the TAT polypeptide causes inhibition of the growth of the cell expressing the TAT polypeptide. In preferred embodiments, the cell is a cancer cell and binding of the antibody, oligopeptide or organic molecule to the TAT polypeptide causes death of the cell expressing the TAT polypeptide. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and TAT binding oligopeptides employed in the methods of the present invention may optionally be produced in CHO cells or bacterial cells.

Yet another embodiment of the present invention is directed to a method of therapeutically treating a mammal having a cancerous tumor comprising cells that express a TAT polypeptide, wherein the method comprises administering to the mammal a therapeutically effective amount of an antibody, an oligopeptide or a small organic molecule that binds to the TAT polypeptide, thereby resulting in the effective therapeutic treatment of the tumor. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

Yet another embodiment of the present invention is directed to a method of determining the presence of a TAT polypeptide in a sample suspected of containing the TAT polypeptide, wherein the method comprises exposing the sample to an antibody, oligopeptide or small organic molecule that binds to the TAT polypeptide and determining binding of the antibody, oligopeptide or organic molecule to the TAT polypeptide in the sample, wherein the presence of such binding is indicative of the presence of the TAT polypeptide in the sample. Optionally, the sample may contain cells (which may be cancer cells) suspected of expressing the TAT polypeptide. The antibody, TAT binding oligopeptide or TAT binding organic molecule employed in the method may optionally be detectably labeled, attached to a solid support, or the like.

A further embodiment of the present invention is directed to a method of diagnosing the presence of a tumor in a mammal, wherein the method comprises detecting the level of expression of a gene encoding a TAT polypeptide (a) in a test sample of tissue cells obtained from said mammal, and (b) in a control sample of known normal non-cancerous cells of the same tissue origin or type, wherein a higher level of expression of the TAT polypeptide in the test sample, as compared to the control sample, is indicative of the presence of tumor in the mammal from which the test sample was obtained.

Another embodiment of the present invention is directed to a method of diagnosing the presence of a tumor in a mammal, wherein the method comprises (a) contacting a test sample comprising tissue cells obtained from the mammal with an antibody, oligopeptide or small organic molecule that binds to a TAT polypeptide and (b) detecting the formation of a complex between the antibody, oligopeptide or small organic molecule and the TAT polypeptide in the test sample, wherein the formation of a complex is indicative of the presence of a tumor in the mammal. Optionally, the antibody, TAT binding oligopeptide or TAT binding organic molecule employed is detectably labeled, attached to a solid support, or the like, and/or the test sample of tissue cells is obtained from an individual suspected of having a cancerous tumor.

Yet another embodiment of the present invention is directed to a method for treating or preventing a cell proliferative disorder associated with altered, preferably increased, expression or activity of a TAT polypeptide, the method comprising administering to a subject in need of such treatment an effective amount of an antagonist of a TAT polypeptide. Preferably, the cell proliferative disorder is cancer and the antagonist of the TAT polypeptide is an anti-TAT polypeptide antibody, TAT binding oligopeptide, TAT binding organic molecule or antisense oligonucleotide. Effective treatment or prevention of the cell proliferative disorder may be a result of direct killing or growth inhibition of cells that express a TAT polypeptide or by antagonizing the cell growth potentiating activity of a TAT polypeptide.

Yet another embodiment of the present invention is directed to a method of binding an antibody, oligopeptide or small organic molecule to a cell that expresses a TAT polypeptide, wherein the method comprises contacting a cell that expresses a TAT polypeptide with said antibody, oligopeptide or small organic molecule under conditions which are suitable for binding of the antibody, oligopeptide or small organic molecule to said TAT polypeptide and allowing binding therebetween.

Other embodiments of the present invention are directed to the use of (a) a TAT polypeptide, (b) a nucleic acid encoding a TAT polypeptide or a vector or host cell comprising that nucleic acid, (c) an anti-TAT polypeptide antibody, (d) a TAT-binding oligopeptide, or (e) a TAT-binding small organic molecule in the preparation of a medicament useful for (i) the therapeutic treatment or diagnostic detection of a cancer or tumor, or (ii) the therapeutic treatment or prevention of a cell proliferative disorder.

Another embodiment of the present invention is directed to a method for inhibiting the growth of a cancer cell, wherein the growth of said cancer cell is at least in part dependent upon the growth potentiating effect(s) of a TAT polypeptide (wherein the TAT polypeptide may be expressed either by the cancer cell itself or a cell that produces polypeptide(s) that have a growth potentiating effect on cancer cells), wherein the method comprises contacting the TAT polypeptide with an antibody, an oligopeptide or a small organic molecule that binds to the TAT polypeptide, thereby antagonizing the growth-potentiating activity of the TAT polypeptide and, in turn, inhibiting the growth of the cancer cell. Preferably the growth of the cancer cell is completely inhibited. Even more preferably, binding of the antibody, oligopeptide or small organic molecule to the TAT polypeptide induces the death of the cancer cell. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and TAT binding oligopeptides employed in the methods of the present invention may optionally be produced in CHO cells or bacterial cells.

Yet another embodiment of the present invention is directed to a method of therapeutically treating a tumor in a mammal, wherein the growth of said tumor is at least in part dependent upon the growth potentiating effect(s) of a TAT polypeptide, wherein the method comprises administering to the mammal a therapeutically effective amount of an antibody, an oligopeptide or a small organic molecule that binds to the TAT polypeptide, thereby antagonizing the growth potentiating activity of said TAT polypeptide and resulting in the effective therapeutic treatment of the tumor. Optionally, the antibody is a monoclonal antibody, antibody fragment, chimeric antibody, humanized antibody, or single-chain antibody. Antibodies, TAT binding oligopeptides and TAT binding organic molecules employed in the methods of the present invention may optionally be conjugated to a growth inhibitory agent or cytotoxic agent such as a toxin, including, for example, a maytansinoid or calicheamicin, an antibiotic, a radioactive isotope, a nucleolytic enzyme, or the like. The antibodies and oligopeptides employed in the methods of the present invention may optionally be produced in CHO cells or bacterial cells.

C. Further Additional Embodiments

In yet further embodiments, the invention is directed to the following set of potential claims for this application:

1. Isolated nucleic acid having a nucleotide sequence that has at least 80% nucleic acid sequence identity to:

(a) a DNA molecule encoding the amino acid sequence shown in any one of FIGS. 57-112, 114, 116, 118 or 120 (SEQ ID NOS:57-112, 114, 116, 118 or 120);

(b) a DNA molecule encoding the amino acid sequence shown in any one of FIGS. 57-112, 114, 116, 118 or 120 (SEQ ID NOS:57-112, 114, 116, 118 or 120), lacking its associated signal peptide;

(c) a DNA molecule encoding an extracellular domain of the polypeptide shown in any one of FIGS. 57-112, 114, 116, 118 or 120 (SEQ ID NOS:57-112, 114, 116, 118 or 120), with its associated signal peptide;

(d) a DNA molecule encoding an extracellular domain of the polypeptide shown in any one of FIGS. 57-112, 114, 116, 118 or 120 (SEQ ID NOS:57-112, 114, 116, 118 or 120), lacking its associated signal peptide;

(e) the nucleotide sequence shown in any one of FIGS. 1-56, 113, 115, 117 or 119 (SEQ ID NOS:1-56, 113, 115, 117 or 119);

(f) the full-length coding region of the nucleotide sequence shown in any one of FIGS. 1-56, 113, 115, 117 or 119 (SEQ ID NOS:1-56, 113, 115, 117 or 119); or (g) the complement of (a), (b), (c), (d), (e) or (f).

2. Isolated nucleic acid having:

(a) a nucleotide sequence that encodes the amino acid sequence shown in any one of FIGS. 57-112, 114, 116, 118 or 120 (SEQ ID NOS:57-112, 114, 116, 118 or 120);

(b) a nucleotide sequence that encodes the amino acid sequence shown in any one of FIGS. 57-112, 114, 116, 118 or 120 (SEQ ID NOS:57-112, 114, 116, 118 or 120), lacking its associated signal peptide;

(c) a nucleotide sequence that encodes an extracellular domain of the polypeptide shown in any one of FIGS. 57-112, 114, 116, 118 or 120 (SEQ ID NOS:57-112, 114, 116, 118 or 120), with its associated signal peptide;

(d) a nucleotide sequence that encodes an extracellular domain of the polypeptide shown in any one of FIGS. 57-112, 114, 116, 118 or 120 (SEQ ID NOS:57-112, 114, 116, 118 or 120), lacking its associated signal peptide;

(e) the nucleotide sequence shown in any one of FIGS. 1-56, 113, 115, 117 or 119 (SEQ ID NOS:1-56, 113, 115, 117 or 119);

(f) the full-length coding region of the nucleotide sequence shown in any one of FIGS. 1-56, 113, 115, 117 or 119 (SEQ ID NOS:1-56, 113, 115, 117 or 119); or (g) the complement of (a), (b), (c), (d), (e) or (f).

3. Isolated nucleic acid that hybridizes to:

(a) a nucleic acid that encodes the amino acid sequence shown in any one of FIGS. 57-112, 114, 116, 118 or 120 (SEQ ID NOS:57-112, 114, 116, 118 or 120);

(b) a nucleic acid that encodes the amino acid sequence shown in any one of FIGS. 57-112, 114, 116, 118 or 120 (SEQ ID NOS:57-112, 114, 116, 118 or 120), lacking its associated signal peptide;

(c) a nucleic acid that encodes an extracellular domain of the polypeptide shown in any one of FIGS. 57-112, 114, 116, 118 or 120 (SEQ ID NOS:57-112, 114, 116, 118 or 120), with its associated signal peptide;

(d) a nucleic acid that encodes an extracellular domain of the polypeptide shown in any one of FIGS. 57-112, 114, 116, 118 or 120 (SEQ ID NOS:57-112, 114, 116, 118 or 120), lacking its associated signal peptide;

(e) the nucleotide sequence shown in any one of FIGS. 1-56, 113, 115, 117 or 119 (SEQ ID NOS:1-56, 113, 115, 117 or 119);

(f) the full-length coding region of the nucleotide sequence shown in any one of FIGS. 1-56, 113, 115, 117 or 119 (SEQ ID NOS:1-56, 113, 115, 117 or 119); or (g) the complement of (a), (b), (c), (d), (e) or (f).

4. The nucleic acid of Claim 3, wherein the hybridization occurs under stringent conditions.

5. The nucleic acid of Claim 3 which is at least about 5 nucleotides in length.

6. An expression vector comprising the nucleic acid of Claim 1, 2 or 3.

7. The expression vector of Claim 6, wherein said nucleic acid is operably linked to control sequences recognized by a host cell transformed with the vector.

8. A host cell comprising the expression vector of Claim 7.

9. The host cell of Claim 8 which is a CHO cell, an *E. coli* cell or a yeast cell.

10. A process for producing a polypeptide comprising culturing the host cell of Claim 8 under conditions suitable for expression of said polypeptide and recovering said polypeptide from the cell culture.

11. An isolated polypeptide having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in any one of FIGS. 1-56, 113, 115, 117 or 119 (SEQ ID NOS:1-56, 113, 115, 117 or 119).

12. An isolated polypeptide having:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

13. A chimeric polypeptide comprising the polypeptide of Claim 11 or 12 fused to a heterologous polypeptide.

14. The chimeric polypeptide of Claim 13, wherein said heterologous polypeptide is an epitope tag sequence or an Fc region of an immunoglobulin.

15. An isolated antibody that binds to a polypeptide having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in any one of FIGS. 1-56, 113, 115, 117 or 119 (SEQ ID NOS:1-56, 113, 115, 117 or 119).

16. An isolated antibody that binds to a polypeptide having:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

17. The antibody of Claim 15 or 16 which is a monoclonal antibody.

18. The antibody of Claim 15 or 16 which is an antibody fragment.

19. The antibody of Claim 15 or 16 which is a chimeric or a humanized antibody.

20. The antibody of Claim 15 or 16 which is conjugated to a growth inhibitory agent.

21. The antibody of Claim 15 or 16 which is conjugated to a cytotoxic agent.

22. The antibody of Claim 21, wherein the cytotoxic agent is selected from the group consisting of toxins, antibiotics, radioactive isotopes and nucleolytic enzymes.

23. The antibody of Claim 21, wherein the cytotoxic agent is a toxin.

24. The antibody of Claim 23, wherein the toxin is selected from the group consisting of maytansinoid and calicheamicin.

25. The antibody of Claim 23, wherein the toxin is a maytansinoid.

26. The antibody of Claim 15 or 16 which is produced bacteria.

27. The antibody of Claim 15 or 16 which is produced in CHO cells.

28. The antibody of Claim 15 or 16 which induces death of a cell to which it binds.

29. The antibody of Claim 15 or 16 which is detectably labeled.

30. An isolated nucleic acid having a nucleotide sequence that encodes the antibody of Claim 15 or 16.

31. An expression vector comprising the nucleic acid of Claim 30 operably linked to control sequences recognized by a host cell transformed with the vector.

32. A host cell comprising the expression vector of Claim 31.

33. The host cell of Claim 32 which is a CHO cell, an *E. coli* cell or a yeast cell.

34. A process for producing an antibody comprising culturing the host cell of Claim 32 under conditions suitable for expression of said antibody and recovering said antibody from the cell culture.

35. An isolated oligopeptide that binds to a polypeptide having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119).

36. An isolated oligopeptide that binds to a polypeptide having:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

37. The oligopeptide of Claim 35 or 36 which is conjugated to a growth inhibitory agent.

38. The oligopeptide of Claim 35 or 36 which is conjugated to a cytotoxic agent.

39. The oligopeptide of Claim 38, wherein the cytotoxic agent is selected from the group consisting of toxins, antibiotics, radioactive isotopes and nucleolytic enzymes.

40. The oligopeptide of Claim 38, wherein the cytotoxic agent is a toxin.

41. The oligopeptide of Claim 40, wherein the toxin is selected from the group consisting of maytansinoid and calicheamicin.

42. The oligopeptide of Claim 40, wherein the toxin is a maytansinoid.

43. The oligopeptide of Claim 35 or 36 which induces death of a cell to which it binds.

44. The oligopeptide of Claim 35 or 36 which is detectably labeled.

45. A TAT binding organic molecule that binds to a polypeptide having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in anyone of FIGS. 57-112, 114, 116, 118 or 120 (SEQ ID NOS:57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in any one of FIGS. 1-56, 113, 115, 117 or 119 (SEQ ID NOS:1-56, 113, 115, 117 or 119).

46. The organic molecule of Claim 45 that binds to a polypeptide having:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in anyone of FIGS. 1-56, 113, 115, 117 or 119 (SEQ ID NOS:1-56, 113, 115, 117 or 119).

47. The organic molecule of Claim 45 or 46 which is conjugated to a growth inhibitory agent.

48. The organic molecule of Claim 45 or 46 which is conjugated to a cytotoxic agent.

49. The organic molecule of Claim 48, wherein the cytotoxic agent is selected from the group consisting of toxins, antibiotics, radioactive isotopes and nucleolytic enzymes.

50. The organic molecule of Claim 48, wherein the cytotoxic agent is a toxin.

51. The organic molecule of Claim 50, wherein the toxin is selected from the group consisting of maytansinoid and calicheamicin.

52. The organic molecule of Claim 50, wherein the toxin is a maytansinoid.

53. The organic molecule of Claim 45 or 46 which induces death of a cell to which it binds.

54. The organic molecule of Claim 45 or 46 which is detectably labeled.

55. A composition of matter comprising:

(a) the polypeptide of Claim 11;

(b) the polypeptide of Claim 12;

(c) the chimeric polypeptide of Claim 13;

(d) the antibody of Claim 15;

(e) the antibody of Claim 16;

(f) the oligopeptide of Claim 35;

(g) the oligopeptide of Claim 36;

(h) the TAT binding organic molecule of Claim 45; or (i) the TAT binding organic molecule of Claim 46; in combination with a carrier.

56. The composition of matter of Claim 55, wherein said carrier is a pharmaceutically acceptable carrier.

57. An article of manufacture comprising:

(a) a container; and (b) the composition of matter of Claim 55 contained within said container.

58. The article of manufacture of Claim 57 further comprising a label affixed to said container, or a package insert included with said container, referring to the use of said composition of matter for the therapeutic treatment of or the diagnostic detection of a cancer.

59. A method of inhibiting the growth of a cell that expresses a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), said method comprising contacting said cell with an antibody, oligopeptide or organic molecule that binds to said protein, the binding of said antibody, oligopeptide or organic molecule to said protein thereby causing an inhibition of growth of said cell.

60. The method of Claim 59, wherein said antibody is a monoclonal antibody.

61. The method of Claim 59, wherein said antibody is an antibody fragment.

62. The method of Claim 59, wherein said antibody is a chimeric or a humanized antibody.

63. The method of Claim 59, wherein said antibody, oligopeptide or organic molecule is conjugated to a growth inhibitory agent.

64. The method of Claim 59, wherein said antibody, oligopeptide or organic molecule is conjugated to a cytotoxic agent.

65. The method of Claim 64, wherein said cytotoxic agent is selected from the group consisting of toxins, antibiotics, radioactive isotopes and nucleolytic enzymes.

66. The method of Claim 64, wherein the cytotoxic agent is a toxin.

67. The method of Claim 66, wherein the toxin is selected from the group consisting of maytansinoid and calicheamicin.

68. The method of Claim 66, wherein the toxin is a maytansinoid.

69. The method of Claim 59, wherein said antibody is produced in bacteria.

70. The method of Claim 59, wherein said antibody is produced in CHO cells.

71. The method of Claim 59, wherein said cell is a cancer cell.

72. The method of Claim 71, wherein said cancer cell is further exposed to radiation treatment or a chemotherapeutic agent.

73. The method of Claim 71, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

74. The method of Claim 71, wherein said protein is more abundantly expressed by said cancer cell as compared to a normal cell of the same tissue origin.

75. The method of Claim 59 which causes the death of said cell.

76. The method of Claim 59, wherein said protein has:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

77. A method of therapeutically treating a mammal having a cancerous tumor comprising cells that express a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in anyone of FIGS. 57-112, 114, 116, 118 or 120 (SEQ ID NOS:57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), said method comprising administering to said mammal a therapeutically effective amount of an antibody, oligopeptide or organic molecule that binds to said protein, thereby effectively treating said mammal.

78. The method of Claim 77, wherein said antibody is a monoclonal antibody.

79. The method of Claim 77, wherein said antibody is an antibody fragment.

80. The method of Claim 77, wherein said antibody is a chimeric or a humanized antibody.

81. The method of Claim 77, wherein said antibody, oligopeptide or organic molecule is conjugated to a growth inhibitory agent.

82. The method of Claim 77, wherein said antibody, oligopeptide or organic molecule is conjugated to a cytotoxic agent.

83. The method of Claim 82, wherein said cytotoxic agent is selected from the group consisting of toxins, antibiotics, radioactive isotopes and nucleolytic enzymes.

84. The method of Claim 82, wherein the cytotoxic agent is a toxin.

85. The method of Claim 84, wherein the toxin is selected from the group consisting of maytansinoid and calicheamicin.

86. The method of Claim 84, wherein the toxin is a maytansinoid.

87. The method of Claim 77, wherein said antibody is produced in bacteria.

88. The method of Claim 77, wherein said antibody is produced in CHO cells.

89. The method of Claim 77, wherein said tumor is further exposed to radiation treatment or a chemotherapeutic agent.

90. The method of Claim 77, wherein said tumor is a breast tumor, a colorectal tumor, a lung tumor, an ovarian tumor, a central nervous system tumor, a liver tumor, a bladder tumor, a pancreatic tumor, or a cervical tumor.

91. The method of Claim 77, wherein said protein is more abundantly expressed by the cancerous cells of said tumor as compared to a normal cell of the same tissue origin.

92. The method of Claim 77, wherein said protein has:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in anyone of FIGS. 1-56, 113, 115, 117 or 119 (SEQ ID NOS:1-56, 113, 115, 117 or 119).

93. A method of determining the presence of a protein in a sample suspected of containing said protein, wherein said protein has at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in anyone of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS: 1-56, 113, 115, 117 or 119); or (f) a polypeptide encoded by the full-length coding region of the nucleotide sequence shown in any one of FIGS. 1-56, 113, 115, 117 or 119 (SEQ ID NOS:1-56, 113, 115, 117 or 119), said method comprising exposing said sample to an antibody, oligopeptide or organic molecule that binds to said protein and determining binding of said antibody, oligopeptide or organic molecule to said protein in said sample, wherein binding of the antibody, oligopeptide or organic molecule to said protein is indicative of the presence of said protein in said sample.

94. The method of Claim 93, wherein said sample comprises a cell suspected of expressing said protein.

95. The method of Claim 94, wherein said cell is a cancer cell.

96. The method of Claim 93, wherein said antibody, oligopeptide or organic molecule is detectably labeled.

97. The method of Claim 93, wherein said protein has:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

98. A method of diagnosing the presence of a tumor in a mammal, said method comprising determining the level of expression of a gene encoding a protein having at least 80% amino acid sequence identity to:

(a) the polypeptide shown in anyone of FIGS. 57-112, 114, 116, 118 or 120 (SEQ ID NOS:57-112, 114, 116, 118 or 120);

(b) the polypeptide shown in anyone of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in any one of FIGS. 1-56, 113, 115, 117 or 119 (SEQ ID NOS:1-56, 113, 115, 117 or 119), in a test sample of tissue cells obtained from said mammal and in a control sample of known normal cells of the same tissue origin, wherein a higher level of expression of said protein in the test sample, as compared to the control sample, is indicative of the presence of tumor in the mammal from which the test sample was obtained.

99. The method of Claim 98, wherein the step of determining the level of expression of a gene encoding said protein comprises employing an oligonucleotide in an in situ hybridization or RT-PCR analysis.

100. The method of Claim 98, wherein the step determining the level of expression of a gene encoding said protein comprises employing an antibody in an immunohistochemistry or Western blot analysis.

101. The method of Claim 98, wherein said protein has:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in anyone of FIGS. 1-56, 113, 115, 117 or 119 (SEQ ID NOS:1-56, 113, 115, 117 or 119).

102. A method of diagnosing the presence of a tumor in a mammal, said method comprising contacting a test sample of tissue cells obtained from said mammal with an antibody, oligopeptide or organic molecule that binds to a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in anyone of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), and detecting the formation of a complex between said antibody, oligopeptide or organic molecule and said protein in the test sample, wherein the formation of a complex is indicative of the presence of a tumor in said mammal.

103. The method of Claim 102, wherein said antibody, oligopeptide or organic molecule is detectably labeled.

104. The method of Claim 102, wherein said test sample sue cells is obtained from an individual suspected of having a cancerous tumor.

105. The method of Claim 102, wherein said protein has:

(a) the amino acid sequence shown in any one of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

106. A method for treating or preventing a cell proliferative disorder associated with increased expression or activity of a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in anyone of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), said method comprising administering to a subject in need of such treatment an effective amount of an antagonist of said protein, thereby effectively treating or preventing said cell proliferative disorder.

107. The method of Claim 106, wherein said cell proliferative disorder is cancer.

108. The method of Claim 106, wherein said antagonist is an anti-TAT polypeptide antibody, TAT binding oligopeptide, TAT binding organic molecule or antisense oligonucleotide.

109. A method of binding an antibody, oligopeptide or organic molecule to a cell that expresses a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide; (c) an extracellular domain of the polypeptide shown in any one of FIGS. 57-112, 114, 116, 118 or 120 (SEQ ID NOS:57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), said method comprising contacting said cell with an antibody, oligopeptide or organic molecule that binds to said protein and allowing the binding of the antibody, oligopeptide or organic molecule to said protein to occur, thereby binding said antibody, oligopeptide or organic molecule to said cell.

110. The method of Claim 109, wherein said antibody is a monoclonal antibody.

111. The method of Claim 109, wherein said antibody is an antibody fragment.

112. The method of Claim 109, wherein said antibody is a chimeric or a humanized antibody.

113. The method of Claim 109, wherein said antibody, oligopeptide or organic molecule is conjugated to a growth inhibitory agent.

114. The method of Claim 109, wherein said antibody, oligopeptide or organic molecule is conjugated to a cytotoxic agent.

115. The method of Claim 114, wherein said cytotoxic agent is selected from the group consisting of toxins, antibiotics, radioactive isotopes and nucleolytic enzymes.

116. The method of Claim 114, wherein the cytotoxic agent is a toxin.

117. The method of Claim 116, wherein the toxin is selected from the group consisting of maytansinoid and calicheamicin.

118. The method of Claim 116, wherein the toxin is a maytansinoid.

119. The method of Claim 109, wherein said antibody is produced in bacteria.

120. The method of Claim 109, wherein said antibody is produced in CHO cells.

121. The method of Claim 109, wherein said cell is a cancer cell.

122. The method of Claim 121, wherein said cancer cell is further exposed to radiation treatment or a chemotherapeutic agent.

123. The method of Claim 121, wherein said cancer cell is selected from the group consisting of a breast cancer cell, a colorectal cancer cell, a lung cancer cell, an ovarian cancer cell, a central nervous system cancer cell, a liver cancer cell, a bladder cancer cell, a pancreatic cancer cell, a cervical cancer cell, a melanoma cell and a leukemia cell.

124. The method of Claim 123, wherein said protein is more abundantly expressed by said cancer cell as compared to a normal cell of the same tissue origin.

125. The method of Claim 109 which causes the death of said cell.

126. Use of a nucleic acid as claimed in any of Claims 1 to 5 or 30 in the preparation of a medicament for the therapeutic treatment or diagnostic detection of a cancer.

127. Use of a nucleic acid as claimed in any of Claims 1 to 5 or 30 in the preparation of a medicament for treating a tumor.

128. Use of a nucleic acid as claimed in any of Claims 1 to 5 or 30 in the preparation of a medicament for treatment or prevention of a cell proliferative disorder.

129. Use of an expression vector as claimed in any of Claims 6, 7 or 31 in the preparation of a medicament for the therapeutic treatment or diagnostic detection of a cancer.

130. Use of an expression vector as claimed in any of Claims 6, 7 or 31 in the preparation of medicament for treating a tumor.

131. Use of an expression vector as claimed in any of Claims 6, 7 or 31 in the preparation of a medicament for treatment or prevention of a cell proliferative disorder.

132. Use of a host cell as claimed in any of Claims 8, 9, 32, or 33 in the preparation of a medicament for the therapeutic treatment or diagnostic detection of a cancer.

133. Use of a host cell as claimed in any of Claims 8, 9, 32 or 33 in the preparation of a medicament for treating a tumor.

134. Use of a host cell as claimed in any of Claims 8, 9, 32 or 33 in the preparation of a medicament for treatment or prevention of a cell proliferative disorder.

135. Use of a polypeptide as claimed in any of Claims 11 to 14 in the preparation of a medicament for the therapeutic treatment or diagnostic detection of a cancer.

136. Use of a polypeptide as claimed in any of Claims 11 to 14 in the preparation of a medicament for treating a tumor.

137. Use of a polypeptide as claimed in any of Claims 11 to 14 in the preparation of a medicament for treatment or prevention of a cell proliferative disorder.

138. Use of an antibody as claimed in any of Claims 15 to 29 in the preparation of a medicament for the therapeutic treatment or diagnostic detection of a cancer.

139. Use of an antibody as claimed in any of Claims 15 to 29 in the preparation of a medicament for treating a tumor.

140. Use of an antibody as claimed in any of Claims 15 to 29 in the preparation of a medicament for treatment or prevention of a cell proliferative disorder.

141. Use of an oligopeptide as claimed in any of Claims 35 to 44 in the preparation of a medicament for the therapeutic treatment or diagnostic detection of a cancer.

142. Use of an oligopeptide as claimed in any of Claims 35 to 44 in the preparation of a medicament for treating a tumor.

143. Use of an oligopeptide as claimed in any of Claims 35 to 44 in the preparation of a medicament for treatment or prevention of a cell proliferative disorder.

144. Use of a TAT binding organic molecule as claimed in any of Claims 45 to 54 in the preparation of a medicament for the therapeutic treatment or diagnostic detection of a cancer.

145. Use of a TAT binding organic molecule as claimed in any of Claims 45 to 54 in the preparation of a medicament for treating a tumor.

146. Use of a TAT binding organic molecule as claimed in any of Claims 45 to 54 in the preparation of a medicament for treatment or prevention of a cell proliferative disorder.

147. Use of a composition of matter as claimed in any of Claims 55 or 56 in the preparation of a medicament for the therapeutic treatment or diagnostic detection of a cancer.

148. Use of a composition of matter as claimed in any of Claims 55 or 56 in the preparation of a medicament for treating a tumor.

149. Use of a composition of matter as claimed in any of Claims 55 or 56 in the preparation of a medicament for treatment or prevention of a cell proliferative disorder.

150. Use of an article of manufacture as claimed in any of Claims 57 or 58 in the preparation of a medicament for the therapeutic treatment or diagnostic detection of a cancer.

151. Use of an article of manufacture as claimed in any of Claims 57 or 58 in the preparation of a medicament for treating a tumor.

152. Use of an article of manufacture as claimed in any of Claims 57 or 58 in the preparation of a medicament for treatment or prevention of a cell proliferative disorder.

153. A method for inhibiting the growth of a cell, wherein the growth of said cell is at least in part dependent upon a growth potentiating effect of a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in anyone of FIGS. 57-112, 114, 116, 118 or 120 (SEQ ID NOS:57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), said method comprising contacting said protein with an antibody, oligopeptide or organic molecule that binds to said protein, there by inhibiting the growth of said cell.

154. The method of Claim 153, wherein said cell is a cancer cell.

155. The method of Claim 153, wherein said protein is expressed by said cell.

156. The method of Claim 153, wherein the binding of said antibody, oligopeptide or organic molecule to said protein antagonizes a cell growth-potentiating activity of said protein.

157. The method of Claim 153, wherein the binding of said antibody, oligopeptide or organic molecule to said protein induces the death of said cell.

158. The method of Claim 153, wherein said antibody is a monoclonal antibody.

159. The method of Claim 153, wherein said antibody is an antibody fragment.

160. The method of Claim 153, wherein said antibody is a chimeric or a humanized antibody.

161. The method of Claim 153, wherein said antibody, oligopeptide or organic molecule is conjugated to a growth inhibitory agent.

162. The method of Claim 153, wherein said antibody, oligopeptide or organic molecule is conjugated to a cytotoxic agent.

163. The method of Claim 162, wherein said cytotoxic agent is selected from the group consisting of toxins, antibiotics, radioactive isotopes and nucleolytic enzymes.

164. The method of Claim 162, wherein the cytotoxic agent is a toxin.

165. The method of Claim 164, wherein the toxin is selected from the group consisting of maytansinoid and calicheamicin.

166. The method of Claim 164, wherein the toxin is a maytansinoid.

167. The method of Claim 153, wherein said antibody is produced in bacteria.

168. The method of Claim 153, wherein said antibody is produced in CHO cells.

169. The method of Claim 153, wherein said protein has:

(a) the amino acid sequence shown in any one of FIGS. 57-112, 114, 116, 118 or 120 (SEQ ID NOS:57-112, 114, 116, 118 or 120);

(b) the amino acid sequence shown in anyone of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

170. A method of therapeutically treating a tumor in a mammal, wherein the growth of said tumor is at least in part dependent upon a growth potentiating effect of a protein having at least 80% amino acid sequence identity to:

(a) the polypeptide shown in any one of FIGS. 57-112, 114, 116, 118 or 120 (SEQ ID NOS:57-112, 114, 116, 118 or 120);

(b) the polypeptide shown in any one of FIGS. 57-112, 114, 116, 118 or 120 (SEQ ID NOS:57-112, 114, 116, 118 or 120), lacking its associated signal peptide;

(c) an extracellular domain of the polypeptide shown in any one of FIGS. 57-112, 114, 116, 118 or 120 (SEQ ID NOS: 57-112, 114, 116, 118 or 120), with its associated signal peptide;

(d) an extracellular domain of the polypeptide shown in any one of FIGS. 57-112, 114, 116, 118 or 120 (SEQ ID NOS:57-112, 114, 116, 118 or 120), lacking its associated signal peptide;

(e) a polypeptide encoded by the nucleotide sequence shown in any one of FIGS. 1-56, 113, 115, 117 or 119 (SEQ ID NOS:1-56, 113, 115, 117 or 119); or (f) a polypeptide encoded by the full-length coding region of the nucleotide sequence shown in anyone of FIGS. 1-56, 113, 115, 117 or 119 (SEQ ID NOS:1-56, 113, 115, 117 or 119), said method comprising contacting said protein with an antibody, oligopeptide or organic molecule that binds to said protein, thereby effectively treating said tumor.

171. The method of Claim 170, wherein said protein is expressed by cells of said tumor.

172. The method of Claim 170, wherein the binding of said antibody, oligopeptide or organic molecule to said protein antagonizes a cell growth-potentiating activity of said protein.

173. The method of Claim 170, wherein said antibody is a monoclonal antibody.

174. The method of Claim 170, wherein said antibody is an antibody fragment.

175. The method of Claim 170, wherein said antibody is a chimeric or a humanized antibody.

176. The method of Claim 170, wherein said antibody, oligopeptide or organic molecule is conjugated to a growth inhibitory agent.

177. The method of Claim 170, wherein said antibody, oligopeptide or organic molecule is conjugated to a cytotoxic agent.

178. The method of Claim 177, wherein said cytotoxic agent is selected from the group consisting of toxins, antibiotics, radioactive isotopes and nucleolytic enzymes.

179. The method of Claim 177, wherein the cytotoxic agent is a toxin.

180. The method of Claim 179, wherein the toxin is selected from the group consisting of maytansinoid and calicheamicin.

181. The method of Claim 179, wherein the toxin is a maytansinoid.

182. The method of Claim 170, wherein said antibody is produced in bacteria.

183. The method of Claim 170, wherein said antibody is produced in CHO cells.

184. The method of Claim 170, wherein said protein has:

(a) the amino acid sequence shown in anyone of FIGS. 57-112, 114, 116, 118 or 120 (SEQ ID NOS:57-112, 114, 116, 118 or 120);

(b) the amino acid sequence shown in any one of FIGS. 57-112, 114, 116, 118 or 120 (SEQ ID NOS:57-112, 114, 116, 118 or 120), lacking its associated signal peptide sequence;

(c) an amino acid sequence of an extracellular domain of the polypeptide shown in any one of FIGS. 57-112, 114, 116, 118 or 120 (SEQ ID NOS:57-112, 114, 116, 118 or 120), with its associated signal peptide sequence;

(d) an amino acid sequence of an extracellular domain of the polypeptide shown in any one of FIGS. 57-112, 114, 116, 118 or 120 (SEQ ID NOS:57-112, 114, 116, 118 or 120), lacking its associated signal peptide sequence;

(e) an amino acid sequence encoded by the nucleotide sequence shown in any one of FIGS. 1-56, 113, 115, 117 or 119 (SEQ ID NOS:1-56, 113, 115, 117 or 119); or (f) an amino acid sequence encoded by the full-length coding region of the nucleotide sequence shown in any one of FIGS. 1-56, 113, 115, 117 or 119 (SEQ ID NOS:1-56, 113, 115, 117 or 119).

Yet further embodiments of the present invention will be evident to the skilled artisan upon a reading of the present specification.

BRIEF DESCRIPTION OF THE DRAWINGS

FIG. 1 shows a nucleotide sequence (SEQ ID NO:1) of a TAT207 cDNA, wherein SEQ ID NO:1 is a clone designated herein as "DNA67962".

FIG. 2 shows a nucleotide sequence (SEQ ID NO:2) of a TAT177 cDNA, wherein SEQ ID NO:2 is a clone designated herein as "DNA77507".

FIG. 3 shows a nucleotide sequence (SEQ ID NO:3) of a TAT235 cDNA, wherein SEQ ID NO:3 is a clone designated herein as "DNA87993".

FIG. 4 shows a nucleotide sequence (SEQ ID NO:4) of a TAT234 cDNA, wherein SEQ ID NO:4 is a clone designated herein as "DNA92980".

FIG. 5 shows a nucleotide sequence (SEQ ID NO:5) of a TAT239 cDNA, wherein SEQ ID NO:5 is a clone designated herein as "DNA96792".

FIG. 6 shows a nucleotide sequence (SEQ ID NO:6) of a TAT193 cDNA, wherein SEQ ID NO:6 is a clone designated herein as "DNA96964".

FIG. 7 shows a nucleotide sequence (SEQ ID NO:7) of a TAT233 cDNA, wherein SEQ ID NO:7 is a clone designated herein as "DNA105792".

FIG. 8 shows a nucleotide sequence (SEQ ID NO:8) of a TAT226 cDNA, wherein SEQ ID NO:8 is a clone designated herein as "DNA119474".

FIG. 9 shows a nucleotide sequence (SEQ ID NO:9) of a TAT199 cDNA, wherein SEQ ID NO:9 is a clone designated herein as "DNA142915".

FIGS. 10A-B show a nucleotide sequence (SEQ ID NO:10) of a TAT204 cDNA, wherein SEQ ID NO:10 is a clone designated herein as "DNA150491".

FIGS. 11A-B show a nucleotide sequence (SEQ ID NO:11) of a TAT248 cDNA, wherein SEQ ID NO:11 is a clone designated herein as "DNA280351".

FIG. 12 shows a nucleotide sequence (SEQ ID NO:12) of a TAT232 cDNA, wherein SEQ ID NO:12 is a clone designated herein as "DNA150648".

FIG. 13 shows a nucleotide sequence (SEQ ID NO:13) of a TAT219 cDNA, wherein SEQ ID NO:13 is a clone designated herein as "DNA172500".

FIG. 14 shows a nucleotide sequence (SEQ ID NO:14) of a TAT224 cDNA, wherein SEQ ID NO:14 is a clone designated herein as "DNA179651".

FIG. 15 shows a nucleotide sequence (SEQ ID NO:15) of a TAT237 cDNA, wherein SEQ ID NO:15 is a clone designated herein as "DNA207698".

FIG. 16 shows a nucleotide sequence (SEQ ID NO:16) of a TAT178 cDNA, wherein SEQ ID NO:16 is a clone designated herein as "DNA208551".

FIGS. 17A-B show a nucleotide sequence (SEQ ID NO:17) of a TAT198 cDNA, wherein SEQ ID NO:17 is a clone designated herein as "DNA210159".

FIGS. 18A-B show a nucleotide sequence (SEQ ID NO:18) of a TAT194 cDNA, wherein SEQ ID NO:18 is a clone designated herein as "DNA225706".

FIGS. 19A-B show a nucleotide sequence (SEQ ID NO:19) of a TAT223 cDNA, wherein SEQ ID NO:19 is a clone designated herein as "DNA225793".

FIG. 20 shows a nucleotide sequence (SEQ ID NO:20) of a TAT196 cDNA, wherein SEQ ID NO:20 is a clone designated herein as "DNA225796".

FIG. 21 shows a nucleotide sequence (SEQ ID NO:21) of a TAT236 cDNA, wherein SEQ ID NO:21 is a clone designated herein as "DNA225886".

FIG. 22 shows a nucleotide sequence (SEQ ID NO:22) of a TAT195 cDNA, wherein SEQ ID NO:22 is a clone designated herein as "DNA225943".

FIG. 23 shows a nucleotide sequence (SEQ ID NO:23) of a TAT203 cDNA, wherein SEQ ID NO:23 is a clone designated herein as "DNA226283".

FIGS. 24A-B show a nucleotide sequence (SEQ ID NO:24) of a TAT200 cDNA, wherein SEQ ID NO:24 is a clone designated herein as "DNA226589".

FIGS. 25A-B show a nucleotide sequence (SEQ ID NO:25) of a TAT205 cDNA, wherein SEQ ID NO:25 is a clone designated herein as "DNA226622".

FIGS. 26A-B show a nucleotide sequence (SEQ ID NO:26) of a TAT185 cDNA, wherein SEQ ID NO:26 is a clone designated herein as "DNA226717".

FIGS. 27A-B show a nucleotide sequence (SEQ ID NO:27) of a TAT225 cDNA, wherein SEQ ID NO:27 is a clone designated herein as "DNA227162".

FIG. 28 shows a nucleotide sequence (SEQ ID NO:28) of a TAT247 cDNA, wherein SEQ ID NO:28 is a clone designated herein as "DNA277804".

FIG. 29 shows a nucleotide sequence (SEQ ID NO:29) of a TAT197 cDNA, wherein SEQ ID NO:29 is a clone designated herein as "DNA227545".

FIG. 30 shows a nucleotide sequence (SEQ ID NO:30) of a TAT175 cDNA, wherein SEQ ID NO:30 is a clone designated herein as "DNA227611".

FIG. 31 shows a nucleotide sequence (SEQ ID NO:31) of a TAT208 cDNA, wherein SEQ ID NO:31 is a clone designated herein as "DNA261021".

FIG. 32 shows a nucleotide sequence (SEQ ID NO:32) of a TAT174 cDNA, wherein SEQ ID NO:32 is a clone designated herein as "DNA233034".

FIG. 33 shows a nucleotide sequence (SEQ ID NO:33) of a TAT214 cDNA, wherein SEQ ID NO:33 is a clone designated herein as "DNA266920".

FIG. 34 shows a nucleotide sequence (SEQ ID NO:34) of a TAT220 cDNA, wherein SEQ ID NO:34 is a clone designated herein as "DNA266921".

FIG. 35 shows a nucleotide sequence (SEQ ID NO:35) of a TAT221 cDNA, wherein SEQ ID NO:35 is a clone designated herein as "DNA266922".

FIG. 36 shows a nucleotide sequence (SEQ ID NO:36) of a TAT201 cDNA, wherein SEQ ID NO:36 is a clone designated herein as "DNA234441".

FIGS. 37A-B show a nucleotide sequence (SEQ ID NO:37) of a TAT179 cDNA, wherein SEQ ID NO:37 is a clone designated herein as "DNA234834".

FIG. 38 shows a nucleotide sequence (SEQ ID NO:38) of a TAT216 cDNA, wherein SEQ ID NO:38 is a clone designated herein as "DNA247587".

FIG. 39 shows a nucleotide sequence (SEQ ID NO:39) of a TAT218 cDNA, wherein SEQ ID NO:39 is a clone designated herein as "DNA255987".

FIG. 40 shows a nucleotide sequence (SEQ ID NO:40) of a TAT206 cDNA, wherein SEQ ID NO:40 is a clone designated herein as "DNA56041".

FIGS. 41A-B show a nucleotide sequence (SEQ ID NO:41) of a TAT374 cDNA, wherein SEQ ID NO:41 is a clone designated herein as "DNA257845".

FIG. 42 shows a nucleotide sequence (SEQ ID NO:42) of a TAT209 cDNA, wherein SEQ ID NO:42 is a clone designated herein as "DNA260655".

FIG. 43 shows a nucleotide sequence (SEQ ID NO:43) of a TAT192 cDNA, wherein SEQ ID NO:43 is a clone designated herein as "DNA260945".

FIG. 44 shows a nucleotide sequence (SEQ ID NO:44) of a TAT180 cDNA, wherein SEQ ID NO:44 is a clone designated herein as "DNA247476".

FIG. 45 shows a nucleotide sequence (SEQ ID NO:45) of a TAT375 cDNA, wherein SEQ ID NO:45 is a clone designated herein as "DNA260990".

FIG. 46 shows a nucleotide sequence (SEQ ID NO:46) of a TAT181 cDNA, wherein SEQ ID NO:46 is a clone designated herein as "DNA261001".

FIG. 47 shows a nucleotide sequence (SEQ ID NO:47) of a TAT176 cDNA, wherein SEQ ID NO:47 is a clone designated herein as "DNA261013".

FIG. 48 shows a nucleotide sequence (SEQ ID NO:48) of a TAT184 cDNA, wherein SEQ ID NO:48 is a clone designated herein as "DNA262144".

FIG. 49 shows a nucleotide sequence (SEQ ID NO:49) of a TAT182 cDNA, wherein SEQ ID NO:49 is a clone designated herein as "DNA266928".

FIGS. 50A-B show a nucleotide sequence (SEQ ID NO:50) of a TAT213 cDNA, wherein SEQ ID NO:50 is a clone designated herein as "DNA267342".

FIGS. 51A-C show a nucleotide sequence (SEQ ID NO:51) of a TAT217 cDNA, wherein SEQ ID NO:51 is a clone designated herein as "DNA267626".

FIG. 52 shows a nucleotide sequence (SEQ ID NO:52) of a TAT222 cDNA, wherein SEQ ID NO:52 is a clone designated herein as "DNA268035".

FIG. 53 shows a nucleotide sequence (SEQ ID NO:53) of a TAT202 cDNA, wherein SEQ ID NO:53 is a clone designated herein as "DNA268334".

FIG. 54 shows a nucleotide sequence (SEQ ID NO:54) of a TAT215 cDNA, wherein SEQ ID NO:54 is a clone designated herein as "DNA269238".

FIG. 55 shows a nucleotide sequence (SEQ ID NO:55) of a TAT238 cDNA, wherein SEQ ID NO:55 is a clone designated herein as "DNA272578".

FIG. 56 shows a nucleotide sequence (SEQ ID NO:56) of a TAT212 cDNA, wherein SEQ ID NO:56 is a clone designated herein as "DNA277797".

FIG. 57 shows the amino acid sequence (SEQ ID NO:57) derived from the coding sequence of SEQ ID NO:1 shown in FIG. 1.

FIG. 58 shows the amino acid sequence (SEQ ID NO:58) derived from the coding sequence of SEQ ID NO:2 shown in FIG. 2.

FIG. 59 shows the amino acid sequence (SEQ ID NO:59) derived from the coding sequence of SEQ ID NO:3 shown in FIG. 3.

FIG. 60 shows the amino acid sequence (SEQ ID NO:60) derived from the coding sequence of SEQ ID NO:4 shown in FIG. 4.

FIG. 61 shows the amino acid sequence (SEQ ID NO:61) derived from the coding sequence of SEQ ID NO:5 shown in FIG. 5.

FIG. 62 shows the amino acid sequence (SEQ ID NO:62) derived from the coding sequence of SEQ ID NO:6 shown in FIG. 6.

FIG. 63 shows the amino acid sequence (SEQ ID NO:63) derived from the coding sequence of SEQ ID NO:7 shown in FIG. 7.

FIG. 64 shows the amino acid sequence (SEQ ID NO:64) derived from the coding sequence of SEQ ID NO:8 shown in FIG. 8.

FIG. 65 shows the amino acid sequence (SEQ ID NO:65) derived from the coding sequence of SEQ ID NO:9 shown in FIG. 9.

FIG. 66 shows the amino acid sequence (SEQ ID NO:66) derived from the coding sequence of SEQ ID NO:10 shown in FIGS. 10A-B.

FIG. 67 shows the amino acid sequence (SEQ ID NO:67) derived from the coding sequence of SEQ ID NO:11 shown in FIGS. 11A-B.

FIG. 68 shows the amino acid sequence (SEQ ID NO:68) derived from the coding sequence of SEQ ID NO:12 shown in FIG. 12.

FIG. 69 shows the amino acid sequence (SEQ ID NO:69) derived from the coding sequence of SEQ ID NO:13 shown in FIG. 13.

FIG. 70 shows the amino acid sequence (SEQ ID NO:70) derived from the coding sequence of SEQ ID NO:14 shown in FIG. 14.

FIG. 71 shows the amino acid sequence (SEQ ID NO:71) derived from the coding sequence of SEQ ID NO:15 shown in FIG. 15.

FIG. 72 shows the amino acid sequence (SEQ ID NO:72) derived from the coding sequence of SEQ ID NO:16 shown in FIG. 16.

FIG. 73 shows the amino acid sequence (SEQ ID NO:73) derived from the coding sequence of SEQ ID NO:17 shown in FIGS. 17A-B.

FIG. 74 shows the amino acid sequence (SEQ ID NO:74) derived from the coding sequence of SEQ ID NO:18 shown in FIGS. 18A-B.

FIG. 75 shows the amino acid sequence (SEQ ID NO:75) derived from the coding sequence of SEQ ID NO:19 shown in FIGS. 19A-B.

FIG. 76 shows the amino acid sequence (SEQ ID NO:76) derived from the coding sequence of SEQ ID NO:20 shown in FIG. 20.

FIG. 77 shows the amino acid sequence (SEQ ID NO:77) derived from the coding sequence of SEQ ID NO:21 shown in FIG. 21.

FIG. 78 shows the amino acid sequence (SEQ ID NO:78) derived from the coding sequence of SEQ ID NO:22 shown in FIG. 22.

FIG. 79 shows the amino acid sequence (SEQ ID NO:79) derived from the coding sequence of SEQ ID NO:23 shown in FIG. 23.

FIG. 80 shows the amino acid sequence (SEQ ID NO:80) derived from the coding sequence of SEQ ID NO:24 shown in FIGS. 24A-B.

FIG. 81 shows the amino acid sequence (SEQ ID NO:81) derived from the coding sequence of SEQ ID NO:25 shown in FIGS. 25A-B.

FIG. 82 shows the amino acid sequence (SEQ ID NO:82) derived from the coding sequence of SEQ ID NO:26 shown in FIGS. 26A-B.

FIG. 83 shows the amino acid sequence (SEQ ID NO:83) derived from the coding sequence of SEQ ID NO:27 shown in FIGS. 27A-B.

FIG. 84 shows the amino acid sequence (SEQ ID NO:84) derived from the coding sequence of SEQ ID NO:28 shown in FIG. 28.

FIG. 85 shows the amino acid sequence (SEQ ID NO:85) derived from the coding sequence of SEQ ID NO:29 shown in FIG. 29.

FIG. 86 shows the amino acid sequence (SEQ ID NO:86) derived from the coding sequence of SEQ ID NO:30 shown in FIG. 30.

FIG. 87 shows the amino acid sequence (SEQ ID NO:87) derived from the coding sequence of SEQ ID NO:31 shown in FIG. 31.

FIG. 88 shows the amino acid sequence (SEQ ID NO:88) derived from the coding sequence of SEQ ID NO:32 shown in FIG. 32.

FIG. 89 shows the amino acid sequence (SEQ ID NO:89) derived from the coding sequence of SEQ ID NO:33 shown in FIG. 33.

FIG. 90 shows the amino acid sequence (SEQ ID NO:90) derived from the coding sequence of SEQ ID NO:34 shown in FIG. 34.

FIG. 91 shows the amino acid sequence (SEQ ID NO:91) derived from the coding sequence of SEQ ID NO:35 shown in FIG. 35.

FIG. 92 shows the amino acid sequence (SEQ ID NO:92) derived from the coding sequence of SEQ ID NO:36 shown in FIG. 36.

FIG. 93 shows the amino acid sequence (SEQ ID NO:93) derived from the coding sequence of SEQ ID NO:37 shown in FIGS. 37A-B.

FIG. 94 shows the amino acid sequence (SEQ ID NO:94) derived from the coding sequence of SEQ ID NO:38 shown in FIG. 38.

FIG. 95 shows the amino acid sequence (SEQ ID NO:95) derived from the coding sequence of SEQ ID NO:39 shown in FIG. 39.

FIG. 96 shows the amino acid sequence (SEQ ID NO:96) derived from the coding sequence of SEQ ID NO:40 shown in FIG. 40.

FIG. 97 shows the amino acid sequence (SEQ ID NO:97) derived from the coding sequence of SEQ ID NO:41 shown in FIGS. 41A-B.

FIG. 98 shows the amino acid sequence (SEQ ID NO:98) derived from the coding sequence of SEQ ID NO:42 shown in FIG. 42.

FIG. 99 shows the amino acid sequence (SEQ ID NO:99) derived from the coding sequence of SEQ ID NO:43 shown in FIG. 43.

FIG. 100 shows the amino acid sequence (SEQ ID NO:100) derived from the coding sequence of SEQ ID NO:44 shown in FIG. 44.

FIG. 101 shows the amino acid sequence (SEQ ID NO:101) derived from the coding sequence of SEQ ID NO:45 shown in FIG. 45.

FIG. 102 shows the amino acid sequence (SEQ ID NO:102) derived from the coding sequence of SEQ ID NO:46 shown in FIG. 46.

FIG. 103 shows the amino acid sequence (SEQ ID NO:103) derived from the coding sequence of SEQ ID NO:47 shown in FIG. 47.

FIG. 104 shows the amino acid sequence (SEQ ID NO:104) derived from the coding sequence of SEQ ID NO:48 shown in FIG. 48.

FIG. 105 shows the amino acid sequence (SEQ ID NO:105) derived from the coding sequence of SEQ ID NO:49 shown in FIG. 49.

FIG. 106 shows the amino acid sequence (SEQ ID NO:106) derived from the coding sequence of SEQ ID NO:50 shown in FIGS. 50A-B.

FIGS. 107A-B show the amino acid sequence (SEQ ID NO:107) derived from the coding sequence of SEQ ID NO:51 shown in FIGS. 51A-C.

FIG. 108 shows the amino acid sequence (SEQ ID NO:108) derived from the coding sequence of SEQ ID NO:52 shown in FIG. 52.

FIG. 109 shows the amino acid sequence (SEQ ID NO:109) derived from the coding sequence of SEQ ID NO:53 shown in FIG. 53.

FIG. 110 shows the amino acid sequence (SEQ ID NO:110) derived from the coding sequence of SEQ ID NO:54 shown in FIG. 54.

FIG. 111 shows the amino acid sequence (SEQ ID NO:111) derived from the coding sequence of SEQ ID NO:55 shown in FIG. 55.

FIG. 112 shows the amino acid sequence (SEQ ID NO:112) derived from the coding sequence of SEQ ID NO:56 shown in FIG. 56.

FIG. 113 shows a nucleotide sequence (SEQ ID NO:113) of a TAT376 cDNA, wherein SEQ ID NO:113 is a clone designated herein as "DNA304853".

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a TAT377 cDNA, wherein SEQ ID NO:115 is a clone designated herein as "DNA304854".

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a TAT378 cDNA, wherein SEQ ID NO:117 is a clone designated herein as "DNA304855".

FIG. 118 shows the amino acid sequence (SEQ ID NO:118) derived from the coding sequence of SEQ ID NO:117 shown in FIG. 117.

FIGS. 119A-B show a nucleotide sequence (SEQ ID NO:119) of a TAT379 cDNA, wherein SEQ ID NO:119 is a clone designated herein as "DNA287971".

FIG. 120 shows the amino acid sequence (SEQ ID NO:120) derived from the coding sequence of SEQ ID NO:119 shown in FIGS. 119A-B.

DETAILED DESCRIPTION OF THE PREFERRED EMBODIMENTS

I. Definitions

The terms "TAT polypeptide" and "TAT" as used herein and when immediately followed by a numerical designation, refer to various polypeptides, wherein the complete designation (i.e., TAT/number) refers to specific polypeptide sequences as described herein. The terms "TAT/number polypeptide" and "TAT/number" wherein the term "number" is provided as an actual numerical designation as used herein encompass native sequence polypeptides, polypeptide variants and fragments of native sequence polypeptides and polypeptide variants (which are further defined herein). The TAT polypeptides described herein may be isolated from a variety of sources, such as from human tissue types or from another source, or prepared by recombinant or synthetic methods. The term "TAT polypeptide" refers to each individual TAT/number polypeptide disclosed herein. All disclosures in this specification which refer to the "TAT polypeptide" refer to each of the polypeptides individually as well as jointly. For example, descriptions of the preparation of, purification of, derivation of, formation of antibodies to or against, formation of TAT binding oligopeptides to or against, formation of TAT binding organic molecules to or against, administration of, compositions containing, treatment of a disease with, etc., pertain to each polypeptide of the invention individually. The term "TAT polypeptide" also includes variants of the TAT/number polypeptides disclosed herein.

A "native sequence TAT polypeptide" comprises a polypeptide having the same amino acid sequence as the corresponding TAT polypeptide derived from nature. Such native sequence TAT polypeptides can be isolated from nature or can be produced by recombinant or synthetic means. The term "native sequence TAT polypeptide" specifically encompasses naturally-occurring truncated or secreted forms of the specific TAT polypeptide (e.g., an extracellular domain sequence), naturally-occurring variant forms (e.g., alternatively spliced forms) and naturally-occurring allelic variants of the polypeptide. In certain embodiments of the invention, the native sequence TAT polypeptides disclosed herein are mature or full-length native sequence polypeptides comprising the full-length amino acids sequences shown in the accompanying figures. Start and stop codons (if indicated) are shown in bold font and underlined in the figures. Nucleic acid residues indicated as "N" in the accompanying figures are any nucleic acid residue. However, while the TAT polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the TAT polypeptides.

The TAT polypeptide "extracellular domain" or "ECD" refers to a form of the TAT polypeptide which is essentially free of the transmembrane and cytoplasmic domains. Ordinarily, a TAT polypeptide ECD will have less than 1% of such transmembrane and/or cytoplasmic domains and preferably, will have less than 0.5% of such domains. It will be understood that any transmembrane domains identified for the TAT polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a TAT polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various TAT polypeptides disclosed herein may be shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"TAT polypeptide variant" means a TAT polypeptide, preferably an active TAT polypeptide, as defined herein having at least about 80% amino acid sequence identity with a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Such TAT polypeptide variants include, for instance, TAT polypeptides wherein one or more amino acid residues are added, or deleted, at the N- or C-terminus of the full-length native amino acid sequence. Ordinarily, a TAT polypeptide variant will have at least about 80% amino acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence TAT polypeptide sequence as disclosed herein, a TAT polypeptide sequence lacking the signal peptide as disclosed herein, an extracellular domain of a TAT polypeptide, with or without the signal peptide, as disclosed herein or any other specifically defined fragment of a full-length TAT polypeptide sequence as disclosed herein. Ordinarily, TAT variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, TAT variant polypeptides will have no more than one conservative amino acid substitution as compared to the native TAT polypeptide sequence, alternatively no more than 2, 3, 4, 5, 6, 7, 8, 9, or 10 conservative amino acid substitution as compared to the native TAT polypeptide sequence.

"Percent (%) amino acid sequence identity" with respect to the TAT polypeptide sequences identified herein is defined as the percentage of amino acid residues in a candidate sequence that are identical with the amino acid residues in the specific TAT polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "TAT", wherein "TAT" represents the amino acid sequence of a hypothetical TAT polypeptide of interest, "Comparison Protein" represents the amino acid sequence of a polypeptide against which the "TAT" polypeptide of interest is being compared, and "X, "Y" and "Z" each represent different hypothetical amino acid residues. Unless specifically stated otherwise, all % amino acid sequence identity values used herein are obtained as described in the immediately preceding paragraph using the ALIGN-2 computer program.

"TAT variant polynucleotide" or "TAT variant nucleic acid sequence" means a nucleic acid molecule which encodes a TAT polypeptide, preferably an active TAT polypeptide, as defined herein and which has at least about 80% nucleic acid sequence identity with a nucleotide acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal peptide, as disclosed herein or any other fragment of a full-length TAT polypeptide sequence as disclosed herein (such as those encoded by a nucleic acid that represents only a portion of the complete coding sequence for a full-length TAT polypeptide). Ordinarily, a TAT variant polynucleotide will have at least about 80% nucleic acid sequence identity, alternatively at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence TAT polypeptide sequence as disclosed herein, a full-length native sequence TAT polypeptide sequence lacking the signal peptide as disclosed herein, an extracellular domain of a TAT polypeptide, with or without the signal sequence, as disclosed herein or any other fragment of a full-length TAT polypeptide sequence as disclosed herein. Variants do not encompass the native nucleotide sequence.

Ordinarily, TAT variant polynucleotides are at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to TAT-encoding nucleic acid sequences identified herein is defined as the percentage of nucleotides in a candidate sequence that are identical with the nucleotides in the TAT nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below.

The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "TAT-DNA", wherein "TAT-DNA" represents a hypothetical TAT-encoding nucleic acid sequence of interest, "Comparison DNA" represents the nucleotide sequence of a nucleic acid molecule against which the "TAT-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

In other embodiments, TAT variant polynucleotides are nucleic acid molecules that encode a TAT polypeptide and which are capable of hybridizing, preferably under stringent hybridization and wash conditions, to nucleotide sequences encoding a full-length TAT polypeptide as disclosed herein. TAT variant polypeptides may be those that are encoded by a TAT variant polynucleotide.

The term "full-length coding region" when used in reference to a nucleic acid encoding a TAT polypeptide refers to the sequence of nucleotides which encode the full-length TAT polypeptide of the invention (which is often shown between start and stop codons, inclusive thereof, in the accompanying figures). The term "full-length coding region" when used in reference to an ATCC deposited nucleic acid refers to the TAT polypeptide-encoding portion of the cDNA that is inserted into the vector deposited with the ATCC (which is often shown between start and stop codons, inclusive thereof, in the accompanying figures).

"Isolated," when used to describe the various TAT polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TAT polypeptide natural environment will not be present. Ordinarily, however, isolated polypeptide will be prepared by at least one purification step.

An "isolated" TAT polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a TAT polypeptide or anti-TAT antibody fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a TAT polypeptide which retain a biological and/or an immunological activity of native or naturally-occurring TAT, wherein "biological" activity refers to a biological function (either inhibitory or stimulatory) caused by a native or naturally-occurring TAT other than the ability to induce the production of an antibody against an antigenic epitope possessed by a native or naturally-occurring TAT and an "immunological" activity refers to the ability to induce the production of an antibody against an antigenic epitope possessed by a native or naturally-occurring TAT.

The term "antagonist" is used in the broadest sense, and includes any molecule that partially or fully blocks, inhibits, or neutralizes a biological activity of a native TAT polypeptide disclosed herein. In a similar manner, the term "agonist" is used in the broadest sense and includes any molecule that mimics a biological activity of a native TAT polypeptide disclosed herein. Suitable agonist or antagonist molecules specifically include agonist or antagonist antibodies or antibody fragments, fragments or amino acid sequence variants of native TAT polypeptides, peptides, antisense oligonucleotides, small organic molecules, etc. Methods for identifying agonists or antagonists of a TAT polypeptide may comprise contacting a TAT polypeptide with a candidate agonist or antagonist molecule and measuring a detectable change in one or more biological activities normally associated with the TAT polypeptide.

"Treating" or "treatment" or "alleviation" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for a TAT polypeptide-expressing cancer if, after receiving a therapeutic amount of an anti-TAT antibody, TAT binding oligopeptide or TAT binding organic molecule according to the methods of the present invention, the patient shows observable and/or measurable reduction in or absence of one or more of the following: reduction in the number of cancer cells or absence of the cancer cells; reduction in the tumor size; inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth; and/or relief to some extent, one or more of the symptoms associated with the specific cancer; reduced morbidity and mortality, and improvement in quality of life issues. To the extent the anti-TAT antibody or TAT binding oligopeptide may prevent growth and/or kill existing cancer cells, it may be cytostatic and/or cytotoxic. Reduction of these signs or symptoms may also be felt by the patient.

The above parameters for assessing successful treatment and improvement in the disease are readily measurable by routine procedures familiar to a physician. For cancer therapy, efficacy can be measured, for example, by assessing the time to disease progression (TTP) and/or determining the response rate (RR). Metastasis can be determined by staging tests and by bone scan and tests for calcium level and other enzymes to determine spread to the bone. CT scans can also be done to look for spread to the pelvis and lymph nodes in the area. Chest X-rays and measurement of liver enzyme levels by known methods are used to look for metastasis to the lungs and liver, respectively. Other routine methods for monitoring the disease include transrectal ultrasonography (TRUS) and transrectal needle biopsy (TRNB).

For bladder cancer, which is a more localized cancer, methods to determine progress of disease include urinary cytologic evaluation by cystoscopy, monitoring for presence of blood in the urine, visualization of the urothelial tract by sonography or an intravenous pyelogram, computed tomography (CT) and magnetic resonance imaging (MRI). The presence of distant metastases can be assessed by CT of the abdomen, chest x-rays, or radionuclide imaging of the skeleton.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of the treatment of, alleviating the symptoms of or diagnosis of a cancer refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

By "solid phase" or "solid support" is meant a non-aqueous matrix to which an antibody, TAT binding oligopeptide or TAT binding organic molecule of the present invention can adhere or attach. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a TAT polypeptide, an antibody thereto or a TAT binding oligopeptide) to a mammal. The components of the liposome are commonly arranged in a bilayer formation, similar to the lipid arrangement of biological membranes.

A "small" molecule or "small" organic molecule is defined herein to have a molecular weight below about 500 Daltons.

An "effective amount" of a polypeptide, antibody, TAT binding oligopeptide, TAT binding organic molecule or an agonist or antagonist thereof as disclosed herein is an amount sufficient to carry out a specifically stated purpose. An "effective amount" may be determined empirically and in a routine manner, in relation to the stated purpose.

The term "therapeutically effective amount" refers to an amount of an antibody, polypeptide, TAT binding oligopeptide, TAT binding organic molecule or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

A "growth inhibitory amount" of an anti-TAT antibody, TAT polypeptide, TAT binding oligopeptide or TAT binding organic molecule is an amount capable of inhibiting the growth of a cell, especially tumor, e.g., cancer cell, either in vitro or in vivo. A "growth inhibitory amount" of an anti-TAT antibody, TAT polypeptide, TAT binding oligopeptide or TAT binding organic molecule for purposes of inhibiting neoplastic cell growth may be determined empirically and in a routine manner.

A "cytotoxic amount" of an anti-TAT antibody, TAT polypeptide, TAT binding oligopeptide or TAT binding organic molecule is an amount capable of causing the destruction of a cell, especially tumor, e.g., cancer cell, either in vitro or in vivo. A "cytotoxic amount" of an anti-TAT antibody, TAT polypeptide, TAT binding oligopeptide or TAT binding organic molecule for purposes of inhibiting neoplastic cell growth may be determined empirically and in a routine manner.

The term "antibody" is used in the broadest sense and specifically covers, for example, single anti-TAT monoclonal antibodies (including agonist, antagonist, and neutralizing antibodies), anti-TAT antibody compositions with polyepitopic specificity, polyclonal antibodies, single chain anti-TAT antibodies, and fragments of anti-TAT antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the $\alpha$ and $\gamma$ chains and four $C_H$ domains for $\mu$ and $\epsilon$ isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated $\alpha$, $\delta$, $\epsilon$, $\gamma$, and $\mu$, respectively. The $\gamma$ and $\alpha$ classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a $\beta$-sheet configuration, connected by three hypervariable regions, which form loops connecting, and in some cases forming part of, the $\beta$-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature,* 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "TAT binding oligopeptide" is an oligopeptide that binds, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

A "TAT binding organic molecule" is an organic molecule other than an oligopeptide or antibody as defined herein that binds, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a diagnostic and/or therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing a TAT polypeptide" or a "growth inhibitory" antibody, oligopeptide or other organic molecule is one which results in measurable growth inhibition of cancer cells expressing or overexpressing the appropriate TAT polypeptide. The TAT polypeptide may be a transmembrane polypeptide expressed on the surface of a cancer cell or may be a polypeptide that is produced and secreted by a cancer cell. Preferred growth inhibitory anti-TAT antibodies, oligopeptides or organic molecules inhibit growth of TAT-expressing tumor cells by greater than 20%, preferably from about 20% to about 50%, and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways such as is described in the Experimental Examples section below. The antibody is growth inhibitory in vivo if administration of the anti-TAT antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses a TAT polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a TAT polypeptide, preferably a cell that overexpresses a TAT polypeptide as compared to a normal cell of the same tissue type. The TAT polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

A "TAT-expressing cell" is a cell which expresses an endogenous or transfected TAT polypeptide either on the cell surface or in a secreted form. A "TAT-expressing cancer" is a cancer comprising cells that have a TAT polypeptide present on the cell surface or that produce and secrete a TAT polypeptide. A "TAT-expressing cancer" optionally produces sufficient levels of TAT polypeptide on the surface of cells thereof, such that an anti-TAT antibody, oligopeptide or other organic molecule can bind thereto and have a therapeutic effect with respect to the cancer. In another embodiment, a "TAT-expressing cancer" optionally produces and secretes sufficient levels of TAT polypeptide, such that an anti-TAT antibody, oligopeptide or other organic molecule antagonist can bind thereto and have a therapeutic effect with respect to the cancer. With regard to the latter, the antagonist may be an antisense oligonucleotide which reduces, inhibits or prevents production and secretion of the secreted TAT polypeptide by tumor cells. A cancer which "overexpresses" a TAT polypeptide is one which has significantly higher levels of TAT polypeptide at the cell surface thereof, or produces and secretes, compared to a noncancerous cell of the same tissue type. Such overexpression may be caused by gene amplification or by increased transcription or translation. TAT polypeptide overexpression may be determined in a diagnostic or prognostic assay by evaluating increased levels of the TAT protein present on the surface of a cell, or secreted by the cell (e.g., via an immunohistochemistry assay using anti-TAT antibodies prepared against an isolated TAT polypeptide which may be prepared using recombinant DNA technology from an isolated nucleic acid encoding the TAT polypeptide; FACS analysis, etc.). Alternatively, or additionally, one may measure levels of TAT polypeptide-encoding nucleic acid or mRNA in the cell, e.g., via fluorescent in situ hybridization using a nucleic acid based probe corresponding to a TAT-encoding nucleic acid or the complement thereof; (FISH; see WO98/45479 published October, 1998), Southern blotting, Northern blotting, or polymerase chain reaction (PCR) techniques, such as real time quantitative PCR (RT-PCR). One may also study TAT polypeptide overexpression by measuring shed antigen in a biological fluid such as serum, e.g, using antibody-based assays (see also, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al., *J. Immunol. Methods* 132:73-80 (1990)). Aside from the above assays, various in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The word "label" when used herein refers to a detectable compound or composition which is conjugated directly or indirectly to the antibody, oligopeptide or other organic molecule so as to generate a "labeled" antibody, oligopeptide or other organic molecule. The label may be detectable by itself (e.g. radioisotope labels or fluorescent labels) or, in the case of an enzymatic label, may catalyze chemical alteration of a substrate compound or composition which is detectable.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "growth inhibitory agent" when used herein refers to a compound or composition which inhibits growth of a cell, especially a TAT-expressing cancer cell, either in vitro or in vivo. Thus, the growth inhibitory agent may be one which significantly reduces the percentage of TAT-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ, colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

TABLE 1

```
/*
 *
 * C-C increased from 12 to 15
 * Z is average of EQ
 * B is average of ND
 * match with stop is _M; stop-stop = 0; J (joker) match = 0
 */
#define     _M     −8          /* value of a match with a stop */
int         _day[26][26] = {
/*          A B C D E F G H I J K L M N O P Q R S T U V W X Y Z */
/* A */     { 2, 0,−2, 0, 0,−4, 1,−1,−1, 0,−1,−2,−1, 0,_M, 1, 0,−2, 1, 1, 0, 0,−6, 0,−3, 0},
/* B */     { 0, 3,−4, 3, 2,−5, 0, 1,−2, 0, 0,−3,−2, 2,_M,−1, 1, 0, 0, 0, 0,−2,−5, 0,−3, 1},
/* C */     {−2,−4,15,−5,−5,−4,−3,−3,−2, 0,−5,−6,−5,−4,_M,−3,−5,−4, 0,−2, 0,−2,−8, 0, 0,−5},
/* D */     { 0, 3,−5, 4, 3,−6, 1, 1,−2, 0, 0,−4,−3, 2,_M,−1, 2,−1, 0, 0, 0,−2,−7, 0,−4, 2},
/* E */     { 0, 2,−5, 3, 4,−5, 0, 1,−2, 0, 0,−3,−2, 1,_M,−1, 2,−1, 0, 0, 0,−2,−7, 0,−4, 3},
/* F */     {−4,−5,−4,−6,−5, 9,−5,−2, 1, 0,−5, 2, 0,−4,_M,−5,−5,−4,−3,−3, 0,−1, 0, 0, 7,−5},
/* G */     { 1, 0,−3, 1, 0,−5, 5,−2,−3, 0,−2,−4,−3, 0,_M,−1,−1,−3, 1, 0, 0,−1,−7, 0,−5, 0},
/* H */     {−1, 1,−3, 1, 1,−2,−2, 6,−2, 0, 0,−2,−2, 2,_M, 0, 3, 2,−1,−1, 0,−2,−3, 0, 0, 2},
/* I */     {−1,−2,−2,−2,−2, 1,−3,−2, 5, 0,−2, 2, 2,−2,_M,−2,−2,−2,−1, 0, 0, 4,−5, 0,−1,−2},
/* J */     { 0, 0, 0, 0, 0, 0, 0, 0, 0, 0, 0, 0, 0, 0,_M, 0, 0, 0, 0, 0, 0, 0, 0, 0, 0, 0},
/* K */     {−1, 0,−5, 0, 0,−5,−2, 0,−2, 0, 5,−3, 0, 1,_M,−1, 1, 3, 0, 0, 0,−2,−3, 0,−4, 0},
/* L */     {−2,−3,−6,−4,−3, 2,−4,−2, 2, 0,−3, 6, 4,−3,_M,−3,−2,−3,−3,−1, 0, 2,−2, 0,−1,−2},
```

TABLE 1-continued

```
/* M */     {-1,-2,-5,-3,-2, 0,-3,-2, 2, 0, 0, 4, 6,-2,_M,-2,-1, 0,-2,-1, 0, 2,-4, 0,-2,-1},
/* N */     { 0, 2,-4, 2, 1,-4, 0, 2,-2, 0, 1,-3,-2, 2,_M,-1, 1, 0, 1, 0, 0,-2,-4, 0,-2, 1},
/* O */     {_M,_M,_M,_M,_M,_M,_M,_M,_M,_M,_M,_M,_M,_M, 0,_M,_M,_M,_M,_M,_M,_M,_M,_M,_M,_M},
/* P */     { 1,-1,-3,-1,-1,-5,-1, 0,-2, 0,-1,-3,-2,-1,_M, 6, 0, 0, 1, 0, 0,-1,-6, 0,-5, 0},
/* Q */     { 0, 1,-5, 2, 2,-5,-1, 3,-2, 0, 1,-2,-1, 1,_M, 0, 4, 1,-1,-1, 0,-2,-5, 0,-4, 3},
/* R */     {-2, 0,-4,-1,-1,-4,-3, 2,-2, 0, 3,-3, 0, 0,_M, 0, 1, 6, 0,-1, 0,-2, 2, 0,-4, 0},
/* S */     { 1, 0, 0, 0, 0,-3, 1,-1,-1, 0, 0,-3,-2, 1,_M, 1,-1, 0, 2, 1, 0,-1,-2, 0,-3, 0},
/* T */     { 1, 0,-2, 0, 0,-3, 0,-1, 0, 0, 0,-1,-1, 0,_M, 0,-1,-1, 1, 3, 0, 0,-5, 0,-3, 0},
/* U */     { 0, 0, 0, 0, 0, 0, 0, 0, 0, 0, 0, 0, 0, 0,_M, 0, 0, 0, 0, 0, 0, 0, 0, 0, 0, 0},
/* V */     { 0,-2,-2,-2,-2,-1,-1,-2, 4, 0,-2, 2, 2,-2,_M,-1,-2,-2,-1, 0, 0, 4,-6, 0,-2,-2},
/* W */     {-6,-5,-8,-7,-7, 0,-7,-3,-5, 0,-3,-2,-4,-4,_M,-6,-5, 2,-2,-5, 0,-6,17, 0, 0,-6},
/* X */     { 0, 0, 0, 0, 0, 0, 0, 0, 0, 0, 0, 0, 0, 0,_M, 0, 0, 0, 0, 0, 0, 0, 0, 0, 0, 0},
/* Y */     {-3,-3, 0,-4,-4, 7,-5, 0,-1, 0,-4,-1,-2,-2,_M,-5,-4,-4,-3,-3, 0,-2, 0, 0,10,-4},
/* Z */     { 0, 1,-5, 2, 3,-5, 0, 2,-2, 0, 0,-2,-1, 1,_M, 0, 3, 0, 0, 0, 0,-2,-6, 0,-4, 4}
};
/*
 */
#include <stdio.h>
#include <ctype.h>
#define  MAXJMP      16     /* max jumps in a diag */
#define  MAXGAP      24     /* don't continue to penalize gaps larger than this */
#define  JMPS        1024   /* max jmps in an path */
#define  MX          4      /* save if there's at least MX-1 bases since last jmp */
#define  DMAT        3      /* value of matching bases */
#define  DMIS        0      /* penalty for mismatched bases */
#define  DINS0       8      /* penalty for a gap */
#define  DINS1       1      /* penalty per base */
#define  PINS0       8      /* penalty for a gap */
#define  PINS1       4      /* penalty per residue */
struct jmp {
        short           n[MAXJMP];      /* size of jmp (neg for dely) */
        unsigned short  x[MAXJMP];      /* base no. of jmp in seq x */
};                                      /* limits seq to 2^16 -1 */
struct diag {
        int             score;          /* score at last jmp */
        long            offset;         /* offset of prev block */
        short           ijmp;           /* current jmp index */
        struct jmp      jp;             /* list of jmps */
};
struct path {
        int     spc;            /* number of leading spaces */
        short   n[JMPS];        /* size of jmp (gap) */
        int     x[JMPS];/* loc of jmp (last elem before gap) */
};
char            *ofile;                 /* output file name */
char            *namex[2];              /* seq names: getseqs( ) */
char            *prog;                  /* prog name for err msgs */
char            *seqx[2];               /* seqs: getseqs( ) */
int             dmax;                   /* best diag: nw( ) */
int             dmax0;                  /* final diag */
int             dna;                    /* set if dna: main( ) */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw( ) */
int             *xbm;                   /* bitmap for matching */
long            offset;                 /* current offset in jmp file */
struct  diag    *dx;                    /* holds diagonals */
struct  path    pp[2];                  /* holds path for seqs */
char            *calloc( ), *malloc( ), *index( ), *strcpy( );
char            *getseq( ), *g_calloc( );
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"
static   _dbval[26] = {
        1,14,2,13,0,0,4,11,0,0,12,0,3,15,0,0,0,5,6,8,8,7,9,0,10,0
};
```

TABLE 1-continued

```
static      _pbval[26] = {
            1, 2|(1<<('D'-'A'))|(1<<('N'-'A')), 4, 8, 16, 32, 64,
            128, 256, 0xFFFFFFF, 1<<10, 1<<11, 1<<12, 1<<13, 1<<14,
            1<<15, 1<<16, 1<<17, 1<<18, 1<<19, 1<<20, 1<<21, 1<<22,
            1<<23, 1<<24, 1<<25|(1<<('E'-'A'))|(1<<('Q'-'A'))
};
main(ac, av)                                                                    main
            int         ac;
            char        *av[ ];
{
            prog = av[0];
            if (ac != 3) {
                        fprintf(stderr,"usage: %s file1 file2\n", prog);
                        fprintf(stderr,"where file1 and file2 are two dna or two protein sequences.\n");
                        fprintf(stderr,"The sequences can be in upper- or lower-case\n");
                        fprintf(stderr,"Any lines beginning with ';' or '<' are ignored\n");
                        fprintf(stderr,"Output is in the file \"align.out\"\n");
                        exit(1);
            }
            namex[0] = av[1];
            namex[1] = av[2];
            seqx[0] = getseq(namex[0], &len0);
            seqx[1] = getseq(namex[1], &len1);
            xbm = (dna)? _dbval : _pbval;
            endgaps = 0;                        /* 1 to penalize endgaps */
            ofile = "align.out";                /* output file */
            nw( );              /* fill in the matrix, get the possible jmps */
            readjmps( );        /* get the actual jmps */
            print( );           /* print stats, alignment */
            cleanup(0);         /* unlink any tmp files */}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                           nw
{
            char                *px, *py;           /* seqs and ptrs */
            int                 *ndely, *dely;      /* keep track of dely */
            int                 ndelx, delx;        /* keep track of delx */
            int                 *tmp;               /* for swapping row0, row1 */
            int                 mis;                /* score for each type */
            int                 ins0, ins1;         /* insertion penalties */
            register            id;                 /* diagonal index */
            register            ij;                 /* jmp index */
            register            *col0, *col1;       /* score for curr, last row */
            register            xx, yy;             /* index into seqs */
            dx = (struct diag *)g_calloc("to get diags", len0+len1+1, sizeof(struct diag));
            ndely = (int *)g_calloc("to get ndely", len1+1, sizeof(int));
            dely = (int *)g_calloc("to get dely", len1+1, sizeof(int));
            col0 = (int *)g_calloc("to get col0", len1+1, sizeof(int));
            col1 = (int *)g_calloc("to get col1", len1+1, sizeof(int));
            ins0 = (dna)? DINS0 : PINS0;
            ins1 = (dna)? DINS1 : PINS1;
            smax = -10000;
            if (endgaps) {
                        for (col0[0] = dely[0] = -ins0, yy = 1; yy <= len1; yy++) {
                                    col0[yy] = dely[yy] = col0[yy-1] - ins1;
                                    ndely[yy] = yy;
                        }
                        col0[0] = 0;            /* Waterman Bull Math Biol 84 */
            }
            else
                        for (yy = 1; yy <= len1; yy++)
                                    dely[yy] = -ins0;
            /* fill in match matrix
             */
            for (px = seqx[0], xx = 1; xx <= len0; px++, xx++) {
                        /* initialize first entry in col
                         */
                        if (endgaps) {
                                    if (xx == 1)
                                                col1[0] = delx = -(ins0+ins1);
                                    else
                                                col1[0] = delx = col0[0] - ins1;
                                    ndelx = xx;
                        }
                        else {
```

TABLE 1-continued

```
                col1[0] = 0;
                delx = -ins0;
                ndelx = 0;
        }
                                                                                        ...nw
        for (py = seqx[1], yy = 1; yy <= len1; py++, yy++) {
                mis = col0[yy-1];
                if (dna)
                        mis += (xbm[*px-'A']&xbm[*py-'A'])? DMAT : DMIS;
                else
                        mis += _day[*px-'A'][*py-'A'];
                /* update penalty for del in x seq;
                 * favor new del over ongong del
                 * ignore MAXGAP if weighting endgaps
                 */
                if (endgaps || ndely[yy] < MAXGAP) {
                        if (col0[yy] - ins0 >= dely[yy]) {
                                dely[yy] = col0[yy] - (ins0+ins1);
                                ndely[yy] = 1;
                        } else {
                                dely[yy] -= ins1;
                                ndely[yy]++;
                        }
                } else {
                        if (col0[yy] - (ins0+ins1) >= dely[yy]) {
                                dely[yy] = col0[yy] - (ins0+ins1);
                                ndely[yy] = 1;
                        } else
                                ndely[yy]++;
                }
                /* update penalty for del in y seq;
                 * favor new del over ongong del
                 */
                if (endgaps || ndelx < MAXGAP) {
                        if (col1[yy-1] - ins0 >= delx) {
                                delx = col1[yy-1] - (ins0+ins1);
                                ndelx = 1;
                        } else {
                                delx -= ins1;
                                ndelx++;
                        }
                } else {
                        if (col1[yy-1] - (ins0+ins1) >= delx) {
                                delx = col1[yy-1] - (ins0+ins1);
                                ndelx = 1;
                        } else
                                ndelx++;
                }
                /* pick the maximum score; we're favoring
                 * mis over any del and delx over dely
                 */
                                                                                        ...nw
                id = xx - yy + len1 - 1;
                if (mis >= delx && mis >= dely[yy])
                        col1[yy] = mis;
                else if (delx >= dely[yy]) {
                        col1[yy] = delx;
                        ij = dx[id].ijmp;
                        if (dx[id].jp.n[0] && (!dna || (ndelx >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
                                        ij = dx[id].ijmp = 0;
                                        dx[id].offset = offset;
                                        offset += sizeof(struct jmp) + sizeof(offset);
                                }
                        }
                        dx[id].jp.n[ij] = ndelx;
                        dx[id].jp.x[ij] = xx;
                        dx[id].score = delx;
                }
                else {
                        col1[yy] = dely[yy];
                        ij = dx[id].ijmp;
    if (dx[id].jp.n[0] && (!dna || (ndely[yy] >= MAXJMP
                        && xx > dx[id].jp.x[ij]+MX) || mis > dx[id].score+DINS0)) {
                                dx[id].ijmp++;
                                if (++ij >= MAXJMP) {
                                        writejmps(id);
```

TABLE 1-continued

```
                        ij = dx[id].ijmp = 0;
                        dx[id].offset = offset;
                        offset += sizeof(struct jmp) + sizeof(offset);
                    }
                }
                dx[id].jp.n[ij] = −ndely[yy];
                dx[id].jp.x[ij] = xx;
                dx[id].score = dely[yy];
            }
            if (xx == len0 && yy < len1) {
                /* last col
                 */
                if (endgaps)
                    col1[yy] −= ins0+ins1*(len1−yy);
                if (col1[yy] > smax) {
                    smax = col1[yy];
                    dmax = id;
                }
            }
        }
        if (endgaps && xx < len0)
            col1[yy−1] −= ins0+ins1*(len0−xx);
        if (col1[yy−1] > smax) {
            smax = col1[yy−1];
            dmax = id;
        }
        tmp = col0; col0 = col1; col1 = tmp;        }
    (void) free((char *)ndely);
    (void) free((char *)dely);
    (void) free((char *)col0);
    (void) free((char *)col1);                }
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
#define SPC         3
#define P_LINE      256     /* maximum output line */
#define P_SPC       3       /* space between name or num and seq */
extern      _day[26][26];
int         olen;           /* set output line length */
FILE        *fx;            /* output file */
print( )                                                              print
{
    int     lx, ly, firstgap, lastgap;      /* overlap */
    if ((fx = fopen(ofile, "w")) == 0) {
        fprintf(stderr,"%s: can't write %s\n", prog, ofile);
        cleanup(1);
    }
    fprintf(fx, "<first sequence: %s (length = %d)\n", namex[0], len0);
    fprintf(fx, "<second sequence: %s (length = %d)\n", namex[1], len1);
    olen = 60;
    lx = len0;
    ly = len1;
    firstgap = lastgap = 0;
    if (dmax < len1 − 1) {      /* leading gap in x */
        pp[0].spc = firstgap = len1 − dmax − 1;
        ly −= pp[0].spc;
    }
    else if (dmax > len1 − 1) {     /* leading gap in y */
        pp[1].spc = firstgap = dmax − (len1 − 1);
        lx −= pp[1].spc;
    }
    if (dmax0 < len0 − 1) {     /* trailing gap in x */
        lastgap = len0 − dmax0 −1;
        lx −= lastgap;
    }
    else if (dmax0 > len0 − 1) {    /* trailing gap in y */
        lastgap = dmax0 − (len0 − 1);
        ly −= lastgap;
    }
```

TABLE 1-continued

```
        getmat(lx, ly, firstgap, lastgap);
        pr_align( );          }
/*
 * trace back the best path, count matches
 */
static
getmat(lx, ly, firstgap, lastgap)                                                    getmat
        int     lx, ly;                   /* "core" (minus endgaps) */
        int     firstgap, lastgap;        /* leading trailing overlap */
{
        int             nm, i0, i1, siz0, siz1;
        char            outx[32];
        double          pct;
        register        n0, n1;
        register char   *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);                            ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
```

TABLE 1-continued

```
                    lastgap, (dna)? "base" : "residue", (lastgap == 1)? "" : "s");
          else
                    fprintf(fx, "<endgaps not penalized\n");
}
static              nm;                 /* matches in core -- for checking */
static              lmax;               /* lengths of stripped file names */
static              ij[2];              /* jmp index for a path */
static              nc[2];              /* number at start of current line */
static              ni[2];              /* current elem number -- for gapping */
static              siz[2];
static char         *ps[2];             /* ptr to current element */
static char         *po[2];             /* ptr to next output char slot */
static char         out[2][P_LINE];     /* output line */
static char         star[P_LINE];       /* set by stars( ) */
/*
 * print alignment of described in struct path pp[ ]
 */
static
pr_align( )                                                                    pr_align
{
          int                 nn;       /* char count */
          int                 more;
          register            i;
          for (i = 0, lmax = 0; i < 2; i++) {
                    nn = stripname(namex[i]);
                    if (nn > lmax)
                              lmax = nn;
                    nc[i] = 1;
                    ni[i] = 1;
                    siz[i] = ij[i] = 0;
                    ps[i] = seqx[i];
                    po[i] = out[i];                   }
          for (nn = nm = 0, more = 1; more; ) {                             ...pr_align
                    for (i = more = 0; i < 2; i++) {
                              /*
                               * do we have more of this sequence?
                               */
                              if (!*ps[i])
                                        continue;
                              more++;
                              if (pp[i].spc) {    /* leading space */
                                        *po[i]++ = ' ';
                                        pp[i].spc--;
                              }
                              else if (siz[i]) {  /* in a gap */
                                        *po[i]++ = '-';
                                        siz[i]--;
                              }
                              else {              /* we're putting a seq element
                                                   */
                                        *po[i] = *ps[i];
                                        if (islower(*ps[i]))
                                                  *ps[i] = toupper(*ps[i]);
                                        po[i]++;
                                        ps[i]++;
                                        /*
                                         * are we at next gap for this seq?
                                         */
                                        if (ni[i] == pp[i].x[ij[i]]) {
                                                  /*
                                                   * we need to merge all gaps
                                                   * at this location
                                                   */
                                                  siz[i] = pp[i].n[ij[i]++];
                                                  while (ni[i] == pp[i].x[ij[i]])
                                                            siz[i] += pp[i].n[ij[i]++];
                                        }
                                        ni[i]++;
                              }
                    }
                    if (++nn == olen || !more && nn) {
                              dumpblock( );
                              for (i = 0; i < 2; i++)
                                        po[i] = out[i];
                              nn = 0;
                    }
          }
}
/*
 * dump a block of lines, including numbers, stars: pr_align( )
```

TABLE 1-continued

```
 */
static
dumpblock( )                                                    dumpblock
{
        register i;
        for (i = 0; i < 2; i++)
                *po[i]−− = '\0';
                                                                ...dumpblock
        (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars( );
                        putline(i);
                        if (i == 0 && *out[1])
                                fprintf(fx, star);
                        if (i == 1)
                                nums(i);
                }
        }
}
/*
 * put out a number line: dumpblock( )
 */
static
nums(ix)                                                        nums
        int     ix;     /* index in out[ ] holding seq line */
{
        char            nline[P_LINE];
        register        i, j;
        register char   *pn, *px, *py;
        for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? −i : i;
                                for (px = pn; j; j /= 10, px−−)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock( )
 */
static
putline(ix)                                                     putline
        int     ix;                     {
                                                                ...putline
        int             i;
        register char   *px;
        for (px = namex[ix], i = 0; *px && *px != ':'; px++, i++)
                (void) putc(*px, fx);
        for (; i < lmax+P_SPC; i++)
                (void) putc(' ', fx);
        /* these count from 1:
         * ni[ ] is current element (from 1)
         * nc[ ] is number at start of current line
         */
        for (px = out[ix]; *px; px++)
                (void) putc(*px&0x7F, fx);
        (void) putc('\n', fx);
}
/*
 * put a line of stars (seqs always in out[0], out[1]): dumpblock( )
```

TABLE 1-continued

```
 */
static
stars( )                                                                stars
{
        int                 i;
        register char       *p0, *p1, cx, *px;
        if (!*out[0] || (*out[0] == ‘ ’ && *(po[0]) == ‘ ’) ||
            !*out[1] || (*out[1] == ‘ ’ && *(po[1]) == ‘ ’))
                return;
        px = star;
        for (i = lmax+P_SPC; i; i−−)
                *px++ = ‘ ’;
        for (p0 = out[0], p1 = out[1]; *p0 && *p1; p0++, p1++) {
                if (isalpha(*p0) && isalpha(*p1)) {
                        if (xbm[*p0−‘A’]&xbm[*p1−‘A’]) {
                                cx = ‘*’;
                                nm++;
                        }
                        else if (!dna && _day[*p0−‘A’][*p1−‘A’] > 0)
                                cx = ‘.’;
                        else
                                cx = ‘ ’;
                }
                else
                        cx = ‘ ’;
                *px++ = cx;
        }
        *px++ = ‘\n’;
        *px = ‘\0’;
}
/*
 * strip path or prefix from pn, return len: pr_align( )
 */
static
stripname(pn)                                                           stripname
        char    *pn;    /* file name (may be path) */
{
        register char       *px, *py;
        py = 0;
        for (px = pn; *px; px++)
                if (*px == ‘/’)
                        py = px + 1;
        if (py)
                (void) strcpy(pn, py);
        return(strlen(pn));
}
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include “nw.h”
#include <sys/file.h>
char    *jname = “/tmp/homgXXXXXX”;             /* tmp file for jmps */
FILE    *fj;
int     cleanup( );                             /* cleanup tmp file */
long    lseek( );
/*
 * remove any tmp file if we blow
 */
cleanup(i)                                                              cleanup
        int     i;
{
        if (fj)
                (void) unlink(jname);
        exit(i);
}
/*
 * read, return ptr to seq, set dna, len, maxlen
 * skip lines starting with ‘;’, ‘<’, or ‘>’
 * seq in upper or lower case
 */
char    *
getseq(file, len)                                                       getseq
        char    *file;  /* file name */
        int     *len;   /* seq len */
{
        char                line[1024], *pseq;
```

TABLE 1-continued

```
        register char   *px, *py;
        int             natgc, tlen;
        FILE            *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
                                                                                ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                                           g_calloc
        char    *msg;           /* program, calling routine */
        int     nx, sz;         /* number and size of elements */
{
        char            *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg, nx, sz);
                        exit(1);
                }
        }
        return(px);
}
/*
 * get final jmps from dx[ ] or tmp file, set pp[ ], reset dmax: main( )
 */
readjmps( )                                                                     readjmps
{
        int             fd = -1;
        int             siz, i0, i1;
        register        i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
                                                                                ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
```

TABLE 1-continued

```
                                        dx[dmax].ijmp = MAXJMP−1;                       }
                              else
                                        break;          }
                    if (i >= JMPS) {
                              fprintf(stderr, "%s: too many gaps in alignment\n", prog);
                              cleanup(1);
                    }
                    if (j >= 0) {
                              siz = dx[dmax].jp.n[j];
                              xx = dx[dmax].jp.x[j];
                              dmax += siz;
                              if (siz < 0) {              /* gap in second seq */
                                        pp[1].n[i1] = −siz;
                                        xx += siz;
                                        /* id = xx − yy + len1 − 1                       */
                                        pp[1].x[i1] = xx − dmax + len1 − 1;
                                        gapy++;
                                        ngapy −= siz;
/* ignore MAXGAP when doing endgaps */
                                        siz = (−siz < MAXGAP || endgaps)? −siz : MAXGAP;
                                        i1++;
                              }
                              else if (siz > 0) { /* gap in first seq */
                                        pp[0].n[i0] = siz;
                                        pp[0].x[i0] = xx;
                                        gapx++;
                                        ngapx += siz;
/* ignore MAXGAP when doing endgaps */
                                        siz = (siz < MAXGAP || endgaps)? siz : MAXGAP;
                                        i0++;
                              }
                    }
                    else
                              break;
          }
          /* reverse the order of jmps           */
          for (j = 0, i0−−; j < i0; j++, i0−−) {
                    i = pp[0].n[j]; pp[0].n[j] = pp[0].n[i0]; pp[0].n[i0] = i;
                    i = pp[0].x[j]; pp[0].x[j] = pp[0].x[i0]; pp[0].x[i0] = i;
          }
          for (j = 0, i1−−; j < i1; j++, i1−−) {
                    i = pp[1].n[j]; pp[1].n[j] = pp[1].n[i1]; pp[1].n[i1] = i;
                    i = pp[1].x[j]; pp[1].x[j] = pp[1].x[i1]; pp[1].x[i1] = i;
          }
          if (fd >= 0)
                    (void) close(fd);
          if (fj) {
                    (void) unlink(jname);
                    fj = 0;
                    offset = 0;
          }                             }
/*
 * write a filled jmp struct offset of the prev one (if any): nw( )
 */
writejmps(ix)                                                                        writejmps
          int       ix;
{
          char      *mktemp( );
          if (!fj) {
                    if (mktemp(jname) < 0) {
                              fprintf(stderr, "%s: can't mktemp( ) %s\n", prog, jname);
                              cleanup(1);
                    }
                    if ((fj = fopen(jname, "w")) == 0) {
                              fprintf(stderr, "%s: can't write %s\n", prog, jname);
                              exit(1);
                    }
          }
          (void) fwrite((char *)&dx[ix].jp, sizeof(struct jmp), 1, fj);
          (void) fwrite((char *)&dx[ix].offset, sizeof(dx[ix].offset), 1, fj);
}
```

TABLE 2

| | | |
|---|---|---|
| TAT | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the TAT polypeptide) = 5 divided by 15 = 33.3%

TABLE 3

| | | |
|---|---|---|
| TAT | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the TAT polypeptide) = 5 divided by 10 = 50%

TABLE 4

| | | |
|---|---|---|
| TAT-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the TAT-DNA nucleic acid sequence) = 6 divided by 14 = 42.9%

TABLE 5

| | | |
|---|---|---|
| TAT-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the TAT-DNA nucleic acid sequence) = 4 divided by 12 = 33.3%

II. Compositions and Methods of the Invention

A. Anti-TAT Antibodies

In one embodiment, the present invention provides anti-TAT antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with 1/5 to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.,* 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130: 151-188 (1992).

In a further embodiment, monoclonal antibodies or antibody fragments can be isolated from antibody phage libraries generated using the techniques described in McCafferty et al., *Nature,* 348:552-554 (1990). Clackson et al., *Nature,* 352: 624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-TAT antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA,* 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

In general, the hypervariable region residues are directly and most substantially involved in influencing antigen binding.

Various forms of a humanized anti-TAT antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a TAT protein as described herein. Other such antibodies may combine a TAT binding site with a binding site for another protein. Alternatively, an anti-TAT arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the TAT-expressing cell. Bispecific antibodies may also be used to localize cytotoxic agents to cells which express TAT. These antibodies possess a TAT-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

In one preferred embodiment, an anti-TAT antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-21neu oncogene. The cytotoxicity of the TA.1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-TAT Polypeptide Antibody-Maytansinoid Conjugates (Immunoconjugates)

Anti-TAT antibody-maytansinoid conjugates are prepared by chemically linking an anti-TAT antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-TAT antibody conjugated to one or more calicheamicin molecules. The calicheamicin family of antibiotics are capable of producing double -stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-TAT antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-TAT antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide -containing linker (Chari et al., *Cancer Research* 52:127-131 (1992); U.S. Pat. No. 5,208,020) may be used.

Alternatively, a fusion protein comprising the anti-TAT antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-TAT antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

B. TAT Binding Oligopeptides

TAT binding oligopeptides of the present invention are oligopeptides that bind, preferably specifically, to a TAT polypeptide as described herein. TAT binding oligopeptides may be chemically synthesized using known oligopeptide synthesis methodology or may be prepared and purified using recombinant technology. TAT binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a TAT polypeptide as described herein. TAT binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708, 871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA, 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren, Z-J. et al. (1998) Gene 215:439; Zhu, Z. (1997) CAN 33:534; Jiang, J. et al. (1997) can 128:44380; Ren, Z-J. et al. (1997) CAN 127:215644; Ren, Z-J. (1996) Protein Sci. 5:1833; Efimov, V. P. et al. (1995) Virus Genes 10:173) and T7 phage display systems (Smith, G. P. and Scott, J. K. (1993) Methods in Enzymology, 217, 228_257; U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphylococcus aureus* protein A as an affinity tag has also been reported (Li et al. (1998) Mol. Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432,018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

C. TAT Binding Organic Molecules

TAT binding organic molecules are organic molecules other than oligopeptides or antibodies as defined herein that bind, preferably specifically, to a TAT polypeptide as described herein. TAT binding organic molecules may be identified and chemically synthesized using known methodology (see, e.g., PCT Publication Nos. WO00/00823 and WO00/39585). TAT binding organic molecules are usually less than about 2000 daltons in size, alternatively less than about 1500, 750, 500, 250 or 200 daltons in size, wherein such organic molecules that are capable of binding, preferably specifically, to a TAT polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). TAT binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

D. Screening for Anti-TAT Antibodies, TAT Binding Oligopeptides and TAT Binding Organic Molecules with the Desired Properties Techniques for generating antibodies, oligopeptides and organic molecules that bind to TAT polypeptides have been described above. One may further select antibodies, oligopeptides or other organic molecules with certain biological characteristics, as desired.

The growth inhibitory effects of an anti-TAT antibody, oligopeptide or other organic molecule of the invention may be assessed by methods known in the art, e.g., using cells which express a TAT polypeptide either endogenously or following transfection with the TAT gene. For example, appropriate tumor cell lines and TAT-transfected cells may treated with an anti-TAT monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^{3}H$-thymidine uptake by the cells treated in the presence or absence an anti-TAT antibody, TAT binding oligopeptide or TAT binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses a TAT polypeptide. Preferably, the anti-TAT antibody, TAT binding oligopeptide or TAT binding organic molecule will inhibit cell proliferation of a TAT-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 μg/ml. Growth inhibition can be measured at an antibody concentration of about 0.5 to 30 μg/ml or about 0.5 nM to 200 nM in cell culture, where the growth inhibition is determined 1-10 days after exposure of the tumor cells to the antibody. The antibody is growth inhibitory in vivo if administration of the anti-TAT antibody at about 1 μg/kg to about 100 mg/kg body weight results in reduction in tumor size or reduction of tumor cell proliferation within about 5 days to 3 months from the first administration of the antibody, preferably within about 5 to 30 days.

To select for an anti-TAT antibody, TAT binding oligopeptide or TAT binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. TAT polypeptide-expressing tumor cells are incubated with medium alone or medium containing the appropriate anti-TAT antibody (e.g, at about 10 μg/ml), TAT binding oligopeptide or TAT binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those anti-TAT antibodies, TAT binding oligopeptides or TAT binding organic molecules that induce statistically significant levels of cell death as determined by PI uptake may be selected as cell death-inducing anti-TAT antibodies, TAT binding oligopeptides or TAT binding organic molecules.

To screen for antibodies, oligopeptides or other organic molecules which bind to an epitope on a TAT polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-TAT antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of a TAT polypeptide can be used in competition assays with the test antibodies or with a test antibody and an antibody with a characterized or known epitope.

E. Antibody Dependent Enzyme Mediated Prodrug Therapy (ADEPT)

The antibodies of the present invention may also be used in ADEPT by conjugating the antibody to a prodrug-activating enzyme which converts a prodrug (e.g., a peptidyl chemotherapeutic agent, see WO81/01145) to an active anti-cancer drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 (1987)). Antibody-abzyme conjugates can be prepared as described herein for delivery of the abzyme to a tumor cell population.

The enzymes of this invention can be covalently bound to the anti-TAT antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature* 312:604-608 (1984).

F. Full-Length TAT Polypeptides

The present invention also provides newly identified and isolated nucleotide sequences encoding polypeptides referred to in the present application as TAT polypeptides. In particular, cDNAs (partial and full-length) encoding various TAT polypeptides have been identified and isolated, as disclosed in further detail in the Examples below.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the TAT polypeptides and encoding nucleic acids described herein, in some cases, Applicants have identified what is believed to be the reading frame best identifiable with the sequence information available at the time.

G. Anti-TAT Antibody and TAT Polypeptide Variants

In addition to the anti-TAT antibodies and full-length native sequence TAT polypeptides described herein, it is contemplated that anti-TAT antibody and TAT polypeptide variants can be prepared. Anti-TAT antibody and TAT polypeptide variants can be prepared by introducing appropriate nucleotide changes into the encoding DNA, and/or by synthesis of the desired antibody or polypeptide. Those skilled in the art will appreciate that amino acid changes may alter post-translational processes of the anti-TAT antibody or TAT polypeptide, such as changing the number or position of glycosylation sites or altering the membrane anchoring characteristics.

Variations in the anti-TAT antibodies and TAT polypeptides described herein, can be made, for example, using any of the techniques and guidelines for conservative and non-conservative mutations set forth, for instance, in U.S. Pat. No. 5,364,934. Variations may be a substitution, deletion or insertion of one or more codons encoding the antibody or polypeptide that results in a change in the amino acid sequence as compared with the native sequence antibody or polypeptide. Optionally the variation is by substitution of at least one amino acid with any other amino acid in one or more of the domains of the anti-TAT antibody or TAT polypeptide. Guidance in determining which amino acid residue may be inserted, substituted or deleted without adversely affecting the desired activity may be found by comparing the sequence of the anti-TAT antibody or TAT polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Anti-TAT antibody and TAT polypeptide fragments are provided herein. Such fragments may be truncated at the N-terminus or C-terminus, or may lack internal residues, for example, when compared with a full length native antibody or protein. Certain fragments lack amino acid residues that are not essential for a desired biological activity of the anti-TAT antibody or TAT polypeptide.

Anti-TAT antibody and TAT polypeptide fragments may be prepared by any of a number of conventional techniques. Desired peptide fragments may be chemically synthesized. An alternative approach involves generating antibody or polypeptide fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired antibody or polypeptide fragment, by polymerase chain reaction (PCR). Oligonucleotides that define the desired termini of the DNA fragment are employed at the 5' and 3' primers in the PCR. Preferably, anti-TAT antibody and TAT polypeptide fragments share at least one biological and/or immunological activity with the native anti-TAT antibody or TAT polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the anti-TAT antibody or TAT polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the anti-TAT antibody or TAT polypeptide variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244:1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

Any cysteine residue not involved in maintaining the proper conformation of the anti-TAT antibody or TAT polypeptide also may be substituted, generally with serine, to improve the oxidative stability of the molecule and prevent aberrant crosslinking. Conversely, cysteine bond(s) may be added to the anti-TAT antibody or TAT polypeptide to improve its stability (particularly where the antibody is an antibody fragment such as an Fv fragment).

A particularly preferred type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage -displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human TAT polypeptide. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the anti-TAT antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-TAT antibody.

H. Modifications of Anti-TAT Antibodies and TAT Polypeptides

Covalent modifications of anti-TAT antibodies and TAT polypeptides are included within the scope of this invention. One type of covalent modification includes reacting targeted amino acid residues of an anti-TAT antibody or TAT polypeptide with an organic derivatizing agent that is capable of reacting with selected side chains or the N- or C-terminal residues of the anti-TAT antibody or TAT polypeptide.

Derivatization with bifunctional agents is useful, for instance, for crosslinking anti-TAT antibody or TAT polypeptide to a water-insoluble support matrix or surface for use in the method for purifying anti-TAT antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the amino groups of lysine, arginine, and histidine side chains [T. E. Creighton, *Proteins: Structure and Molecular Properties*, W.H. Freeman & Co., San Francisco, pp. 79-86 (1983)], acetylation of the N -terminal amine, and amidation of any C-terminal carboxyl group.

Another type of covalent modification of the anti-TAT antibody or TAT polypeptide included within the scope of this invention comprises altering the native glycosylation pattern of the antibody or polypeptide. "Altering the native glycosylation pattern" is intended for purposes herein to mean deleting one or more carbohydrate moieties found in native sequence anti-TAT antibody or TAT polypeptide (either by removing the underlying glycosylation site or by deleting the glycosylation by chemical and/or enzymatic means), and/or adding one or more glycosylation sites that are not present in the native sequence anti-TAT antibody or TAT polypeptide. In addition, the phrase includes qualitative changes in the glycosylation of the native proteins, involving a change in the nature and proportions of the various carbohydrate moieties present.

Glycosylation of antibodies and other polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the anti-TAT antibody or TAT polypeptide is conveniently accomplished by altering the amino acid sequence such that it contains one or more of the above -described tripeptide sequences (for N-linked glycosylation sites). The alteration may also be made by the addition of, or substitution by, one or more serine or threonine residues to the sequence of the original anti-TAT antibody or TAT polypeptide (for O-linked glycosylation sites). The anti-TAT antibody or TAT polypeptide amino acid sequence may optionally be altered through changes at the DNA level, particularly by mutating the DNA encoding the anti-TAT antibody or TAT polypeptide at preselected bases such that codons are generated that will translate into the desired amino acids.

Another means of increasing the number of carbohydrate moieties on the anti-TAT antibody or TAT polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the anti-TAT antibody or TAT polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of anti-TAT antibody or TAT polypeptide comprises linking the antibody or polypeptide to one of a variety of nonproteinaceous polymers, e.g., polyethylene glycol (PEG), polypropylene glycol, or polyoxyalkylenes, in the manner set forth in U.S. Pat. No. 4,640,835; 4,496,689; 4,301,144; 4,670,417; 4,791,192 or 4,179,337. The antibody or polypeptide also may be entrapped in microcapsules prepared, for example, by coacervation techniques or by interfacial polymerization (for example, hydroxymethylcellulose or gelatin-microcapsules and poly -(methylmethacylate) microcapsules, respectively), in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The anti-TAT antibody or TAT polypeptide of the present invention may also be modified in a way to form chimeric molecules comprising an anti-TAT antibody or TAT polypeptide fused to another, heterologous polypeptide or amino acid sequence.

In one embodiment, such a chimeric molecule comprises a fusion of the anti-TAT antibody or TAT polypeptide with a tag polypeptide which provides an epitope to which an anti-tag antibody can selectively bind. The epitope tag is generally placed at the amino- or carboxyl-terminus of the anti-TAT antibody or TAT polypeptide. The presence of such epitope-tagged forms of the anti-TAT antibody or TAT polypeptide can be detected using an antibody against the tag polypeptide. Also, provision of the epitope tag enables the anti-TAT antibody or TAT polypeptide to be readily purified by affinity purification using an anti-tag antibody or another type of affinity matrix that binds to the epitope tag. Various tag polypeptides and their respective antibodies are well known in the art. Examples include poly -histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag -peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

In an alternative embodiment, the chimeric molecule may comprise a fusion of the anti-TAT antibody or TAT polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an anti-TAT antibody or TAT polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule. For the production of immunoglobulin fusions see also U.S. Pat. No. 5,428,130 issued Jun. 27, 1995.

I. Preparation of Anti-TAT Antibodies and TAT Polypeptides

The description below relates primarily to production of anti-TAT antibodies and TAT polypeptides by culturing cells transformed or transfected with a vector containing anti-TAT antibody- and TAT polypeptide-encoding nucleic acid. It is, of course, contemplated that alternative methods, which are well known in the art, may be employed to prepare anti-TAT antibodies and TAT polypeptides. For instance, the appropriate amino acid sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the anti-TAT antibody or TAT polypeptide may be chemically synthesized separately and combined using chemical or enzymatic methods to produce the desired anti-TAT antibody or TAT polypeptide.

1. Isolation of DNA Encoding Anti-TAT Antibody or TAT Polypeptide

DNA encoding anti-TAT antibody or TAT polypeptide may be obtained from a cDNA library prepared from tissue believed to possess the anti-TAT antibody or TAT polypeptide mRNA and to express it at a detectable level. Accordingly, human anti-TAT antibody or TAT polypeptide DNA can be conveniently obtained from a cDNA library prepared from human tissue. The anti-TAT antibody- or TAT polypeptide-encoding gene may also be obtained from a genomic library or by known synthetic procedures (e.g., automated nucleic acid synthesis).

Libraries can be screened with probes (such as oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding anti-TAT antibody or TAT polypeptide is to use PCR methodology [Sambrook et al., supra; Dieffenbach et al., *PCR Primer: A Laboratory Manual* (Cold Spring Harbor Laboratory Press, 1995)].

Techniques for screening a cDNA library are well known in the art. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}P$-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for anti-TAT antibody or TAT polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* $K_{12}$ strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella*

*typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac) 169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

Full length antibody, antibody fragments, and antibody fusion proteins can be produced in bacteria, in particular when glycosylation and Fc effector function are not needed, such as when the therapeutic antibody is conjugated to a cytotoxic agent (e.g., a toxin) and the immunoconjugate by itself shows effectiveness in tumor cell destruction. Full length antibodies have greater half life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation regio (TIR) and signal sequences for optimizing expression and secretion, these patents incorporated herein by reference. After expression, the antibody is isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for anti-TAT antibody- or TAT polypeptide-encoding vectors. *Saccharomyces cerevisiae* is a commonly used lower eukaryotic host microorganism. Others include *Schizosaccharomyces pombe* (Beach and Nurse, *Nature,* 290:140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2): 737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans*, and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs,* 269 (1982).

Suitable host cells for the expression of glycosylated anti-TAT antibody or TAT polypeptide are derived from multicellular organisms. Examples of invertebrate cells include insect cells such as *Drosophila* S2 and *Spodoptera* Sf9, as well as plant cells, such as cell cultures of cotton, corn, potato, soybean, petunia, tomato, and tobacco. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L -1 variant of *Autographa californica* NPV and the Bm-5 strain of *Bombyx mori* NPV, and such viruses may be used as the virus herein according to the present invention, particularly for transfection of *Spodoptera frugiperda* cells.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/−DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for anti-TAT antibody or TAT polypeptide production and cultured in conventional nutrient media modified as appropriate for inducing promoters, selecting transformants, or amplifying the genes encoding the desired sequences.

3. Selection and Use of a Replicable Vector

The nucleic acid (e.g., cDNA or genomic DNA) encoding anti-TAT antibody or TAT polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The TAT may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the anti-TAT antibody- or TAT polypeptide-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the anti-TAT antibody- or TAT polypeptide-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the anti-TAT antibody- or TAT polypeptide-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding anti-TAT antibody or TAT polypeptide.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

Anti-TAT antibody or TAT polypeptide transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the anti-TAT antibody or TAT polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the anti-TAT antibody or TAT polypeptide coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-TAT antibody or TAT polypeptide.

Still other methods, vectors, and host cells suitable for adaptation to the synthesis of anti-TAT antibody or TAT polypeptide in recombinant vertebrate cell culture are described in Gething et al., *Nature,* 293:620-625 (1981); Mantei et al., *Nature,* 281:40-46 (1979); EP 117,060; and EP 117,058.

4. Culturing the Host Cells

The host cells used to produce the anti-TAT antibody or TAT polypeptide of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102: 255 (1980), U.S. Pat. No. 4,767,704; 4,657,866; 4,927,762; 4,560,655; or 5,122,469; WO 90/03430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

5. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TAT polypeptide or against a synthetic peptide based on the DNA sequences provided herein or against exogenous sequence fused to TAT DNA and encoding a specific antibody epitope.

6. Purification of Anti-TAT Antibody and TAT Polypeptide

Forms of anti-TAT antibody and TAT polypeptide may be recovered from culture medium or from host cell lysates. If membrane-bound, it can be released from the membrane using a suitable detergent solution (e.g. Triton-X 100) or by enzymatic cleavage. Cells employed in expression of anti-TAT antibody and TAT polypeptide can be disrupted by various physical or chemical means, such as freeze-thaw cycling, sonication, mechanical disruption, or cell lysing agents.

It may be desired to purify anti-TAT antibody and TAT polypeptide from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the anti-TAT antibody and TAT polypeptide. Various methods of protein purification may be employed and such methods are known in the art and described for example in Deutscher, *Methods in Enzymology,* 182 (1990); Scopes, *Protein Purification: Principles and Practice*, Springer -Verlag, New York (1982). The purification step(s) selected will depend, for example, on the nature of the production process used and the particular anti-TAT antibody or TAT polypeptide produced.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli.* Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on humanyl, γ1, γ2 or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

J. Pharmaceutical Formulations

Therapeutic formulations of the anti-TAT antibodies, TAT binding oligopeptides, TAT binding organic molecules and/or TAT polypeptides used in accordance with the present invention are prepared for storage by mixing the antibody, polypeptide, oligopeptide or organic molecule having the desired degree of purity with optional pharmaceutically acceptable carriers, excipients or stabilizers (*Remington's Pharmaceu-*

*tical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as acetate, Tris, phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt -forming counter-ions such as sodium; metal complexes (e.g., Zn-protein complexes); and/or non-ionic surfactants such as TWEEN®, PLURONICS® or polyethylene glycol (PEG). The antibody preferably comprises the antibody at a concentration of between 5-200 mg/ml, preferably between 10-100 mg/ml.

The formulations herein may also contain more than one active compound as necessary for the particular indication being treated, preferably those with complementary activities that do not adversely affect each other. For example, in addition to an anti-TAT antibody, TAT binding oligopeptide, or TAT binding organic molecule, it may be desirable to include in the one formulation, an additional antibody, e.g., a second anti-TAT antibody which binds a different epitope on the TAT polypeptide, or an antibody to some other target such as a growth factor that affects the growth of the particular cancer. Alternatively, or additionally, the composition may further comprise a chemotherapeutic agent, cytotoxic agent, cytokine, growth inhibitory agent, anti-hormonal agent, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences,* 16th edition, Osol, A. Ed. (1980).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

K. Diagnosis and Treatment with Anti-TAT Antibodies. TAT Binding Oligopeptides and TAT Binding Organic Molecules To determine TAT expression in the cancer, various diagnostic assays are available. In one embodiment, TAT polypeptide overexpression may be analyzed by immunohistochemistry (IHC). Parrafin embedded tissue sections from a tumor biopsy may be subjected to the IHC assay and accorded a TAT protein staining intensity criteria as follows:

Score 0—no staining is observed or membrane staining is observed in less than 10% of tumor cells.

Score 1+—a faint/barely perceptible membrane staining is detected in more than 10% of the tumor cells. The cells are only stained in part of their membrane.

Score 2+—a weak to moderate complete membrane staining is observed in more than 10% of the tumor cells.

Score 3+—a moderate to strong complete membrane staining is observed in more than 10% of the tumor cells.

Those tumors with 0 or 1+ scores for TAT polypeptide expression may be characterized as not overexpressing TAT, whereas those tumors with 2+ or 3+ scores may be characterized as overexpressing TAT.

Alternatively, or additionally, FISH assays such as the INFORM® (sold by Ventana, Ariz.) or PATHVISION® (Vysis, Ill.) may be carried out on formalin-fixed, paraffin-embedded tumor tissue to determine the extent (if any) of TAT overexpression in the tumor.

TAT overexpression or amplification may be evaluated using an in vivo diagnostic assay, e.g., by administering a molecule (such as an antibody, oligopeptide or organic molecule) which binds the molecule to be detected and is tagged with a detectable label (e.g., a radioactive isotope or a fluorescent label) and externally scanning the patient for localization of the label.

As described above, the anti-TAT antibodies, oligopeptides and organic molecules of the invention have various non-therapeutic applications. The anti-TAT antibodies, oligopeptides and organic molecules of the present invention can be useful for diagnosis and staging of TAT polypeptide -expressing cancers (e.g., in radioimaging). The antibodies, oligopeptides and organic molecules are also useful for purification or immunoprecipitation of TAT polypeptide from cells, for detection and quantitation of TAT polypeptide in vitro, e.g., in an ELISA or a Western blot, to kill and eliminate TAT-expressing cells from a population of mixed cells as a step in the purification of other cells.

Currently, depending on the stage of the cancer, cancer treatment involves one or a combination of the following therapies: surgery to remove the cancerous tissue, radiation therapy, and chemotherapy. Anti-TAT antibody, oligopeptide or organic molecule therapy may be especially desirable in elderly patients who do not tolerate the toxicity and side effects of chemotherapy well and in metastatic disease where radiation therapy has limited usefulness. The tumor targeting anti-TAT antibodies, oligopeptides and organic molecules of the invention are useful to alleviate TAT-expressing cancers upon initial diagnosis of the disease or during relapse. For therapeutic applications, the anti-TAT antibody, oligopeptide or organic molecule can be used alone, or in combination therapy with, e.g., hormones, antiangiogens, or radiolabelled compounds, or with surgery, cryotherapy, and/or radiotherapy. Anti-TAT antibody, oligopeptide or organic molecule treatment can be administered in conjunction with other forms of conventional therapy, either consecutively with, pre- or post-conventional therapy. Chemotherapeutic drugs such as TAXOTERE® (docetaxel), TAXOL® (palictaxel), estramustine and mitoxantrone are used in treating cancer, in particular, in good risk patients. In the present method of the invention for treating or alleviating cancer, the cancer patient can be administered anti-TAT antibody, oligopeptide or organic molecule in conjuction with treatment with the one or more of the preceding chemotherapeutic agents. In particular, combination therapy with palictaxel and modified derivatives (see, e.g., EP0600517) is contemplated. The anti-TAT antibody, oligopeptide or organic molecule will be administered with a therapeutically effective dose of the chemotherapeutic agent. In another embodiment, the anti-TAT antibody, oligopeptide or organic molecule is administered in conjunction with chemotherapy to enhance the activity and efficacy of the chemotherapeutic agent, e.g., paclitaxel. The Physicians' Desk Reference (PDR) discloses dosages of these agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician.

In one particular embodiment, a conjugate comprising an anti-TAT antibody, oligopeptide or organic molecule conjugated with a cytotoxic agent is administered to the patient. Preferably, the immunoconjugate bound to the TAT protein is internalized by the cell, resulting in increased therapeutic efficacy of the immunoconjugate in killing the cancer cell to which it binds. In a preferred embodiment, the cytotoxic agent targets or interferes with the nucleic acid in the cancer cell. Examples of such cytotoxic agents are described above and include maytansinoids, calicheamicins, ribonucleases and DNA endonucleases.

The anti-TAT antibodies, oligopeptides, organic molecules or toxin conjugates thereof are administered to a human patient, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody, oligopeptide or organic molecule is preferred.

Other therapeutic regimens may be combined with the administration of the anti-TAT antibody, oligopeptide or organic molecule. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect.

It may also be desirable to combine administration of the anti-TAT antibody or antibodies, oligopeptides or organic molecules, with administration of an antibody directed against another tumor antigen associated with the particular cancer.

In another embodiment, the therapeutic treatment methods of the present invention involves the combined administration of an anti-TAT antibody (or antibodies), oligopeptides or organic molecules and one or more chemotherapeutic agents or growth inhibitory agents, including co-administration of cocktails of different chemotherapeutic agents. Chemotherapeutic agents include estramustine phosphate, prednimustine, cisplatin, 5-fluorouracil, melphalan, cyclophosphamide, hydroxyurea and hydroxyureataxanes (such as paclitaxel and doxetaxel) and/or anthracycline antibiotics. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The antibody, oligopeptide or organic molecule may be combined with an anti-hormonal compound; e.g., an anti-estrogen compound such as tamoxifen; an anti-progesterone such as onapristone (see, EP 616 812); or an anti-androgen such as flutamide, in dosages known for such molecules. Where the cancer to be treated is androgen independent cancer, the patient may previously have been subjected to anti-androgen therapy and, after the cancer becomes androgen independent, the anti-TAT antibody, oligopeptide or organic molecule (and optionally other agents as described herein) may be administered to the patient.

Sometimes, it may be beneficial to also co-administer a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy, before, simultaneously with, or post antibody, oligopeptide or organic molecule therapy. Suitable dosages for any of the above co-administered agents are those presently used and may be lowered due to the combined action (synergy) of the agent and anti-TAT antibody, oligopeptide or organic molecule.

For the prevention or treatment of disease, the dosage and mode of administration will be chosen by the physician according to known criteria. The appropriate dosage of antibody, oligopeptide or organic molecule will depend on the type of disease to be treated, as defined above, the severity and course of the disease, whether the antibody, oligopeptide or organic molecule is administered for preventive or therapeutic purposes, previous therapy, the patient's clinical history and response to the antibody, oligopeptide or organic molecule, and the discretion of the attending physician. The antibody, oligopeptide or organic molecule is suitably administered to the patient at one time or over a series of treatments. Preferably, the antibody, oligopeptide or organic molecule is administered by intravenous infusion or by subcutaneous injections. Depending on the type and severity of the disease, about 1 μg/kg to about 50 mg/kg body weight (e.g., about 0.1-15 mg/kg/dose) of antibody can be an initial candidate dosage for administration to the patient, whether, for example, by one or more separate administrations, or by continuous infusion. A dosing regimen can comprise administering an initial loading dose of about 4 mg/kg, followed by a weekly maintenance dose of about 2 mg/kg of the anti-TAT antibody. However, other dosage regimens may be useful. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. The progress of this therapy can be readily monitored by conventional methods and assays and based on criteria known to the physician or other persons of skill in the art.

Aside from administration of the antibody protein to the patient, the present application contemplates administration of the antibody by gene therapy. Such administration of nucleic acid encoding the antibody is encompassed by the expression "administering a therapeutically effective amount of an antibody". See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retroviral vector.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). For review of the currently known gene marking and gene therapy protocols see Anderson et al., *Science* 256:808-813 (1992). See also WO 93/25673 and the references cited therein.

The anti-TAT antibodies of the invention can be in the different forms encompassed by the definition of "antibody" herein. Thus, the antibodies include full length or intact antibody, antibody fragments, native sequence antibody or amino acid variants, humanized, chimeric or fusion antibodies, immunoconjugates, and functional fragments thereof. In fusion antibodies an antibody sequence is fused to a heterologous polypeptide sequence. The antibodies can be modified in the Fc region to provide desired effector functions. As discussed in more detail in the sections herein, with the appropriate Fc regions, the naked antibody bound on the cell surface can induce cytotoxicity, e.g., via antibody-dependent cellular cytotoxicity (ADCC) or by recruiting complement in complement dependent cytotoxicity, or some other mechanism. Alternatively, where it is desirable to eliminate or reduce effector function, so as to minimize side effects or therapeutic complications, certain other Fc regions may be used.

In one embodiment, the antibody competes for binding or bind substantially to, the same epitope as the antibodies of the invention. Antibodies having the biological characteristics of the present anti-TAT antibodies of the invention are also contemplated, specifically including the in vivo tumor targeting and any cell proliferation inhibition or cytotoxic characteristics.

Methods of producing the above antibodies are described in detail herein.

The present anti-TAT antibodies, oligopeptides and organic molecules are useful for treating a TAT-expressing cancer or alleviating one or more symptoms of the cancer in a mammal. Such a cancer includes prostate cancer, cancer of the urinary tract, lung cancer, breast cancer, colon cancer and ovarian cancer, more specifically, prostate adenocarcinoma, renal cell carcinomas, colorectal adenocarcinomas, lung adenocarcinomas, lung squamous cell carcinomas, and pleural mesothelioma. The cancers encompass metastatic cancers of any of the preceding. The antibody, oligopeptide or organic molecule is able to bind to at least a portion of the cancer cells that express TAT polypeptide in the mammal. In a preferred embodiment, the antibody, oligopeptide or organic molecule is effective to destroy or kill TAT-expressing tumor cells or inhibit the growth of such tumor cells, in vitro or in vivo, upon binding to TAT polypeptide on the cell. Such an antibody includes a naked anti-TAT antibody (not conjugated to any agent). Naked antibodies that have cytotoxic or cell growth inhibition properties can be further harnessed with a cytotoxic agent to render them even more potent in tumor cell destruction. Cytotoxic properties can be conferred to an anti-TAT antibody by, e.g., conjugating the antibody with a cytotoxic agent, to form an immunoconjugate as described herein. The cytotoxic agent or a growth inhibitory agent is preferably a small molecule. Toxins such as calicheamicin or a maytansinoid and analogs or derivatives thereof, are preferable.

The invention provides a composition comprising an anti-TAT antibody, oligopeptide or organic molecule of the invention, and a carrier. For the purposes of treating cancer, compositions can be administered to the patient in need of such treatment, wherein the composition can comprise one or more anti-TAT antibodies present as an immunoconjugate or as the naked antibody. In a further embodiment, the compositions can comprise these antibodies, oligopeptides or organic molecules in combination with other therapeutic agents such as cytotoxic or growth inhibitory agents, including chemotherapeutic agents. The invention also provides formulations comprising an anti-TAT antibody, oligopeptide or organic molecule of the invention, and a carrier. In one embodiment, the formulation is a therapeutic formulation comprising a pharmaceutically acceptable carrier.

Another aspect of the invention is isolated nucleic acids encoding the anti-TAT antibodies. Nucleic acids encoding both the H and L chains and especially the hypervariable region residues, chains which encode the native sequence antibody as well as variants, modifications and humanized versions of the antibody, are encompassed.

The invention also provides methods useful for treating a TAT polypeptide-expressing cancer or alleviating one or more symptoms of the cancer in a mammal, comprising administering a therapeutically effective amount of an anti-TAT antibody, oligopeptide or organic molecule to the mammal. The antibody, oligopeptide or organic molecule therapeutic compositions can be administered short term (acute) or chronic, or intermittent as directed by physician. Also provided are methods of inhibiting the growth of, and killing a TAT polypeptide-expressing cell.

The invention also provides kits and articles of manufacture comprising at least one anti-TAT antibody, oligopeptide or organic molecule. Kits containing anti-TAT antibodies, oligopeptides or organic molecules find use, e.g., for TAT cell killing assays, for purification or immunoprecipitation of TAT polypeptide from cells. For example, for isolation and purification of TAT, the kit can contain an anti-TAT antibody, oligopeptide or organic molecule coupled to beads (e.g., sepharose beads). Kits can be provided which contain the antibodies, oligopeptides or organic molecules for detection and quantitation of TAT in vitro, e.g., in an ELISA or a Western blot. Such antibody, oligopeptide or organic molecule useful for detection may be provided with a label such as a fluorescent or radiolabel.

L. Articles of Manufacture and Kits

Another embodiment of the invention is an article of manufacture containing materials useful for the treatment of anti-TAT expressing cancer. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the cancer condition and may have a sterile access port (for example the container may be an intravenous solution bag or a vial having a stopper pierceable by a hypodermic injection needle). At least one active agent in the composition is an anti-TAT antibody, oligopeptide or organic molecule of the invention. The label or package insert indicates that the composition is used for treating cancer. The label or package insert will further comprise instructions for administering the antibody, oligopeptide or organic molecule composition to the cancer patient. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for TAT-expressing cell killing assays, for purification or immunoprecipitation of TAT polypeptide from cells. For isolation and purification of TAT polypeptide, the kit can contain an anti-TAT antibody, oligopeptide or organic molecule coupled to beads (e.g., sepharose beads). Kits can be provided which contain the antibodies, oligopeptides or organic molecules for detection and quantitation of TAT polypeptide in vitro, e.g., in an ELISA or a Western blot. As with the article of manufacture, the kit comprises a container and a label or package insert on or associated with the container. The container holds a composition comprising at least one anti-TAT antibody, oligopeptide or organic molecule of the invention. Additional containers may be included that contain, e.g., diluents and buffers, control antibodies. The label or package insert may provide a description of the composition as well as instructions for the intended in vitro or diagnostic use.

M. Uses for TAT Polypeptides and TAT-Polypeptide Encoding Nucleic Acids

Nucleotide sequences (or their complement) encoding TAT polypeptides have various applications in the art of molecular biology, including uses as hybridization probes, in chromosome and gene mapping and in the generation of anti-sense RNA and DNA probes. TAT-encoding nucleic acid will also be useful for the preparation of TAT polypeptides by the recombinant techniques described herein, wherein those TAT polypeptides may find use, for example, in the preparation of anti-TAT antibodies as described herein.

The full-length native sequence TAT gene, or portions thereof, may be used as hybridization probes for a cDNA library to isolate the full-length TAT cDNA or to isolate still other cDNAs (for instance, those encoding naturally-occurring variants of TAT or TAT from other species) which have a desired sequence identity to the native TAT sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence TAT. By way of example, a screening method will comprise isolating the coding region of the TAT gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the TAT gene of the present invention can be used to screen libraries of human cDNA, genomic DNA or mRNA to determine which members of such libraries the probe hybridizes to. Hybridization techniques are described in further detail in the Examples below. Any EST sequences disclosed in the present application may similarly be employed as probes, using the methods disclosed herein.

Other useful fragments of the TAT-encoding nucleic acids include antisense or sense oligonucleotides comprising a singe-stranded nucleic acid sequence (either RNA or DNA) capable of binding to target TAT mRNA (sense) or TAT DNA (antisense) sequences. Antisense or sense oligonucleotides, according to the present invention, comprise a fragment of the coding region of TAT DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. Such methods are encompassed by the present invention. The antisense oligonucleotides thus may be used to block expression of TAT proteins, wherein those TAT proteins may play a role in the induction of cancer in mammals. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Preferred intragenic sites for antisense binding include the region incorporating the translation initiation/start codon (5'-AUG/5'-ATG) or termination/stop codon (5'-UAA, 5'-UAG and 5-UGA/5'-TM, 5'-TAG and 5'-TGA) of the open reading frame (ORF) of the gene. These regions refer to a portion of the mRNA or gene that encompasses from about 25 to about 50 contiguous nucleotides in either direction (i.e., 5' or 3') from a translation initiation or termination codon. Other preferred regions for antisense binding include: introns; exons; intron-exon junctions; the open reading frame (ORF) or "coding region," which is the region between the translation initiation codon and the translation termination codon; the 5' cap of an mRNA which comprises an N7-methylated guanosine residue joined to the 5'-most residue of the mRNA via a 5'-5' triphosphate linkage and includes 5' cap structure itself as well as the first 50 nucleotides adjacent to the cap; the 5' untranslated region (5'UTR), the portion of an mRNA in the 5' direction from the translation initiation codon, and thus including nucleotides between the 5' cap site and the translation initiation codon of an mRNA or corresponding nucleotides on the gene; and the 3' untranslated region (3'UTR), the portion of an mRNA in the 3' direction from the translation termination codon, and thus including nucleotides between the translation termination codon and 3' end of an mRNA or corresponding nucleotides on the gene.

Specific examples of preferred antisense compounds useful for inhibiting expression of TAT proteins include oligonucleotides containing modified backbones or non-natural internucleoside linkages. Oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Preferred modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included. Representative United States patents that teach the preparation of phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH.sub.2 component parts. Representative United States patents that teach the preparation of such oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

In other preferred antisense oligonucleotides, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Preferred antisense oligonucleotides incorporate phosphorothioate backbones and/or heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] described in the above referenced U.S. Pat. No. 5,489,677, and the amide backbones of the above referenced U.S. Pat. No. 5,602,240. Also preferred are antisense oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-alkyl, S-alkyl, or N-alkyl; O-alkenyl, S-alkenyl, or N-alkenyl; O-alkynyl, S-alkynyl or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred antisense oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy ($2'-O-CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethylaminoethoxyethyl or 2'-DMAEOE), i.e., $2'-O-CH_2-O-CH_2-N(CH_2)$.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methylene $(-CH_2-)_n$ group bridging the 2' oxygen atom and the 4' carbon atom wherein n is 1 or 2. LNAs and preparation thereof are described in WO 98/39352 and WO 99/14226.

Other preferred modifications include 2'-methoxy ($2'-O-CH_3$), 2'-aminopropoxy ($2'-OCH_2CH_2CH_2NH_2$), 2'-allyl ($2'-CH_2-CH=CH_2$), 2'-O-allyl ($2'-O-CH_2-CH=CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$ or $-CH_2-C{\equiv}CH$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido [5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi et al, Antisense Research and Applications, CRC Press, Boca Raton, 1993, pp. 276-278) and are preferred base substitutions, even more particularly when combined with 2'-O-methoxyethyl sugar modifications. Representative United States patents that teach the preparation of modified nucleobases include, but are not limited to: U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,681,941 and 5,750,692, each of which is herein incorporated by reference.

Another modification of antisense oligonucleotides chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, cation lipids, phospholipids, cationic phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., *Nucl. Acids Res.,* 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl -oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) and U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Preferred chimeric antisense oligonucleotides incorporate at least one 2' modified sugar (preferably 2'-O—$(CH_2)_2$—O—$CH_3$) at the 3' terminal to confer nuclease resistance and a region with at least 4 contiguous 2'-H sugars to confer RNase H activity. Such compounds have also been referred to in the art as hybrids or gapmers. Preferred gapmers have a region of 2' modified sugars (preferably 2'-O—$(CH_2)_2$—O—$CH_3$) at the 3'-terminal and at the 5' terminal separated by at least one region having at least 4 contiguous 2'-H sugars and preferably incorporate phosphorothioate backbone linkages. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 nucleotides in length, alternatively at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

The probes may also be employed in PCR techniques to generate a pool of sequences for identification of closely related TAT coding sequences.

Nucleotide sequences encoding a TAT can also be used to construct hybridization probes for mapping the gene which encodes that TAT and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for TAT encode a protein which binds to another protein (example, where the TAT is a receptor), the TAT can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor TAT can be used to isolate correlative ligand(s). Screening assays can be designed to find lead compounds that mimic the biological activity of a native TAT or a receptor for TAT. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein -protein binding assays, biochemical screening assays, immunoassays and cell based assays, which are well characterized in the art.

Nucleic acids which encode TAT or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding TAT can be used to clone genomic DNA encoding TAT in accordance with established techniques and the genomic sequences used to generate transgenic animals that contain cells which express DNA encoding TAT. Methods for generating transgenic animals, particularly animals such as mice or rats, have become conventional in the art and are described, for example, in U.S. Pat. Nos. 4,736,866 and 4,870,009. Typically, particular cells would be targeted for TAT transgene incorporation with tissue -specific enhancers. Transgenic animals that include a copy of a transgene encoding TAT introduced into the germ line of the animal at an embryonic stage can be used to examine the effect of increased expression of DNA encoding TAT. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of TAT can be used to construct a TAT "knock out" animal which has a defective or altered gene encoding TAT as a result of homologous recombination between the endogenous gene encoding TAT and altered genomic DNA encoding TAT introduced into an embryonic stem cell of the animal. For example, cDNA encoding TAT can be used to clone genomic DNA encoding TAT in accordance with established techniques. A portion of the genomic DNA encoding TAT can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the TAT polypeptide.

Nucleic acid encoding the TAT polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE -dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The nucleic acid molecules encoding the TAT polypeptides or fragments thereof described herein are useful for chromosome identification. In this regard, there exists an ongoing need to identify new chromosome markers, since relatively few chromosome marking reagents, based upon actual sequence data are presently available. Each TAT nucleic acid molecule of the present invention can be used as a chromosome marker.

The TAT polypeptides and nucleic acid molecules of the present invention may also be used diagnostically for tissue typing, wherein the TAT polypeptides of the present invention may be differentially expressed in one tissue as compared to another, preferably in a diseased tissue as compared to a normal tissue of the same tissue type. TAT nucleic acid molecules will find use for generating probes for PCR, Northern analysis, Southern analysis and Western analysis.

This invention encompasses methods of screening compounds to identify those that mimic the TAT polypeptide (agonists) or prevent the effect of the TAT polypeptide (antagonists). Screening assays for antagonist drug candidates are designed to identify compounds that bind or complex with the TAT polypeptides encoded by the genes identified herein, or otherwise interfere with the interaction of the encoded polypeptides with other cellular proteins, including e.g., inhibiting the expression of TAT polypeptide from cells. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a TAT polypeptide encoded by a nucleic acid identified herein under conditions and for a time sufficient to allow these two components to interact.

In binding assays, the interaction is binding and the complex formed can be isolated or detected in the reaction mixture. In a particular embodiment, the TAT polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the TAT polypeptide and drying. Alternatively, an immobilized antibody, e.g., a monoclonal antibody, specific for the TAT polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular TAT polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (*London*), 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a TAT polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the TAT polypeptide may be added to a cell along with the compound to be screened for a particular activity and the ability of the compound to inhibit the activity of interest in the presence of the TAT polypeptide indicates that the compound is an antagonist to the TAT polypeptide. Alternatively, antagonists may be detected by combining the TAT polypeptide and a potential antagonist with membrane-bound TAT polypeptide receptors or recombinant receptors under appropriate conditions for a competitive inhibition assay. The TAT polypeptide can be labeled, such as by radioactivity, such that the number of TAT polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the TAT polypeptide and a cDNA library created from this RNA is divided into pools and used to transfect COS cells or other cells that are not responsive to the TAT polypeptide. Transfected cells that are grown on glass slides are exposed to labeled TAT polypeptide. The TAT polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled TAT polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro -sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled TAT polypeptide in the presence of the candidate compound. The ability of the compound to enhance or block this interaction could then be measured.

More specific examples of potential antagonists include an oligonucleotide that binds to the fusions of immunoglobulin with TAT polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the TAT polypeptide that recognizes the receptor but imparts no effect, thereby competitively inhibiting the action of the TAT polypeptide.

Another potential TAT polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature TAT polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the TAT polypeptide. The antisense RNA oligonucleotide hybridizes to the mRNA in vivo and blocks translation of the mRNA molecule into the TAT polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the TAT polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the TAT polypeptide, thereby blocking the normal biological activity of the TAT polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Isolated TAT polypeptide-encoding nucleic acid can be used herein for recombinantly producing TAT polypeptide using techniques well known in the art and as described herein. In turn, the produced TAT polypeptides can be employed for generating anti-TAT antibodies using techniques well known in the art and as described herein.

Antibodies specifically binding a TAT polypeptide identified herein, as well as other molecules identified by the screening assays disclosed hereinbefore, can be administered for the treatment of various disorders, including cancer, in the form of pharmaceutical compositions.

If the TAT polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993).

The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly upregulated in a particular tumor tissue(s) of interest as compared to other tumor(s) and/or normal tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The following is a list of molecules whose tissue expression profile as determined from an analysis of the GeneExpress® database evidences high tissue expression and significant upregulation of expression in a specific tumor or tumors as compared to other tumor(s) and/or normal tissues and optionally relatively low expression in normal essential and/or normal proliferating tissues. As such, the molecules listed below are excellent polypeptide targets for the diagnosis and therapy of cancer in mammals.

| Molecule | upregulation of expression in: | as compared to: |
|---|---|---|
| DNA96792 (TAT239) | colon tumor | normal colon tissue |
| DNA96792 (TAT239) | rectum tumor | normal rectum tissue |
| DNA96792 (TAT239) | pancreas tumor | normal pancreas tissue |
| DNA96792 (TAT239) | lung tumor | normal lung tissue |
| DNA96792 (TAT239) | stomach tumor | normal stomach tissue |
| DNA96792 (TAT239) | esophagus tumor | normal esophagus tissue |
| DNA96792 (TAT239) | breast tumor | normal breast tissue |
| DNA96792 (TAT239) | uterus tumor | normal uterus tissue |
| DNA225793 (TAT223) | ovarian tumor | normal ovarian tissue |
| DNA225793 (TAT223) | kidney tumor | normal kidney tissue |
| DNA227611 (TAT175) | prostate tumor | normal prostate tissue |
| DNA227611 (TAT175) | colon tumor | normal colon tissue |
| DNA227611 (TAT175) | breast tumor | normal breast tissue |
| DNA261021 (TAT208) | breast tumor | normal breast tissue |
| DNA260655 (TAT209) | lung tumor | normal lung tissue |
| DNA260655 (TAT209) | colon tumor | normal colon tissue |
| DNA260655 (TAT209) | breast tumor | normal breast tissue |
| DNA260655 (TAT209) | liver tumor | normal liver tissue |
| DNA260655 (TAT209) | ovarian tumor | normal ovarian tissue |
| DNA260655 (TAT209) | skin tumor | normal skin tissue |
| DNA260655 (TAT209) | spleen tumor | normal spleen tissue |
| DNA260655 (TAT209) | myeloid tumor | normal myeloid tissue |
| DNA260655 (TAT209) | muscle tumor | normal muscle tissue |
| DNA260655 (TAT209) | bone tumor | normal bone tissue |
| DNA261001 (TAT181) | bone tumor | normal bone tissue |
| DNA261001 (TAT181) | lung tumor | normal lung tissue |
| DNA266928 (TAT182) | bone tumor | normal bone tissue |
| DNA266928 (TAT182) | lung tumor | normal lung tissue |
| DNA268035 (TAT222) | breast tumor | normal breast tissue |
| DNA268035 (TAT222) | colon tumor | normal colon tissue |
| DNA268035 (TAT222) | ovarian tumor | normal ovarian tissue |
| DNA268035 (TAT222) | uterine tumor | normal uterine tissue |
| DNA77509 (TAT177) | colon tumor | normal colon tissue |
| DNA87993 (TAT235) | breast tumor | normal breast tissue |
| DNA87993 (TAT235) | pancreatic tumor | normal pancreatic tissue |
| DNA87993 (TAT235) | lung tumor | normal lung tissue |
| DNA87993 (TAT235) | colon tumor | normal colon tissue |
| DNA87993 (TAT235) | rectum tumor | normal rectum tissue |
| DNA87993 (TAT235) | gallbladder tumor | normal gallbladder tissue |
| DNA92980 (TAT234) | bone tumor | normal bone tissue |
| DNA92980 (TAT234) | breast tumor | normal breast tissue |
| DNA92980 (TAT234) | cervical tumor | normal cervical tissue |
| DNA92980 (TAT234) | colon tumor | normal colon tissue |
| DNA92980 (TAT234) | rectum tumor | normal rectum tissue |
| DNA92980 (TAT234) | endometrial tumor | normal endometrial tissue |
| DNA92980 (TAT234) | liver tumor | normal liver tissue |
| DNA92980 (TAT234) | lung tumor | normal lung tissue |
| DNA92980 (TAT234) | ovarian tumor | normal ovarian tissue |
| DNA92980 (TAT234) | pancreatic tumor | normal pancreatic tissue |
| DNA92980 (TAT234) | skin tumor | normal skin tissue |
| DNA92980 (TAT234) | soft tissue tumor | normal soft tissue |
| DNA92980 (TAT234) | stomach tumor | normal stomach tissue |
| DNA92980 (TAT234) | bladder tumor | normal bladder tissue |

-continued

| Molecule | upregulation of expression in: | as compared to: |
|---|---|---|
| DNA92980 (TAT234) | thyroid tumor | normal thyroid tissue |
| DNA105792 (TAT233) | bone tumor | normal bone tissue |
| DNA105792 (TAT233) | breast tumor | normal breast tissue |
| DNA105792 (TAT233) | endometrial tumor | normal endometrial tissue |
| DNA105792 (TAT233) | esophagus tumor | normal esophagus tissue |
| DNA105792 (TAT233) | kidney tumor | normal kidney tissue |
| DNA105792 (TAT233) | lung tumor | normal lung tissue |
| DNA105792 (TAT233) | ovarian tumor | normal ovarian tissue |
| DNA105792 (TAT233) | pancreatic tumor | normal pancreatic tissue |
| DNA105792 (TAT233) | prostate tumor | normal prostate tissue |
| DNA105792 (TAT233) | soft tissue tumor | normal soft tissue |
| DNA105792 (TAT233) | stomach tumor | normal stomach tissue |
| DNA105792 (TAT233) | thyroid tumor | normal thyroid tissue |
| DNA105792 (TAT233) | bladder tumor | normal bladder tissue |
| DNA105792 (TAT233) | brain tumor | normal brain tissue |
| DNA105792 (TAT233) | Wilm's tumor | normal associated tissue |
| DNA119474 (TAT228) | uterine tumor | normal uterine tissue |
| DNA119474 (TAT228) | ovarian tumor | normal ovarian tissue |
| DNA280351 (TAT248) | squamous cell lung tumor | normal squamous cell lung tissue |
| DNA280351 (TAT248) | colon tumor | normal colon tissue |
| DNA150648 (TAT232) | liver tumor | normal liver tissue |
| DNA150648 (TAT232) | breast tumor | normal breast tissue |
| DNA150648 (TAT232) | brain tumor | normal brain tissue |
| DNA150648 (TAT232) | lung tumor | normal lung tissue |
| DNA150648 (TAT232) | colon tumor | normal colon tissue |
| DNA150648 (TAT232) | rectum tumor | normal rectum tissue |
| DNA150648 (TAT232) | kidney tumor | normal kidney tissue |
| DNA150648 (TAT232) | bladder tumor | normal bladder tissue |
| DNA179651 (TAT224) | breast tumor | normal breast tissue |
| DNA179651 (TAT224) | cervical tumor | normal cervical tissue |
| DNA179651 (TAT224) | colon tumor | normal colon tissue |
| DNA179651 (TAT224) | rectum tumor | normal rectum tissue |
| DNA179651 (TAT224) | uterine tumor | normal uterine tissue |
| DNA179651 (TAT224) | lung tumor | normal lung tissue |
| DNA179651 (TAT224) | ovarian tumor | normal ovarian tissue |
| DNA207698 (TAT237) | breast tumor | normal breast tissue |
| DNA207698 (TAT237) | colon tumor | normal colon tissue |
| DNA207698 (TAT237) | ovarian tumor | normal ovarian tissue |
| DNA207698 (TAT237) | pancreatic tumor | normal pancreatic tissue |
| DNA207698 (TAT237) | stomach tumor | normal stomach tissue |
| DNA225886 (TAT236) | breast tumor | normal breast tissue |
| DNA225886 (TAT236) | colon tumor | normal colon tissue |
| DNA225886 (TAT236) | rectum tumor | normal rectum tissue |
| DNA225886 (TAT236) | endometrial tumor | normal endometrial tissue |
| DNA225886 (TAT236) | lung tumor | normal lung tissue |
| DNA225886 (TAT236) | ovarian tumor | normal ovarian tissue |
| DNA225886 (TAT236) | pancreas tumor | normal pancreas tissue |
| DNA225886 (TAT236) | prostate tumor | normal prostate tissue |
| DNA225886 (TAT236) | bladder tumor | normal bladder tissue |
| DNA226717 (TAT185) | glioma | normal glial tissue |
| DNA226717 (TAT185) | brain tumor | normal brain tissue |
| DNA227162 (TAT225) | breast tumor | normal breast tissue |
| DNA227162 (TAT225) | endometrial tumor | normal endometrial tissue |
| DNA227162 (TAT225) | lung tumor | normal lung tissue |
| DNA227162 (TAT225) | ovarian tumor | normal ovarian tissue |
| DNA277804 (TAT247) | breast tumor | normal breast tissue |
| DNA277804 (TAT247) | endometrial tumor | normal endometrial tissue |
| DNA277804 (TAT247) | lung tumor | normal lung tissue |
| DNA277804 (TAT247) | ovarian tumor | normal ovarian tissue |
| DNA233034 (TAT174) | glioma | normal glial tissue |
| DNA233034 (TAT174) | brain tumor | normal brain tissue |
| DNA266920 (TAT214) | glioma | normal glial tissue |
| DNA266920 (TAT214) | brain tumor | normal brain tissue |
| DNA266921 (TAT220) | glioma | normal glial tissue |
| DNA266921 (TAT220) | brain tumor | normal brain tissue |
| DNA266922 (TAT221) | glioma | normal glial tissue |
| DNA266922 (TAT221) | brain tumor | normal brain tissue |
| DNA234441 (TAT201) | colon tumor | normal colon tissue |
| DNA234441 (TAT201) | rectum tumor | normal rectum tissue |
| DNA234834 (TAT179) | breast tumor | normal breast tissue |
| DNA234834 (TAT179) | colon tumor | normal colon tissue |
| DNA234834 (TAT179) | rectum tumor | normal rectum tissue |
| DNA234834 (TAT179) | prostate tumor | normal prostate tissue |
| DNA234834 (TAT179) | pancreatic tumor | normal pancreatic |

-continued

| Molecule | upregulation of expression in: | as compared to: |
|---|---|---|
| | | tissue |
| DNA234834 (TAT179) | endometrial tumor | normal endometrial tissue |
| DNA234834 (TAT179) | lung tumor | normal lung tissue |
| DNA234834 (TAT179) | ovarian tumor | normal ovarian tissue |
| DNA247587 (TAT216) | breast tumor | normal breast tissue |
| DNA247587 (TAT216) | lung tumor | normal lung tissue |
| DNA247587 (TAT216) | ovarian tumor | normal ovarian tissue |
| DNA247587 (TAT216) | pancreatic tumor | normal pancreatic tissue |
| DNA247587 (TAT216) | stomach tumor | normal stomach tissue |
| DNA247587 (TAT216) | urinary tumor | normal urinary tissue |
| DNA255987 (TAT218) | breast tumor | normal breast tissue |
| DNA56041 (TAT206) | lymphoid tumor | normal lymphoid tissue |
| DNA257845 (TAT374) | lymphoid tumor | normal lymphoid tissue |
| DNA247476 (TAT180) | bone tumor | normal bone tissue |
| DNA247476 (TAT180) | breast tumor | normal breast tissue |
| DNA247476 (TAT180) | colon tumor | normal colon tissue |
| DNA247476 (TAT180) | rectum tumor | normal rectum tissue |
| DNA247476 (TAT180) | kidney tumor | normal kidney tissue |
| DNA247476 (TAT180) | lung tumor | normal lung tissue |
| DNA247476 (TAT180) | pancreatic tumor | normal pancreatic tissue |
| DNA247476 (TAT180) | prostate tumor | normal prostate tissue |
| DNA247476 (TAT180) | skin tumor | normal skin tissue |
| DNA247476 (TAT180) | soft tissue tumor | normal soft tissue |
| DNA247476 (TAT180) | stomach tumor | normal stomach tissue |
| DNA260990 (TAT375) | bone tumor | normal bone tissue |
| DNA260990 (TAT375) | breast tumor | normal breast tissue |
| DNA260990 (TAT375) | colon tumor | normal colon tissue |
| DNA260990 (TAT375) | rectum tumor | normal rectum tissue |
| DNA260990 (TAT375) | kidney tumor | normal kidney tissue |
| DNA260990 (TAT375) | lung tumor | normal lung tissue |
| DNA260990 (TAT375) | pancreatic tumor | normal pancreatic tissue |
| DNA260990 (TAT375) | prostate tumor | normal prostate tissue |
| DNA260990 (TAT375) | skin tumor | normal skin tissue |
| DNA260990 (TAT375) | soft tissue tumor | normal soft tissue |
| DNA260990 (TAT375) | stomach tumor | normal stomach tissue |
| DNA261013 (TAT176) | breast tumor | normal breast tissue |
| DNA261013 (TAT176) | colon tumor | normal colon tissue |
| DNA261013 (TAT176) | rectum tumor | normal rectum tissue |
| DNA261013 (TAT176) | lung tumor | normal lung tissue |
| DNA261013 (TAT176) | ovarian tumor | normal ovarian tissue |
| DNA261013 (TAT176) | stomach tumor | normal stomach tissue |
| DNA262144 (TAT184) | breast tumor | normal breast tissue |
| DNA262144 (TAT184) | colon tumor | normal colon tissue |
| DNA262144 (TAT184) | rectum tumor | normal rectum tissue |
| DNA262144 (TAT184) | endometrial tumor | normal endometrial tissue |
| DNA262144 (TAT184) | kidney tumor | normal kidney tissue |
| DNA262144 (TAT184) | lung tumor | normal lung tissue |
| DNA262144 (TAT184) | ovarian tumor | normal ovarian tissue |
| DNA267342 (TAT213)) | stroma associated with the following tumors: bone, breast, colon, rectum, lung, ovarian, pancreas, soft tissue, bladder | normal associated tissues, respectively |
| DNA267626 (TAT217) | breast tumor | normal breast tissue |
| DNA267626 (TAT217) | colon tumor | normal colon tissue |
| DNA267626 (TAT217) | rectum tumor | normal rectum tissue |
| DNA267626 (TAT217) | endometrial tumor | normal endometrial tissue |
| DNA267626 (TAT217) | lung tumor | normal lung tissue |
| DNA267626 (TAT217) | pancreatic tumor | normal pancreatic tissue |
| DNA268334 (TAT202) | kidney tumor | normal kidney tissue |
| DNA269238 (TAT215) | kidney tumor | normal kidney tissue |
| DNA272578 (TAT238) | liver tumor | normal liver tissue |
| DNA272578 (TAT238) | lung tumor | normal lung tissue |
| DNA272578 (TAT238) | ovarian tumor | normal ovarian tissue |
| DNA304853 (TAT376) | breast tumor | normal breast tissue |
| DNA304853 (TAT376) | colon tumor | normal colon tissue |
| DNA304853 (TAT376) | rectum tumor | normal rectum tissue |
| DNA304853 (TAT376) | prostate tumor | normal prostate tissue |
| DNA304853 (TAT376) | pancreatic tumor | normal pancreatic tissue |
| DNA304853 (TAT376) | endometrial tumor | normal endometrial tissue |
| DNA304853 (TAT376) | lung tumor | normal lung tissue |
| DNA304853 (TAT376) | ovarian tumor | normal ovarian tissue |
| DNA304854 (TAT377) | breast tumor | normal breast tissue |
| DNA304854 (TAT377) | colon tumor | normal colon tissue |

-continued

| Molecule | upregulation of expression in: | as compared to: |
|---|---|---|
| DNA304854 (TAT377) | rectum tumor | normal rectum tissue |
| DNA304854 (TAT377) | prostate tumor | normal prostate tissue |
| DNA304854 (TAT377) | pancreatic tumor | normal pancreatic tissue |
| DNA304854 (TAT377) | endometrial tumor | normal endometrial tissue |
| DNA304854 (TAT377) | lung tumor | normal lung tissue |
| DNA304854 (TAT377) | ovarian tumor | normal ovarian tissue |
| DNA304855 (TAT378) | breast tumor | normal breast tissue |
| DNA304855 (TAT378) | colon tumor | normal colon tissue |
| DNA304855 (TAT378) | rectum tumor | normal rectum tissue |
| DNA304855 (TAT378) | prostate tumor | normal prostate tissue |
| DNA304855 (TAT378) | pancreatic tumor | normal pancreatic tissue |
| DNA304855 (TAT378) | endometrial tumor | normal endometrial tissue |
| DNA304855 (TAT378) | lung tumor | normal lung tissue |
| DNA304855 (TAT378) | ovarian tumor | normal ovarian tissue |
| DNA287971 (TAT379) | bone tumor | normal bone tissue |
| DNA287971 (TAT379) | breast tumor | normal breast tissue |
| DNA287971 (TAT379) | colon tumor | normal colon tissue |
| DNA287971 (TAT379) | rectum tumor | normal rectum tissue |
| DNA287971 (TAT379) | kidney tumor | normal kidney tissue |
| DNA287971 (TAT379) | lung tumor | normal lung tissue |
| DNA287971 (TAT379) | pancreatic tumor | normal pancreatic tissue |
| DNA287971 (TAT379) | prostate tumor | normal prostate tissue |
| DNA287971 (TAT379) | skin tumor | normal skin tissue |
| DNA287971 (TAT379) | soft tissue tumor | normal soft tissue |
| DNA287971 (TAT379) | stomach tumor | normal stomach tissue |

Example 2

Microarray Analysis to Detect Upregulation of TAT Polypeptides in Cancerous Tumors Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In one example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In the present example, cancerous tumors derived from various human tissues were studied for upregulated gene expression relative to cancerous tumors from different tissue types and/or non-cancerous human tissues in an attempt to identify those polypeptides which are overexpressed in a particular cancerous tumor(s). In certain experiments, cancerous human tumor tissue and non-cancerous human tumor tissue of the same tissue type (often from the same patient) were obtained and analyzed for TAT polypeptide expression. Additionally, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described TAT polypeptide-encoding nucleic acid sequences were used in the creation of the microarray and RNA from various tumor tissues were used for the hybridization thereto. Below is shown the results of these experiments, demonstrating that various TAT polypeptides of the present invention are significantly overexpressed in various human tumor tissues as compared to their normal counterpart tissue(s). Moreover, all of the molecules shown below are significantly overexpressed in their specific tumor tissue(s) as compared to in the "universal" epithelial control. As described above, these data demonstrate that the TAT polypeptides of the present invention are useful not only as diagnostic markers for the presence of one or more cancerous tumors, but also serve as therapeutic targets for the treatment of those tumors.

| Molecule | upregulation of expression in: | as compared to: |
|---|---|---|
| DNA172500 (TAT219) | renal cell carcinoma | normal kidney (renal cell) tissue |

Example 3

Quantitative Analysis of TAT mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), were used to find genes that are significantly overexpressed in a cancerous tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen was mRNA isolated from a variety of different cancerous tissues. The mRNA is quantitated precisely, e.g., fluorometrically. As a negative control, RNA was isolated from various normal tissues of the same tissue type as the cancerous tissues being tested.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. Using this technique, the molecules listed below have been identified as being significantly overexpressed in a particular tumor(s) as compared to their normal non-cancerous counterpart tissue(s) (from both the same and different tissue donors) and thus, represent excellent polypeptide targets for the diagnosis and therapy of cancer in mammals.

| Molecule | upregulation of expression in: | as compared to: |
|---|---|---|
| DNA261021 (TAT208) | lung tumor | normal lung tissue |
| DNA77509 (TAT177) | colon tumor | normal colon tissue |
| DNA119474 (TAT226) | ovarian tumor | normal ovarian tissue |
| DNA179651 (TAT224) | ovarian tumor | normal ovarian tissue |
| DNA226717 (TAT185) | glioma | normal glial/brain tissue |
| DNA227162 (TAT225) | ovarian tumor | normal ovarian tissue |
| DNA277804 (TAT247) | ovarian tumor | normal ovarian tissue |
| DNA233034 (TAT174) | glioma | normal glial/brain tissue |
| DNA266920 (TAT214) | glioma | normal glial/brain tissue |
| DNA266921 (TAT220) | glioma | normal glial/brain tissue |
| DNA266922 (TAT221) | glioma | normal glial/brain tissue |
| DNA234441 (TAT201) | colon tumor | normal colon tissue |
| DNA234834 (TAT179) | colon tumor | normal colon tissue |
| DNA247587 (TAT216) | squamous cell lung tumor | normal squamous cell lung tissue |
| DNA255987 (TAT218) | breast tumor | normal breast tissue |
| DNA247476 (TAT180) | colon tumor | normal colon tissue |
| DNA260990 (TAT375) | colon tumor | normal colon tissue |
| DNA261013 (TAT176) | breast tumor | normal breast tissue |
| DNA262144 (TAT184) | kidney tumor | normal kidney tissue |
| DNA267342 (TAT213) | breast tumor | normal breast tissue |
| DNA267626 (TAT217) | breast tumor | normal breast tissue |
| DNA268334 (TAT202) | kidney tumor | normal kidney tissue |
| DNA269238 (TAT215) | kidney tumor | normal kidney tissue |
| DNA87993 (TAT235) | lung tumor | normal lung tissue |
| DNA92980 (TAT234) | ovarian tumor | normal ovarian tissue |
| DNA105792 (TAT233) | lung tumor | normal lung tissue |
| DNA207698 (TAT237) | colon tumor | normal colon tissue |
| DNA225886 (TAT236) | colon tumor | normal colon tissue |
| DNA272578 (TAT238) | ovarian tumor | normal ovarian tissue |
| DNA304853 (TAT376) | colon tumor | normal colon tissue |
| DNA304854 (TAT377) | colon tumor | normal colon tissue |
| DNA304855 (TAT378) | colon tumor | normal colon tissue |
| DNA287971 (TAT379) | colon tumor | normal colon tissue |

Example 4

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 μl (125 mCi) of $^{33}$P-UTP (Amersham BF 1002, SA<2000 Ci/mmol) were speed vac dried. To each tube containing dried $^{33}$P-UTP, the following ingredients were added:

2.0 μl 5× transcription buffer 1.0 μl DTT (100 mM)

2.0 μl NTP mix (2.5 mM: 10μ; each of 10 mM GTP, CTP & ATP+10 μl $H_2O$)

1.0 μl UTP (50 μM)

1.0 μl Rnasin 1.0 μl DNA template (1 μg)

1.0 μl $H_2O$ 1.0 μl RNA polymerase (for PCR products T3=AS, T7=S, usually)

The tubes were incubated at 37° C. for one hour. 1.0 μl RQ1 DNase were added, followed by incubation at 37° C. for 15 minutes. 90 μl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 μl TE were added. 1 μl of the final product was pipetted on DE81 paper and counted in 6 ml of Biofluor II.

The probe was run on a TBE/urea gel. 1-3 μl of the probe or 5 μl of RNA Mrk III were added to 3 μl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ $H_2O$). After deproteination in 0.5 μg/ml proteinase K for 10 minutes at 37° C. (12.5 μl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ $H_2O$, and rinsed twice in 2×SSC at room temperature, for 5 minutes each time. The sections were deproteinated in 20 μg/ml proteinase K (500 μl of 10 mg/ml in 250 ml RNase-free RNase buffer; 37° C., 15 minutes)—human embryo, or 8× proteinase K (100 μl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization 1.0×10$^6$ cpm probe and 1.0 μl tRNA (50 mg/ml stock) per slide were heated at 95° C. for 3 minutes. The slides were cooled on ice, and 48 μl hybridization buffer were added per slide. After vortexing, 50 μl $^{33}$P mix were added to 50 μl prehybridization on slide. The slides were incubated overnight at 55° C.

E. Washes

Washing was done 2×10 minutes with 2×SSC, EDTA at room temperature (400 ml 20×SSC+16 ml 0.25M EDTA, $V_f$=4 L), followed by RNaseA treatment at 37° C. for 30 minutes (500 μl of 10 mg/ml in 250 ml Rnase buffer=20 μg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4 L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

In situ analysis was performed on a variety of DNA sequences disclosed herein. The results from these analyses are as follows.

(1) DNA119474 (TAT226)

Positive expression is observed in 2 of 3 non-small cell lung carcinomas, 2 of 3 pancreatic adenocarcinomas, 1 of 2 hepatocellular carcinomas and 2 of 3 endometrial adenocarcinomas. In a separate analysis, 10 of 16 ovarian adenocarcinomas are positive and 3 of 9 endometrial adenocarcinomas are positive. All normal tissues examined are negative for expression.

(2) DNA179651 (TAT224)

In one analysis, expression is seen in 5 of 7 uterine adenocarcinomas and in 7 of 16 ovarian adenocarcinomas. Two cases of dysgerminoma are positive as is one case of a Brenner's tumor.

In another analysis, 33 of 68 ovarian adenocarcinomas (serous, mucinous, endometrioid, clear cell) are positive for expression. Moderate to strong expression is seen in normal endometrium (no other normal tissues) and normal ovarian stroma is negative.

In yet another analysis, positive:expression is seen in 3/3 endometrial, 2/2 colorectal, 1/3 transitional cell, 3/3 lung and 1/2 ovarian cancers.

(3) DNA227162 (TAT225)

Expression is seen in the following tumors: 1 of 3 lung cancers, 1 of 2 colon cancers, 1 of 1 pancreatic cancer, 2 of 3 transitional cell carcinomas, 3 of 3 endometrial carcinomas, 2 of 2 ovarian carcinomas and 2 of 3 malignant melanomas.

In a separate analysis, positive expression is seen in 6 of 9 uterine adenocarcinomas and 6 of 14 ovarian tumors.

With regard to expression in normal tissues, weak expression is seen in one core of urothelium (superficial cell layer positive) and one core of gall bladder mucosa. All other normal tissues are negative for expression.

(4) DNA277804 (TAT247)

Expression is seen in the following tumors: 1 of 3 lung cancers, 1 of 2 colon cancers, 1 of 1 pancreatic cancer, 2 of 3 transitional cell carcinomas, 3 of 3 endometrial carcinomas, 2 of 2 ovarian carcinomas and 2 of 3 malignant melanomas.

In a separate analysis, positive expression is seen in 6 of 9 uterine adenocarcinomas and 6 of 14 ovarian tumors.

With regard to expression in normal tissues, weak expression is seen in one core of urothelium (superficial cell layer positive) and one core of gall bladder mucosa. All other normal tissues are negative for expression.

(5) DNA234441 (TAT201)

Weak (and inconsistent) expression is seen in normal kidney, normal colon mucosa and normal gallbladder. Weak to moderate, though somewhat inconsistent expression is seen in normal gastrointestinal mucosa (esophagus, stomach, small intestine, colon, anus). Significant expression in tumors is seen as follows: 11 of 12 colorectal adenocarcinomas, 4 of 4 gastric adenocarcinomas, 6 of 8 metastatic adenocarcinomas, 4 of 4 esophageal cancers and 1 of 2 pancreatic adenocarcinomas.

(6) DNA234834 (TAT179)

With regard to normal tissues, it appears that there is a weak signal in colon mucosa and breast epithelium. With regard to tumor tissues, expression is seen in 1 of 2 non-small cell lung carcinomas, 2 of 2 colon cancers, 1 of 2 pancreatic cancers, 1 of 2 hepatocellular carcinomas, 3 of 3 endometrial carcinomas, 1 of 2 ovarian carcinomas and 2 of 3 malignant melanomas.

In a separate analysis, 12 of 16 colorectal carcinomas are positive for expression; 2 of 8 gastric adenocarcinoma are positive for expression, 2 of 4 esophageal carcinomas are positive for expression; 7 of 10 metastatic adenocarcinoma are positive for expression and 1 of 2 cholangiocarcinomas are positive for expression. Expression level is tumor tissues is consistently higher than in normal tissues.

(7) DNA247587 (TAT216)

Expression is seen in 13 of 16 non-small cell lung carcinomas. Expression is also seen in benign bronchial mucosa and occasional activated pneumocytes. Moreover, 65 of 89 cases of invasive breast cancer are positive for expression. Strong expression is seen in normal skin and normal urothelium. Moderate expression is seen in normal mammary epithelium and trophoblasts of the placenta, weak expression in normal prostate and normal gall bladder epithelium and distal renal tubules.

(8) DNA56041 (TAT206)

In non-malignant lymphoid tissue expression is seen in occasional larger lymphoid cells within germinal centers and in interfollicular regions. Positive cells account for less than 5% of all lymphoid cells. In section of spleen scattered positive cells are seen within the periarteriolar lymphoid sheath and in the marginal zone.

In four cases of Hodgkin's disease Reed-Sternberg cells are negative, positive signal is observed in scattered lymphocytes. Three of four cases of follicular lymphoma are positive (weak to moderate), four of six cases of diffuse large cell lymphoma are positive (weak to moderate). Two cases of small lymphocytic lymphoma show a weak signal in variable proportion of cells.

(9) DNA257845 (TAT374)

In non-malignant lymphoid tissue expression is seen in occasional larger lymphoid cells within germinal centers and in interfollicular regions. Positive cells account for less than 5% of all lymphoid cells. In section of spleen scattered positive cells are seen within the periarteriolar lymphoid sheath and in the marginal zone.

In four cases of Hodgkin's disease Reed-Sternberg cells are negative, positive signal is observed in scattered lymphocytes. Three of four cases of follicular lymphoma are positive (weak to moderate), four of six cases of diffuse large cell lymphoma are positive (weak to moderate). Two cases of small lymphocytic lymphoma show a weak signal in variable proportion of cells.

(10) DNA247476 (TAT180)

With regard to normal tissues, strong expression is seen in prostatic epithelium and in a section of peripheral nerve. Moderate expression is seen in renal glomeruli. Weak expression is seen in bile duct epithelium and mammary epithelium. Two sections of stomach show weak expression in a subset of gastric glands. Sections of colon and small intestine show a signal in lamina propria and/or submucosa, most likely in small autonomic nerve fibers. Another independent ISH study fails to show expression in peripheral nerves of prostatectomy sections, despite adequate signal in prostatic epithelium.

In a separate analysis, 42 of 77 breast tumors are positive (55%) for expression.

In yet another analysis, 8 of 11 breast cancers are positive for expression.

In yet another analysis, expression is seen in 1/2 non-small cell lung carcinomas, 1/3 colorectal adenocarcinomas, 2/3 pancreatic adenocarcinomas, 1/1 prostate cancers, 1/3 transitional cell carcinomas, 3/3 renal cell carcinomas, 3/3 endometrial adenocarcinomas, 1/2 ovarian adenocarcinomas and 1/3 malignant melanomas.

In yet another analysis, expression is seen in 42 of 45 (93%) prostate cancers.

In yet another analysis, expression is seen in all of 23 primary and in 12 of 15 (80%) metastatic prostate cancers analyzed.

In yet another analysis, expression is observed in the following carcinomas as follows: pancreatic adenocarcinoma-2 of 2 cases are positive; colorectal adenocarcinoma-12 of 14 cases are positive; gastric adenocarcinoma-6 of 8 cases are positive; esophageal carcinoma-2 of 3 cases are positive; cholangiocarcinoma-1 of 1 case is positive; metastatic adenocarcinoma (ovary, liver, lymph node, diaphragm)-8 of 12 cases are positive.

(11) DNA260990 (TAT375)

With regard to normal tissues, strong expression is seen in prostatic epithelium and in a section of peripheral nerve. Moderate expression is seen in renal glomeruli. Weak expression is seen in bile duct epithelium and mammary epithelium. Two sections of stomach show weak expression in a subset of gastric glands. Sections of colon and small intestine show a signal in lamina propria and/or submucosa, most likely in small autonomic nerve fibers. Another independent ISH study fails to show expression in peripheral nerves of prostatectomy sections, despite adequate signal in prostatic epithelium.

In a separate analysis, 42 of 77 breast tumors are positive (55%) for expression.

In yet another analysis, 8 of 11 breast cancers are positive for expression.

In yet another analysis, expression is seen in 1/2 non-small cell lung carcinomas, 1/3 colorectal adenocarcinomas, 2/3 pancreatic adenocarcinomas, 1/1 prostate cancers, 1/3 transitional cell carcinomas, 3/3 renal cell carcinomas, 3/3 endometrial adenocarcinomas, 1/2 ovarian adenocarcinomas and 1/3 malignant melanomas.

In yet another analysis, expression is seen in 42 of 45 (93%) prostate cancers.

In yet another analysis, expression is seen in all of 23 primary and in 12 of 15 (80%) metastatic prostate cancers analyzed.

In yet another analysis, expression is observed in the following carcinomas as follows: pancreatic adenocarcinoma-2 of 2 cases are positive; colorectal adenocarcinoma-12 of 14 cases are positive; gastric adenocarcinoma-6 of 8 cases are positive; esophageal carcinoma-2 of 3 cases are positive; cholangiocarcinoma-1 of 1 case is positive; metastatic adenocarcinoma (ovary, liver, lymph node, diaphragm)-8 of 12 cases are positive.

(12) DNA261013 (TAT176)

With regard to normal tissues, prostate epithelium shows a weak positive signal. Also, one core of colonic mucosa shows a weak signal in mucosal epithelium. Two cores of a testicular neoplasm are positive.

In another analysis, 87 cases of infiltrating ductal breast cancer are available for review. 40 cases are positive for expression. Additionally, all tested cell lines (A549, SK-MES, SKBR3, MDA231, MDA453, MDA175, MCF7) are positive for expression.

In another analysis, there is no consistent expression in benign colon, small intestinal, liver, pancreatic, gastric or esophageal tissue. In malignant tumors expression is observed as follows: colorectal adenocarcinoma: 10 of 14 cases are positive, gastric adenocarcinoma: 4 of 8 cases are positive, esophageal carcinoma: 3 of 4 cases are positive and metastatic adenocarcinoma: 8 of 11 cases are positive.

(13) DNA262144 (TAT184)

Two of 4 cases of non-small cell lung carcinoma are positive for expression while no signal is observed in non-neoplastic lung. In a separate analysis, three cases of non-small cell lung carcinoma are positive

(14) DNA267342 (TAT213)

Expression is not observed in any of the normal adult tissues tested. Seventy four cases of breast cancer are available for review and 30 cases give a positive signal Expression localizes to tumor-associated stroma.

In a separate analysis, expression is seen in a minority of sarcomas; moderate and occasionally strong expression is seen in a case of a synovial sarcoma, angiosarcoma, fibrosarcoma, gliosarcoma and malignant fibrohistiocytoma. In most cases expression appears to localize to the malignant cell population.

(15) DNA267626 (TAT217)

Expression is seen in 6 of 9 invasive breast cancers. Expression is in most cases of moderate intensity, expression is also seen in benign mammary epithelium and fibroadenoma. The large sections included in this study show expression in 1 of 1 endometrial adenocarcinomas, in 2 of 3 invasive ductal breast cancers, in benign renal tubules, in normal breast epithelium and in epidermis. Sections of lung, brain, myometrium and eye are negative.

(16) DNA268334 (TAT202)

No expression is seen in any of the adult, normal tissues tested while expression is observed in 3 of 3 renal cell carcinomas.

(17) DNA269238 (TAT215)

Tumor-associated vasculature was strongly positive in all renal cell carcinomas tested (n=6), in all hepatocellular carcinomas tested (n=3), in all gastric adenocarcinomas tested (n=5), in all endometrial adenocarcinomas tested (n=3), in all malignant melanomas tested (n=3), in all malignant lymphomas tested (n=3), in all pancreatic adenocarcinomas tested (n=1), in all esophageal carcinomas tested (n=4), in all cholangiocarcinomas tested (n=2), in 93% of all non-small cell lung cancers tested (n=15), in 86% of all invasive ductal breast cancers tested (n=88), in 83% of all colorectal adenocarcinomas tested (n=12), in 67% of all metastatic adenocarcinomas tested (n=6), in 75% of all transitional cell carcinomas tested (n=4). While TAT215 expression is also observed in endothelial components of various normal non-cancerous tissues, the expression level is significantly lower in these non-cancerous tissues as compared to their cancerous counterparts and the expression pattern in the tumor tissues was distinct from that in the normal tissues, thereby providing a means for both therapy and diagnosis of the cancerous condition.

(18) DNA304853 (TAT376)

With regard to normal tissues, it appears that there is a weak signal in colon mucosa and breast epithelium. With regard to tumor tissues, expression is seen in 1 of 2 non-small cell lung carcinomas, 2 of 2 colon cancers, 1 of 2 pancreatic cancers, 1 of 2 hepatocellular carcinomas, 3 of 3 endometrial carcinomas, 1 of 2 ovarian carcinomas and 2 of 3 malignant melanomas.

In a separate analysis, 12 of 16 colorectal carcinomas are positive for expression; 2 of 8 gastric adenocarcinoma are positive for expression, 2 of 4 esophageal carcinomas are positive for expression; 7 of 10 metastatic adenocarcinoma are positive for expression and 1 of 2 cholangiocarcinomas are positive for expression. Expression level is tumor tissues is consistently higher than in normal tissues.

(19) DNA304854 (TAT377)

With regard to normal tissues, it appears that there is a weak signal in colon mucosa and breast epithelium. With regard to tumor tissues, expression is seen in 1 of 2 non-small cell lung carcinomas, 2 of 2 colon cancers, 1 of 2 pancreatic cancers, 1 of 2 hepatocellular carcinomas, 3 of 3 endometrial carcinomas, 1 of 2 ovarian carcinomas and 2 of 3 malignant melanomas.

In a separate analysis, 12 of 16 colorectal carcinomas are positive for expression; 2 of 8 gastric adenocarcinoma are positive for expression, 2 of 4 esophageal carcinomas are positive for expression; 7 of 10 metastatic adenocarcinoma are positive for expression and 1 of 2 cholangiocarcinomas are positive for expression. Expression level is tumor tissues is consistently higher than in normal tissues.

(20) DNA304855 (TAT378)

With regard to normal tissues, it appears that there is a weak signal in colon mucosa and breast epithelium. With regard to tumor tissues, expression is seen in 1 of 2 non-small cell lung carcinomas, 2 of 2 colon cancers, 1 of 2 pancreatic cancers, 1 of 2 hepatocellular carcinomas, 3 of 3 endometrial carcinomas, 1 of 2 ovarian carcinomas and 2 of 3 malignant melanomas.

In a separate analysis, 12 of 16 colorectal carcinomas are positive for expression; 2 of 8 gastric adenocarcinoma are positive for expression, 2 of 4 esophageal carcinomas are positive for expression; 7 of 10 metastatic adenocarcinoma are positive for expression and 1 of 2 cholangiocarcinomas are positive for expression. Expression level is tumor tissues is consistently higher than in normal tissues.

(21) DNA287971 (TAT379)

With regard to normal tissues, strong expression is seen in prostatic epithelium and in a section of peripheral nerve. Moderate expression is seen in renal glomeruli. Weak expression is seen in bile duct epithelium and mammary epithelium. Two sections of stomach show weak expression in a subset of gastric glands. Sections of colon and small intestine show a signal in lamina propria and/or submucosa, most likely in small autonomic nerve fibers. Another independent ISH study fails to show expression in peripheral nerves of prostatectomy sections, despite adequate signal in prostatic epithelium.

In a separate analysis, 42 of 77 breast tumors are positive (55%) for expression.

In yet another analysis, 8 of 11 breast cancers are positive for expression.

In yet another analysis, expression is seen in 1/2 non-small cell lung carcinomas, 1/3 colorectal adenocarcinomas, 2/3 pancreatic adenocarcinomas, 1/1 prostate cancers, 1/3 transitional cell carcinomas, 3/3 renal cell carcinomas, 3/3 endometrial adenocarcinomas, 1/2 ovarian adenocarcinomas and 1/3 malignant melanomas.

In yet another analysis, expression is seen in 42 of 45 (93%) prostate cancers.

In yet another analysis, expression is seen in all of 23 primary and in 12 of 15 (80%) metastatic prostate cancers analyzed.

In yet another analysis, expression is observed in the following carcinomas as follows: pancreatic adenocarcinoma-2 of 2 cases are positive; colorectal adenocarcinoma-12 of 14 cases are positive; gastric adenocarcinoma-6 of 8 cases are positive; esophageal carcinoma-2 of 3 cases are positive; cholangiocarcinoma-1 of 1 case is positive; metastatic adenocarcinoma (ovary, liver, lymph node, diaphragm)-8 of 12 cases are positive.

Example 5

Verification and Analysis of Differential TAT Polypeptide Expression by GEPIS

TAT polypeptides which may have been identified as a tumor antigen as described in one or more of the above Examples were analyzed and verified as follows. An expressed sequence tag (EST) DNA database (LIFESEQ®, Incyte Pharmaceuticals, Palo Alto, Calif.) was searched and interesting EST sequences were identified by GEPIS. Gene expression profiling in silico (GEPIS) is a bioinformatics tool developed at Genentech, Inc. that characterizes genes of interest for new cancer therapeutic targets. GEPIS takes advantage of large amounts of EST sequence and library information to determine gene expression profiles. GEPIS is capable of determining the expression profile of a gene based upon its proportional correlation with the number of its occurrences in EST databases, and it works by integrating the LIFESEQ® EST relational database and Genentech proprietary information in a stringent and statistically meaningful way. In this example, GEPIS is used to identify and cross-validate novel tumor antigens, although GEPIS can be configured to perform either very specific analyses or broad screening tasks. For the initial screen, GEPIS is used to identify EST sequences from the LIFESEQ® database that correlate to expression in a particular tissue or tissues of interest (often a tumor tissue of interest). The EST sequences identified in this initial screen (or consensus sequences obtained from aligning multiple related and overlapping EST sequences obtained from the initial screen) were then subjected to a screen intended to identify the presence of at least one transmembrane domain in the encoded protein. Finally, GEPIS was employed to generate a complete tissue expression profile for the various sequences of interest. Using this type of screening bioinformatics, various TAT polypeptides (and their encoding nucleic acid molecules) were identified as being significantly overexpressed in a particular type of cancer or certain cancers as compared to other cancers and/or normal non-cancerous tissues. The rating of GEPIS hits is based upon several criteria including, for example, tissue specificity, tumor specificity and expression level in normal essential and/or normal proliferating tissues. The following is a list of molecules whose tissue expression profile as determined by GEPIS evidences high tissue expression and significant upregulation of expression in a specific tumor or tumors as compared to other tumor(s) and/or normal tissues and optionally relatively low expression in normal essential and/or normal proliferating tissues. As such, the molecules listed below are excellent polypeptide targets for the diagnosis and therapy of cancer in mammals.

| Molecule | upregulation of expression in: | as compared to: |
|---|---|---|
| DNA67962 (TAT207) | colon tumor | normal colon tissue |
| DNA67962 (TAT207) | uterus tumor | normal uterus tissue |
| DNA67962 (TAT207) | lung tumor | normal lung tissue |
| DNA67962 (TAT207) | prostate tumor | normal prostate tissue |
| DNA67962 (TAT207) | breast tumor | normal breast tissue |
| DNA96792 (TAT239) | colon tumor | normal colon tissue |
| DNA96792 (TAT239) | rectum tumor | normal rectum tissue |
| DNA96792 (TAT239) | pancreas tumor | normal pancreas tissue |
| DNA96792 (TAT239) | lung tumor | normal lung tissue |
| DNA96792 (TAT239) | stomach tumor | normal stomach tissue |
| DNA96792 (TAT239) | esophagus tumor | normal esophagus tissue |
| DNA96792 (TAT239) | breast tumor | normal breast tissue |
| DNA96792 (TAT239) | uterus tumor | normal uterus tissue |
| DNA96964 (TAT193) | breast tumor | normal breast tissue |
| DNA96964 (TAT193) | brain tumor | normal brain tissue |
| DNA142915 (TAT199) | breast tumor | normal breast tissue |
| DNA142915 (TAT199) | ovary tumor | normal ovary tissue |
| DNA142915 (TAT199) | brain tumor | normal brain tissue |
| DNA208551 (TAT178) | prostate tumor | normal prostate tissue |
| DNA208551 (TAT178) | colon tumor | normal colon tissue |
| DNA210159 (TAT198) | prostate tumor | normal prostate tissue |
| DNA210159 (TAT198) | uterus tumor | normal uterus tissue |
| DNA210159 (TAT198) | breast tumor | normal breast tissue |
| DNA210159 (TAT198) | ovarian tumor | normal ovarian tissue |
| DNA225706 (TAT194) | adrenal tumor | normal adrenal tissue |
| DNA225706 (TAT194) | prostate tumor | normal prostate tissue |
| DNA225706 (TAT194) | breast tumor | normal breast tissue |
| DNA225706 (TAT194) | connective tissue tumor | normal connective tissue |
| DNA225793 (TAT223) | ovarian tumor | normal ovarian tissue |
| DNA225793 (TAT223) | fallopian tube tumor | normal fallopian tube tissue |
| DNA225793 (TAT223) | kidney tumor | normal kidney tissue |
| DNA225796 (TAT196) | breast tumor | normal breast tissue |
| DNA225943 (TAT195) | liver tumor | normal liver tissue |
| DNA225943 (TAT195) | lung tumor | normal lung tissue |
| DNA225943 (TAT195) | breast tumor | normal breast tissue |
| DNA226283 (TAT203) | uterine tumor | normal uterine tissue |
| DNA226283 (TAT203) | breast tumor | normal breast tissue |
| DNA226283 (TAT203) | squamous cell lung tumor | normal squamous cell lung tissue |
| DNA226283 (TAT203) | colon tumor | normal colon tissue |
| DNA226283 (TAT203) | ovarian tumor | normal ovarian tissue |
| DNA226589 (TAT200) | brain tumor | normal brain tissue |
| DNA226589 (TAT200) | colon tumor | normal colon tissue |
| DNA226589 (TAT200) | breast tumor | normal breast tissue |
| DNA226589 (TAT200) | prostate tumor | normal prostate tissue |

-continued

| Molecule | upregulation of expression in: | as compared to: |
|---|---|---|
| DNA226622 (TAT205) | squamous cell lung tumor | normal squamous cell lung tissue |
| DNA226622 (TAT205) | kidney tumor | normal kidney tissue |
| DNA226622 (TAT205) | uterine tumor | normal uterine tissue |
| DNA226622 (TAT205) | breast tumor | normal breast tissue |
| DNA226622 (TAT205) | colon tumor | normal colon tissue |
| DNA227545 (TAT197) | breast tumor | normal breast tissue |
| DNA227611 (TAT175) | prostate tumor | normal prostate tissue |
| DNA227611 (TAT175) | colon tumor | normal colon tissue |
| DNA227611 (TAT175) | breast tumor | normal breast tissue |
| DNA227611 (TAT175) | uterine tumor | normal uterine tissue |
| DNA261021 (TAT208) | prostate tumor | normal prostate tissue |
| DNA261021 (TAT208) | colon tumor | normal colon tissue |
| DNA261021 (TAT208) | breast tumor | normal breast tissue |
| DNA261021 (TAT208) | uterine tumor | normal uterine tissue |
| DNA260655 (TAT209) | lung tumor | normal lung tissue |
| DNA260655 (TAT209) | colon tumor | normal colon tissue |
| DNA260655 (TAT209) | breast tumor | normal breast tissue |
| DNA260655 (TAT209) | liver tumor | normal liver tissue |
| DNA260655 (TAT209) | ovarian tumor | normal ovarian tissue |
| DNA260655 (TAT209) | skin tumor | normal skin tissue |
| DNA260655 (TAT209) | spleen tumor | normal spleen tissue |
| DNA260655 (TAT209) | myeloid tumor | normal myeloid tissue |
| DNA260655 (TAT209) | muscle tumor | normal muscle tissue |
| DNA260655 (TAT209) | bone tumor | normal bone tissue |
| DNA260945 (TAT192) | brain tumor | normal brain tissue |
| DNA260945 (TAT192) | breast tumor | normal breast tissue |
| DNA260945 (TAT192) | colon tumor | normal colon tissue |
| DNA260945 (TAT192) | ovarian tumor | normal ovarian tissue |
| DNA260945 (TAT192) | pancreatic tumor | normal pancreatic tissue |
| DNA261001 (TAT181) | bone tumor | normal bone tissue |
| DNA261001 (TAT181) | lung tumor | normal lung tissue |
| DNA266928 (TAT182) | bone tumor | normal bone tissue |
| DNA266928 (TAT182) | lung tumor | normal lung tissue |
| DNA268035 (TAT222) | ovarian tumor | normal ovarian tissue |
| DNA277797 (TAT212) | breast tumor | normal breast tissue |
| DNA277797 (TAT212) | pancreatic tumor | normal pancreatic tissue |
| DNA77509 (TAT177) | colon tumor | normal colon tissue |
| DNA77509 (TAT177) | testis tumor | normal testis tissue |
| DNA87993 (TAT235) | breast tumor | normal breast tissue |
| DNA87993 (TAT235) | prostate tumor | normal prostate tissue |
| DNA87993 (TAT235) | colon tumor | normal colon tissue |
| DNA87993 (TAT235) | ovarian tumor | normal ovarian tissue |
| DNA92980 (TAT234) | bone tumor | normal bone tissue |
| DNA92980 (TAT234) | breast tumor | normal breast tissue |
| DNA92980 (TAT234) | cervical tumor | normal cervical tissue |
| DNA92980 (TAT234) | colon tumor | normal colon tissue |
| DNA92980 (TAT234) | rectum tumor | normal rectum tissue |
| DNA92980 (TAT234) | endometrial tumor | normal endometrial tissue |
| DNA92980 (TAT234) | liver tumor | normal liver tissue |
| DNA92980 (TAT234) | lung tumor | normal lung tissue |
| DNA92980 (TAT234) | ovarian tumor | normal ovarian tissue |
| DNA92980 (TAT234) | pancreatic tumor | normal pancreatic tissue |
| DNA92980 (TAT234) | skin tumor | normal skin tissue |
| DNA92980 (TAT234) | soft tissue tumor | normal soft tissue |
| DNA92980 (TAT234) | stomach tumor | normal stomach tissue |
| DNA92980 (TAT234) | bladder tumor | normal bladder tissue |
| DNA92980 (TAT234) | thyroid tumor | normal thyroid tissue |
| DNA92980 (TAT234) | esophagus tumor | normal esophagus tissue |
| DNA92980 (TAT234) | testis tumor | normal testis tissue |
| DNA105792 (TAT233) | adrenal tumor | normal adrenal tissue |
| DNA105792 (TAT233) | breast tumor | normal breast tissue |
| DNA105792 (TAT233) | endometrial tumor | normal endometrial tissue |
| DNA105792 (TAT233) | esophagus tumor | normal esophagus tissue |
| DNA105792 (TAT233) | kidney tumor | normal kidney tissue |
| DNA105792 (TAT233) | lung tumor | normal lung tissue |
| DNA105792 (TAT233) | ovarian tumor | normal ovarian tissue |
| DNA105792 (TAT233) | pancreatic tumor | normal pancreatic tissue |
| DNA105792 (TAT233) | prostate tumor | normal prostate tissue |
| DNA105792 (TAT233) | soft tissue tumor | normal soft tissue |
| DNA105792 (TAT233) | myeloid tumor | normal myeloid tissue |
| DNA105792 (TAT233) | thyroid tumor | normal thyroid tissue |
| DNA105792 (TAT233) | bladder tumor | normal bladder tissue |
| DNA105792 (TAT233) | brain tumor | normal brain tissue |
| DNA105792 (TAT233) | testis tumor | normal testis tissue |
| DNA119474 (TAT226) | kidney tumor | normal kidney tissue |
| DNA119474 (TAT226) | adrenal tumor | normal adrenal tissue |
| DNA119474 (TAT226) | uterine tumor | normal uterine tissue |

-continued

| Molecule | upregulation of expression in: | as compared to: |
|---|---|---|
| DNA119474 (TAT226) | ovarian tumor | normal ovarian tissue |
| DNA150491 (TAT204) | squamous cell lung tumor | normal squamous cell lung tissue |
| DNA150491 (TAT204) | colon tumor | normal colon tissue |
| DNA280351 (TAT248) | squamous cell lung tumor | normal squamous cell lung tissue |
| DNA280351 (TAT248) | colon tumor | normal colon tissue |
| DNA150648 (TAT232) | liver tumor | normal liver tissue |
| DNA150648 (TAT232) | breast tumor | normal breast tissue |
| DNA150648 (TAT232) | brain tumor | normal brain tissue |
| DNA150648 (TAT232) | lung tumor | normal lung tissue |
| DNA150648 (TAT232) | colon tumor | normal colon tissue |
| DNA150648 (TAT232) | rectum tumor | normal rectum tissue |
| DNA150648 (TAT232) | kidney tumor | normal kidney tissue |
| DNA150648 (TAT232) | bladder tumor | normal bladder tissue |
| DNA179651 (TAT224) | colon tumor | normal colon tissue |
| DNA179651 (TAT224) | uterine tumor | normal uterine tissue |
| DNA179651 (TAT224) | lung tumor | normal lung tissue |
| DNA179651 (TAT224) | kidney tumor | normal kidney tissue |
| DNA225886 (TAT236) | breast tumor | normal breast tissue |
| DNA225886 (TAT236) | colon tumor | normal colon tissue |
| DNA225886 (TAT236) | rectum tumor | normal rectum tissue |
| DNA225886 (TAT236) | ovarian tumor | normal ovarian tissue |
| DNA225886 (TAT236) | pancreas tumor | normal pancreas tissue |
| DNA225886 (TAT236) | prostate tumor | normal prostate tissue |
| DNA225886 (TAT236) | bladder tumor | normal bladder tissue |
| DNA225886 (TAT236) | testis tumor | normal testis tissue |
| DNA226717 (TAT185) | glioma | normal glial tissue |
| DNA226717 (TAT185) | brain tumor | normal brain tissue |
| DNA227162 (TAT225) | myeloid tumor | normal myeloid tissue |
| DNA227162 (TAT225) | uterine tumor | normal uterine tissue |
| DNA227162 (TAT225) | prostate tumor | normal prostate tissue |
| DNA277804 (TAT247) | myeloid tumor | normal myeloid tissue |
| DNA277804 (TAT247) | uterine tumor | normal uterine tissue |
| DNA277804 (TAT247) | prostate tumor | normal prostate tissue |
| DNA233034 (TAT174) | glioma | normal glial tissue |
| DNA233034 (TAT174) | brain tumor | normal brain tissue |
| DNA233034 (TAT174) | kidney tumor | normal kidney tissue |
| DNA233034 (TAT174) | adrenal tumor | normal adrenal tissue |
| DNA266920 (TAT214) | glioma | normal glial tissue |
| DNA266920 (TAT214) | brain tumor | normal brain tissue |
| DNA266920 (TAT214) | kidney tumor | normal kidney tissue |
| DNA266920 (TAT214) | adrenal tumor | normal adrenal tissue |
| DNA266921 (TAT220) | glioma | normal glial tissue |
| DNA266921 (TAT220) | brain tumor | normal brain tissue |
| DNA266921 (TAT220) | kidney tumor | normal kidney tissue |
| DNA266921 (TAT220) | adrenal tumor | normal adrenal tissue |
| DNA266922 (TAT221) | glioma | normal glial tissue |
| DNA266922 (TAT221) | brain tumor | normal brain tissue |
| DNA266922 (TAT221) | kidney tumor | normal kidney tissue |
| DNA266922 (TAT221) | adrenal tumor | normal adrenal tissue |
| DNA234834 (TAT179) | colon tumor | normal colon tissue |
| DNA234834 (TAT179) | uterine tumor | normal uterine tissue |
| DNA234834 (TAT179) | breast tumor | normal breast tissue |
| DNA234834 (TAT179) | prostate tumor | normal prostate tissue |
| DNA247587 (TAT216) | breast tumor | normal breast tissue |
| DNA247587 (TAT216) | prostate tumor | normal prostate tissue |
| DNA247587 (TAT216) | bladder tumor | normal bladder tissue |
| DNA247587 (TAT216) | lymphoid tumor | normal lymphoid tissue |
| DNA255987 (TAT218) | brain tumor | normal brain tissue |
| DNA255987 (TAT218) | breast tumor | normal breast tissue |
| DNA247476 (TAT180) | prostate tumor | normal prostate tissue |
| DNA247476 (TAT180) | pancreas tumor | normal pancreas tissue |
| DNA247476 (TAT180) | brain tumor | normal brain tissue |
| DNA247476 (TAT180) | stomach tumor | normal stomach tissue |
| DNA247476 (TAT180) | bladder tumor | normal bladder tissue |
| DNA247476 (TAT180) | soft tissue tumor | normal soft tissue |
| DNA247476 (TAT180) | skin tumor | normal skin tissue |
| DNA247476 (TAT180) | kidney tumor | normal kidney tissue |
| DNA260990 (TAT375) | prostate tumor | normal prostate tissue |
| DNA260990 (TAT375) | pancreas tumor | normal pancreas tissue |
| DNA260990 (TAT375) | brain tumor | normal brain tissue |
| DNA260990 (TAT375) | stomach tumor | normal stomach tissue |
| DNA260990 (TAT375) | bladder tumor | normal bladder tissue |
| DNA260990 (TAT375) | soft tissue tumor | normal soft tissue |
| DNA260990 (TAT375) | skin tumor | normal skin tissue |
| DNA260990 (TAT375) | kidney tumor | normal kidney tissue |
| DNA261013 (TAT176) | prostate tumor | normal prostate tissue |

-continued

| Molecule | upregulation of expression in: | as compared to: |
|---|---|---|
| DNA261013 (TAT176) | colon tumor | normal colon tissue |
| DNA261013 (TAT176) | small intestine tumor | normal small intestine tissue |
| DNA261013 (TAT176) | pancreatic tumor | normal pancreatic tissue |
| DNA261013 (TAT176) | uterine tumor | normal uterine tissue |
| DNA261013 (TAT176) | ovarian tumor | normal ovarian tissue |
| DNA261013 (TAT176) | bladder tumor | normal bladder tissue |
| DNA261013 (TAT176) | stomach tumor | normal stomach tissue |
| DNA267342 (TAT213) | breast tumor | normal breast tissue |
| DNA267342 (TAT213) | uterine tumor | normal uterine tissue |
| DNA267342 (TAT213) | colon tumor | normal colon tissue |
| DNA267342 (TAT213) | kidney tumor | normal kidney tissue |
| DNA267342 (TAT213) | bladder tumor | normal bladder tissue |
| DNA267342 (TAT213) | bone tumor | normal bone tissue |
| DNA267342 (TAT213) | ovarian tumor | normal ovarian tissue |
| DNA267342 (TAT213) | pancreatic tumor | normal pancreatic tissue |
| DNA267626 (TAT217) | breast tumor | normal breast tissue |
| DNA267626 (TAT217) | colon tumor | normal colon tissue |
| DNA267626 (TAT217) | pancreatic tumor | normal pancreatic tissue |
| DNA267626 (TAT217) | ovarian tumor | normal ovarian tissue |
| DNA268334 (TAT202) | kidney tumor | normal kidney tissue |
| DNA269238 (TAT215) | colon tumor | normal colon tissue |
| DNA269238 (TAT215) | kidney tumor | normal kidney tissue |
| DNA269238 (TAT215) | adrenal tumor | normal adrenal tissue |
| DNA269238 (TAT215) | bladder tumor | normal bladder tissue |
| DNA272578 (TAT238) | adrenal tumor | normal adrenal tissue |
| DNA272578 (TAT238) | lung tumor | normal lung tissue |
| DNA272578 (TAT238) | ovarian tumor | normal ovarian tissue |
| DNA272578 (TAT238) | uterine tumor | normal uterine tissue |
| DNA304853 (TAT376) | colon tumor | normal colon tissue |
| DNA304853 (TAT376) | uterine tumor | normal uterine tissue |
| DNA304853 (TAT376) | breast tumor | normal breast tissue |
| DNA304853 (TAT376) | prostate tumor | normal prostate tissue |
| DNA304854 (TAT377) | colon tumor | normal colon tissue |
| DNA304854 (TAT377) | uterine tumor | normal uterine tissue |
| DNA304854 (TAT377) | breast tumor | normal breast tissue |
| DNA304854 (TAT377) | prostate tumor | normal prostate tissue |
| DNA304855 (TAT378) | colon tumor | normal colon tissue |
| DNA304855 (TAT378) | uterine tumor | normal uterine tissue |
| DNA304855 (TAT378) | breast tumor | normal breast tissue |
| DNA304855 (TAT378) | prostate tumor | normal prostate tissue |
| DNA287971 (TAT379) | prostate tumor | normal prostate tissue |
| DNA287971 (TAT379) | pancreas tumor | normal pancreas tissue |
| DNA287971 (TAT379) | brain tumor | normal brain tissue |
| DNA287971 (TAT379) | stomach tumor | normal stomach tissue |
| DNA287971 (TAT379) | bladder tumor | normal bladder tissue |
| DNA287971 (TAT379) | soft tissue tumor | normal soft tissue |
| DNA287971 (TAT379) | skin tumor | normal skin tissue |
| DNA287971 (TAT379) | kidney tumor | normal kidney tissue |

Example 6

Use of TAT as a Hybridization Probe

The following method describes use of a nucleotide sequence encoding TAT as a hybridization probe for, i.e., diagnosis of the presence of a tumor in a mammal.

DNA comprising the coding sequence of full-length or mature TAT as disclosed herein can also be employed as a probe to screen for homologous DNAs (such as those encoding naturally-occurring variants of TAT) in human tissue cDNA libraries or human tissue genomic libraries.

Hybridization and washing of filters containing either library DNAs is performed under the following high stringency conditions. Hybridization of radiolabeled TAT-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence TAT can then be identified using standard techniques known in the art.

Example 7

Expression of TAT in *E. coli*

This example illustrates preparation of an unglycosylated form of TAT by recombinant expression in *E. coli*.

The DNA sequence encoding TAT is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the TAT coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized TAT protein can then be purified using a metal chelating column under conditions that allow tight binding of the protein.

TAT may be expressed in *E. coli* in a poly-His tagged form, using the following procedure. The DNA encoding TAT is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) Ion galE rpoHts(htpRts) cipP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded TAT polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Certain of the TAT polypeptides disclosed herein have been successfully expressed and purified using this technique(s).

Example 8

Expression of TAT in Mammalian Cells

This example illustrates preparation of a potentially glycosylated form of TAT by recombinant expression in mammalian cells.

The vector, pRK5 (see EP 307,247, published Mar. 15, 1989 employed as the expression vector. Optionally, the TAT DNA is ligated into pRK5 with selected restriction enzymes to allow insertion of the TAT DNA using ligation methods such as described in Sambrook et al., supra. The resulting vector is called pRK5-TAT.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-TAT DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S methionine. After a 12 hour incubation, the conditioned medium is collected, concentrated on a spin filter, and loaded onto a 15% SDS gel. The processed gel may be dried and exposed to film for a selected period of time to reveal the presence of TAT polypeptide. The cultures containing transfected cells may undergo further incubation (in serum free medium) and the medium is tested in selected bioassays.

In an alternative technique, TAT may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-TAT DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed TAT can then be concentrated and purified by any selected method, such as dialysis and/or column chromatography.

In another embodiment, TAT can be expressed in CHO cells. The pRK5-TAT can be transfected into CHO cells using known reagents such as $CaPO_4$ or DEAE-dextran. As described above, the cell cultures can be incubated, and the medium replaced with culture medium (alone) or medium containing a radiolabel such as $^{35}S$-methionine. After determining the presence of TAT polypeptide, the culture medium may be replaced with serum free medium. Preferably, the cultures are incubated for about 6 days, and then the conditioned medium is harvested. The medium containing the expressed TAT can then be concentrated and purified by any selected method.

Epitope-tagged TAT may also be expressed in host CHO cells. The TAT may be subcloned out of the pRK5 vector. The subclone insert can undergo PCR to fuse in frame with a selected epitope tag such as a poly-his tag into a Baculovirus expression vector. The poly-his tagged TAT insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged TAT can then be concentrated and purified by any selected method, such as by $Ni^{2+}$-chelate affinity chromatography.

TAT may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Certain of the TAT polypeptides disclosed herein have been successfully expressed and purified using this technique(s).

Example 9

Expression of TAT in Yeast

The following method describes recombinant expression of TAT in yeast.

First, yeast expression vectors are constructed for intracellular production or secretion of TAT from the ADH2/GAPDH promoter. DNA encoding TAT and the promoter is inserted into suitable restriction enzyme sites in the selected plasmid to direct intracellular expression of TAT. For secretion, DNA encoding TAT can be cloned into the selected plasmid, together with DNA encoding the ADH2/GAPDH promoter, a native TAT signal peptide or other mammalian signal peptide, or, for example, a yeast alpha-factor or invertase secretory signal/leader sequence, and linker sequences (if needed) for expression of TAT.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant TAT can subsequently be isolated and purified by removing the yeast cells from the fermentation medium by centrifugation and then concentrating the medium using selected cartridge filters. The concentrate containing TAT may further be purified using selected column chromatography resins.

Certain of the TAT polypeptides disclosed herein have been successfully expressed and purified using this technique(s).

Example 10

Expression of TAT in Baculovirus-Infected Insect Cells

The following method describes recombinant expression of TAT in Baculovirus-infected insect cells.

The sequence coding for TAT is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding TAT or the desired portion of the coding sequence of TAT such as the sequence encoding an extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged TAT can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged TAT are pooled and dialyzed against loading buffer.

Alternatively, purification of the IgG tagged (or Fc tagged) TAT can be performed using known chromatography techniques, including for instance, Protein A or protein G column chromatography.

Certain of the TAT polypeptides disclosed herein have been successfully expressed and purified using this technique(s).

Example 11

Preparation of Antibodies that Bind TAT

This example illustrates preparation of monoclonal antibodies which can specifically bind TAT.

Techniques for producing the monoclonal antibodies are known in the art and are described, for instance, in Goding, supra. Immunogens that may be employed include purified TAT, fusion proteins containing TAT, and cells expressing recombinant TAT on the cell surface. Selection of the immunogen can be made by the skilled artisan without undue experimentation.

Mice, such as Balb/c, are immunized with the TAT immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-TAT antibodies.

After a suitable antibody titer has been detected, the animals "positive" for antibodies can be injected with a final intravenous injection of TAT. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against TAT. Determination of "positive" hybridoma cells secreting the desired monoclonal antibodies against TAT is within the skill in the art.

The positive hybridoma cells can be injected intraperitoneally into syngeneic Balb/c mice to produce ascites containing the anti-TAT monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 12

Purification of TAT Polypeptides Using Specific Antibodies

Native or recombinant TAT polypeptides may be purified by a variety of standard techniques in the art of protein purification. For example, pro-TAT polypeptide, mature TAT polypeptide, or pre-TAT polypeptide is purified by immunoaffinity chromatography using antibodies specific for the TAT polypeptide of interest. In general, an immunoaffinity column is constructed by covalently coupling the anti-TAT polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of TAT polypeptide by preparing a fraction from cells containing TAT polypeptide in a soluble form. This preparation is derived by solubilization of the whole cell or of a subcellular fraction obtained via differential centrifugation by the addition of detergent or by other methods well known in the art. Alternatively, soluble TAT polypeptide containing a signal sequence may be secreted in useful quantity into the medium in which the cells are grown.

A soluble TAT polypeptide-containing preparation is passed over the immunoaffinity column, and the column is washed under conditions that allow the preferential absorbance of TAT polypeptide (e.g., high ionic strength buffers in the presence of detergent). Then, the column is eluted under conditions that disrupt antibody/TAT polypeptide binding (e.g., a low pH buffer such as approximately pH 2-3, or a high concentration of a chaotrope such as urea or thiocyanate ion), and TAT polypeptide is collected.

Example 13

In Vitro Tumor Cell Killing Assay

Mammalian cells expressing the TAT polypeptide of interest may be obtained using standard expression vector and cloning techniques. Alternatively, many tumor cell lines expressing TAT polypeptides of interest are publicly available, for example, through the ATCC and can be routinely identified using standard ELISA or FACS analysis. Anti-TAT polypeptide monoclonal antibodies (and toxin conjugated derivatives thereof) may then be employed in assays to determine the ability of the antibody to kill TAT polypeptide expressing cells in vitro.

For example, cells expressing the TAT polypeptide of interest are obtained as described above and plated into 96 well dishes. In one analysis, the antibody/toxin conjugate (or naked antibody) is included throughout the cell incubation for a period of 4 days. In a second independent analysis, the cells are incubated for 1 hour with the antibody/toxin conjugate (or naked antibody) and then washed and incubated in the absence of antibody/toxin conjugate for a period of 4 days. Cell viability is then measured using the CellTiter-Glo Luminescent Cell Viability Assay from Promega (Cat# G7571). Untreated cells serve as a negative control.

Example 14

In Vivo Tumor Cell Killing Assay

To test the efficacy of conjugated or unconjugated anti-TAT polypeptide monoclonal antibodies, anti-TAT antibody is injected intraperitoneally into nude mice 24 hours prior to receiving tumor promoting cells subcutaneously in the flank. Antibody injections continue twice per week for the remainder of the study. Tumor volume is then measured twice per week.

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of diagnosing the presence of colon cancer in a mammal, said method comprising contacting a test sample of tissue cells suspected of containing cancerous tumor cells obtained from said mammal with an anti-SEQ ID NO:92 antibody that specifically binds to a protein comprising the amino acid sequence of SEQ ID NO:92, and detecting the formation of a complex between said antibody and said protein in the test sample, and classifying a higher level of formation of such a complex in the test sample, as compared to the level of formation of such a complex in a control sample of normal tissue cells from the same type of tissue as the test sample, as diagnostic of the presence of colon cancer in said mammal.

2. The method of claim 1, wherein said anti-SEQ ID NO: 92 antibody is detectably labeled.

3. A method of diagnosing the presence of colon cancer in a mammal, said method comprising determining the level of expression of a gene encoding a protein comprising the amino acid sequence of SEQ ID NO:92 in a test sample of tissue cells obtained from tissue suspected of containing cancerous tumor cells in said mammal and in a control sample of known normal cells taken from the same type of tissue as the test sample, wherein determining the level of expression of a gene encoding said protein comprises employing an anti-SEQ ID NO:92 antibody that specifically binds to a protein comprising the amino acid sequence of SEQ ID NO:92, and classifying a higher level of expression of said protein in the test sample, as compared to the control sample, as diagnostic of the presence of colon cancer in the mammal from which the test sample was obtained.

4. The method of claim 3, wherein the step employing an anti-SEQ ID NO:92 antibody that specifically binds to a protein comprising the amino acid sequence of SEQ ID NO:92 comprises an immunohistochemistry or Western blot analysis.

* * * * *

UNITED STATES PATENT AND TRADEMARK OFFICE

CERTIFICATE OF CORRECTION

PATENT NO. : 7,951,546 B2
APPLICATION NO. : 12/156180
DATED : May 31, 2011
INVENTOR(S) : Frantz et al.

It is certified that error appears in the above-identified patent and that said Letters Patent is hereby corrected as shown below:

Title Page
The Assignee item (73) instead of
"(73) Genetech, Inc., South San Francisco, CA (US)"

Should Read

"(73) Assignee: GENENTECH, Inc., South San Francisco, CA (US)"

Signed and Sealed this
Sixteenth Day of August, 2011

David J. Kappos
*Director of the United States Patent and Trademark Office*